US012565501B2

(12) United States Patent
Baccei et al.

(10) Patent No.: US 12,565,501 B2
(45) Date of Patent: Mar. 3, 2026

(54) MUSCARINIC ACETYLCHOLINE $M_1$ RECEPTOR ANTAGONISTS

(71) Applicant: Contineum Therapeutics, Inc., San Diego, CA (US)

(72) Inventors: Jill Melissa Baccei, San Diego, CA (US); Yalda Bravo, San Diego, CA (US); Austin Chih-Yu Chen, San Diego, CA (US); Jeffrey Roppe, Temecula, CA (US); Thomas Schrader, San Diego, CA (US); Yifeng Xiong, San Diego, CA (US)

(73) Assignee: Contineum Therapeutics, Inc., San Diego, CA (US)

( * ) Notice: Subject to any disclaimer, the term of this patent is extended or adjusted under 35 U.S.C. 154(b) by 923 days.

(21) Appl. No.: 17/762,683

(22) PCT Filed: Oct. 6, 2020

(86) PCT No.: PCT/US2020/054412

§ 371 (c)(1),
(2) Date: Mar. 22, 2022

(87) PCT Pub. No.: WO2021/071843

PCT Pub. Date: Apr. 15, 2021

(65) Prior Publication Data

US 2023/0089921 A1 Mar. 23, 2023

Related U.S. Application Data

(60) Provisional application No. 62/911,807, filed on Oct. 7, 2019.

(51) Int. Cl.

| | |
|---|---|
| ***C07D 487/08*** | (2006.01) |
| ***A61K 31/444*** | (2006.01) |
| ***A61K 31/4709*** | (2006.01) |
| ***A61K 31/506*** | (2006.01) |
| ***A61K 45/06*** | (2006.01) |
| ***A61P 25/00*** | (2006.01) |
| ***C07D 471/08*** | (2006.01) |
| ***C07D 498/08*** | (2006.01) |
| ***C07D 519/00*** | (2006.01) |

(52) U.S. Cl.

CPC .......... *C07D 487/08* (2013.01); *A61K 31/444* (2013.01); *A61K 31/4709* (2013.01); *A61K 31/506* (2013.01); *A61K 45/06* (2013.01); *A61P 25/00* (2018.01); *C07D 471/08* (2013.01); *C07D 498/08* (2013.01); *C07D 519/00* (2013.01)

(58) Field of Classification Search

None

See application file for complete search history.

(56) References Cited

U.S. PATENT DOCUMENTS

| | | | | |
|---|---|---|---|---|
| 4,803,203 | A | 2/1989 | Caprathe et al. | |
| 4,873,331 | A | 10/1989 | Childers, Jr. et al. | |
| 5,089,497 | A | 2/1992 | Jaen et al. | |
| 5,846,514 | A | 12/1998 | Foster | |
| 6,334,997 | B1 | 1/2002 | Foster | |
| 7,071,335 | B2 | 7/2006 | Kyle et al. | |
| 8,648,074 | B2 | 2/2014 | Li et al. | |
| 8,906,924 | B2 | 12/2014 | Baroni et al. | |
| 8,999,974 | B2 | 4/2015 | Morita et al. | |
| 9,446,030 | B2 | 9/2016 | Dooley | |
| 9,592,288 | B2 | 3/2017 | Schultz | |
| 9,616,052 | B2 | 4/2017 | Dooley | |
| 10,464,919 | B2 | 11/2019 | Lee | |
| 10,550,105 | B2 * | 2/2020 | Vasbinder | C07D 401/14 |
| 10,596,378 | B2 | 3/2020 | Rustick | |
| 11,512,090 | B2 | 11/2022 | Xiong et al. | |
| 11,752,149 | B2 | 9/2023 | Xiong et al. | |
| 12,054,487 | B2 | 8/2024 | Schrader | |
| 12,180,243 | B2 | 12/2024 | Zhao et al. | |
| 2006/0233843 | A1 | 10/2006 | Conn et al. | |
| 2007/0129378 | A1 | 6/2007 | Siddiqui et al. | |
| 2013/0178458 | A1 | 7/2013 | Lindsley et al. | |
| 2013/0289019 | A1 | 10/2013 | Chau | |
| 2018/0258085 | A1 | 9/2018 | Brown et al. | |
| 2020/0181166 | A1 | 6/2020 | Lindsley | |
| 2020/0231592 | A1 | 7/2020 | Lindsley et al. | |
| 2021/0061779 | A1 | 3/2021 | Wipf | |

(Continued)

FOREIGN PATENT DOCUMENTS

| | | |
|---|---|---|
| CN | 107663159 A | 2/2018 |
| CN | 108349936 A | 7/2018 |

(Continued)

OTHER PUBLICATIONS

CAS Registry No. 2249464-92-2, entered STN Nov. 18, 2018, 1 page.

(Continued)

*Primary Examiner* — Juliet C Switzer
*Assistant Examiner* — Dawanna Shar-Day White
(74) *Attorney, Agent, or Firm* — Morrison & Foerster LLP

(57) ABSTRACT

Provided herein, inter alia, are compounds which are useful as antagonists of the muscarinic acetylcholine receptor $M_1$ (mAChR $M_1$); synthetic methods for making the compounds; pharmaceutical compositions comprising the compounds; and methods of treating neurological and psychiatric disorders associated with muscarinic acetylcholine receptor dysfunction using the compounds and compositions.

38 Claims, No Drawings

(56) References Cited

U.S. PATENT DOCUMENTS

| | | | |
|---|---|---|---|
| 2021/0113532 | A1 | 4/2021 | Sidrauski |
| 2021/0137910 | A1 | 5/2021 | Jones |
| 2021/0155629 | A1 | 5/2021 | Schrader et al. |
| 2021/0161889 | A1 | 6/2021 | Xiong et al. |
| 2021/0186963 | A1 | 6/2021 | Wipf |
| 2022/0332721 | A1 | 10/2022 | Xiong |
| 2023/0364082 | A1 | 11/2023 | Xiong et al. |
| 2024/0217981 | A1 | 7/2024 | Roppe et al. |
| 2025/0026758 | A1 | 1/2025 | Schrader et al. |
| 2025/0171455 | A1 | 5/2025 | Baccei et al. |

FOREIGN PATENT DOCUMENTS

| | | | |
|---|---|---|---|
| EP | 2675893 | A1 | 12/2013 |
| EP | 3171867 | A1 | 5/2017 |
| JP | 2008507575 | A | 3/2008 |
| JP | 2009520689 | A | 5/2009 |
| JP | 2021523104 | A | 9/2021 |
| JP | 2021536505 | A | 12/2021 |
| WO | WO-97/23482 | A1 | 7/1997 |
| WO | 200200651 | A2 | 1/2002 |
| WO | WO-2006/010751 | A1 | 2/2006 |
| WO | 2007064732 | A1 | 6/2007 |
| WO | WO-2007/077508 | A2 | 7/2007 |
| WO | WO-2007/077508 | A3 | 7/2007 |
| WO | 2009117421 | A2 | 9/2009 |
| WO | 2011080445 | A1 | 7/2011 |
| WO | 2012020567 | A1 | 2/2012 |
| WO | 2012112933 | A1 | 8/2012 |
| WO | WO-2013/103931 | A1 | 7/2013 |
| WO | 2016014117 | A1 | 1/2016 |
| WO | 2016084866 | A1 | 6/2016 |
| WO | 2016107602 | A1 | 7/2016 |
| WO | 2017066705 | A1 | 4/2017 |
| WO | 2017079641 | A1 | 5/2017 |
| WO | 2017165822 | A1 | 9/2017 |
| WO | 2017223474 | A1 | 12/2017 |
| WO | WO-2018/089433 | A1 | 5/2018 |
| WO | 2018160891 | A1 | 9/2018 |
| WO | 2019073251 | A1 | 4/2019 |
| WO | WO-2019/126559 | A1 | 6/2019 |
| WO | WO-2019/158572 | A1 | 8/2019 |
| WO | 2019173790 | A1 | 9/2019 |
| WO | 2019179515 | A1 | 9/2019 |
| WO | WO-2019/212937 | A1 | 11/2019 |
| WO | WO-2019/241131 | A1 | 12/2019 |
| WO | 2020021021 | A1 | 1/2020 |
| WO | WO-2020/051153 | A1 | 3/2020 |
| WO | 2020123675 | A1 | 6/2020 |
| WO | 2020231806 | A1 | 11/2020 |
| WO | 2020231808 | A1 | 11/2020 |
| WO | 2020257180 | A1 | 12/2020 |
| WO | 2021071806 | A1 | 4/2021 |
| WO | 2021071837 | A1 | 4/2021 |
| WO | WO-2021/071843 | A1 | 4/2021 |
| WO | 2021094210 | A1 | 5/2021 |
| WO | 2022221450 | A1 | 10/2022 |
| WO | 2024088408 | A1 | 5/2024 |
| WO | 2024094170 | A1 | 5/2024 |
| WO | 2024169895 | A1 | 8/2024 |
| WO | 2024217531 | A1 | 10/2024 |

OTHER PUBLICATIONS

Cheng, H. et al. (Nov. 25, 2006). "Expression of mACh receptor m1-m5 subunits in the vestibular endorgans of rat," *Journal of Clinical Otorhinolaryngology* 20(22): 1027-1029. (*Translation of Abstract only*).

Zipp, G.G. et al. (Aug. 15, 2014). "Novel inhibitors of the high-affinity L-proline transporter as potential therapeutic agents for the treatment of cognitive disorders," *Bioorg Med Chem Lett* 24(16):3886-3890.

Extended European Search Report mailed on Oct. 10, 2023, for EP Patent Application No. 20875038.0, 7 pages.

International Search Report mailed on Jul. 15, 2022, for PCT Application No. PCT/US2022/024684, filed on Apr. 13, 2022, 2 pages.

Jicha. G. et al. (Feb. 2019). "Hippocampal Sclerosis, Argyrophilic Grain Disease, and Primary Age-Related Tauopathy," Continuum 25(1):208-233.

Klein J. (Apr. 29, 2020). "Can a person prevent multiple sclerosis?" Medical News Today 9 pages.

Liu, X. et al. (2019). "Parkinsonism Caused by Viral Encephalitis Affecting the Bilateral Substantia Nigra," *Clin Neuroradiol* 29(3):571-573.

Smith, S. et al. (Aug. 3, 2022). "Prevention and Management Strategies for Diabetic Neuropathy" *Life* (*Basel*) 12(8):1185.

Teylan, M. et al. (Jul. 2019). "Clinical diagnoses *among individuals with primary age-related tauopathy versus Alzheimer's neuropathology," Lab Invest* 99:1049-1055.

Written Opinion mailed on Jul. 15, 2022, for PCT Application No. PCT/US2022/024684, filed on Apr. 13, 2022, 3 pages.

Zuev, D. et al. (2005). "Stereoselective synthesis of new conformationally restricted analogues of a potent CGRP receptor antagonist," Organic Letters 7(12):2465-2468.

Ablordeppey, S. Y. et al. (Aug. 1, 2008). "Identification of A Butyrophenone Analog as a Potential Atypical Antipsychotic Agent: 4-[4-(4-Chlorophenyl)-1,4-diazepan-1-yl]-1-(4-fluorophenyl)butan-1-one," Bioorg Med Chem. 16 (15):7291-7301.

Berge, S. M. et al. (Jan. 1977). "Pharmaceutical Salts," Journal of Pharmaceutical Sciences 66(1):19 pages.

Busch-Petersen, J. et al. (2011, e-pub. Sep. 23, 2011). "Inhaled Long-Acting Muscarinic Antagonists in Chronic Obstructive Pulmonary Disease," Future Medical Chemistry 3(13):1623-1634.

Dean, D.C. (Jul. 2000). "Recent Advances in the Synthesis and Applications of Radiolabeled Compounds for Drug Discovery and Development," Current Pharm. Des. 6(10):113, TOC Only, 2 pages.

Evans, A.E. (Mar. 1981, e-pub. Jan. 9, 2007). "Synthesis of Radiolabelled Compounds," J Radio Anal. Chem. 64(1-2):9-32.

FDA Center for Drug Evaluation and Research. (2009). "Application No. 22-527," Pharmacology Review (s), 252 pages.

Fleisher, D. et al. (May 22, 1996). "Improved Oral Drug Delivery: Solubility Limitations Overcome by the Use of Prodrugs," Advanced Drug Delivery Reviews 19(2):115-130.

Frothingham, S. et al. (Nov. 10, 2022). "The Possibility of Multiple Sclerosis Prevention," Healthline, located at https://www.healthline.com/health/multiple-sclerosis-prevention, last visited on Jan. 6, 2025, 18 pages.

Kabalka, G.W. et al. (1989). "The Synthesis of Radiolabeled Compounds via Organometallic Intermediates," Tetrahedron 45(21):6601-6621.

Lochner, M. et al. (Sep. 2016, e-pub. Apr. 22, 2016). "The Muscarinic Antagonists Scopolamine and Atropine are Competitive Antagonists at 5-HT3 Receptors," Neuropharmacology 108:220-228.

Mei, F. et al. (Sep. 27, 2016). "Accelerated Remyelination During Inflammatory Demyelination Prevents Axonal Loss and Improves Functional Recovery," eLIFE 5:1-21.

Schrader, T. O. et al. (Dec. 24, 2020, e-pub. Jan. 14, 2021). "Discovery of PIPE-359, a Brain-Penetrant, Selective M1 Receptor Antagonist with Robust Efficacy in Murine MOG-EAE," ACS Med Chem Lett 12(1):155-161.

U.S. Appl. No. 16/827,546, filed Mar. 23, 2020, for Rustick et al. (Copy not submitted herewith pursuant to the waiver of 37 C.F.R. 1.98(a)(2)(iii) issued by the Office on Sep. 21, 2004).

Zhao, M. et al. (Jul. 23, 1998). "A Novel Chromium Trioxide Catalyzed Oxidation of Primary Alcohols to the Carboxylic Acids," Tetrahedron Letters 39(30):5323-5326.

Bender, A.M. et al. (Aug. 1, 2017, e-published May 15, 2017). "Discovery and optimization of 3-(4-aryl/heteroarylsulfonyl)piperazin-1-yl)-6-(piperidin-1-yl)pyridazines as novel, CNS penetrant pan-muscarinic antagonists," *Bioorg Med Chem Lett* 27(15):3576-3581.

Extended European Search Report mailed on May 6, 2022, for EP Patent Application No. 19857624.1, 8 pages.

International Search Report mailed Oct. 18, 2019, for PCT Application No. PCT/US2019/036345, filed Jun. 10, 2019, 4 pages.

(56) References Cited

OTHER PUBLICATIONS

International Search Report mailed on Nov. 21, 2019, for PCT Application No. PCT/US2019/049374, filed Sep. 3, 2019, 3 pages.
International Search Report mailed on Dec. 29, 2020 for PCT Application No. PCT/US2020/054412, filed Oct. 6, 2020, 3 pages.
Manetti, D. et al. (May 18, 2000). "Design, synthesis, and preliminary pharmacological evaluation of 1, 4-diazabicyclo[4.3.0]nonan-9-ones as a new class of highly potent nootropic agents," *Journal of Medicinal Chemistry* 43(10):1969-1974.
Melancon, B.J. et al. (Jan. 15, 2012, e-published Dec. 6, 2011). "Development of a more highly selective M1 antagonist from the continued optimization of the MLPCN Probe ML012," *Bioorg Med Chem Lett* 22(2):1044-1048.
Melancon, B.J. et al. (Aug. 1, 2012, e-published Jun. 15, 2012). "Development of novel M1 antagonist scaffolds through the continued optimization of the MLPCN probe ML012," *Bioorg Med Chem Lett* 22(15):5035-5040.
PubChem CID 70746046, (Create Date Mar. 4, 2013), located at <https://pubchem.ncbi.nlm.nih.gov/compound/70746046>, 5 pages.
PubChem CID 101131894, (Create Date Dec. 17, 2015), located at <https://pubchem.ncbi.nlm.nih.gov/compound/101131894>, 7 pages.
PubChem CID 101131895, (Create Date Dec. 17, 2015), located at <https://pubchem.ncbi.nlm.nih.gov/compound/101131895>, 8 pages.
PubChem CID 102350371, (Create Date Dec. 25, 2015), located at <https://pubchem.ncbi.nlm.nih.gov/compound/102350371>, 7 pages.
Sheffler, D.J. et al. (Aug. 2009, e-published Apr. 30, 2009). "A novel selective muscarinic acetylcholine receptor subtype 1 antagonist reduces seizures without impairing hippocampus-dependent learning," *Mol Pharmacol* 76(2):356-368.
Weaver, C.D. et al. (2009). "Discovery and development of a potent and highly selective small molecule muscarinic acetylcholine receptor subtype I (mAChR 1 or M1) antagonist in vitro and in vivo probe," *Current Topics in Medicinal Chemistry* 9(13):1217-1226.
Written Opinion mailed Oct. 18, 2019, for PCT Application No. PCT/US2019/036345, filed Jun. 10, 2019, 6 pages.
Written Opinion mailed on Nov. 21, 2019, for PCT Application No. PCT/US2019/049374, filed Sep. 3, 2019, 4 pages.
Written Opinion mailed on Dec. 29, 2020 for PCT Application No. PCT/US2020/054412, filed Oct. 6, 2020, 3 pages.
Contineum Therapeutics, Inc. (Nov. 20, 2025). "Contineum Therapeutics Reports Topline Data From Its Phase 2 PIPE-307 VISTA Trial for the Treatment of Relapsing-Remitting Multiple Sclerosis (RRMS)," Press Release from Contineum Therapeutics, Inc., 2 pages, as retrieved from https://ir.contineum-tx.com/news-releases/news-release-details/contineum-therapeutics-reports-topline-data-its-phase-2-pipe-307.

* cited by examiner

MUSCARINIC ACETYLCHOLINE $M_1$ RECEPTOR ANTAGONISTS

CROSS REFERENCE TO RELATED APPLICATIONS

This application is the national stage filing under 35 U.S.C. § 371 of International Application No. PCT/US2020/054412 filed Oct. 6, 2020, which claims priority to U.S. Provisional Application No. 62/911,807, filed Oct. 7, 2019, which are hereby incorporated by reference in their entirety and for all purposes.

BACKGROUND

The human muscarinic acetylcholine receptor $M_1$ (mAChR $M_1$) is a protein of 479 amino acids encoded by the CHRM1 gene. The mAChR $M_1$ is one of five members of the family of muscarinic acetylcholine receptors ($M_1$-$M_5$), which are widely expressed throughout the body where they have varying roles in cognitive, sensory, motor, and autonomic functions. The $M_1$ mAChR is found in both the central and peripheral nervous systems, particularly in the cerebral cortex and sympathetic ganglia. Based on the potential role of mAChR $M_1$ in seizure activity and motor control, highly selective mAChR $M_1$ antagonists may have potential utility in the treatment of some epileptic disorders, as well as certain movement disorders, including Parkinson's disease, dystonia, and fragile X syndrome.

BRIEF SUMMARY

This disclosure provides, for example, compounds and compositions which are antagonists of the muscarinic acetylcholine $M_1$ receptor (mAChR $M_1$), and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of muscarinic acetylcholine M1 receptor activity in patients.

In an aspect is provided a compound, or a pharmaceutically acceptable salt or solvate thereof, having the structure of Formula (IA-1) or (IB-1):

Formula (IA-1)

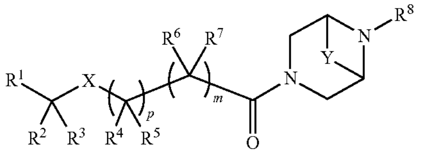

Formula (IB-1)

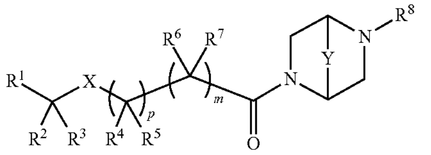

wherein:

X is a bond, —C($R^9$)($R^{10}$)—, —N($R^{11}$)—, —O—, —S(O)$_n$—, —$CH_2$N($R^{11}$)—, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene;

Y is a substituted or unsubstituted alkylene, substituted or unsubstituted alkenylene, or substituted or unsubstituted heteroalkylene;

$R^1$ is

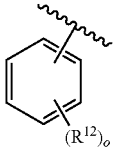 , 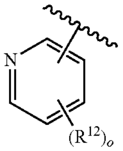 , 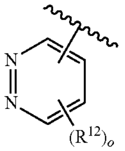 , 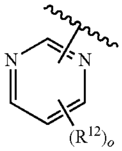 ,

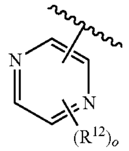 , 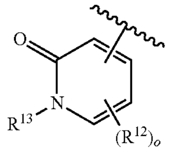 , 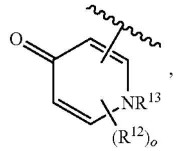 ,

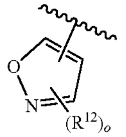 , 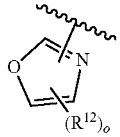 , 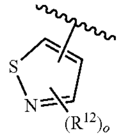 , 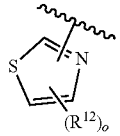 ,

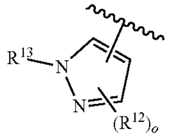 , 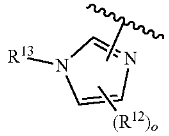 ,

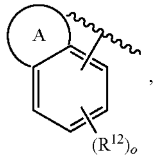 , or 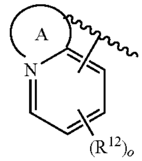 , wherein ring A is a heteroaryl ring or a heterocycloalkyl ring optionally substituted with hydroxyl, halogen, cyano, —N($R^{14}$)($R^{15}$), substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted heterocycloalkyl, substituted or unsubstituted aryl, substituted or unsubstituted heteroaryl, —S(O)$_n$($R^{16}$), or —$SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted alkylhydroxyl, substituted or unsubstituted heterocycloalkyl, substituted or unsubstituted aryl, or substituted or unsubstituted heteroaryl;

$R^3$ is halogen, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted alkylhydroxyl, substituted or unsubstituted heterocycloalkyl, substituted or unsubstituted aryl, or substituted or unsubstituted heteroaryl; or $R^2$ and $R^3$ combine to form a cycloalkyl or heterocycloalkyl ring optionally substituted with halogen, substituted or unsubstituted alkyl, or substituted or unsubstituted cycloalkyl;

$R^4$ and $R^5$ are independently selected from hydrogen, deuterium, halogen, and substituted or unsubstituted alkyl; or $R^3$ and $R^4$ combine to form a cycloalkyl or heterocycloalkyl ring optionally substituted with halogen, substituted or unsubstituted alkyl, or substituted or unsubstituted cycloalkyl; or $R^4$ and $R^5$ combine to form a cycloalkyl or heterocycloalkyl ring optionally substituted with halogen, substituted or unsubstituted alkyl, or substituted or unsubstituted cycloalkyl;

$R^6$ and $R^7$ are independently selected from hydrogen, deuterium, halogen, and substituted or unsubstituted alkyl; or $R^3$ and $R^7$ combine to form a cycloalkyl or heterocycloalkyl ring optionally substituted with halogen, substituted or unsubstituted alkyl, or substituted or unsubstituted cycloalkyl; or $R^4$ and $R^6$ combine to form a cycloalkyl or heterocycloalkyl ring optionally substituted with halogen, substituted or unsubstituted alkyl, or substituted or unsubstituted cycloalkyl; or $R^5$ and $R^7$ combine to form a bond;

$R^8$ is

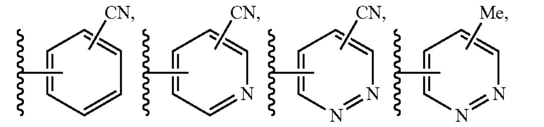

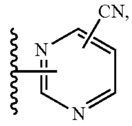

or

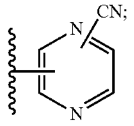

$R^9$ and $R^{10}$ are independently selected from hydrogen, deuterium, halogen, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted heterocycloalkyl, substituted or unsubstituted aryl, or substituted or unsubstituted heteroaryl; or $R^3$ and $R^{10}$ combine to form a cycloalkyl or heterocycloalkyl ring optionally substituted with halogen, substituted or unsubstituted alkyl, or substituted or unsubstituted cycloalkyl; or $R^4$ and $R^{10}$ combine to form a cycloalkyl or heterocycloalkyl ring optionally substituted with halogen, substituted or unsubstituted alkyl, or substituted or unsubstituted cycloalkyl; or $R^6$ and $R^{10}$ combine to form a cycloalkyl or heterocycloalkyl ring optionally substituted with halogen, substituted or unsubstituted alkyl, or substituted or unsubstituted cycloalkyl; or $R^9$ and $R^{10}$ combine to form a cycloalkyl or heterocycloalkyl ring optionally substituted with halogen, substituted or unsubstituted alkyl, or substituted or unsubstituted cycloalkyl;

$R^{11}$ is hydrogen, substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl; or $R^3$ and $R^{11}$ combine to form a heteroalkyl ring optionally substituted with halogen, substituted or unsubstituted alkyl, or substituted or unsubstituted cycloalkyl; or $R^4$ and $R^{11}$ combine to form a heteroalkyl ring optionally substituted with halogen, substituted or unsubstituted alkyl, or substituted or unsubstituted cycloalkyl; or $R^6$ and $R^{11}$ combine to form a heteroalkyl ring optionally substituted with halogen, substituted or unsubstituted alkyl, or substituted or unsubstituted cycloalkyl;

each $R^{12}$ is independently selected from hydroxyl, halogen, cyano, —$N(R^{14})(R^{15})$, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted alkylhydroxyl, substituted or unsubstituted heterocycloalkyl, substituted or unsubstituted aryl, substituted or unsubstituted heteroaryl, —$S(O)_n(R^{16})$, or —$SF_5$; or $R^3$ and one $R^{12}$ combine to form a cycloalkyl or heteroalkyl ring optionally substituted with halogen, substituted or unsubstituted alkyl, or substituted or unsubstituted cycloalkyl; or $R^{10}$ and one $R^{12}$ combine to form a cycloalkyl or heteroalkyl ring optionally substituted with halogen, substituted or unsubstituted alkyl, or substituted or unsubstituted cycloalkyl; or $R^{11}$ and one $R^{12}$ combine to form a heteroalkyl ring optionally substituted with halogen, substituted or unsubstituted alkyl, or substituted or unsubstituted cycloalkyl;

$R^{13}$ is hydrogen, substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl;

$R^{14}$ and $R^{15}$ are independently selected from hydrogen, substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl; or $R^{14}$ and $R^{15}$ combine to form a heterocycloalkyl ring optionally substituted with halogen, substituted or unsubstituted alkyl, or substituted or unsubstituted cycloalkyl;

$R^{16}$ is substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl;

m is 0 or 1;

n is 0, 1, or 2;

o is 0, 1, 2, or 3; and p is 0 or 1.

In one aspect is provided a compound of Formula (IA) or (IB):

Formula (IA)

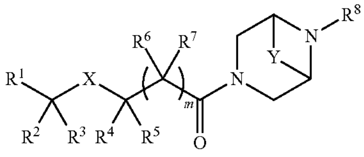

Formula (IB)

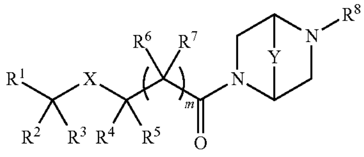

wherein:

X is a bond, —C($R^9$)($R^{10}$)—, —N($R^{11}$)—, —O—, —S(O)$_n$—, —$CH_2N$($R^{11}$)—, or —$CH_2O$—;

Y is a —$CH_2$—, —$CH_2CH_2$—, —CH═CH—, or —$CH_2OCH_2$—;

$R^1$ is

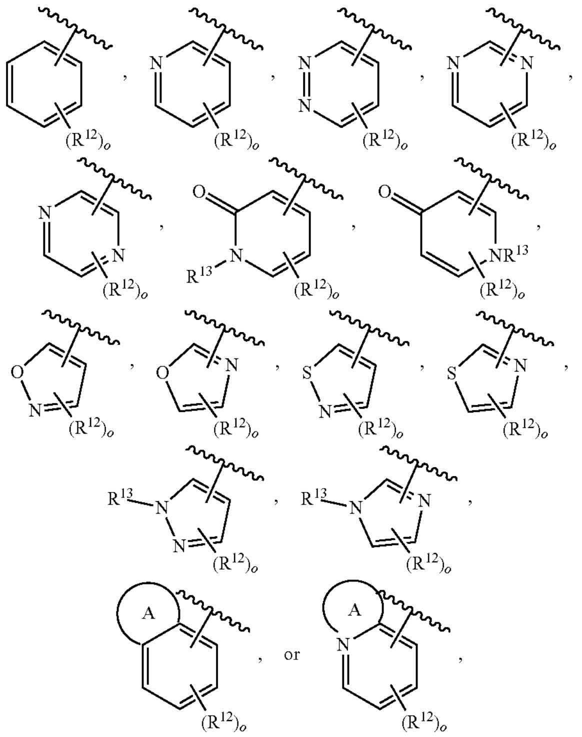

, or , wherein ring A is a 5- or 6-membered heteroaryl ring or a 5- or 6-membered heterocycloalkyl ring optionally substituted with halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, S(O)$_n$($R^{16}$), or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^4$ and $R^5$ are independently selected from hydrogen, deuterium, halogen, and $C_{1-3}$ alkyl; or $R^3$ and $R^4$ combine to form a cycloalkyl or heterocycloalkyl ring optionally substituted with halogen, $C_{1-6}$ alkyl, or $C_{3-6}$ cycloalkyl; or $R^4$ and $R^5$ combine to form a cycloalkyl or heterocycloalkyl ring optionally substituted with halogen, $C_{1-6}$ alkyl, or $C_{3-6}$ cycloalkyl;

$R^6$ and $R^7$ are independently selected from hydrogen, deuterium, halogen, and $C_{1-3}$ alkyl; or $R^3$ and $R^7$ combine to form a cycloalkyl or heterocycloalkyl ring optionally substituted with halogen, $C_{1-6}$ alkyl, or $C_{3-6}$ cycloalkyl; or $R^4$ and $R^6$ combine to form a cycloalkyl or heterocycloalkyl ring optionally substituted with halogen, $C_{1-6}$ alkyl, or $C_{3-6}$ cycloalkyl; or $R^5$ and $R^7$ combine to form a bond;

$R^8$ is

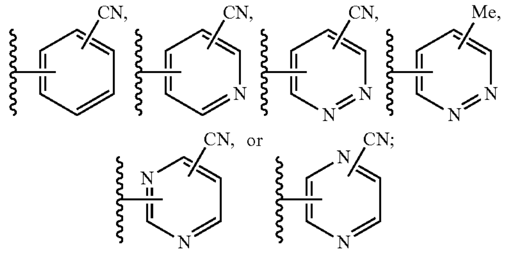

or $R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^4$ and $R^{10}$ combine to form a cycloalkyl or heterocycloalkyl ring optionally substituted with halogen, $C_{1-6}$ alkyl, or $C_{3-6}$ cycloalkyl; or $R^6$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl; or $R^4$ and $R^{11}$ combine to form a heteroalkyl ring optionally substituted with halogen, $C_{1-6}$ alkyl, or $C_{3-6}$ cycloalkyl; or $R^6$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and is 0, 1, 2, or 3;

or a pharmaceutically acceptable salt or solvate thereof, provided that the aforementioned combinations do not violate the rules of valency known to those skilled in the art.

In one aspect is provided a compound of Formula (IIA) or (IIB):

Formula (IIA)

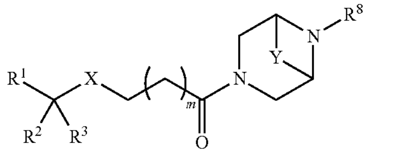

Formula (IIB)

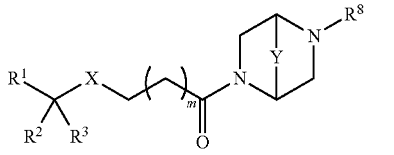

wherein:

X is a bond, —$C(R^9)(R^{10})$—, —$N(R^{11})$—, —O—, —$S(O)_n$—, —$CH_2N(R^{11})$—, or —$CH_2O$—;

Y is a —$CH_2$—, —$CH_2CH_2$—, —CH═CH—, or —$CH_2OCH_2$—;

$R^1$ is

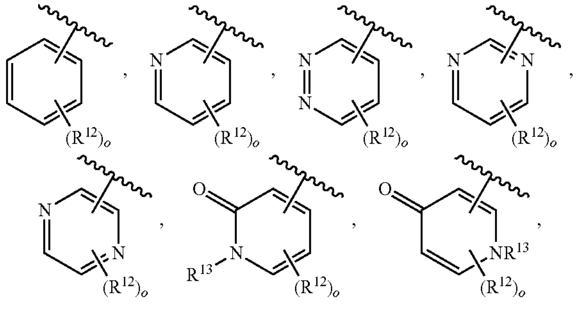

-continued

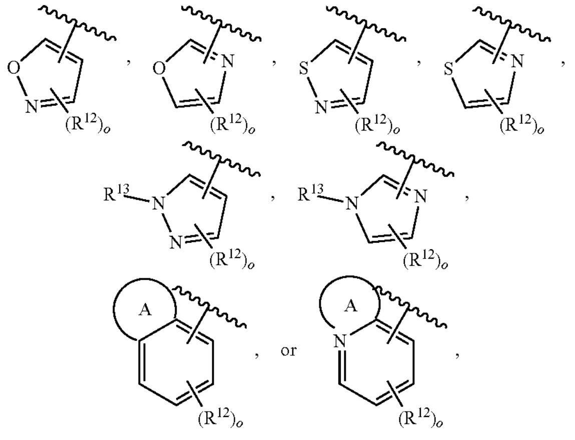

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

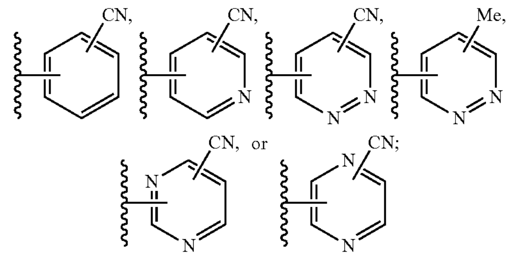

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and is 0, 1, 2, or 3;

or a pharmaceutically acceptable salt or solvate thereof, provided that the aforementioned combinations do not violate the rules of valency known to those skilled in the art.

In another aspect is provided a compound of Formula (III):

Formula (III)

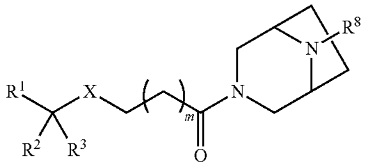

wherein:

X is a bond, —$C(R^9)(R^{10})$—, —$N(R^{11})$—, —O—, —$S(O)_n$—, —$CH_2N(R^{11})$—, or —$CH_2O$—;

$R^1$ is

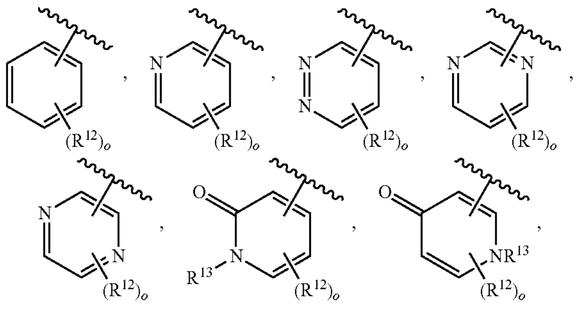

-continued

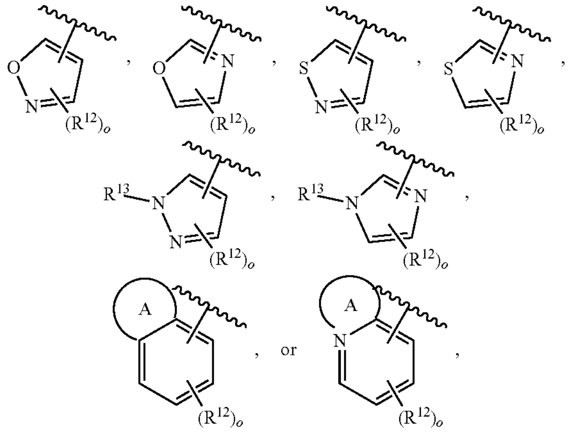

or wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

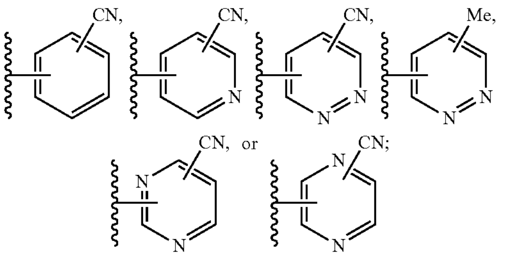

or $R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and is 0, 1, 2, or 3;

or a pharmaceutically acceptable salt or solvate thereof, provided that the aforementioned combinations do not violate the rules of valency known to those skilled in the art.

In some embodiments of a compound of Formula (IA), (IB), (IIA), (IIB), or (III), or a pharmaceutically acceptable salt or solvate thereof, X is a bond, —$C(R^9)(R^{10})$—, —$N(R^{11})$—, or —O—. In some embodiments, X is a bond, —$N(R^{11})$—, or —O—.

In some embodiments of a compound of Formula (IA), (IB), (IIA), (IIB), or (III), or a pharmaceutically acceptable salt or solvate thereof, $R^1$ is

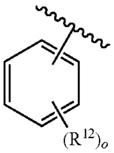, 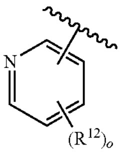, 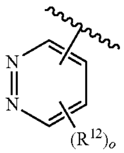, 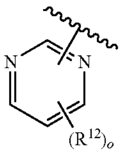, 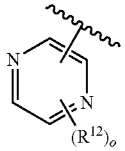, 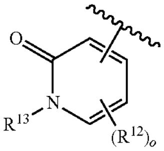, 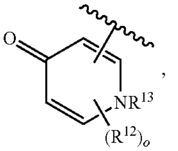, 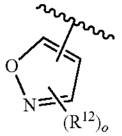, 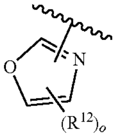, 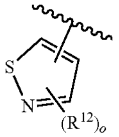, 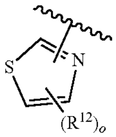, 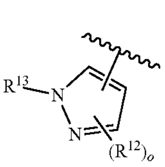, 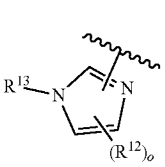, 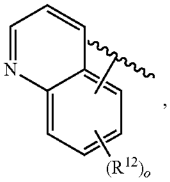, -continued

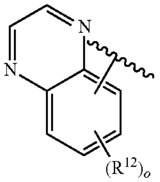, 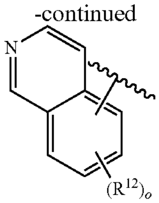, 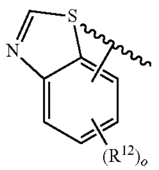, 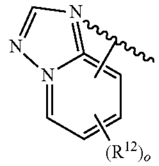, or 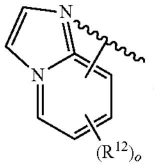.

In some embodiments, $R^1$ is

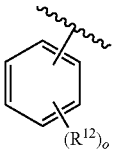, 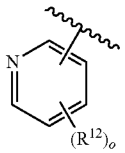, 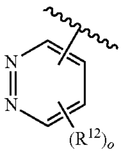, 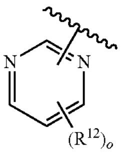, 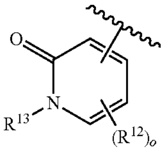, 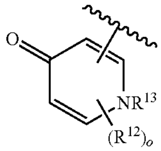, 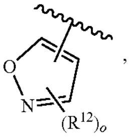, 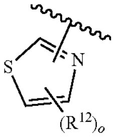, 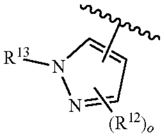, 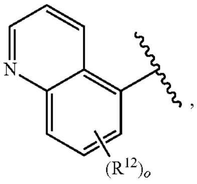, 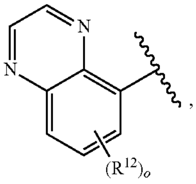, 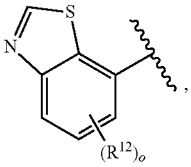, 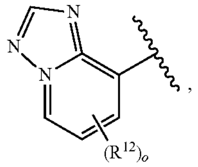, 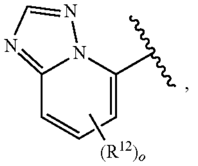, or 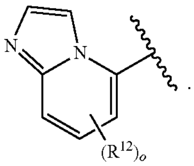.

In some embodiments of a compound of Formula (IA), (IB), (IIA), (IIB), or (III), or a pharmaceutically acceptable salt or solvate thereof, $R^8$ is

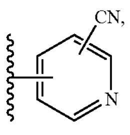 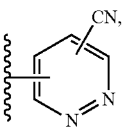 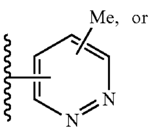

-continued

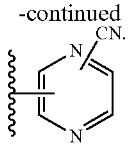

In some embodiments, $R^8$ is

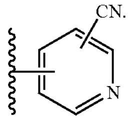

Any combination of the groups described above or below for the various variables is contemplated herein. Throughout the specification, groups and substituents thereof are chosen by one skilled in the field to provide stable moieties and compounds.

In another aspect is a pharmaceutical composition comprising a compound of Formula (IA), (IB), (IIA), (IIB), or (III), a pharmaceutically acceptable salt or solvate thereof, and at least one pharmaceutically acceptable excipient.

In another aspect is a method of treating a neurodegenerative disorder in a subject in need thereof, comprising administering to subject a therapeutically effective amount of a compound of Formula (IA), (IB), (IIA), (IIB), or (III), or a pharmaceutically acceptable salt or solvate thereof.

In another aspect is a method of treating neuropathy in a subject in need thereof, comprising administering to subject a therapeutically effective amount of a compound of Formula (IA), (IB), (IIA), (IIB), or (III), or a pharmaceutically acceptable salt or solvate thereof. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is diabetic neuropathy.

In another aspect is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the peripheral nervous system.

In some embodiments of the methods described herein, the method further comprises the administration of one or more immunomodulatory agents. In some embodiments, the one or more immunomodulatory agents are selected from: an IFN-01 molecule, or the like; a corticosteroid, or the like; a polymer of glutamic acid, lysine, alanine and tyrosine or glatiramer, or the like; an antibody or fragment thereof against alpha-4 integrin or natalizumab, or the like; an anthracenedione molecule or mitoxantrone, or the like; a S1P1 functional modulator or fingolimod, or the like; a NRF2 functional modulator or dimethyl fumarate, or the like; an antibody to the alpha subunit of the IL-2 receptor of T cells (CD25) or daclizumab, or the like; an antibody against CD52 or alemtuzumab, or the like; an antibody against CD20 or ocrelizumab, or the like; and an inhibitor of a dihydroorotate dehydrogenase or teriflunomide, or the like.

In another aspect is a method of modulating muscarinic acetylcholine receptor $M_1$ activity in a subject comprising administering to the subject a compound of Formula (IA), (IB), (IIA), (IIB), or (III), or a pharmaceutically acceptable salt or solvate thereof. In some embodiments, the compound of Formula (IA), (IB), (IIA), (IIB), or (III), or a pharmaceutically acceptable salt or solvate thereof, acts as a selective $M_1$ antagonist.

DETAILED DESCRIPTION

This disclosure is directed, at least in part, to compounds capable of inhibiting the muscarinic acetylcholine $M_1$ receptor.

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. In embodiments, about means within a standard deviation using measurements generally acceptable in the art. In embodiments, about means a range extending to +/−10% of the specified value. In embodiments, about includes the specified value. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

I. DEFINITIONS

As used in the specification and appended claims, unless specified to the contrary, the following terms have the meaning indicated below.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents). Similarly, $C_{1-x}$ includes $C_{1-2}$, $C_{1-3}$ . . . $C_{1-x}$. $C_{1-x}$ refers to the number of carbon atoms that make up the moiety to which it designates (excluding optional substituents).

"Amino" refers to the —$NH_2$ radical.

"Cyano" refers to the —CN radical.

"Hydroxyl" refers to the —OH radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl or $C_{1-15}$ alkyl). In certain embodiments, an alkyl comprises one to thirteen carbon atoms (e.g., $C_1$-$C_{13}$ alkyl or $C_{1-13}$ alkyl). In certain embodiments, an alkyl comprises one to eight carbon atoms (e.g., $C_1$-$C_8$ alkyl or $C_{1-8}$ alkyl). In other embodiments, an alkyl comprises one to six carbon atoms (e.g., $C_1$-$C_6$ alkyl or $C_{1-6}$ alkyl). In other embodiments, an alkyl comprises one to five carbon atoms (e.g., $C_1$-$C_5$ alkyl or $C_{1-5}$ alkyl). In other embodiments, an alkyl comprises one to four carbon atoms (e.g., $C_1$-$C_4$ alkyl or $C_{1-4}$ alkyl). In other embodiments, an alkyl comprises one to three carbon atoms (e.g., $C_1$-$C_3$ alkyl or $C_{1-3}$ alkyl). In other embodiments, an alkyl comprises one to two carbon atoms (e.g., $C_1$-$C_2$ alkyl or $C_{1-2}$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl or $C_{5-15}$ alkyl). In other embodiments, an alkyl comprises five to eight carbon atoms (e.g., $C_5$-$C_8$alkyl or $C_{5-8}$ alkyl). In other embodiments, an alkyl comprises two to five carbon atoms (e.g., $C_2$-$C_5$ alkyl or $C_{2-5}$ alkyl). In other embodiments, an alkyl comprises three to five carbon atoms (e.g., $C_3$-$C_5$ alkyl or $C_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halogen, cyano, nitro, oxo, thioxo, imino, oximo, trimethylsilyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl. Thus, an alkyl group can be substituted or unsubstituted. In embodiments, the alkyl group is substituted with at least one substituent group, wherein if the alkyl group is substituted with a plurality of substituent groups, each substituent group may optionally be different. In embodiments, the alkyl group is substituted with at least one size-limited substituent group, wherein if the alkyl group is substituted with a plurality of size-limited substituent groups, each size-limited substituent group may optionally be different. In embodiments, the alkyl group is substituted with at least one lower substituent group, wherein if the alkyl group is substituted with a plurality of lower substituent groups, each lower substituent group may optionally be different.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halogen, cyano, nitro, oxo, thioxo, imino, oximo, trimethylsilyl, —$OR^a$, —$SR^a$, —OC(O)—$R^f$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl. Thus, an alkenyl group can be substituted or unsubstituted. In embodiments, the alkenyl group is substituted with at least one substituent group, wherein if the alkenyl group is substituted with a plurality of substituent groups, each substituent group may optionally be different. In embodiments, the alkenyl group is substituted with at least one size-limited substituent group, wherein if the alkenyl group is substituted with a plurality of size-limited substituent groups, each size-limited substituent group may optionally be different. In embodiments, the alkenyl group is substituted with at least one lower substituent group, wherein if the alkenyl group is substituted with a plurality of lower substituent groups, each lower substituent group may optionally be different.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halogen, cyano, nitro, oxo, thioxo, imino, oximo, trimethylsilyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl. Thus, an alkynyl group can be substituted or unsubstituted. In embodiments, the alkynyl group is substituted with at least one substituent group, wherein if the alkynyl group is substituted with a plurality of substituent groups, each substituent group may optionally be different. In embodiments, the alkynyl group is substituted with at least one size-limited substituent group, wherein if the alkynyl group is substituted with a plurality of size-limited substituent groups, each size-limited substituent group may optionally be different. In embodiments, the alkynyl group is substituted with at least one lower substituent group, wherein if the alkynyl group is substituted with a plurality of lower substituent groups, each lower substituent group may optionally be different.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized, and containing no unsaturation. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-S-CH_2$, $-S(O)-CH_3$, $-CH_2-CH_2-S(O)_2-CH_3$, $-Si(CH_3)_3$, $-O-CH_3$, $-O-CH_2-CH_3$, and $-CN$. Up to two or three heteroatoms may be consecutive, such as, for example, $-CH_2-NH-OCH_3$ and $-CH_2-O-Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to eight optionally different heteroatoms (e.g., O, N, S, Si, or P). A heteroalkyl group can be substituted or unsubstituted. In embodiments, the heteroalkyl group is substituted with at least one substituent group, wherein if the heteroalkyl group is substituted with a plurality of substituent groups, each substituent group may optionally be different. In embodiments, the heteroalkyl group is substituted with at least one size-limited substituent group, wherein if the heteroalkyl group is substituted with a plurality of size-limited substituent groups, each size-limited substituent group may optionally be different. In embodiments, the heteroalkyl group is substituted with at least one lower substituent group, wherein if the heteroalkyl group is substituted with a plurality of lower substituent groups, each lower substituent group may optionally be different.

"Heteroalkenyl" refers to a stable straight or branched chain, or combinations thereof, including at least one carbon-carbon double bond and at least one heteroatom (e.g., O, N, P, Si, and S), and wherein the nitrogen and sulfur atoms may optionally be oxidized, and the nitrogen heteroatom may optionally be quaternized. A heteroalkenyl group can be substituted or unsubstituted. In embodiments, the heteroalkenyl group is substituted with at least one substituent group, wherein if the heteroalkenyl group is substituted with a plurality of substituent groups, each substituent group may optionally be different. In embodiments, the heteroalkenyl group is substituted with at least one size-limited substituent group, wherein if the heteroalkenyl group is substituted with a plurality of size-limited substituent groups, each size-limited substituent group may optionally be different. In embodiments, the heteroalkenyl group is substituted with at least one lower substituent group, wherein if the heteroalkenyl group is substituted with a plurality of lower substituent groups, each lower substituent group may optionally be different.

"Heteroalkynyl" refers to a stable straight or branched chain, or combinations thereof, including at least one carbon-carbon triple bond and at least one heteroatom (e.g., O, N, P, Si, and S), and wherein the nitrogen and sulfur atoms may optionally be oxidized, and the nitrogen heteroatom may optionally be quaternized. A heteroalkynyl group can be substituted or unsubstituted. In embodiments, the heteroalkynyl group is substituted with at least one substituent group, wherein if the heteroalkynyl group is substituted with a plurality of substituent groups, each substituent group may optionally be different. In embodiments, the heteroalkynyl group is substituted with at least one size-limited substituent group, wherein if the heteroalkynyl group is substituted with a plurality of size-limited substituent groups, each size-limited substituent group may optionally be different. In embodiments, the heteroalkynyl group is substituted with at least one lower substituent group, wherein if the heteroalkynyl group is substituted with a plurality of lower substituent groups, each lower substituent group may optionally be different.

The term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

The term "heteroalkenylene," by itself or as part of another substituent, means, unless otherwise stated, a divalent radical derived from a heteroalkenyl.

The term "heteroalkynylene," by itself or as part of another substituent, means, unless otherwise stated, a divalent radical derived from a heteroalkynyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized $(4n+2)$ π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halogen, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, haloalkyl, cycloalkyl, cycloalkylalkyl, aryl (optionally substituted with one or more halogen groups), aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain. Thus, an aryl group can be substituted or unsubstituted. In embodiments, the aryl group is substituted with at least one substituent group, wherein if the aryl group is substituted with a plurality of substituent groups, each substituent group may optionally be different. In embodiments, the aryl group is substituted with at least one size-limited substituent group, wherein if the aryl group is substituted with a plurality of size-limited substituent groups, each size-limited substituent group may optionally be different. In embodiments, the aryl group is substituted with at least one lower substituent group, wherein if the aryl group is substituted with a plurality of lower substituent groups, each lower substituent group may optionally be different.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused, bridged or spirocyclic ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds). Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl or $C_{3-8}$ cycloalkyl). In other embodiments, a cycloalkyl comprises three to seven carbon atoms (e.g., $C_3$-$C_7$ cycloalkyl or $C_{3-7}$ cycloalkyl). In other embodiments, a cycloalkyl comprises three to six carbon atoms (e.g., $C_3$-$C_6$ cycloalkyl or $C_{3-6}$ cycloalkyl). In other embodiments, a cycloalkyl comprises three to five carbon atoms (e.g., $C_3$-$C_5$ cycloalkyl or $C_{3-5}$ cycloalkyl). In other embodiments, a cycloalkyl comprises three to four carbon atoms (e.g., $C_3$-$C_4$ cycloalkyl or $C_{3-4}$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbomyl (i.e., bicyclo[2.2.1]heptanyl), norbornenyl, decalinyl, 7,7-dimethyl-bicyclo[2.2.1]heptanyl, bicyclo[1.1.1]pentanyl, spiro[3.3]heptanyl, spiro[4.4]nonanyl, and the like. Unless otherwise stated specifically in the specification, the term "cycloalkyl" is meant to include cycloalkyl radicals optionally substituted by one or more substituents independently selected from alkyl, alkenyl, alkynyl, halogen, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, haloalkyl, cycloalkyl, cycloalkylalkyl, aryl (optionally substituted with one or more halogen groups), aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain. Thus, a cycloalkyl group can be substituted or unsubstituted. In embodiments, the cycloalkyl group is substituted with at least one substituent group, wherein if the cycloalkyl group is substituted with a plurality of substituent groups, each substituent group may optionally be different. In embodiments, the cycloalkyl group is substituted with at least one size-limited substituent group, wherein if the cycloalkyl group is substituted with a plurality of size-limited substituent groups, each size limited substituent group may optionally be different. In embodiments, the cycloalkyl group is substituted with at least one lower substituent group, wherein if the cycloalkyl group is substituted with a plurality of lower substituent groups, each lower substituent group may optionally be different.

"Cycloalkoxy" refers to a radical bonded through an oxygen atom of the formula —O-cycloalkyl, where cycloalkyl is as defined above.

"Halo" or "halogen" refers to bromo, chloro, fluoro or iodo substituents.

"Haloalkyl" refers to an alkyl radical, as defined above, that is substituted by one or more halogen radicals, as defined above.

"Haloalkoxy" refers to an alkoxy radical, as defined above, that is substituted by one or more halogen radicals, as defined above.

"Halocycloalkyl" refers to a cycloalkyl radical, as defined above, that is substituted by one or more halogen radicals, as defined above.

"Halocycloalkoxy" refers to an alkoxy radical, as defined above, that is substituted by one or more halogen radicals, as defined above.

"Alkylhydroxyl" refers to an alkyl radical, as defined above, that is substituted by one or more hydroxyl radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halogen, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain. In embodiments, a heterocycloalkyl group can be substituted or unsubstituted. In embodiments, the heterocycloalkyl group is substituted with at least one substituent group, wherein if the heterocycloalkyl group is substituted with a plurality of substituent groups, each substituent group may optionally be different. In embodiments, the heterocycloalkyl group is substituted with at least one size-limited substituent group, wherein if the heterocycloalkyl group is substituted with a plurality of size-limited substituent groups, each size-limited substituent group may optionally be different. In embodiments, the heterocycloalkyl group is substituted with at least one lower substituent group, wherein if the heterocycloalkyl group is substituted with a plurality of lower substituent groups, each lower substituent group may optionally be different. In embodiments, the term "heteroalkyl ring" as used herein is a heterocycloalkyl ring.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2) and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain. Thus, a heteroaryl group can be substituted or unsubstituted. In embodiments, the heteroaryl group is substituted with at least one substituent group, wherein if the heteroaryl group is substituted with a plurality of substituent groups, each substituent group may optionally be different. In embodiments, the heteroaryl group is substituted with at least one size-limited substituent group, wherein if the heteroaryl group is substituted with a plurality of size-limited substituent groups, each size-limited substituent group may optionally be different. In embodiments, the heteroaryl group is substituted with at least one lower substituent group, wherein if the heteroaryl group is substituted with a plurality of lower substituent groups, each lower substituent group may optionally be different.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula $-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula $-O-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

"Optional" or "optionally" means that a subsequently described event or circumstance may or may not occur and that the description includes instances when the event or circumstance occurs and instances in which it does not. For example, "optionally substituted aryl" means that the aryl radical is or is not substituted and that the description includes both substituted aryl radicals and aryl radicals having no substitution.

In embodiments, each of the above terms (e.g., "alkyl," "alkenyl," "alkynyl," "heteroalkyl," "heteroalkenyl," "heteroalkynkyl," "cycloalkyl," "heterocycloalkyl," "aryl," and "heteroaryl") includes both substituted and unsubstituted forms of the indicated radical. Preferred substituents for each type of radical are provided below.

A "substituent group," as used herein, means a group selected from the following moieties:

(A) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$ alkyl, $C_1$-$C_6$ alkyl, or $C_1$-$C_4$ alkyl), unsubstituted alkenyl (e.g., $C_2$-$C_8$ alkenyl, $C_2$-$C_6$ alkenyl, or $C_2$-$C_4$ alkenyl), unsubstituted alkynyl (e.g., $C_2$-$C_8$ alkynyl, $C_2$-$C_6$ alkynyl, or $C_2$-$C_4$ alkynyl), unsubstituted heteroalkyl (e.g., 2 to 8 membered heteroalkyl, 2 to 6 membered heteroalkyl, or 2 to 4 membered heteroalkyl), unsubstituted heteroalkenyl (e.g., 3 to 8 membered heteroalkenyl, 3 to 6 membered heteroalkenyl, or 3 to 4 membered heteroalkenyl), unsubstituted heteroalkynyl (e.g., 3 to 8 membered heteroalkynyl, 3 to 6 membered heteroalkynyl, or 3 to 4 membered heteroalkynyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_{20}$, $C_1$-$C_{12}$, $C_1$-$C_8$, $C_1$-$C_6$, $C_1$-$C_4$, or $C_1$-$C_2$), alkenyl (e.g., $C_2$-$C_{20}$, $C_2$-$C_{12}$, $C_2$-$C_8$, $C_2$-$C_6$, or $C_2$-$C_4$), alkynyl (e.g., $C_2$-$C_{20}$, $C_2$-$C_{12}$, $C_2$-$C_8$, $C_2$-$C_6$, or $C_2$-$C_4$), heteroalkyl (e.g., 2 to 20 membered, 2 to 12 membered, 2 to 8 membered, 2 to 6 membered, 4 to 6 membered, 2 to 3 membered, or 4 to 5 membered), heteroalkenyl (e.g., 3 to 20 membered, 3 to 12 membered, 3 to 8 membered, 3 to 6 membered, 4 to 6 membered, or 4 to 5 membered), heteroalkynyl (e.g., 3 to 20 membered, 3 to 12 membered, 3 to 8 membered, 3 to 6 membered, 4 to 6 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$ alkyl, $C_1$—$C_6$ alkyl, or $C_1$-$C_4$ alkyl), unsubstituted alkenyl (e.g., $C_2$-$C_8$ alkenyl, $C_2$-$C_6$ alkenyl, or $C_2$-$C_4$ alkenyl), unsubstituted alkynyl (e.g., $C_2$-$C_8$ alkynyl, $C_2$-$C_6$ alkynyl, or $C_2$-$C_4$ alkynyl), unsubstituted heteroalkyl (e.g., 2 to 8 membered heteroalkyl, 2 to 6 membered heteroalkyl, or 2 to 4 membered heteroalkyl), unsubstituted heteroalkenyl (e.g., 3 to 8 membered heteroalkenyl, 3 to 6 membered heteroalkenyl, or 3 to 4 membered heteroalkenyl), unsubstituted heteroalkynyl (e.g., 3 to 8 membered heteroalkynyl, 3 to 6 membered heteroalkynyl, or 3 to 4 membered heteroalkynyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_{20}$, $C_1$-$C_{12}$, $C_1$-$C_8$, $C_1$-$C_6$, $C_1$-$C_4$, or $C_1$-$C_2$), alkenyl (e.g., $C_2$-$C_{20}$, $C_2$-$C_{12}$, $C_2$-$C_8$, $C_2$-$C_6$, or $C_2$-$C_4$), alkynyl (e.g., $C_2$-$C_{20}$, $C_2$-$C_{12}$, $C_2$-$C_8$, $C_2$-$C_6$, or $C_2$-$C_4$), heteroalkyl (e.g., 2 to 20 membered, 2 to 12 membered, 2 to 8 membered, 2 to 6 membered, 4 to 6 membered, 2 to 3 membered, or 4 to 5 membered), heteroalkenyl (e.g., 3 to 20 membered, 3 to 12 membered, 3 to 8 membered, 3 to 6 membered, 4 to 6 membered, or 4 to 5 membered), heteroalkynyl (e.g., 3 to 20 membered, 3 to 12 membered, 3 to 8 membered, 3 to 6 membered, 4 to 6 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, $—CCl_3$, $—CBr_3$, $—CF_3$, $—CI_3$, $—CHCl_2$, $—CHBr_2$, $—CHF_2$, $—CHI_2$, $—CH_2C_1$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$ alkyl, $C_1$-$C_6$ alkyl, or $C_1$-$C_4$ alkyl), unsubstituted alkenyl (e.g., $C_2$-$C_8$ alkenyl, $C_2$-$C_6$ alkenyl, or $C_2$-$C_4$ alkenyl), unsubstituted alkynyl (e.g., $C_2$—$C_8$ alkynyl, $C_2$-$C_6$ alkynyl, or $C_2$-$C_4$ alkynyl), unsubstituted heteroalkyl (e.g., 2 to 8 membered heteroalkyl, 2 to 6 membered heteroalkyl, or 2 to 4 membered heteroalkyl), unsubstituted heteroalkenyl (e.g., 3 to 8 membered heteroalkenyl, 3 to 6 membered heteroalkenyl, or 3 to 4 membered heteroalkenyl), unsubstituted heteroalkynyl (e.g., 3 to 8 membered heteroalkynyl, 3 to 6 membered heteroalkynyl, or 3 to 4 membered heteroalkynyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), alkenyl (e.g., $C_2$-$C_{20}$, $C_2$-$C_{12}$, $C_2$-$C_8$, $C_2$-$C_6$, or $C_2$-$C_4$), alkynyl (e.g., $C_2$-$C_{20}$, $C_2$-$C_{12}$, $C_2$-$C_8$, $C_2$-$C_6$, or $C_2$-$C_4$), heteroalkyl (e.g., 2 to 20 membered, 2 to 12 membered, 2 to 8 membered, 2 to 6 membered, 4 to 6 membered, 2 to 3 membered, or 4 to 5 membered), heteroalkenyl (e.g., 3 to 20 membered, 3 to 12 membered, 3 to 8 membered, 3 to 6 membered, 4 to 6 membered, or 4 to 5 membered), heteroalkynyl (e.g., 3 to 20 membered, 3 to 12 membered, 3 to 8 membered, 3 to 6 membered, 4 to 6 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, $—CCl_3$, $—CBr_3$, $—CF_3$, $—CI_3$, $—CHCl_2$, $—CHBr_2$, $—CHF_2$, $—CHI_2$, $—CH_2C_1$, $—CH_2Br$, $—CH_2F$, $—CH_2I$, $—OCCl_3$, $—OCF_3$, $—OCBr_3$, $—OCI_3$, $—OCHCl_2$, $—OCHBr_2$, $—OCHI_2$, $—OCHF_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$ alkyl, $C_1$-$C_6$ alkyl, or $C_1$-$C_4$ alkyl), unsubstituted alkenyl (e.g., $C_2$-$C_8$ alkenyl, $C_2$-$C_6$ alkenyl, or $C_2$-$C_4$ alkenyl), unsubstituted alkynyl (e.g., $C_2$-$C_8$ alkynyl, $C_2$-$C_6$ alkynyl, or $C_2$-$C_4$ alkynyl), unsubstituted heteroalkyl (e.g., 2 to 8 membered heteroalkyl, 2 to 6 membered heteroalkyl, or 2 to 4 membered heteroalkyl), unsubstituted heteroalkenyl (e.g., 3 to 8 membered heteroalkenyl, 3 to 6 membered heteroalkenyl, or 3 to 4 membered heteroalkenyl), unsubstituted heteroalkynyl (e.g., 3 to 8 membered heteroalkynyl, 3 to 6 membered heteroalkynyl, or 3 to 4 membered heteroalkynyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted alkenyl is a substituted or unsubstituted $C_2$-$C_{20}$ alkenyl, each substituted or unsubstituted alkynyl is a substituted or unsubstituted $C_2$-$C_{20}$ alkynyl, each substituted or unsubstituted heteroalkyl is a substituted or unsubstituted 2 to 20 membered heteroalkyl, each substituted or unsubstituted heteroalkenyl is a substituted or unsubstituted 3 to 20 membered heteroalkenyl, each substituted or unsubstituted heteroalkynyl is a substituted or unsubstituted 3 to 20 membered heteroalkynyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted alkenyl is a substituted or unsubstituted $C_2$-$C_8$ alkenyl, each substituted or unsubstituted alkynyl is a substituted or unsubstituted $C_2$-$C_8$ alkynyl, each substituted or unsubstituted heteroalkyl is a substituted or unsubstituted 2 to 8 membered heteroalkyl, each substituted or unsubstituted heteroalkenyl is a substituted or unsubstituted 3 to 8 membered heteroalkenyl, each substituted or unsubstituted heteroalkynyl is a substituted or unsubstituted 3 to 8 membered heteroalkynyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted alkenyl, substituted alkynyl, substituted heteroalkyl, substituted heteroalkenyl, substituted heteroalkynyl, substituted cycloalkyl, substituted heterocycloalkyl, substituted aryl, substituted heteroaryl, substituted alkylene, substituted alkenylene, substituted alkynylene, substituted heteroalkylene, substituted heteroalkenylene, substituted heteroalkynylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted alkenyl may be a substituted or unsubstituted $C_2$-$C_{20}$ alkenyl, each substituted or unsubstituted alkynyl may be a substituted or unsubstituted $C_2$-$C_{20}$ alkynyl, each substituted or unsubstituted heteroalkyl is a substituted or unsubstituted 2 to 20 membered heteroalkyl, each substituted or unsubstituted heteroalkenyl is a substituted or unsubstituted 3 to 20 membered heteroalkenyl, each substituted or unsubstituted heteroalkynyl is a substituted or unsubstituted 3 to 20 membered heteroalkynyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted alkenylene is a substituted or unsubstituted $C_2$-$C_{20}$ alkenylene, each substituted or unsubstituted alkynylene is a substituted or unsubstituted $C_2$-$C_{20}$ alkynylene, each substituted or unsubstituted heteroalkylene is a substituted or unsubstituted 2 to 20 membered heteroalkylene, each substituted or unsubstituted heteroalkenylene is a substituted or unsubstituted 3 to 20 membered heteroalkenylene, each substituted or unsubstituted heteroalkynylene is a substituted or unsubstituted 3 to 20 membered heteroalkynylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted alkenyl is a substituted or unsubstituted $C_2$-$C_8$ alkenyl, each substituted or unsubstituted alkynyl is a substituted or unsubstituted $C_2$-$C_8$ alkynyl, each substituted or unsubstituted heteroalkyl is a substituted or unsubstituted 2 to 8 membered heteroalkyl, each substituted or unsubstituted heteroalkenyl is a substituted or unsubstituted 3 to 8 membered heteroalkenyl, each substituted or unsubstituted heteroalkynyl is a substituted or unsubstituted 3 to 8 membered heteroalkynyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted alkenylene is a substituted or unsubstituted $C_2$-$C_8$ alkenylene, each substituted or unsubstituted alkynylene is a substituted or unsubstituted $C_2$-$C_8$ alkynylene, each substituted or unsubstituted heteroalkylene is a substituted or unsubstituted 2 to 8 membered heteroalkylene, each substituted or unsubstituted heteroalkenylene is a substituted or unsubstituted 3 to 8 membered heteroalkenylene, each substituted or unsubstituted heteroalkynylene is a substituted or unsubstituted 3 to 8 membered heteroalkynylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound is a chemical species set forth in the application (e.g., Examples section, figures, or tables below).

In embodiments, a substituted or unsubstituted moiety (e.g., substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted alkenylene, substituted or unsubstituted alkynylene, substituted or unsubstituted heteroalkylene, substituted or unsubstituted heteroalkenylene, substituted or unsubstituted heteroalkynylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted alkenyl, unsubstituted alkynyl, unsubstituted heteroalkyl, unsubstituted heteroalkenyl, unsubstituted heteroalkynyl, unsubstituted cycloalkyl, unsubstituted heterocycloalkyl, unsubstituted aryl, unsubstituted heteroaryl, unsubstituted alkylene, unsubstituted alkenylene, unsubstituted alkynylene, unsubstituted heteroalkylene, unsubstituted heteroalkenylene, unsubstituted heteroalkynylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted alkenylene, substituted or unsubstituted alkynylene, substituted or unsubstituted heteroalkylene, substituted or unsubstituted heteroalkenylene, substituted or unsubstituted heteroalkynylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted alkenyl, substituted alkynyl, substituted heteroalkyl, substituted heteroalkenyl, substituted heteroalkynyl, substituted cycloalkyl, substituted heterocycloalkyl, substituted aryl, substituted heteroaryl, substituted alkylene, substituted alkenylene, substituted alkynylene, substituted heteroalkylene, substituted heteroalkenylene, substituted heteroalkynylene, substituted cycloalkylene, substituted heterocycloalkylene, substituted arylene, and/or substituted heteroarylene, respectively).

In embodiments, a substituted moiety (e.g., substituted alkyl, substituted alkenyl, substituted alkynyl, substituted heteroalkyl, substituted heteroalkenyl, substituted heteroalkynyl, substituted cycloalkyl, substituted heterocycloalkyl, substituted aryl, substituted heteroaryl, substituted alkylene, substituted alkenylene, substituted alkynylene, substituted heteroalkylene, substituted heteroalkenylene, substituted heteroalkynylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted alkenyl, substituted alkynyl, substituted heteroalkyl, substituted heteroalkenyl, substituted heteroalkynyl, substituted cycloalkyl, substituted heterocycloalkyl, substituted aryl, substituted heteroaryl, substituted alkylene, substituted alkenylene, substituted alkynylene, substituted heteroalkylene, substituted heteroalkenylene, substituted heteroalkynylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted alkenyl, substituted alkynyl, substituted heteroalkyl, substituted heteroalkenyl, substituted heteroalkynyl, substituted cycloalkyl, substituted heterocycloalkyl, substituted aryl, substituted heteroaryl, substituted alkylene, substituted alkenylene, substituted alkynylene, substituted heteroalkylene, substituted heteroalkenylene, substituted heteroalkynylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted alkenyl, substituted alkynyl, substituted heteroalkyl, substituted heteroalkenyl, substituted heteroalkynyl, substituted cycloalkyl, substituted heterocycloalkyl, substituted aryl, substituted heteroaryl, substituted alkylene, substituted alkenylene, substituted alkynylene, substituted heteroalkylene, substituted heteroalkenylene, substituted heteroalkynylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

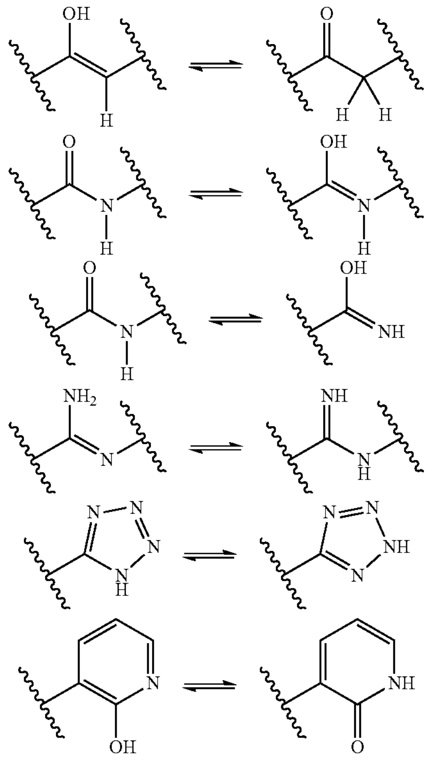

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, for example, Bundgard, H., *Design of Prodrugs*, Amsterdam: Elsevier, 1985). Discussions of prodrugs can also be found in Higuchi, T. et al., "Pro-drugs as Novel Delivery Systems," *A.C.S. Symposium Series*, Vol. 14, and in Roche, E. B., ed. *Bioreversible Carriers in Drug Design*, Oxford: Pergamon Press, 1987.

The term "prodrug" is also meant to include any covalently bonded carriers, which release the active compound in vivo when such prodrug is administered to a mammalian subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol in the active compounds and the like.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. "Hydrates" are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The terms "allosteric site" and "allosteric binding site" refer to a ligand binding site that is topographically distinct from the orthosteric binding site.

The terms "orthosteric site" and "orthosteric binding site" refer to the primary binding site on a receptor that is recognized by an endogenous ligand or agonist for the receptor. For example, the orthosteric site on the muscarinic acetylcholine $M_1$ receptor is the site that acetylcholine binds.

The term "ligand" refers to a natural or synthetic molecule that is capable of binding to or associating with a receptor to form a complex and mediate, prevent, or modify a biological effect. The term "ligand" is meant to encompass allosteric modulators, inhibitors, activators, agonists, antagonists, natural substrates, and analogs of natural substrates.

The terms "natural ligand" and "endogenous ligand" refer to a naturally occurring ligand which binds to a receptor.

In embodiments, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In embodiments inhibition means negatively affecting (e.g., decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

In embodiments, the terms "inhibitor", "repressor", "antagonist", or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

In embodiments, the term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "mAChR $M_1$ receptor antagonist" refers to any exogenously administered compound or agent that is capable of partially or completely inhibiting, or reversing, the effect of an agonist (e.g. acetylcholine) on the mAChR $M_1$ receptor. The term is inclusive of compounds or agents characterized or described as antagonists, partial antagonists, and negative allosteric modulators. For example, mAChR $M_1$ receptor antagonists can mediate their effects by binding to the orthosteric site or to allosteric sites, or they may interact at unique binding sites not normally involved in the biological regulation of the receptor's activity. Thus, a mAChR $M_1$ receptor antagonist directly or indirectly inhibits the activity of the mAChR $M_1$ receptor in the presence or in the absence of acetylcholine, or another agonist, in an animal, in particular a mammal, for example a human. In various aspects, a mAChR $M_1$ receptor antagonist decreases the activity of the mAChR $M_1$ receptor in a cell in the presence of extracellular acetylcholine. In some embodiments, a compound that is a "mAChR $M_1$ receptor antagonist" includes a compound that is a "mAChR $M_1$ receptor competitive antagonist," a "mAChR $M_1$ receptor noncompetitive antagonist," a "mAChR $M_1$ receptor partial antagonist," or a "mAChR $M_1$ receptor negative allosteric modulator."

The term "mAChR $M_1$ receptor competitive antagonist" refers to any exogenously administered compound or agent that is capable of binding to the orthosteric site of mAChR $M_1$ receptors without activating the receptor. Thus, a competitive antagonist can interact with a mAChR $M_1$ receptor and compete with the endogenous ligand, acetylcholine, for binding to the receptor and decrease the ability of the receptor to transduce an intracellular signal in response to endogenous ligand binding.

The term "mAChR $M_1$ receptor noncompetitive antagonist" refers to any exogenously administered compound or agent that binds to site that is not the orthosteric binding site of mAChR $M_1$ receptors, and is capable of partially or completely inhibiting, or reversing, the effect of an agonist (e.g. acetylcholine) on the mAChR $M_1$ receptor. Thus, a non-competitive antagonist can interact with a mAChR $M_1$ receptor and decrease the binding of the endogenous ligand, acetylcholine, to the receptor and/or decrease the ability of the receptor to transduce an intracellular signal in response to endogenous ligand binding.

The term "mAChR $M_1$ partial antagonist" refers to any exogenously administered compound or agent that can bind to an orthosteric or an allosteric site, but the effect of binding is to only partially block effect of mAChR $M_1$ receptor response to an agonist, e.g. acetylcholine. Thus, a partial antagonist can interact with a mAChR $M_1$ receptor and but is not capable of fully inhibiting the response of the mAChR $M_1$ receptor to an agonist, e.g. acetylcholine.

The term "mAChR $M_1$ negative allosteric modulator" refers to any exogenously administered compound or agent that binds an allosteric site that directly or indirectly inhibits the activity of the mAChR $M_1$ receptor in the presence of acetylcholine, or another agonist, in an animal, in particular a mammal, for example a human. For example, while not intended to be limiting towards the present disclosure, a selective muscarinic $M_1$ negative allosteric modulator can preferentially bind to the muscarinic $M_1$ receptor and decrease muscarinic $M_1$ signaling by acting as a non-competitive antagonist. In one aspect, a mAChR $M_1$ receptor negative allosteric modulator decreases the activity of the mAChR $M_1$ receptor in a cell in the presence of extracellular acetylcholine.

In embodiments, "selective" or "selectivity" or the like in reference to a compound or agent refers to the compound's or agent's ability to cause an increase or decrease in activity of a particular molecular target (e.g., protein, enzyme, etc.) preferentially over one or more different molecular targets (e.g., a compound having selectivity toward muscarinic acetylcholine $M_1$ receptor (mAChR $M_1$) would preferentially inhibit mAChR $M_1$ over other muscarinic receptors). In embodiments, a "muscarinic acetylcholine $M_1$ receptor selective compound" or "mAChR $M_1$-selective compound" refers to a compound (e.g., compounds described herein) having selectivity towards muscarinic acetylcholine $M_1$ receptor (mAChR $M_1$). In embodiments, the compound (e.g., compound described herein) is about 5-fold, 10-fold, 20-fold, 30-fold, 40-fold, 50-fold, or about 100-fold more selective for muscarinic acetylcholine $M_1$ receptor (mAChR $M_1$) over one or more of the mAChR $M_2$, $M_3$, $M_4$, or $M_5$ receptors. In embodiments, the compound (e.g., compound described herein) is at least 5-fold, 10-fold, 20-fold, 30-fold, 40-fold, 50-fold, or at least 100-fold more selective for muscarinic acetylcholine $M_1$ receptor (mAChR $M_1$) over one or more of the mAChR $M_2$, $M_3$, $M_4$, or $M_5$ receptors.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the subject is a human.

As used herein, "treatment" or "treating" or "palliating" or "ameliorating" are used interchangeably herein. These terms refer to an approach for obtaining beneficial or desired results including but not limited to therapeutic benefit and/or prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "$EC_{50}$" is intended to refer to the concentration of a substance (e.g., a compound or a drug) that is required for 50% activation or enhancement of a biological process, or component of a process, including a protein, subunit, organelle, ribonucleoprotein, etc. For example, $EC_{50}$ can refer to the concentration of agonist that provokes a response halfway between the baseline and maximum response in an in vitro assay. In some embodiments, in vitro assay systems utilize a cell line that either expresses endogenously a target of interest or has been transfected with a suitable expression vector that directs expression of a recombinant form of the target.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. For example, $IC_{50}$ refers to the half maximal (50%) inhibitory concentration (IC) of a substance as determined in a suitable assay. For example, an $IC_{50}$ for mAChR $M_1$ receptor can be determined in an in vitro assay system.

II. COMPOUNDS

This disclosure provides compounds which are antagonists of the muscarinic acetylcholine $M_1$ receptor (mAChR $M_1$). These compounds, and compositions comprising these compounds, are useful for the treatment or prevention of neurological disorders. In some embodiments, the compounds described herein are useful for treating multiple sclerosis.

In an aspect is provided a compound, or a pharmaceutically acceptable salt or solvate thereof, having the structure of Formula (IA-1) or (IB-1):

Formula (IA-1)

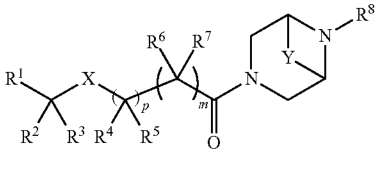

Formula (IB-1)

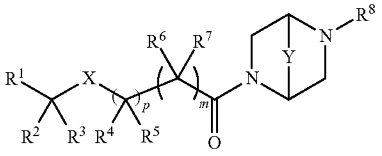

wherein:

X is a bond, —C($R^9$)($R^{10}$)—, —N($R^{11}$)—, —O—, —S(O)$_n$—, —$CH_2N$($R^{11}$)—, substituted or unsubstituted alkylene (e.g., $C_1$-$C_8$, $C_1$-$C_6$, $C_1$-$C_4$, or $C_1$-$C_2$), substituted or unsubstituted alkenylene (e.g., $C_2$-$C_8$, $C_2$-$C_6$, or $C_2$-$C_4$), substituted or unsubstituted alkynylene (e.g., $C_2$-$C_8$, $C_2$-$C_6$, or $C_2$-$C_4$), substituted or unsubstituted heteroalkylene (e.g., 2 to 8 membered, 2 to 6 membered, 4 to 6 membered, or 2 to 3 membered), substituted or unsubstituted heteroalkenylene (e.g., 3 to 8 membered, 3 to 6 membered, or 4 to 6 membered), or substituted or unsubstituted heteroalkynylene (e.g., 3 to 8 membered, 3 to 6 membered, or 4 to 6 membered);

Y is a substituted or unsubstituted alkylene (e.g., $C_1$-$C_8$, $C_1$-$C_6$, $C_1$-$C_4$, or $C_1$-$C_2$), substituted or unsubstituted alkenylene (e.g., $C_2$-$C_8$, $C_2$-$C_6$, or $C_2$-$C_4$), or substituted or unsubstituted heteroalkylene (e.g., 2 to 8 membered, 2 to 6 membered, 4 to 6 membered, or 2 to 3 membered);

$R^1$ is

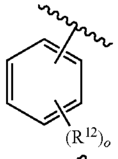, 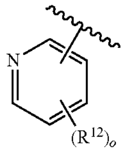, 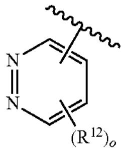, 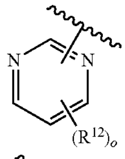,

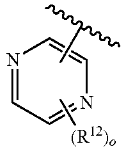, 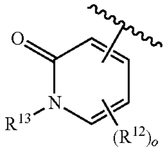, 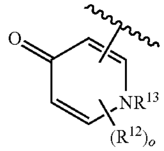,

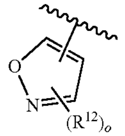, 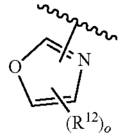, 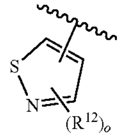, 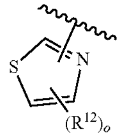,

-continued

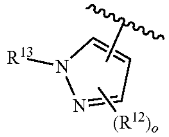, 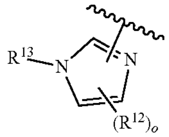,

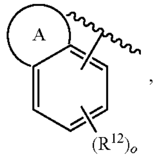, or 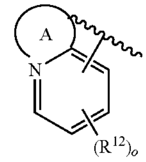, wherein ring A is a heteroaryl ring or a heterocycloalkyl ring optionally substituted with hydroxyl, halogen, cyano, —N($R^{14}$)($R^{15}$), substituted or unsubstituted alkyl (e.g., $C_1$-$C_8$, $C_1$-$C_6$, $C_1$-$C_4$, or $C_1$-$C_2$), substituted or unsubstituted alkoxy (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted haloalkoxy (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted cycloalkoxy (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted halocycloalkoxy (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), —S(O)$_n$($R^{16}$), or —$SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, substituted or unsubstituted alkyl (e.g., $C_1$-$C_8$, $C_1$-$C_6$, $C_1$-$C_4$, or $C_1$-$C_2$), substituted or unsubstituted alkoxy (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted haloalkoxy (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted cycloalkoxy (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted halocycloalkoxy (e.g., $C_3$-$C_8$, $C_3$-$C_6$, $C_4$-$C_6$, or $C_5$-$C_6$), substituted or unsubstituted alkylhydroxyl (e.g., $C_1$-$C_8$, $C_1$-$C_6$, $C_1$-$C_4$, or $C_1$-$C_2$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered);

$R^3$ is halogen, substituted or unsubstituted alkyl (e.g., $C_1$-$C_8$, $C_1$-$C_6$, $C_1$-$C_4$, or $C_1$-$C_2$), substituted or unsubstituted alkoxy (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted haloalkoxy (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted cycloalkoxy (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted halocycloalkoxy (e.g., $C_3$-$C_8$, $C_3$-$C_6$, $C_4$-$C_6$, or $C_5$-$C_6$), substituted or unsubstituted alkylhydroxyl (e.g., $C_1$-$C_8$, $C_1$-$C_6$, $C_1$-$C_4$, or $C_1$-$C_2$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); or $R^2$ and $R^3$ combine to form a cycloalkyl (e.g., $C_3$-$C_8$, $C_3$-$C_6$, $C_4$-$C_6$, or $C_5$-$C_6$) or heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$);

$R^4$ and $R^5$ are independently selected from hydrogen, deuterium, halogen, and substituted or unsubstituted alkyl (e.g., $C_1$-$C_8$, $C_1$-$C_6$, $C_1$-$C_4$, or $C_1$-$C_2$); or $R^3$ and $R^4$ combine to form a cycloalkyl (e.g., $C_3$-$C_8$, $C_3$-$C_6$, $C_4$-$C_6$, or $C_5$-$C_6$) or heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^4$ and $R^5$ combine to form a cycloalkyl (e.g., $C_3$-$C_8$, $C_3$-$C_6$, $C_4$-$C_6$, or $C_5$-$C_6$) or heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$);

$R^6$ and $R^7$ are independently selected from hydrogen, deuterium, halogen, and substituted or unsubstituted alkyl (e.g., $C_1$-$C_8$, $C_1$-$C_6$, $C_1$-$C_4$, or $C_1$-$C_2$); or $R^3$ and $R^7$ combine to form a cycloalkyl (e.g., $C_4$-$C_8$, $C_4$-$C_6$, or $C_5$-$C_6$) or heterocycloalkyl (e.g., 4 to 8 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^4$ and $R^6$ combine to form a cycloalkyl (e.g., $C_4$-$C_8$, $C_4$-$C_6$, or $C_5$-$C_6$) or heterocycloalkyl (e.g., 4 to 8 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^5$ and $R^7$ combine to form a bond;

$R^8$ is

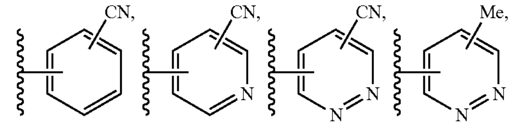

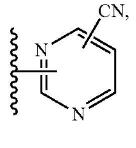

or

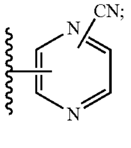

$R^9$ and $R^{10}$ are independently selected from hydrogen, deuterium, halogen, substituted or unsubstituted alkyl (e.g., $C_1$-$C_8$, $C_1$-$C_6$, $C_1$-$C_4$, or $C_1$-$C_2$), substituted or unsubstituted alkoxy (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted haloalkoxy (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted cycloalkoxy (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted halocycloalkoxy (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); or $R^3$ and $R^{10}$ combine to form a cycloalkyl (e.g., $C_4$-$C_8$, $C_4$-$C_6$, or $C_5$-$C_6$) or heterocycloalkyl (e.g., 4 to 8 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^4$ and $R^{10}$ combine to form a cycloalkyl (e.g., $C_4$-$C_8$, $C_4$-$C_6$, or $C_5$-$C_6$) or heterocycloalkyl (e.g., 4 to 8 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^6$ and $R^{10}$ combine to form a cycloalkyl (e.g., $C_4$-$C_8$, $C_4$-$C_6$, or $C_5$-$C_6$) or heterocycloalkyl (e.g., 4 to 8 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^9$ and $R^{10}$ combine to form a cycloalkyl (e.g., $C_3$-$C_8$, $C_3$-$C_6$, $C_4$-$C_6$, or $C_5$-$C_6$) or heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$);

$R^{11}$ is hydrogen, substituted or unsubstituted alkyl (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); or $R^3$ and $R^{11}$ combine to form a heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^4$ and $R^{11}$ combine to form a heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^6$ and $R^{11}$ combine to form a heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$);

each $R^{12}$ is independently selected from hydroxyl, halogen, cyano, —$N(R^{14})(R^{15})$, substituted or unsubstituted alkyl (e.g., $C_1$-$C_8$, $C_1$-$C_6$, $C_1$-$C_4$, or $C_1$-$C_2$), substituted or unsubstituted alkoxy (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted haloalkoxy (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted cycloalkoxy (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted halocycloalkoxy (e.g., $C_3$-$C_8$, $C_3$-$C_6$, $C_4$-$C_6$, or $C_5$-$C_6$), substituted or unsubstituted alkylhydroxyl (e.g., $C_1$-$C_8$, $C_1$-$C_6$, $C_1$-$C_4$, or $C_1$-$C_2$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered), —$S(O)_n(R^{16})$, or —$SF_5$; or $R^3$ and one $R^{12}$ combine to form a cycloalkyl (e.g., $C_3$-$C_8$, $C_3$-$C_6$, $C_4$-$C_6$, or $C_5$-$C_6$) or heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^{10}$ and one $R^{12}$ combine to form a cycloalkyl (e.g., $C_3$-$C_8$, $C_3$-$C_6$, $C_4$-$C_6$, or $C_5$-$C_6$) or heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$); or $R^{11}$ and one $R^{12}$ combine to form a heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$);

$R^{13}$ is hydrogen, substituted or unsubstituted alkyl (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered);

$R^{14}$ and $R^{15}$ are independently selected from hydrogen, substituted or unsubstituted alkyl (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); or $R^{14}$ and $R^{15}$ combine to form a heterocycloalkyl (e.g., 3 to 8 membered, 3 to 6 membered, 4 to 6 membered, 4 to 5 membered, or 5 to 6 membered) ring optionally substituted with halogen, substituted or unsubstituted alkyl (e.g., $C_1$-$C_8$, $C_1$-$C_6$, $C_1$-$C_4$, or $C_1$-$C_2$), or substituted or unsubstituted cycloalkyl (e.g., $C_3$-$C_8$, $C_3$-$C_6$, $C_4$-$C_6$, or $C_5$-$C_6$);

$R^{16}$ is substituted or unsubstituted alkyl (e.g., $C_1$-$C_8$, $C_1$-$C_6$, $C_1$-$C_4$, or $C_1$-$C_2$), substituted or unsubstituted haloalkyl (e.g., $C_1$-$C_8$, $C_1$-$C_6$, $C_1$-$C_4$, or $C_1$-$C_2$), substituted or unsubstituted cycloalkyl (e.g., $C_3$-$C_8$, $C_3$-$C_6$, $C_4$-$C_6$, or $C_5$-$C_6$), substituted or unsubstituted halocycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered);

m is 0 or 1;

n is 0, 1, or 2;

o is 0, 1, 2, or 3; and p is 0 or 1.

In one aspect is provided a compound of Formula (IA) or (IB):

Formula (IA)

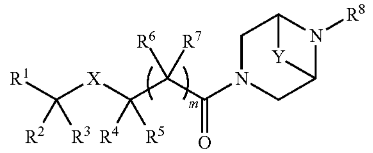

Formula (IB)

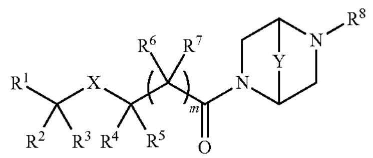

wherein:

X is a bond, —$C(R^9)(R^{10})$—, —$N(R^{11})$—, —O—, —$S(O)_n$—, —$CH_2N(R^{11})$—, or —$CH_2O$—;

Y is a —$CH_2$—, —$CH_2CH_2$—, —CH═CH—, or —$CH_2OCH_2$—;

$R^1$ is

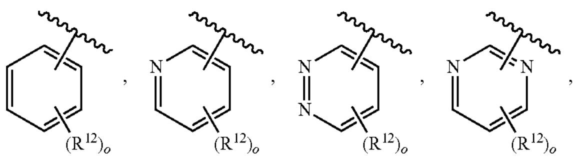

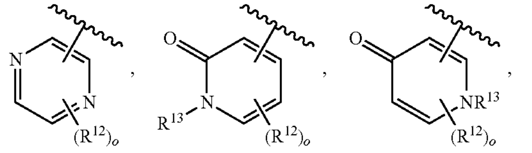

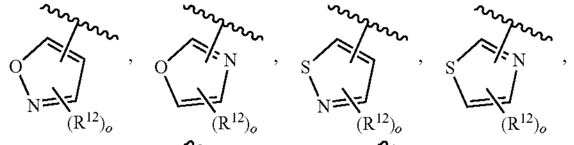

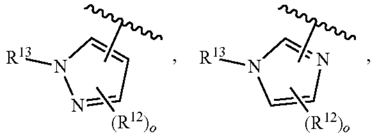

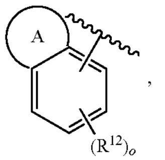

or

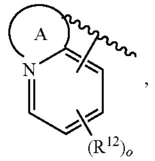

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^4$ and $R^5$ are independently selected from hydrogen, deuterium, halogen, and $C_{1-3}$ alkyl; or $R^3$ and $R^4$ combine to form a cycloalkyl or heterocycloalkyl ring optionally substituted with halogen, $C_{1-6}$ alkyl, or $C_{3-6}$ cycloalkyl; or $R^4$ and $R^5$ combine to form a cycloalkyl or heterocycloalkyl ring optionally substituted with halogen, $C_{1-6}$ alkyl, or $C_{3-6}$ cycloalkyl;

$R^6$ and $R^7$ are independently selected from hydrogen, deuterium, halogen, and $C_{1-3}$ alkyl; or $R^3$ and $R^7$ combine to form a cycloalkyl or heterocycloalkyl ring optionally substituted with halogen, $C_{1-6}$ alkyl, or $C_{3-6}$ cycloalkyl; or $R^4$ and $R^6$ combine to form a cycloalkyl or heterocycloalkyl ring optionally substituted with halogen, $C_{1-6}$ alkyl, or $C_{3-6}$ cycloalkyl; or $R^5$ and $R^7$ combine to form a bond;

$R^8$ is

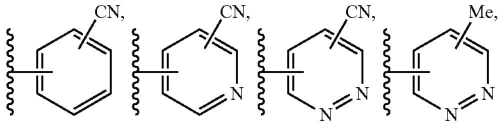

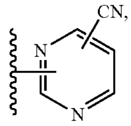

or

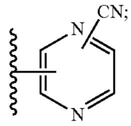

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^4$ and $R^{10}$ combine to form a cycloalkyl or heterocycloalkyl ring optionally substituted with halogen, $C_{1-6}$ alkyl, or $C_{3-6}$ cycloalkyl; or $R^6$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl; or $R^4$ and $R^{11}$ combine to form a heteroalkyl ring optionally substituted with halogen, $C_{1-6}$ alkyl, or $C_{3-6}$ cycloalkyl; or $R^6$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3;

or a pharmaceutically acceptable salt or solvate thereof, provided that the aforementioned combinations do not violate the rules of valency known to those skilled in the art.

In one aspect is provided a compound of Formula (IIA) or (IIB):

Formula (IIA)

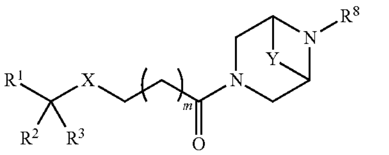

Formula (IIB)

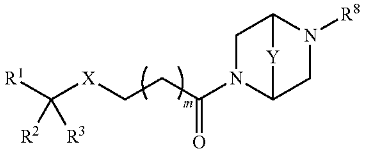

wherein:

X is a bond, —C($R^9$)($R^{10}$)—, —N($R^{11}$)—, —O—, —S(O)$_n$—, —$CH_2N(R^{11})$—, or —$CH_2O$—;

Y is a —$CH_2$—, —$CH_2CH_2$—, —CH═CH—, or —$CH_2OCH_2$—;

$R^1$ is

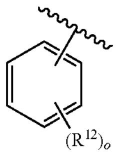, 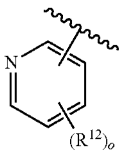, 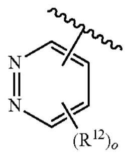, 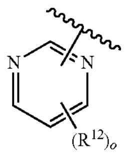, 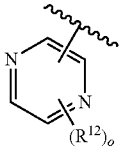, 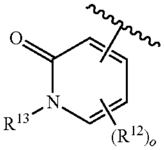, 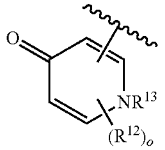, 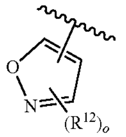, 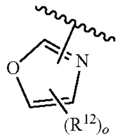, 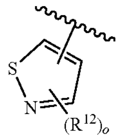, 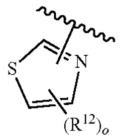, 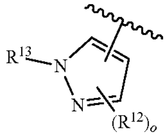, 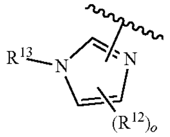, 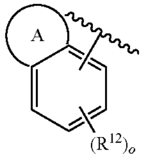, or 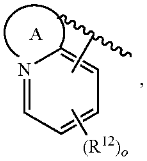, wherein ring A is a 5- or 6-membered heteroaryl ring or a 5- or 6-membered heterocycloalkyl ring optionally substituted with halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, S(O)$_n$($R^{16}$), or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

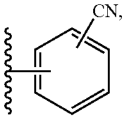 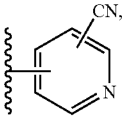 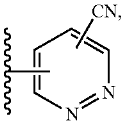 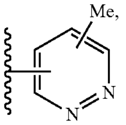 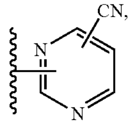 or 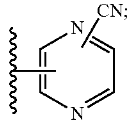

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, S(O)$_n$($R^{16}$), or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and is 0, 1, 2, or 3;

or a pharmaceutically acceptable salt or solvate thereof, provided that the aforementioned combinations do not violate the rules of valency known to those skilled in the art.

In another aspect is provided a compound of Formula (III):

Formula (III)

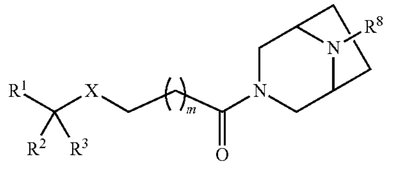

wherein:

X is a bond, —C($R^9$)($R^{10}$)—, —N($R^{11}$)—, —O—, —S(O)$_n$—, —$CH_2$N($R^{11}$)—, or —$CH_2$O—;

$R^1$ is

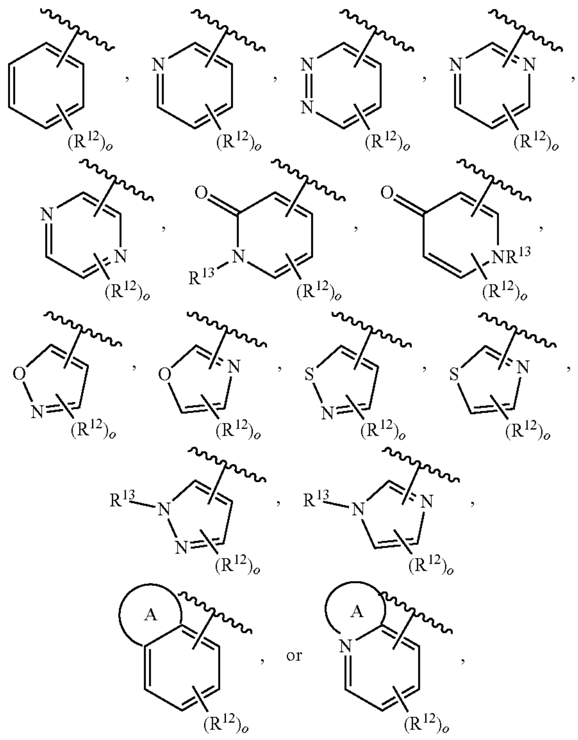

wherein ring A is a 5- or 6-membered heteroaryl ring or a 5- or 6-membered heterocycloalkyl ring optionally substituted with halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, S(O)$_n$($R^{16}$), or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

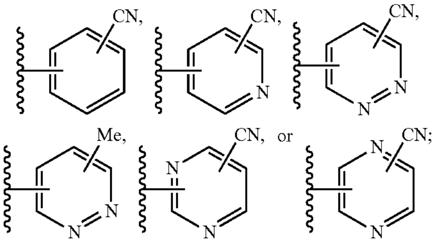

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, S(O)$_n$($R^{16}$), or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3;

or a pharmaceutically acceptable salt or solvate thereof, provided that the aforementioned combinations do not violate the rules of valency known to those skilled in the art.

In embodiments of a compound described herein (e.g., of Formula (IA-1), (IB-1), (IA), (IB), (IIA), (IIB), or (III)), or a pharmaceutically acceptable salt or solvate thereof, X is a bond, —C($R^9$)($R^{10}$)—, —N($R^{11}$)—, or —O—. In some embodiments, X is a bond, —N($R^{11}$)—, or —O—.

In some embodiments of a compound of Formula (IA), (IB), (IIA), (IIB), or (III), or a pharmaceutically acceptable salt or solvate thereof, X is a bond, —C($R^9$)($R^{10}$)—, —N($R^{11}$)—, or —O—. In some embodiments, X is a bond, —N($R^{11}$)—, or —O—.

In embodiments, a substituted X (e.g., substituted alkylene, substituted alkenylene, substituted alkynylene, substituted heteroalkylene, substituted heteroalkenylene, and/or substituted heteroalkynylene) is substituted with at least one substituent group, size-limited substituent group, or lower substituent group; wherein if the substituted X is substituted with a plurality of groups selected from substituent groups, size-limited substituent groups, and lower substituent groups; each substituent group, size-limited substituent group, and/or lower substituent group may optionally be different. In embodiments, when X is substituted, it is substituted with at least one substituent group. In embodiments, when X is substituted, it is substituted with at least one size-limited substituent group. In embodiments, when X is substituted, it is substituted with at least one lower substituent group.

In embodiments, a substituted Y (e.g., substituted alkylene, substituted alkenylene, and/or substituted heteroalkylene) is substituted with at least one substituent group, size-limited substituent group, or lower substituent group; wherein if the substituted Y is substituted with a plurality of groups selected from substituent groups, size-limited substituent groups, and lower substituent groups; each substituent group, size-limited substituent group, and/or lower substituent group may optionally be different. In embodiments, when Y is substituted, it is substituted with at least one substituent group. In embodiments, when Y is substituted, it is substituted with at least one size-limited substituent group. In embodiments, when Y is substituted, it is substituted with at least one lower substituent group.

In embodiments, Ring A may be substituted with hydroxyl, in addition to the substituents listed.

In embodiments of a compound described herein (e.g., of Formula (IA-1), (IB-1), (IA), (IB), (IIA), (IIB), or (III)), or a pharmaceutically acceptable salt or solvate thereof, $R^1$ is

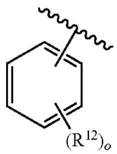, 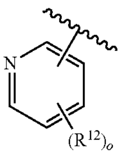, 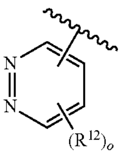, 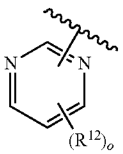,

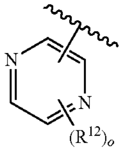, 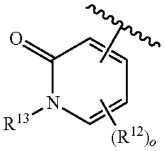, 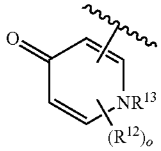,

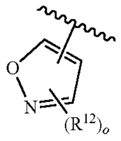, 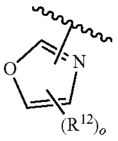, 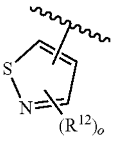, 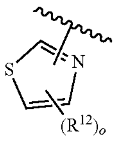,

-continued

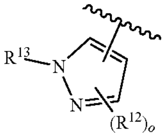, 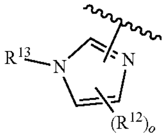, 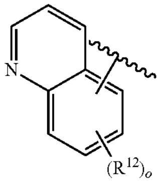,

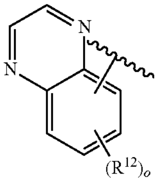, 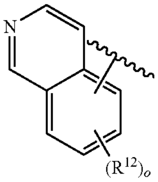, 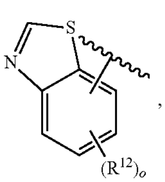,

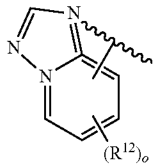, or 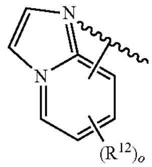.

In some embodiments, $R^1$ is

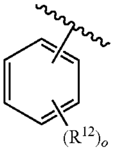, 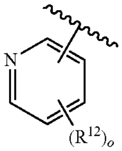, 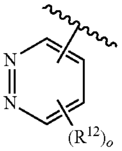, 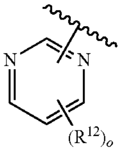,

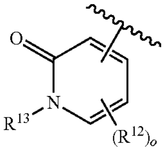, 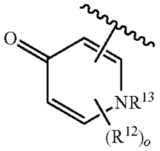,

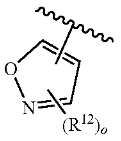, 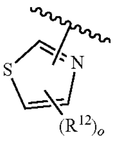, 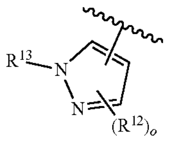,

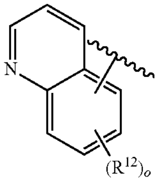, 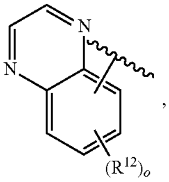,

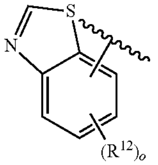, 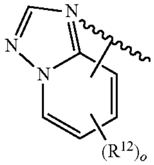, 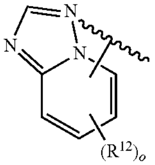, or

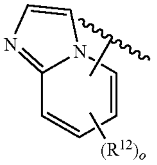.

In some embodiments of a compound of Formula (IA), (IB), (IIA), (IIB), or (III), or a pharmaceutically acceptable salt or solvate thereof, $R^1$ is

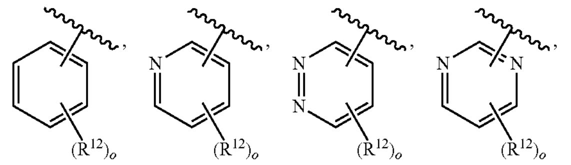

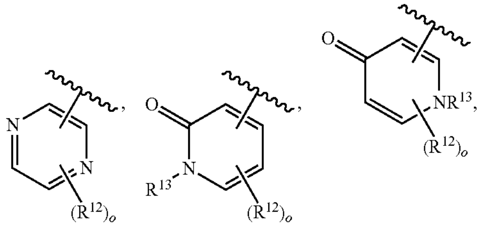

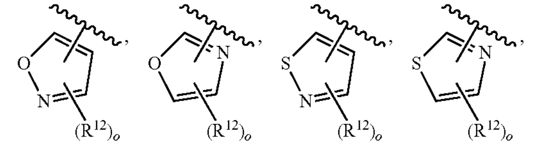

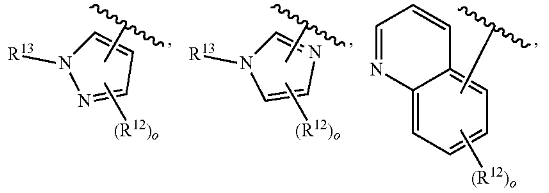

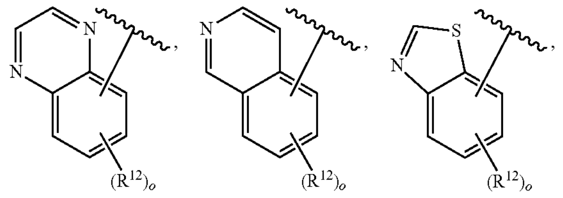

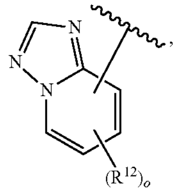

or

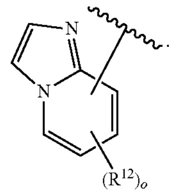

In some embodiments, $R^1$ is

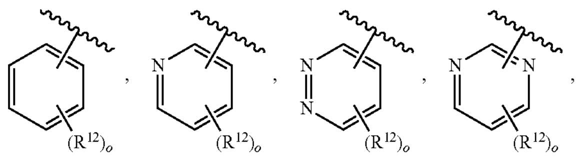

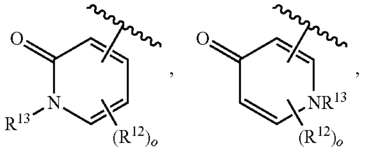

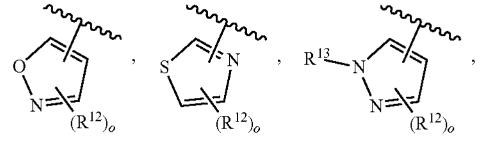

-continued

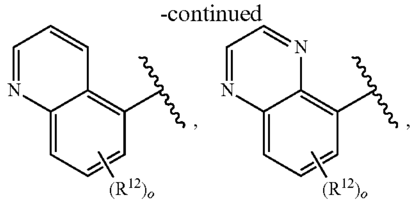

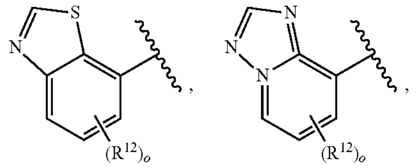

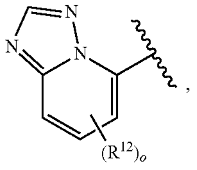

or

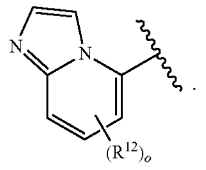

In embodiments, $R^2$ is hydrogen, deuterium, halogen, hydroxyl, substituted or unsubstituted $C_{1-6}$ alkyl, substituted or unsubstituted $C_{1-6}$ alkoxy, substituted or unsubstituted $C_{1-6}$ haloalkyl, substituted or unsubstituted $C_{1-6}$ haloalkoxy, substituted or unsubstituted $C_{3-6}$ cycloalkyl, substituted or unsubstituted $C_{3-6}$ cycloalkoxy, substituted or unsubstituted $C_{3-6}$ halocycloalkyl, substituted or unsubstituted $C_{3-6}$ halocycloalkoxy, substituted or unsubstituted $C_{1-6}$ alkylhydroxyl, substituted or unsubstituted heterocycloalkyl, substituted or unsubstituted aryl or substituted or unsubstituted heteroaryl.

In embodiments, a substituted $R^2$ (e.g., substituted alkyl, substituted alkoxy, substituted haloalkyl, substituted haloalkoxy, substituted cycloalkyl, substituted cycloalkoxy, substituted halocycloalkyl, substituted halocycloalkoxy, substituted alkylhydroxyl, substituted heterocycloalkyl, substituted aryl and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, a substituted $R^3$ (e.g., substituted alkyl, substituted alkoxy, substituted haloalkyl, substituted haloalkoxy, substituted cycloalkyl, substituted cycloalkoxy, substituted halocycloalkyl, substituted halocycloalkoxy, substituted alkylhydroxyl, substituted heterocycloalkyl, substituted aryl and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, a substituted $R^4$ (e.g., substituted alkyl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, a substituted $R^5$ (e.g., substituted alkyl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, a substituted $R^6$ (e.g., substituted alkyl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, a substituted $R^7$ (e.g., substituted alkyl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments of a compound described herein (e.g., of Formula (IA-1), (IB-1), (IA), (IB), (IIA), (IIB), or (III)), or a pharmaceutically acceptable salt or solvate thereof, $R^8$ is

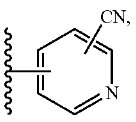
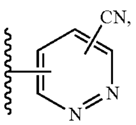
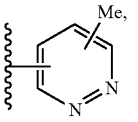
or
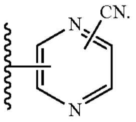

In some embodiments, $R^8$ is

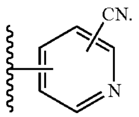

In some embodiments of a compound of Formula (IA), (IB), (IIA), (IIB), or (III), or a pharmaceutically acceptable salt or solvate thereof, $R^8$ is

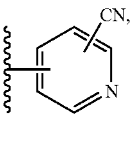
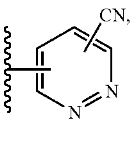
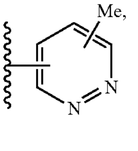
or
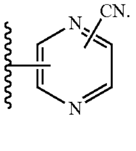

In some embodiments, $R^8$ is

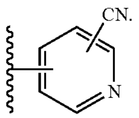

In embodiments, a substituted $R^9$ (e.g., substituted alkyl, substituted alkoxy, substituted haloalkyl, substituted haloalkoxy, substituted cycloalkyl, substituted cycloalkoxy, substituted halocycloalkyl, substituted halocycloalkoxy, substituted heterocycloalkyl, substituted aryl and/or substituted heteroaryl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, a substituted $R^{10}$ (e.g., substituted alkyl, substituted alkoxy, substituted haloalkyl, substituted haloalkoxy, substituted cycloalkyl, substituted cycloalkoxy, substituted halocycloalkyl, substituted halocycloalkoxy, substituted heterocycloalkyl, substituted aryl and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, a substituted $R^{11}$ (e.g., substituted alkyl, substituted haloalkyl, substituted cycloalkyl, substituted halocycloalkyl, substituted heterocycloalkyl, substituted aryl and/or substituted heteroaryl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when $R^{11}$ is substituted, it is substituted with at least one substituent group. In embodiments, when $R^{11}$ is substituted, it is substituted with at least one size-limited substituent group. In embodiments, when $R^{11}$ is substituted, it is substituted with at least one lower substituent group.

In embodiments, a substituted $R^{12}$ (e.g., substituted alkyl, substituted alkoxy, substituted haloalkyl, substituted haloalkoxy, substituted cycloalkyl, substituted cycloalkoxy, substituted halocycloalkyl, substituted halocycloalkoxy, substituted alkylhydroxyl, substituted heterocycloalkyl, substituted aryl and/or substituted heteroaryl) is substituted with at least one substituent group, size-limited substituent group, or lower substituent group; wherein if the substituted $R^{12}$ is substituted with a plurality of groups selected from substituent groups, size-limited substituent groups, and lower substituent groups; each substituent group, size-limited substituent group, and/or lower substituent group may optionally be different. In embodiments, when $R^{12}$ is substituted, it is substituted with at least one substituent group. In embodiments, when $R^{12}$ is substituted, it is substituted with at least one size-limited substituent group. In embodiments, when $R^{12}$ is substituted, it is substituted with at least one lower substituent group.

In embodiments, a substituted $R^{13}$ (e.g., substituted alkyl, substituted haloalkyl, substituted cycloalkyl, substituted halocycloalkyl, substituted heterocycloalkyl, substituted aryl and/or substituted heteroaryl) is substituted with at least one substituent group, size-limited substituent group, or lower substituent group; wherein if the substituted $R^{13}$ is substituted with a plurality of groups selected from substituent groups, size-limited substituent groups, and lower substituent groups; each substituent group, size-limited substituent group, and/or lower substituent group may optionally be different. In embodiments, when $R^{13}$ is substituted, it is substituted with at least one substituent group. In embodiments, when $R^{13}$ is substituted, it is substituted with at least one size-limited substituent group. In embodiments, when $R^{13}$ is substituted, it is substituted with at least one lower substituent group.

In embodiments, a substituted $R^{14}$ (e.g., substituted alkyl, substituted haloalkyl, substituted cycloalkyl, substituted halocycloalkyl, substituted heterocycloalkyl, substituted aryl and/or substituted heteroaryl) is substituted with at least one substituent group, size-limited substituent group, or lower substituent group; wherein if the substituted $R^{14}$ is substituted with a plurality of groups selected from substituent groups, size-limited substituent groups, and lower substituent groups; each substituent group, size-limited substituent group, and/or lower substituent group may optionally be different. In embodiments, when $R^{14}$ is substituted, it is substituted with at least one substituent group. In embodiments, when $R^{14}$ is substituted, it is substituted with at least one size-limited substituent group. In embodiments, when $R^{14}$ is substituted, it is substituted with at least one lower substituent group.

In embodiments, a substituted $R^{15}$ (e.g., substituted alkyl, substituted haloalkyl, substituted cycloalkyl, substituted halocycloalkyl, substituted heterocycloalkyl, substituted aryl and/or substituted heteroaryl) is substituted with at least one substituent group, size-limited substituent group, or lower substituent group; wherein if the substituted $R^{15}$ is substituted with a plurality of groups selected from substituent groups, size-limited substituent groups, and lower substituent groups; each substituent group, size-limited substituent group, and/or lower substituent group may optionally be different. In embodiments, when $R^{15}$ is substituted, it is substituted with at least one substituent group. In embodiments, when $R^{15}$ is substituted, it is substituted with at least one size-limited substituent group. In embodiments, when $R^{15}$ is substituted, it is substituted with at least one lower substituent group.

In embodiments, a substituted $R^{16}$ (e.g., substituted alkyl, substituted haloalkyl, substituted cycloalkyl, substituted halocycloalkyl, substituted heterocycloalkyl, substituted aryl and/or substituted heteroaryl) is substituted with at least one substituent group, size-limited substituent group, or lower substituent group; wherein if the substituted $R^{16}$ is substituted with a plurality of groups selected from substituent groups, size-limited substituent groups, and lower substituent groups; each substituent group, size-limited substituent group, and/or lower substituent group may optionally be different. In embodiments, when $R^{16}$ is substituted, it is substituted with at least one substituent group. In embodiments, when $R^{16}$ is substituted, it is substituted with at least one size-limited substituent group. In embodiments, when $R^{16}$ is substituted, it is substituted with at least one lower substituent group.

Any combination of the groups described above or below for the various variables is contemplated herein. Throughout the specification, groups and substituents thereof are chosen by one skilled in the field to provide stable moieties and compounds.

In some embodiments is a compound selected from:

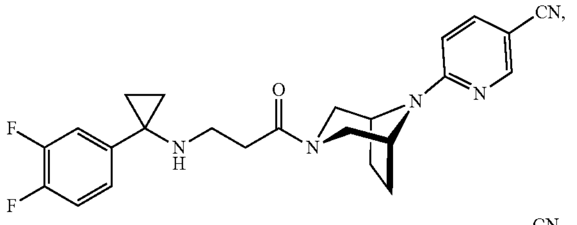
,

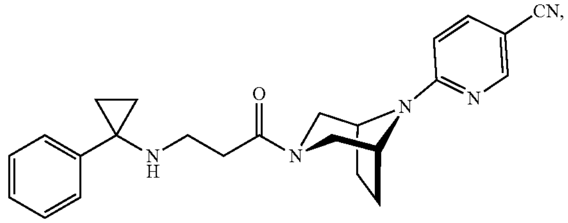
,

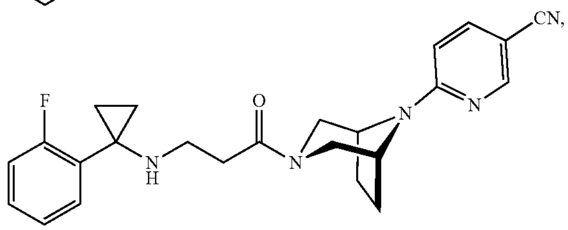
,

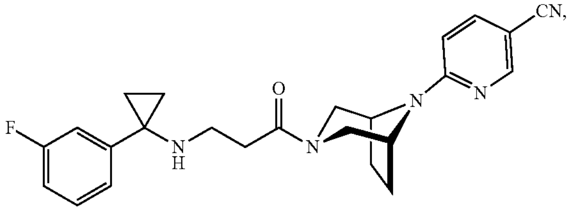
,

-continued
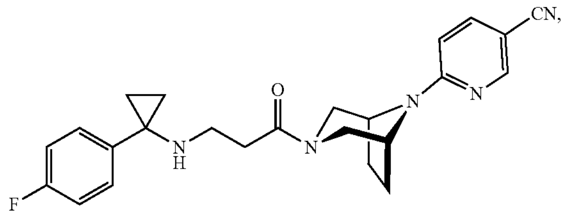
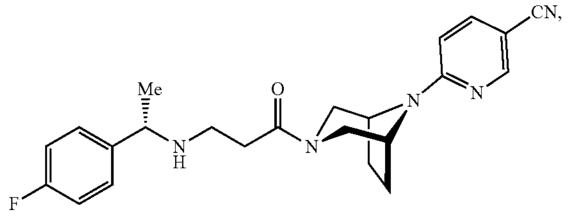
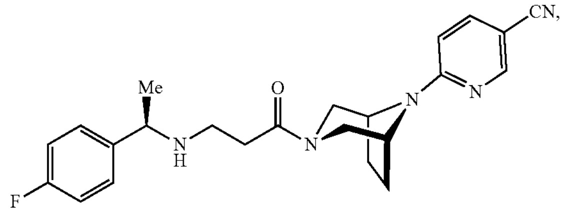
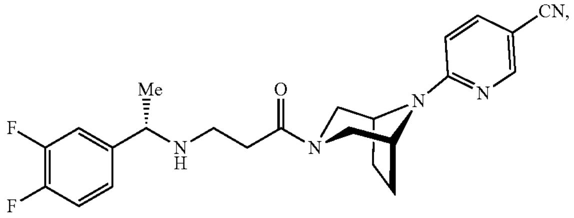
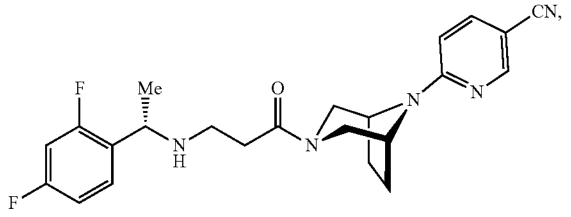
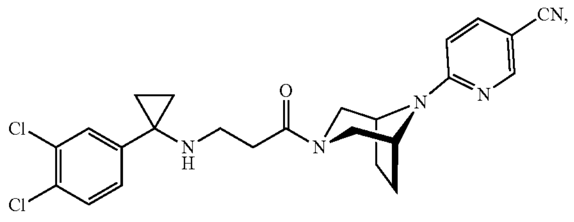
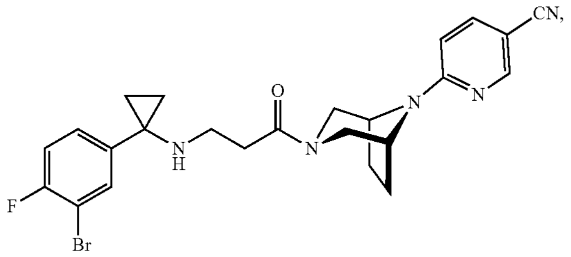
-continued
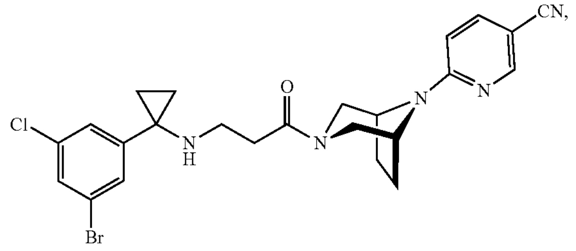
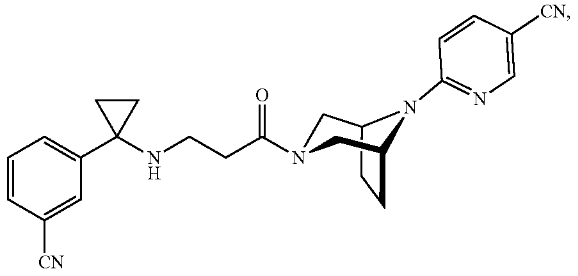
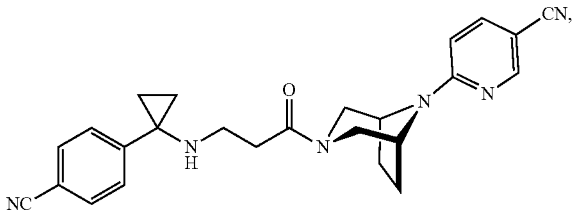
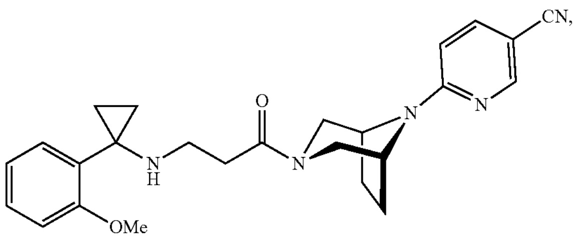
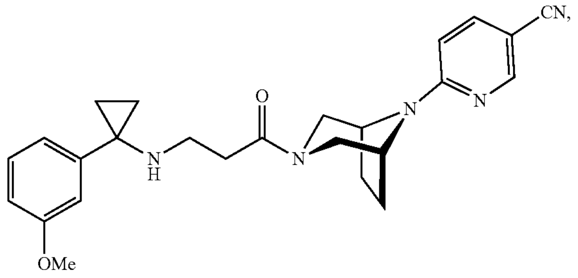
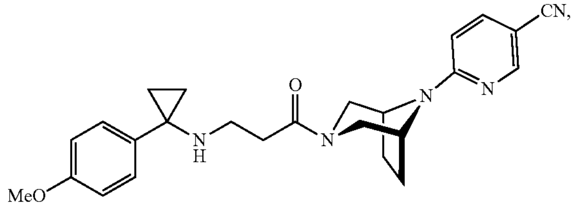
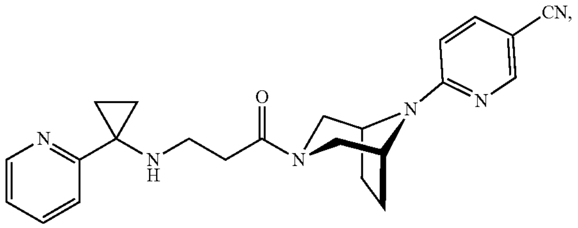

-continued
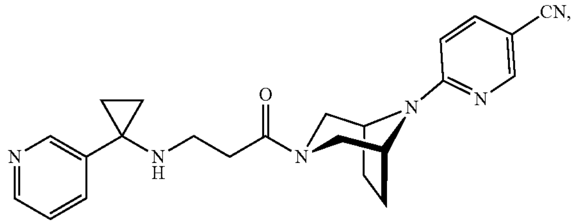
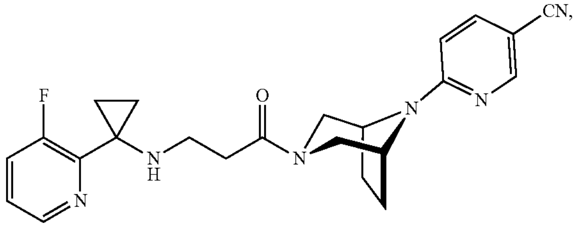
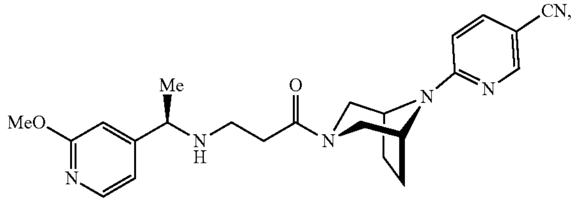
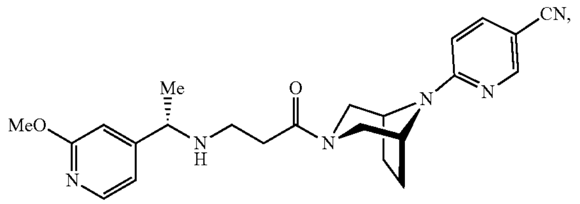
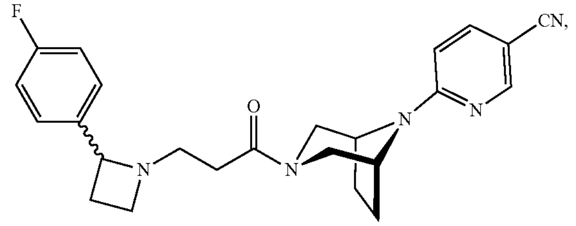
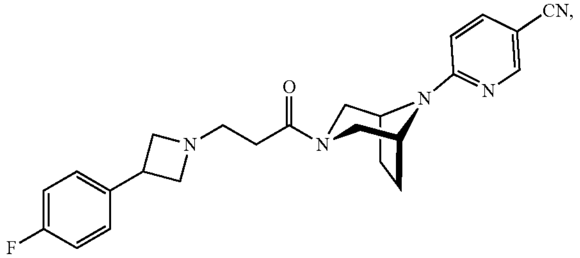
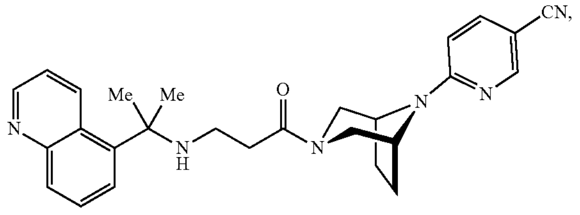
-continued
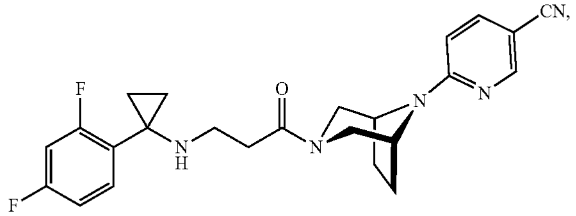
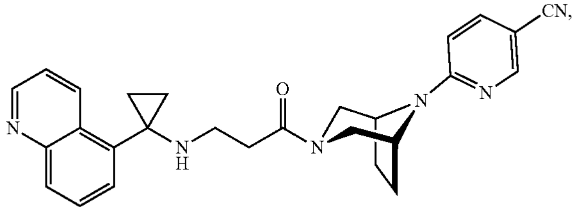
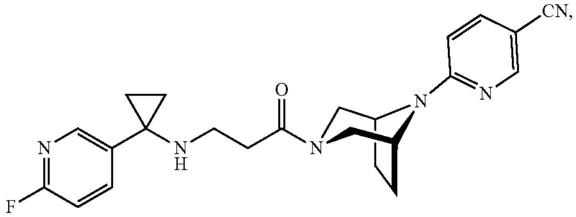
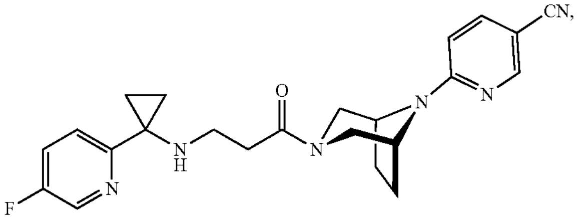
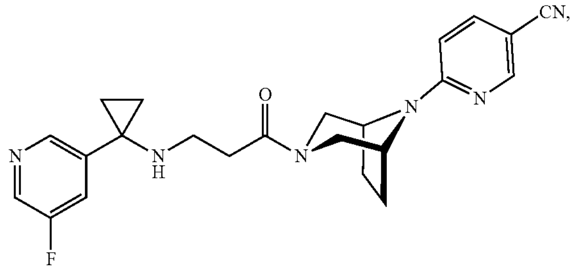
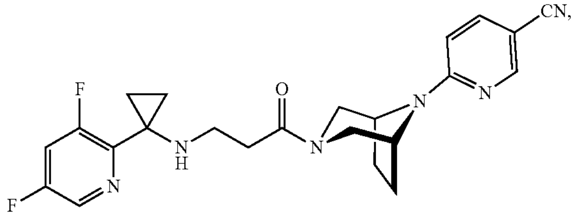
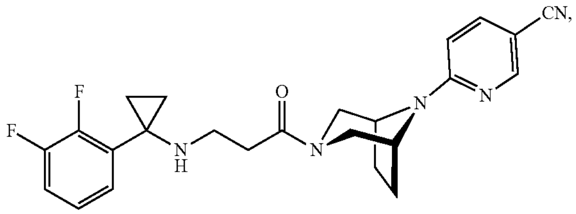

-continued
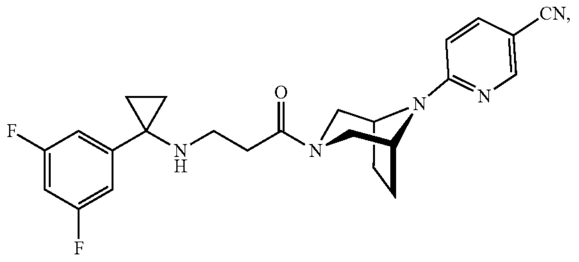
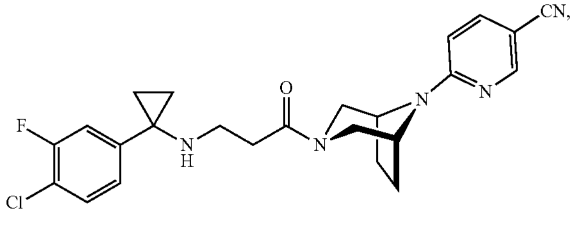
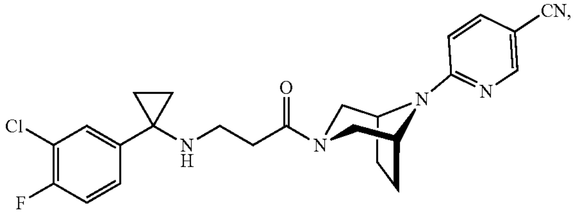
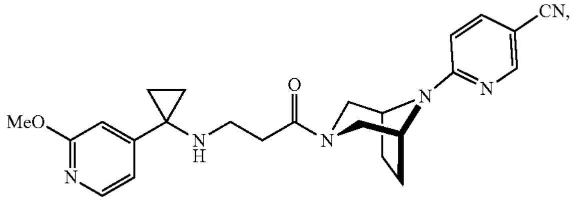
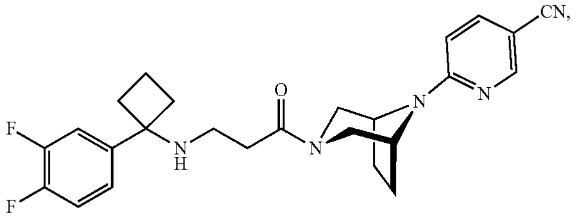
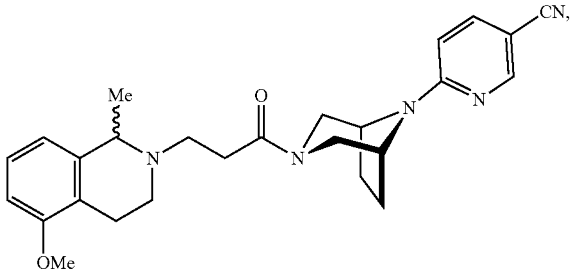
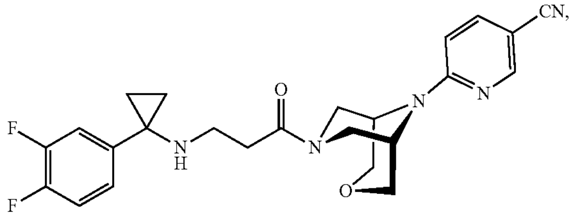
-continued
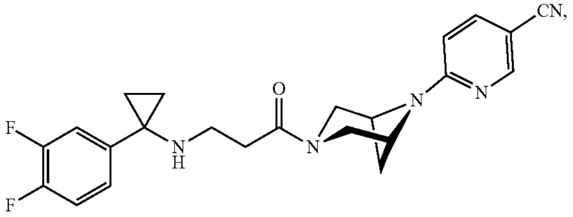
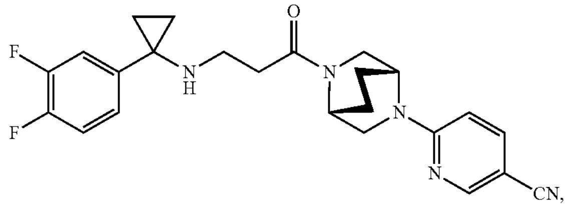
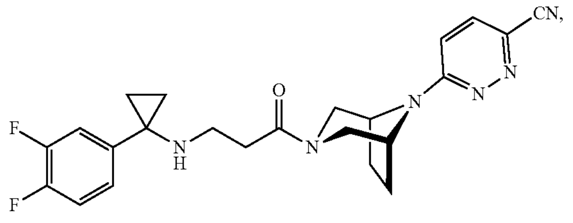
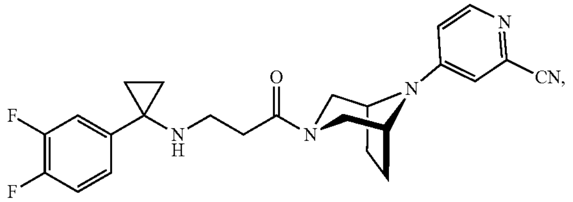
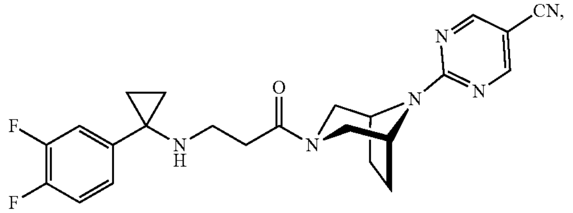
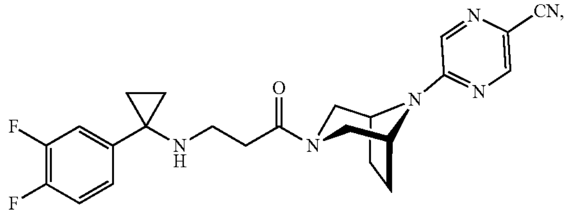
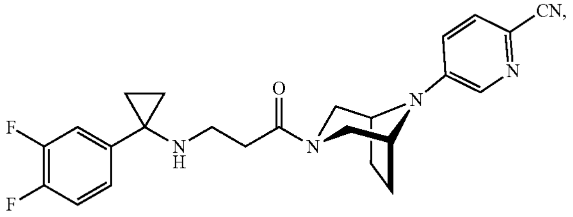
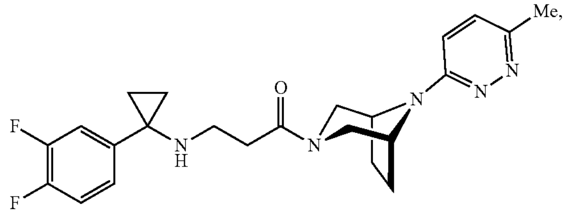

-continued
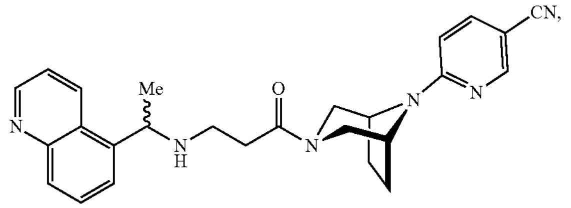
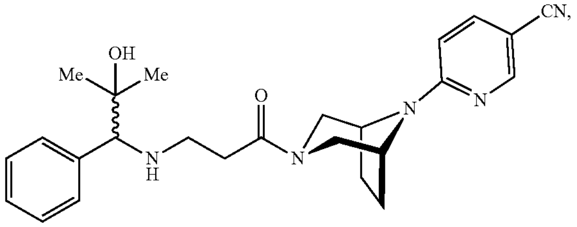
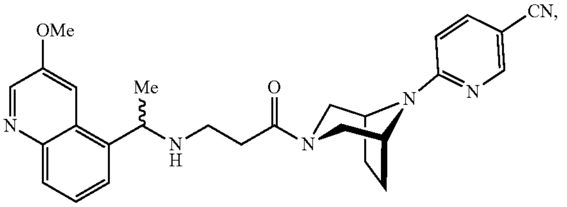
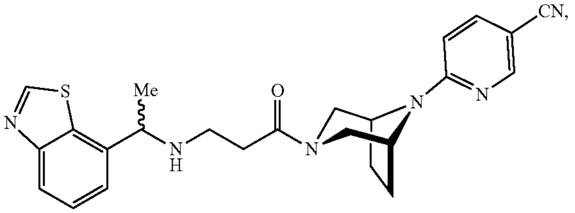
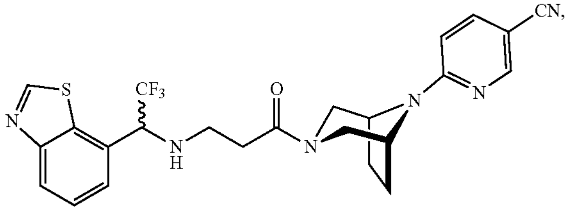
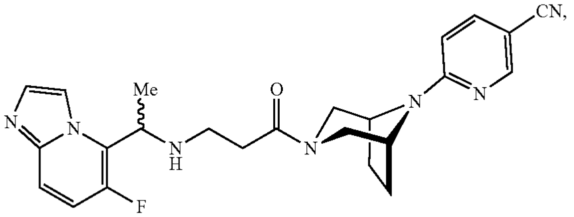
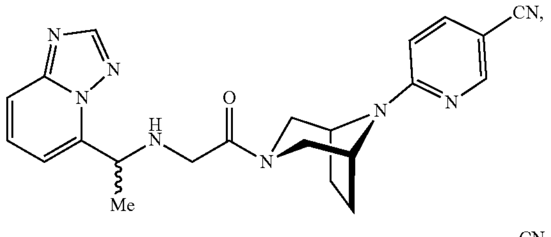
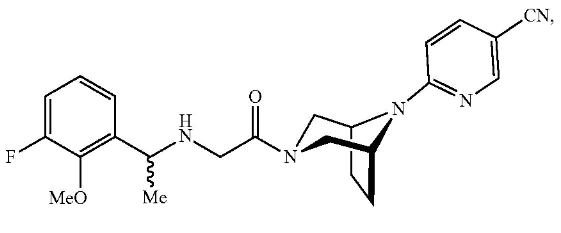
-continued
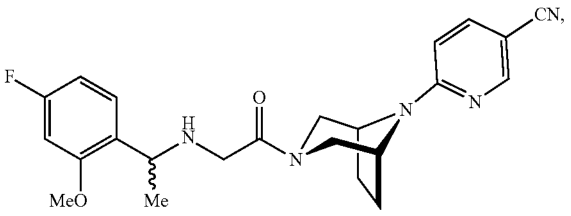
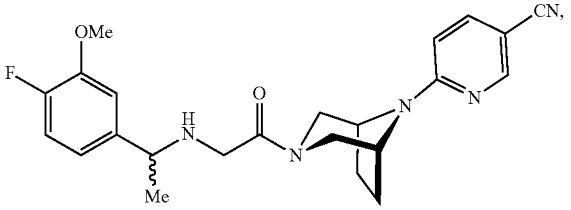
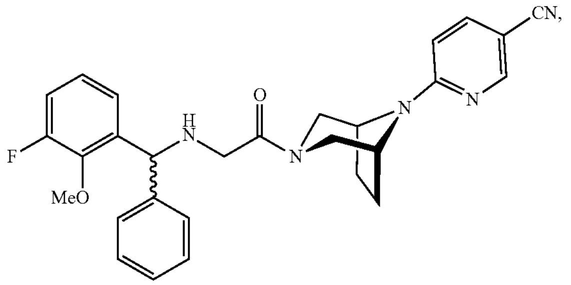
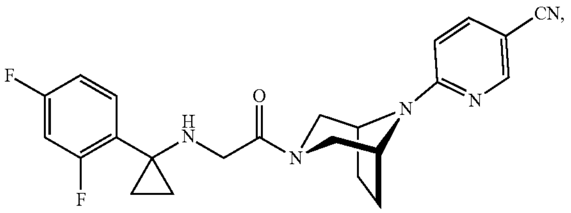
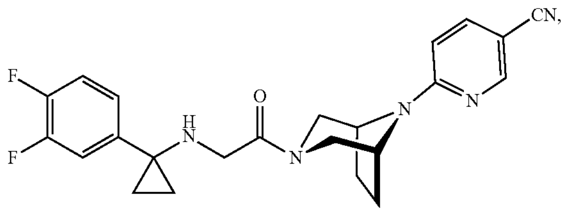
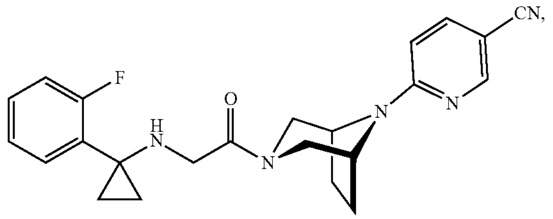
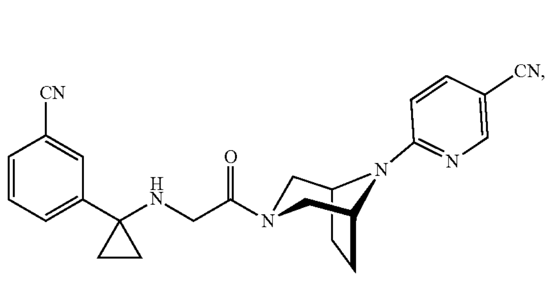

-continued
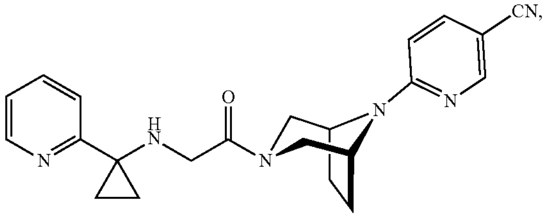
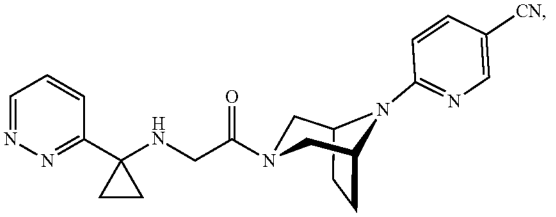
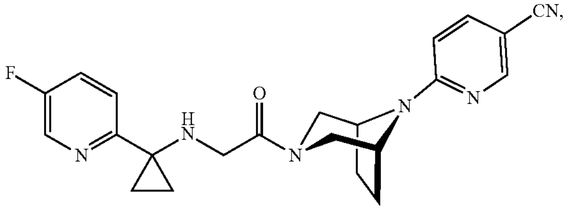
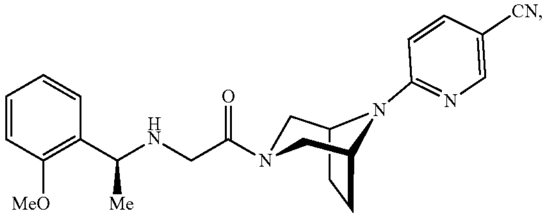
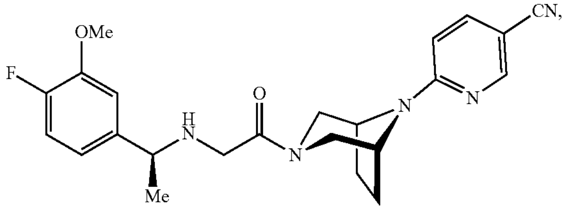
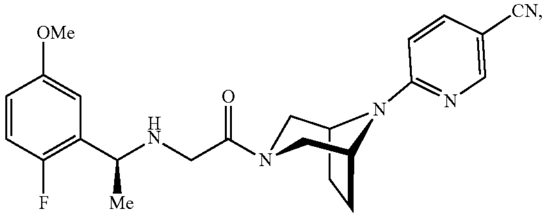
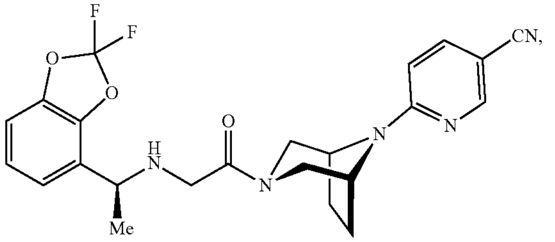
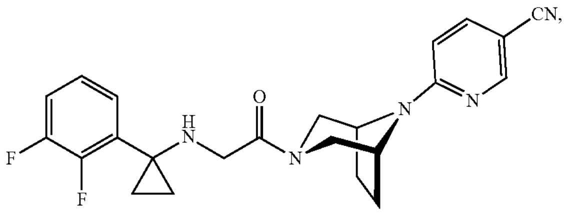
-continued
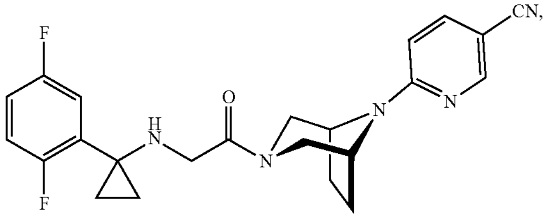
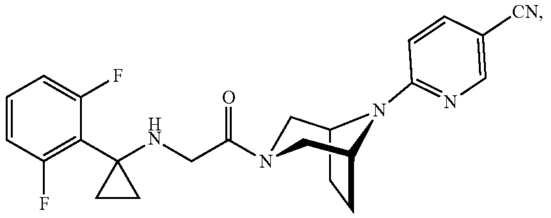
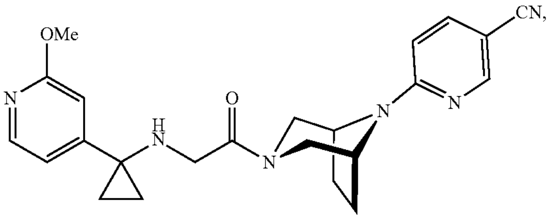
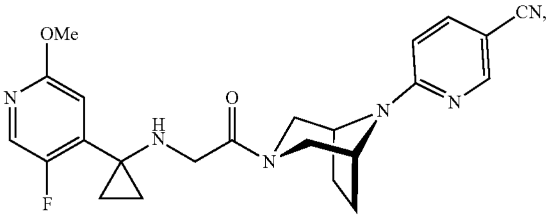
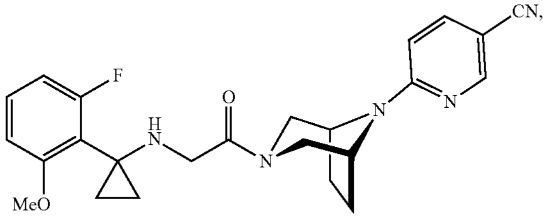
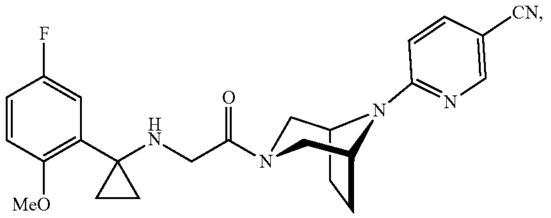
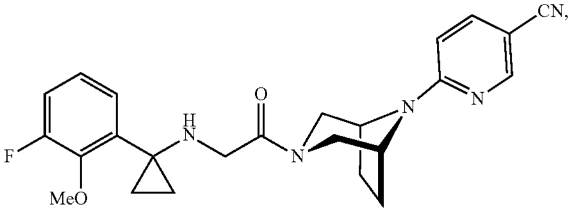
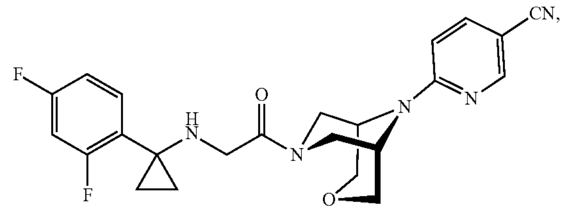

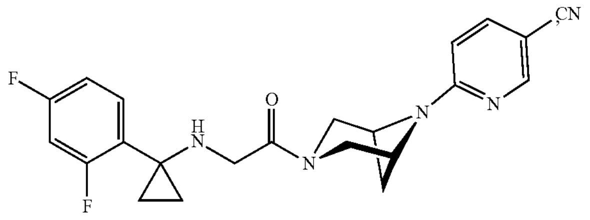
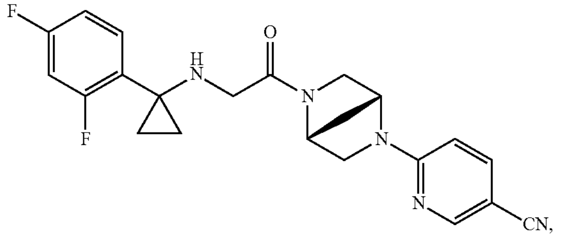
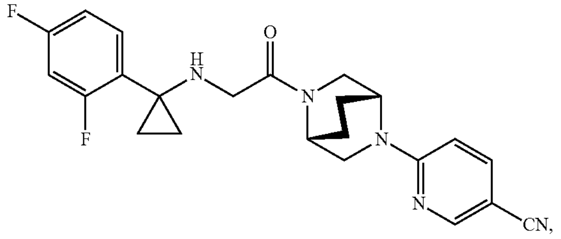
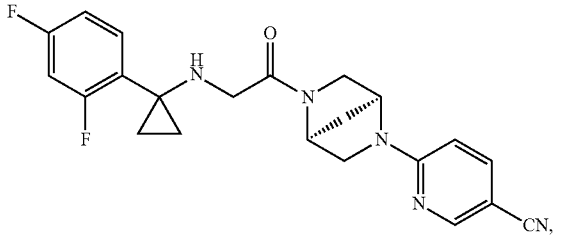
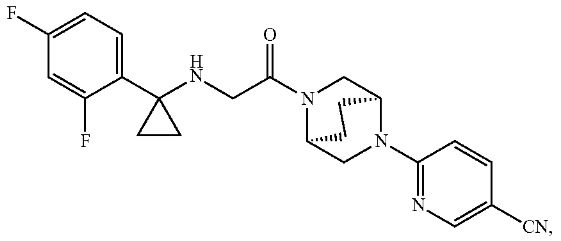
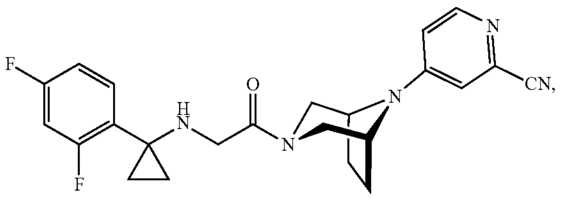
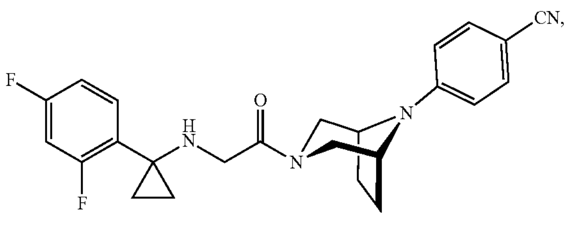
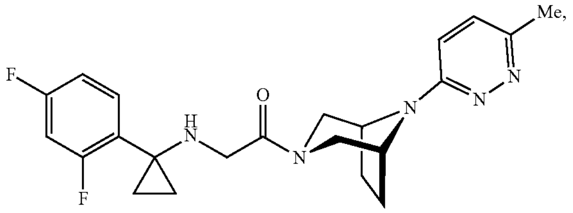
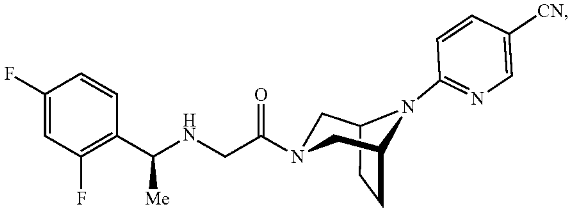
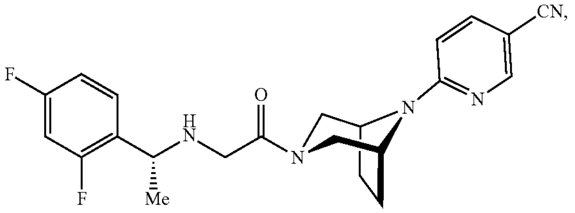
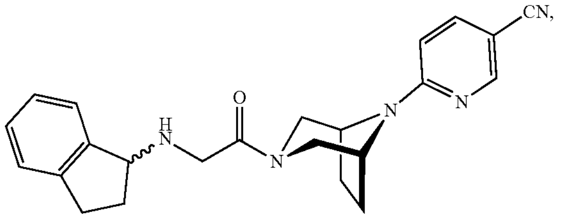
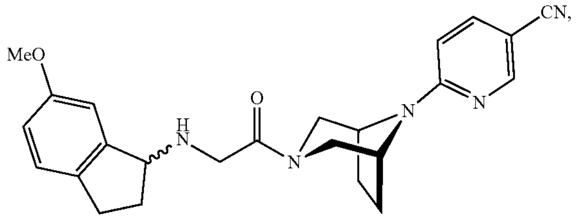
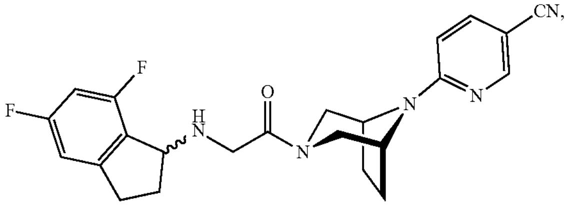
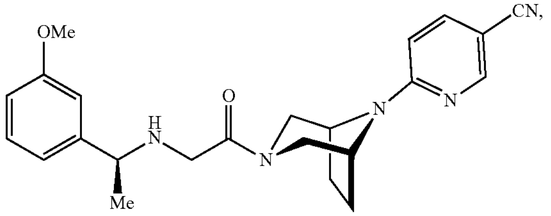
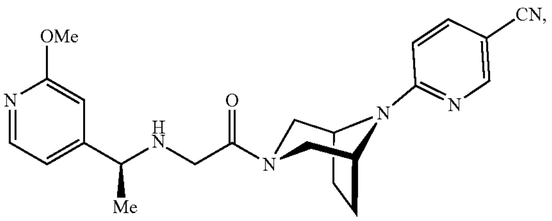

-continued
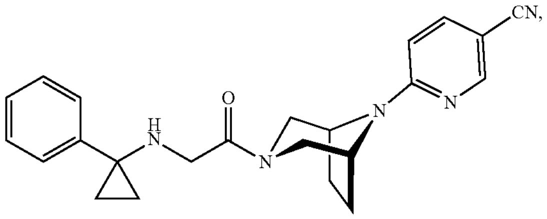
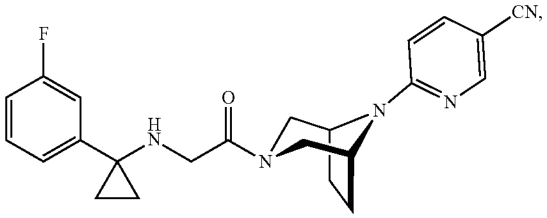
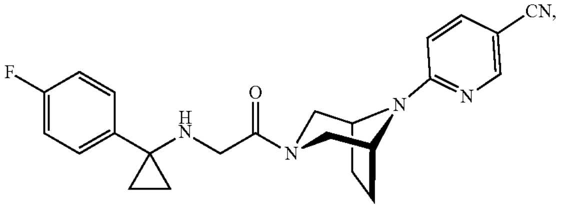
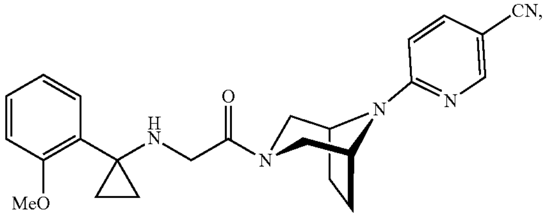
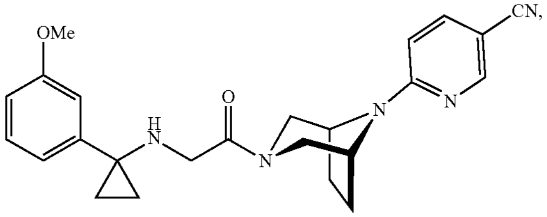
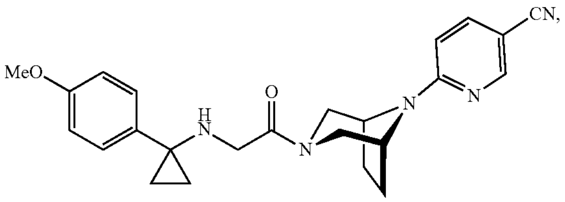
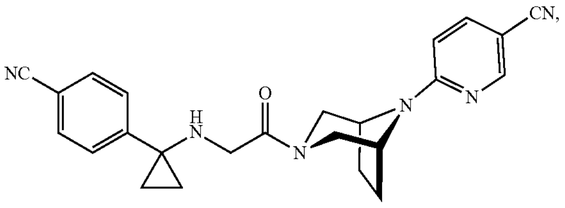
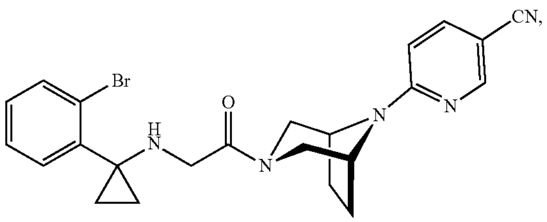
-continued
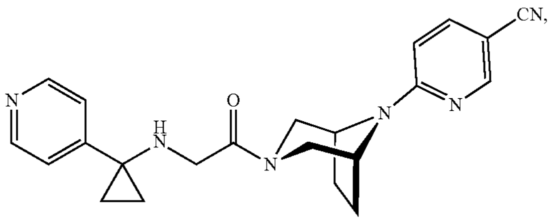
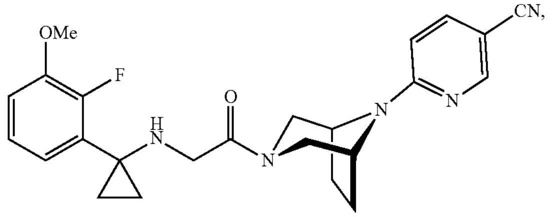
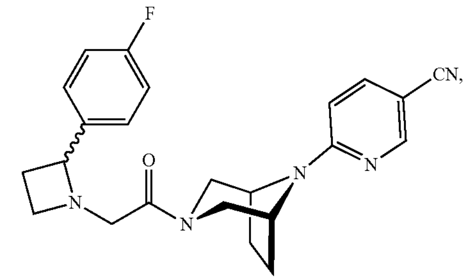
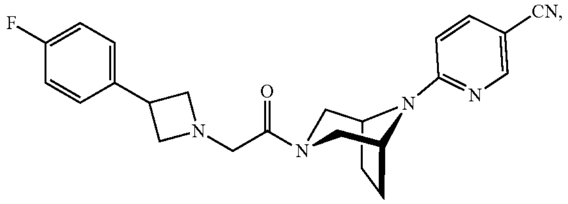
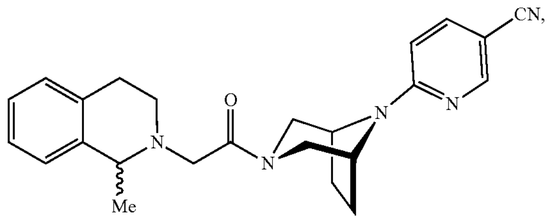
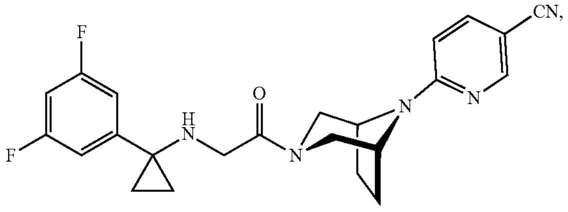
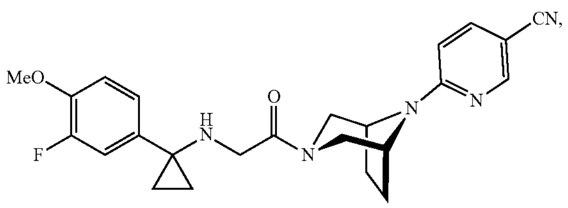

-continued
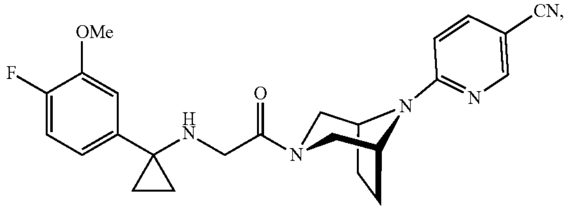
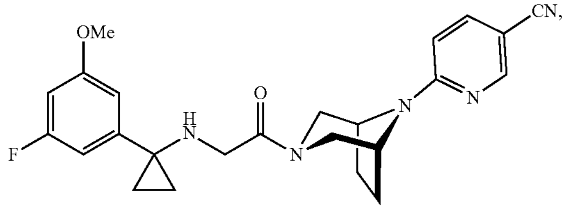
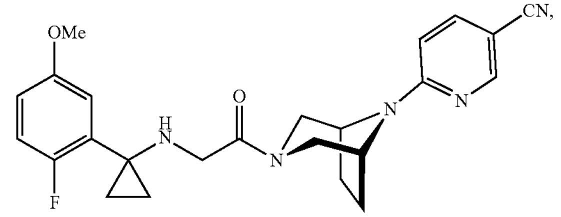
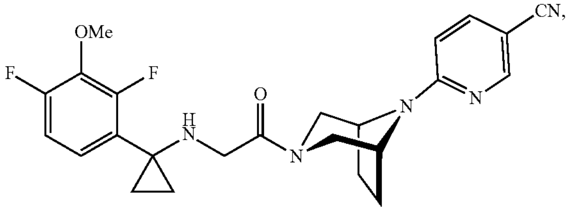
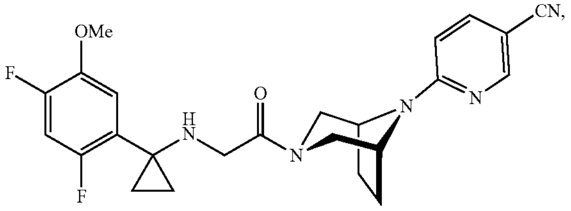
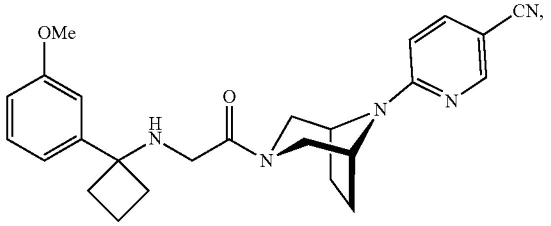
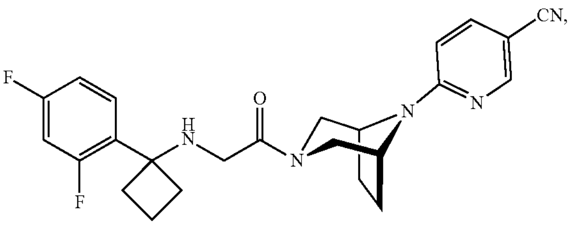
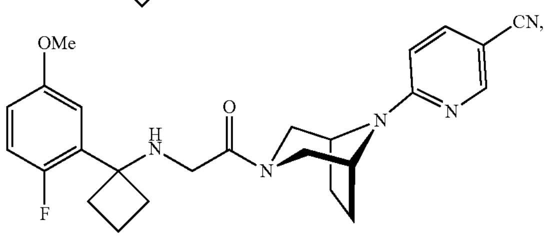
-continued
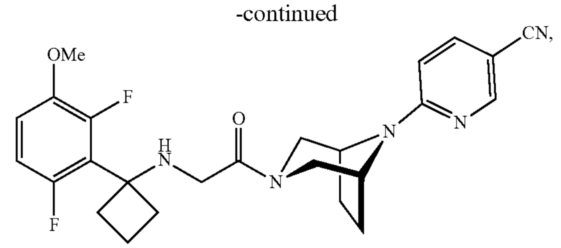
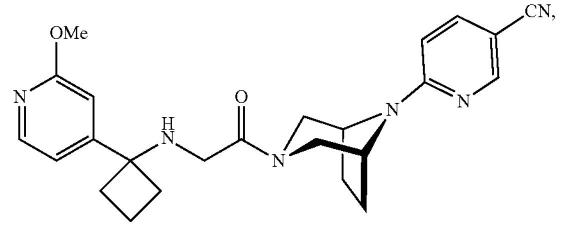
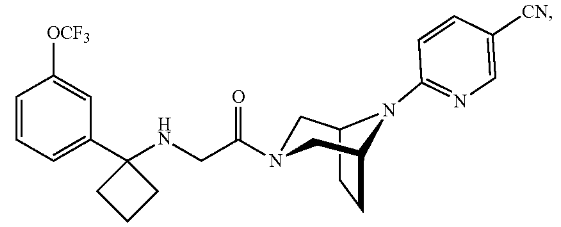
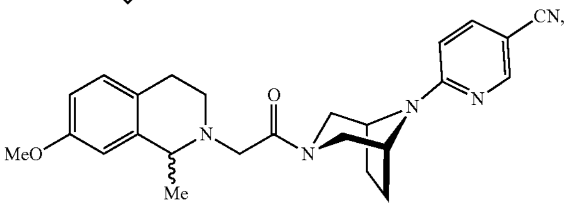
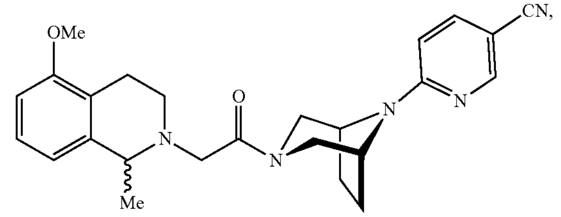
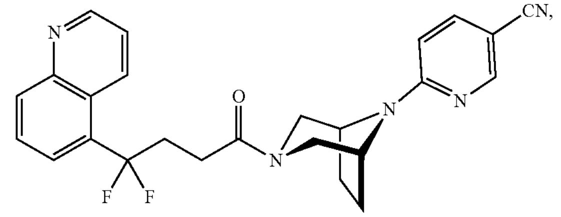
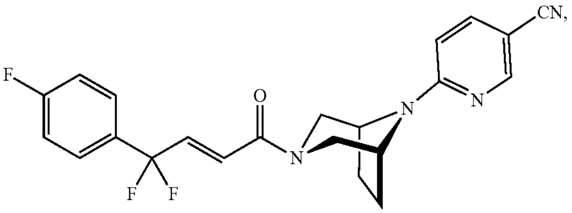
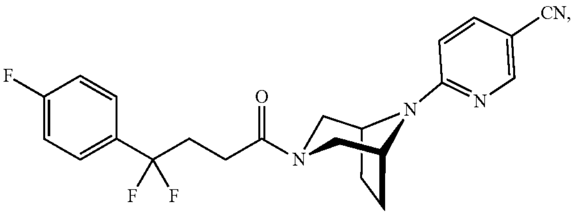

-continued
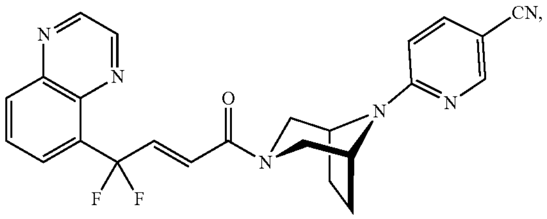
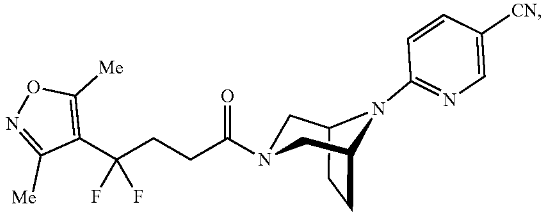
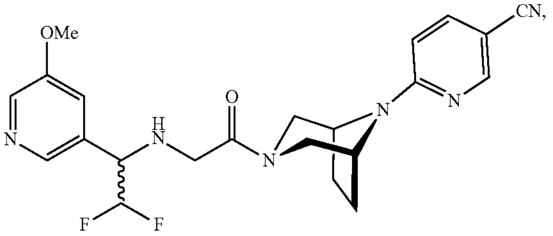
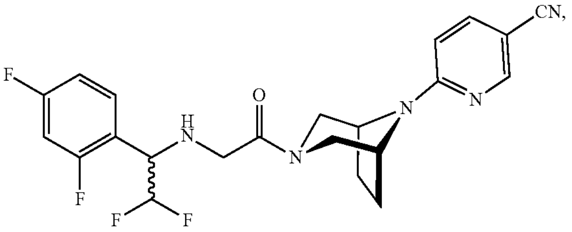
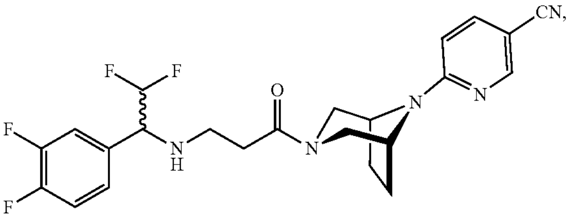
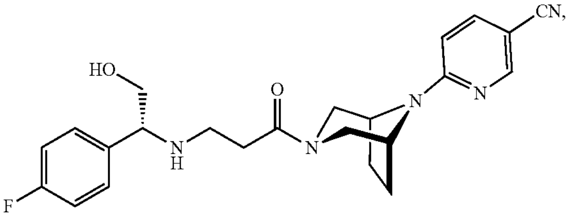
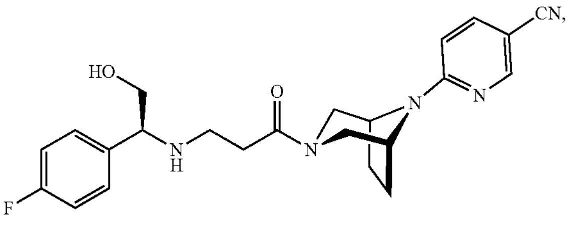
-continued
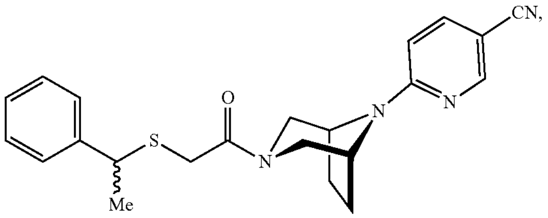
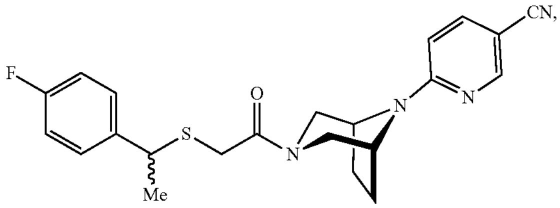
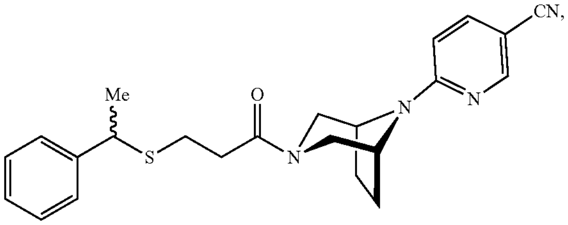
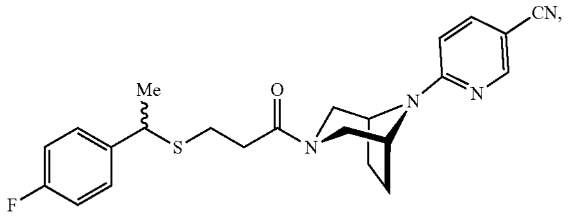
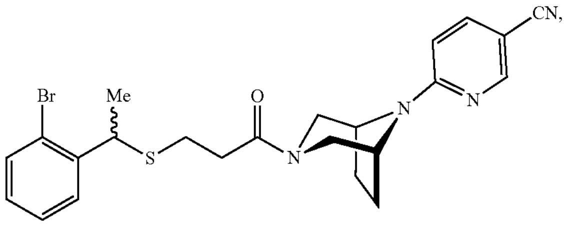
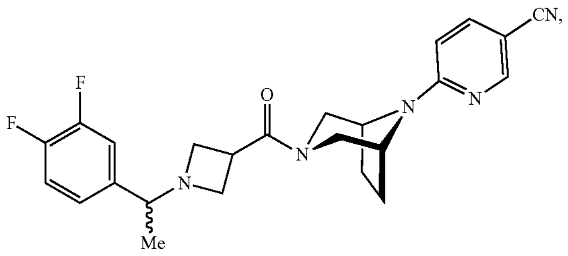
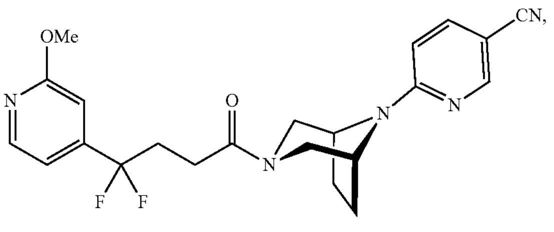

-continued
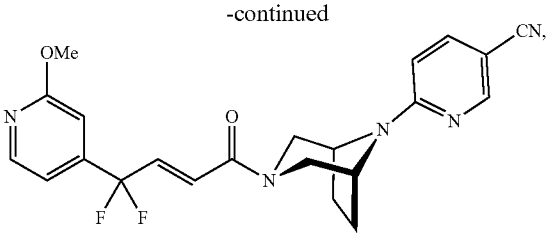
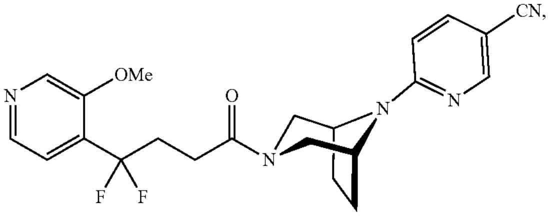
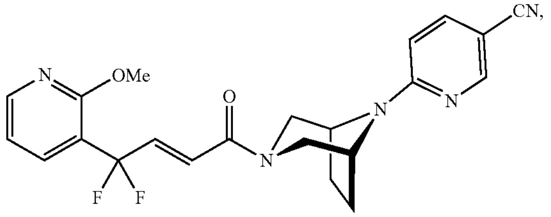
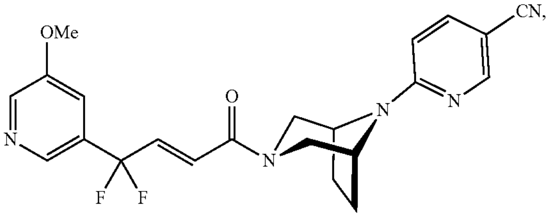
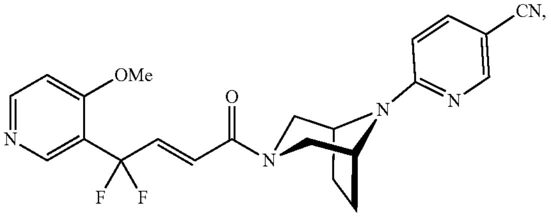
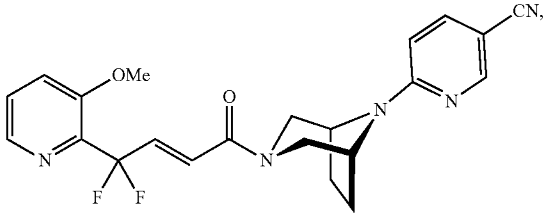
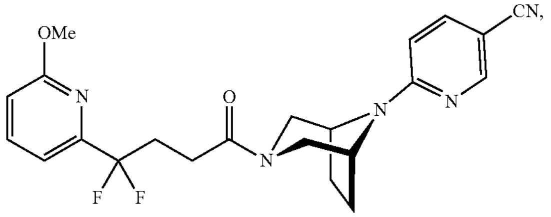
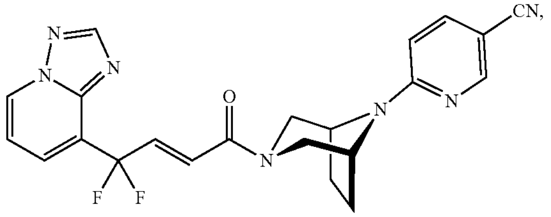
-continued
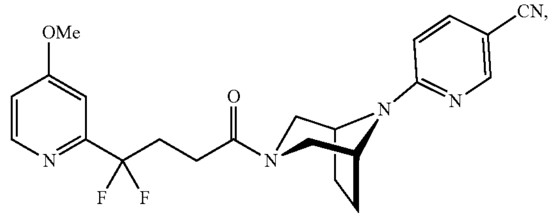
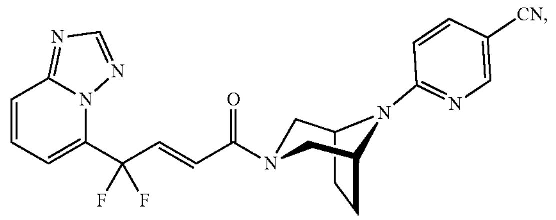
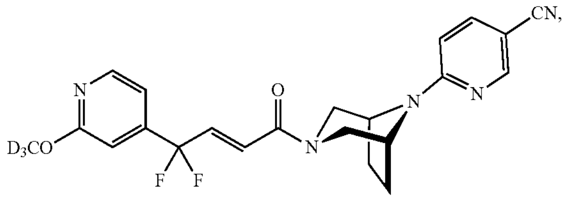
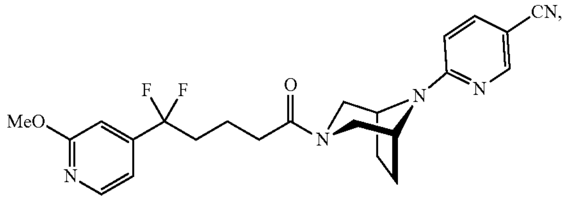
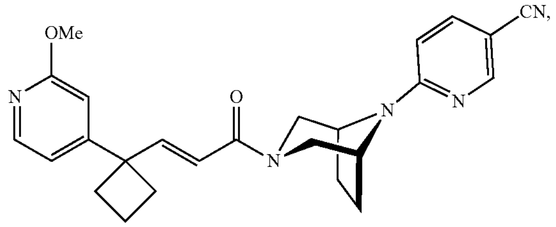
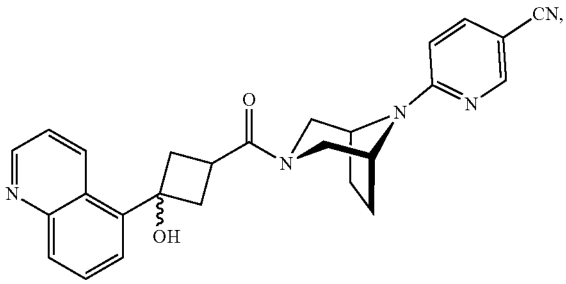
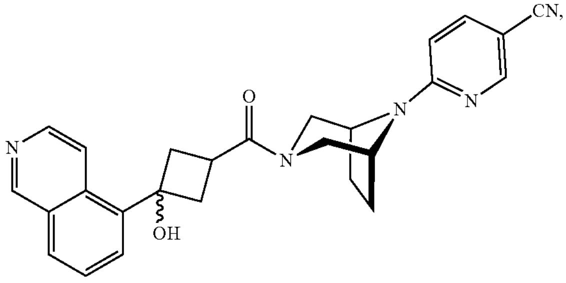

-continued
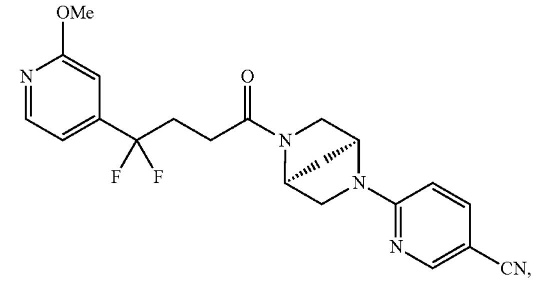,
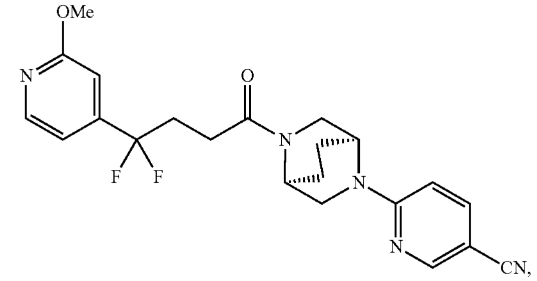,
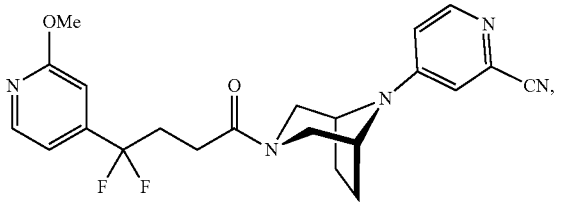,
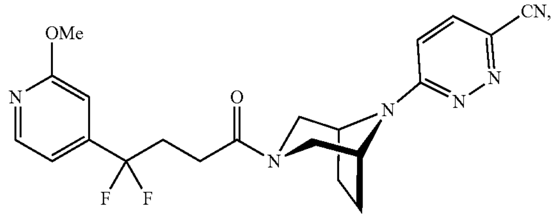,
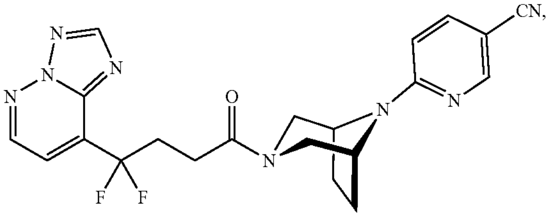,
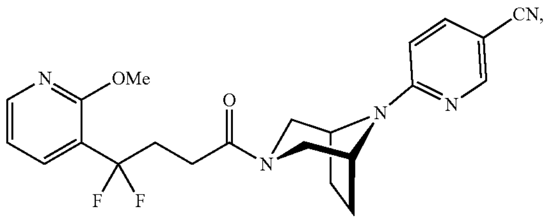,
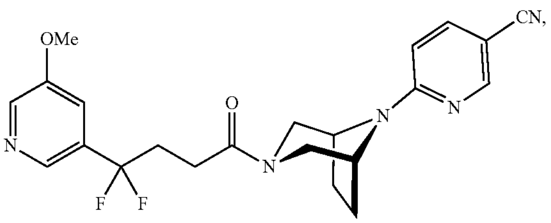,
-continued
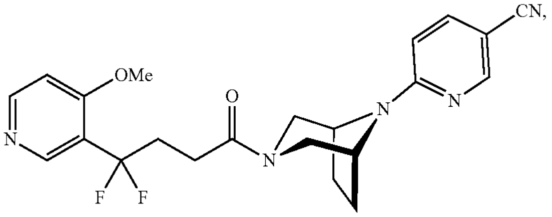,
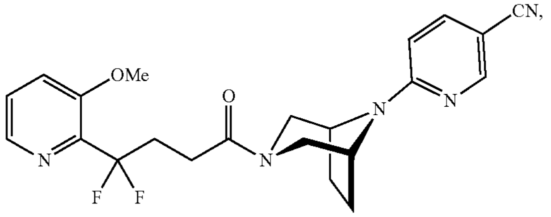,
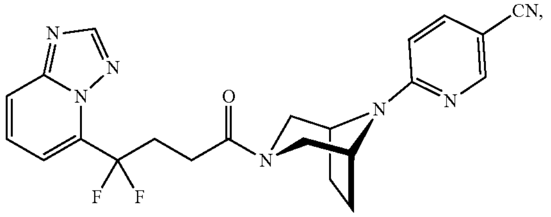,
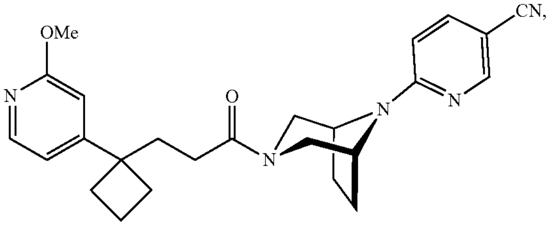,
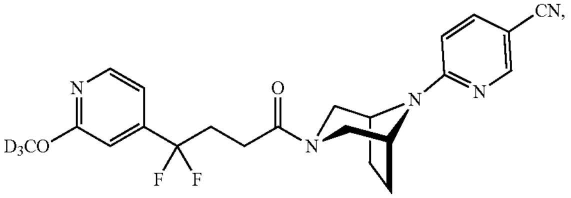,
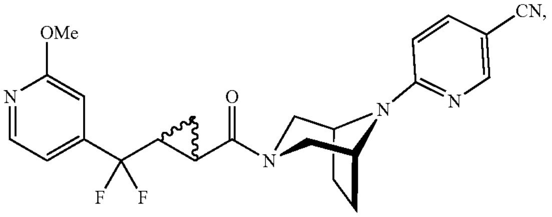,
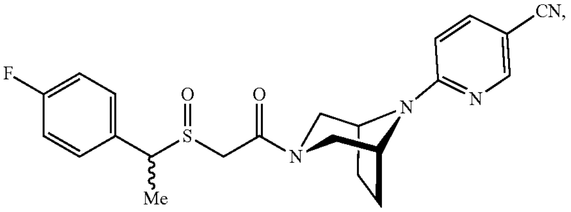,
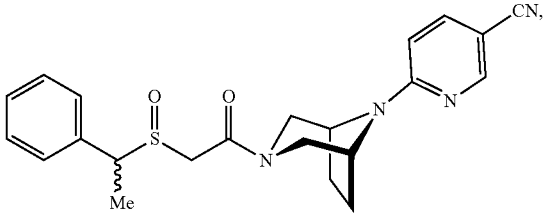, -continued
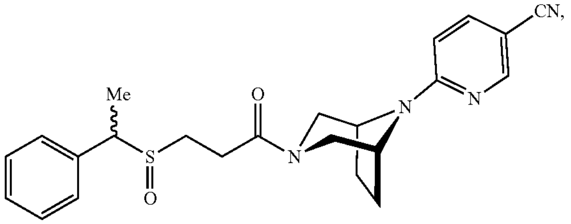
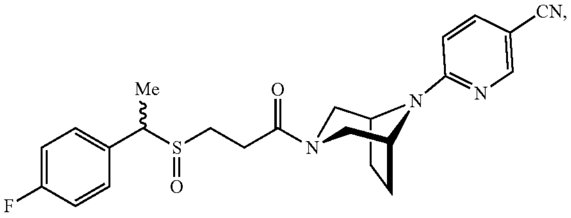
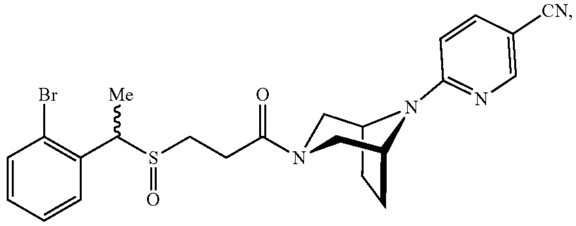
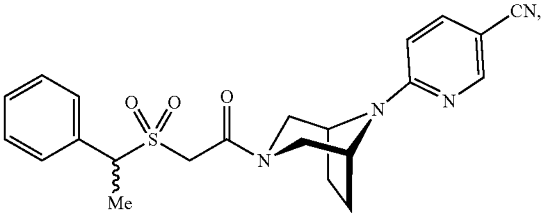
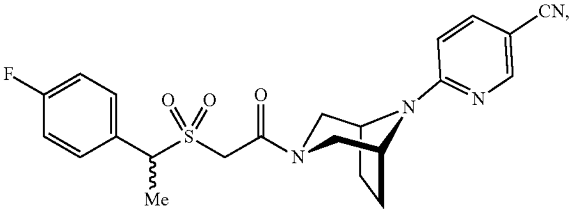
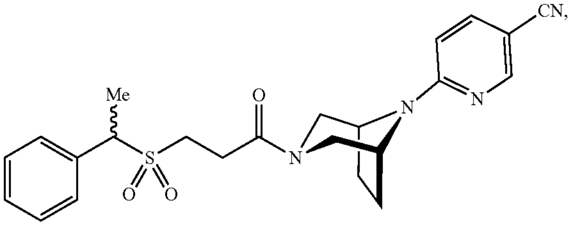
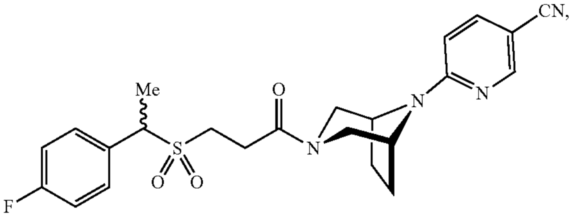
-continued
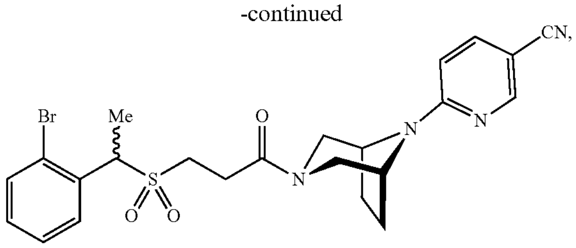
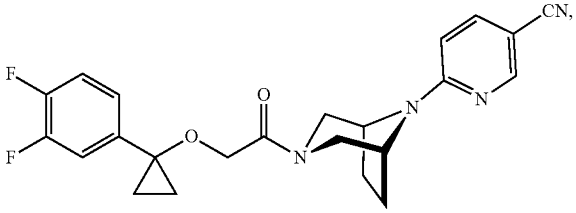
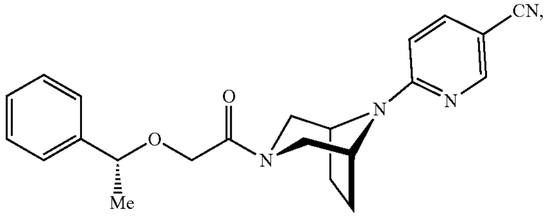
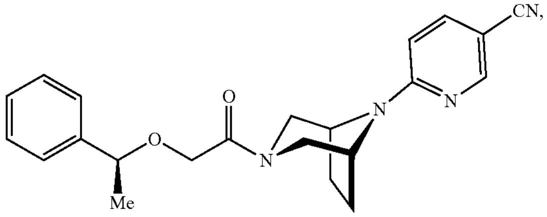
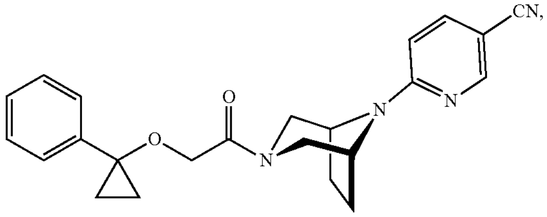
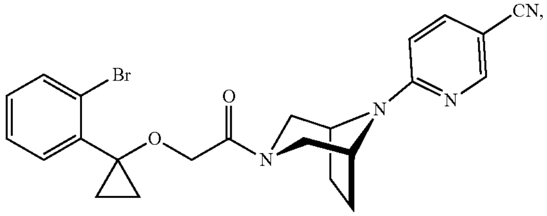
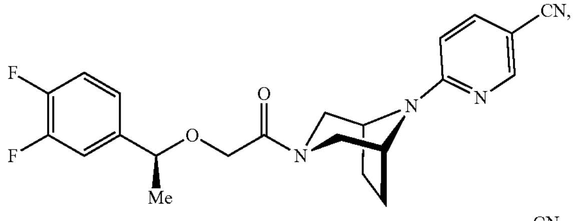
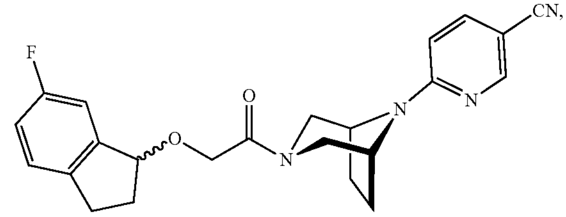

-continued
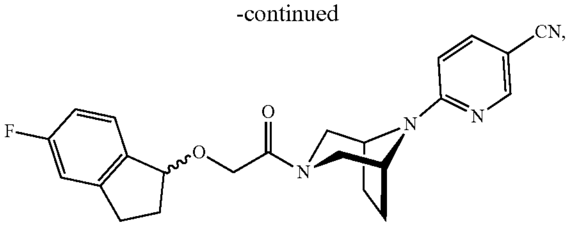
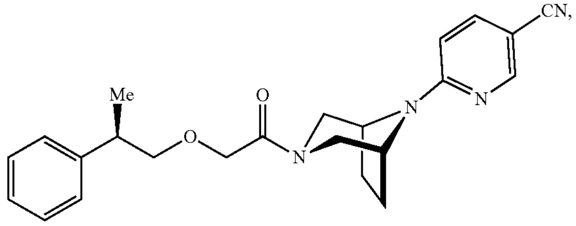
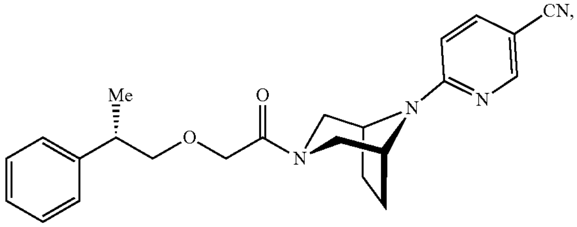
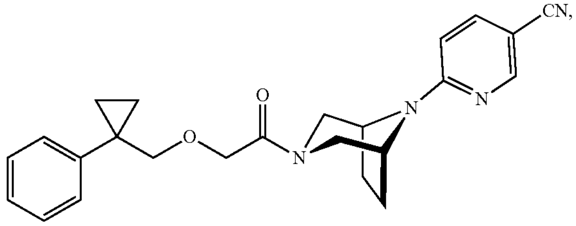
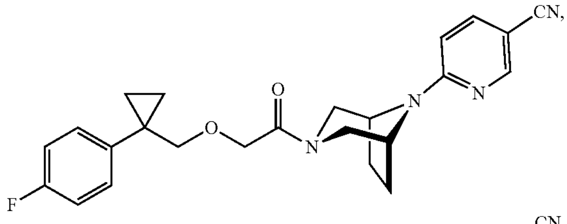
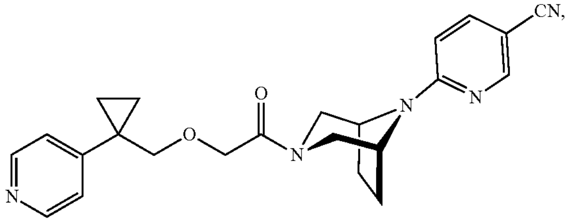
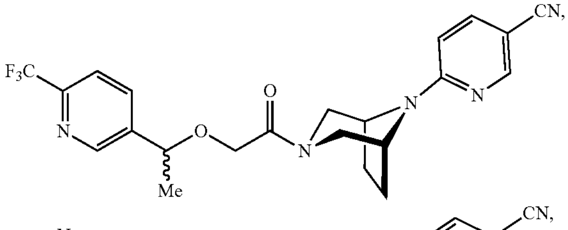
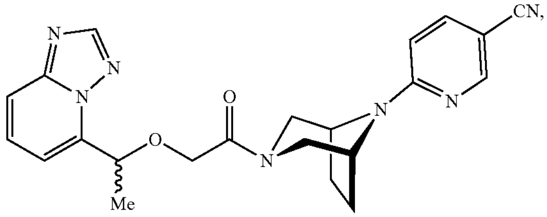
-continued
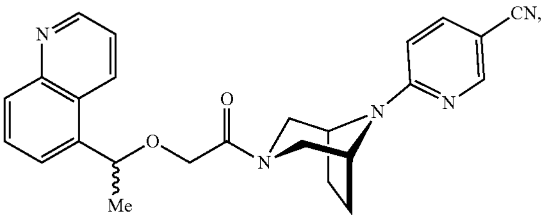
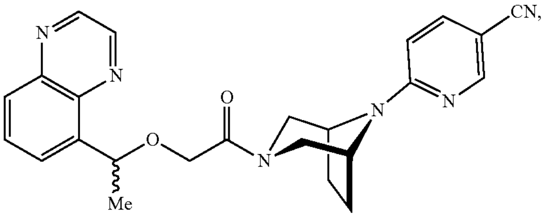
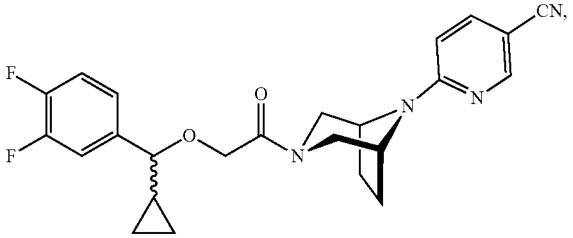
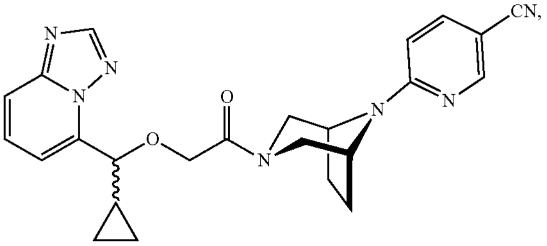
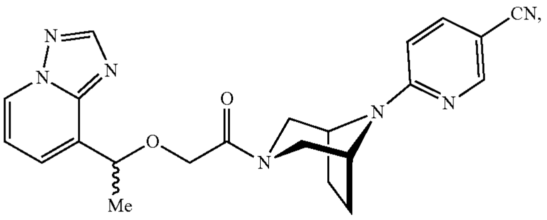
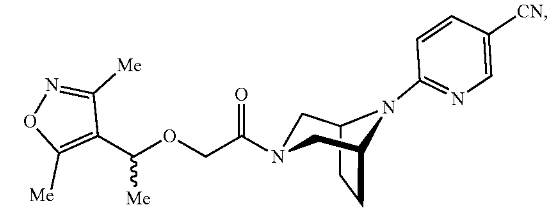
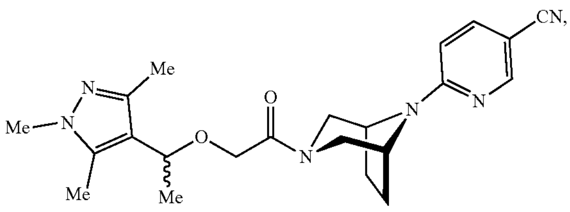

-continued
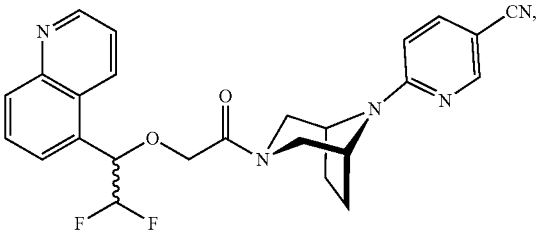
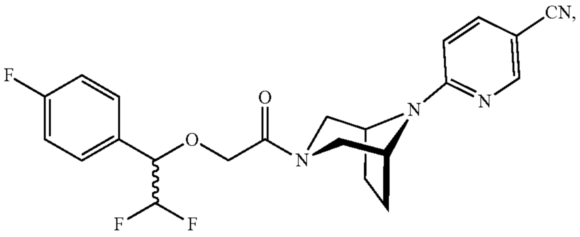
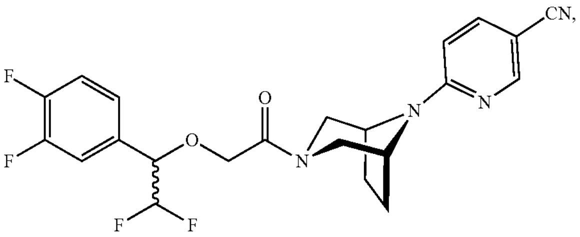
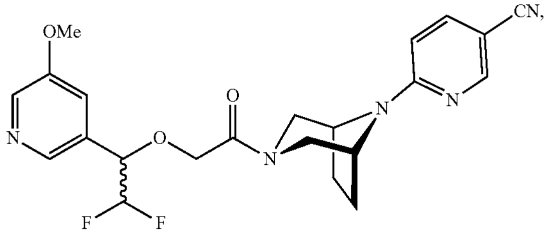
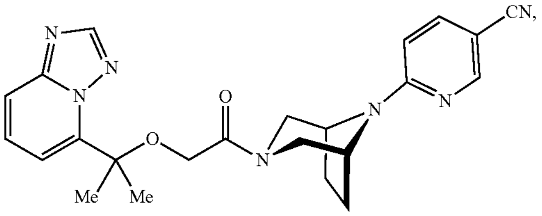
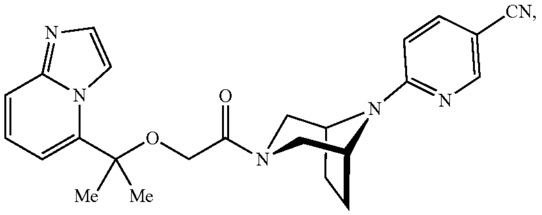
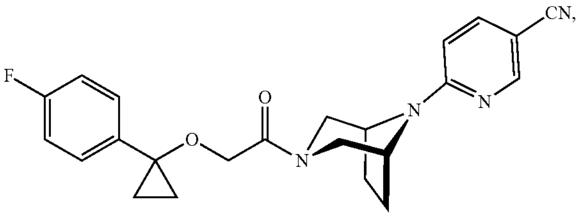
-continued
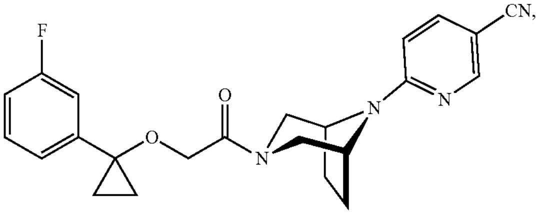
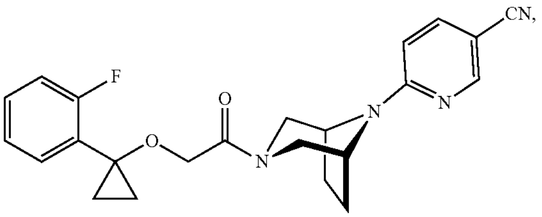
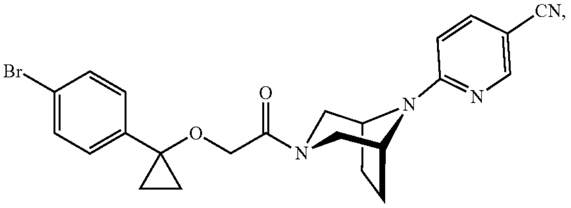
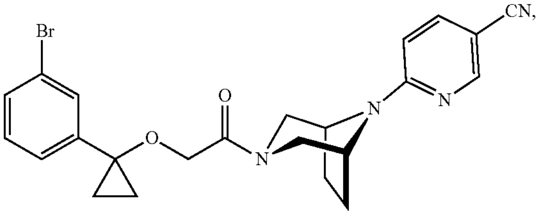
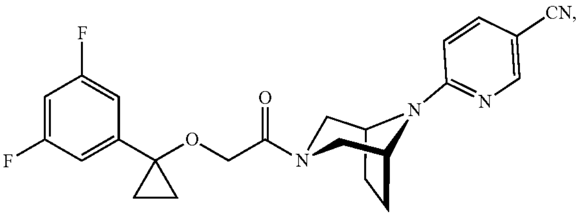
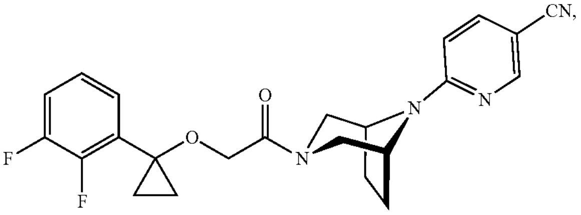
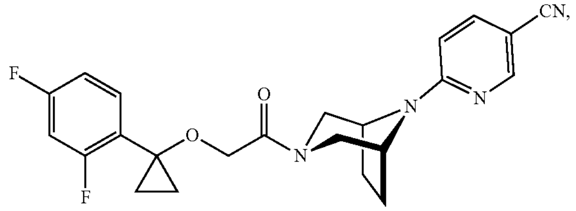
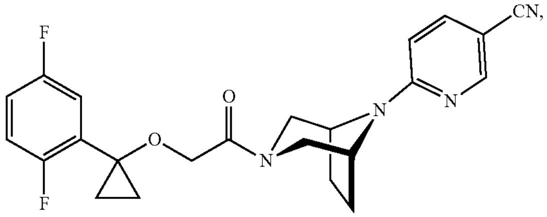

-continued
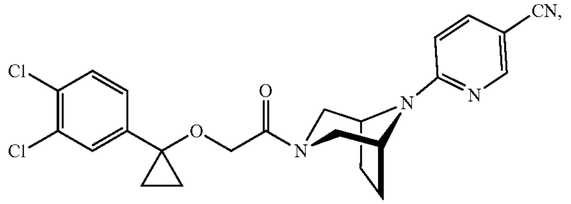
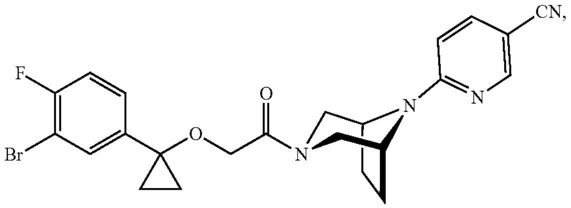
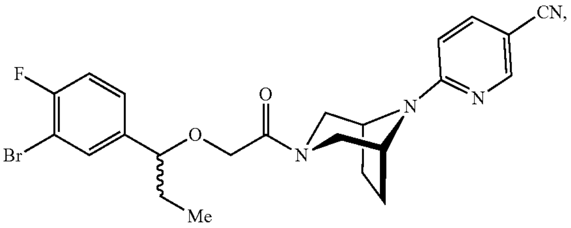
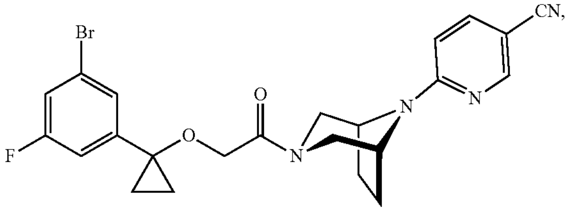
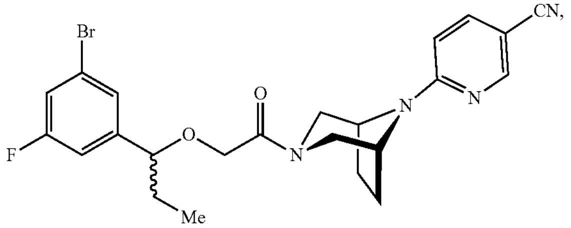
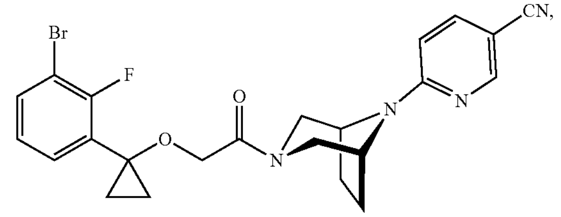
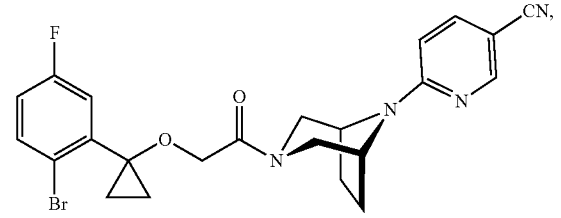
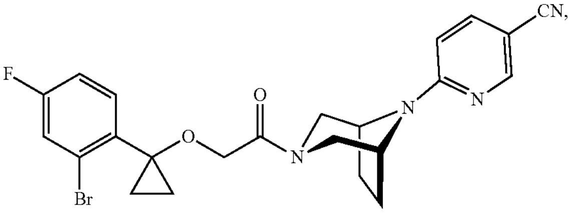
-continued
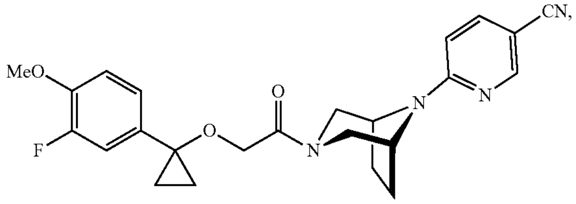
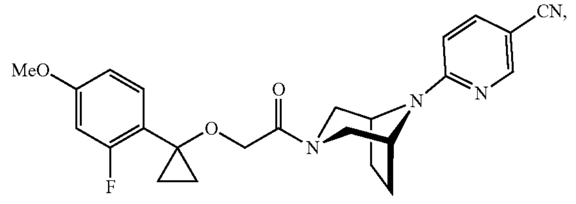
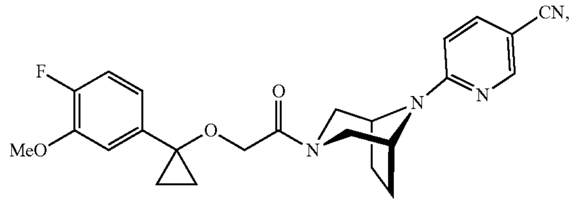
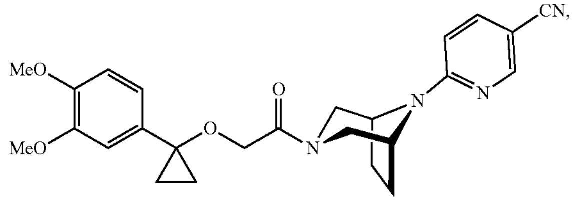
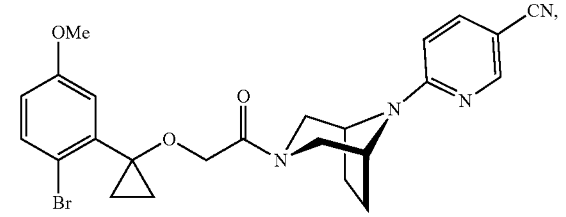
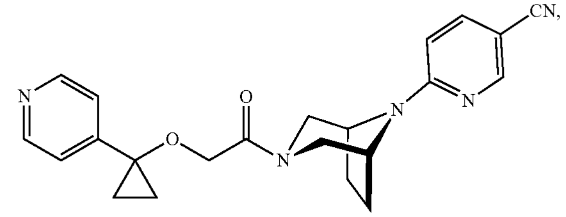
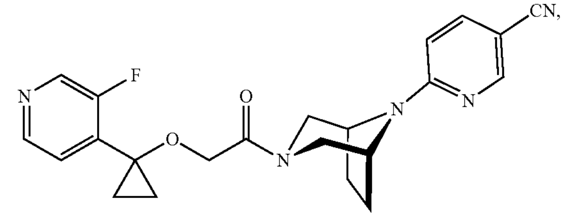
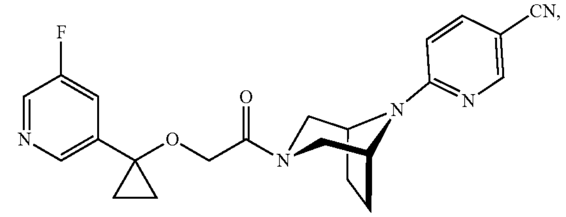

-continued
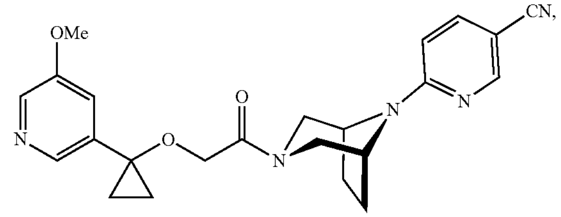
,
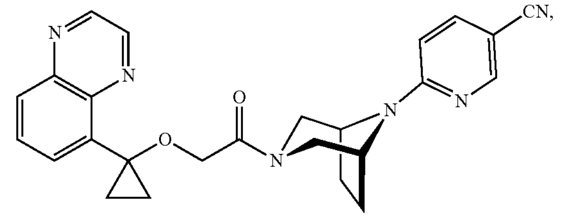
,
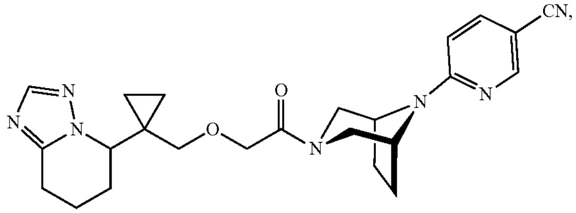
,
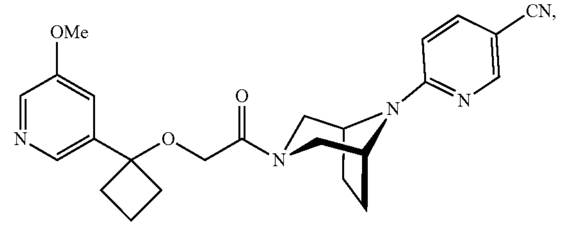
,
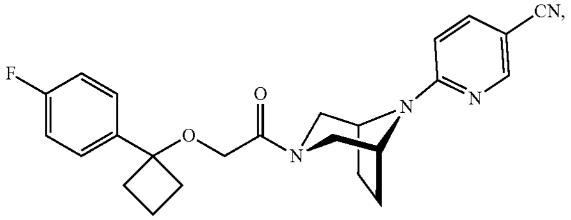
,
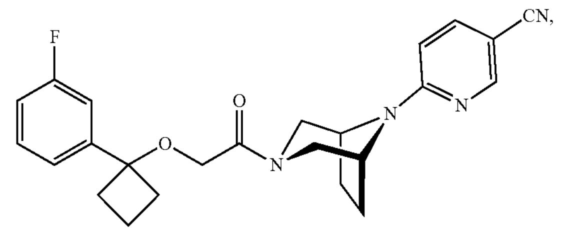
,
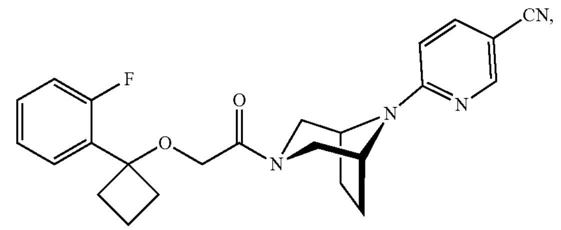
,
-continued
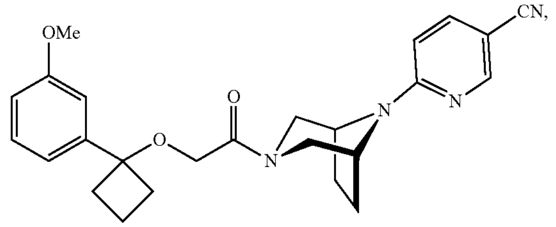
,
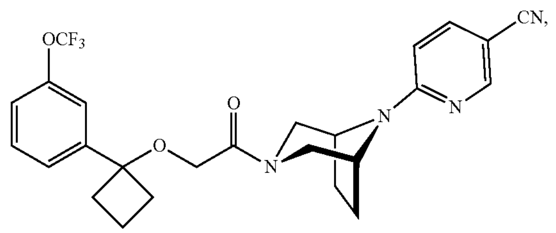
,
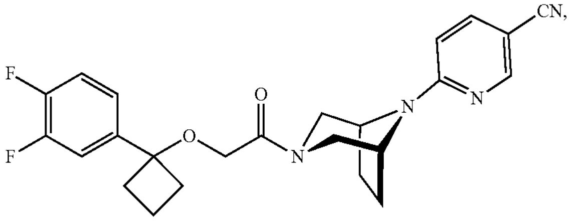
,
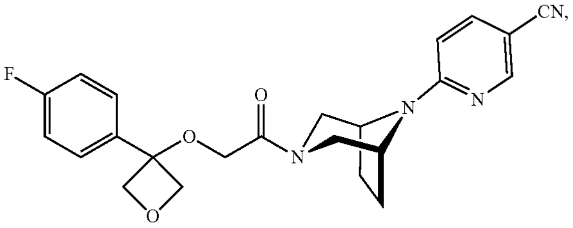
,
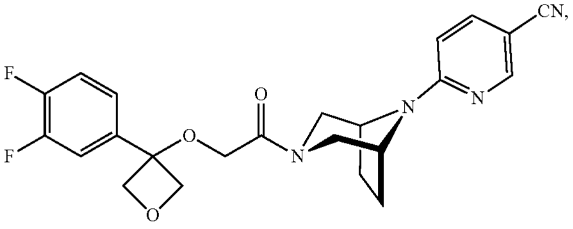
,
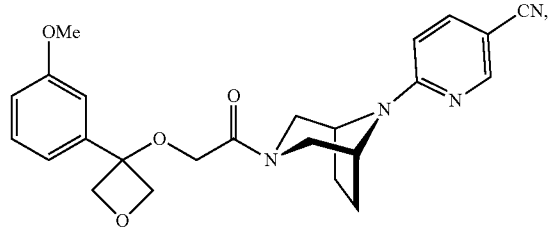
,
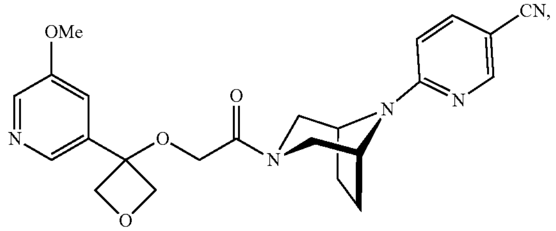
, -continued
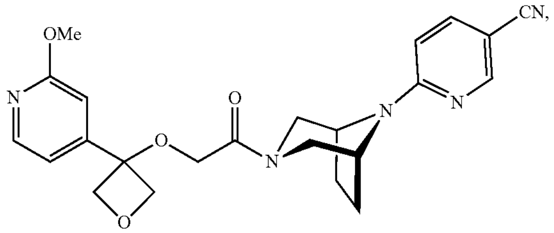
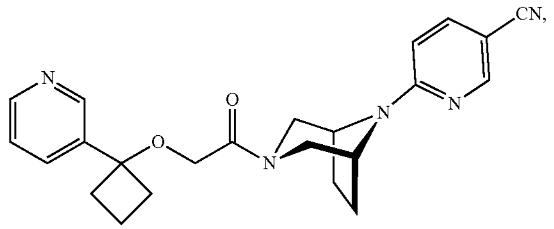
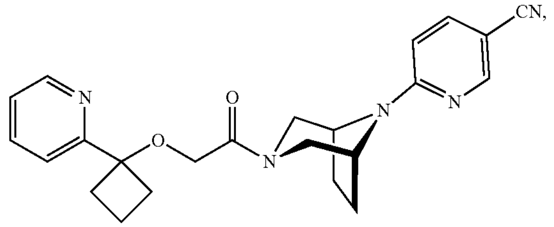
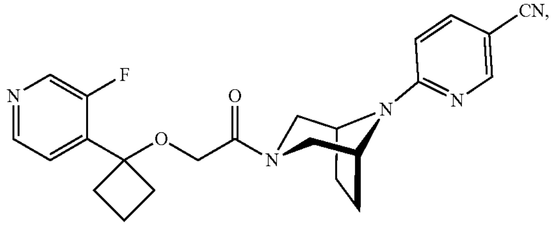
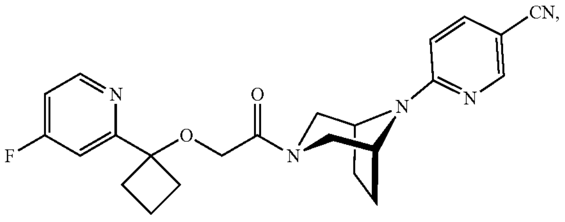
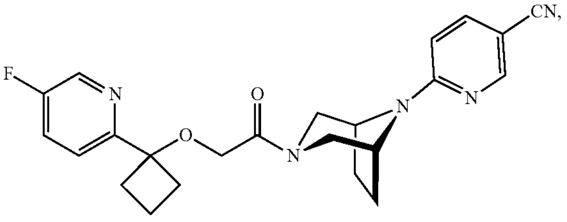
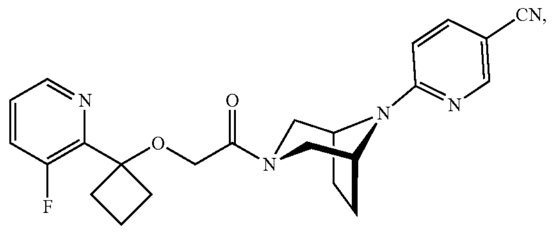
-continued
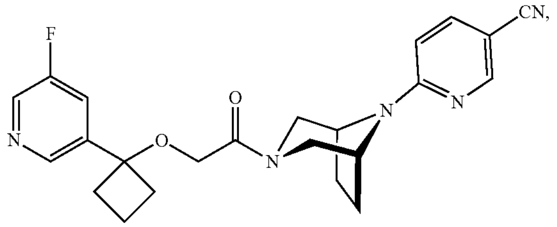
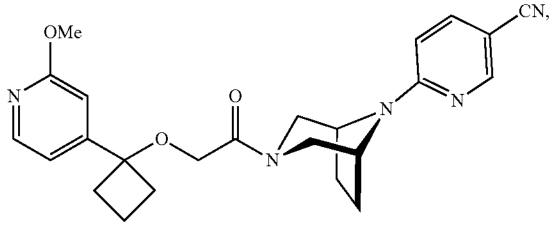
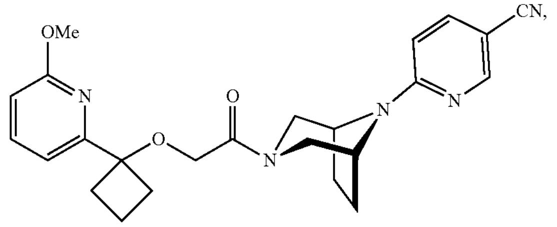
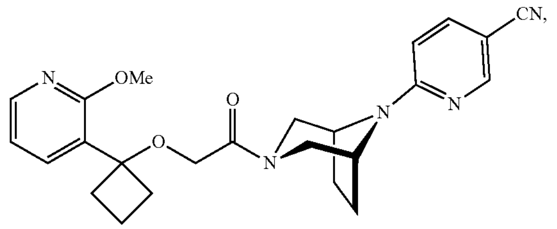
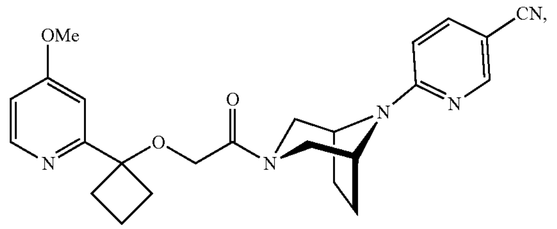
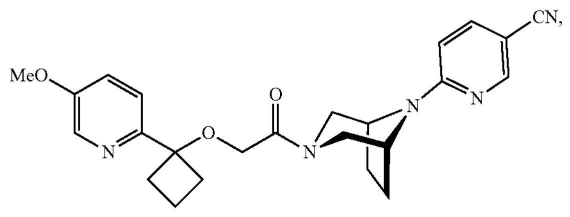
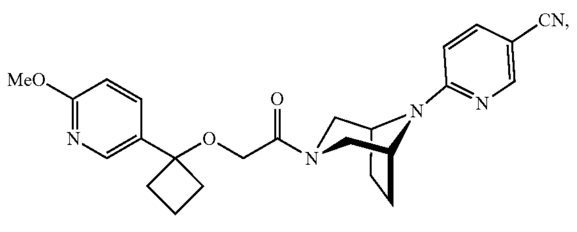

-continued
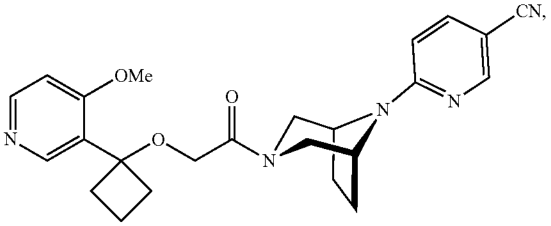
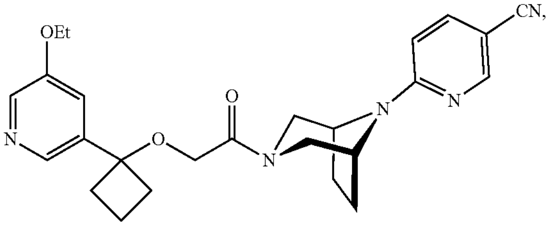
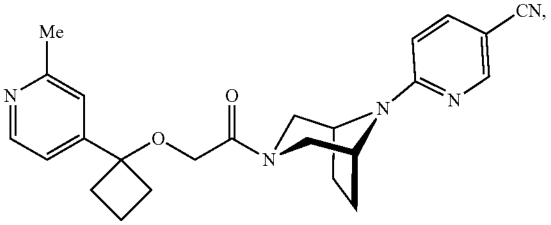
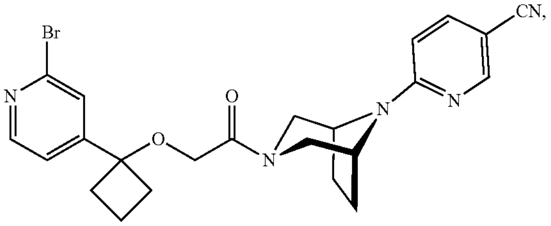
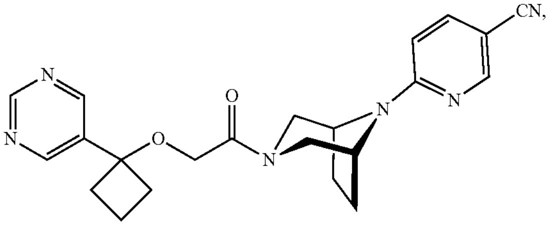
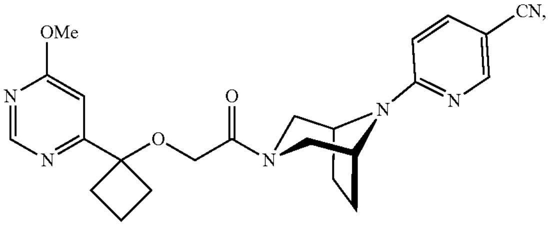
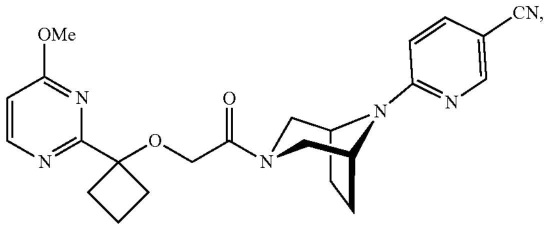
-continued
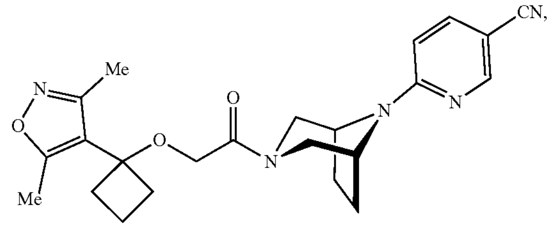
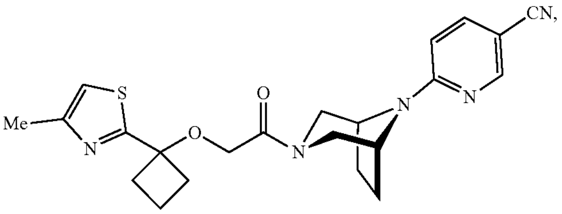
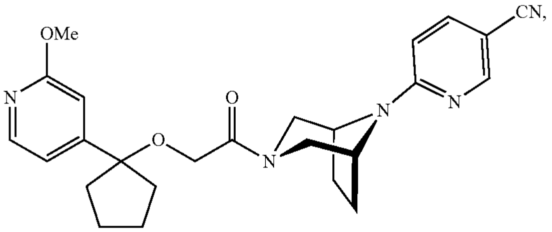
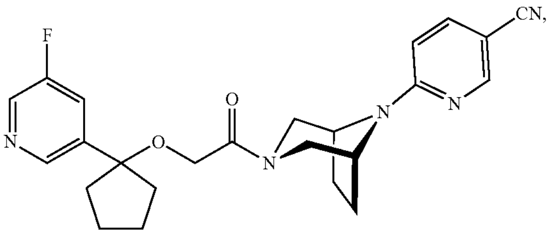
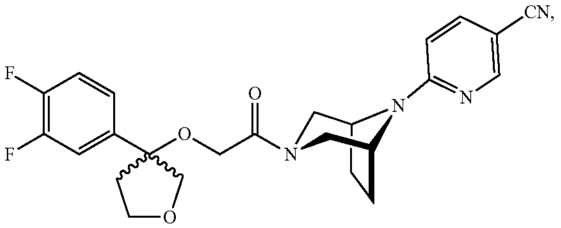
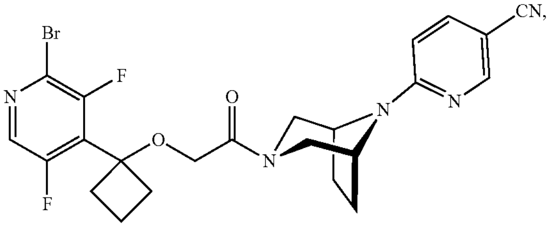
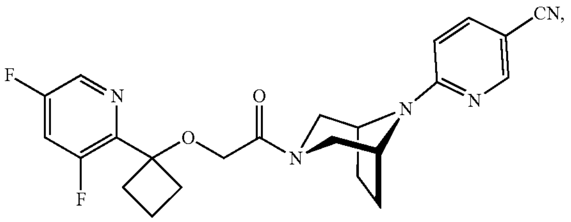

-continued
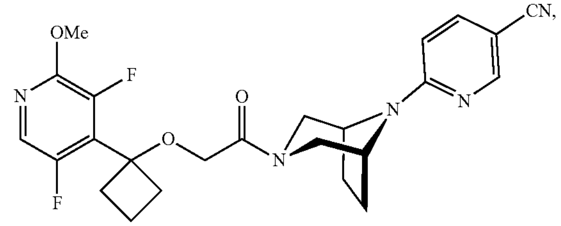
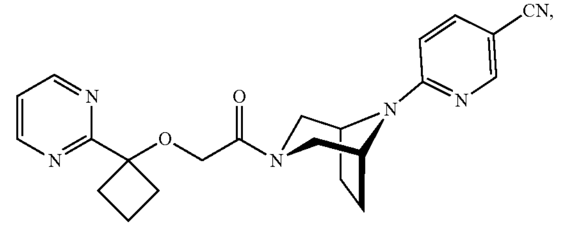
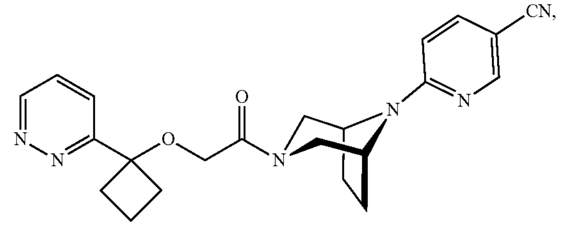
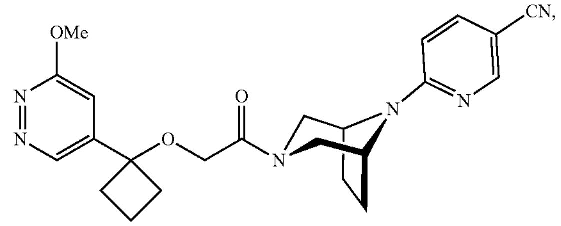
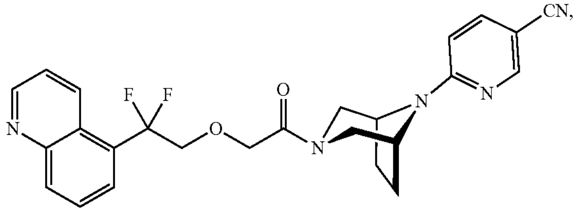
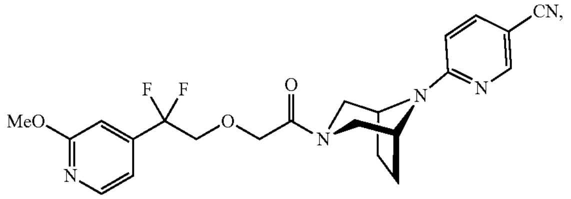
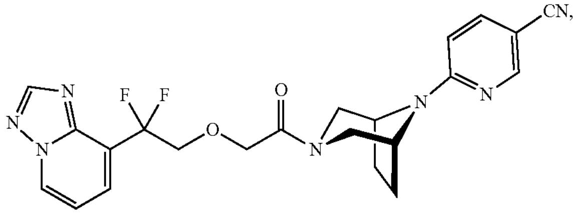
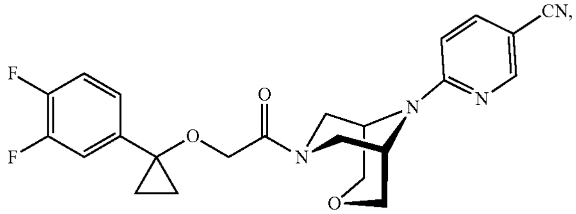
-continued
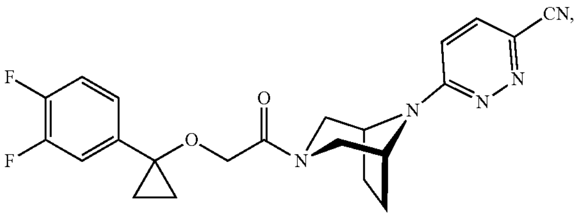
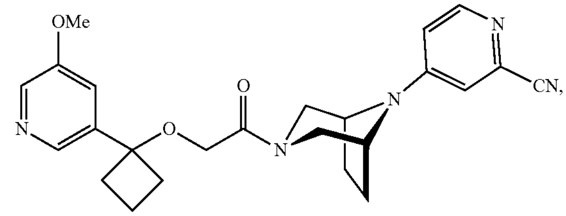
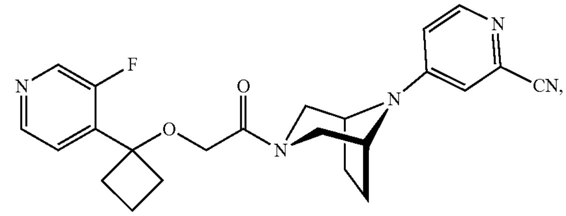
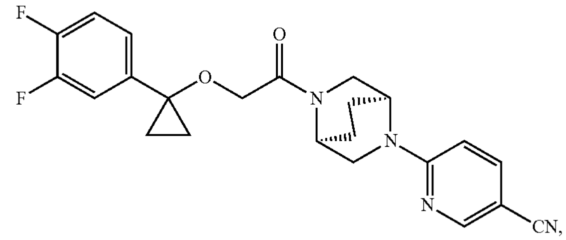
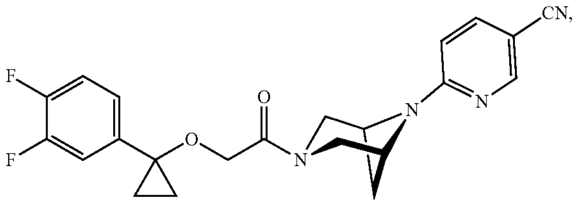
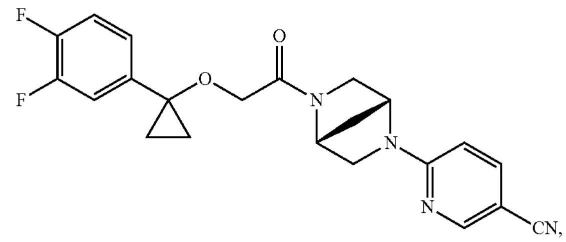
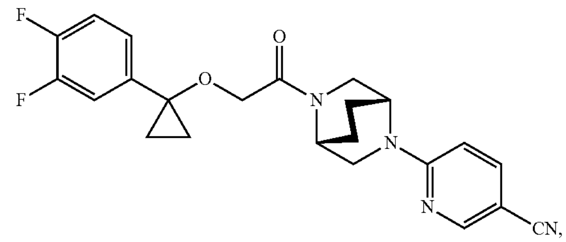

-continued
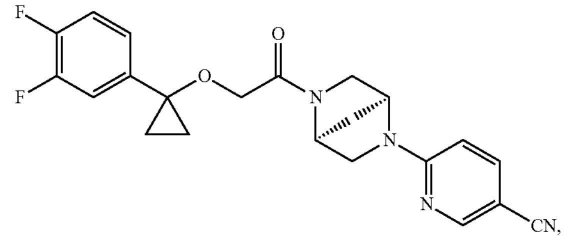
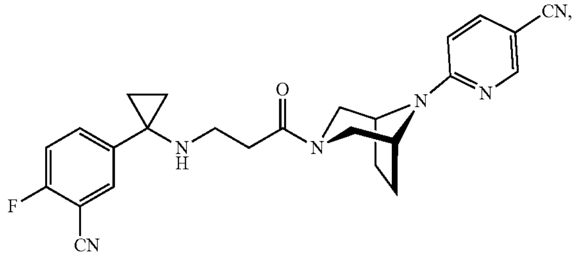
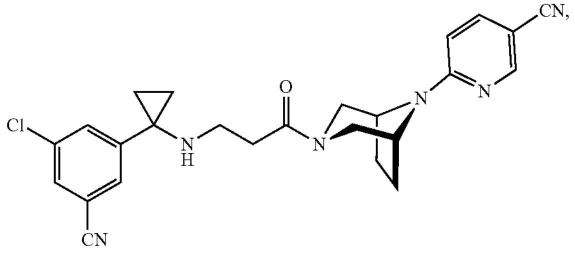
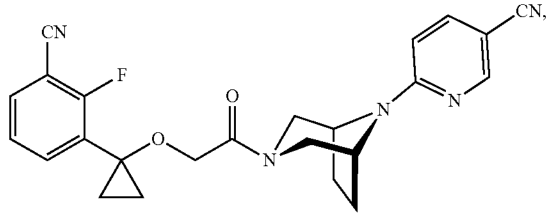
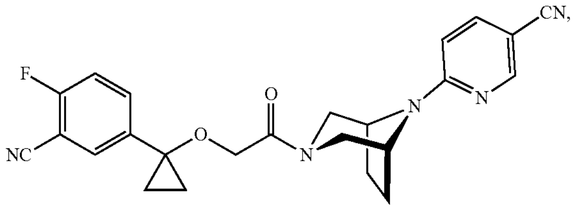
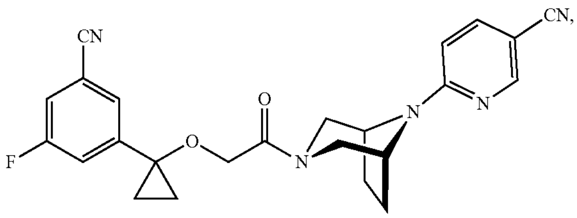
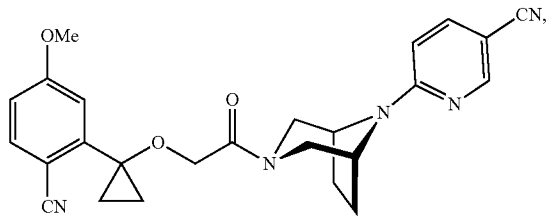
-continued
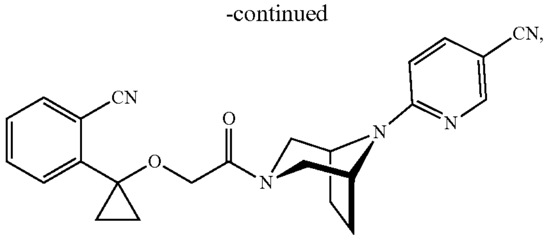
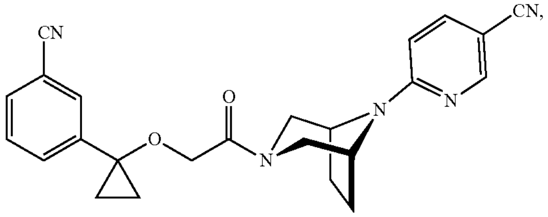
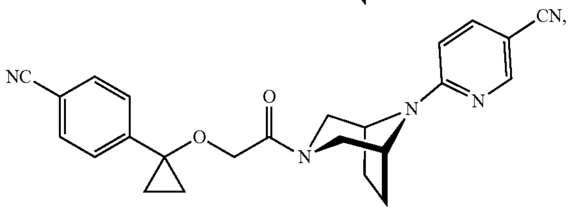
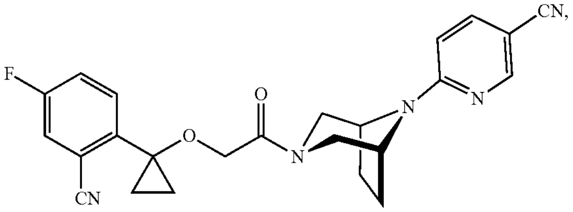
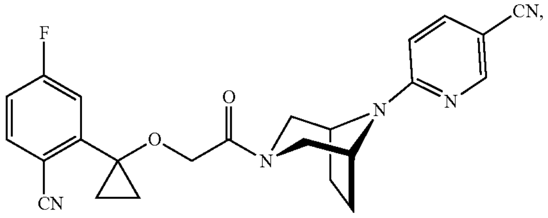
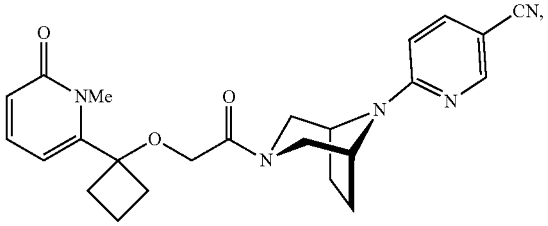
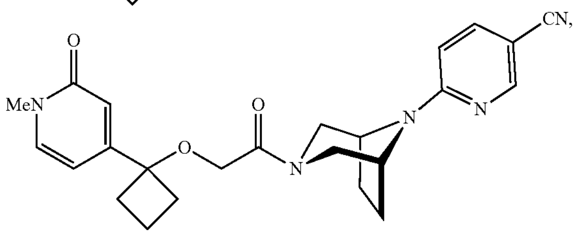
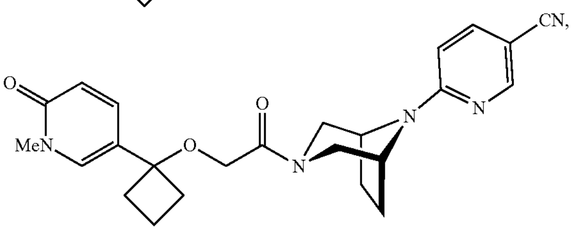

-continued
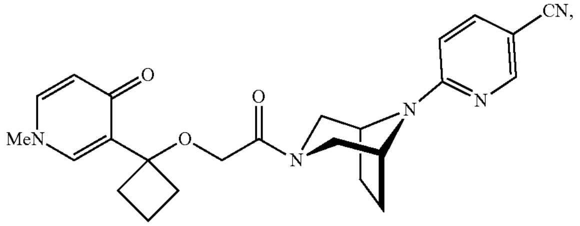
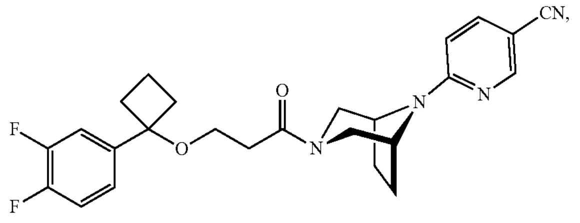
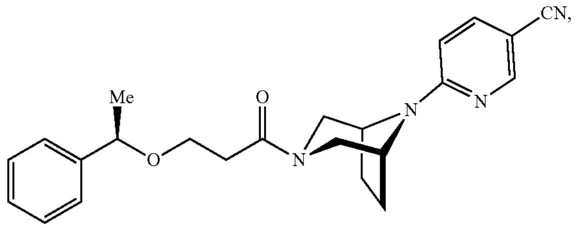
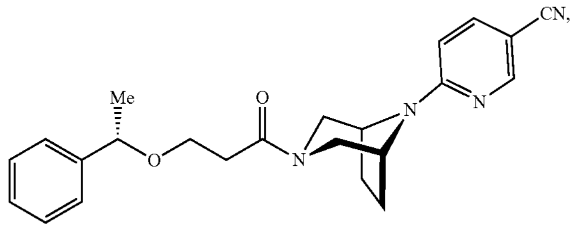
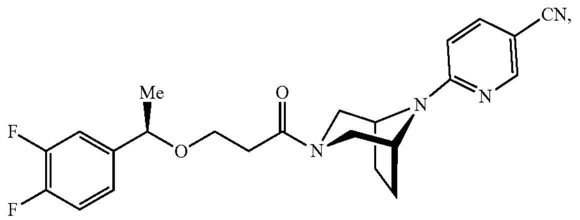
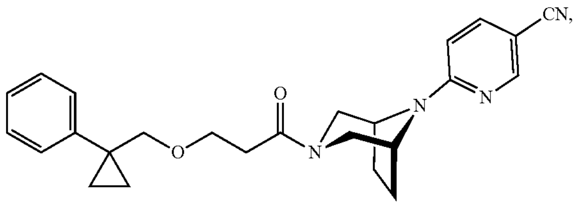
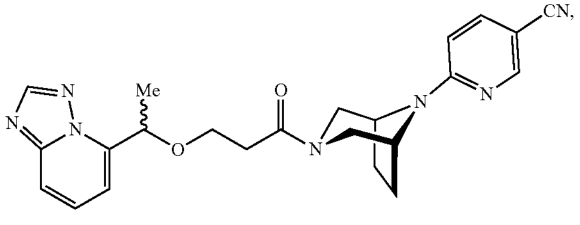
-continued
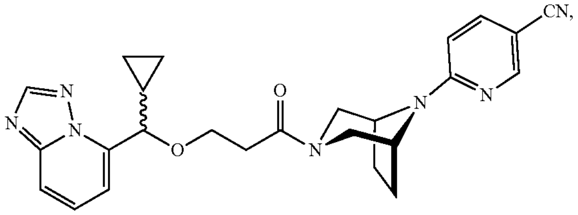
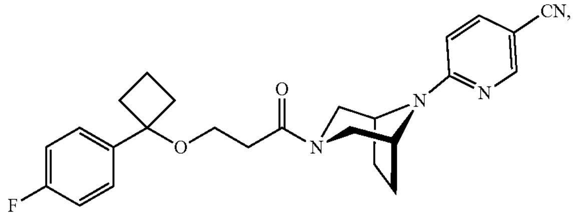
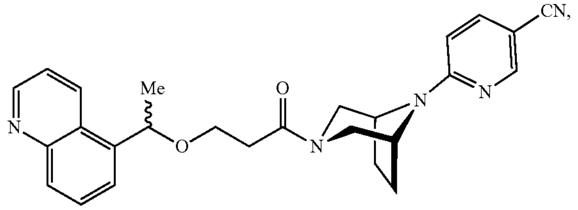
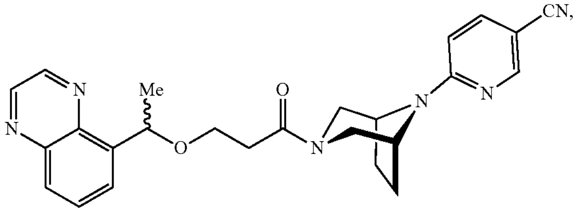
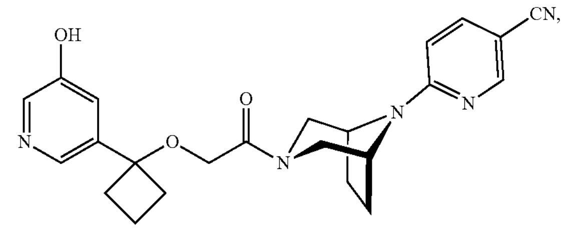
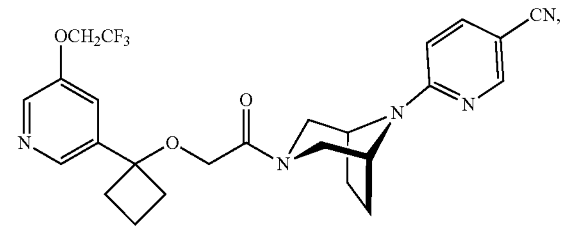
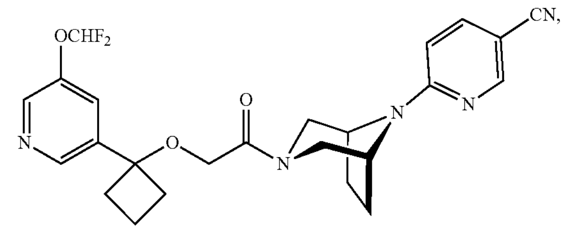

-continued
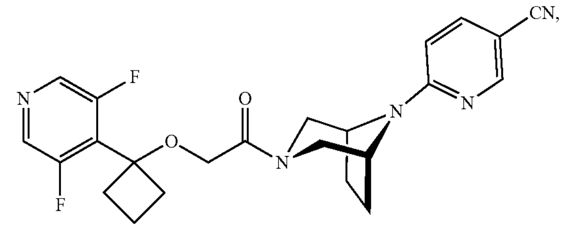
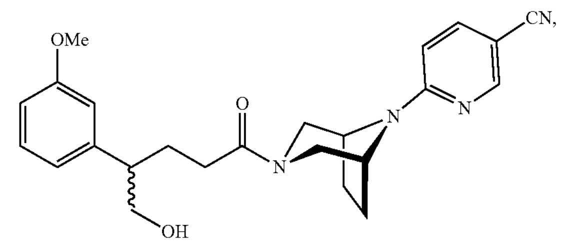
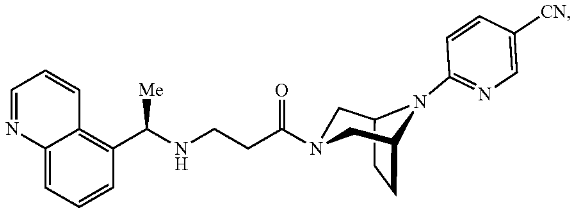
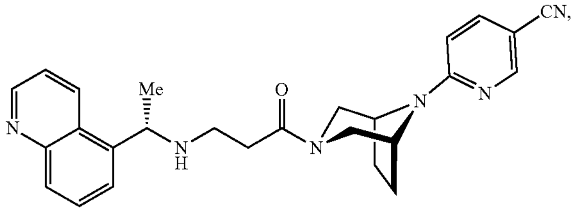
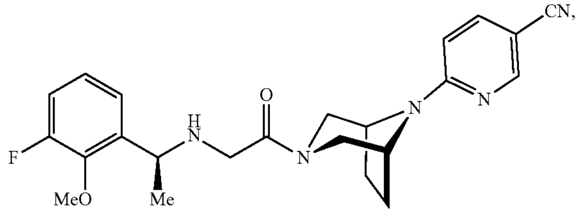
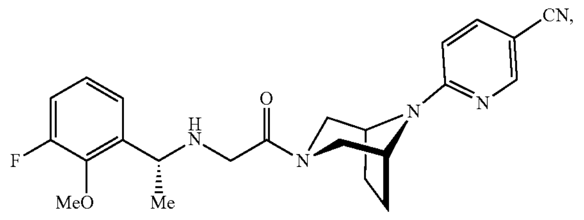
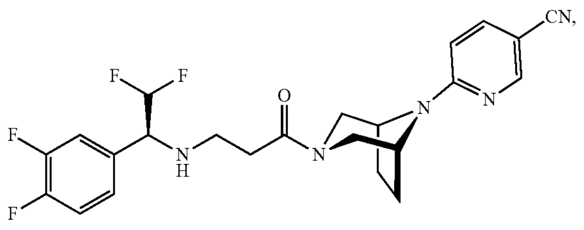
-continued
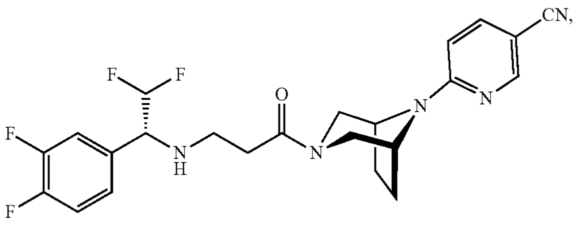
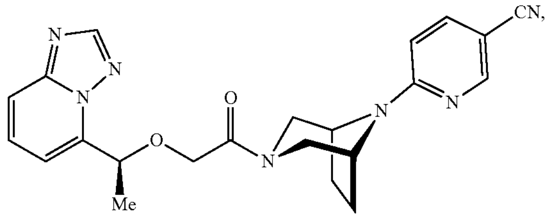
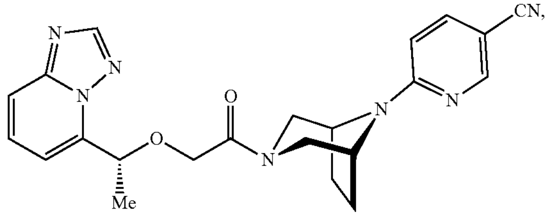
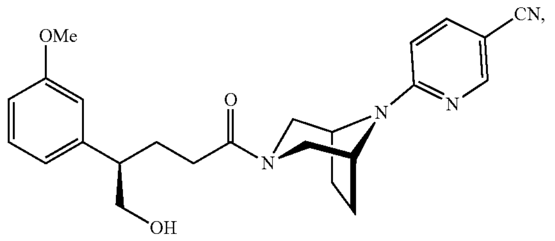
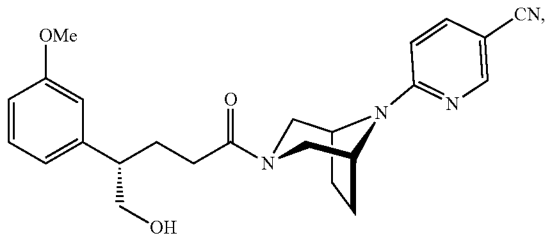
or a pharmaceutically acceptable salt or solvate thereof. The list of compounds immediately preceding this sentence is hereinafter referred to as "Compound List 1".
In embodiments, the compound is
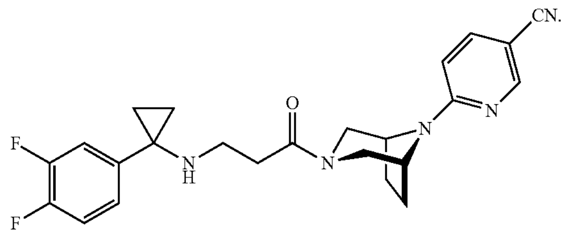

In embodiments, the compound is
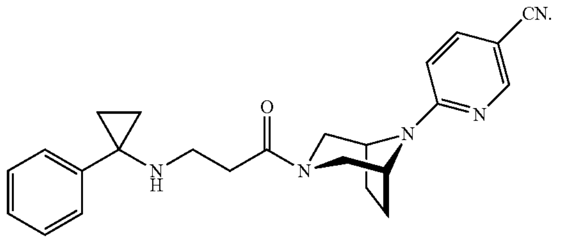
In embodiments, the compound is
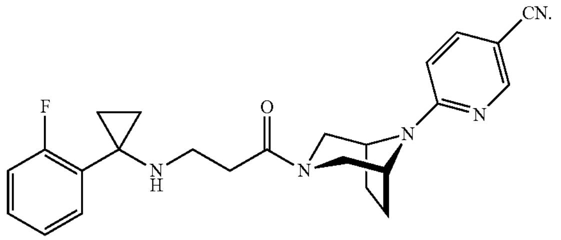
In embodiments, the compound is
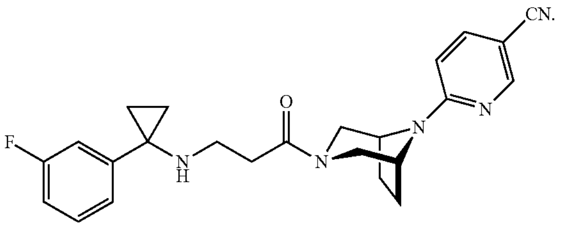
In embodiments, the compound is
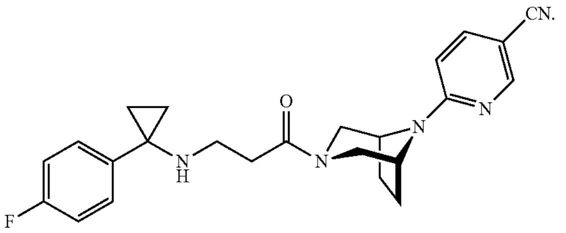
In embodiments, the compound is
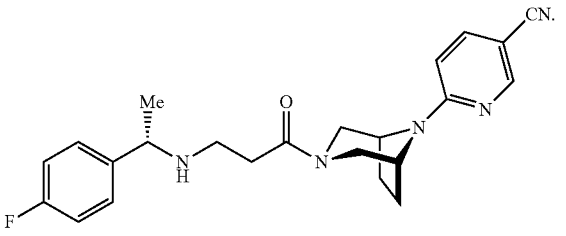
In embodiments, the compound is
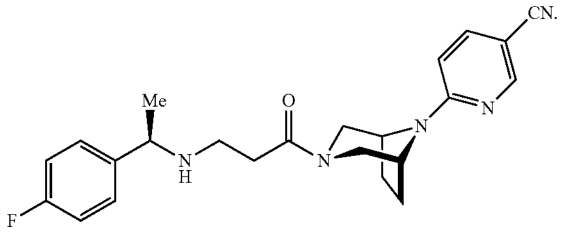
In embodiments, the compound is
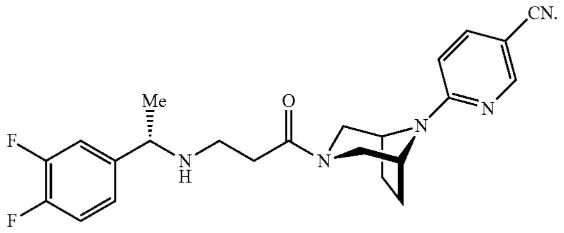
In embodiments, the compound is
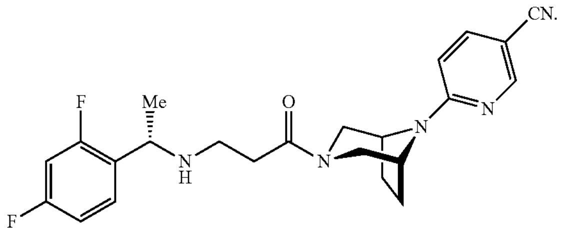
In embodiments, the compound is
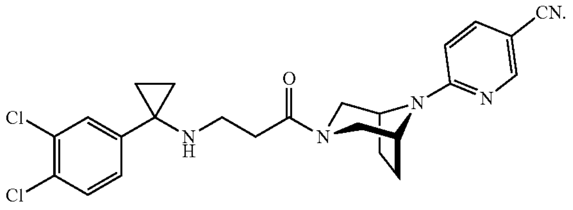
In embodiments, the compound is
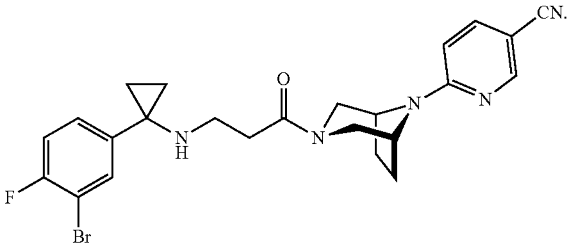

In embodiments, the compound is
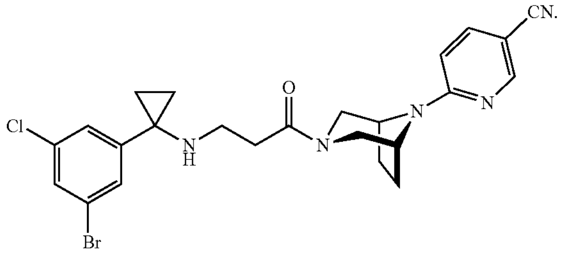
In embodiments, the compound is
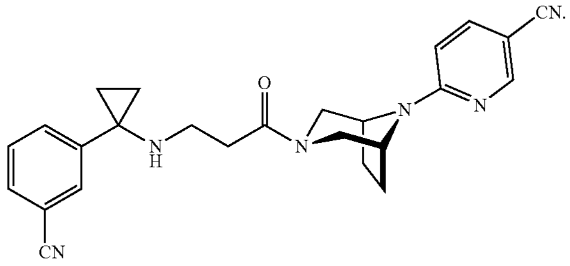
In embodiments, the compound is
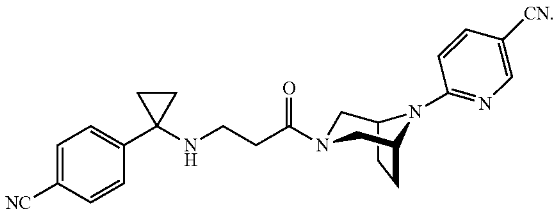
In embodiments, the compound is
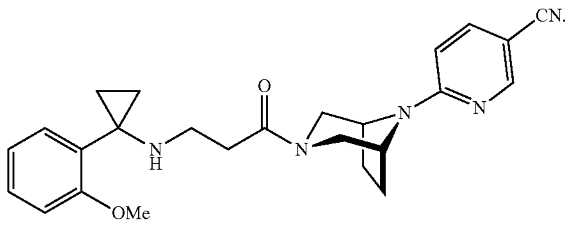
In embodiments, the compound is
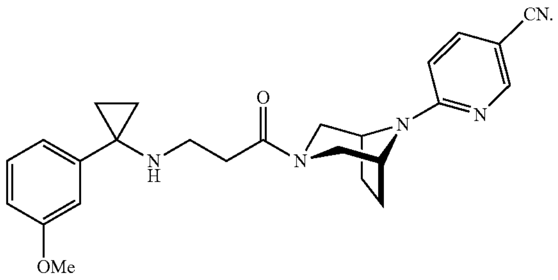
In embodiments, the compound is
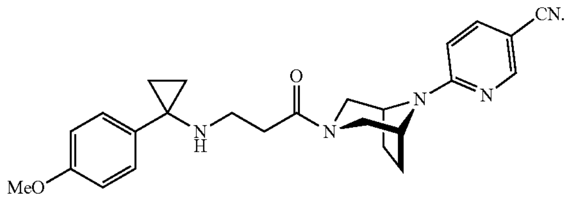
In embodiments, the compound is
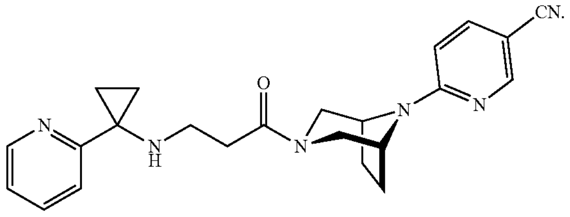
In embodiments, the compound is
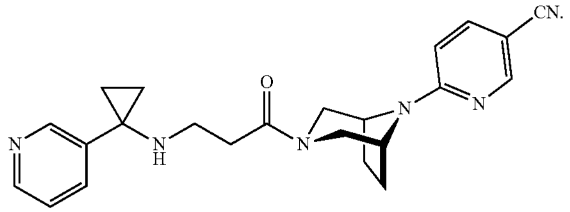
In embodiments, the compound is
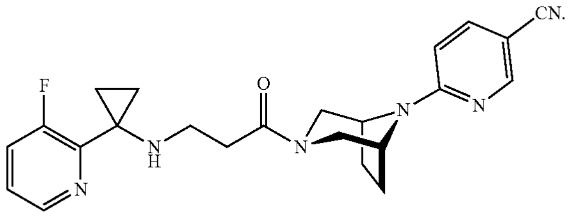
In embodiments, the compound is
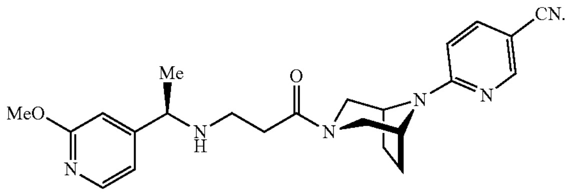

In embodiments, the compound is
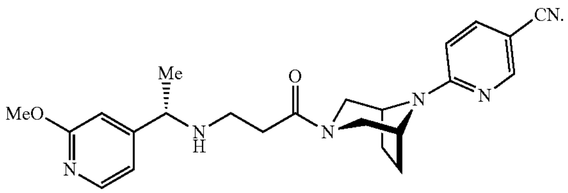
In embodiments, the compound is
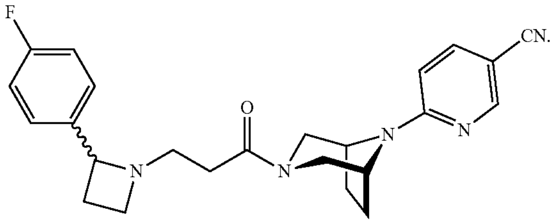
In embodiments, the compound is
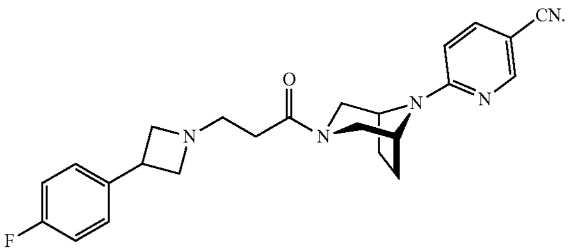
In embodiments, the compound is
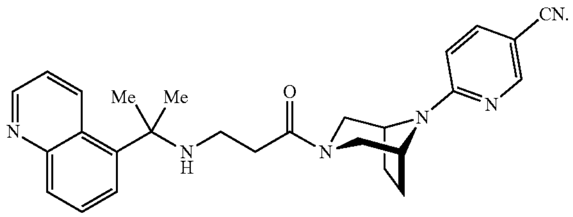
In embodiments, the compound is
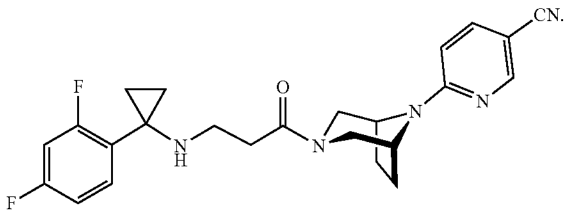
In embodiments, the compound is
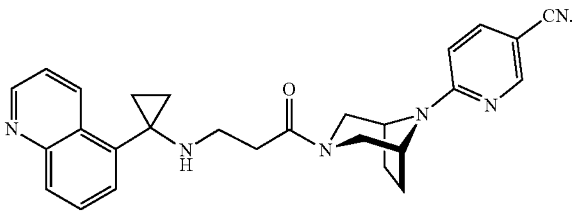
In embodiments, the compound is
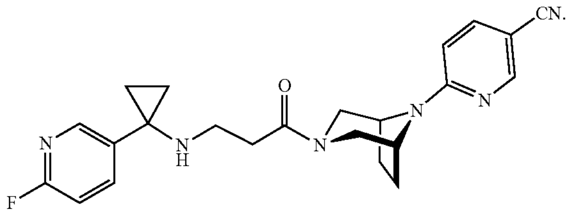
In embodiments, the compound is
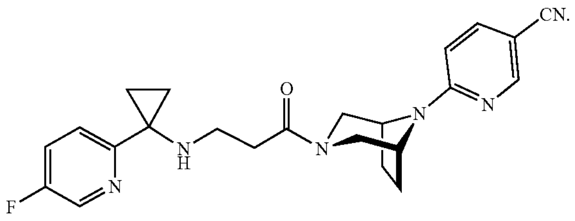
In embodiments, the compound is
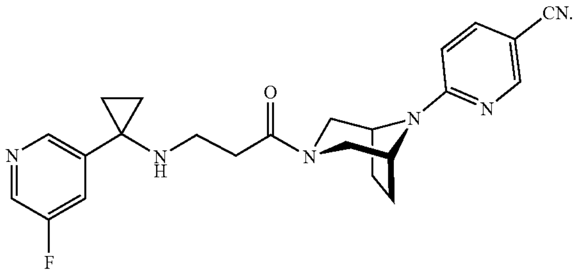
In embodiments, the compound is
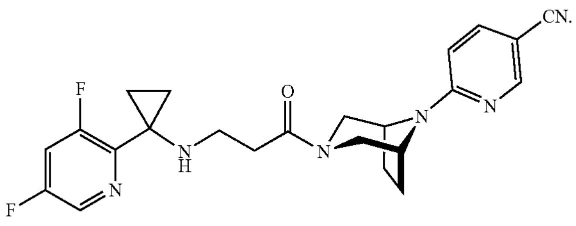

In embodiments, the compound is
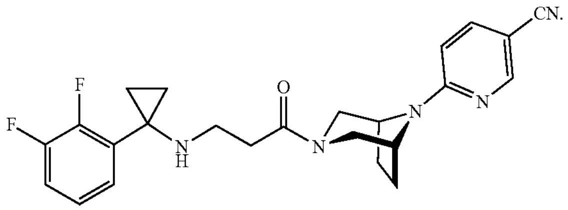
In embodiments, the compound is
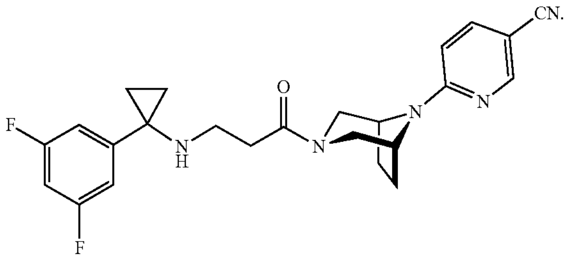
In embodiments, the compound is
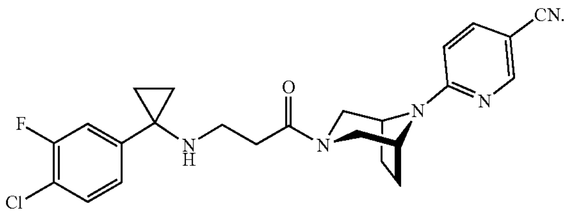
In embodiments, the compound is
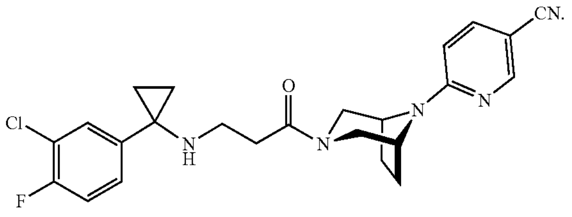
In embodiments, the compound is
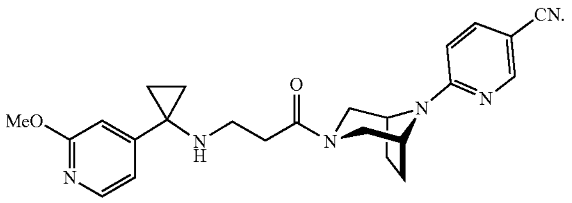
In embodiments, the compound is
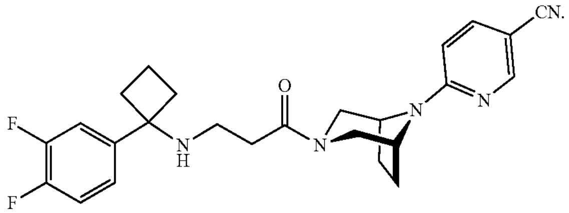
In embodiments, the compound is
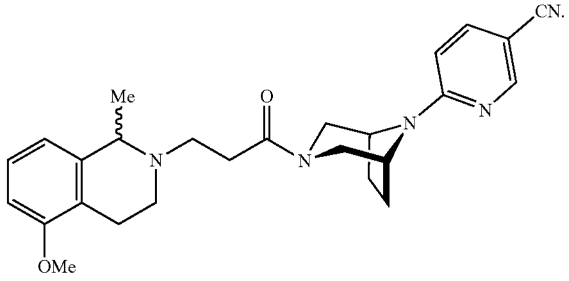
In embodiments, the compound is
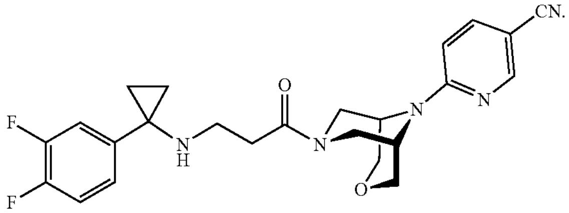
In embodiments, the compound is
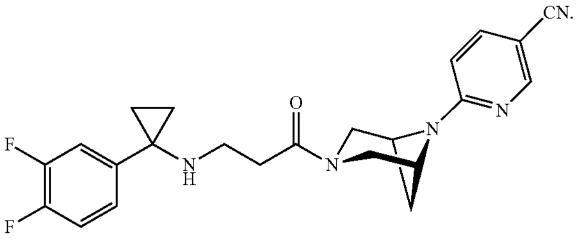
In embodiments, the compound is
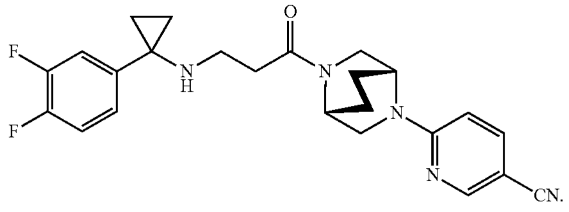

In embodiments, the compound is
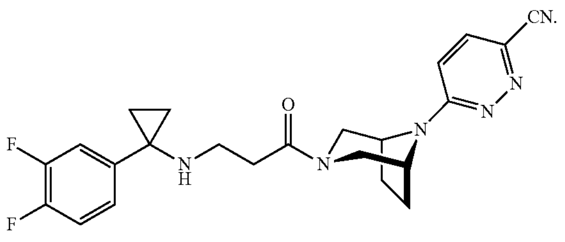
In embodiments, the compound is
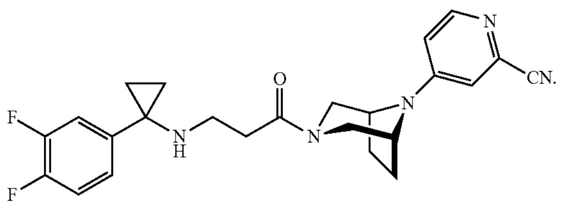
In embodiments, the compound is
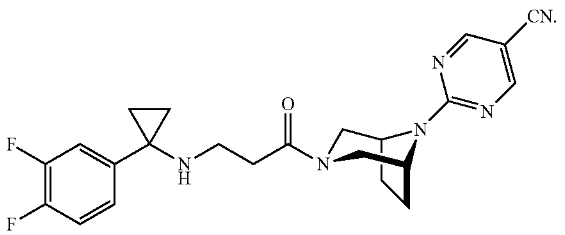
In embodiments, the compound is
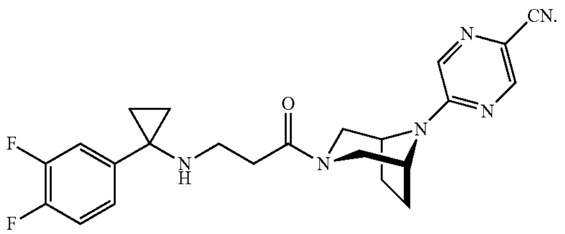
In embodiments, the compound is
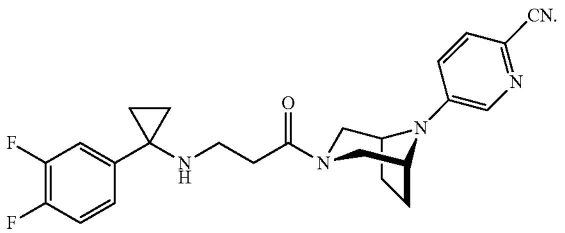
In embodiments, the compound is
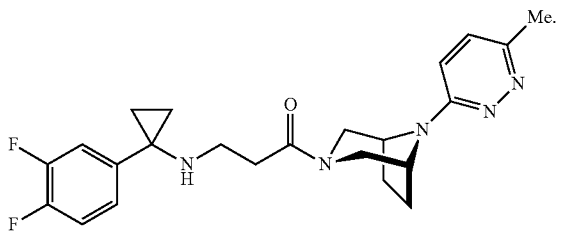
In embodiments, the compound is
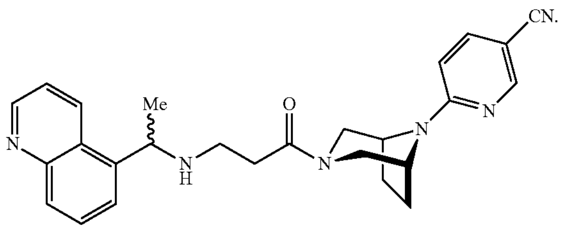
In embodiments, the compound is
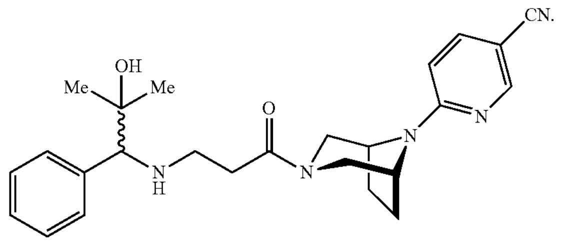
In embodiments, the compound is
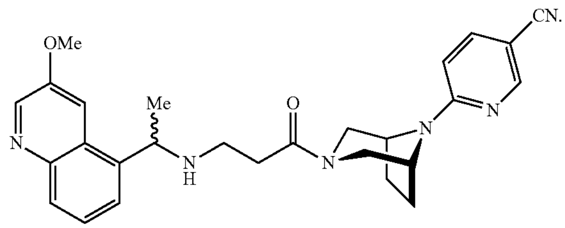
In embodiments, the compound is
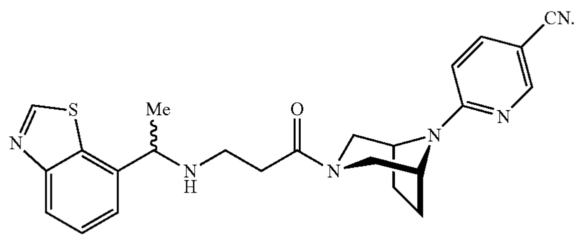

In embodiments, the compound is
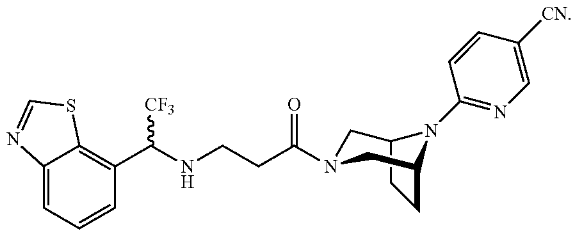
In embodiments, the compound is
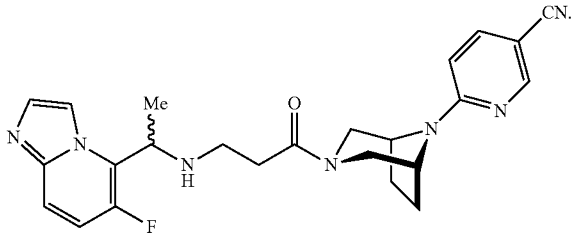
In embodiments, the compound is
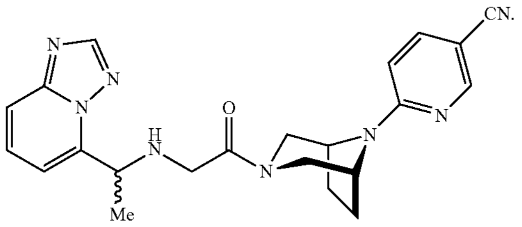
In embodiments, the compound is
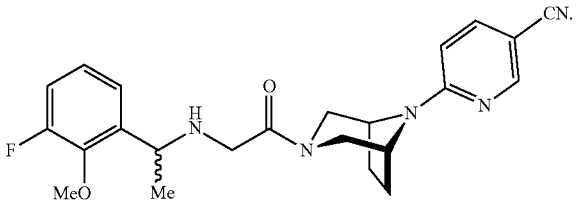
In embodiments, the compound is
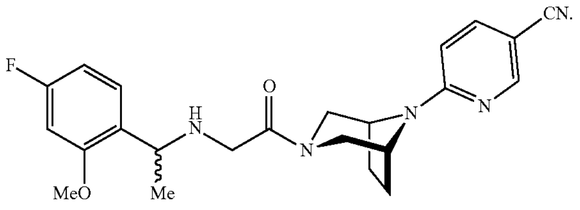
In embodiments, the compound is
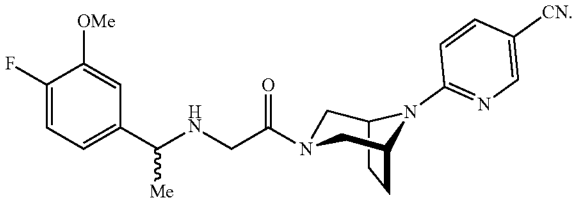
In embodiments, the compound is
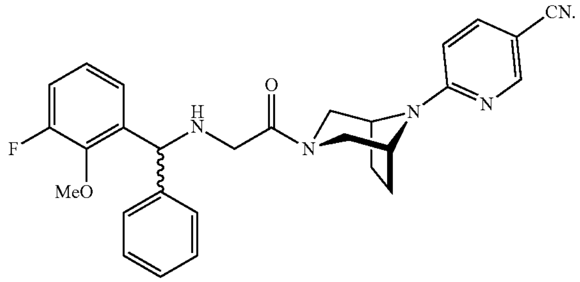
In embodiments, the compound is
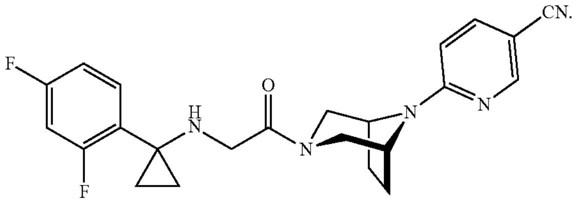
In embodiments, the compound is
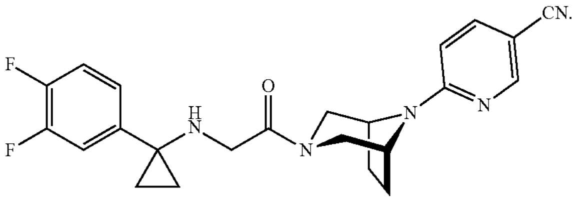
In embodiments, the compound is
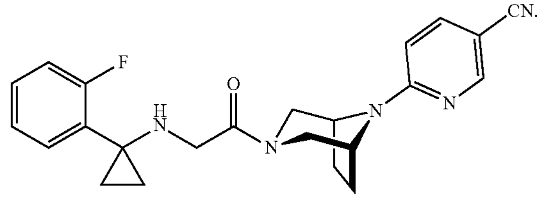

In embodiments, the compound is
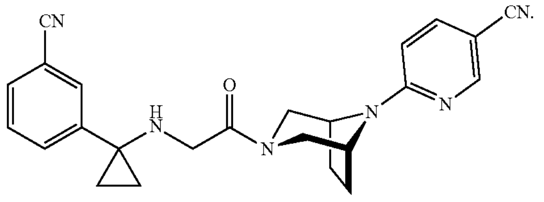
In embodiments, the compound is
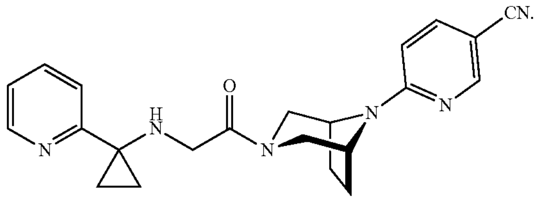
In embodiments, the compound is
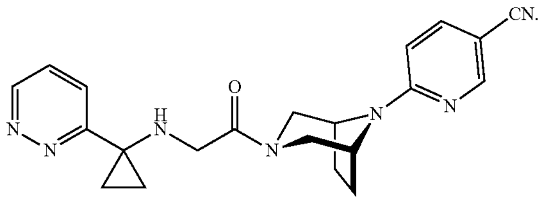
In embodiments, the compound is
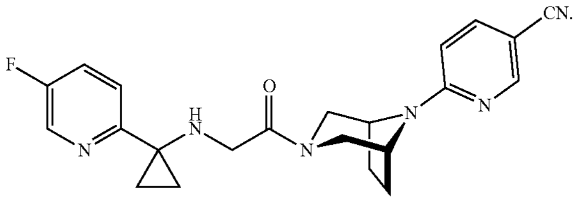
In embodiments, the compound is
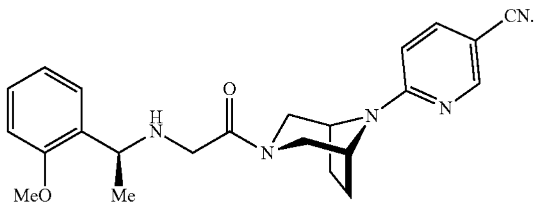
In embodiments, the compound is
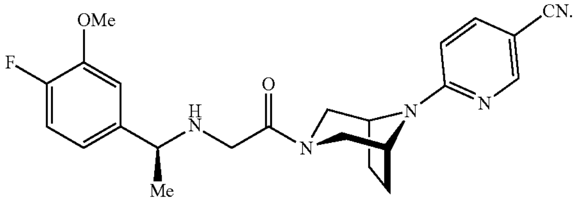
In embodiments, the compound is
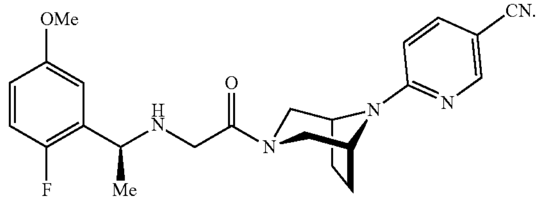
In embodiments, the compound is
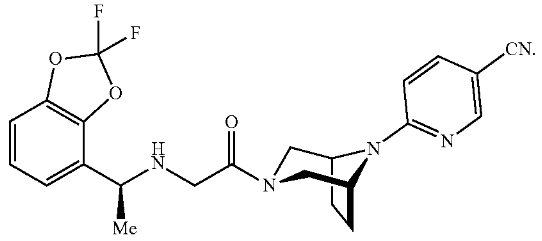
In embodiments, the compound is
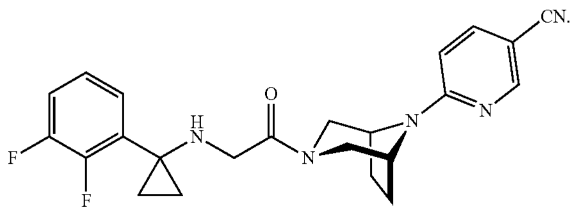
In embodiments, the compound is
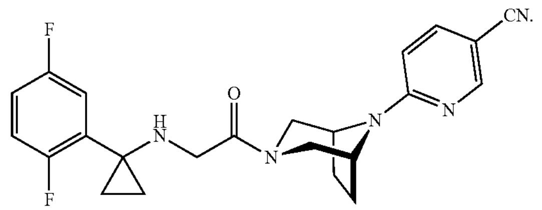

In embodiments, the compound is
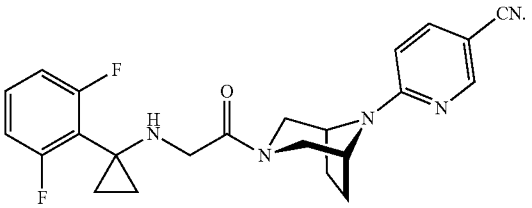
In embodiments, the compound is
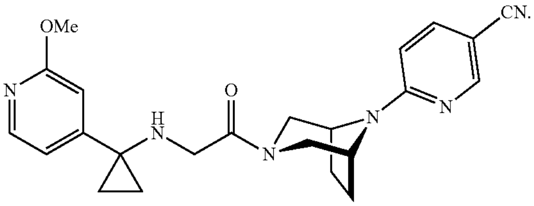
In embodiments, the compound is
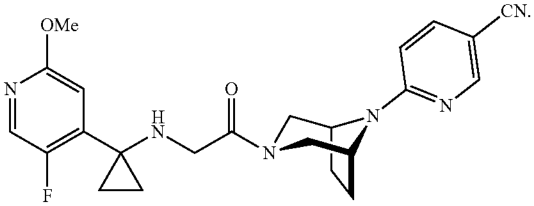
In embodiments, the compound is
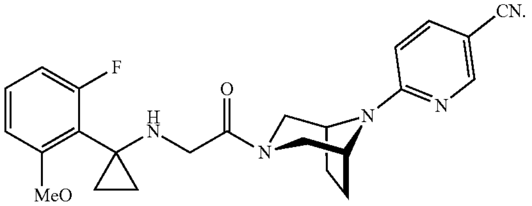
In embodiments, the compound is
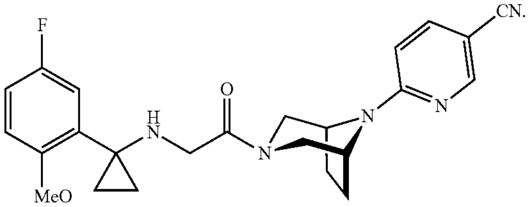
In embodiments, the compound is
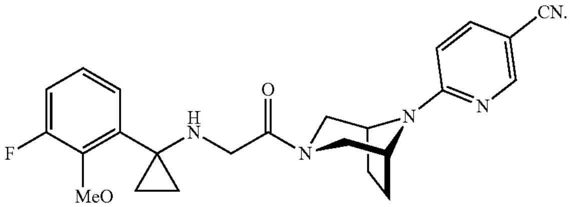
In embodiments, the compound is
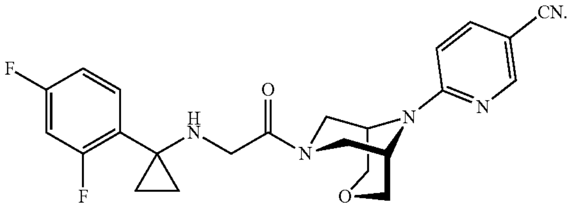
In embodiments, the compound is
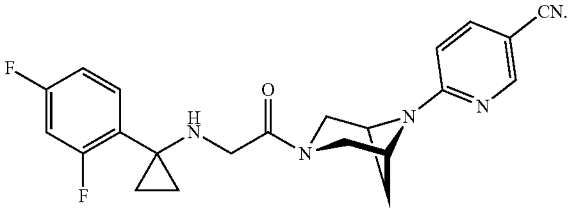
In embodiments, the compound is
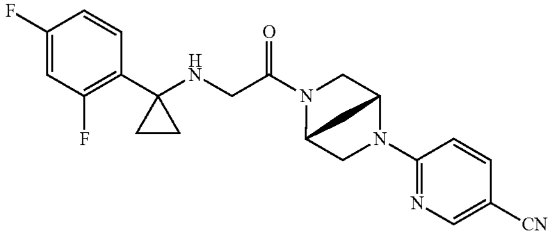 [SMILES: N#Cc1ccc(N2C[C@H]3C[C@@H]2CN3C(=O)CNC2(c3ccc(F)cc3F)CC2)nc1]
In embodiments, the compound is
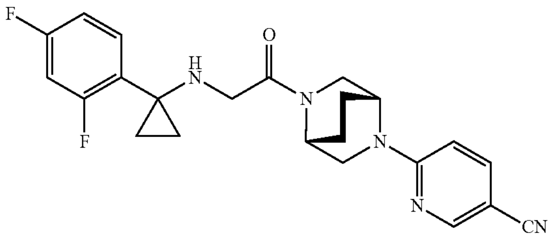

In embodiments, the compound is
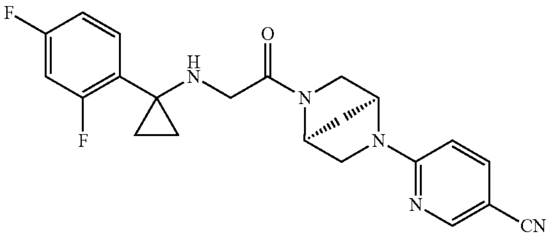 [SMILES: N#Cc1ccc(N2C[C@@H]3C[C@H]2CN3C(=O)CNC2(c3ccc(F)cc3F)CC2)nc1]
In embodiments, the compound is
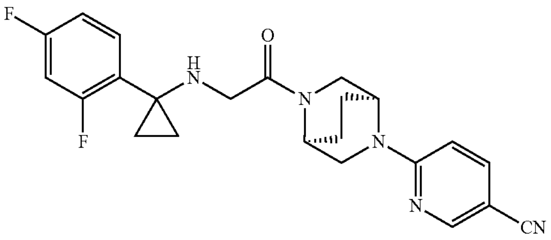 [SMILES: N#Cc1ccc(N2C[C@@H]3CC[C@H]2CN3C(=O)CNC2(c3ccc(F)cc3F)CC2)nc1]
In embodiments, the compound is
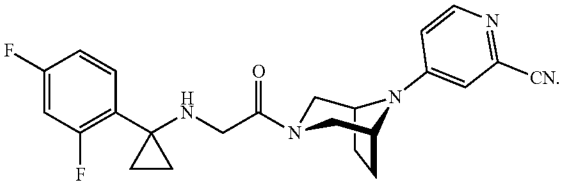
In embodiments, the compound is
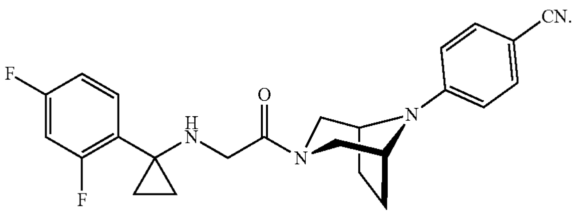
In embodiments, the compound is
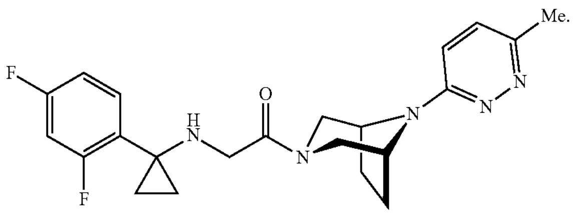
In embodiments, the compound is
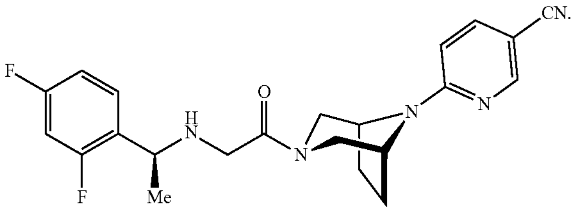
In embodiments, the compound is
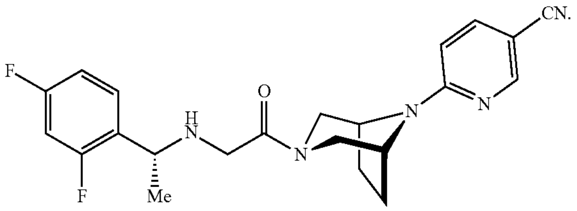
In embodiments, the compound is
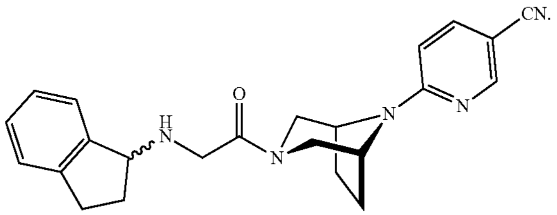
In embodiments, the compound is
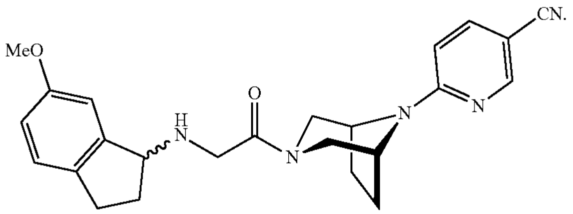
In embodiments, the compound is
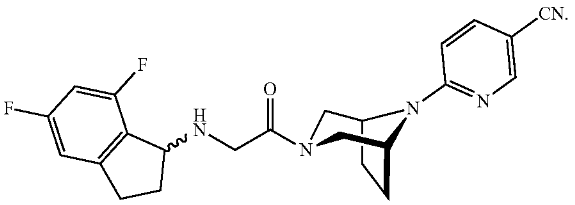

In embodiments, the compound is
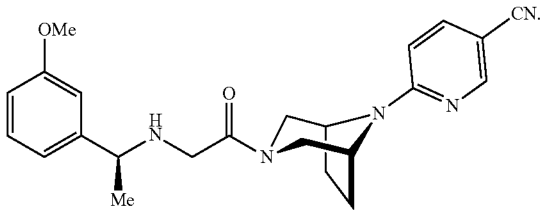
In embodiments, the compound is
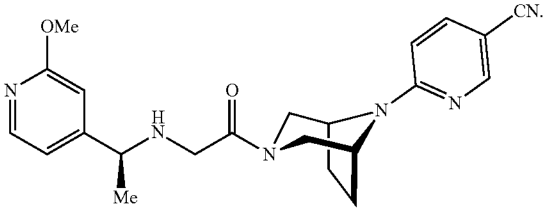
In embodiments, the compound is
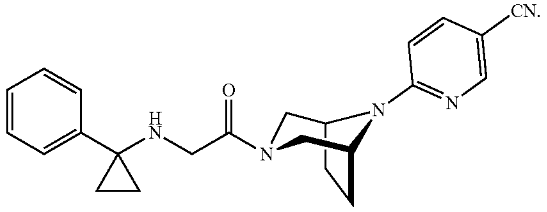
In embodiments, the compound is
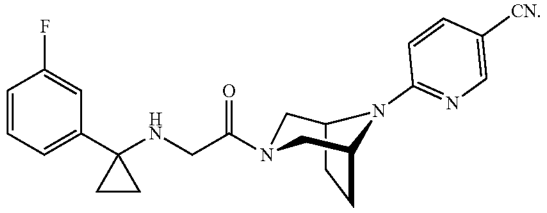
In embodiments, the compound is
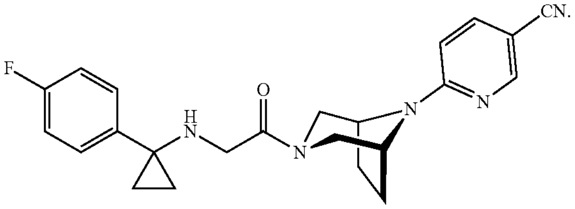
In embodiments, the compound is
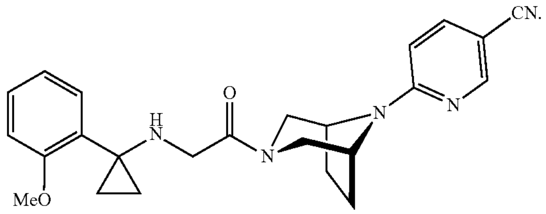
In embodiments, the compound is
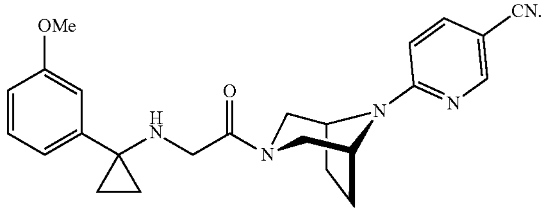
In embodiments, the compound is
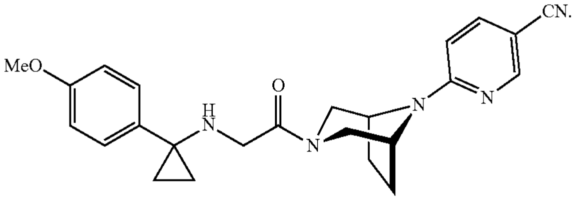
In embodiments, the compound is
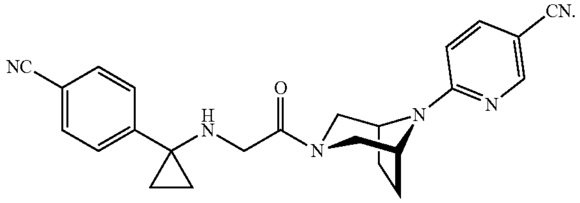
In embodiments, the compound is
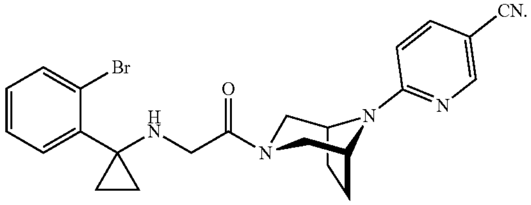

In embodiments, the compound is
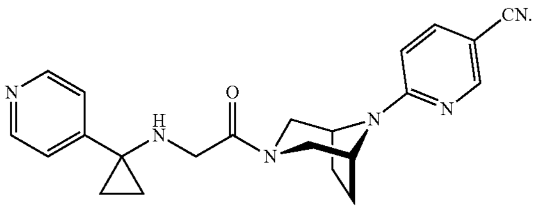
In embodiments, the compound is
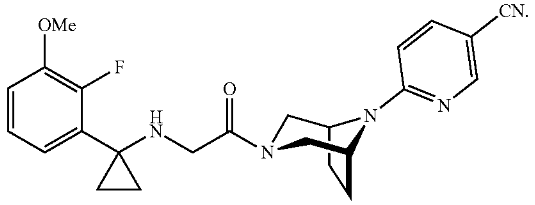
In embodiments, the compound is
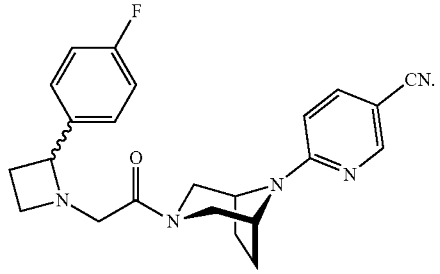
In embodiments, the compound is
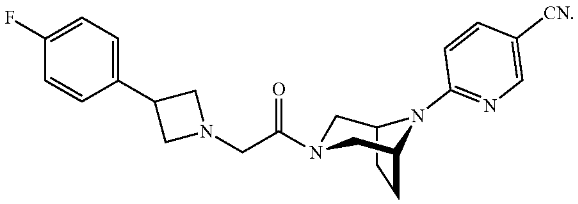
In embodiments, the compound is
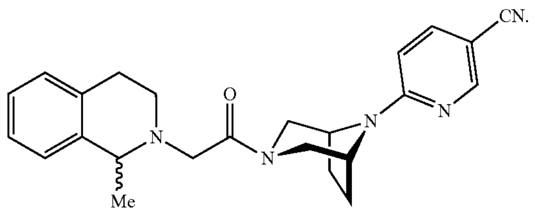
In embodiments, the compound is
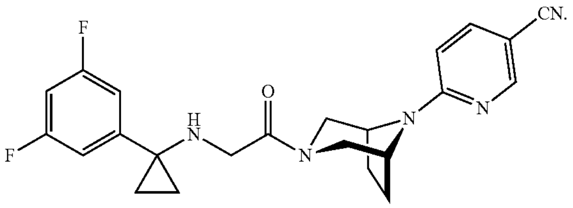
In embodiments, the compound is
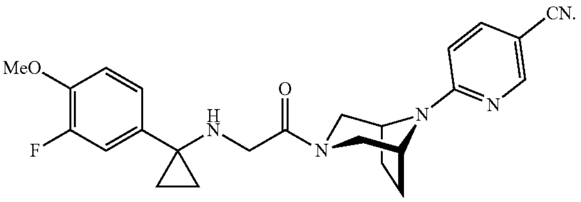
In embodiments, the compound is
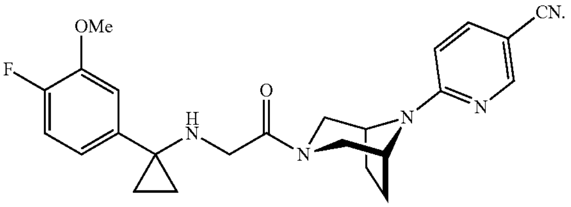
In embodiments, the compound is
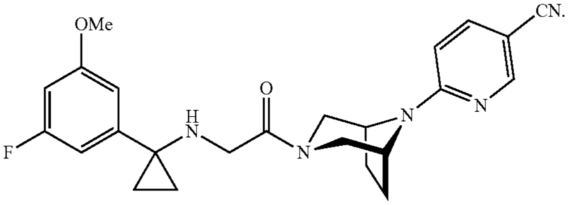
In embodiments, the compound is
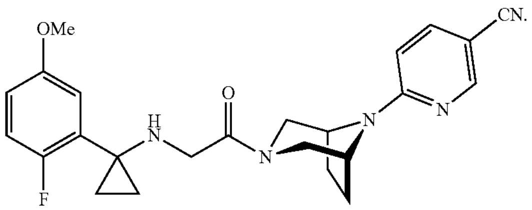

In embodiments, the compound is
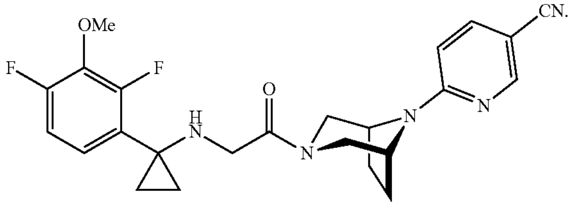
In embodiments, the compound is
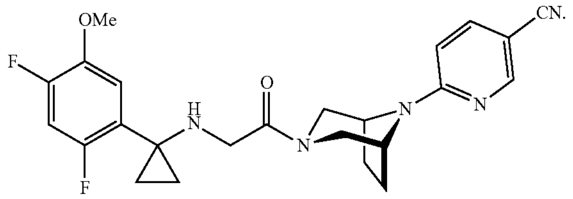
In embodiments, the compound is
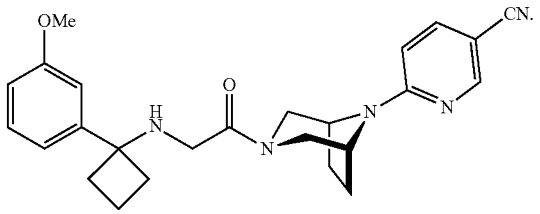
In embodiments, the compound is
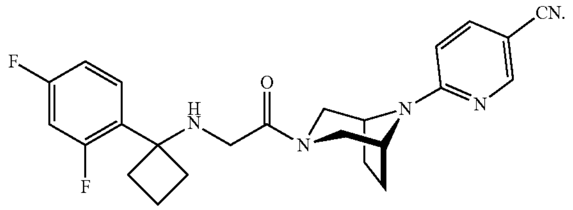
In embodiments, the compound is
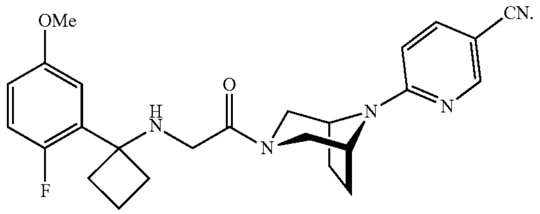
In embodiments, the compound is
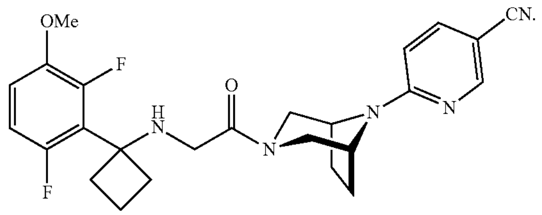
In embodiments, the compound is
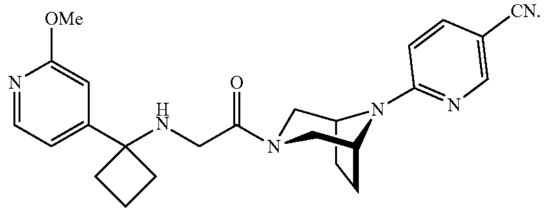
In embodiments, the compound is
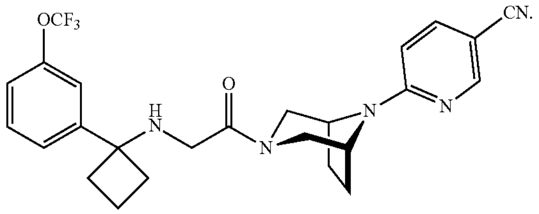
In embodiments, the compound is
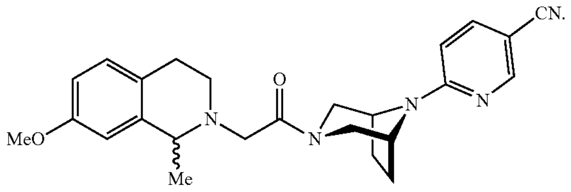
In embodiments, the compound is
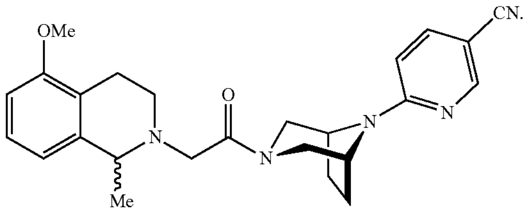

In embodiments, the compound is
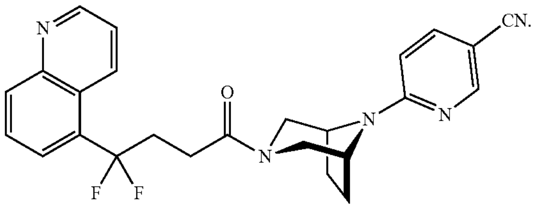
In embodiments, the compound is
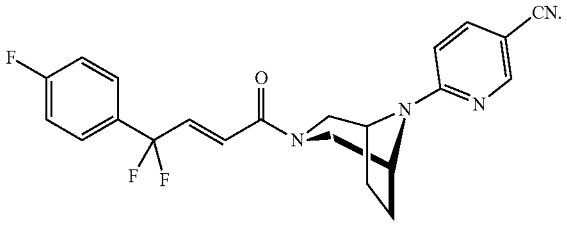
In embodiments, the compound is
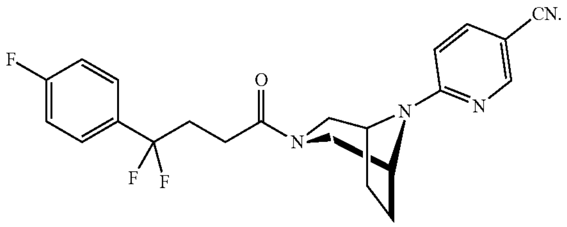
In embodiments, the compound is
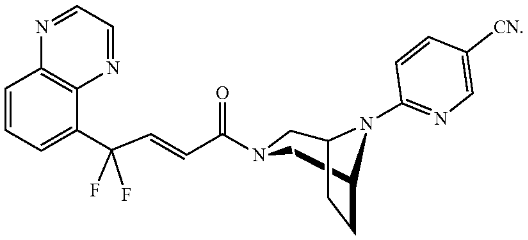
In embodiments, the compound is
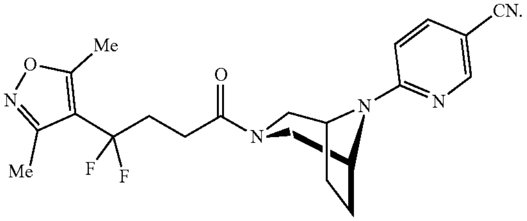
In embodiments, the compound is
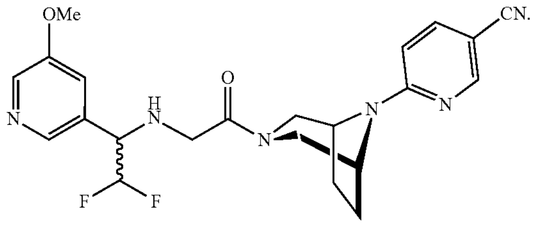
In embodiments, the compound is
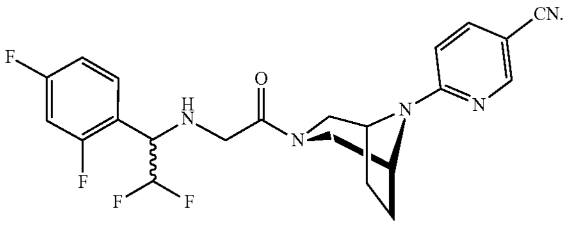
In embodiments, the compound is
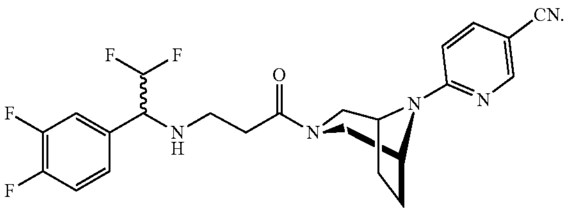
In embodiments, the compound is
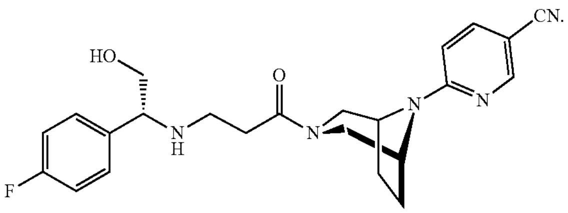
In embodiments, the compound is
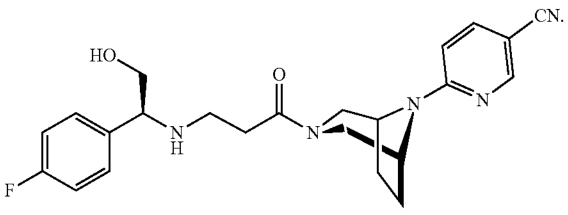

In embodiments, the compound is
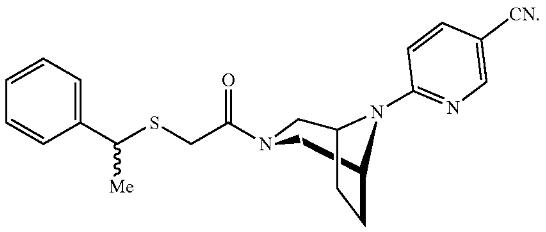
In embodiments, the compound is
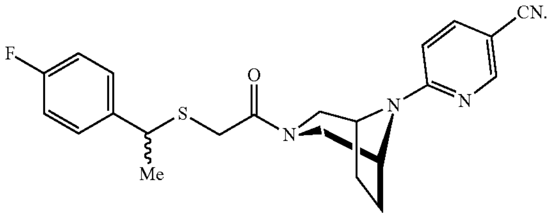
In embodiments, the compound is
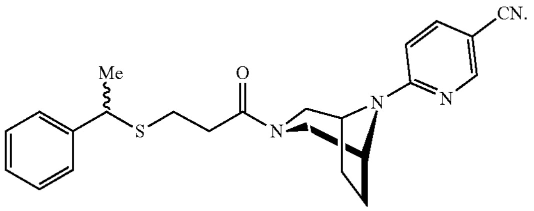
In embodiments, the compound is
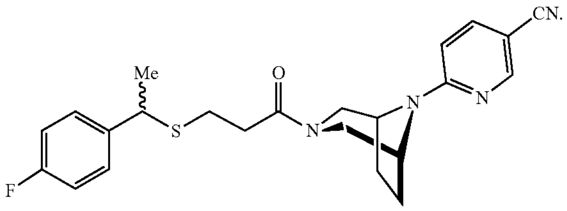
In embodiments, the compound is
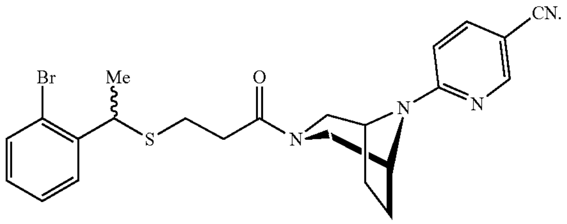
In embodiments, the compound is
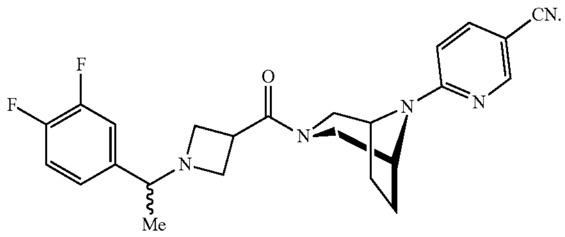
In embodiments, the compound is
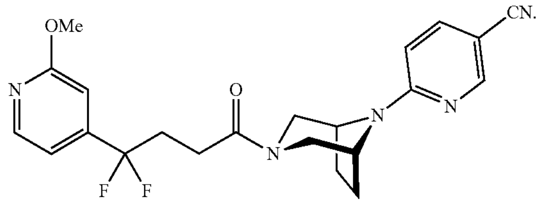
In embodiments, the compound is
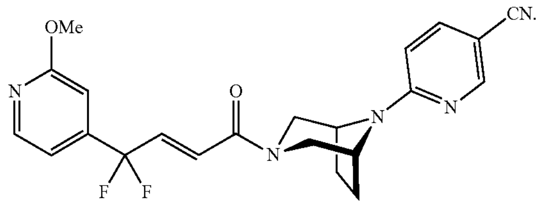
In embodiments, the compound is
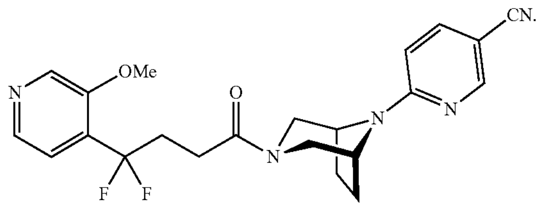
In embodiments, the compound is
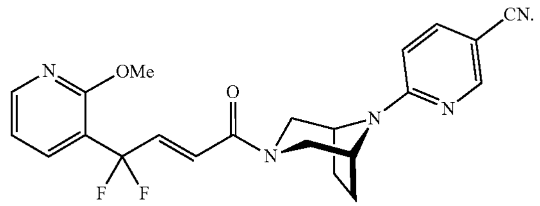

In embodiments, the compound is
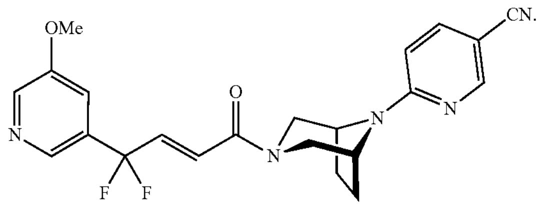
In embodiments, the compound is
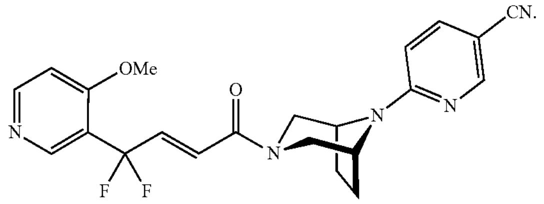
In embodiments, the compound is
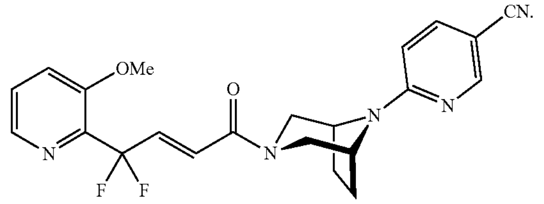
In embodiments, the compound is
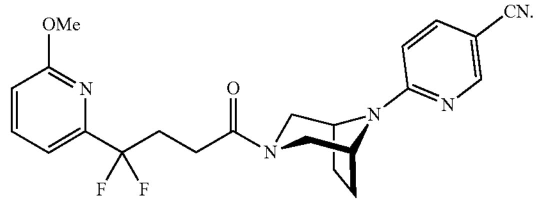
In embodiments, the compound is
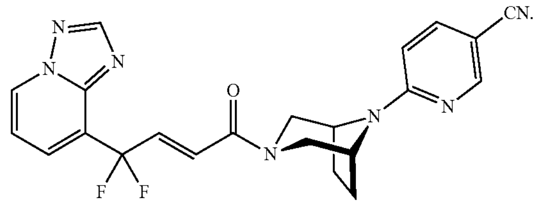
In embodiments, the compound is
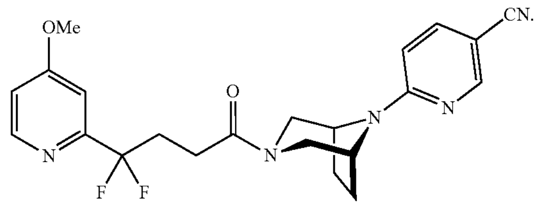
In embodiments, the compound is
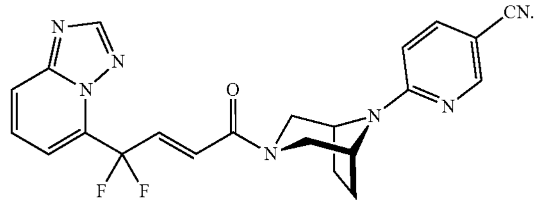
In embodiments, the compound is
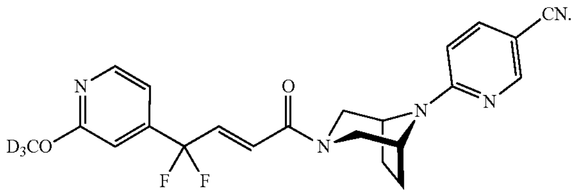
In embodiments, the compound is
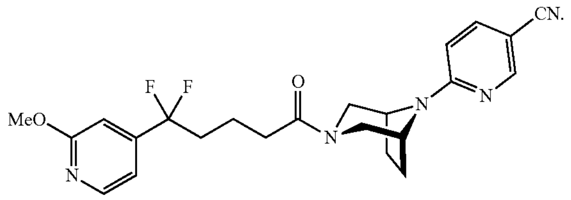
In embodiments, the compound is
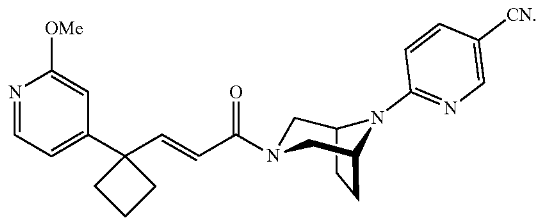

In embodiments, the compound is
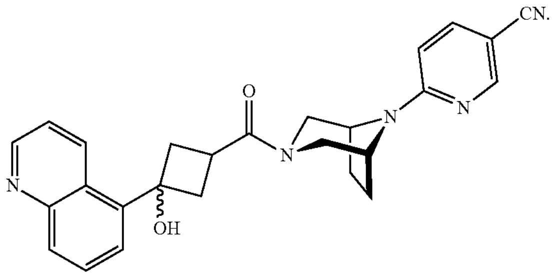
In embodiments, the compound is
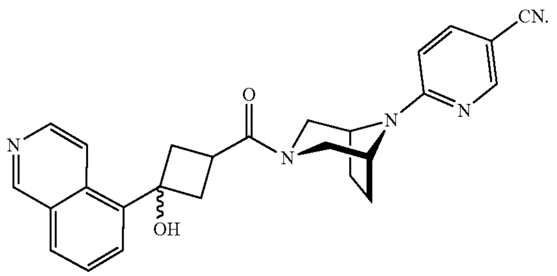
In embodiments, the compound is
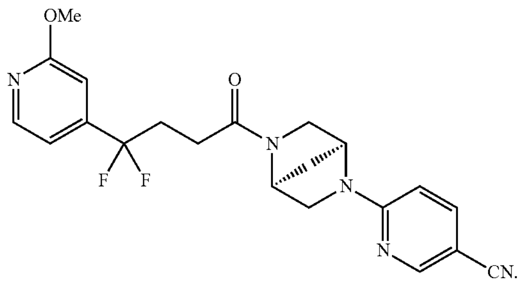 [SMILES: COc1cc(C(F)(F)CCC(=O)N2C[C@@H]3C[C@H]2CN3c2ccc(C#N)cn2)ccn1]
In embodiments, the compound is
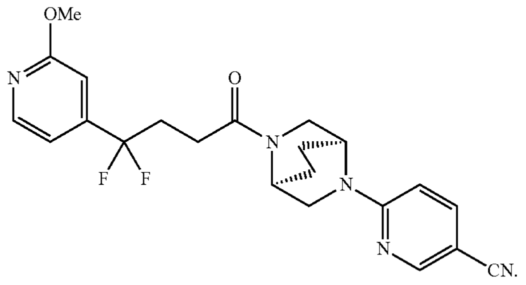 [SMILES: COc1cc(C(F)(F)CCC(=O)N2C[C@@H]3CC[C@H]2CN3c2ccc(C#N)cn2)ccn1]
In embodiments, the compound is
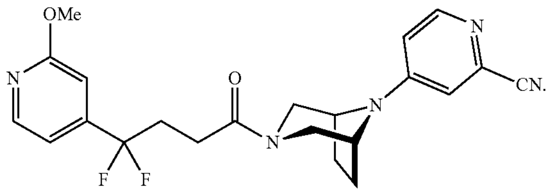
In embodiments, the compound is
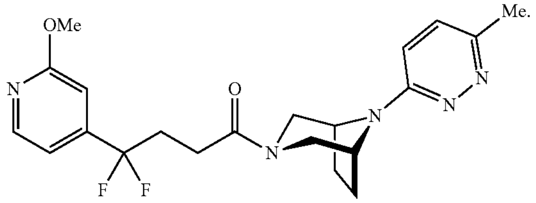
In embodiments, the compound is
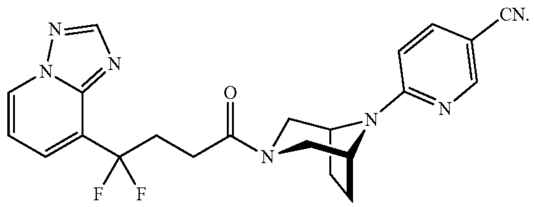
In embodiments, the compound is
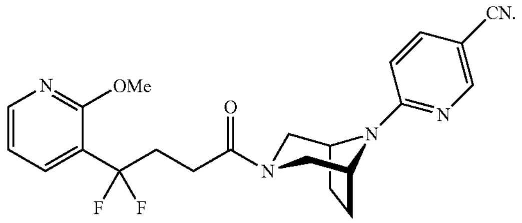
In embodiments, the compound is
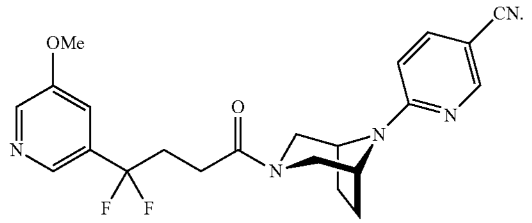

In embodiments, the compound is
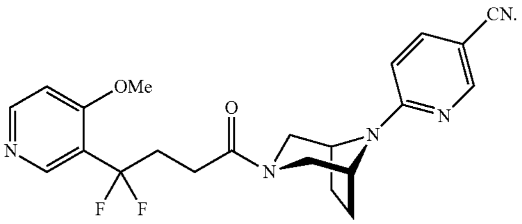
In embodiments, the compound is
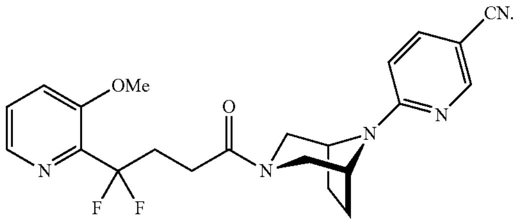
In embodiments, the compound is
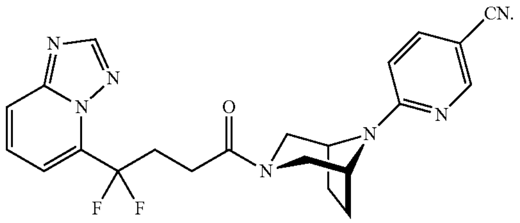
In embodiments, the compound is
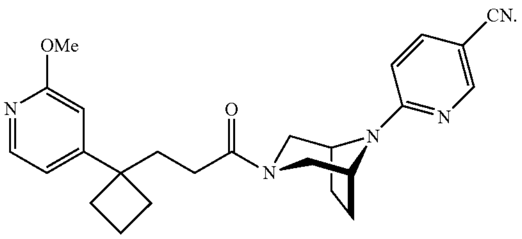
In embodiments, the compound is
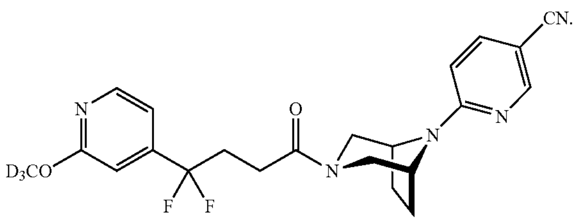
In embodiments, the compound is
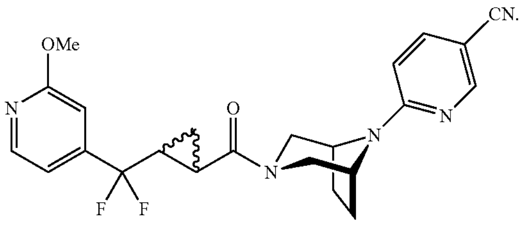
In embodiments, the compound is
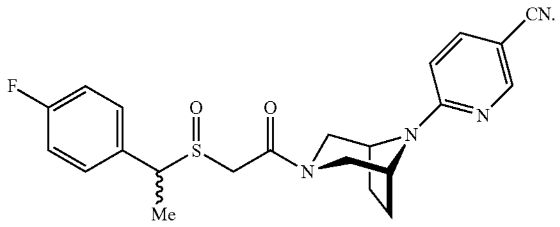
In embodiments, the compound is
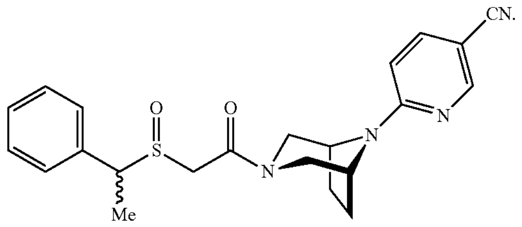
In embodiments, the compound is
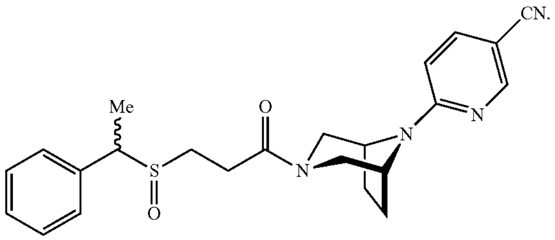
In embodiments, the compound is
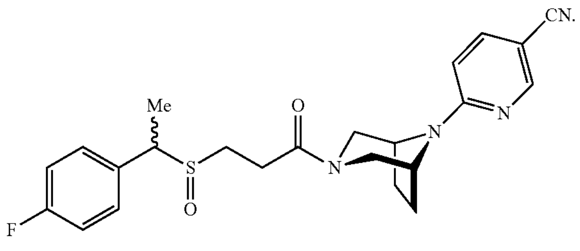

In embodiments, the compound is
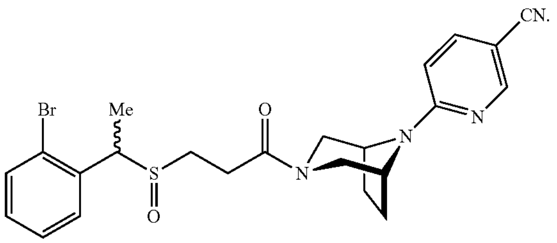
In embodiments, the compound is
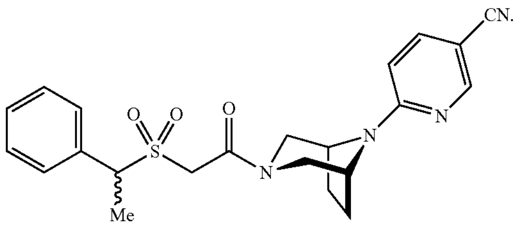
In embodiments, the compound is
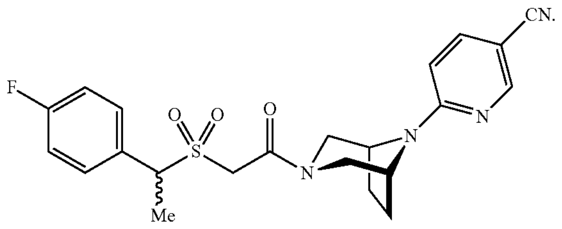
In embodiments, the compound is
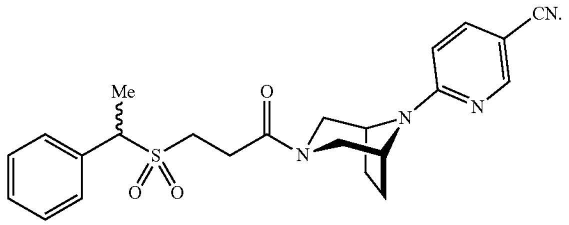
In embodiments, the compound is
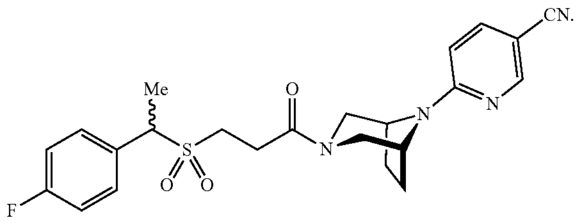
In embodiments, the compound is
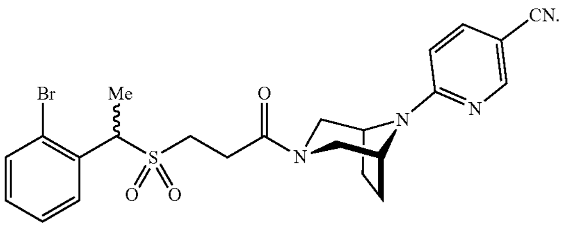
In embodiments, the compound is
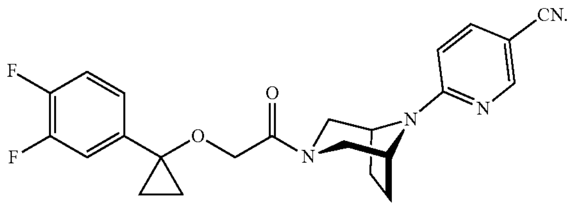
In embodiments, the compound is
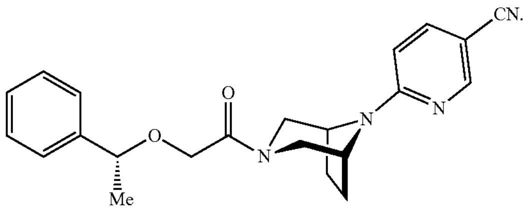
In embodiments, the compound is
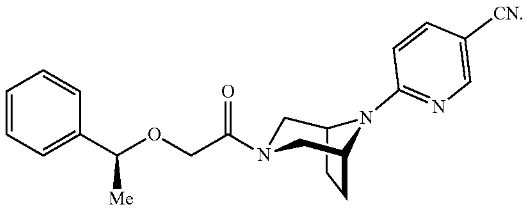
In embodiments, the compound is
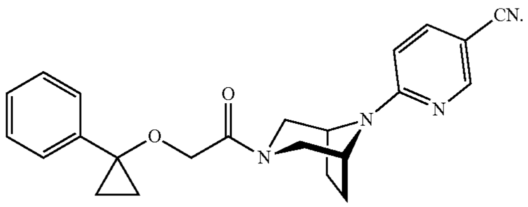

In embodiments, the compound is
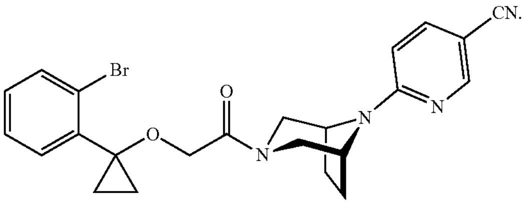
In embodiments, the compound is
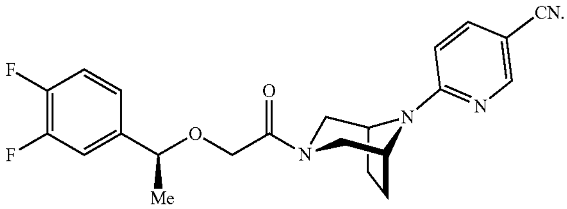
In embodiments, the compound is
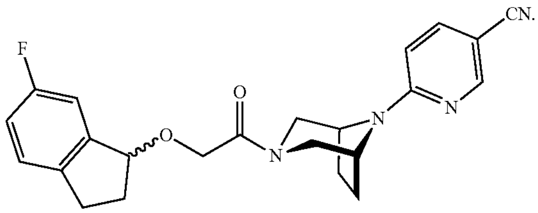
In embodiments, the compound is
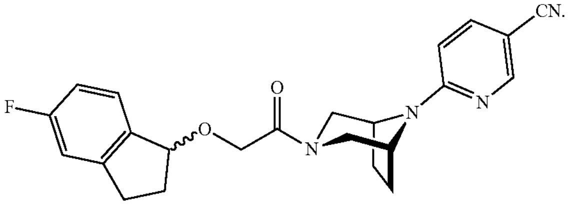
In embodiments, the compound is
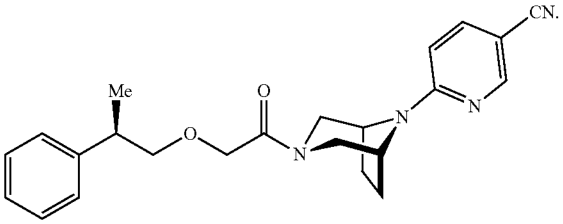
In embodiments, the compound is
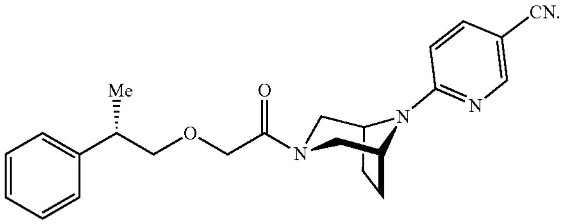
In embodiments, the compound is
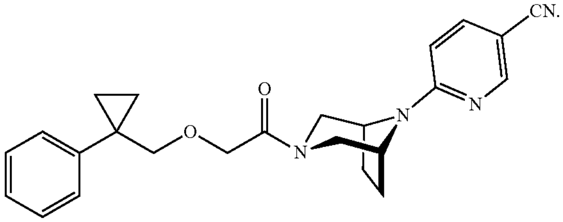
In embodiments, the compound is
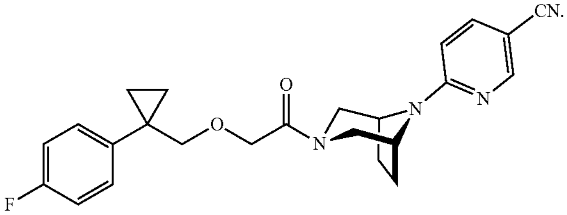
In embodiments, the compound is
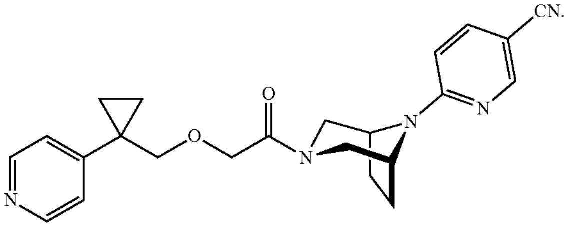
In embodiments, the compound is
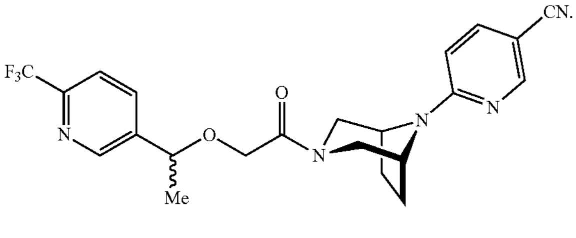

In embodiments, the compound is
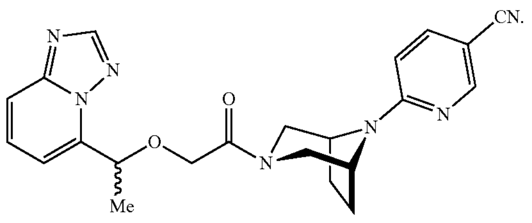
In embodiments, the compound is
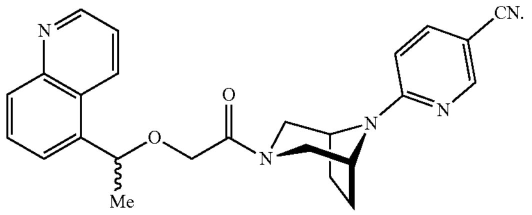
In embodiments, the compound is
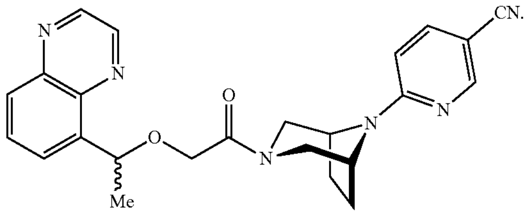
In embodiments, the compound is
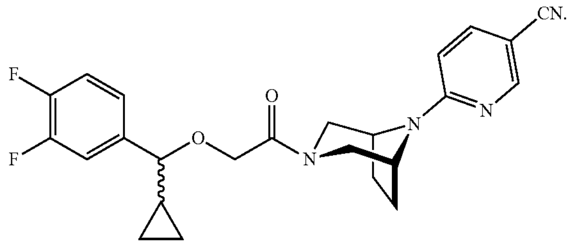
In embodiments, the compound is
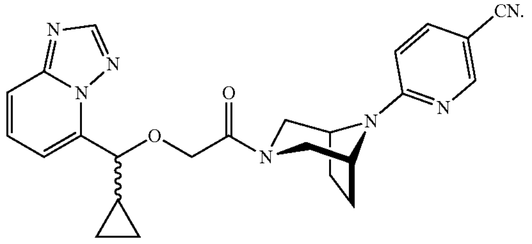
In embodiments, the compound is
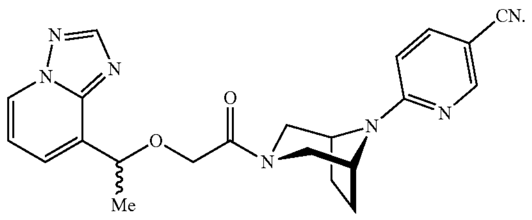
In embodiments, the compound is
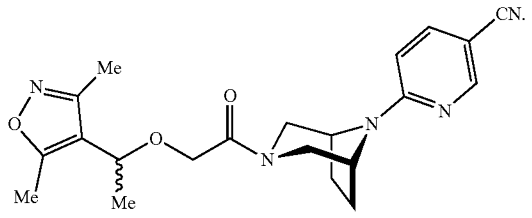
In embodiments, the compound is
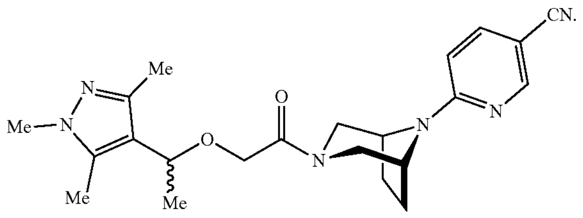
In embodiments, the compound is
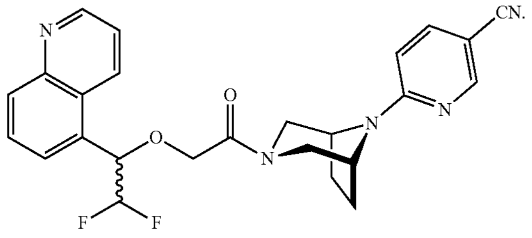
In embodiments, the compound is
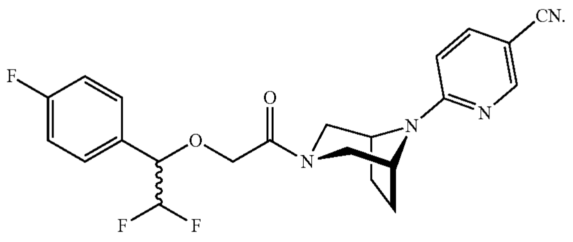

In embodiments, the compound is
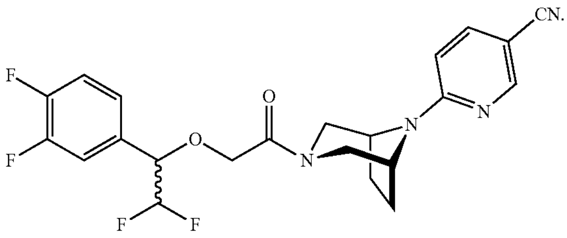
In embodiments, the compound is
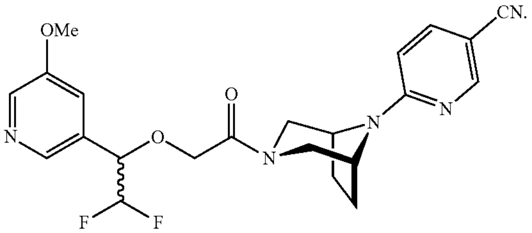
In embodiments, the compound is
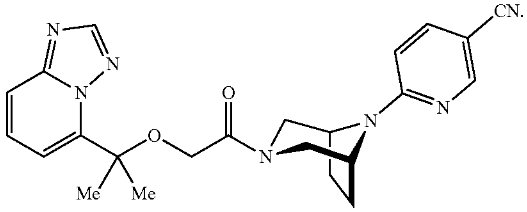
In embodiments, the compound is
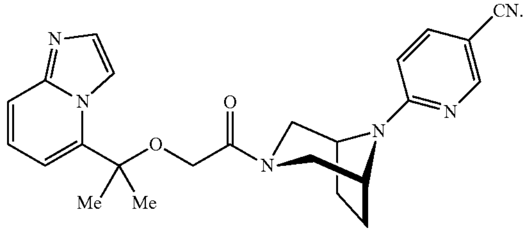
In embodiments, the compound is
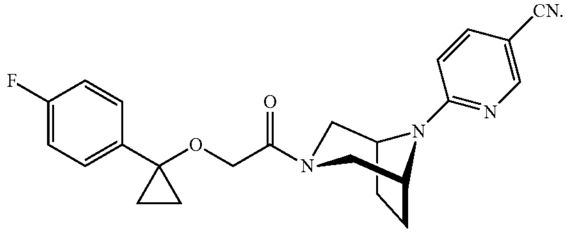
In embodiments, the compound is
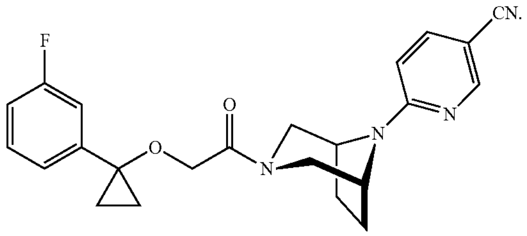
In embodiments, the compound is
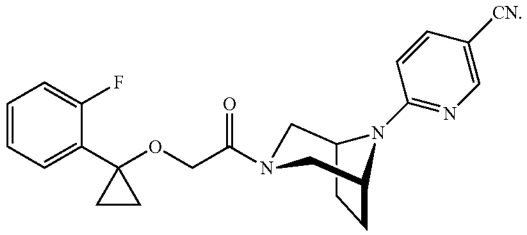
In embodiments, the compound is
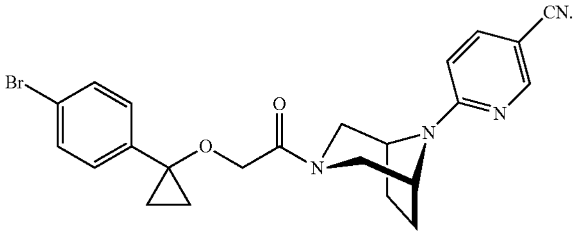
In embodiments, the compound is
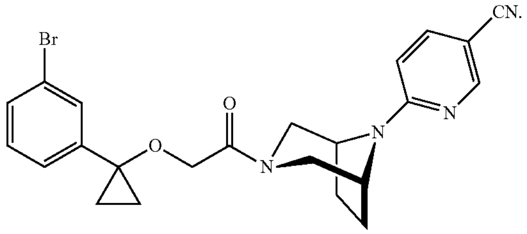
In embodiments, the compound is
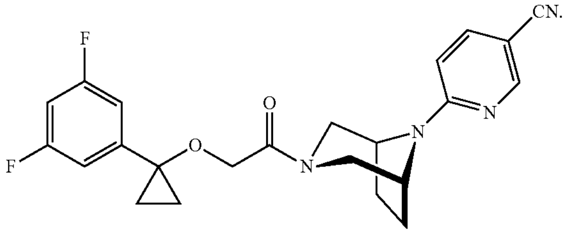

In embodiments, the compound is
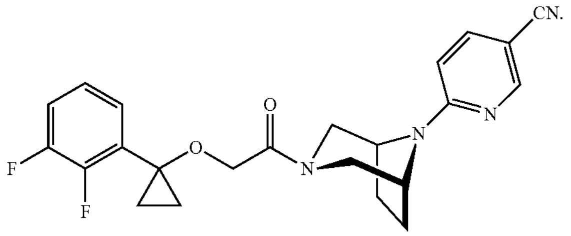
In embodiments, the compound is
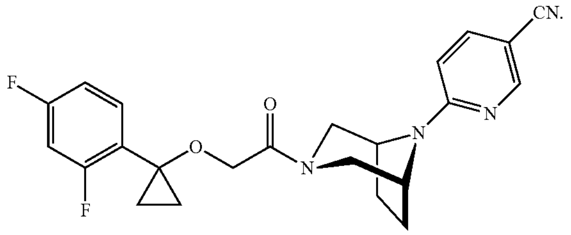
In embodiments, the compound is
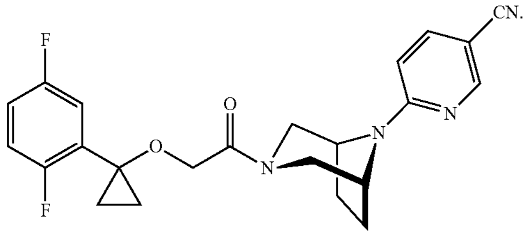
In embodiments, the compound is
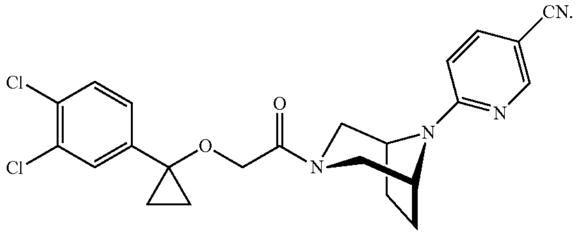
In embodiments, the compound is
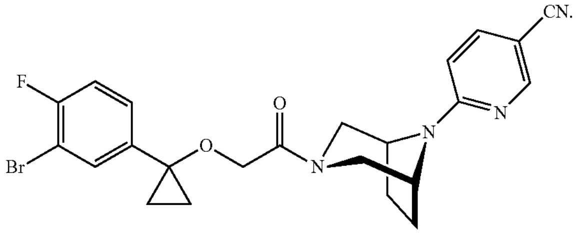
In embodiments, the compound is
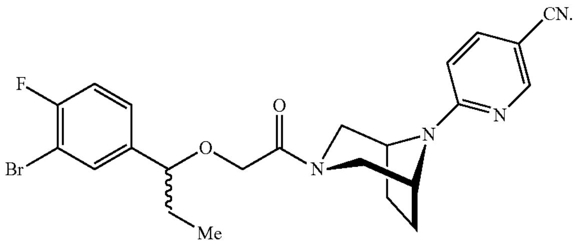
In embodiments, the compound is
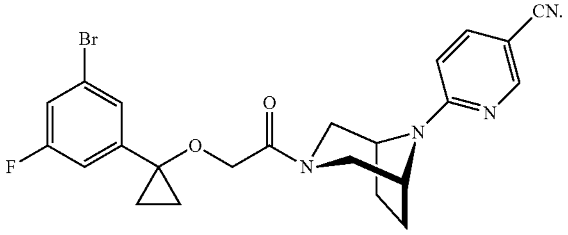
In embodiments, the compound is
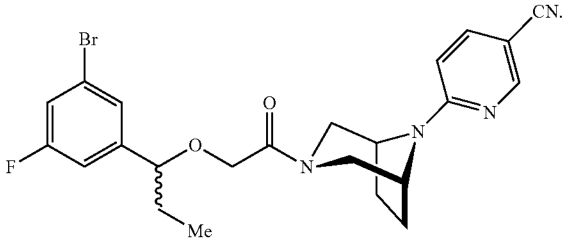
In embodiments, the compound is
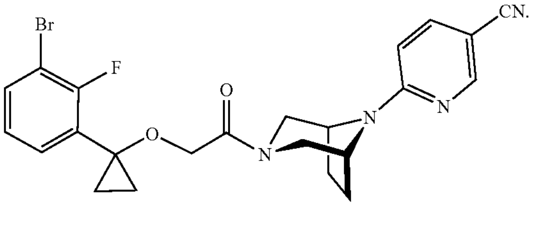
In embodiments, the compound is
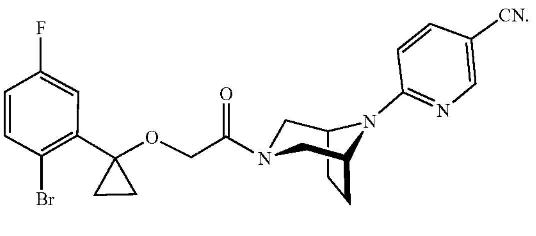

In embodiments, the compound is
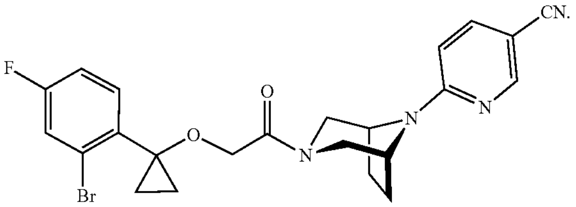
In embodiments, the compound is
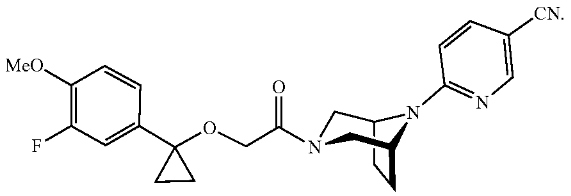
In embodiments, the compound is
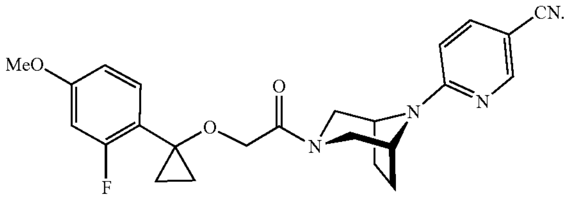
In embodiments, the compound is
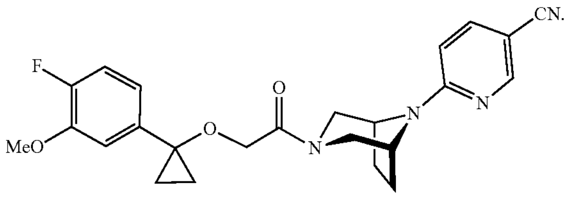
In embodiments, the compound is
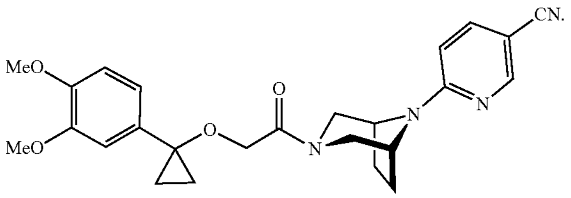
In embodiments, the compound is
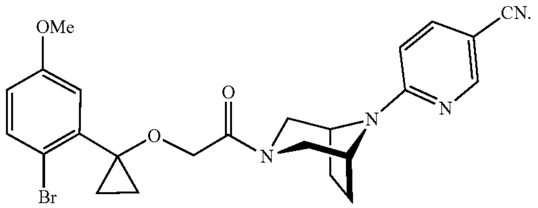
In embodiments, the compound is
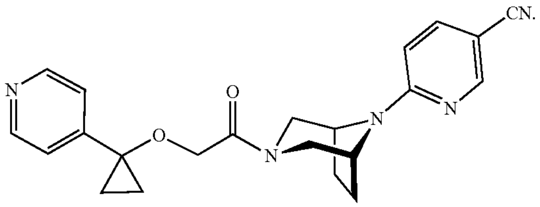
In embodiments, the compound is
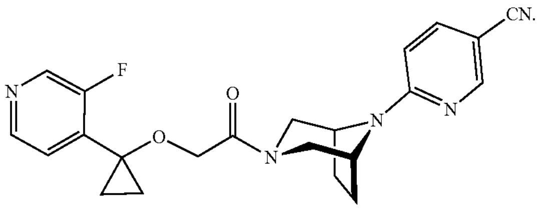
In embodiments, the compound is
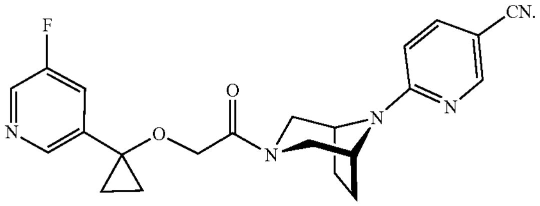
In embodiments, the compound is
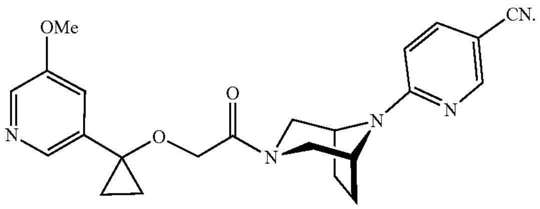

In embodiments, the compound is
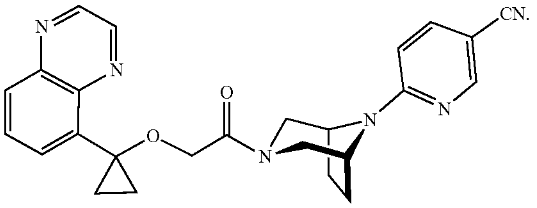
In embodiments, the compound is
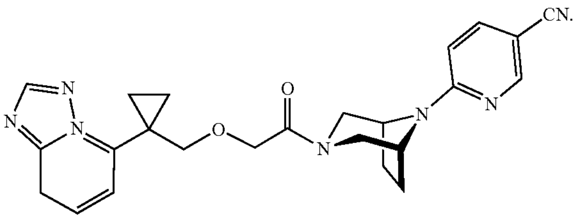
In embodiments, the compound is
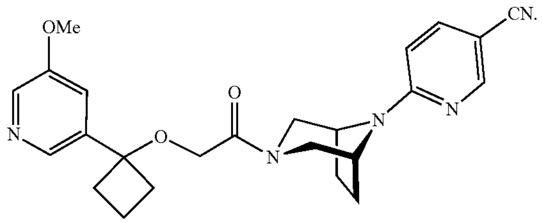
In embodiments, the compound is
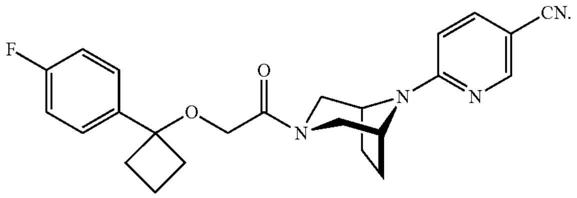
In embodiments, the compound is
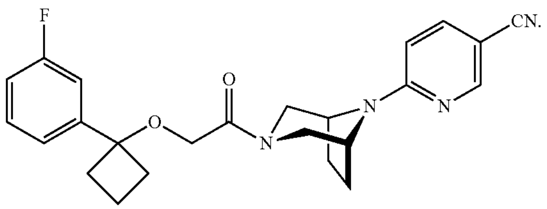
In embodiments, the compound is
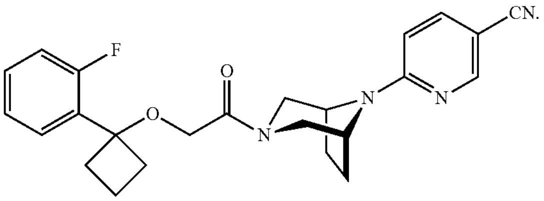
In embodiments, the compound is
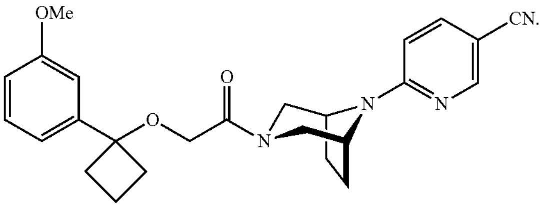
In embodiments, the compound is
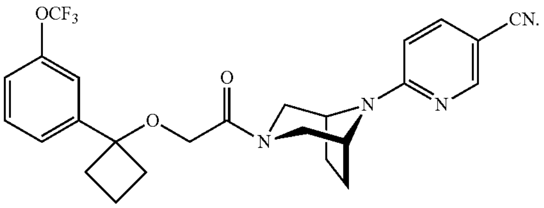
In embodiments, the compound is
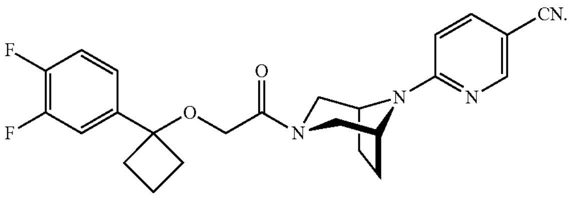
In embodiments, the compound is
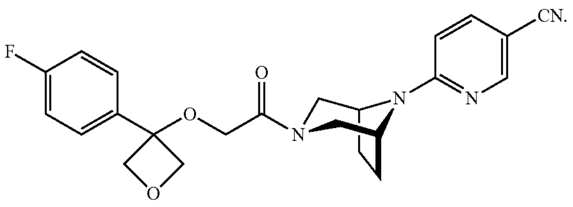

In embodiments, the compound is
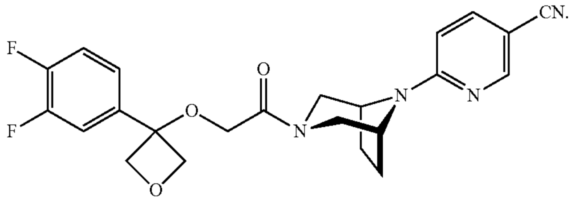
In embodiments, the compound is
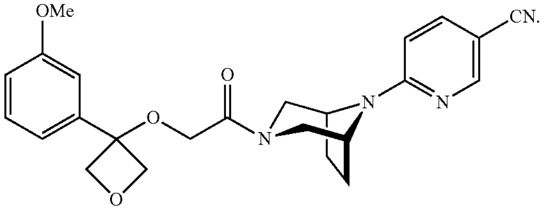
In embodiments, the compound is
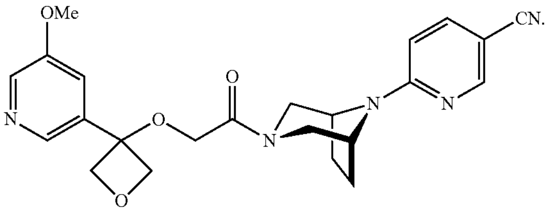
In embodiments, the compound is
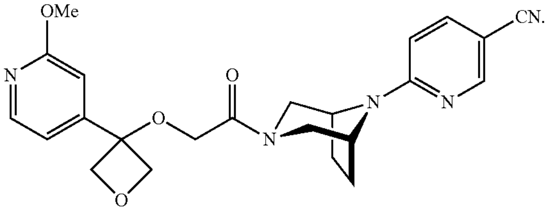
In embodiments, the compound is
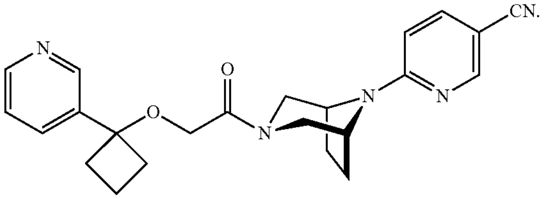
In embodiments, the compound is
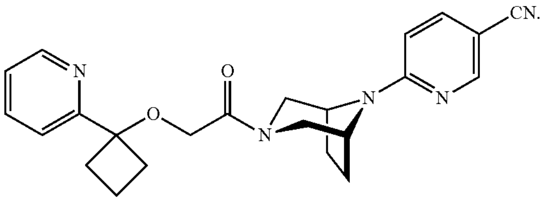
In embodiments, the compound is
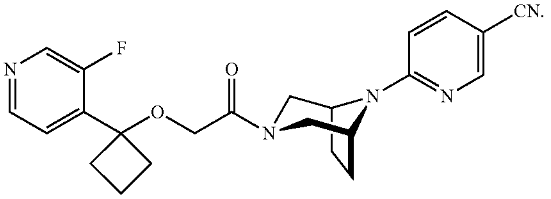
In embodiments, the compound is
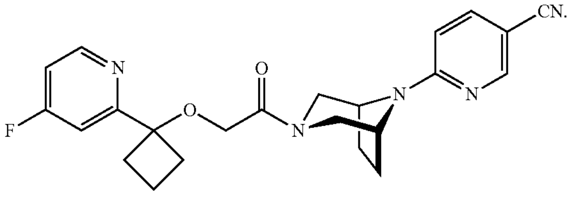
In embodiments, the compound is
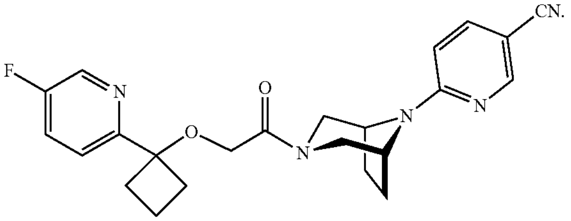
In embodiments, the compound is
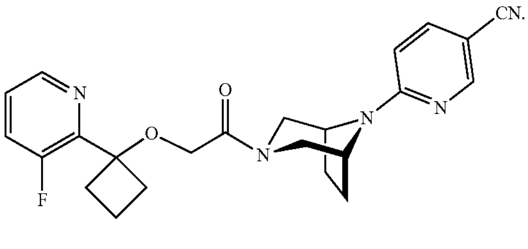

In embodiments, the compound is
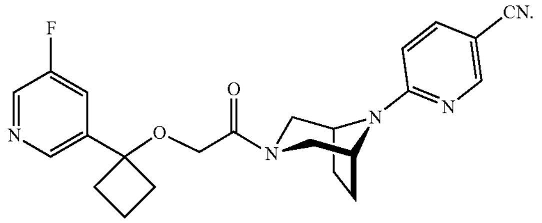
In embodiments, the compound is
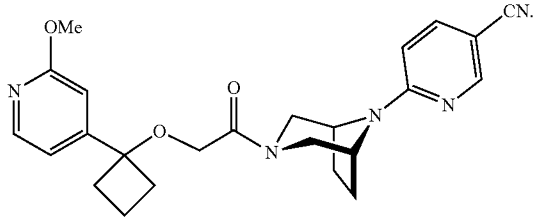
In embodiments, the compound is
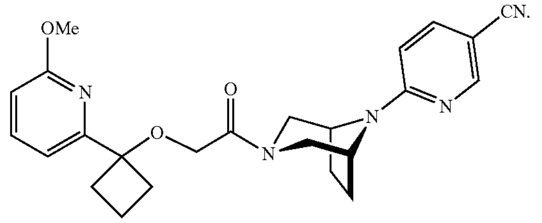
In embodiments, the compound is
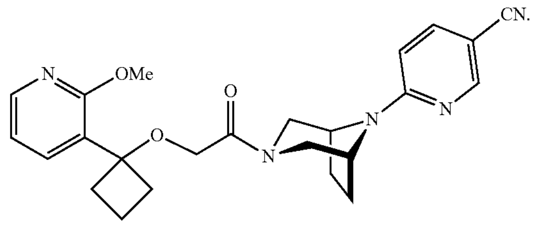
In embodiments, the compound is
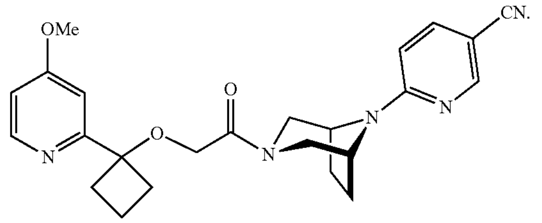
In embodiments, the compound is
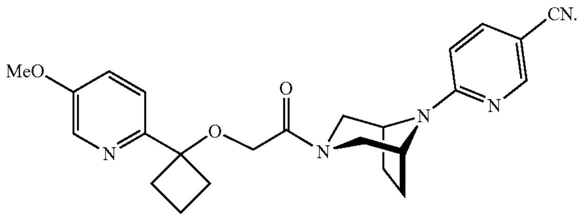
In embodiments, the compound is
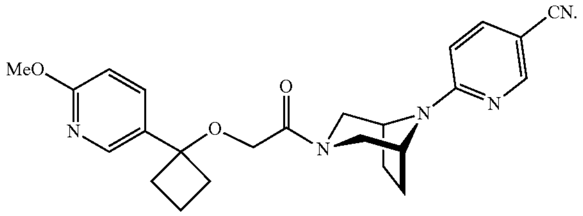
In embodiments, the compound is
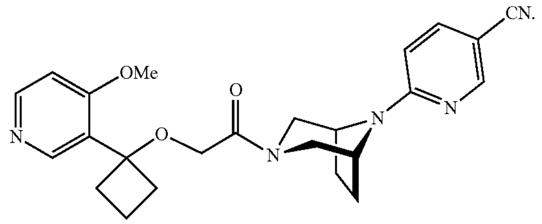
In embodiments, the compound is
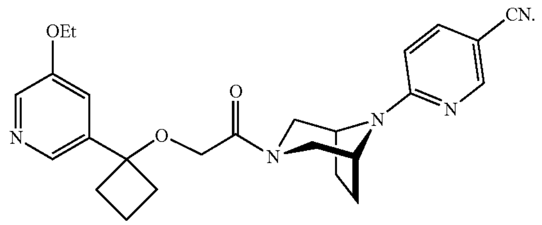
In embodiments, the compound is
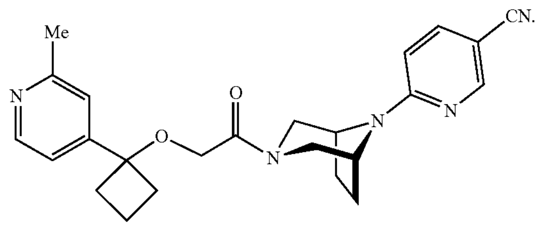

In embodiments, the compound is
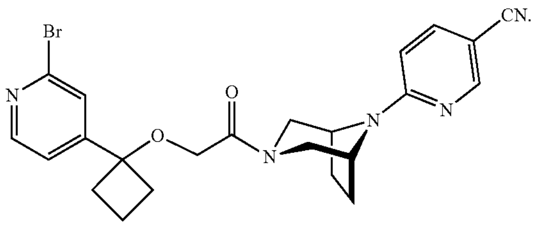
In embodiments, the compound is
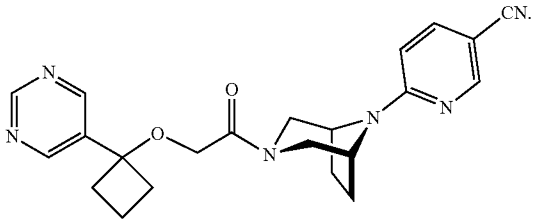
In embodiments, the compound is
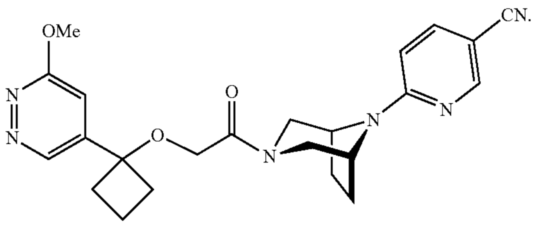
In embodiments, the compound is
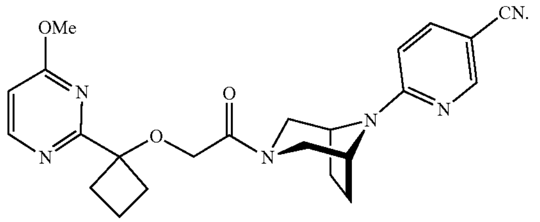
In embodiments, the compound is
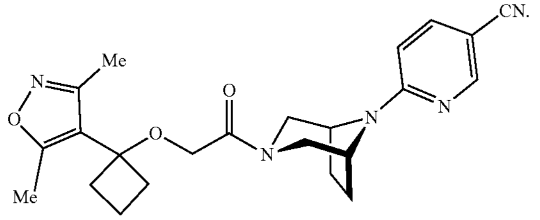
In embodiments, the compound is
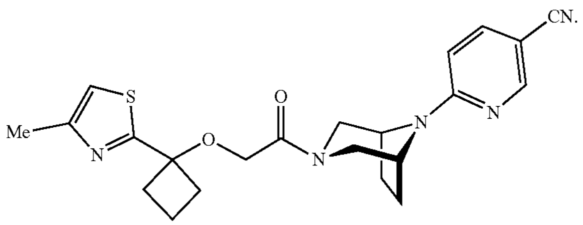
In embodiments, the compound is
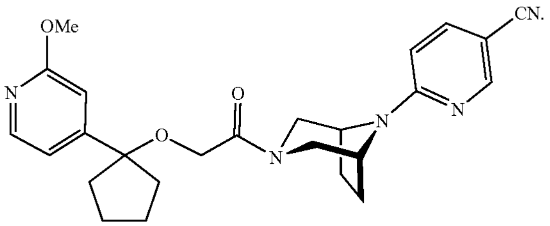
In embodiments, the compound is
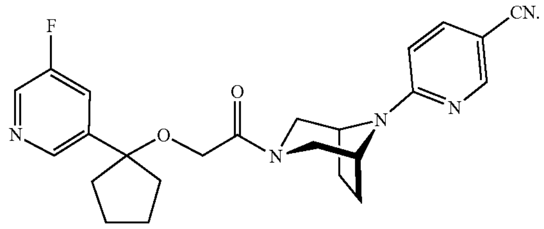
In embodiments, the compound is
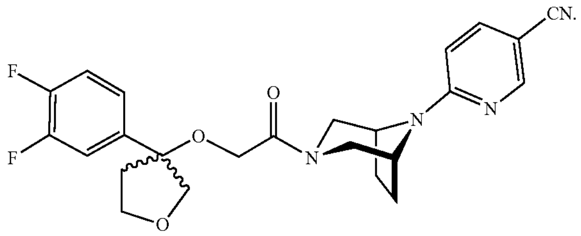
In embodiments, the compound is
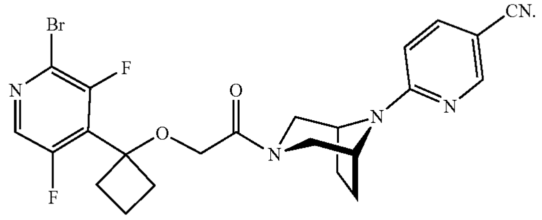

In embodiments, the compound is
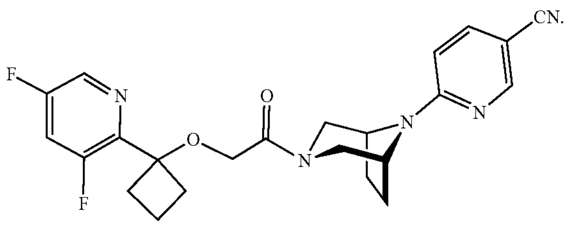
In embodiments, the compound is
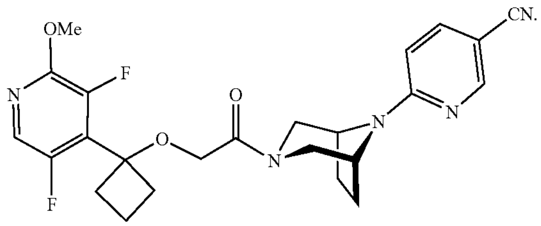
In embodiments, the compound is
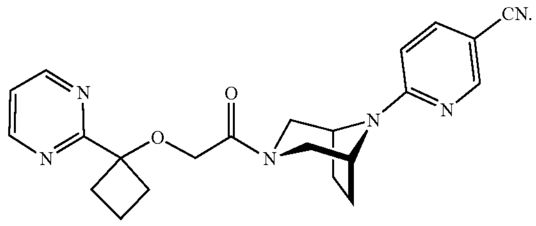
In embodiments, the compound is
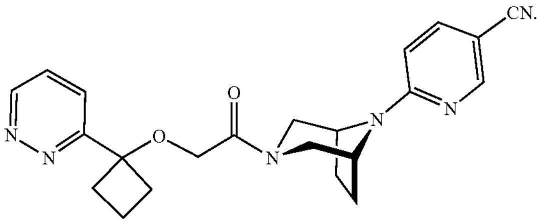
In embodiments, the compound is
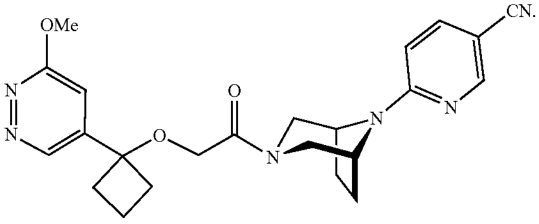
In embodiments, the compound is
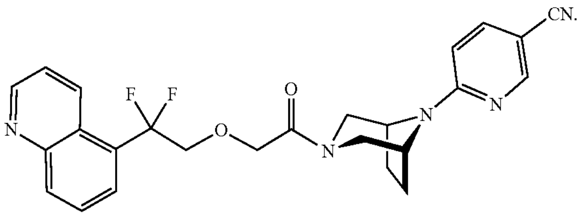
In embodiments, the compound is
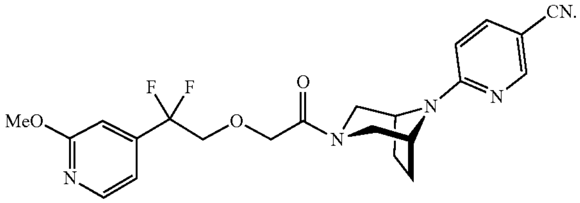
In embodiments, the compound is
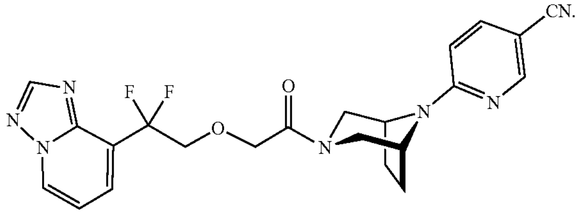
In embodiments, the compound is
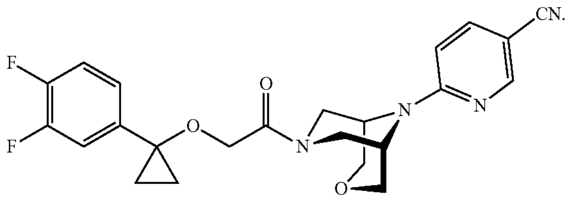
In embodiments, the compound is
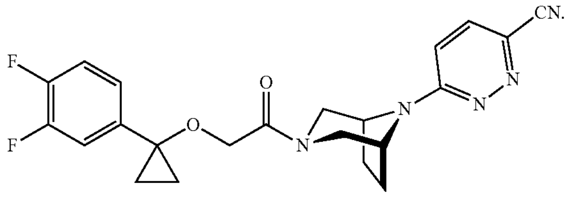

In embodiments, the compound is
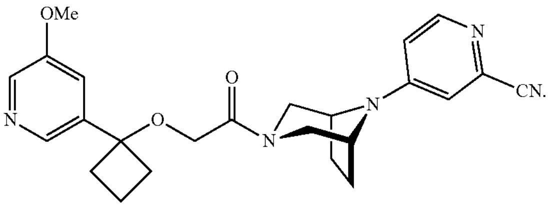
In embodiments, the compound is
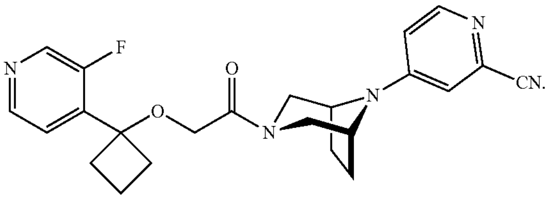
In embodiments, the compound is
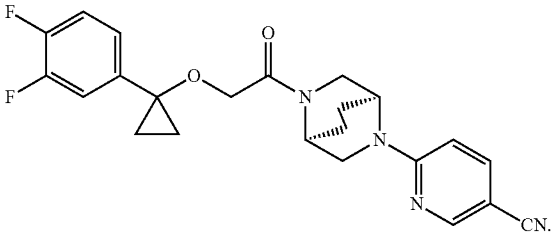 [SMILES: N#Cc1ccc(N2C[C@@H]3CC[C@H]2CN3C(=O)COC2(c3ccc(F)c(F)c3)CC2)nc1]
In embodiments, the compound is
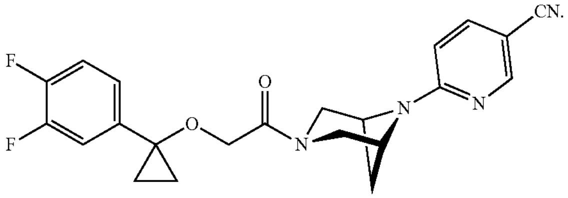
In embodiments, the compound is
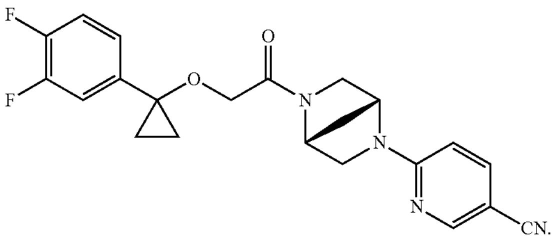 [SMILES: N#Cc1ccc(N2C[C@H]3C[C@@H]2CN3C(=O)COC2(c3ccc(F)c(F)c3)CC2)nc1]
In embodiments, the compound is
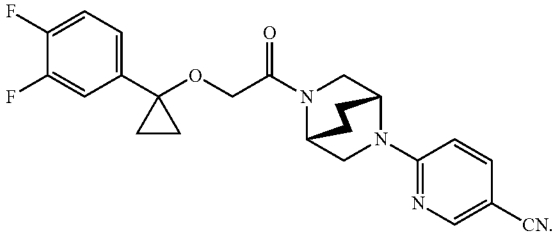
In embodiments, the compound is
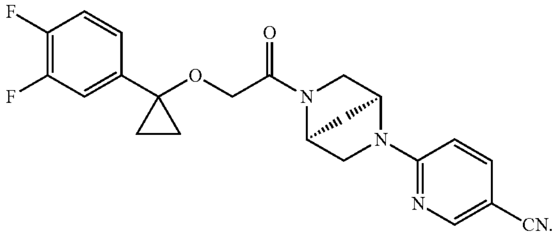 [SMILES: N#Cc1ccc(N2C[C@@H]3C[C@H]2CN3C(=O)COC2(c3ccc(F)c(F)c3)CC2)nc1]
In embodiments, the compound is
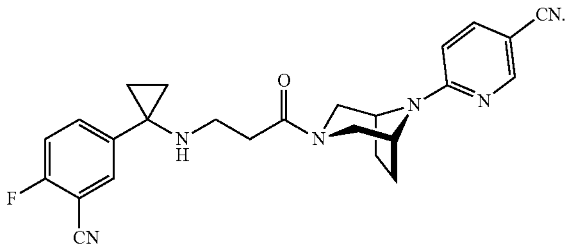
In embodiments, the compound is
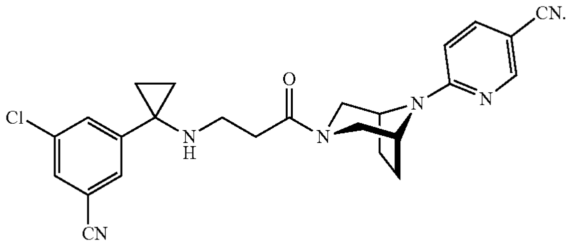
In embodiments, the compound is
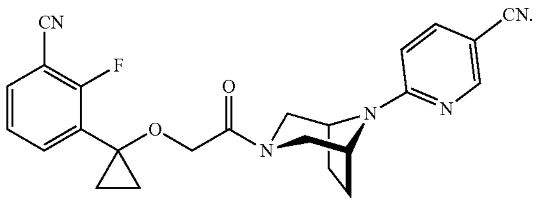

In embodiments, the compound is
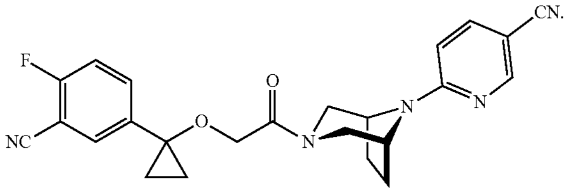
In embodiments, the compound is
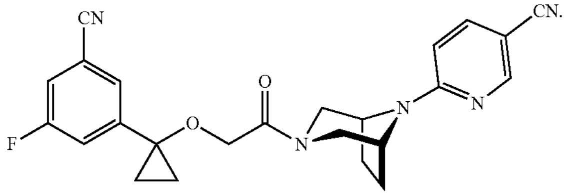
In embodiments, the compound is
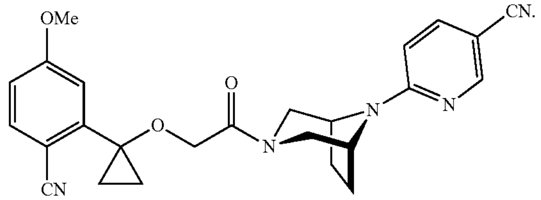
In embodiments, the compound is
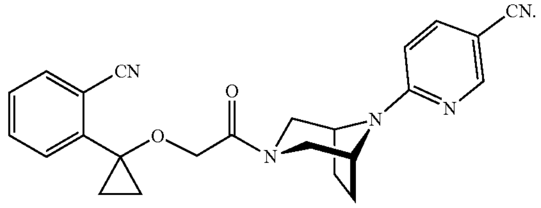
In embodiments, the compound is
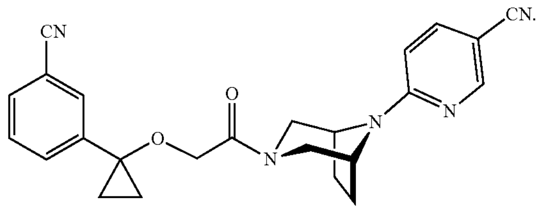
In embodiments, the compound is
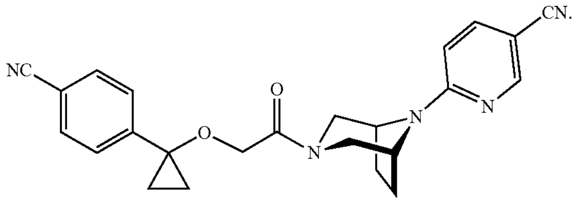
In embodiments, the compound is
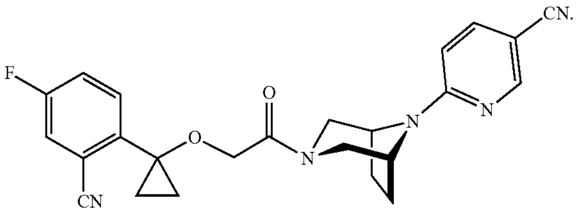
In embodiments, the compound is
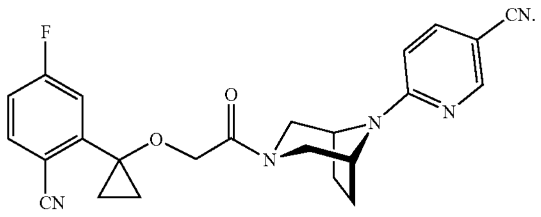
In embodiments, the compound is
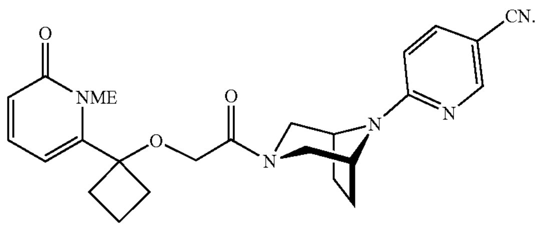
In embodiments, the compound is
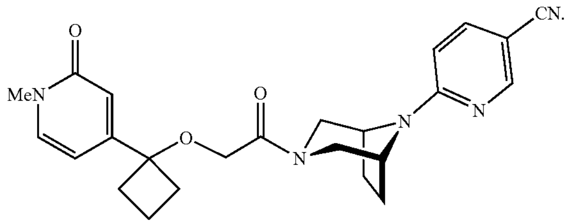

In embodiments, the compound is
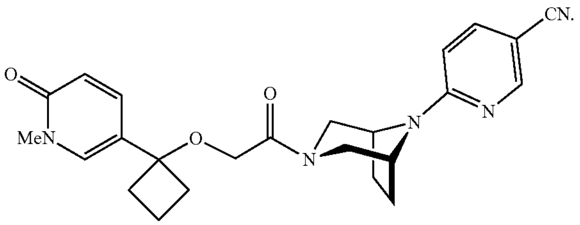
In embodiments, the compound is
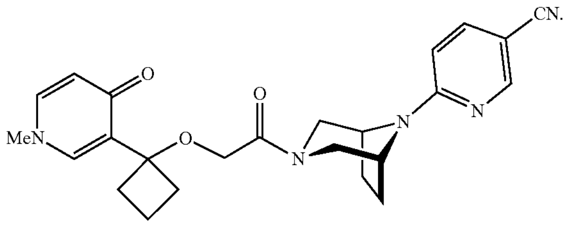
In embodiments, the compound is
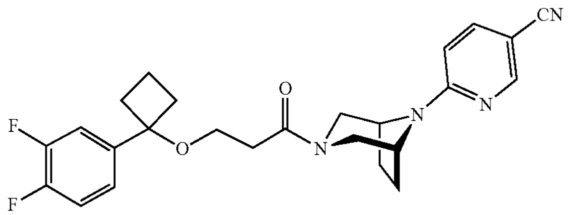
In embodiments, the compound is
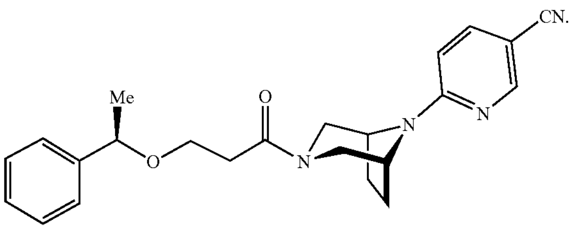
In embodiments, the compound is
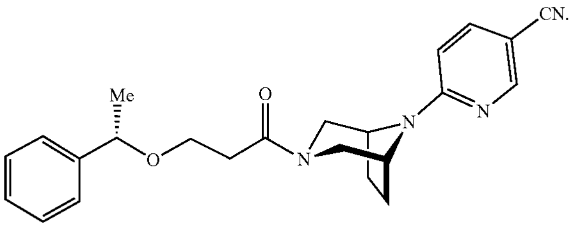
In embodiments, the compound is
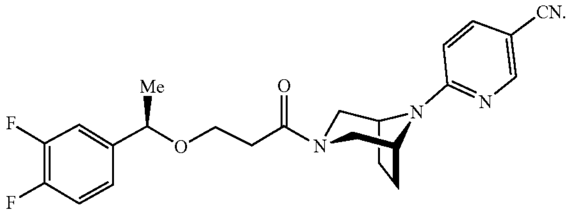
In embodiments, the compound is
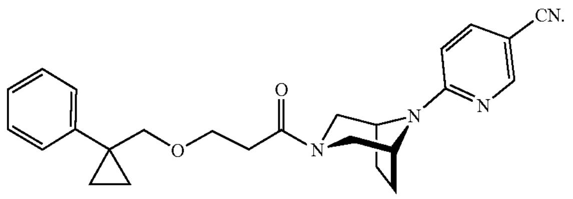
In embodiments, the compound is
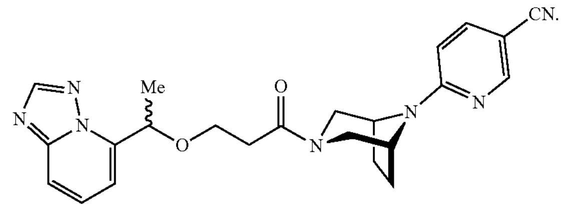
In embodiments, the compound is
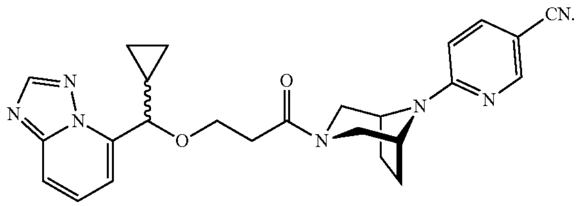
In embodiments, the compound is
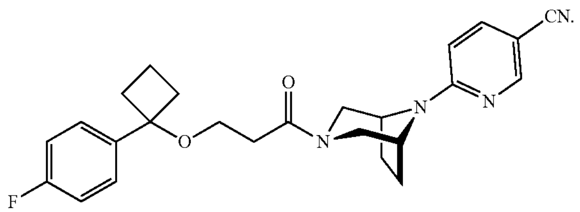

In embodiments, the compound is
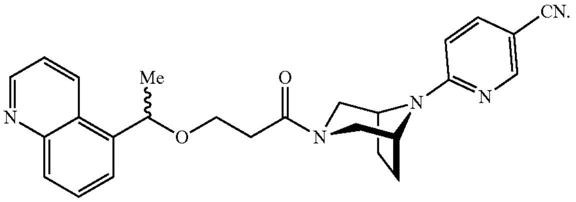
In embodiments, the compound is
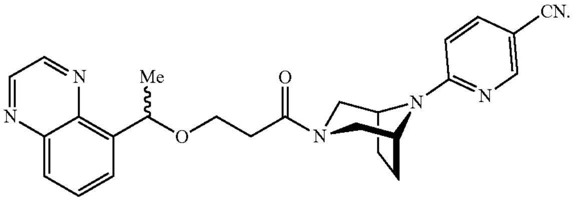
In embodiments, the compound is
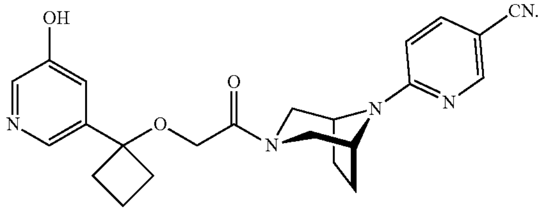
In embodiments, the compound is
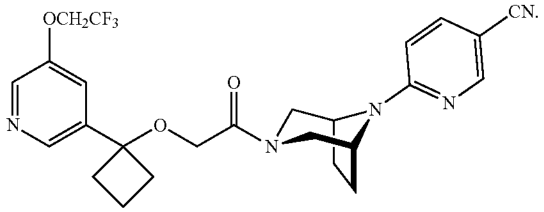
In embodiments, the compound is
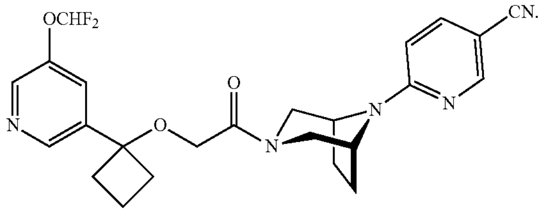
In embodiments, the compound is
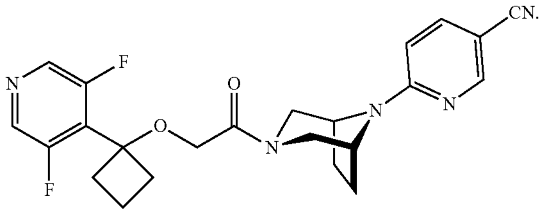
In embodiments, the compound is
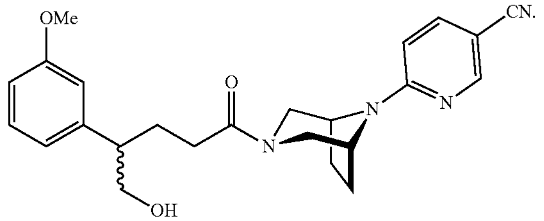
In embodiments, the compound is
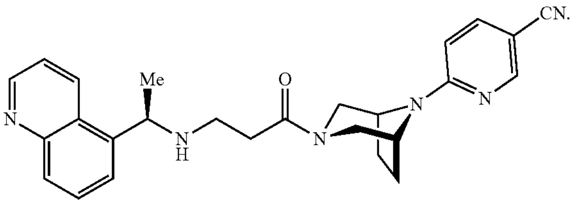
In embodiments, the compound is
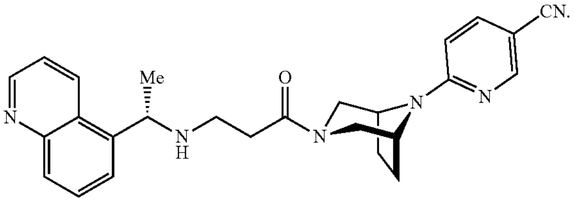
In embodiments, the compound is
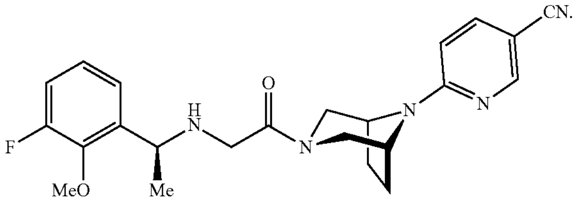

In embodiments, the compound is

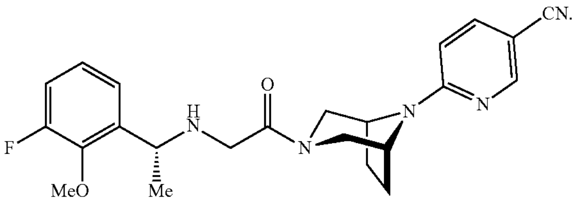

In embodiments, the compound is

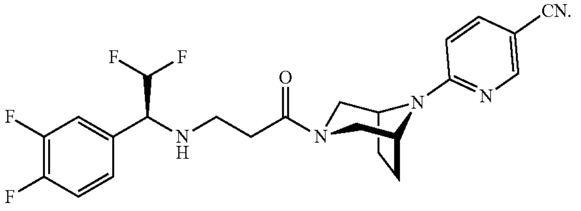

In embodiments, the compound is

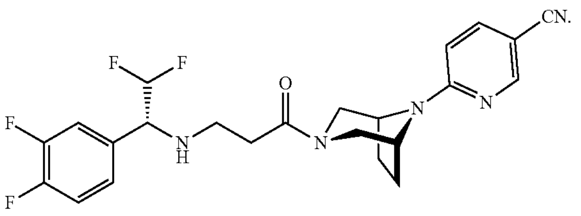

In embodiments, the compound is

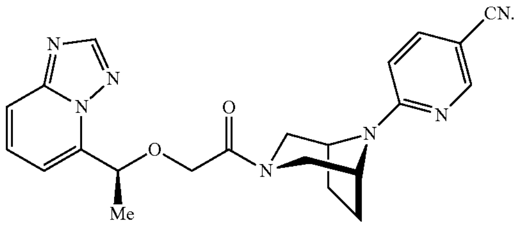

In embodiments, the compound is

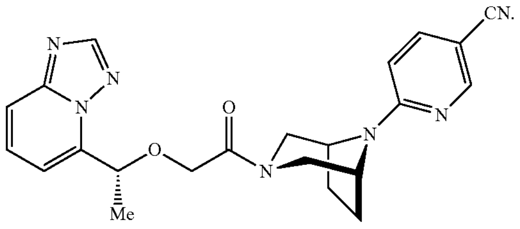

In embodiments, the compound is

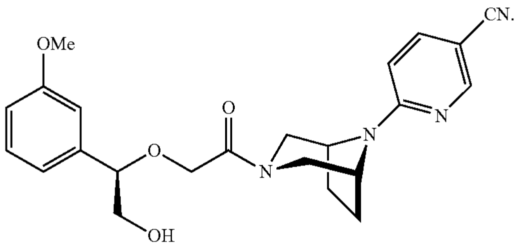

In embodiments, the compound is

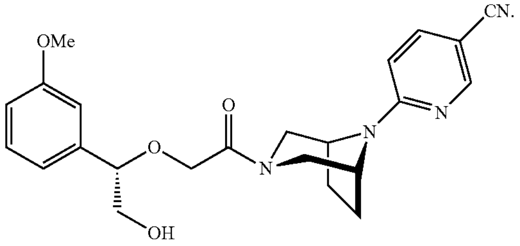

In embodiments, the compounds listed in this paragraph may exist as a pharmaceutically acceptable salt or solvate thereof.

In embodiments, the compound is useful as a comparator compound. In embodiments, the comparator compound can be used to assess the activity of a test compound in an assay (e.g., an assay as described herein, for example in the examples section, figures, or tables).

In embodiments, the compound is a compound described herein (e.g., in the Compounds section, Examples Section, Methods Section, or in a claim, table, or figure).

III. FURTHER FORMS OF THE COMPOUNDS

Isomers

The compounds described herein include all possible tautomers within the formulas described herein. Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

In some situations, the compounds described herein possess one or more chiral centers and each center exists in the (R)-configuration, or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term “geometric isomer” refers to E or Z geometric isomers (e.g., cis or trans) of an alkene double bond. The term “positional isomer” refers to structural isomers around a central ring, such as ortho-, meta-, and para-isomers around a benzene ring.

Labeled Compounds

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present disclosure, whether radioactive or not, are encompassed within the scope of the present disclosure.

In certain embodiments, the compounds disclosed herein have some or all of the $^{1}H$ atoms replaced with $^{2}H$ atoms. The methods of synthesis for deuterium-containing compounds are known in the art. In some embodiments deuterium substituted compounds are synthesized using various methods such as described in: Dean, D. C.; “Recent Advances in the Synthesis and Applications of Radiolabeled Compounds for Drug Discovery and Development,” *Curr. Pharm. Des.,* 2000, 6(10); George W; Varma, R. S., “The Synthesis of Radiolabeled Compounds via Organometallic Intermediates,” *Tetrahedron,* 1989, 45(21), 6601-21; and Evans, E. A., “Synthesis of radiolabeled compounds,” *J. Radioanal. Chem.,* 1981, 64(1-2), 9-32.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The present disclosure provides for methods of treating diseases by administering such solvates. The present disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The present disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present disclosure. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in Fleisher, D. et al., "Improved oral drug delivery: solubility limitations overcome by the use of prodrugs," *Advanced Drug Delivery Reviews,* 1996, 19, 115-130.

Amine derived prodrugs include, but are not limited to the following groups and combinations of groups:

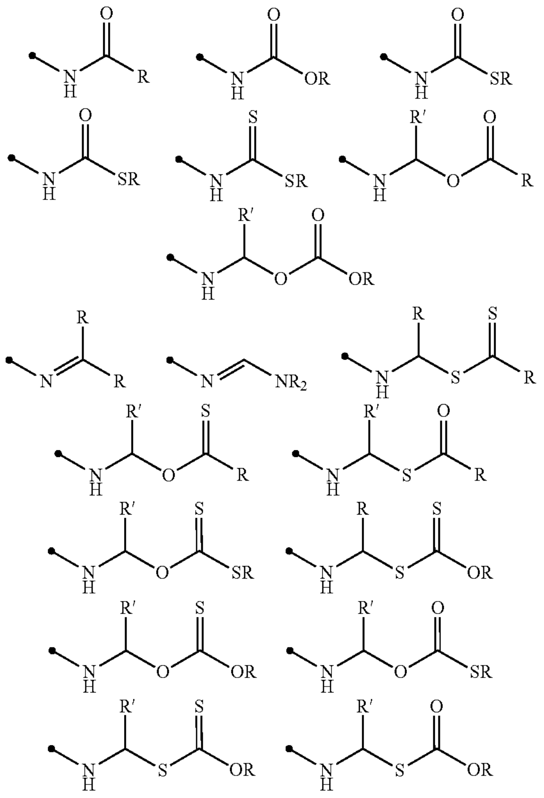

as well as sulfonamides and phosphonamides.

IV. PHARMACEUTICAL COMPOSITIONS

In embodiments, the compound described herein (e.g., of Formula (IA-1), (IB-1), (IA), (IB), (IIA), (IIB), or (III)) is administered as a pure chemical. In embodiments, the compound as described herein (e.g., of Formula (IA-1), (IB-1), (IA), (IB), (IIA), (IIB), or (III)) is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Gennaro, A. R., "Remington: The Science and Practice of Pharmacy," $21^{st}$ ed., Easton: Lippincott Williams & Wilkins, 2005.

In certain embodiments, the compound of Formula (IA), (IB), (IIA), (IIB), or (III) as described herein is administered as a pure chemical. In some embodiments, the compound of Formula (IA), (IB), (IIA), (IIB), or (III) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Gennaro, A. R., "Remington: The Science and Practice of Pharmacy," $21^{st}$ ed., Easton: Lippincott Williams & Wilkins, 2005.

Accordingly, provided herein is a pharmaceutical composition comprising at least one compound of Formula (IA-1), (IB-1), (IA), (IB), (IIA), (IIB), or (III) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

Accordingly, provided herein is a pharmaceutical composition comprising at least one compound of Formula (IA), (IB), (IIA), (IIB), or (III) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (IA-1), or a pharmaceutically acceptable salt thereof.

One embodiment provides a pharmaceutical composition comprising a pharmaceutically acceptable excipient and a compound of Formula (IB-1), or a pharmaceutically acceptable salt thereof.

One embodiment provides a pharmaceutical composition comprising a pharmaceutically acceptable excipient and a compound of Formula (IA), or a pharmaceutically acceptable salt thereof.

One embodiment provides a pharmaceutical composition comprising a pharmaceutically acceptable excipient and a compound of Formula (IB), or a pharmaceutically acceptable salt thereof.

One embodiment provides a pharmaceutical composition comprising a pharmaceutically acceptable excipient and a compound of Formula (IIA), or a pharmaceutically acceptable salt thereof.

One embodiment provides a pharmaceutical composition comprising a pharmaceutically acceptable excipient and a compound of Formula (IIB), or a pharmaceutically acceptable salt thereof.

One embodiment provides a pharmaceutical composition comprising a pharmaceutically acceptable excipient and a compound of Formula (III), or a pharmaceutically acceptable salt thereof.

In embodiments, the pharmaceutical composition includes a compound selected from Compound List 1, or a pharmaceutically acceptable salt thereof, and a pharmaceutically acceptable excipient.

In embodiments, the compound described herein (e.g., of Formula (IA-1), (IB-1), (IA), (IB), (IIA), (IIB), or (III)) is substantially pure, in that it contains less than about 5%, or less than about 1%, or less than about 0.1%, of other organic small molecules, such as contaminating intermediates or by-products that are created, for example, in one or more of the steps of a synthesis method.

In certain embodiments, the compound of Formula (IA), (IB), (IIA), (IIB), or (III) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous), vaginal, ophthalmic, or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid pre-formulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (e.g., Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound described herein (e.g., of Formula (IA-1), (IB-1), (IA), (IB), (IIA), (IIB), or (III)) differs, depending upon the patient's (e.g., human) condition, that is, stage of the disease, general health status, age, and other factors.

The dose of the composition comprising at least one compound of Formula (IA), (IB), (IIA), (IIB), or (III) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Disclosed compounds are administered to subjects or patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

V. METHODS OF USING THE COMPOUNDS AND COMPOSITIONS

Antagonists of mAChR $M_1$

The muscarinic acetylcholine receptor $M_1$ (mAChR $M_1$) is found in both the central and peripheral nervous systems, particularly in the cerebral cortex and sympathetic ganglia.

Notably, $M_1$ is expressed on oligodendrocyte precursor cells (OPCs) in the central nervous system. Over time, OPCs will differentiate into myelin-producing oligodendrocytes. Myelin is indispensable for action potential conduction along the axon and its loss has been attributed to neurodegenerative disorders, specifically multiple sclerosis. In some embodiments, selective mAChR $M_1$ antagonists accelerate OPC differentiation into oligodendrocytes. In some embodiments, selective mAChR $M_1$ antagonists are useful in the treatment of demyelinating disorders, such as multiple sclerosis. In some embodiments, selective mAChR $M_1$ antagonists are useful in treating epileptic disorders and certain movement disorders, including Parkinson's disease, dystonia, and fragile X syndrome.

In one aspect, the compounds disclosed herein are selective antagonists of the muscarinic acetylcholine $M_1$ receptor (mAChR $M_1$). In some embodiments, the compounds disclosed herein are selective antagonists of the muscarinic acetylcholine $M_1$ receptor (mAChR $M_1$) over one or more of the mAChR $M_2$, $M_3$, $M_4$, or $M_5$ receptors. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_3$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_4$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_5$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$, $M_3$, $M_4$, or $M_5$, or combinations thereof.

Treatment Methods

The compounds disclosed herein are useful for treating, preventing, ameliorating, controlling or reducing the risk of a variety of disorders wherein the patient or subject would benefit from antagonism of the muscarinic acetylcholine $M_1$ receptor.

In one aspect, a treatment can include selective $M_1$ receptor antagonism to an extent effective to affect cholinergic activity. Thus, disorders for which the compounds disclosed herein are useful can be associated with cholinergic activity, for example cholinergic hyperfunction. In some embodiments, provided herein is a method of treating or preventing a disorder in a subject comprising the step of administering to the subject a compound disclosed herein, or a pharmaceutically acceptable salt or solvate thereof, or a pharmaceutical composition described herein in a dosage and amount effective to treat the disorder in the subject.

Provided herein is a method for the treatment of one or more disorders, for which muscarinic acetylcholine receptor inhibition is predicted to be beneficial, in a subject comprising the step of administering to the subject a compound disclosed herein, or a pharmaceutically acceptable salt or solvate thereof, or a pharmaceutical composition described herein in a dosage and amount effective to treat the disorder in the subject.

In some embodiments provided herein is a method of treating a neurodegenerative disorder in a subject in need thereof, comprising administering to subject a therapeutically effective amount of a compound described herein (e.g., of Formula (IA-1), (IB-1), (IA), (IB), (IIA), (IIB), or (III)), or a pharmaceutically acceptable salt or solvate thereof.

In some embodiments provided herein is a method of treating a neurodegenerative disorder in a subject in need thereof, comprising administering to subject a therapeutically effective amount of a compound of Formula (IA), (IB), (IIA), (IIB), or (III), or a pharmaceutically acceptable salt or solvate thereof.

In embodiments, the method of treating a neurodegenerative disorder in a subject in need thereof includes administering an effective amount of a compound selected from Compound List 1, or a pharmaceutically acceptable salt or solvate thereof.

In some embodiments provided herein is a method of treating neuropathy in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof. In some embodiments is a method of treating neuropathy in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof, wherein the neuropathy is diabetic neuropathy.

In some embodiments provided herein is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is diabetic neuropathy.

In embodiments, the method of treating neuropathy in a subject in need thereof includes administering an effective amount of a compound selected from Compound List 1, or a pharmaceutically acceptable salt or solvate thereof.

In some embodiments is a method of treating a demyelinating disease in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof. In some embodiments is a method of treating a demyelinating disease in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound described herein (e.g., of Formula (IA-1), (IB-1), (IA), (IB), (IIA), (IIB), or (III)), or a pharmaceutically acceptable salt or solvate thereof, wherein the demyelinating disease is a demyelinating disease of the peripheral nervous system.

In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the peripheral nervous system.

In embodiments, the method of treating a demyelinating disease in a subject in need thereof includes administering an effective amount of a compound selected from Compound List 1, or a pharmaceutically acceptable salt or solvate thereof.

In some embodiments is a method of modulating muscarinic acetylcholine receptor $M_1$ activity in a subject comprising administering to the subject a compound described herein (e.g., of Formula (IA-1), (IB-1), (IA), (IB), (IIA), (IIB), or (III)), or a pharmaceutically acceptable salt or solvate thereof. In some embodiments, the compound described herein (e.g., of Formula (IA-1), (IB-1), (IA), (IB), (IIA), (IIB), or (III)), or a pharmaceutically acceptable salt or solvate thereof acts as a selective $M_1$ antagonist.

In some embodiments is a method of modulating muscarinic acetylcholine receptor $M_1$ activity in a subject comprising administering to the subject a compound of Formula (IA), (IB), (IIA), (IIB), or (III), or a pharmaceutically acceptable salt or solvate thereof. In some embodiments, the compound of Formula (IA), (IB), (IIA), (IIB), or (III), or a pharmaceutically acceptable salt or solvate thereof acts as a selective $M_1$ antagonist.

In embodiments, the method of modulating muscarinic acetylcholine receptor $M_1$ activity in a subject includes administering a compound selected from Compound List 1, or a pharmaceutically acceptable salt or solvate thereof.

VI. COMBINATION THERAPY

Also contemplated herein are combination therapies, for example, co-administering a disclosed compound and an additional active agent, as part of a specific treatment regimen intended to provide the beneficial effect from the co-action of these therapeutic agents. In some embodiments, a compound described herein is administered in combination with one or more immunomodulatory agents. In some embodiments, a compound described herein is administered in combination with one or more immunomodulatory agents, wherein the immunomodulatory agents are selected from an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or other SIP1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide. In some embodiments, the immunomodulatory agent is an IFN-β 1 molecule. In some embodiments, the immunomodulatory agent is a corticosteroid. In some embodiments, the immunomodulatory agent is a polymer of glutamic acid, lysine, alanine and tyrosine or glatiramer. In some embodiments, the immunomodulatory agent is an antibody or fragment thereof against alpha-4 integrin or natalizumab. In some embodiments, the immunomodulatory agent is an anthracenedione molecule or mitoxantrone. In some embodiments, the immunomodulatory agent is a fingolimod or other S1P1 functional modulator. In some embodiments, the immunomodulatory agent is a dimethyl fumarate or other NRF2 functional modulator. In some embodiments, the immunomodulatory agent is an antibody to the alpha subunit of the IL-2 receptor of T cells (CD25) or daclizumab. In some embodiments, the immunomodulatory agent is an antibody against CD52 or alemtuzumab. In some embodiments, the immunomodulatory agent is an antibody against CD20 or ocrelizumab. In some embodiments, the immunomodulatory agent is an inhibitor of a dihydroorotate dehydrogenase or teriflunomide.

The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

The following examples are provided merely as illustrative of various embodiments and shall not be construed to limit the invention in any way.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

VII. PREPARATION OF THE COMPOUNDS

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Comwall, U.K.), Lancaster Synthesis (Windham, NH), Matrix Scientific, (Columbia, SC), Maybridge Chemical Co. Ltd. (Comwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry," New York: John Wiley & Sons, Inc., 1982; Sandler S. R. et al., "Organic Functional Group Preparations," $2^{nd}$ ed., New York: Academic Press, 1983; House, H. O., "Modern Synthetic Reactions," $2^{nd}$ ed., Menlo Park: W. A. Benjamin, Inc., 1972; Gilchrist, T. L., "Heterocyclic Chemistry," $2^{nd}$ ed., New York: Wiley, 1992; March, J., "Advanced Organic Chemistry: Reactions, Mechanisms and Structure," $4^{th}$ ed., New York: Wiley, 1992. Additional suitable reference books and treatises that detail the synthesis of reactants useful in the preparation of compounds described herein, or provide references to articles that describe the preparation, include for example, Fuhrhop, J., Penzlin, G., "Organic Synthesis: Concepts, Methods, Starting Materials," $2^{nd}$ ed., New York: Wiley, 1994; Hoffman, R. V., "Organic Chemistry, An Intermediate Text," Oxford: Oxford University Press, 1996; Larock, R. C., "Comprehensive Organic Transformations: A Guide to Functional Group Preparations," $2^{nd}$ ed., New York: Wiley, 1999; Otera, J., "Modern Carbonyl Chemistry," New York: Wiley, 2000; Solomons, T. W. G., "Organic Chemistry," $7^{th}$ ed., New York: Wiley, 2000; Stowell, J. C., "Intermediate Organic Chemistry," $2^{nd}$ ed., New York: Wiley, 1993; "Industrial Organic Chemicals: Starting Materials and Intermediates: An Ullmann's Encyclopedia," New York: Wiley, in 8 volumes; "Organic Reactions," New York: Wiley, in over 55 volumes; and "Chemistry of Functional Groups," New York: Wiley, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is Stahl, P. H., Wermuth, C. G., "Handbook of Pharmaceutical Salts," Zurich: Verlag Helvetica Chimica Acta, 2002.

LIST OF ABBREVIATIONS

As used above, and throughout the description of the present disclosure, the following abbreviations, unless otherwise indicated, shall be understood to have the following meanings:

ACN or MeCN acetonitrile
aq aqueous
Bn benzyl
Bu butyl
BOC or Boc tert-butyl carbamate
BrettPhos 2-(dicyclohexylphosphino)-3,6-dimethoxy-2'4'6'-triisopropyl-1,1'-biphenyl
BSA bovine serum albumin
CDI 1,1'-carbonyldiimidazole
CHO Chinese hamster ovary
Cy cyclohexyl dba dibenzylideneacetone
DAST diethylaminosulfur trifluoride
DCC N,N'-dicyclohexylcarbodiimide
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DME 1,2-dimethoxyethane
DMEM Dulbecco's modified eagle medium
DMF N,N-dimethylformamide
DMA N,N-dimethylacetamide
DMSO dimethylsulfoxide
EDC N-(3-dimethylaminopropyl)-N'-ethylcarbodiimide
equiv equivalent(s)
Et ethyl
EtOH ethanol
EtOAc ethyl acetate
FBS fetal bovine serum
h hour(s)
HATU 1-[bis(dimethylamino)methylene]-1H-1,2,3-triazolo[4,5-b]pyridinium 3-oxide hexafluorophosphate
HEPES 4-(2-hydroxyethyl)-1-piperazineethanesulfonic acid
Hex hexanes
HPLC high performance liquid chromatography
LAH lithium aluminum hydride
LCMS or LC-MS liquid chromatography-mass spectrometry
LG leaving group
M molar
mCPBA meta-chloroperoxybenzoic acid
Me methyl
MeOH methanol
min minute(s)
MS mass spectroscopy
NMM N-methylmorpholine
NMP N-methyl-2-pyrrolidone
NMR nuclear magnetic resonance
Pd/C palladium on carbon
PG protecting group
PMB para-methoxybenzyl
RT room temperature
RuPhos Pd G3 (2-dicyclohexylphosphino-2',6'-diisopropoxy-1,1'-biphenyl)[2-(2'-amino-1,1'-biphenyl)] palladium(II) methanesulfonate
sec seconds
T3P propylphosphonic anhydride
$^t$BuXPhos Pd G3 [(2-di-tert-butylphosphino-2',4'6'-triisopropyl-1,1'-biphenyl)-2-(2'-amino-1,1'-biphenyl)]palladium(II) methanesulfonate
TBAF tetrabutylammonium fluoride
TEA triethylamine
TFA trifluoroacetic acid
THF tetrahydrofuran
TLC thin layer chromatography
XantPhos 4,5-bis(diphenylphosphino)-9,9-dimethylxanthene
XPhos 2-dicyclohexylphosphino-2'4'6'-triisopropylbiphenyl
XtalFluor-E® (diethylamino)difluorosulfonium tetrafluoroborate General Synthetic Scheme Compounds of Formula (IA) or (IB) of the present disclosure may be prepared, for example from amine (1a) or (1b), or its corresponding ammonium salt, and a carboxylic acid (2) in the presence of an appropriate coupling reagent such as HATU, CDI, T3P, or the like, and an appropriate base such as TEA, DIEA, or the like (Scheme 1). Alternatively, the acid may be pre-activated via its conversion into the corresponding acid chloride using an agent such as thionyl chloride, oxalyl chloride, or the like. The resulting amide (3a) or (3b), which itself may be a compound of Formula (IA) or (IB), can be further functionalized using synthetic methodologies known to those skilled in the art to deliver another compound of Formula (IA) or (IB). Examples of such transformations include, but are not limited to:

(a) reduction of an alkene or an alkyne in the presence of a catalyst such as Pd/C, $Pd(OH)_2$, or the like, and a reducing agent such as hydrogen gas, deuterium gas, or the like.
(b) cyclopropanation of an alkene in the presence of a methylene source such as trimethylsulfonium iodide, diazomethane, or the like, and a promoter such as potassium tert-butoxide, palladium(II) acetate, or the like.
(c) oxidation of a sulfide in the presence of an oxidant such as oxone, mCPBA, or the like.
(d) conversion of an appropriately functionalized 2- or 4-methoxypyridine into its corresponding 1-methylpyridin-2(1H)-one or 1-methylpyridin-4(1H)-one in the presence of a methyl source such as iodomethane, dimethyl sulfate, or the like, and a promoter such as sodium iodide, potassium iodide, or the like.
(e) conversion of an appropriate functionalized (hetero) aryl halide into its corresponding (hetero)aryl cyanide in the presence of a suitable palladium ligand complex as the catalyst and zinc cyanide as the cyanide source, or the like.
(f) separation of a mixture of stereoisomers into its stereochemically-enriched constituents utilizing an appropriate chiral column such as ChiralPAK OD, ChiralPAK AD, or the like.

Scheme 1

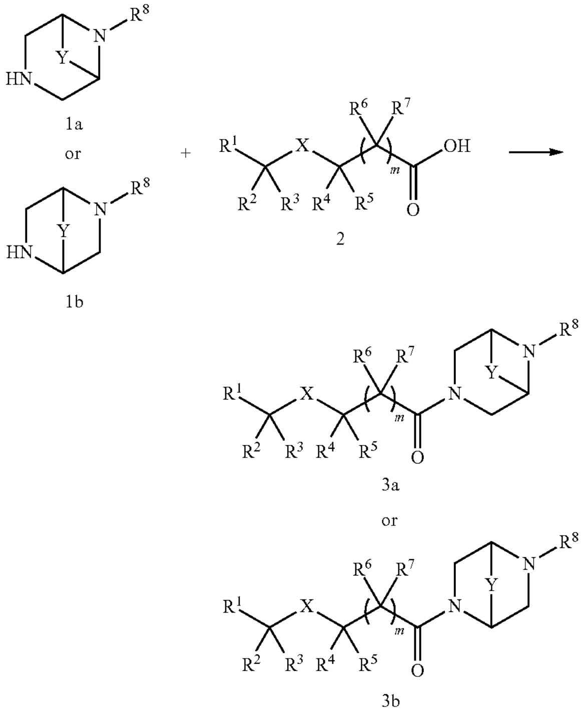

1a or 1b + 2 → 3a or 3b

Alternatively, it may be more advantageous to instead prepare compounds of Formula (IA) or (IB) via a three-step sequence (Scheme 2) involving the initial coupling of a suitably protected amine (4a) or (4b) with carboxylic acid (2), followed by the removal of the protecting group (PG) in amide (5a) or (5b) using conditions known to those skilled in the art (i.e. by treatment with HCl, TFA, or the like, when N-PG is a tert-butyl carbamate), and finally by reacting the resulting amine (6a) or (6b) with an appropriately functionalized (hetereo)aryl halide using, for example, standard nucleophilic aromatic substitution conditions (i.e. by heating the reactants in a polar, aprotic solvent in the presence of an appropriate base) or Buchwald-Hartwig coupling conditions (i.e. by coupling in the presence of a suitable palladium ligand complex as the catalyst and a metal alkoxide as the base), or the like.

Scheme 2

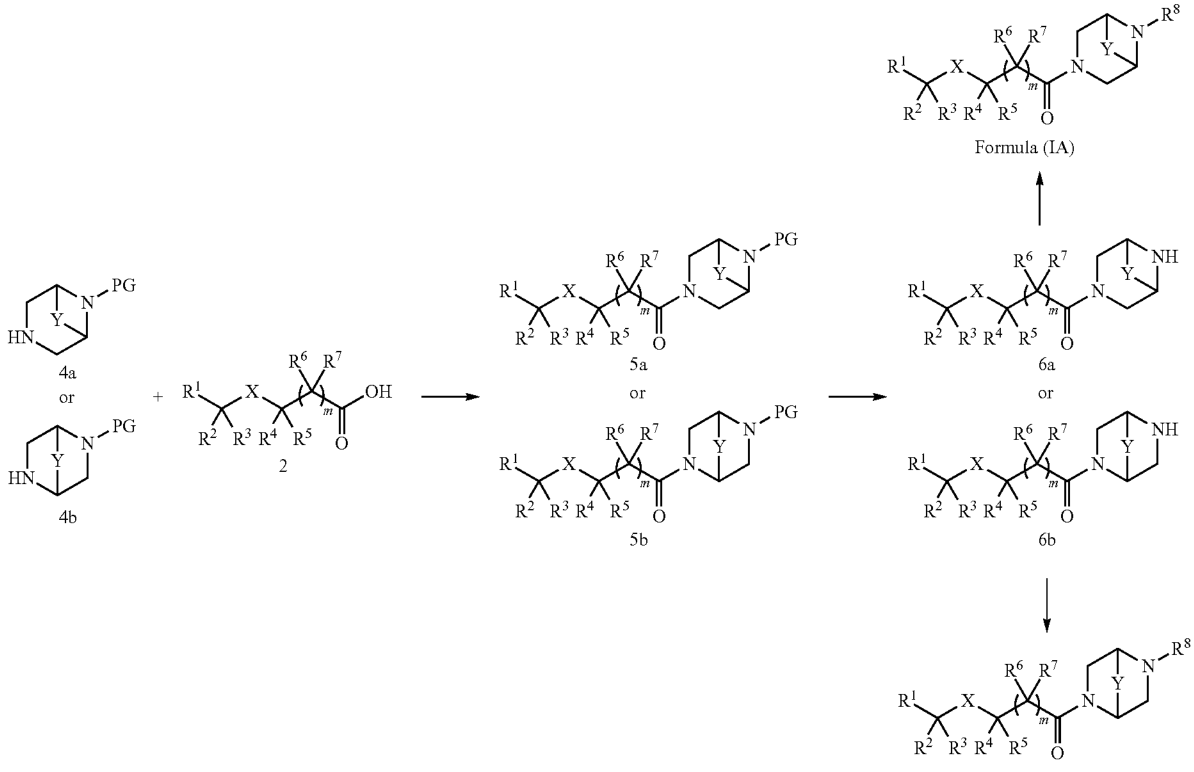

4a or 4b + 2 → 5a or 5b → 6a or 6b → Formula (IA) / Formula (IB)

For certain embodiments, a person skilled in the art can also access compounds of Formula (IA) or (IB) via the union of nucleophile (9) with electrophile (8a) or (8b) via direct nucleophilic displacement of the leaving group (LG) in (8a) or (8b) using conditions described in reference books and treatises that were highlighted previously (Scheme 3). In certain cases, especially when nucleophile (9) is an amine, it may be beneficial if (9) is first activated by its pretreatment with an agent such as the lithium chloride complex of isopropylmagnesium chloride, or the like. Electrophile (8a) or (8b) can itself be readily synthesized, for example, from amine (1a) or (1b) and acid chloride (7) in the presence of a suitable base like TEA, DIEA, or the like.

Scheme 3

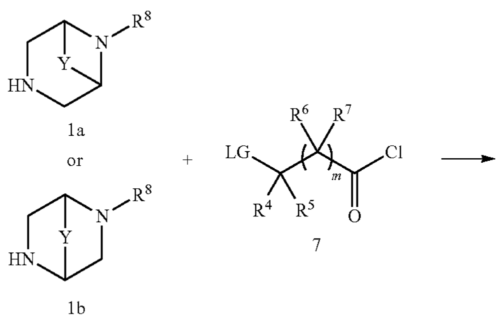

1a or 1b + 7

-continued

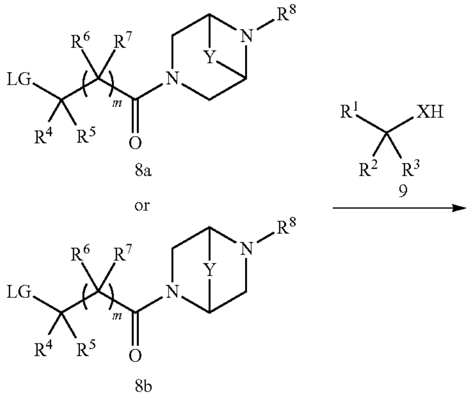

8a or 8b; 9

-continued

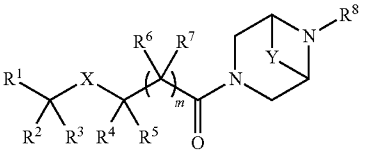

Formula (IA)

or

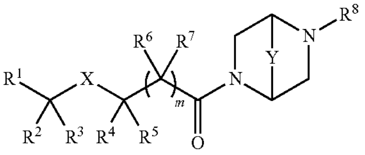

Formula (IB)

For certain embodiments, the aforementioned direct nucleophilic displacement may be best accomplished by using amide (11a) or (11b) as the nucleophile, itself readily prepared from amine (1a) or (1b) and acid (10) by, for example, a two-step amide coupling-deprotection sequence, and appropriately functionalized (12) as the electrophile (Scheme 4).

Scheme 4

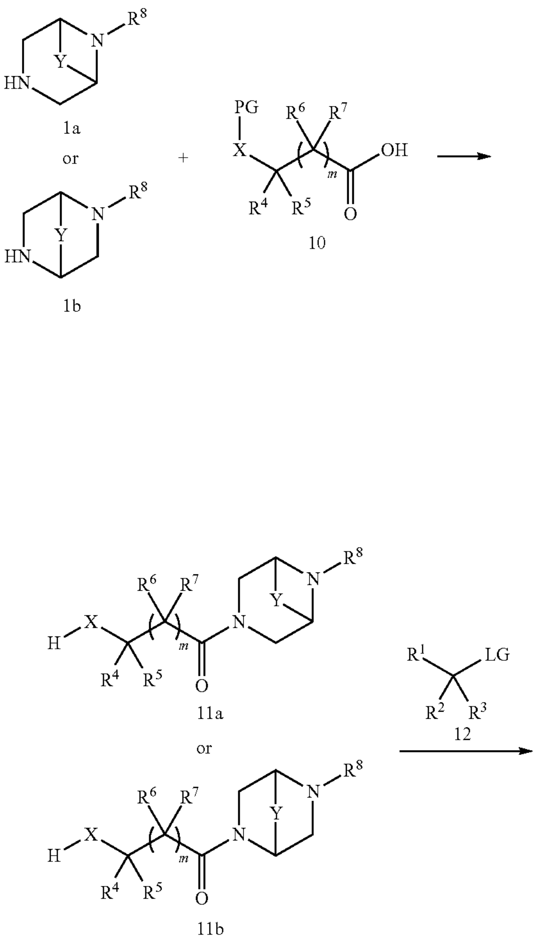

1a or 1b; 10; 11a or 11b; 12

-continued

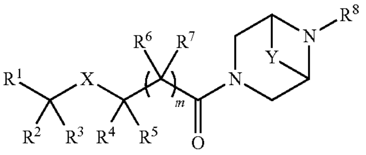

Formula (IA)

or

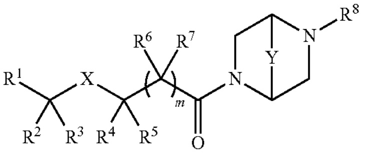

Formula (IB)

For certain embodiments where X in Formula (IA) or (IB) is NH, it may prove more advantageous to form the requisite bonds using ketone (14) and amine (13a) or (13b) under dehydrating conditions well known to a person skilled in the art (Scheme 5). The resulting Schiff base (15a) or (15b) can either be reduced, using a reagent such as lithium borohydride, sodium cyanoborohydride, or the like, or trapped with an organometallic compound such as Grignard reagent, (hetereo)aryl lithium reagent, or the like. In instances where the organometallic compound is an organosilicon reagent, it may be beneficial to add a fluoride activator such as TBAF, cesium fluoride, or the like.

Scheme 5

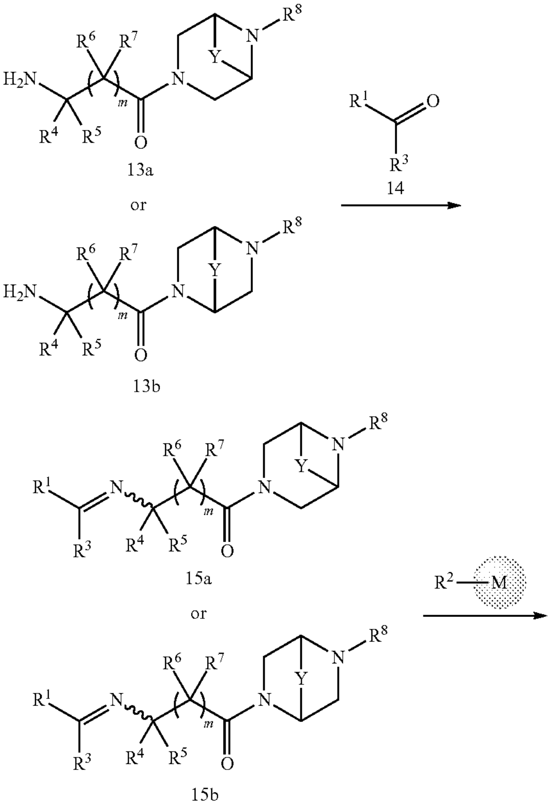

13a or 13b; 14; 15a or 15b

-continued

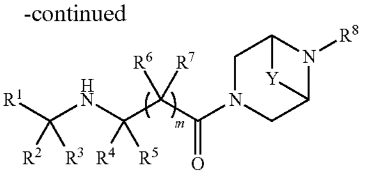

Formula (IA)

or

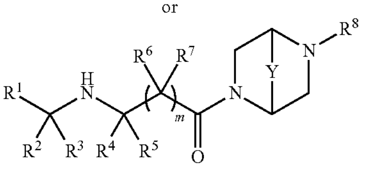

Formula (IB)

The general synthetic schemes above have been described in an illustrative manner and is intended to be in the nature of description rather than of limitation. It will also be appreciated that many of the reagents provided in the following examples may be substituted with other suitable reagents (see, e.g., is Fieser, L., et al., "Encyclopedia of Reagents for Organic Synthesis," $2^{nd}$ ed., New York: Wiley, 2009). In addition, it will be appreciated that conditions such as choice of solvent, temperature of reaction, volumes and reaction time may vary while still producing the desired compounds. Such changes and modifications, including without limitation, those relating to the chemical structures, substituents, derivatives, intermediates and/or syntheses provided herein, may be made without departing from the spirit and scope thereof.

VIII. EMBODIMENTS

Embodiment P1. A compound, or a pharmaceutically acceptable salt or solvate thereof, having the structure of Formula (IA) or (IB):

Formula (IA)

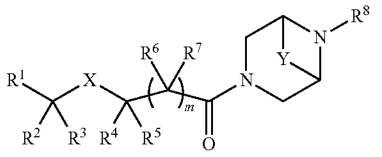

Formula (IB)

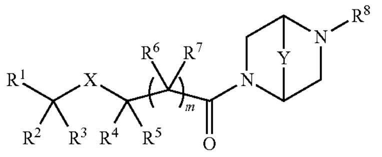

wherein:

X is a bond, —C($R^9$)($R^{10}$)—, —N($R^{11}$)—, —O—, —S(O)$_n$—, —$CH_2N$($R^{11}$)—, or —$CH_2O$—;

Y is a —$CH_2$—, —$CH_2CH_2$—, —CH═CH—, or —$CH_2OCH_2$—;

$R^1$ is

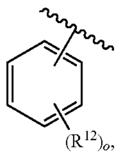 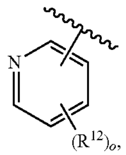 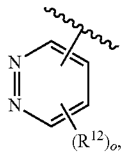 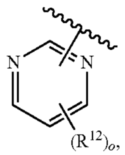 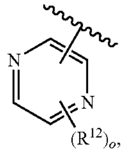 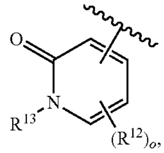 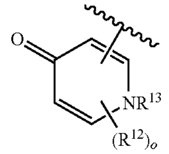 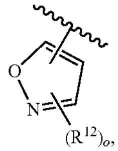 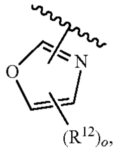 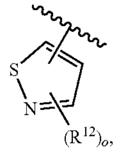 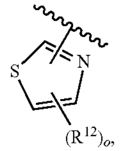 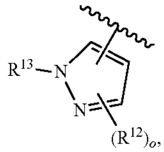 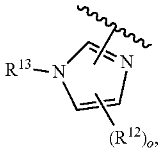 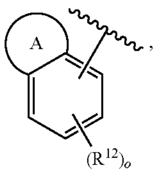 or 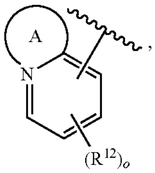

wherein ring A is a 5- or 6-membered heteroaryl ring or a 5- or 6-membered heterocycloalkyl ring optionally substituted with halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, S(O)$_n$($R^{16}$), or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^4$ and $R^5$ are independently selected from hydrogen, deuterium, halogen, and $C_{1-3}$ alkyl; or $R^3$ and $R^4$ combine to form a cycloalkyl or heterocycloalkyl ring optionally substituted with halogen, $C_{1-6}$ alkyl, or $C_{3-6}$ cycloalkyl; or $R^4$ and $R^5$ combine to form a cycloalkyl or heterocycloalkyl ring optionally substituted with halogen, $C_{1-6}$ alkyl, or $C_{3-6}$ cycloalkyl;

$R^6$ and $R^7$ are independently selected from hydrogen, deuterium, halogen, and $C_{1-3}$ alkyl; or $R^3$ and $R^7$ combine to form a cycloalkyl or heterocycloalkyl ring optionally substituted with halogen, $C_{1-6}$ alkyl, or $C_{3-6}$ cycloalkyl; or $R^4$ and $R^6$ combine to form a cycloalkyl or heterocycloalkyl ring optionally substituted with halogen, $C_{1-6}$ alkyl, or $C_{3-6}$ cycloalkyl; or $R^5$ and $R^7$ combine to form a bond;

$R^8$ is

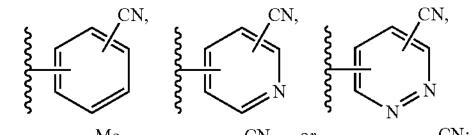

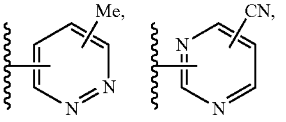

or

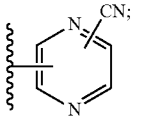

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^4$ and $R^{10}$ combine to form a cycloalkyl or heterocycloalkyl ring optionally substituted with halogen, $C_{1-6}$ alkyl, or $C_{3-6}$ cycloalkyl; or $R^6$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl; or $R^4$ and $R^{11}$ combine to form a heteroalkyl ring optionally substituted with halogen, $C_{1-6}$ alkyl, or $C_{3-6}$ cycloalkyl; or $R^6$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, $—N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment P2. The compound of embodiment P1, or a pharmaceutically acceptable salt or solvate thereof, having the structure of Formula (IIA) or (IIB):

Formula (IIA)

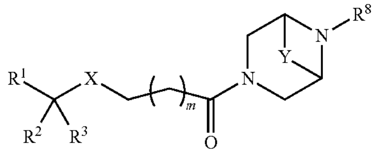

Formula (IIB)

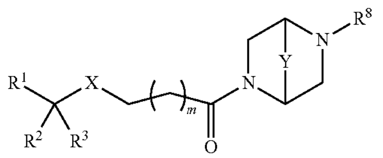

wherein:

X is a bond, $—C(R^9)(R^{10})—$, $—N(R^{11})—$, $—O—$, $—S(O)_n—$, $—CH_2N(R^{11})—$, or $—CH_2O—$;

Y is a $—CH_2—$, $—CH_2CH_2—$, $—CH{=}CH—$, or $—CH_2OCH_2—$;

$R^1$ is

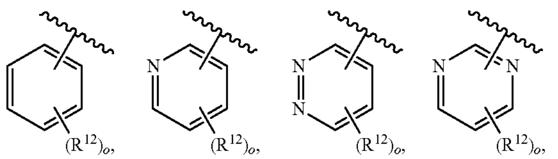

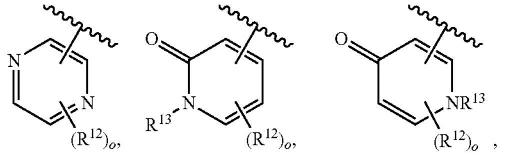

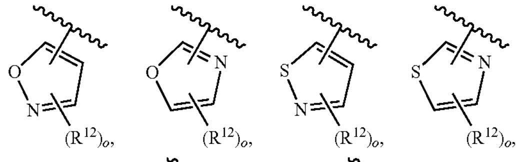

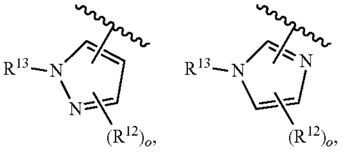

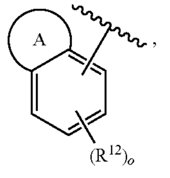

, or

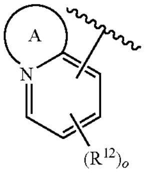

, wherein ring A is a 5- or 6-membered heteroaryl ring or a 5- or 6-membered heterocycloalkyl ring optionally substituted with halogen, cyano, $—N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

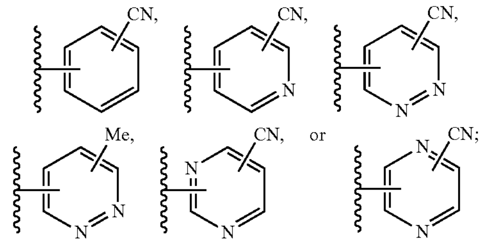

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment P3. The compound of embodiment P1, or a pharmaceutically acceptable salt or solvate thereof, having the structure of Formula (III):

Formula (III)

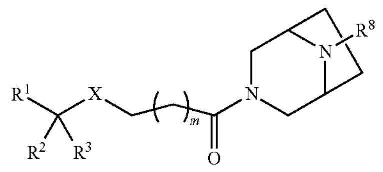

wherein:

X is a bond, —$C(R^9)(R^{10})$—, —$N(R^{11})$—, —O—, —$S(O)_n$—, —$CH_2N(R^{11})$—, or —$CH_2O$—;

$R^1$ is

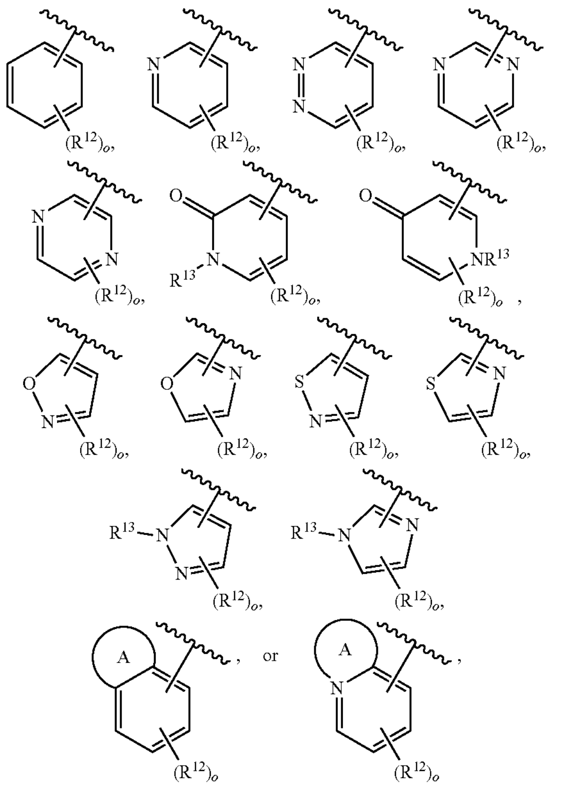

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

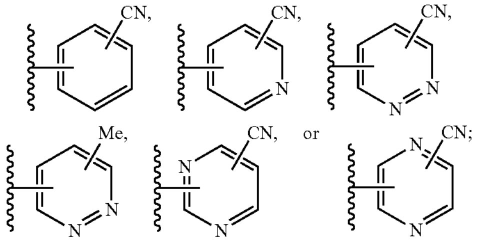

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl;

each $R^{12}$ is independently selected from hydroxyl, halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heteroalkyl ring optionally substituted with halogen, $C_{1-6}$ alkyl, or $C_{3-6}$ cycloalkyl; or $R^{10}$ and one $R^{12}$ combine to form a cycloalkyl or heteroalkyl ring optionally substituted with halogen, $C_{1-6}$ alkyl, or $C_{3-6}$ cycloalkyl; or $R^{11}$ and one $R^{12}$ combine to form a heteroalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment P4. The compound of any one of embodiments P1-P3, or a pharmaceutically acceptable salt or solvate thereof, wherein X is a bond.

Embodiment P5. The compound of any one of embodiments P1-P3, or a pharmaceutically acceptable salt or solvate thereof, wherein X is —C($R^9$)($R^{10}$)—.

Embodiment P6. The compound of any one of embodiments P1-P3, or a pharmaceutically acceptable salt or solvate thereof, wherein X is —N($R^{11}$)—

Embodiment P7. The compound of any one of embodiments P1-P3, or a pharmaceutically acceptable salt or solvate thereof, wherein X is —O—.

Embodiment P8. The compound of any one of embodiments P1-P3, or a pharmaceutically acceptable salt or solvate thereof, wherein X is —S—.

Embodiment P9. The compound of any one of embodiments P1-P3, or a pharmaceutically acceptable salt or solvate thereof, wherein X is —S(O)—.

Embodiment P10. The compound of any one of embodiments P1-P3, or a pharmaceutically acceptable salt or solvate thereof, wherein X is —$S(O)_2$—.

Embodiment P11. The compound of any one of embodiments P1-P10, or a pharmaceutically acceptable salt or solvate thereof, wherein $R^1$ is

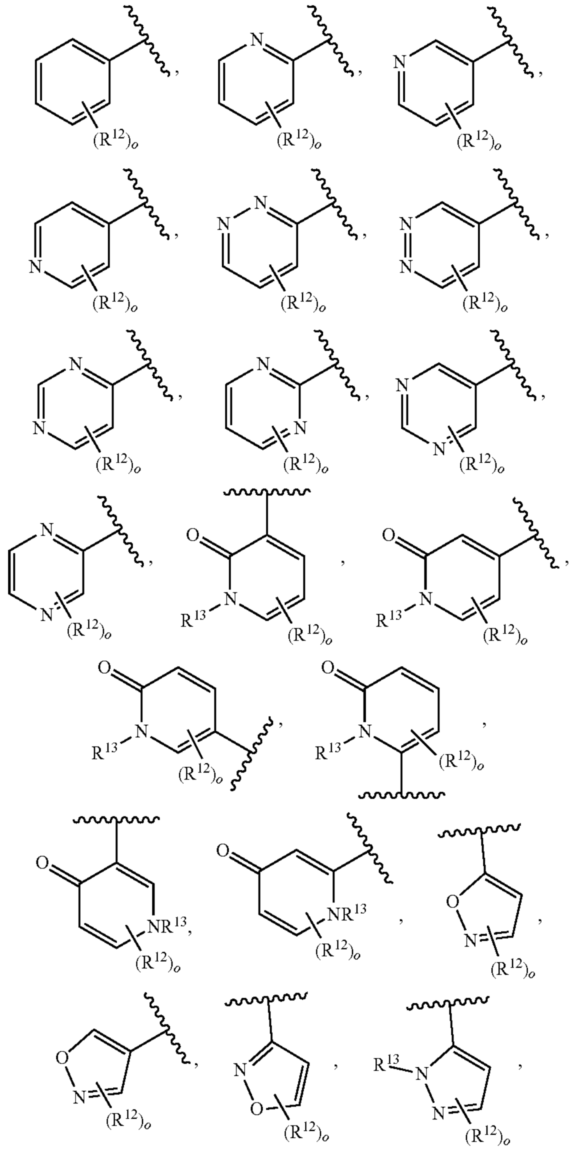

-continued

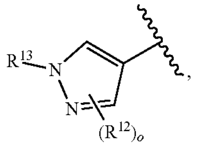, 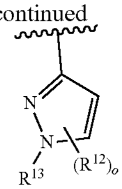, 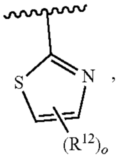,

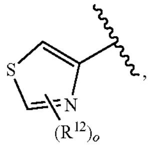, 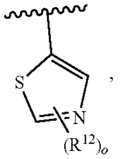, 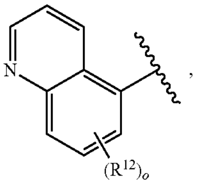,

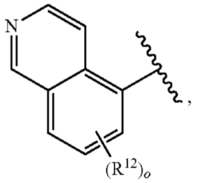, 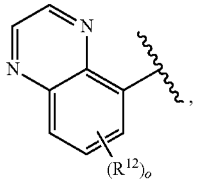,

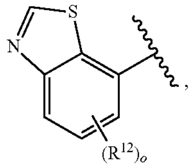, 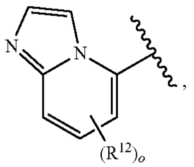,

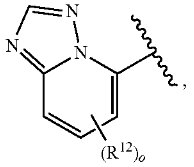,

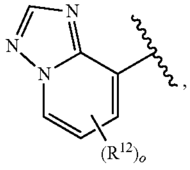, or 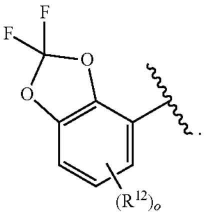.

Embodiment P12. The compound of any one of embodiments P1-P11, wherein $R^2$ is hydrogen, —F, —$CH_3$, —$CH_2CH_3$, —$CF_2H$, —$CF_3$, —$CH_2OH$, —$C(CH_3)_2OH$, phenyl, or cyclopropyl.

Embodiment P13. The compound of any one of embodiments P1-P12, wherein $R^3$ is —F, —$CH_3$, —$CH_2CH_3$, —$CF_2H$, —$CF_3$, —$CH_2OH$, —$C(CH_3)_2OH$, phenyl, or cyclopropyl.

Embodiment P14. The compound of any one of embodiments P1-P11, wherein $R^2$ and $R^3$ combine to form a cyclopropyl, cyclobutyl, or cyclopentyl ring.

Embodiment P15. The compound of any one of embodiments P1-P11, wherein $R^2$ and $R^3$ combine to form an oxetanyl or tetrahydrofuranyl ring.

Embodiment P16. The compound of any one of embodiments P1-P15, or a pharmaceutically acceptable salt or solvate thereof, wherein m is 0.

Embodiment P17. The compound of any one of embodiments P1-P15, or a pharmaceutically acceptable salt or solvate thereof, wherein m is 1.

Embodiment P18. The compound of any one of embodiments P1-P17, or a pharmaceutically acceptable salt or solvate thereof, wherein o is 0.

Embodiment P19. The compound of any one of embodiments P1-P17, or a pharmaceutically acceptable salt or solvate thereof, wherein o is 1.

Embodiment P20. The compound of any one of embodiments P1-P17, or a pharmaceutically acceptable salt or solvate thereof, wherein o is 2.

Embodiment P21. The compound of any one of embodiments P1-P17, or a pharmaceutically acceptable salt or solvate thereof, wherein o is 3.

Embodiment P22. The compound of any one of embodiments P1-P21, or a pharmaceutically acceptable salt or solvate thereof, wherein $R^8$ is

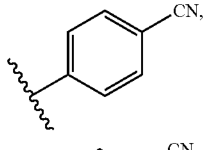 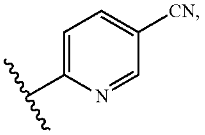

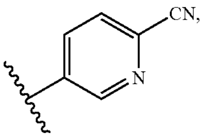, 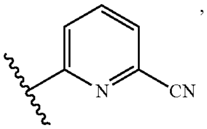

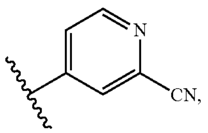 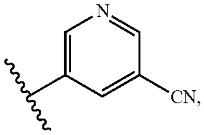

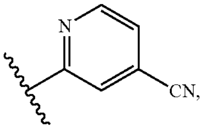 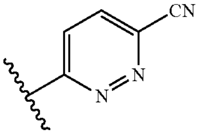,

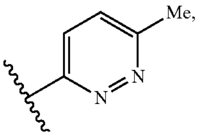 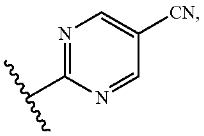 or

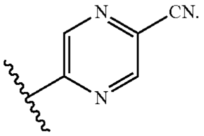

Embodiment P23. A compound selected from Compound List 1, or a pharmaceutically acceptable salt thereof.

Embodiment P24. A pharmaceutical composition comprising a compound of any one of embodiments P1-P23, or a pharmaceutically acceptable salt or solvate thereof, and at least one pharmaceutically acceptable excipient.

Embodiment P25. A method of treating a neurodegenerative disorder in a subject in need thereof, comprising administering to the subject a therapeutically effective amount of a compound of any one of embodiments P1-P23, or a pharmaceutically acceptable salt or solvate thereof.

Embodiment P26. A method of treating a demyelinating disease in a subject in need thereof, comprising administering to the subject a therapeutically effective amount of a compound of any one of embodiments P1-P23, or a pharmaceutically acceptable salt or solvate thereof.

Embodiment P27. The method of embodiment P26, wherein the demyelinating disease is a demyelinating disease of the central nervous system.

Embodiment P28. The method of embodiment P27, wherein the disease is multiple sclerosis.

Embodiment P29. The method of embodiment P26, wherein the demyelinating disease is a demyelinating disease of the peripheral nervous system.

Embodiment P30. A method of treating a neuropathic disease, optionally a peripheral neuropathy, in a subject in need thereof, comprising administering to the subject a therapeutically effective amount of a compound of any one of embodiments P1-P23, or a pharmaceutically acceptable salt or solvate thereof.

Embodiment P31. The method of embodiment P30, wherein the neuropathic disease disease is diabetic neuropathy.

Embodiment P32. The method of any one of embodiments P25-P31, further comprising the administration of one or more immunomodulatory agents.

Embodiment P33. The method of embodiment P32, wherein the one or more immunomodulatory agents are selected from: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other S1P1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide.

Embodiment P34. A method of modulating muscarinic acetylcholine receptor $M_1$ activity in a subject comprising administering to the subject a compound of any one of embodiments P1-P23, or a pharmaceutically acceptable salt or solvate thereof.

Embodiment P35. The method of embodiment P34, wherein the compound acts as a selective $M_1$ antagonist.

IX. ADDITIONAL EMBODIMENTS

Embodiment PPT. A compound, or a pharmaceutically acceptable salt or solvate thereof, having the structure of Formula (IA-1) or (IB-1):

Formula (IA-1)

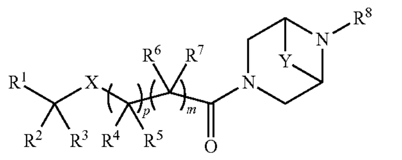

Formula (IB-1)

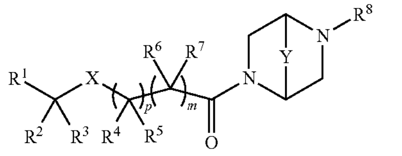

wherein:

X is a bond, —C($R^9$)($R^{10}$)—, —N($R^{11}$)—, —O—, —S(O)$_1$—, —$CH_2$N($R^{11}$)—, substituted or unsubstituted alkylene, substituted or unsubstituted alkenylene, substituted or unsubstituted alkynylene, substituted or unsubstituted heteroalkylene, substituted or unsubstituted heteroalkenylene, or substituted or unsubstituted heteroalkynylene;

Y is a substituted or unsubstituted alkylene, substituted or unsubstituted alkenylene, or substituted or unsubstituted heteroalkylene;

$R^1$ is

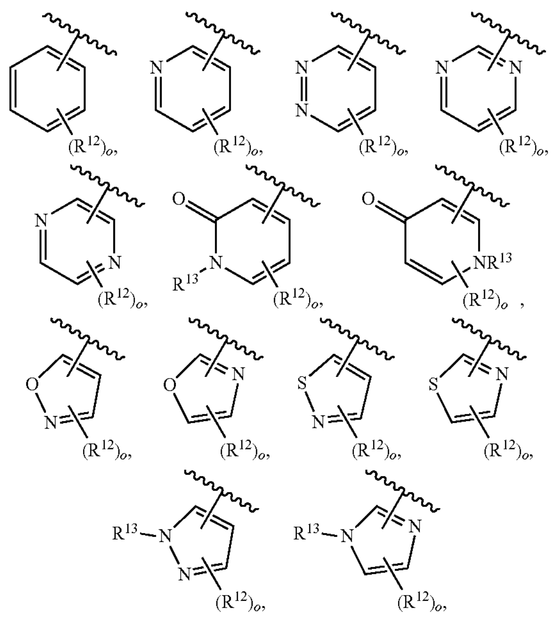

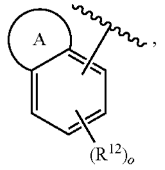

, or

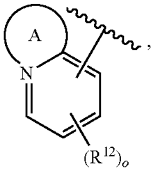

, wherein ring A is a heteroaryl ring or a heterocycloalkyl ring optionally substituted with hydroxyl, halogen, cyano, —N($R^{14}$)($R^{15}$), substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted heterocycloalkyl, substituted or unsubstituted aryl, substituted or unsubstituted heteroaryl, —S(O)$_n$($R^{16}$), or —$SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted alkylhydroxyl, substituted or unsubstituted heterocycloalkyl, substituted or unsubstituted aryl, or substituted or unsubstituted heteroaryl;

$R^3$ is halogen, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted alkylhydroxyl, substituted or unsubstituted heterocycloalkyl, substituted or unsubstituted aryl, or substituted or unsubstituted heteroaryl; or $R^2$ and $R^3$ combine to form a cycloalkyl or heterocycloalkyl ring optionally substituted with halogen, substituted or unsubstituted alkyl, or substituted or unsubstituted cycloalkyl;

$R^4$ and $R^5$ are independently selected from hydrogen, deuterium, halogen, and substituted or unsubstituted alkyl; or $R^3$ and $R^4$ combine to form a cycloalkyl or heterocycloalkyl ring optionally substituted with halogen, substituted or unsubstituted alkyl, or substituted or unsubstituted cycloalkyl; or $R^4$ and $R^5$ combine to form a cycloalkyl or heterocycloalkyl ring optionally substituted with halogen, substituted or unsubstituted alkyl, or substituted or unsubstituted cycloalkyl;

$R^6$ and $R^7$ are independently selected from hydrogen, deuterium, halogen, and substituted or unsubstituted alkyl; or $R^3$ and $R^7$ combine to form a cycloalkyl or heterocycloalkyl ring optionally substituted with halogen, substituted or unsubstituted alkyl, or substituted or unsubstituted cycloalkyl; or $R^4$ and $R^6$ combine to form a cycloalkyl or heterocycloalkyl ring optionally substituted with halogen, substituted or unsubstituted alkyl, or substituted or unsubstituted cycloalkyl; or $R^5$ and $R^7$ combine to form a bond;

$R^8$ is

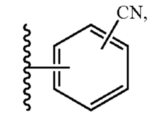 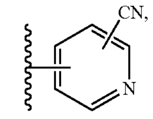 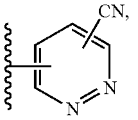

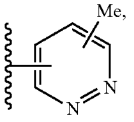 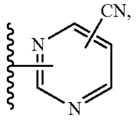 or 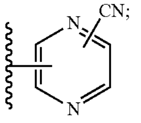

$R^9$ and $R^{10}$ are independently selected from hydrogen, deuterium, halogen, substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted heterocycloalkyl, substituted or unsubstituted aryl, or substituted or unsubstituted heteroaryl; or $R^3$ and $R^{10}$ combine to form a cycloalkyl or heterocycloalkyl ring optionally substituted with halogen, substituted or unsubstituted alkyl, or substituted or unsubstituted cycloalkyl; or $R^4$ and $R^{10}$ combine to form a cycloalkyl or heterocycloalkyl ring optionally substituted with halogen, substituted or unsubstituted alkyl, or substituted or unsubstituted cycloalkyl; or $R^6$ and $R^{10}$ combine to form a cycloalkyl or heterocycloalkyl ring optionally substituted with halogen, substituted or unsubstituted alkyl, or substituted or unsubstituted cycloalkyl; or $R^9$ and $R^{10}$ combine to form a cycloalkyl or heterocycloalkyl ring optionally substituted with halogen, substituted or unsubstituted alkyl, or substituted or unsubstituted cycloalkyl;

$R^{11}$ is hydrogen, substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl; or $R^3$ and $R^{11}$ combine to form a heteroalkyl ring optionally substituted with halogen, substituted or unsubstituted alkyl, or substituted or unsubstituted cycloalkyl; or $R^4$ and $R^{11}$ combine to form a heterocycloalkyl ring optionally substituted with halogen, substituted or unsubstituted alkyl, or substituted or unsubstituted cycloalkyl; or $R^6$ and $R^{11}$ combine to form a heterocycloalkyl ring optionally substituted with halogen, substituted or unsubstituted alkyl, or substituted or unsubstituted cycloalkyl;

each $R^{12}$ is independently selected from hydroxyl, halogen, cyano, —$N(R^{14})(R^{15})$ substituted or unsubstituted alkyl, substituted or unsubstituted alkoxy, substituted or unsubstituted haloalkyl, substituted or unsubstituted haloalkoxy, substituted or unsubstituted cycloalkyl, substituted or unsubstituted cycloalkoxy, substituted or unsubstituted halocycloalkyl, substituted or unsubstituted halocycloalkoxy, substituted or unsubstituted alkylhydroxyl, substituted or unsubstituted heterocycloalkyl, substituted or unsubstituted aryl, substituted or unsubstituted heteroaryl, —$S(O)_n(R^{16})$, or —$SF_5$; or $R^3$ and one $R^{12}$ combine to form a cycloalkyl or heterocycloalkyl ring optionally substituted with halogen, substituted or unsubstituted alkyl, or substituted or unsubstituted cycloalkyl; or $R^{10}$ and one $R^{12}$ combine to form a cycloalkyl or heterocycloalkyl ring optionally substituted with halogen, substituted or unsubstituted alkyl, or substituted or unsubstituted cycloalkyl; or $R^{11}$ and one $R^{12}$ combine to form a heterocycloalkyl ring optionally substituted with halogen, substituted or unsubstituted alkyl, or substituted or unsubstituted cycloalkyl;

$R^{13}$ is hydrogen, substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl;

$R^{14}$ and $R^{15}$ are independently selected from hydrogen, substituted or unsubstituted alkyl, substituted or unsubstituted haloalkyl, substituted or unsubstituted cycloalkyl, substituted or unsubstituted halocycloalkyl, substituted or unsubstituted heterocycloalkyl, substituted or unsubstituted aryl, or substituted or unsubstituted heteroaryl; or $R^{14}$ and $R^{15}$ combine to form a heterocycloalkyl ring optionally substituted with halogen, substituted or unsubstituted alkyl, or substituted or unsubstituted cycloalkyl;

$R^{16}$ is substituted or unsubstituted alkyl, substituted or unsubstituted haloalkyl, substituted or unsubstituted cycloalkyl, halocycloalkyl, substituted or unsubstituted heterocycloalkyl, substituted or unsubstituted aryl, or substituted or unsubstituted heteroaryl;

m is 0 or 1;

n is 0, 1, or 2;

o is 0, 1, 2, or 3; and p is 0 or 1.

Embodiment PP2. The compound of embodiment PP1, or a pharmaceutically acceptable salt or solvate thereof, having the structure of Formula (IA) or (IB):

Formula (IA)

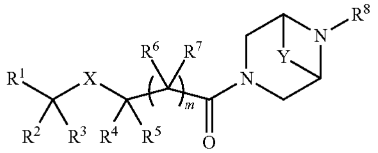

Formula (IB)

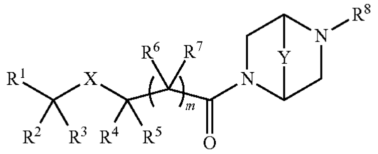

wherein:

X is a bond, —C($R^9$)($R^{10}$)—, —N($R^{11}$)—, —O—, —S(O)$_n$—, —$CH_2N$($R^{11}$)—, or —$CH_2O$—;

Y is a —$CH_2$—, —$CH_2CH_2$—, —CH═CH—, or —$CH_2OCH_2$—;

$R^1$ is

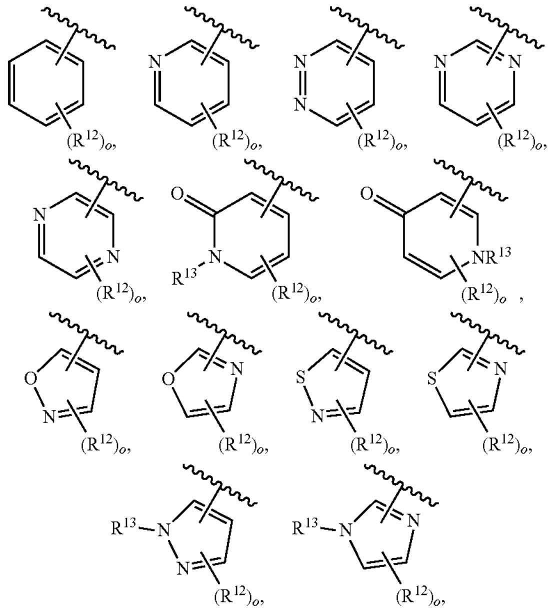

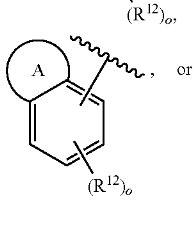

or

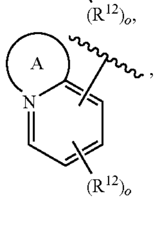

wherein ring A is a 5- or 6-membered heteroaryl ring or a 5- or 6-membered heterocycloalkyl ring optionally substituted with halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, S(O)$_n$($R^{16}$), or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^4$ and $R^5$ are independently selected from hydrogen, deuterium, halogen, and $C_{1-3}$ alkyl; or $R^3$ and $R^4$ combine to form a cycloalkyl or heterocycloalkyl ring optionally substituted with halogen, $C_{1-6}$ alkyl, or $C_{3-6}$ cycloalkyl; or $R^4$ and $R^5$ combine to form a cycloalkyl or heterocycloalkyl ring optionally substituted with halogen, $C_{1-6}$ alkyl, or $C_{3-6}$ cycloalkyl;

$R^6$ and $R^7$ are independently selected from hydrogen, deuterium, halogen, and $C_{1-3}$ alkyl; or $R^3$ and $R^7$ combine to form a cycloalkyl or heterocycloalkyl ring optionally substituted with halogen, $C_{1-6}$ alkyl, or $C_{3-6}$ cycloalkyl; or $R^4$ and $R^6$ combine to form a cycloalkyl or heterocycloalkyl ring optionally substituted with halogen, $C_{1-6}$ alkyl, or $C_{3-6}$ cycloalkyl; or $R^5$ and $R^7$ combine to form a bond;

$R^8$ is

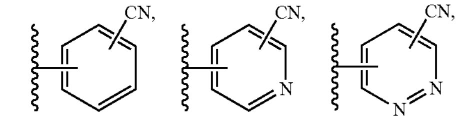

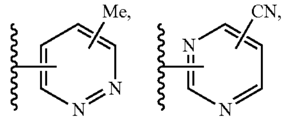

or

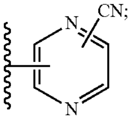

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^4$ and $R^{10}$ combine to form a cycloalkyl or heterocycloalkyl ring optionally substituted with halogen, $C_{1-6}$ alkyl, or $C_{3-6}$ cycloalkyl; or $R^6$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heteroalkyl ring optionally substituted with halogen, $C_{1-6}$ alkyl, or $C_{3-6}$ cycloalkyl; or $R^4$ and $R^{11}$ combine to form a heterocycloalkyl ring optionally substituted with halogen, $C_{1-6}$ alkyl, or $C_{3-6}$ cycloalkyl; or $R^6$ and $R^{11}$ combine to form a heterocycloalkyl ring optionally substituted with halogen, $C_{1-6}$ alkyl, or $C_{3-6}$ cycloalkyl;

each $R^{12}$ is independently selected from hydroxyl, halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heterocycloalkyl ring optionally substituted with halogen, $C_{1-6}$ alkyl, or $C_{3-6}$ cycloalkyl; or $R^{10}$ and one $R^{12}$ combine to form a cycloalkyl or heterocycloalkyl ring optionally substituted with halogen, $C_{1-6}$ alkyl, or $C_{3-6}$ cycloalkyl; or $R^{11}$ and one $R^{12}$ combine to form a heterocycloalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment PP3. The compound of any one of embodiments PP1-PP2, or a pharmaceutically acceptable salt or solvate thereof, having the structure of Formula (IIA) or (IIB):

Formula (IIA)

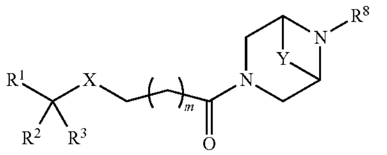

Formula (IIB)

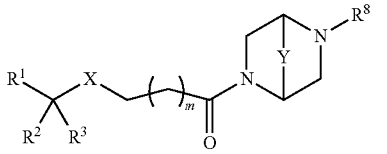

wherein:

X is a bond, —$C(R^9)(R^{10})$—, —$N(R^{11})$—, —O—, —$S(O)_n$—, —$CH_2N(R^{11})$—, or —$CH_2O$—;

Y is a —$CH_2$—, —$CH_2CH_2$—, —CH═CH—, or —$CH_2OCH_2$—;

$R^1$ is

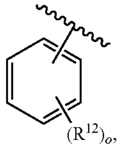
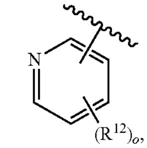
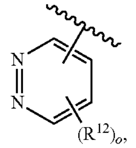
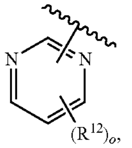
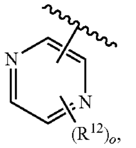
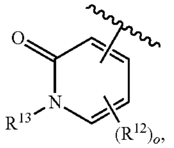

-continued

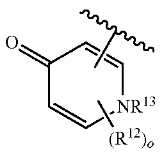
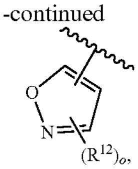
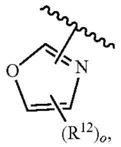
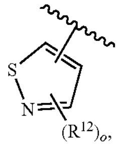
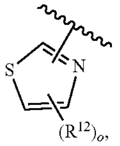
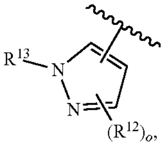
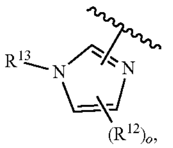
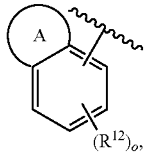
or
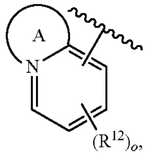

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

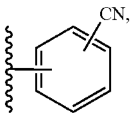
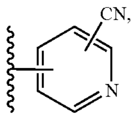
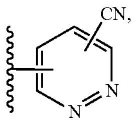
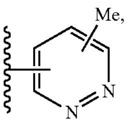
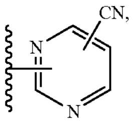
or
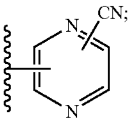

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heterocycloalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heterocycloalkyl ring optionally substituted with halogen, $C_{1-6}$ alkyl, or $C_{3-6}$ cycloalkyl; or $R^{10}$ and one $R^{12}$ combine to form a cycloalkyl or heterocycloalkyl ring optionally substituted with halogen, $C_{1-6}$ alkyl, or $C_{3-6}$ cycloalkyl; or $R^{11}$ and one $R^{12}$ combine to form a heterocycloalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment PP4. The compound of any one of embodiments PP1-PP2, or a pharmaceutically acceptable salt or solvate thereof, having the structure of Formula (III):

Formula (III)

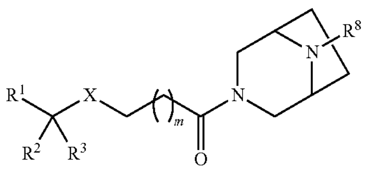

wherein:

X is a bond, —$C(R^9)(R^{10})$—, —$N(R^{11})$—, —O—, —$S(O)_n$—, —$CH_2N(R^{11})$—, or —$CH_2O$—;

$R^1$ is

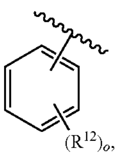
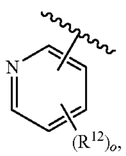
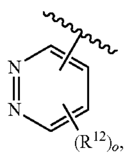
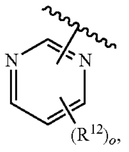
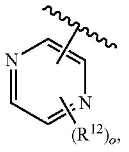
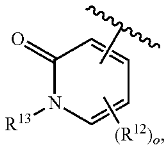
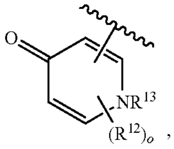
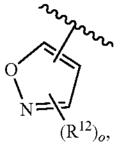
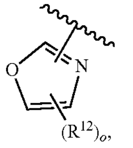

-continued

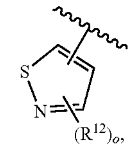
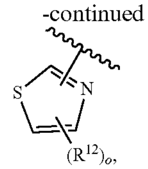
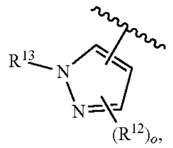
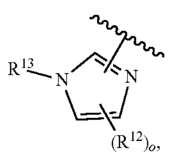
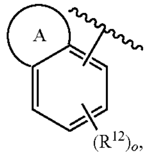

or

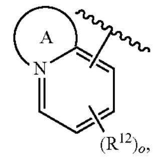

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, $S(O)_n(R^{16})$, or $SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

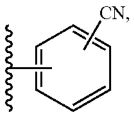
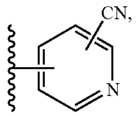
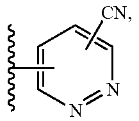
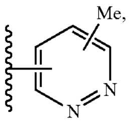
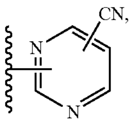

or

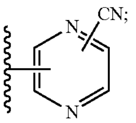

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heterocycloalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, $S(O)_n(R^{16})$, or $SF_5$; or $R^3$ and one $R^{12}$ combine to form a cycloalkyl or heterocycloalkyl ring optionally substituted with halogen, $C_{1-6}$ alkyl, or $C_{3-6}$ cycloalkyl; or $R^{10}$ and one $R^{12}$ combine to form a cycloalkyl or heterocycloalkyl ring optionally substituted with halogen, $C_{1-6}$ alkyl, or $C_{3-6}$ cycloalkyl; or $R^{11}$ and one $R^{12}$ combine to form a heterocycloalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment PP5. The compound of any one of embodiments PP1-PP4, or a pharmaceutically acceptable salt or solvate thereof, wherein X is a bond.

Embodiment PP6. The compound of any one of embodiments PP1-PP4, or a pharmaceutically acceptable salt or solvate thereof, wherein X is —C(R$^9$)(R$^{10}$)—.

Embodiment PP7. The compound of any one of embodiments PP1-PP4, or a pharmaceutically acceptable salt or solvate thereof, wherein X is —N(R$^{11}$)—.

Embodiment PP8. The compound of any one of embodiments PP1-PP4, or a pharmaceutically acceptable salt or solvate thereof, wherein X is —O—.

Embodiment PP9. The compound of any one of embodiments PP1-PP4, or a pharmaceutically acceptable salt or solvate thereof, wherein X is —S—.

Embodiment PP10. The compound of any one of embodiments PP1-PP4, or a pharmaceutically acceptable salt or solvate thereof, wherein X is —S(O)—.

Embodiment PP11. The compound of any one of embodiments PP1-PP4, or a pharmaceutically acceptable salt or solvate thereof, wherein X is —S(O)$_2$—.

Embodiment PP12. The compound of any one of embodiments PP1-PP11, or a pharmaceutically acceptable salt or solvate thereof, wherein $R^1$ is

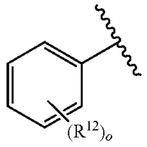 , 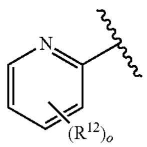 , 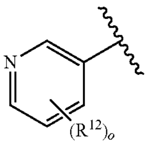 ,

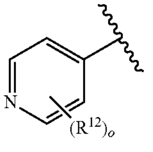 , 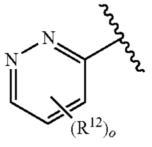 , 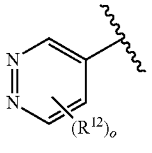 ,

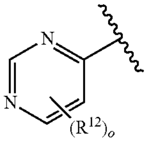 , 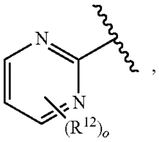 , 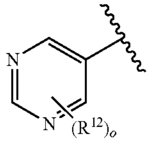 ,

-continued

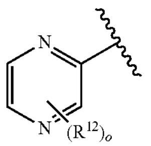 , 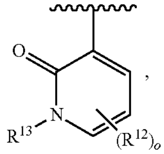 ,

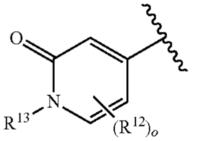 , 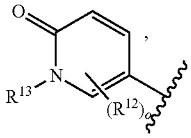 ,

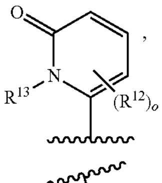 , 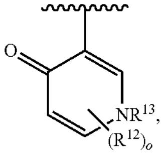 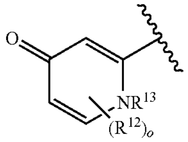 ,

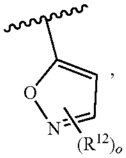 , 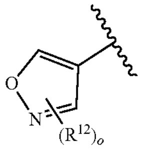 , 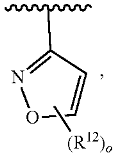 ,

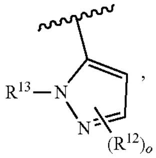 , 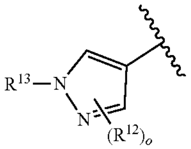 ,

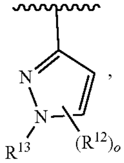 , 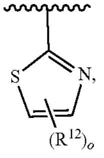 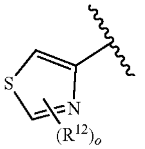 ,

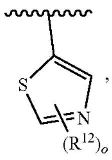 , 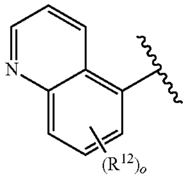 ,

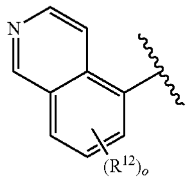 , 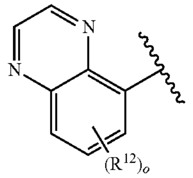 ,

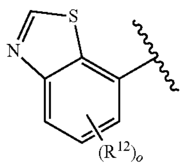 , 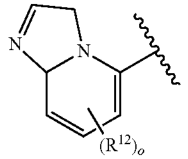 ,

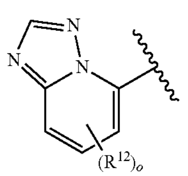 , 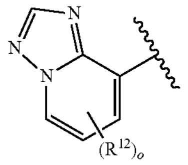 ,

-continued

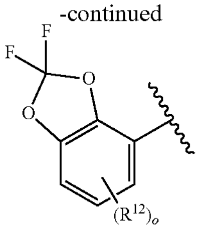,

Embodiment PP13. The compound of any one of embodiments PP1-PP12, wherein $R^2$ is hydrogen, —F, —$CH_3$, —$CH_2CH_3$, —$CF_2H$, —$CF_3$, —$CH_2OH$, —$C(CH_3)_2OH$, phenyl, or cyclopropyl.

Embodiment PP14. The compound of any one of embodiments PP1-PP13, wherein $R^3$ is —F, —$CH_3$, —$CH_2CH_3$, —$CF_2H$, —$CF_3$, —$CH_2OH$, —$C(CH_3)_2OH$, phenyl, or cyclopropyl.

Embodiment PP15. The compound of any one of embodiments PP1-PP12, wherein $R^2$ and $R^3$ combine to form a cyclopropyl, cyclobutyl, or cyclopentyl ring.

Embodiment PP16. The compound of any one of embodiments PP1-PP12, wherein $R^2$ and $R^3$ combine to form an oxetanyl or tetrahydrofuranyl ring.

Embodiment PP17. The compound of any one of embodiments PP1-PP16, or a pharmaceutically acceptable salt or solvate thereof, wherein m is 0.

Embodiment PP18. The compound of any one of embodiments PP1-PP16, or a pharmaceutically acceptable salt or solvate thereof, wherein m is 1.

Embodiment PP19. The compound of any one of embodiments PP1-PP18, or a pharmaceutically acceptable salt or solvate thereof, wherein o is 0.

Embodiment PP20. The compound of any one of embodiments PP1-PP18, or a pharmaceutically acceptable salt or solvate thereof, wherein o is 1.

Embodiment PP21. The compound of any one of embodiments PP1-PP18, or a pharmaceutically acceptable salt or solvate thereof, wherein o is 2.

Embodiment PP22. The compound of any one of embodiments PP1-PP18, or a pharmaceutically acceptable salt or solvate thereof, wherein o is 3.

Embodiment PP23. The compound of any one of embodiments PP1-PP22, or a pharmaceutically acceptable salt or solvate thereof, wherein $R^8$ is,

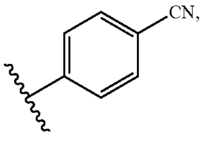
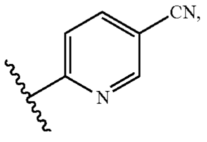
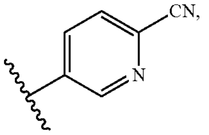
,
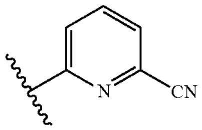
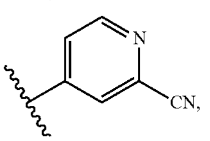
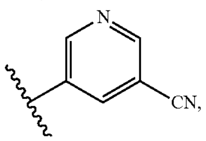

-continued

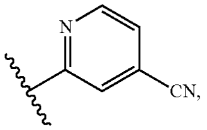
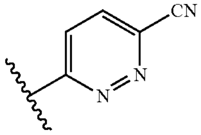
,
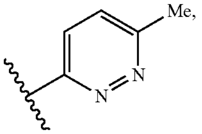
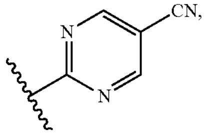
or
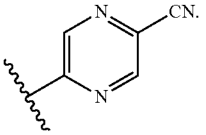

Embodiment PP24. A compound selected from Compound List 1, or a pharmaceutically acceptable salt thereof.

Embodiment PP25. A pharmaceutical composition comprising a compound of any one of embodiments PP1-PP24, or a pharmaceutically acceptable salt or solvate thereof, and at least one pharmaceutically acceptable excipient.

Embodiment PP26. A method of treating a neurodegenerative disorder in a subject in need thereof, comprising administering to the subject a therapeutically effective amount of a compound of any one of embodiments PP1-PP24, or a pharmaceutically acceptable salt or solvate thereof.

Embodiment PP27. A method of treating a demyelinating disease in a subject in need thereof, comprising administering to the subject a therapeutically effective amount of a compound of any one of embodiments PP1-PP24, or a pharmaceutically acceptable salt or solvate thereof.

Embodiment PP28. The method of embodiment PP27, wherein the demyelinating disease is a demyelinating disease of the central nervous system.

Embodiment PP29. The method of embodiment PP28, wherein the disease is multiple sclerosis.

Embodiment PP30. The method of embodiment PP27, wherein the demyelinating disease is a demyelinating disease of the peripheral nervous system.

Embodiment PP31. A method of treating a neuropathic disease, optionally a peripheral neuropathy, in a subject in need thereof, comprising administering to the subject a therapeutically effective amount of a compound of any one of embodiments PP1-PP24, or a pharmaceutically acceptable salt or solvate thereof.

Embodiment PP32. The method of embodiment PP31, wherein the neuropathic disease disease is diabetic neuropathy.

Embodiment PP33. The method of any one of embodiments PP26-PP32, further comprising the administration of one or more immunomodulatory agents.

Embodiment PP34. The method of embodiment PP33, wherein the one or more immunomodulatory agents are selected from: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other S1P1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide.

Embodiment PP35. A method of modulating muscarinic acetylcholine receptor $M_1$ activity in a subject comprising administering to the subject a compound of any one of embodiments PP1-PP24, or a pharmaceutically acceptable salt or solvate thereof.

Embodiment PP36. The method of embodiment PP35, wherein the compound acts as a selective $M_1$ antagonist.

X. FURTHER EMBODIMENTS

Embodiment 1. A compound, or a pharmaceutically acceptable salt or solvate thereof, having the structure of Formula (IA) or (IB):

Formula (IA)

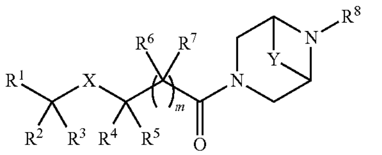

Formula (IB)

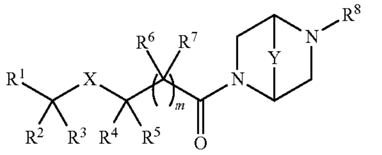

wherein:

X is a bond, —C($R^9$)($R^{10}$)—, —N($R^{11}$)—, —O—, —S(O)$_n$—, —$CH_2$N($R^{11}$)—, or —$CH_2$O—;

Y is a —$CH_2$—, —$CH_2CH_2$—, —CH═CH—, or —$CH_2OCH_2$—;

$R^1$ is

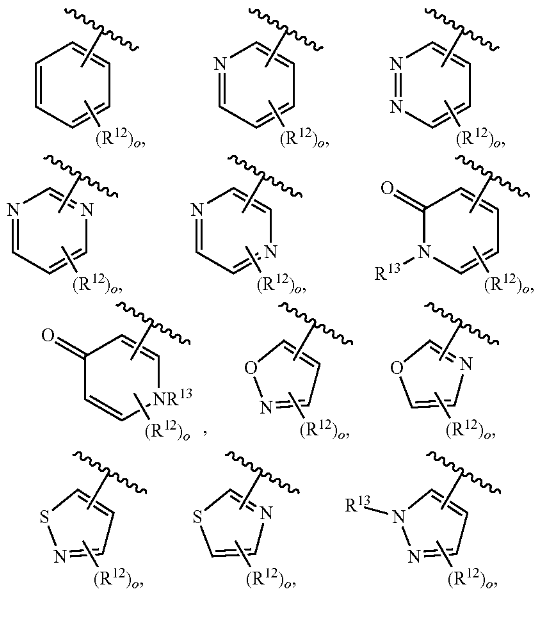

-continued

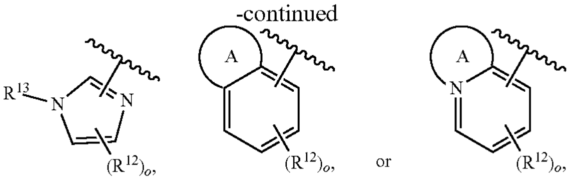

or wherein ring A is a 5- or 6-membered heteroaryl ring or a 5- or 6-membered heterocycloalkyl ring optionally substituted with halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, —S(O)$_n$($R^{16}$), or —$SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^4$ and $R^5$ are independently selected from hydrogen, deuterium, halogen, and $C_{1-3}$ alkyl; or $R^3$ and $R^4$ combine to form a cycloalkyl or heterocycloalkyl ring optionally substituted with halogen, $C_{1-6}$ alkyl, or $C_{3-6}$ cycloalkyl; or $R^4$ and $R^5$ combine to form a cycloalkyl or heterocycloalkyl ring optionally substituted with halogen, $C_{1-6}$ alkyl, or $C_{3-6}$ cycloalkyl;

$R^6$ and $R^7$ are independently selected from hydrogen, deuterium, halogen, and $C_{1-3}$ alkyl; or $R^3$ and $R^7$ combine to form a cycloalkyl or heterocycloalkyl ring optionally substituted with halogen, $C_{1-6}$ alkyl, or $C_{3-6}$ cycloalkyl; or $R^4$ and $R^6$ combine to form a cycloalkyl or heterocycloalkyl ring optionally substituted with halogen, $C_{1-6}$ alkyl, or $C_{3-6}$ cycloalkyl; or $R^5$ and $R^7$ combine to form a bond;

$R^8$ is

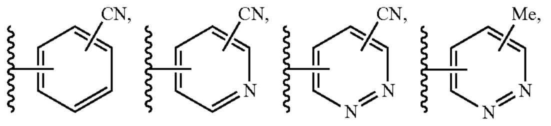

or

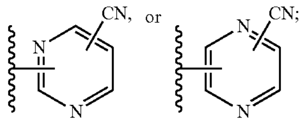

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^4$ and $R^{10}$ combine to form a cycloalkyl or heterocycloalkyl ring optionally substituted with halogen, $C_{1-6}$ alkyl, or $C_{3-6}$ cycloalkyl; or $R^6$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heterocycloalkyl ring optionally substituted with halogen, $C_{1-6}$ alkyl, or $C_{3-6}$ cycloalkyl; or $R^4$ and $R^{11}$ combine to form a heterocycloalkyl ring optionally substituted with halogen, $C_{1-6}$ alkyl, or $C_{3-6}$ cycloalkyl; or $R^6$ and $R^{11}$ combine to form a heterocycloalkyl ring optionally substituted with halogen, $C_{1-6}$ alkyl, or $C_{3-6}$ cycloalkyl;

each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, —$S(O)_n(R^{16})$, or —$SF_5$; or $R^3$ and one $R^{12}$ combine to form a cycloalkyl or heterocycloalkyl ring optionally substituted with halogen, $C_{1-6}$ alkyl, or $C_{3-6}$ cycloalkyl; or $R^{10}$ and one $R^{12}$ combine to form a cycloalkyl or heterocycloalkyl ring optionally substituted with halogen, $C_{1-6}$ alkyl, or $C_{3-6}$ cycloalkyl; or $R^{11}$ and one $R^{12}$ combine to form a heterocycloalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment 2. The compound of embodiment 1, or a pharmaceutically acceptable salt or solvate thereof, having the structure of Formula (IIA) or (IIB):

Formula (IIA)

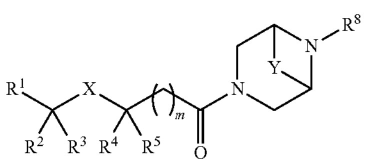

Formula (IIB)

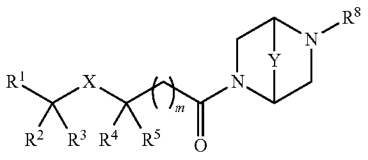

wherein:

X is a bond, —$C(R^9)(R^{10})$—, —$N(R^{11})$—, —O—, —$S(O)_n$—, —$CH_2N(R^{11})$—, or —$CH_2O$—;

Y is a —$CH_2$—, —$CH_2CH_2$—, —CH═CH—, or —$CH_2OCH_2$—;

$R^1$ is

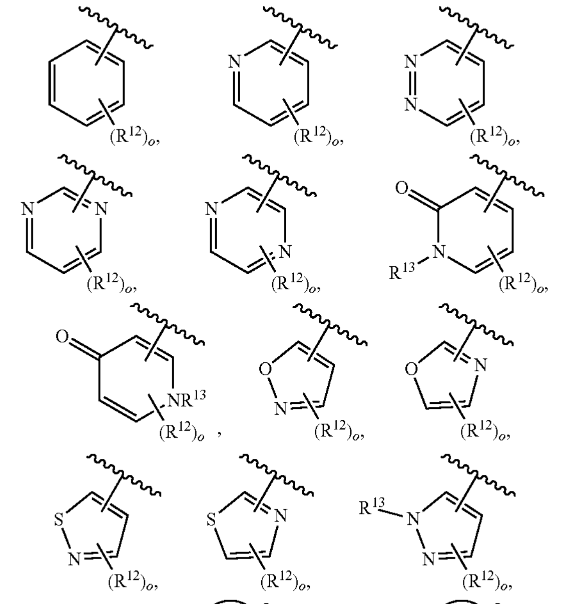

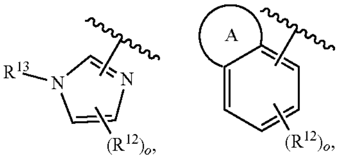

or

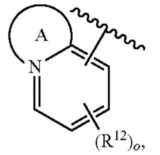

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, —$S(O)_n(R^{16})$, or —$SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

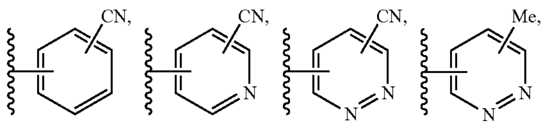

-continued

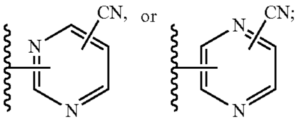

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heterocycloalkyl ring optionally substituted with halogen, $C_{1-6}$ alkyl, or $C_{3-6}$ cycloalkyl; each $R^{12}$ is independently selected from hydroxyl, halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, —$S(O)_n(R^{16})$, or —$SF_5$; or $R^3$ and one $R^{12}$ combine to form a cycloalkyl or heterocycloalkyl ring optionally substituted with halogen, $C_{1-6}$ alkyl, or $C_{3-6}$ cycloalkyl; or $R^{10}$ and one $R^{12}$ combine to form a cycloalkyl or heterocycloalkyl ring optionally substituted with halogen, $C_{1-6}$ alkyl, or $C_{3-6}$ cycloalkyl; or $R^{11}$ and one $R^{12}$ combine to form a heterocycloalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment 3. The compound of embodiment 1, or a pharmaceutically acceptable salt or solvate thereof, having the structure of Formula (III):

Formula (III)

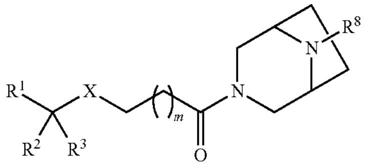

wherein:

X is a bond, —$C(R^9)(R^{10})$—, —$N(R^{11})$—, —O—, —$S(O)_n$—, —$CH_2N(R^{11})$—, or —$CH_2O$—;

$R^1$ is

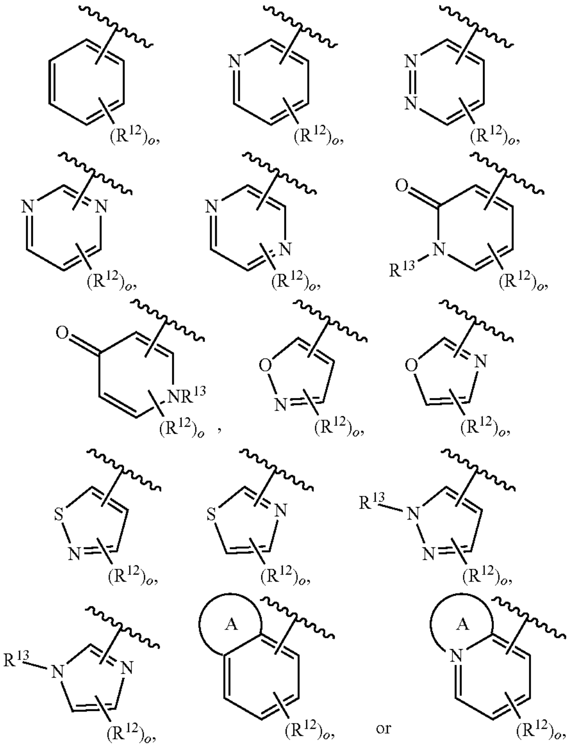

wherein ring A is a 5- or 6-membered heteroaryl ring or a 5- or 6-membered heterocycloalkyl ring optionally substituted with halogen, cyano, —$N(R^{14})(R^{15})$, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl, heteroaryl, —$S(O)_n(R^{16})$, or —$SF_5$, wherein the heteroaryl or heterocycloalkyl ring contains 1, 2 or 3 heteroatoms selected from the group consisting of O, N or S;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl or heteroaryl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

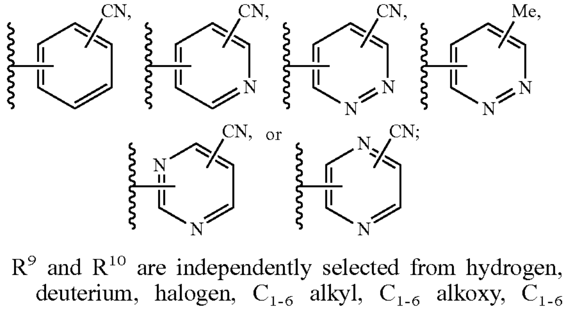

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

$R^{11}$ is hydrogen, $C_{1-6}$ alkyl, $C_{1-6}$ haloalkyl, $C_{3-6}$ cycloalkyl, $C_{3-6}$ halocycloalkyl, heterocycloalkyl aryl or heteroaryl; or $R^3$ and $R^{11}$ combine to form a heterocycloalkyl ring optionally substituted with halogen, $C_{1-6}$ alkyl, or $C_{3-6}$ cycloalkyl;

each $R^{12}$ is independently selected from hydroxyl, halogen, cyano, —N($R^{14}$)($R^{15}$), $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, —S(O)$_n$($R^{16}$), or —$SF_5$; or $R^3$ and one $R^{12}$ combine to form a cycloalkyl or heterocycloalkyl ring optionally substituted with halogen, $C_{1-6}$ alkyl, or $C_{3-6}$ cycloalkyl; or $R^{10}$ and one $R^{12}$ combine to form a cycloalkyl or heterocycloalkyl ring optionally substituted with halogen, $C_{1-6}$ alkyl, or $C_{3-6}$ cycloalkyl; or $R^{11}$ and one $R^{12}$ combine to form a heterocycloalkyl ring optionally substituted with halogen, $C_{1-6}$ alkyl, or $C_{3-6}$ cycloalkyl;

$R^{13}$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

$R^{14}$ and $R^{15}$ are independently selected from hydrogen, $C_{1-6}$ alkyl, $C_{1-6}$ haloalkyl, $C_{3-6}$ cycloalkyl, $C_{3-6}$ halocycloalkyl, heterocycloalkyl, aryl or heteroaryl; or $R^{14}$ and $R^{15}$ combine to form a heterocycloalkyl ring optionally substituted with halogen, $C_{1-6}$ alkyl, or $C_{3-6}$ cycloalkyl;

$R^{16}$ is $C_{1-6}$ alkyl, $C_{1-6}$ haloalkyl, $C_{3-6}$ cycloalkyl, $C_{3-6}$ halocycloalkyl, heterocycloalkyl, aryl or heteroaryl;

m is 0 or 1;

n is 0, 1, or 2; and o is 0, 1, 2, or 3.

Embodiment 4. The compound of any one of embodiments 1-3, or a pharmaceutically acceptable salt or solvate thereof, wherein X is a bond.

Embodiment 5. The compound of any one of embodiments 1-3, or a pharmaceutically acceptable salt or solvate thereof, wherein X is —C($R^9$)($R^{10}$)—.

Embodiment 6. The compound of any one of embodiments 1-3, or a pharmaceutically acceptable salt or solvate thereof, wherein X is —N($R^{11}$)—.

Embodiment 7. The compound of any one of embodiments 1-3, or a pharmaceutically acceptable salt or solvate thereof, wherein X is —O—.

Embodiment 8. The compound of any one of embodiments 1-3, or a pharmaceutically acceptable salt or solvate thereof, wherein X is —S—.

Embodiment 9. The compound of any one of embodiments 1-3, or a pharmaceutically acceptable salt or solvate thereof, wherein X is —S(O)—.

Embodiment 10. The compound of any one of embodiments 1-3, or a pharmaceutically acceptable salt or solvate thereof, wherein X is —S$(O)_2$—.

Embodiment 11. The compound of any one of embodiments 1-10 or a pharmaceutically acceptable salt or solvate thereof, wherein $R^1$ is

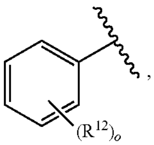,
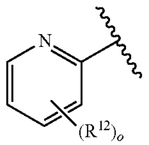,
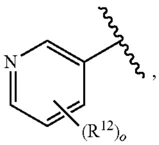,
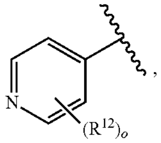,
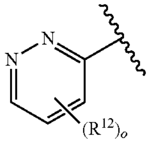,
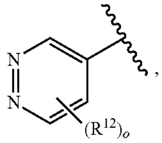,
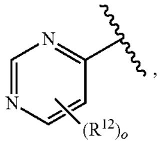,
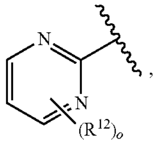,
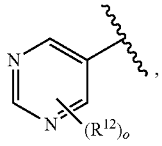,
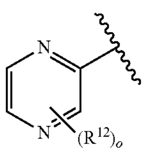,
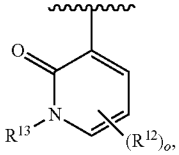,
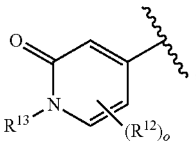,
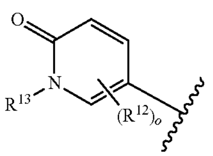,
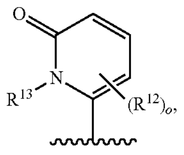,
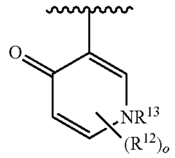,
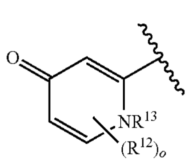,
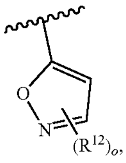,
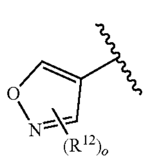,
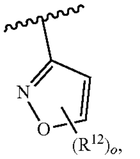,
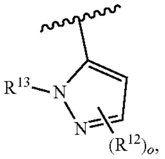,
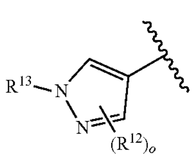,
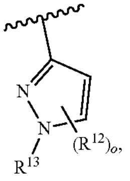,
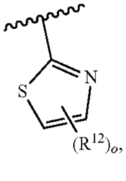,
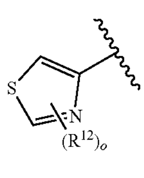,
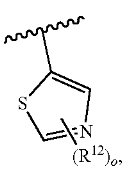,
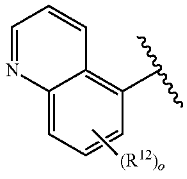,
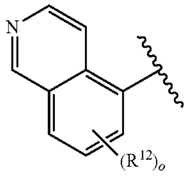, -continued

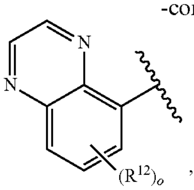 ,

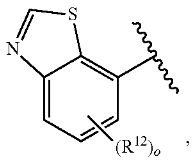 ,

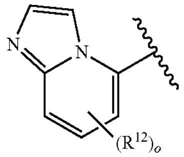 ,

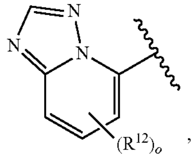 ,

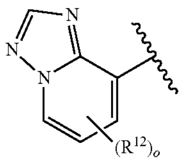 , or

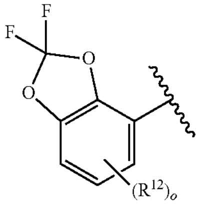 .

Embodiment 12. The compound of any one of embodiments 1-11, or a pharmaceutically acceptable salt or solvate thereof, wherein $R^2$ is hydrogen, —F, —$CH_3$, —$CH_2CH_3$, —$CF_2H$, —$CF_3$, —$CH_2OH$, —$C(CH_3)_2OH$, phenyl, or cyclopropyl.

Embodiment 13. The compound ofany one of embodiments 1-12, or a pharmaceutically acceptable salt or solvate thereof, wherein $R^3$ is —F, —$CH_3$, —$CH_2CH_3$, —$CF_2H$, —$CF_3$, —$CH_2OH$, —$C(CH_3)_2OH$, phenyl, or cyclopropyl.

Embodiment 14. The compound of any one of embodiments 1-11, or a pharmaceutically acceptable salt or solvate thereof, wherein $R^2$ and $R^3$ combine to form a cyclopropyl, cyclobutyl, or cyclopentyl ring.

Embodiment 15. The compound of any one of embodiments 1-11, or a pharmaceutically acceptable salt or solvate thereof, wherein $R^2$ and $R^3$ combine to form an oxetanyl or tetrahydrofuranyl ring.

Embodiment 16. The compound of any one of embodiments 1-15, or a pharmaceutically acceptable salt or solvate thereof, wherein m is 0.

Embodiment 17. The compound of any one of embodiments 1-15, or a pharmaceutically acceptable salt or solvate thereof, wherein m is 1.

Embodiment 18. The compound of any one of embodiments 1-17, or a pharmaceutically acceptable salt or solvate thereof, wherein o is 0.

Embodiment 19. The compound of any one of embodiments 1-17, or a pharmaceutically acceptable salt or solvate thereof, wherein o is 1.

Embodiment 20. The compound of any one of embodiments 1-17, or a pharmaceutically acceptable salt or solvate thereof, wherein o is 2.

Embodiment 21. The compound of any one of embodiments 1-17, or a pharmaceutically acceptable salt or solvate thereof, wherein o is 3.

Embodiment 22. The compound of any one of embodiments 1-21, or a pharmaceutically acceptable salt or solvate thereof, wherein $R^8$ is

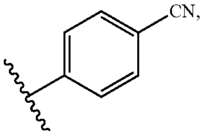

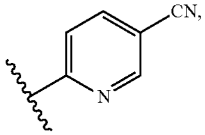

-continued

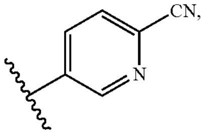 ,

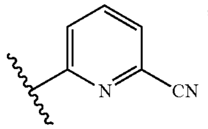

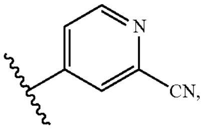

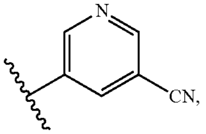

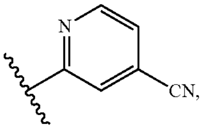

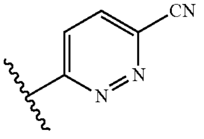 ,

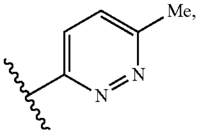

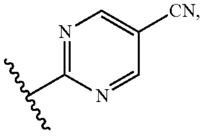 or

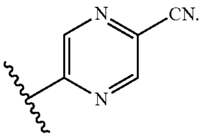

Embodiment 23. A compound selected from Compound List 1, or a pharmaceutically acceptable salt thereof.

Embodiment 24. A pharmaceutical composition comprising a compound of any one of embodiments 1-23, or a pharmaceutically acceptable salt or solvate thereof, and at least one pharmaceutically acceptable excipient.

Embodiment 25. A method of treating a neurodegenerative disorder in a subject in need thereof, comprising administering to the subject a therapeutically effective amount of a compound of any one of embodiments 1-23, or a pharmaceutically acceptable salt or solvate thereof.

Embodiment 26. A method of treating a demyelinating disease in a subject in need thereof, comprising administering to the subject a therapeutically effective amount of a compound of any one of embodiments 1-23, or a pharmaceutically acceptable salt or solvate thereof.

Embodiment 27. The method of embodiment 26, wherein the demyelinating disease is a demyelinating disease of the central nervous system.

Embodiment 28. The method of embodiment 27, wherein the demyelinating disease is multiple sclerosis.

Embodiment 29. The method of embodiment 26, wherein the demyelinating disease is a demyelinating disease of the peripheral nervous system.

Embodiment 30. A method of treating a neuropathic disease, optionally a peripheral neuropathy, in a subject in need thereof, comprising administering to the subject a therapeutically effective amount of a compound of any one of embodiments 1-23, or a pharmaceutically acceptable salt or solvate thereof.

Embodiment 31. The method of embodiment 30, wherein the neuropathic disease is diabetic neuropathy.

Embodiment 32. The method of any one of embodiments 25-31, further comprising the administration of one or more immunomodulatory agents.

Embodiment 33. The method of embodiment 32, wherein the one or more immunomodulatory agents are selected from: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other S1P1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide.

Embodiment 34. A method of modulating muscarinic acetylcholine receptor $M_1$ activity in a subject comprising administering to the subject a compound of any one of embodiments 1-23, or a pharmaceutically acceptable salt or solvate thereof.

Embodiment 35. The method of embodiment 34, wherein the compound acts as a selective $M_1$ antagonist.

EXAMPLES

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Intermediate amine 1: Preparation of 1-(quinolin-5-yl)cyclopropan-1-amine

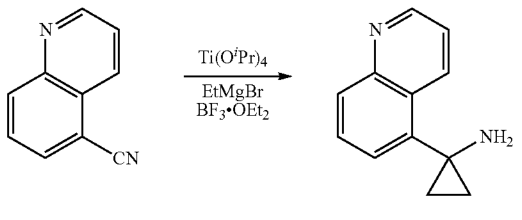

Intermediate amine 1

In a dried round-bottom flask equipped with a magnetic stirrer was dissolved quinoline-5-carbonitrile (1 equiv, Combi-Blocks) and titanium(IV) isopropoxide (1.1 equiv, Combi-Blocks) in diethyl ether (0.2 M). To this was then added ethyl magnesium bromide (2 equiv, 3 M solution in ether, Sigma-Aldrich) dropwise at −78° C. over a period of 5 min. The resulting brown suspension was stirred at −78° C. for 10 more min and then allowed to warm to RT over 1 h. Finally, to the reaction mixture was added neat boron trifluoride diethyl etherate (2 equiv, Sigma-Aldrich) dropwise over a period of 5 min. The now brown-black suspension was allowed to stir at RT for another 2 h. The reaction was then quenched with the addition of 1 M aq. HCl and the resulting biphasic mixture was poured into a separatory funnel. The golden aqueous layer was separated, washed further with diethyl ether (3×) and carefully basified with the addition of 1 M aq. NaOH. The resulting suspension was then extracted with EtOAc (3×). The combined EtOAc extracts were washed further with water and brine, dried over $MgSO_4$, filtered and the filtrate concentrated in vacuo to afford a viscous, golden oil. Purification of the crude product thus obtained by way of column chromatography ($SiO_2$, gradient elution: EtOAc→9:1 (v/v) EtOAc: MeOH) afforded the title compound as a yellow oil that solidified upon standing (44% yield).

The following amines were prepared in an analogous fashion to Intermediate amine 1 but substituting quinoline-5-carbonitrile for the requisite carbonitrile:

| Name | Structure |
| --- | --- |
| Intermediate amine 2 | 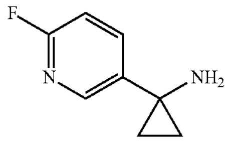 [SMILES: NC1(c2ccc(F)nc2)CC1] |
| Intermediate amine 3 | 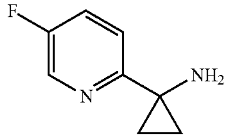 [SMILES: NC1(c2ccc(F)cn2)CC1] |
| Intermediate amine 4 | 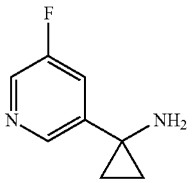 [SMILES: NC1(c2cncc(F)c2)CC1] |
| Intermediate amine 5 | 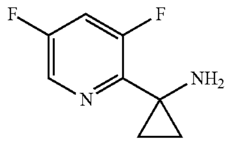 [SMILES: NC1(c2ncc(F)cc2F)CC1] |
| Intermediate amine 6 | 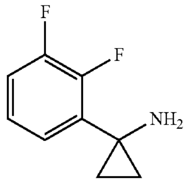 [SMILES: NC1(c2cccc(F)c2F)CC1] |
| Intermediate amine 7 | 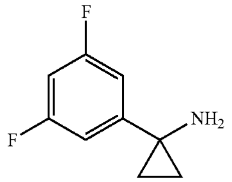 [SMILES: NC1(c2cc(F)cc(F)c2)CC1] |
| Intermediate amine 8 | 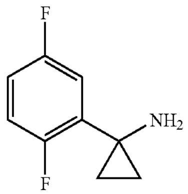 [SMILES: NC1(c2cc(F)ccc2F)CC1] |
| Intermediate amine 9 | 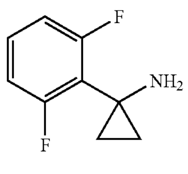 [SMILES: NC1(c2c(F)cccc2F)CC1] |

-continued

| Name | Structure |
|---|---|
| Intermediate amine 10 | 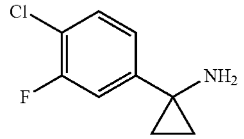 [SMILES: NC1(c2ccc(Cl)c(F)c2)CC1] |
| Intermediate amine 11 | 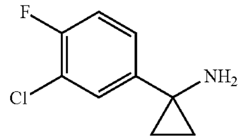 [SMILES: NC1(c2ccc(F)c(Cl)c2)CC1] |
| Intermediate amine 12 | 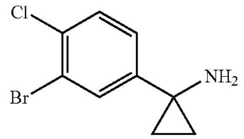 [SMILES: NC1(c2ccc(Cl)c(Br)c2)CC1] |
| Intermediate amine 13 | 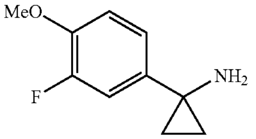 [SMILES: COc1ccc(C2(N)CC2)cc1F] |
| Intermediate amine 14 | 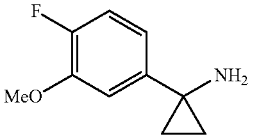 [SMILES: COc1cc(C2(N)CC2)ccc1F] |
| Intermediate amine 15 | 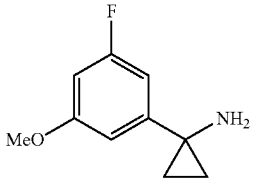 [SMILES: COc1cc(F)cc(C2(N)CC2)c1] |
| Intermediate amine 16 | 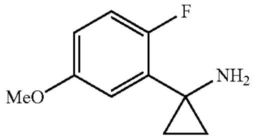 [SMILES: COc1ccc(F)c(C2(N)CC2)c1] |

Intermediate amine 17: Preparation of 1-(2-methoxypyridin-4-yl)cyclopropan-1-amine

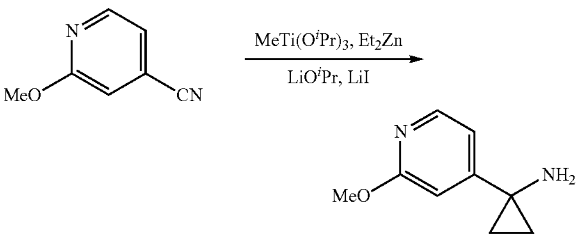

Intermediate amine 17

In a dried round-bottom flask equipped with a magnetic stirrer was combined lithium isopropoxide (2.5 equiv, 3 M solution in THF, Sigma-Aldrich) and lithium iodide (2.5 equiv, Sigma-Aldrich) in THF (0.31 M). To this was then carefully added methyltitanium(IV) triisopropoxide (1.2 equiv, 1 M solution in THF, Sigma-Aldrich) and 4-cyano-2-methoxypyridine (1 equiv, 1.9 M solution in THF, Combi-Blocks) dropwise over a period of 15 min. Finally, diethylzinc (1.2 equiv, 1 M solution in toluene, Sigma-Aldrich) was added dropwise within 60 min. The resulting mixture was stirred at RT for 16 h before the reaction was quenched by the careful addition of water. The resulting slurry was stirred until the color turned yellow and the precipitate was removed via filtration. The insolubles were rinsed further with diethyl ether. The combined filtrates were washed sequentially with water and brine, dried over $Na_2SO_4$, filtered and the filtrate concentrated in vacuo. Purification of the crude product thus obtained by way of reverse phase column chromatography (Cis, gradient elution: 9:1 (v/v) $H_2O$:MeCN+0.1% formic acid→MeCN+0.1% formic acid) afforded the title compound after freebasing (14% yield).

The following amines were prepared in an analogous fashion to Intermediate amine 17 but substituting 4-cyano-2-methoxypyridine for the requisite carbonitrile:

| Name | Structure |
|---|---|
| Intermediate amine 18 | 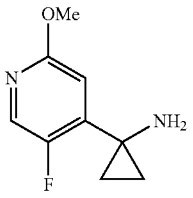 [SMILES: COc1cc(C2(N)CC2)c(F)cn1] |
| Intermediate amine 19 | 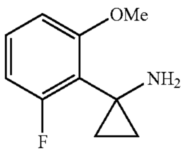 [SMILES: COc1cccc(F)c1C1(N)CC1] |
| Intermediate amine 20 | 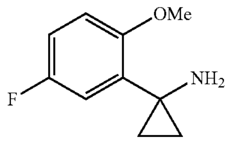 [SMILES: COc1ccc(F)cc1C1(N)CC1] |
| Intermediate amine 21 | 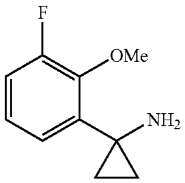 [SMILES: COc1c(F)cccc1C1(N)CC1] |
| Intermediate amine 22 | 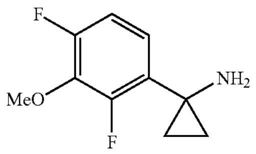 [SMILES: COc1c(F)ccc(C2(N)CC2)c1F] |
| Intermediate amine 23 | 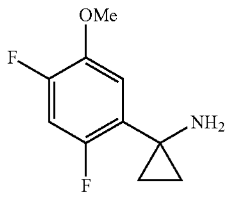 [SMILES: COc1cc(C2(N)CC2)c(F)cc1F] |

Intermediate amine 24: Preparation of 1-(3-methoxyphenyl)cyclobutan-1-amine

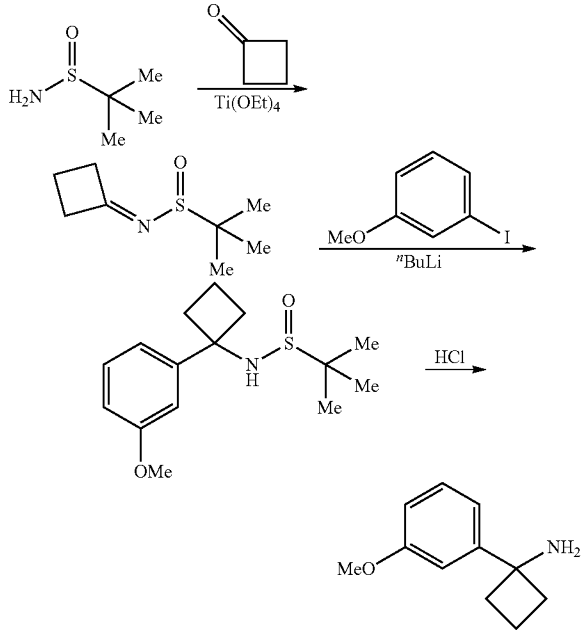

Intermediate amine 24

Step 1: In a dried round-bottom flask equipped with a magnetic stirrer was dissolved cyclobutanone (1.2 equiv, Combi-Blocks) in THF (0.5 M). To this was then added sequentially titanium(IV) ethoxide (1.8 equiv, Acros) and 2-methylpropane-2-sulfinamide (1 equiv, Combi-Blocks). The resulting mixture was allowed to stir at RT for 16 h. The volatiles were then removed in vacuo and the resulting residue was partitioned between EtOAc and saturated aq. $NaHCO_3$. The resulting suspension was then filtered through a pad of celite and the insoluble was washed further with EtOAc. The filtrate was then poured into a separatory funnel. The organic layer was separated, washed further with brine, dried over $MgSO_4$, filtered and the filtrate concentrated in vacuo. Purification of the crude product thus obtained by way of column chromatography ($SiO_2$, gradient elution: Hex→EtOAc) afforded N-cyclobutylidene-2-methylpropane-2-sulfinamide as a yellow oil (64% yield).

Step 2: In a dried round-bottom flask equipped with a magnetic stirrer was dissolved 1-iodo-3-methoxybenzene (1 equiv, Acros) in diethyl ether (0.43 M). The resulting solution was then cooled to −78° C. before $^n$BuLi (1.1 equiv, 2.5 M solution in hexanes, Sigma-Aldrich) was added dropwise over 5 min to afford a bright yellow solution. After 30 min of stirring at −78° C., N-cyclobutylidene-2-methylpropane-2-sulfinamide (1.1 equiv) from the previous step was then added. The resulting mixture was allowed to warm to RT over 30 min before the reaction was quenched with the addition of saturated aq. $NH_4Cl$. The aqueous phase was separated and back extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution: Hex→EtOAc) afforded N-(1-(3-methoxyphenyl)cyclobutyl)-2-methylpropane-2-sulfinamide as a colorless oil (39% yield).

Step 3: In a dried round-bottom flask equipped with a magnetic stirrer was dissolved N-(1-(3-methoxyphenyl)cyclobutyl)-2-methylpropane-2-sulfinamide (1 equiv) from the previous step in methanol (0.83 M). To this was then added HCl (3 equiv, 4 M solution in dioxane, Sigma-Aldrich) and the resulting solution was allowed to stir at RT for 30 min. The reaction was then quenched with saturated aq. $NaHCO_3$ and extracted with EtOAc. The combined organic extracts were washed further with brine, dried over $Na_2SO_4$, and filtered. Concentration of the filtrate in vacuo afforded the title compound (45% crude yield).

The following amines were prepared in an analogous fashion to Intermediate amine 24 but substituting 1-iodo-3-methoxybenzene in step 2 for the requisite (hetero)aryl halide:

| Name | Structure |
| --- | --- |
| Intermediate amine 25 | 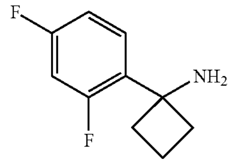 [SMILES: NC1(c2ccc(F)cc2F)CCC1] |
| Intermediate amine 26 | 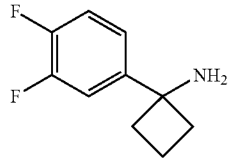 [SMILES: NC1(c2ccc(F)c(F)c2)CCC1] |
| Intermediate amine 27 | 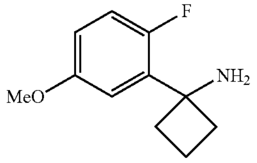 [SMILES: COc1ccc(F)c(C2(N)CCC2)c1] |
| Intermediate amine 28 | 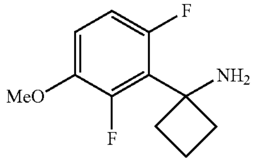 [SMILES: COc1ccc(F)c(C2(N)CCC2)c1F] |
| Intermediate amine 29 | 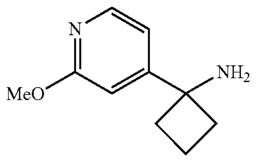 [SMILES: COc1cc(C2(N)CCC2)ccn1] |
| Intermediate amine 30 | 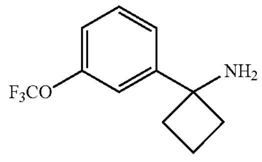 [SMILES: NC1(c2cccc(OC(F)(F)F)c2)CCC1] |

Intermediate amine 31: Preparation of 7-methoxy-1-methyl-1,2,3,4-tetrahydroisoquinoline

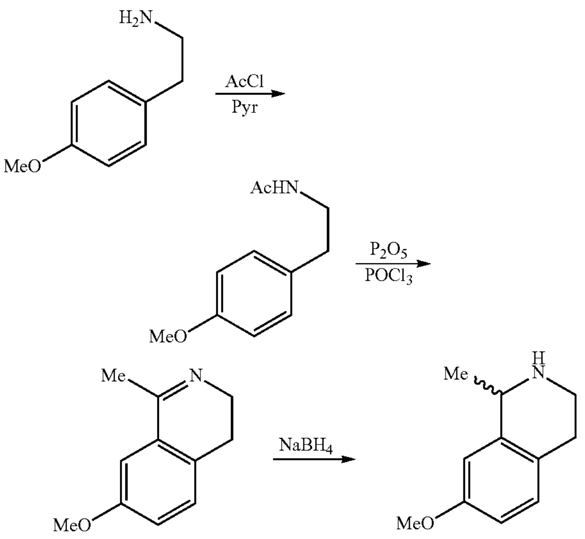

Intermediate amine 31

Step 1: In a dried round-bottom flask equipped with a magnetic stirrer was combined 4-methoxyphenethylamine (1 equiv, Combi-Blocks) and pyridine (2.5 equiv, Sigma-Aldrich) in dichloromethane (0.34 M). To this was then added acetyl chloride (2 equiv, Sigma-Aldrich) neat and dropwise over a period of 5 min. The resulting mixture was allowed to stir at RT for 3 h. The volatiles were then removed in vacuo and the resulting residue was directly subjected to purification by way of column chromatography ($SiO_2$, gradient elution:Hex→EtOAc) to afford N-(4-methoxyphenethyl)acetamide as a yellow oil (63% yield).

Step 2: In a dried round-bottom flask equipped with a magnetic stirrer was combined N-(4-methoxyphenethyl)acetamide (1 equiv) from the previous step, phosphorus pentoxide (2 equiv, Sigma-Aldich), and phosphorus (V) oxychloride (2 equiv, Sigma-Aldich) in toluene (0.21 M). The resulting solution was heated at 110° C. for 2 h. The volatiles were then removed in vacuo and the resulting residue was directly subjected to purification by way of reverse phase column chromatography (Cis, gradient elution: 10:1 (v/v) $H_2O$:MeCN→MeCN) to afford 7-methoxy-1-methyl-3,4-dihydroisoquinoline as a yellow oil (77% yield).

Step 3: In a dried round-bottom flask equipped with a magnetic stirrer was dissolved 7-methoxy-1-methyl-3,4-dihydroisoquinoline (1 equiv) from the previous step in methanol (0.32 M). To this was then added at 0° C. sodium borohydride (4 equiv, Sigma-Aldrich) portionwise and the resulting solution was allowed to stir at 0° C. for 2 h. The reaction was then quenched with water and extracted with DCM. The combined organic extracts were washed further with brine, dried over $Na_2SO_4$, filtered, and the filtrate concentrated in vacuo. Purification of the crude product this obtained by way of reverse phase column chromatography (Cis, gradient elution: 10:1 (v/v) $H_2O$:MeCN→MeCN) afforded the title compound as a pale yellow oil (74% yield).

The following amine was prepared in an analogous fashion to Intermediate amine 31 but substituting 4-methoxyphenethylamine in step 1 for 2-(2-methoxyphenyl)ethylamine (TCI):

| Name | Structure |
| --- | --- |
| Intermediate amine 32 | 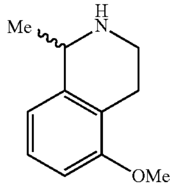 [SMILES: COc1cccc2c1CCNC2C] |

Intermediate amine 33: Preparation of 6-(3,8-diazabicyclo[3.2.1]octan-8-yl)nicotinonitrile bis hydrochloride

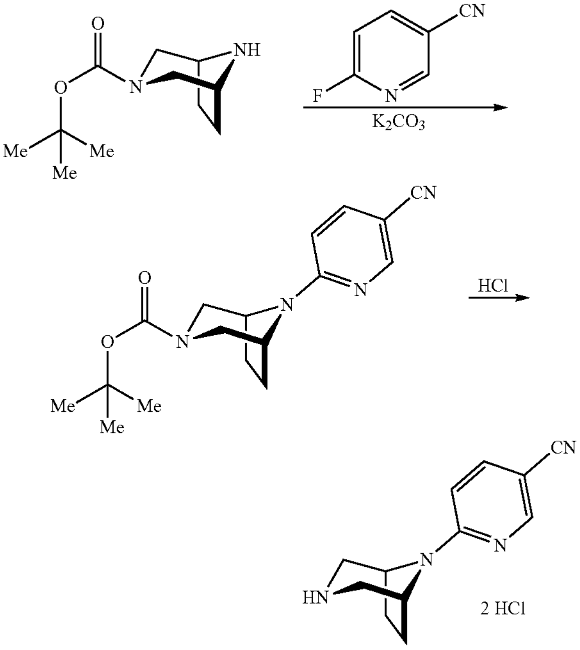

Intermediate amine 33

Step 1: In a dried round-bottom flask equipped with a magnetic stirrer and a reflux condenser was dissolved tert-butyl 3,8-diazabicyclo[3.2.1]octane-3-carboxylate (1 equiv, PharmaBlock, Inc.) and 5-cyano-2-fluoropyridine (1.2 equiv, Combi-Blocks) in acetonitrile (0.45 M). To this was then added potassium carbonate (2 equiv, Sigma-Aldrich) in one rapid portion and the resulting suspension was stirred at reflux for 3 h. The reaction suspension was then cooled to RT and filtered. The insoluble was rinsed further with acetonitrile and the filtrate was concentrated in vacuo. The resulting residue was then partitioned between EtOAc and water. The organic layer was separated and washed further with water (2×) and brine. The combined aqueous washes were backextracted with EtOAc (2×). The EtOAc extracts were then combined, dried over $MgSO_4$, filtered and the filtrate concentrated in vacuo. The resulting oil, which solidified upon standing, was taken up in warm EtOAc and then added an equal volume of hexanes. Upon cooling to RT, slow precipitation of white crystalline solid was observed. This solid impurity was removed via filtration and discarded. The filtrate was then concentrated in vacuo and the crude product thus obtained was purified further by way of column chromatography ($SiO_2$, gradient elution:Hex→1:1 (v/v) Hex:EtOAc) to afford tert-butyl 8-(5-cyanopyridin-2-yl)-3,8-diazabicyclo[3.2.1]octane-3-carboxylate as a white, crystalline solid (94% yield).

Step 2: In a dried round-bottom flask equipped with a magnetic stirrer was dissolved tert-butyl 8-(5-cyanopyridin-2-yl)-3,8-diazabicyclo[3.2.1]octane-3-carboxylate (1 equiv) from the previous step in dichloromethane (0.42 M). To this was then added at 0° C. HCl (4 equiv, 4 M solution in dioxane, Sigma-Aldrich) in three portions over a period of 30 min. The resulting suspension was stirred at 0° C. for 1 h and then allowed to warm slowly to RT over 16 h. The reaction mixture was added tert-butyl methyl ether and the resulting thick suspension was vigorously stirred at RT for 1 h. Finally, the suspension was filtered, washed further with tert-butyl methyl ether and air-dried to afford the title compound as a white crystalline solid (96% yield).

The following amines were prepared in an analogous fashion to Intermediate amine 33 but substituting tert-butyl 3,8-diazabicyclo[3.2.1]octane-3-carboxylate in step 1 for the requisite amine. For the synthesis of Intermediate amine 34, Intermediate amine 40, Intermediate amine 42 and Intermediate amine 43, potassium carbonate was also substituted with DIPEA (Sigma-Aldrich) as the base and acetonitrile was substituted with NMP as the solvent in step 1. In addition, for the synthesis of Intermediate amine 42 and Intermediate amine 43, the deprotection was carried out with TFA (Fisher Scientific) instead of HCl and the resulting product was also freebased. For the synthesis of Intermediate amine 35, Intermediate amine 36, Intermediate amine 37, Intermediate amine 38, and Intermediate amine 39, potassium carbonate was also substituted with cesium carbonate (Sigma-Aldrich) as the base in step 1.

| Name | Structure |
|---|---|
| Intermediate amine 34 | 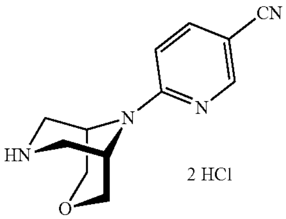 2 HCl |
| Intermediate amine 35 | 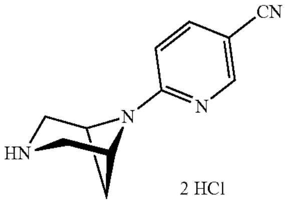 2 HCl |
| Intermediate amine 36 | 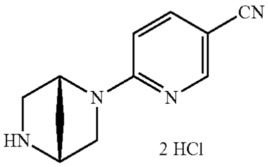 2 HCl |

-continued

| Name | Structure |
|---|---|
| Intermediate amine 37 | 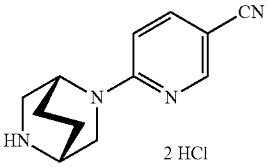 2 HCl |
| Intermediate amine 38 | 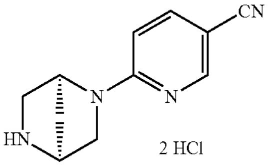 [SMILES: N#Cc1ccc(N2C[C@@H]3C[C@H]2CN3)nc1] 2 HCl |
| Intermediate amine 39 | 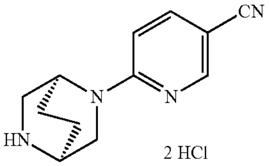 [SMILES: N#Cc1ccc(N2C[C@@H]3CC[C@H]2CN3)nc1] 2 HCl |
| Intermediate amine 40 | 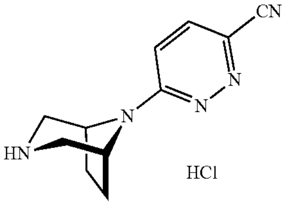 HCl |
| Intermediate amine 41 | 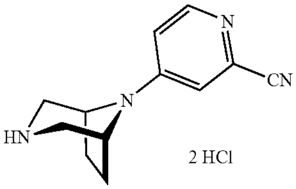 2 HCl |
| Intermediate amine 42 | 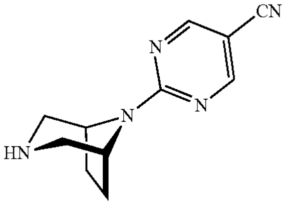 |
| Intermediate amine 43 | 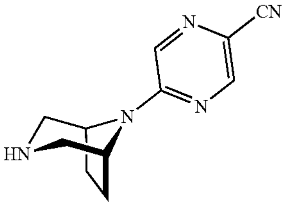 |

Intermediate amine 44: Preparation of 5-(3,8-diazabicyclo[3.2.1]octan-8-yl)picolinonitrile

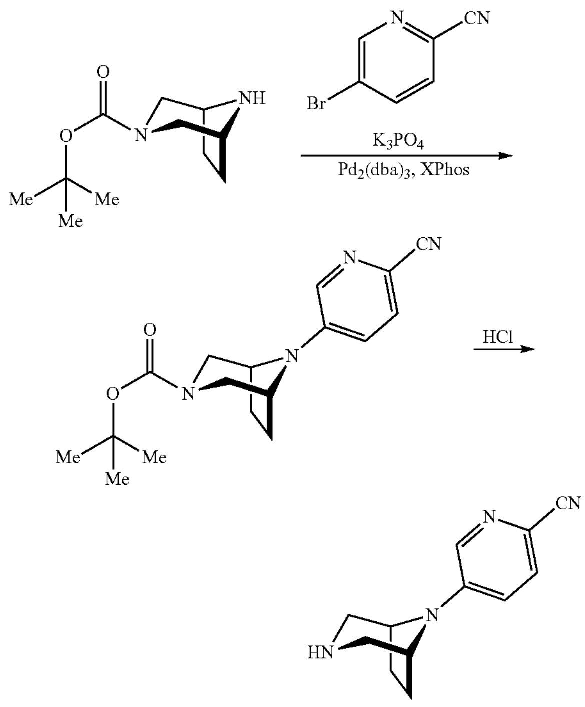

Intermediate amine 44

Step 1: In a dried round-bottom flask equipped with a magnetic stirrer was combined tert-butyl 3,8-diazabicyclo[3.2.1]octane-3-carboxylate (1 equiv, PharmaBlock, Inc.), 3-bromopyridine-2-carbonitrile (1.2 equiv, Combi-Blocks), $K_3PO_4$ (2.5 equiv, Sigma-Aldrich), $Pd_2(dba)_3$ (0.2 equiv, Sigma-Aldrich), and XPhos (0.4 equiv, Strem) in DME (0.29 M). The reaction suspension was then deoxygenated via sub-surface purging with $N_2$ for 10 min. Finally, the reaction vessel was tightly sealed and heated at 90° C. for 3 h. The reaction mixture was allowed to cool to RT, diluted with water and extracted with DCM. The combined organic extracts were dried over $MgSO_4$, filtered and the filtrate concentrated in vacuo. Purification of the crude product thus obtained by way of column chromatography ($SiO_2$, isocratic elution: 1:1 (v/v) Hex:EtOAc) afforded tert-butyl 8-(6-cyanopyridin-3-yl)-3,8-diazabicyclo[3.2.1]octane-3-carboxylate as an off-white solid (49% yield).

Step 2: In a dried round-bottom flask equipped with a magnetic stirrer was dissolved tert-butyl 8-(6-cyanopyridin-3-yl)-3,8-diazabicyclo[3.2.1]octane-3-carboxylate (1 equiv) from the previous step in dichloromethane (0.076 M). To this was then added TFA (45 equiv, Fisher Scientific) and the resulting solution was stirred at RT for 1 h. The pH of the reaction solution was then adjusted to 8-9 with ammonia (7 M solution in methanol, Sigma-Aldrich) before the volatiles were removed in vacuo. Purification of the crude product thus obtained by way of column chromatography ($SiO_2$, gradient elution: EtOAc→10:1 (v/v) EtOAc: MeOH) afforded the title compound as a yellow solid (65% yield).

Intermediate amine 45: Preparation of 4-(3,8-diazabicyclo[3.2.1]octan-8-yl)benzonitrile bis hydrochloride

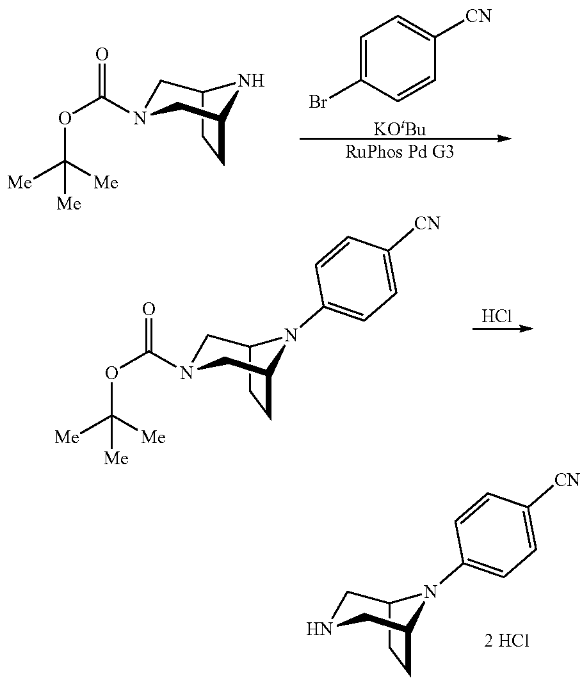

Intermediate amine 45

Step 1: In a sealable reaction vessel equipped with a magnetic stirrer and a Teflon screwcap was combined tert-butyl 3,8-diazabicyclo[3.2.1]octane-3-carboxylate (1 equiv, PharmaBlock, Inc.), 4-bromobenzonitrile (1.1 equiv, Combi-Blocks) and potassium tert-butoxide (2 equiv, Sigma-Aldrich) in dioxane (0.33 M). The reaction suspension was then deoxygenated via sub-surface purging with $N_2$ for 10 min. Finally, RuPhos Pd G3 (0.05 equiv, Sigma-Aldrich) was added in one rapid fashion and the reaction vessel was tightly sealed and heated at 80° C. for 16 h. The reaction mixture was allowed to cool to RT, diluted with water and extracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution: Hex→EtOAc) afforded tert-butyl 8-(4-cyanophenyl)-3,8-diazabicyclo[3.2.1]octane-3-carboxylate as a tan solid (29% yield).

Step 2: In a dried round-bottom flask equipped with a magnetic stirrer was dissolved tert-butyl 8-(4-cyanophenyl)-3,8-diazabicyclo[3.2.1]octane-3-carboxylate (1 equiv) from the previous step in dichloromethane (0.2 M). To this was then added HCl (4 equiv, 4 M solution in dioxane, Sigma-Aldrich) and the resulting suspension was stirred at RT for 16 h. The reaction mixture was added tert-butyl methyl ether and the resulting thick suspension was vigorously stirred at RT for 1 h. Finally, the suspension was filtered, washed further with tert-butyl methyl ether and air-dried to afford the title compound as a white crystalline solid (91% yield).

Intermediate amine 46: Preparation of 8-(6-methylpyridazin-3-yl)-3,8-diazabicyclo[3.2.1]octane bis hydrochloride

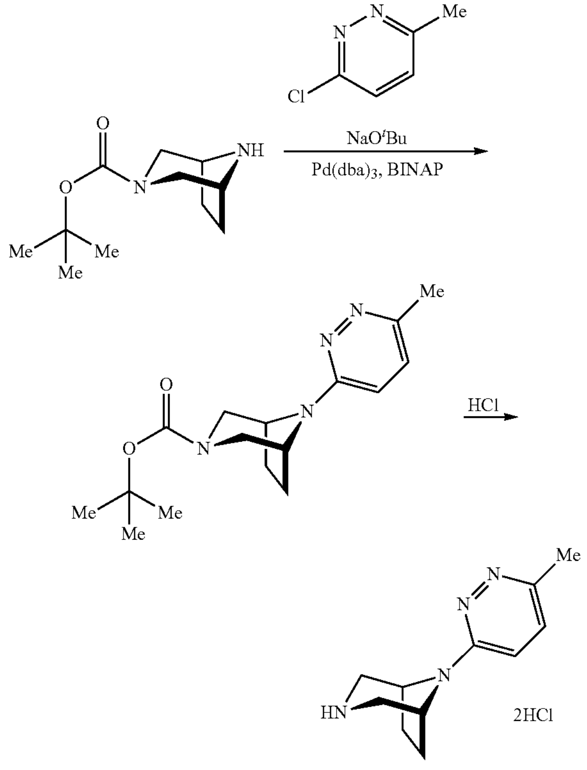

Intermediate amine 46

Step 1: In a sealable reaction vessel equipped with a magnetic stirrer and a Teflon screwcap was combined tert-butyl 3,8-diazabicyclo[3.2.1]octane-3-carboxylate (1.2 equiv, PharmaBlock, Inc.), 3-chloro-6-methylpyridazine (1 equiv, Combi-Blocks), sodium tert-butoxide (1.2 equiv, Sigma-Aldrich), $Pd_2(dba)_3$ (0.02 equiv, Sigma-Aldrich), and BINAP (0.04 equiv, ArkPharm) in toluene (0.68 M). The reaction suspension was then deoxygenated via sub-surface purging with $N_2$ for 10 min. Finally, the reaction vessel was tightly sealed and heated at 100° C. for 16 h. The reaction mixture was allowed to cool to RT, diluted with water and extracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution:Hex→EtOAc→10:1 (v/v) EtOAc: MeOH) afforded tert-butyl 8-(6-methylpyridazin-3-yl)-3,8-diazabicyclo[3.2.1]octane-3-carboxylate as an off-white solid (69% yield).

Step 2: In a dried round-bottom flask equipped with a magnetic stirrer was dissolved tert-butyl 8-(6-methylpyridazin-3-yl)-3,8-diazabicyclo[3.2.1]octane-3-carboxylate (1 equiv) from the previous step in dichloromethane (0.25 M). To this was then added HCl (8 equiv, 4 M solution in dioxane, Sigma-Aldrich) and the resulting suspension was stirred at RT for 8 h. The reaction mixture was added tert-butyl methyl ether and the resulting thick suspension was vigorously stirred at RT for 1 h. Finally, the suspension was filtered, washed further with tert-butyl methyl ether and air-dried to afford the title compound as a white crystalline solid (83% yield).

Intermediate Ketone 1: Preparation of 1-(quinolin-5-yl)ethan-1-one

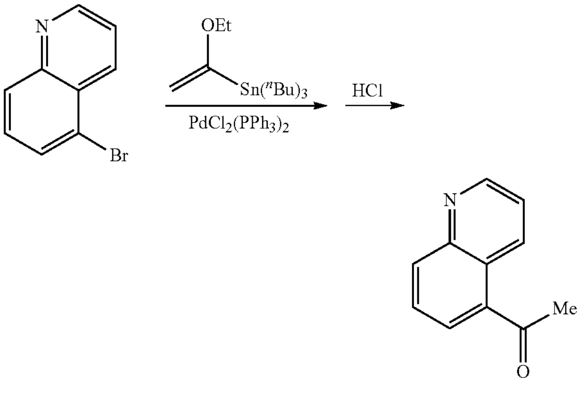

Intermediate ketone 1

In a sealable reaction vessel equipped with a magnetic stirrer and a Teflon screwcap was combined 5-bromoquinoline (1 equiv, Enamine), tributyl(1-ethoxyvinyl)tin (1 equiv, Sigma-Aldrich), and bis(triphenylphosphine)palladium(II) dichloride (0.05 equiv, Sigma-Aldrich) in dioxane (0.61 M). The reaction suspension was then deoxygenated via sub-surface purging with $N_2$ for 5 min. Finally, the reaction vessel was tightly sealed and heated at 100° C. for 2 h. The reaction mixture was allowed to cool to RT, diluted with water and added HCl (8 equiv, 8 M solution in water). The resulting mixture was vigorously stirred at RT for 45 min before its pH was adjusted to ~10 with the addition of 1 M aq. NaOH. The aqueous layer was then separated and backextracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution:Hex→EtOAc) afforded the title compound as a tan solid (84% yield).

The following ketones were prepared in an analogous fashion to Intermediate ketone 1 but substituting 5-bromoquinoline for the requisite heteroaryl halide:

| Name | Structure |
| --- | --- |
| Intermediate ketone 2 | 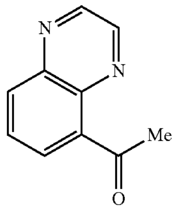 [SMILES: CC(=O)c1cccc2nccnc12] |

-continued

| Name | Structure |
|---|---|
| Intermediate ketone 3 | 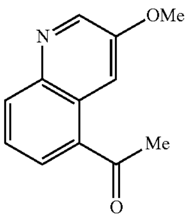 [SMILES: COc1cnc2cccc(C(C)=O)c2c1] |

| Name | Structure |
|---|---|
| Intermediate ketone 5 | 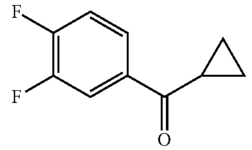 [SMILES: O=C(c1ccc(F)c(F)c1)C1CC1] |

Intermediate Ketone 4: Preparation of 1-(benzo[d]thiazol-7-yl)ethan-1-one

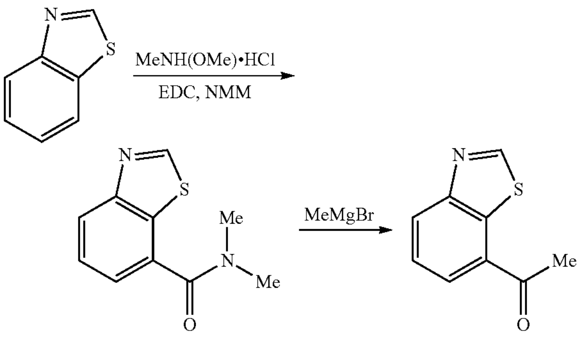

Intermediate ketone 4

Step 1: In a dried round-bottom flask equipped with a magnetic stirrer was combined benzo[d]thiazole-7-carboxylic acid (1 equiv, AstaTech), N, O-dimethylhydroxylamine hydrochloride (1.2 equiv, Combi-Blocks), and EDC (1.5 equiv, Sigma-Aldrich) in dichloromethane (0.28 M). To the reaction mixture was then added NMM (3 equiv, Sigma-Aldrich) and the resulting solution was allowed to stir at RT for 1 h. The volatiles were removed in vacuo and the resulting residue was directly subjected to purification by way of column chromatography ($SiO_2$, gradient elution: Hex→EtOAc) to afford N-methoxy-N-methylbenzo[d]thiazole-7-carboxamide as a yellow oil (64% yield).

Step 2: In a dried round-bottom flask equipped with a magnetic stirrer was dissolved N-methoxy-N-methylbenzo[d]thiazole-7-carboxamide (1 equiv) from the previous step in THF (0.17 M). To this was then added at −78° C. methylmagnesium bromide (1.1 equiv, 1 M solution in dibutyl ether, Sigma-Aldrich) dropwise over a period of 5 min. The resulting reaction mixture was allowed to warm slowly to RT over 5 h and then carefully quenched with 1 M aq. HCl. The aqueous layer was separated and backextracted with EtOAc. The organic extracts were then combined and concentrated in vacuo. The resulting residue was directly subjected to purification by way of column chromatography ($SiO_2$, gradient elution:Hex→EtOAc) to afford the title compound as a yellow oil (88% yield).

The following ketone was prepared in an analogous fashion to Intermediate ketone 4 but substituting benzo[d]thiazole-7-carboxylic acid for 3,4-difluorobenzoic acid (Combi-Blocks) in step 1 and methylmagnesium bromide for cyclopropylmagnesium bromide (Sigma-Aldrich) in step 2:

Intermediate Ketone 6: Preparation of 1-(benzo[d]thiazol-7-yl)-2,2,2-trifluoroethan-1-one

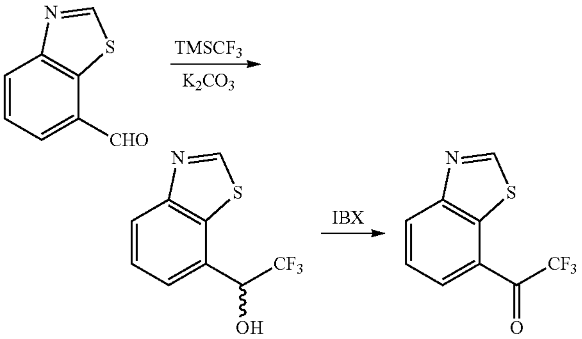

Intermediate ketone 6

Step 1: In a sealable reaction vessel equipped with a magnetic stirrer and a Teflon screwcap was combined benzo[d]thiazole-7-carbaldehyde (1 equiv, AstaTech), trimethyl(trifluoromethyl)silane (1.5 equiv, Sigma-Aldrich), and potassium carbonate (2 equiv, Sigma-Aldrich) in DMF (0.17 M). The reaction suspension was then deoxygenated via sub-surface purging with $N_2$ for 5 min. Finally, the reaction vessel was tightly sealed and heated at 80° C. for 2 h. The volatiles were removed in vacuo and the resulting residue was directly subjected to purification by way of column chromatography ($SiO_2$, gradient elution: Hex 4 EtOAc) to afford 1-(benzo[d]thiazole-7-yl)-2,2,2-trifluoroethan-1-ol as a yellow solid (76% yield).

Step 2: In a dried round-bottom flask equipped with a magnetic stirrer was dissolved 1-(benzo[d]thiazole-7-yl)-2,2,2-trifluoroethan-1-ol (1 equiv) from the previous step in EtOAc (0.11 M). To this was then added 2-iodoxybenzoic acid (2 equiv, Matrix Scientific) in one rapid portion and the resulting solution was heated at 80° C. for 12 h. The volatiles were removed in vacuo and the resulting residue was directly subjected to purification by way of column chromatography ($SiO_2$, gradient elution:Hex→EtOAc) to afford the title compound was as a yellow solid (76% yield).

Intermediate Ketone 7: Preparation of 1-(6-fluoroimidazol[1,2-a]pyridin-5-yl)ethan-1-one

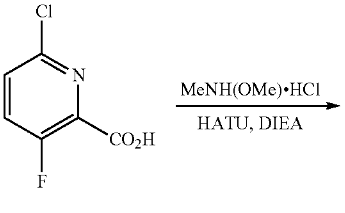

-continued

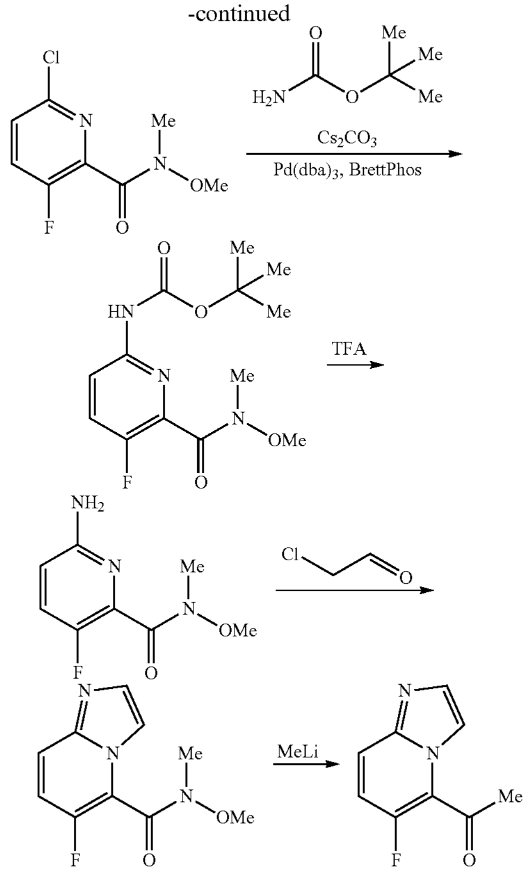

Intermediate ketone 7

Step 1: In a dried round-bottom flask equipped with a magnetic stirrer was combined 6-chloro-3-fluoropicolinic acid (1 equiv, AstaTech), N, O-dimethylhydroxylamine hydrochloride (1.2 equiv, Combi-Blocks), and HATU (1.5 equiv, Combi-Blocks) in DMF (0.85 M). To the reaction mixture was then added DIEA (3 equiv, Sigma-Aldrich) and the resulting solution was allowed to stir at RT for 1 h. The reaction mixture was then diluted with EtOAc and washed further with water (3×). The organic layer was then concentrated in vacuo and the resulting residue was directly subjected to purification by way of column chromatography ($SiO_2$, isocratic elution: 1:1 (v/v) Hex:EtOAc) to afford 6-chloro-3-fluoro-N-methoxy-N-methylpicolinamide as a yellow solid (80% yield).

Step 2: In a sealable reaction vessel equipped with a magnetic stirrer and a Teflon screwcap was dissolved 6-chloro-3-fluoro-N-methoxy-N-methylpicolinamide (1 equiv) from the previous step in dioxane (0.34 M). To this was then added $Pd_2(dba)_3$ (0.2 equiv, Sigma-Aldrich), BrettPhos (0.4 equiv, Sigma-Aldrich), cesium carbonate (3 equiv, Sigma-Aldrich) and tert-butyl carbamate (5 equiv, AstaTech). The reaction suspension was then deoxygenated via sub-surface purging with $N_2$ for 5 min. Finally, the reaction vessel was tightly sealed and heated at 90° C. for 2 h. The now black reaction suspension was allowed to cool to RT and filtered through a bed of celite. The filtrate was then concentrated in vacuo to afford a black tar. Purification of the crude product thus obtained by way of column chromatography ($SiO_2$, isocratic elution: 2:1 (v/v) Hex:EtOAc) afforded tert-butyl (5-fluoro-6-(methoxy(methyl)carbamoyl)pyridin-2-yl)carbamate as a brown oil (68% yield).

Step 3: In a dried round-bottom flask equipped with a magnetic stirrer was dissolved tert-butyl (5-fluoro-6-(methoxy(methyl)carbamoyl)pyridin-2-yl)carbamate (1 equiv) from the previous step in dichloromethane (0.47 M). To this was then added TFA (7 equiv, Fisher Scientific) and the resulting solution was stirred at RT for 2.5 h. The pH of the reaction solution was then adjusted to 8-9 with ammonia (7 M solution in methanol, Sigma-Aldrich) before the volatiles were removed in vacuo. Purification of the crude product thus obtained by way of reverse phase column chromatography (Cis, gradient elution: 10:1 (v/v) $H_2O$: MeCN→MeCN) afforded 6-amino-3-fluoro-N-methoxy-N-methylpicolinamide as a yellow oil (97% yield).

Step 4: In a dried round-bottom flask equipped with a magnetic stirrer was dissolved 6-amino-3-fluoro-N-methoxy-N-methylpicolinamide (1 equiv) from the previous step in ethanol (0.47 M). To this was then added chloroacetaldehyde (6 equiv, Enamine) and the resulting solution was heated at 80° C. for 2.5 h. The volatiles were then removed in vacuo. Purification of the crude product thus obtained by way of column chromatography ($SiO_2$, gradient elution: Hex→EtOAc) afforded 6-fluoro-N-methoxy-N-methylimidazol[1,2-a]pyridine-5-carboxamide as a yellow solid (97% yield).

Step 5: In a dried round-bottom flask equipped with a magnetic stirrer was dissolved 6-fluoro-N-methoxy-N-methylimidazol[1,2-a]pyridine-5-carboxamide (1 equiv) from the previous step in THF (0.067 M). To this was then added at −70° C. methyllithium (1.2 equiv, 1.6 M solution in diethyl ether, Sigma-Aldrich) dropwise over a period of 10 min. The resulting reaction mixture was allowed to stir at −70° C. for 1 h and then at 0° C. for another 45 min. Finally, the reaction was quenched with the careful addition of saturated aqueous $NH_4Cl$ at 0° C. The aqueous layer was separated and backextracted with EtOAc. The organic extracts were then combined and concentrated in vacuo. The resulting residue was directly subjected to purification by way of column chromatography ($SiO_2$, gradient elution: Hex→EtOAc) to afford the title compound as a yellow solid (21% yield).

Intermediate Ketone 8: Preparation of 1-([1,2,4]triazolo[1,5-a]pyridin-5-yl)ethan-1-one

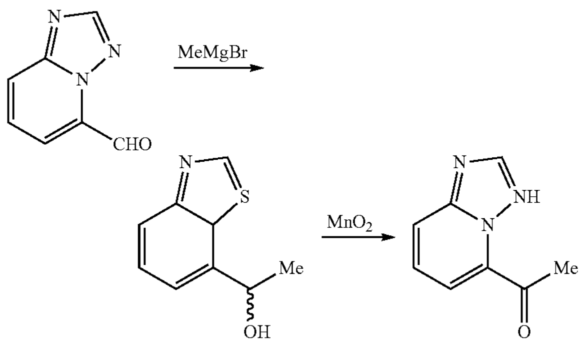

Intermediate alcohol 1 Intermediate ketone 8

Step 1: In a dried round-bottom flask equipped with a magnetic stirrer was dissolved [1,2,4]triazolo[1,5-a]pyridine-5-carbaldehyde (1 equiv, Enamine) in THF (0.5 M). To this was then added at −78° C. methylmagnesium bromide (2 equiv, 1 M solution in dibutyl ether, Sigma-Aldrich)

dropwise over a period of 10 min. The resulting reaction mixture was stirred at −50° C. for 1 h and then carefully quenched with saturated aq. $NH_4Cl$. The aqueous layer was separated and backextracted with DCM. The combined organic extracts were then washed further with water (3×) and brine, dried over $Na_2SO_4$, filtered and the filtrate concentrated in vacuo. The resulting residue was directly subjected to purification by way of column chromatography ($SiO_2$, isocratic elution: 95:5 (v/v) $CHCl_3$:MeOH) to afford 1-([1,2,4]triazolo[1,4-a]pyridin-5-yl)ethan-1-ol (Intermediate alcohol 1) as an off-white solid (78% yield).

Step 2: In a dried round-bottom flask equipped with a magnetic stirrer and a reflux condenser was dissolved Intermediate alcohol 1 (1 equiv) from the previous step in $CCl_4$ (0.12 M). To this was then added manganese (IV) oxide (5 equiv, Sigma-Aldrich) in one rapid portion and the resulting suspension was heated at 70° C. for 16 h. The reaction mixture was then cooled to RT, filtered through a bed of celite and the filtrate was concentrated in vacuo. The resulting residue was directly subjected to purification by way of column chromatography ($SiO_2$, gradient elution:Hex→EtOAc) to afford the title compound as an off-white solid (67% yield).

The following ketone was prepared in an analogous fashion to Intermediate ketone 8 but substituting [1,2,4]triazolo[1,5-a]pyridine-5-carbaldehyde for 3-fluoro-2-methoxybenzaldehyde (AstaTech) and methylmagnesium bromide for phenyllithium (1.9 M solution in dibutyl ether, Sigma-Aldrich) in step 1, as well as substituting manganese (IV) oxide for Dess-Martin Periodinane (2 equiv, Sigma-Aldrich) and $CCl_4$ for dichloromethane (0.26 M) in step 2:

| Name | Structure |
|---|---|
| Intermediate ketone 9 | 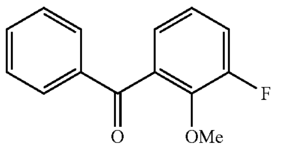 [SMILES: COc1c(F)cccc1C(=O)c1ccccc1] |

Intermediate Alcohol 2: Preparation of 1-(quinolin-5-yl)ethan-1-ol

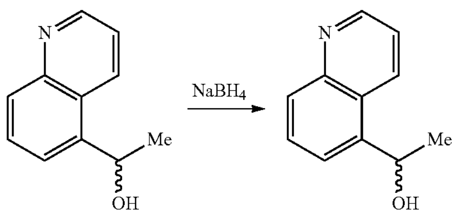

Intermediate ketone 1    Intermediate alcohol 2

In a dried round-bottom flask equipped with a magnetic stirrer was dissolved Intermediate ketone 1 (1 equiv) in methanol (0.1 M). To this was then added sodium borohydride (1.5 equiv, Sigma-Aldrich) portionwise over a period of 2 min. Following an initial period gas evolution, the resulting mixture was stirred at RT for an additional 10 min. The unreacted borohydride was first quenched with the addition of 1 M aq. HCl and then the pH of the resulting mixture was adjusted to ~10 with the addition of 1 M aq. NaOH. The volatiles were then removed in vacuo and the resulting aqueous suspension was extracted with EtOAc (3×). The combined EtOAc extracts were washed further with water and brine, dried over $MgSO_4$ and filtered. Concentration of the filtrate in vacuo afforded the title compound as white solid (77% yield).

The following alcohols were prepared in an analogous fashion to Intermediate alcohol 2 but substituting Intermediate ketone 1 for the requisite ketone:

| Name | Structure |
|---|---|
| Intermediate alcohol 3 | 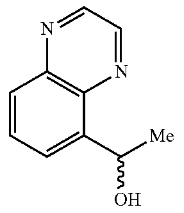 [SMILES: CC(O)c1cccc2nccnc12] |
| Intermediate alcohol 4 | 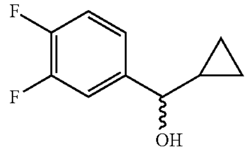 [SMILES: OC(c1ccc(F)c(F)c1)C1CC1] |

Intermediate Alcohol 5: Preparation of [1,2,4]triazolo[1,5-a]pyridin-5-yl(cyclopropyl)methanol

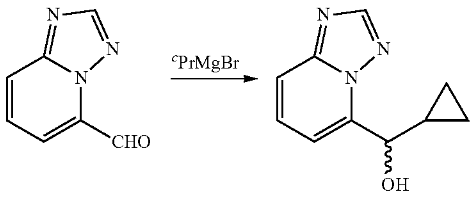

Intermediate alcohol 5

In a dried round-bottom flask equipped with a magnetic stirrer was dissolved [1,2,4]triazolo[1,5-a]pyridine-5-carbaldehyde (1 equiv, Enamine) in THF (0.35 M). To this was then added at −78° C. cyclopropylmagnesium bromide (2 equiv, 0.5 M solution in THF, Sigma-Aldrich) dropwise over a period of 10 min. The resulting reaction mixture was allowed to stir for 1 h at −78° C. and then 1 h at 0° C., before the reaction was carefully quenched with saturated aq. $NH_4Cl$. The aqueous layer was separated and back extracted with DCM. The combined organic extracts were then washed further with water (3×) and brine, dried over $Na_2SO_4$, filtered and the filtrate concentrated in vacuo. The resulting residue was directly subjected to purification by way of column chromatography ($SiO_2$, gradient elution: DCM→90:10 (v/v) DCM:MeOH) to afford the title compound as an off-white solid (38% yield).

The following alcohols were prepared in an analogous fashion to Intermediate alcohol 5 but substituting [1,2,4]triazolo[1,5-a]pyridine-5-carbaldehyde for the requisite aldehyde in step 1 and cyclopropyl magnesium bromide for methylmagnesium bromide for step 2:

| Name | Structure |
|---|---|
| Intermediate alcohol 6 | 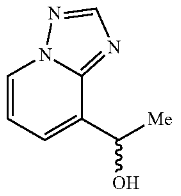 [SMILES: CC(O)c1cccn2ncnc12] |
| Intermediate alcohol 7 | 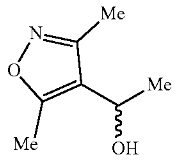 |
| Intermediate alcohol 8 | 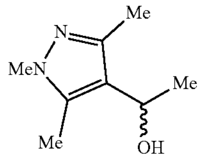 [SMILES: Cc1nn(C)c(C)c1C(C)O] |

Intermediate Alcohol 9: Preparation of 2,2-difluoro-1-(quinolin-5-yl)ethan-1-ol

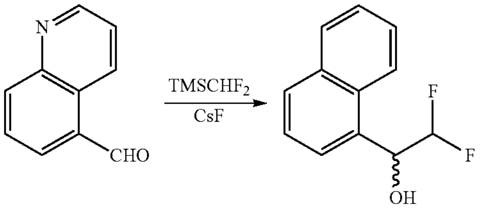

Intermediate alcohol 9

In a dried round-bottom flask equipped with a magnetic stirrer was combined quinoline-5-carbaldehyde (1 equiv, Combi-Blocks) and cesium fluoride (0.5 equiv, Sigma-Aldrich) in DMF (0.25 M). To this was then added trimethyl (difluoromethyl)silane (1.5 equiv, Sigma-Aldrich) in one rapid portion. The resulting reaction mixture was allowed to stir at RT for 15 min and then TBAF (1 equiv, 1 M solution in THF, Sigma-Aldrich) was added. After another 15 min of stirring at RT, the reaction mixture was diluted with 1:1 (v/v) Hex:EtOAc and washed with brine. The volatiles were then removed in vacuo and the resulting residue was directly subjected to purification by way of column chromatography ($SiO_2$, gradient elution:Hex→4:1 (v/v) EtOAc:Hex) to afford the title compound as a colorless oil (47% yield).

The following alcohols were prepared in an analogous fashion to Intermediate alcohol 9 but substituting quinoline-5-carbaldehyde for the requisite aldehyde:

| Name | Structure |
|---|---|
| Intermediate alcohol 10 | 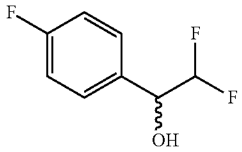 [SMILES: OC(c1ccc(F)cc1)C(F)F] |

-continued

| Name | Structure |
|---|---|
| Intermediate alcohol 11 | 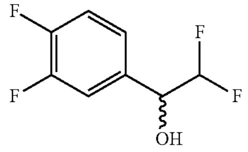 [SMILES: OC(c1ccc(F)c(F)c1)C(F)F] |
| Intermediate alcohol 12 | 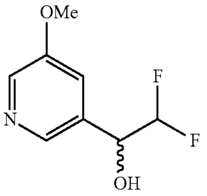 [SMILES: COc1cncc(C(O)C(F)F)c1] |

Intermediate Alcohol 13: Preparation of 2-([1,2,4]triazolo[1,5-a]pyridin-5-yl)propan-2-ol

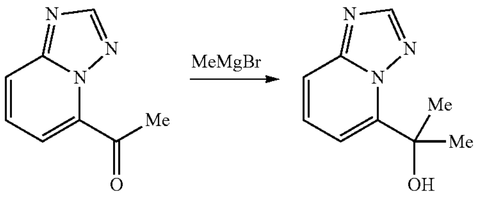

Intermediate ketone 8 Intermediate alcohol 13

In a dried round-bottom flask equipped with a magnetic stirrer was dissolved Intermediate ketone 8 (1 equiv) in THF (0.18 M). To this was then added at −78° C. methylmagnesium bromide (2 equiv, 1 M solution in dibutyl ether, Sigma-Aldrich) dropwise over a period of 5 min. The resulting reaction mixture was stirred at −78° C. for 1 h and then carefully quenched with saturated aq. $NH_4Cl$. The aqueous layer was separated and back extracted with DCM. The combined organic extracts were then washed further with water (3×) and brine, dried over $Na_2SO_4$, filtered and the filtrate concentrated in vacuo. The resulting residue was directly subjected to purification by way of column chromatography ($SiO_2$, isocratic elution: 5:1 (v/v) $CH_2Cl_2$:MeOH) to afford the title compound as an off-white solid (91% yield).

The following alcohol was prepared in an analogous fashion to Intermediate alcohol 13 but substituting Intermediate ketone 8 for methyl imidazole[1,2-a]pyridine-5-carboxylate (AstaTech):

| Name | Structure |
|---|---|
| Intermediate alcohol 14 | 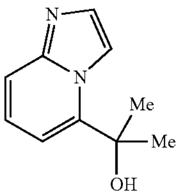 [SMILES: CC(C)(O)c1cccc2nccn12] |

Intermediate Alcohol 15: Preparation of 1-(3,4-difluorophenyl)cyclopropan-1-ol

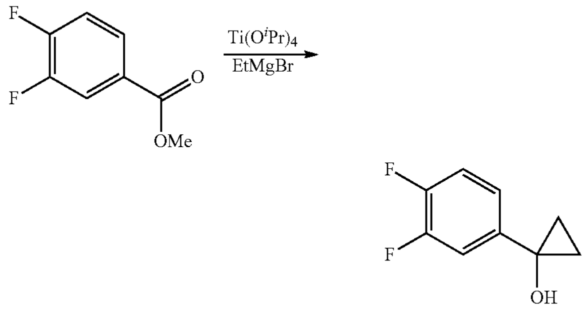

Intermediate alcohol 15

In a dried round-bottom flask equipped with a magnetic stirrer was dissolved methyl 3,4-difluorobenzoate (1 equiv, Combi-Blocks) and titanium(IV) isopropoxide (1.4 equiv, Combi-Blocks) in THF (0.3 M). To this was then added ethyl magnesium bromide (2 equiv, 3 M solution in ether, Sigma-Aldrich) dropwise at 0° C. over a period of 5 min. The reaction was then allowed to warm slowly to RT and stirred at RT for 16 h. Finally, the reaction was quenched with the addition of 1 M aq. HCl and diluted further with EtOAc. The resulting emulsion was then filtered through a pad of celite and the insolubles were washed further with EtOAc. The biphasic filtrate was then poured into a separatory funnel. The organic layer was separated, washed further with water and brine, dried over $Na_2SO_4$, filtered and the filtrate concentrated in vacuo. Purification of the crude product thus obtained by way of column chromatography ($SiO_2$, gradient elution:Hex 4~1:1 (v/v) Hex:EtOAc) afforded the title compound that was stored in a −20° C. freezer until use (41% yield).

The following alcohols were prepared in an analogous fashion to Intermediate alcohol 15 but substituting methyl 3,4-difluorobenzoate for the requisite ester:

| Name | Structure |
| --- | --- |
| Intermediate alcohol 16 | 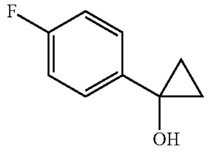 [SMILES: OC1(c2ccc(F)cc2)CC1] |
| Intermediate alcohol 17 | 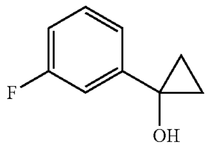 [SMILES: OC1(c2cccc(F)c2)CC1] |
| Intermediate alcohol 18 | 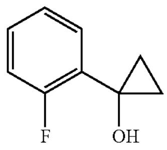 [SMILES: OC1(c2ccccc2F)CC1] |

-continued

| Name | Structure |
| --- | --- |
| Intermediate alcohol 19 | 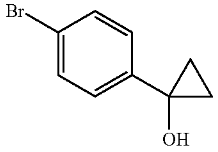 [SMILES: OC1(c2ccc(Br)cc2)CC1] |
| Intermediate alcohol 20 | 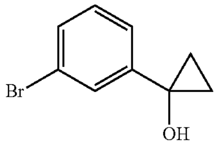 [SMILES: OC1(c2cccc(Br)c2)CC1] |
| Intermediate alcohol 21 | 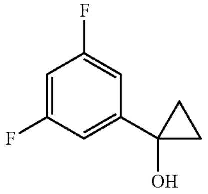 [SMILES: OC1(c2cc(F)cc(F)c2)CC1] |
| Intermediate alcohol 22 | 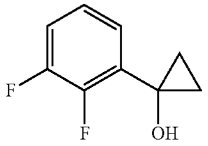 [SMILES: OC1(c2cccc(F)c2F)CC1] |
| Intermediate alcohol 23 | 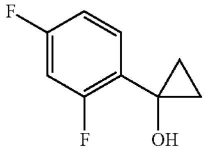 [SMILES: OC1(c2ccc(F)cc2F)CC1] |
| Intermediate alcohol 24 | 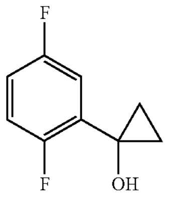 [SMILES: OC1(c2cc(F)ccc2F)CC1] |
| Intermediate alcohol 25 | 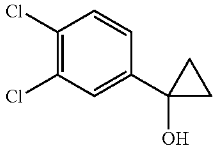 [SMILES: OC1(c2ccc(Cl)c(Cl)c2)CC1] |
| Intermediate alcohol 26 | 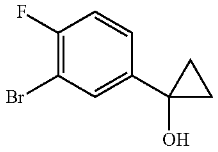 |
| Intermediate alcohol 27 | 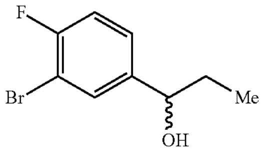 [SMILES: CCC(O)c1ccc(F)c(Br)c1] |

-continued

| Name | Structure |
|---|---|
| Intermediate alcohol 28 | 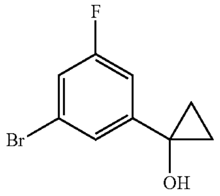 [SMILES: OC1(c2cc(F)cc(Br)c2)CC1] |
| Intermediate alcohol 29 | 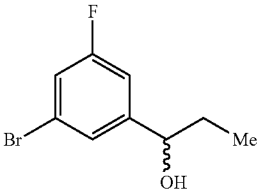 [SMILES: CCC(O)c1cc(F)cc(Br)c1] |

Intermediate Alcohol 38: Preparation of 1-(pyridin-4-yl)cyclopropan-1-ol

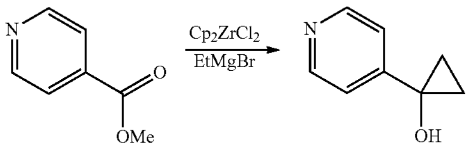

Intermediate alcohol 38

In a dried round-bottom flask equipped with a magnetic stirrer was dissolved bis(cyclopentadienyl)zirconium (IV) dichloride (2 equiv, Sigma-Aldrich) in toluene (0.14 M). To this was then added ethyl magnesium bromide (4 equiv, 3 M solution in ether, Sigma-Aldrich) dropwise at 0° C. over a period of 5 min and the resulting solution was stirred at 0° C. for 1 h. Finally, methyl isonicotinate (1 equiv, Combi-Blocks) was added dropwise at 0° C. to the reaction mixture as a toluene solution (0.36 M). The reaction was then allowed to warm slowly to RT and stirred at RT for 16 h. The reaction was quenched with the addition of saturated aq. $NH_4Cl$ and diluted further with DCM. The resulting orange suspension was then filtered through a pad of celite and the biphasic filtrate was poured into a separatory funnel. The aqueous layer was separated and backextracted with 2-methyltetrahydrofuran (3×). The combined 2-methyltetrahydrofuran extracts were then washed further with brine, dried over $Na_2SO_4$, filtered and the filtrate concentrated in vacuo. The crude title compound thus obtained (22% yield) was used directly in the next step without further purification.

The following alcohols were prepared in an analogous fashion to Intermediate alcohol 38 but substituting methyl isonicotinate for the requisite ester:

| Name | Structure |
|---|---|
| Intermediate alcohol 39 | 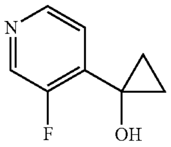 |

-continued

| Name | Structure |
|---|---|
| Intermediate alcohol 40 | 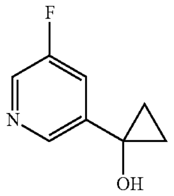 [SMILES: OC1(c2cncc(F)c2)CC1] |
| Intermediate alcohol 41 | 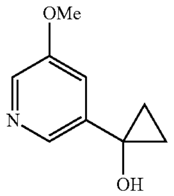 [SMILES: COc1cncc(C2(O)CC2)c1] |

Intermediate Alcohol 42: Preparation of 1-(quinoxalin-5-yl)cyclopropan-1-ol

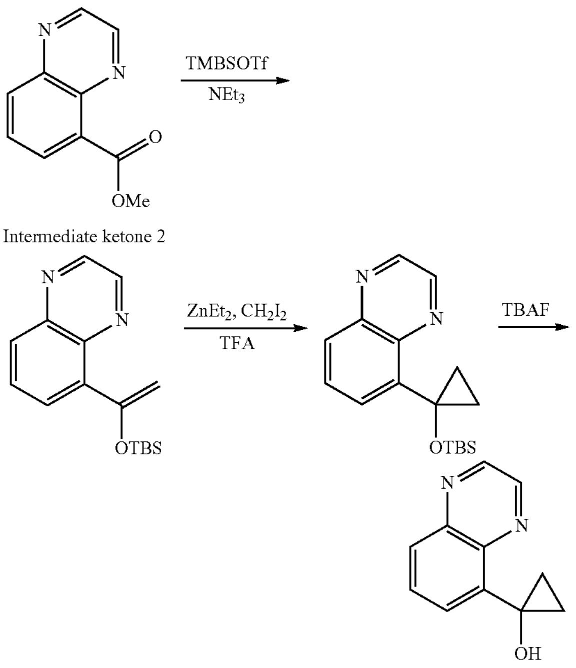

Intermediate alcohol 42

Step 1: In a dried round-bottom flask equipped with a magnetic stirrer was combined Intermediate ketone 2 (1 equiv) and tert-butyldimethylsilyl triflate (2 equiv, Sigma-Aldrich) in dichloromethane (0.21 M). To the reaction mixture was then added TEA (3 equiv, Sigma-Aldrich) and the resulting solution was stirred at RT for 1 h. The reaction was then quenched with the addition of saturated aq. $NH_4Cl$. The organic layer was separated, washed further with water (5×), dried over $Na_2S04$ and filtered. Concentration of the filtrate in vacuo afforded crude 5-(1-((tert-butyldimethylsilyl)oxy)vinyl)quinoxaline which was used directly in the next step without further purification.

Step 2: In a dried round-bottom flask equipped with a magnetic stirrer was combined diethylzinc (2 equiv, Sigma-Aldrich) and TFA (2 equiv, Sigma-Aldrich) at 0° C. in dichloromethane (0.11 M). To this was then carefully added at 0° C. diiodomethane (2 equiv, 1 M solution in dichloromethane, Sigma-Aldrich) dropwise over a period of 5 min. The resulting reaction mixture was stirred at 0° C. for another 20 min before 5-(1-((tert-butyldimethylsilyl)oxy)vinyl)quinoxaline (1 equiv) from the previous step was added dropwise as a dichloromethane solution (0.42 M) over a period of 5 min. The cooling bath was then removed and the mixture was allowed to stir at RT for 12 h. The reaction was finally quenched with the addition of saturated aq. $NH_4Cl$ and extracted with DCM (6×). The combined organic extracts were washed further with brine, dried over $Na_2SO_4$, filtered and the filtrate concentrated in vacuo. Purification of the crude product thus obtained by way of column chromatography ($SiO_2$, isocratic elution: 14:1 (v/v) Hex:EtOAc) afforded 5-(1-((tert-butyldimethylsilyl)oxy)cyclopropyl)quinoxaline as a yellow oil (24% yield over two steps).

Step 3: In a dried round-bottom flask equipped with a magnetic stirrer was dissolved 5-(1-((tert-butyldimethylsilyl)oxy)cyclopropyl)quinoxaline (1 equiv) from the previous step in THF (0.06 M). To this was then added TBAF (3 equiv, 1 M solution in THF, Sigma-Aldrich) and the resulting reaction mixture was stirred at RT for 20 min. The reaction was then quenched with the addition of water and extracted with DCM (3×). The combined organic extracts were washed further with water (6×) and brine, dried over $Na_2SO_4$, and filtered. Concentration of the filtrate in vacuo afforded the title compound which was used crude without further purification.

Intermediate Alcohol 43: Preparation of (1-([1,2,4]triazolo[1,5-a]pyridin-5-yl)cyclopropyl)methanol

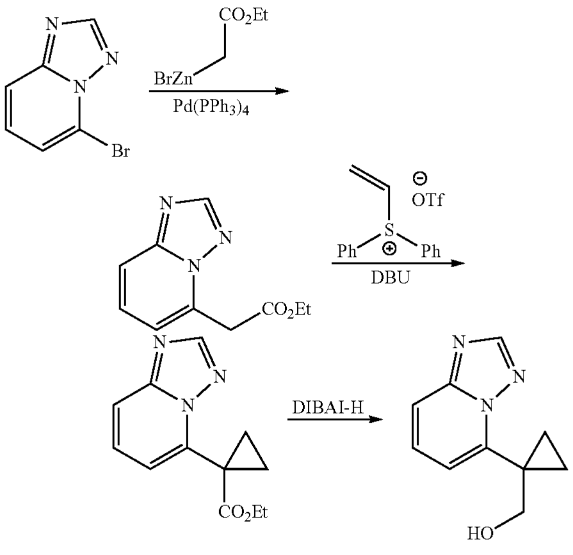

Intermediate alcohol 43

Step 1: In a dried round-bottom flask equipped with a magnetic stirrer was combined 5-bromo-[1,2,4]triazolo[1,5-a]pyridine (1 equiv, Sigma-Aldrich), 2-ethoxy-2-oxoethylzinc bromide (1.5 equiv, 0.5 M solution in THF, Rieke Metals), and $Pd(PPh_3)_4$(0.05 equiv, Sigma-Aldrich) in THF (0.21 M). The resulting solution was then deoxygenated via sub-surface purging with $N_2$ for 10 min. Finally, the reaction vessel was tightly sealed and heated at 60° C. for 16 h. The reaction mixture was allowed to cool to RT and the volatiles were removed in vacuo. Purification of the crude product thus obtained by way of column chromatography ($SiO_2$, isocratic elution: 4:1 (v/v) Hex:EtOAc) afforded ethyl 2-([1,2,4]triazolo[1,5-a]pyridin-5-yl)acetate as an off-white solid (55% yield).

Step 2: In a dried round-bottom flask equipped with a magnetic stirrer was combined ethyl 2-([1,2,4]triazolo[1,5-a]pyridin-5-yl)acetate (1 equiv) from the previous step and diphenylvinyl sulfonium triflate (1.2 equiv, Combi-Blocks) in DMSO (0.23 M). To this was then added DBU (3 equiv, Sigma-Aldrich) and the resulting solution was stirred at RT for 12 h. The reaction mixture was then directly subjected to purification by way of column chromatography (Cis, isocratic elution: 3:1 (v/v) $H_2O$:MeCN) to afford ethyl 1-([1,2,4]triazolo[1,5-a]pyridin-5-yl)cyclopropane-1-carboxylate as a yellow oil (57% yield).

Step 3: In a dried round-bottom flask equipped with a magnetic stirrer was dissolved ethyl 1-([1,2,4]triazolo[1,5-a]pyridin-5-yl)cyclopropane-1-carboxylate (1 equiv) from the previous step in THF (0.13 M). To this was then added at 0° C. diisobutylaluminum hydride (3 equiv, 1 M solution in THF, Sigma-Aldrich) over a period of 5 min. The resulting reaction mixture was first stirred at 0° C. for 30 min and then at RT for another 45 min. The reaction was then carefully quenched with saturated aq. $NH_4Cl$ and extracted with DCM (3×). The combined organic extracts were washed further with water (3×), dried over $Na_2SO_4$, filtered and the filtrate concentrated in vacuo. Purification of the crude product thus obtained by way of reverse phase column chromatography (Cis, gradient elution: 10:1 (v/v) $H_2O$: MeCN 4 MeCN) afforded the title compound as a yellow solid (54% yield).

Intermediate Alcohol 44: Preparation of 1-(5-methoxypyridin-3-yl)cyclobutan-1-ol

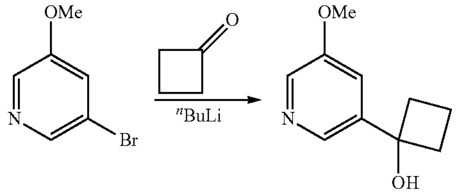

intermediate alcohol 44

In a dried round-bottom flask equipped with a magnetic stirrer was dissolved 3-bromo-5-methoxypyridine (1 equiv, Combi-Blocks) in THF (0.25 M). The resulting solution was then cooled to −78° C. before $^n$BuLi (1 equiv, 2.5 M solution in hexanes, Sigma-Aldrich) was added dropwise over 5 min to afford a dark purple solution. After 20 min of stirring at −78° C., cyclobutanone (1.1 equiv, Combi-Blocks) was then added neat and dropwise over 5 min. The resulting mixture was allowed to warm to RT over 30 min before the reaction was quenched with the addition of saturated aq. $NH_4Cl$. The aqueous phase was separated and backextracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex 4 EtOAc) afforded the title compound as a viscous oil that solidified upon standing (17% yield).

The following alcohols were prepared in an analogous fashion to Intermediate alcohol 44 but substituting 3-bromo-5-methoxypyridine for the requisite (hetero)aryl bromide or (hetero)aryl iodide. For the synthesis of Intermediate alcohol 45, Intermediate alcohol 46, Intermediate alcohol 47, Intermediate alcohol 48, Intermediate alcohol 55, Intermediate alcohol 58, Intermediate alcohol 59, Intermediate alcohol 61, Intermediate alcohol 63, Intermediate alcohol 72, Intermediate alcohol 74, Intermediate alcohol 75, Intermediate alcohol 78, and Intermediate alcohol 79, $^n$BuLi was also substituted with Turbo Grignard (1.3 M solution in THF, Sigma-Aldrich) and the transmetallation was carried out at −10° C. instead of −78° C. For the synthesis of Intermediate alcohol 51, Intermediate alcohol 52, Intermediate alcohol 53, Intermediate alcohol 54, and Intermediate alcohol 55, cyclobutanone was also substituted with 3-oxetanone (Combi-Blocks). For the synthesis of Intermediate alcohol 78 and Intermediate alcohol 79, cyclobutanone was also substituted with cyclopentanone (Combi-Blocks). For the synthesis of Intermediate alcohol 80, cyclobutanone was also substituted with dihydrofuran-3(2H)-one (Combi-Blocks):

| Name | Structure |
| --- | --- |
| Intermediate alcohol 45 | 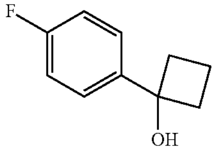 [SMILES: OC1(c2ccc(F)cc2)CCC1] |
| Intermediate alcohol 46 | 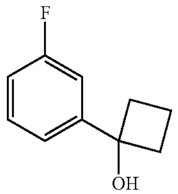 [SMILES: OC1(c2cccc(F)c2)CCC1] |
| Intermediate alcohol 47 | 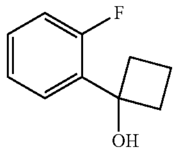 [SMILES: OC1(c2ccccc2F)CCC1] |
| Intermediate alcohol 48 | 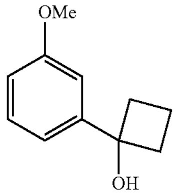 [SMILES: COc1cccc(C2(O)CCC2)c1] |
| Intermediate alcohol 49 | 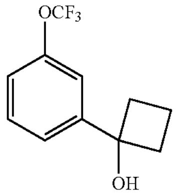 [SMILES: OC1(c2cccc(OC(F)(F)F)c2)CCC1] |

-continued

| Name | Structure |
| --- | --- |
| Intermediate alcohol 50 | 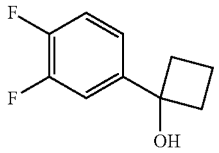 [SMILES: OC1(c2ccc(F)c(F)c2)CCC1] |
| Intermediate alcohol 51 | 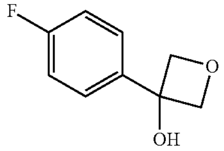 [SMILES: OC1(c2ccc(F)cc2)COC1] |
| Intermediate alcohol 52 | 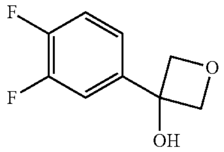 [SMILES: OC1(c2ccc(F)c(F)c2)COC1] |
| Intermediate alcohol 53 | 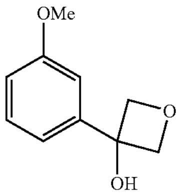 [SMILES: COc1cccc(C2(O)COC2)c1] |
| Intermediate alcohol 54 | 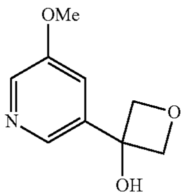 [SMILES: COc1cncc(C2(O)COC2)c1] |
| Intermediate alcohol 55 | 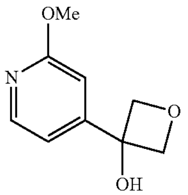 [SMILES: COc1cc(C2(O)COC2)ccn1] |
| Intermediate alcohol 56 | 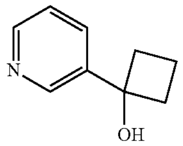 [SMILES: OC1(c2cccnc2)CCC1] |
| Intermediate alcohol 57 | 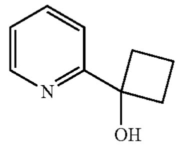 [SMILES: OC1(c2ccccn2)CCC1] |
| Intermediate alcohol 58 | 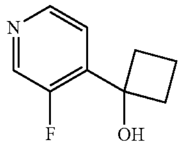 [SMILES: OC1(c2ccncc2F)CCC1] |

-continued

| Name | Structure |
| --- | --- |
| Intermediate alcohol 59 | 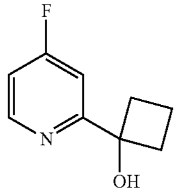 [SMILES: OC1(c2cc(F)ccn2)CCC1] |
| Intermediate alcohol 60 | 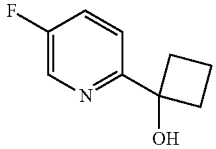 [SMILES: OC1(c2ccc(F)cn2)CCC1] |
| Intermediate alcohol 61 | 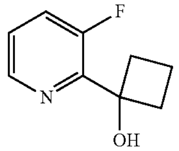 [SMILES: OC1(c2ncccc2F)CCC1] |
| Intermediate alcohol 62 | 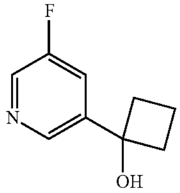 [SMILES: OC1(c2cncc(F)c2)CCC1] |
| Intermediate alcohol 63 | 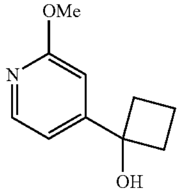 [SMILES: COc1cc(C2(O)CCC2)ccn1] |
| Intermediate alcohol 64 | 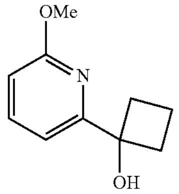 [SMILES: COc1cccc(C2(O)CCC2)n1] |
| Intermediate alcohol 65 | 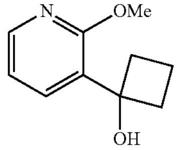 [SMILES: COc1ncccc1C1(O)CCC1] |
| Intermediate alcohol 66 | 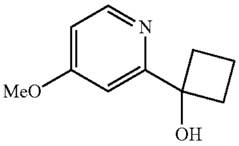 [SMILES: COc1ccnc(C2(O)CCC2)c1] |
| Intermediate alcohol 67 | 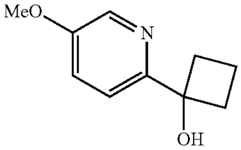 [SMILES: COc1ccc(C2(O)CCC2)nc1] |
| Intermediate alcohol 68 | 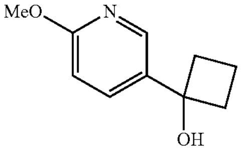 [SMILES: COc1ccc(C2(O)CCC2)cn1] |
| Intermediate alcohol 69 | 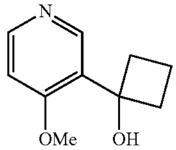 [SMILES: COc1ccncc1C1(O)CCC1] |
| Intermediate alcohol 70 | 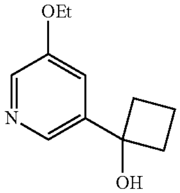 [SMILES: CCOc1cncc(C2(O)CCC2)c1] |
| Intermediate alcohol 71 | 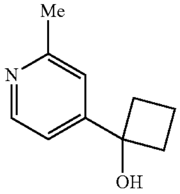 [SMILES: Cc1cc(C2(O)CCC2)ccn1] |
| Intermediate alcohol 72 | 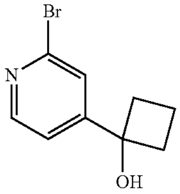 [SMILES: OC1(c2ccnc(Br)c2)CCC1] |
| Intermediate alcohol 73 | 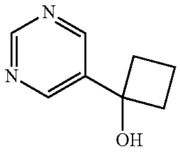 [SMILES: OC1(c2cncnc2)CCC1] |
| Intermediate alcohol 74 | 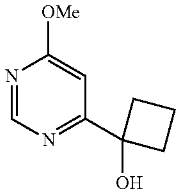 [SMILES: COc1cc(C2(O)CCC2)ncn1] |

-continued

| Name | Structure |
|---|---|
| Intermediate alcohol 75 | 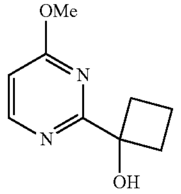 [SMILES: COc1ccnc(C2(O)CCC2)n1] |
| Intermediate alcohol 76 | 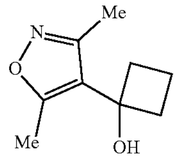 [SMILES: Cc1noc(C)c1C1(O)CCC1] |
| Intermediate alcohol 77 | 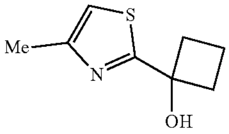 [SMILES: Cc1csc(C2(O)CCC2)n1] |
| Intermediate alcohol 78 | 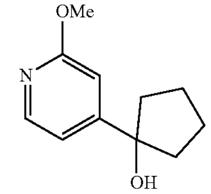 [SMILES: COc1cc(C2(O)CCCC2)ccn1] |
| Intermediate alcohol 79 | 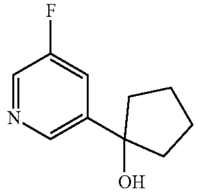 [SMILES: OC1(c2cncc(F)c2)CCCC1] |
| Intermediate alcohol 80 | 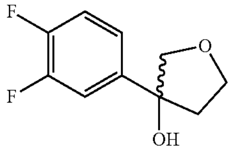 [SMILES: OC1(c2ccc(F)c(F)c2)CCOC1] |

Intermediate Alcohol 81 & Intermediate alcohol 82: Preparation of 1-(2-bromo-3,5-difluoropyridin-4-yl)cyclobutan-1-ol & 1-(3,5-difluoropyridin-2-yl)cyclobutan-1-ol

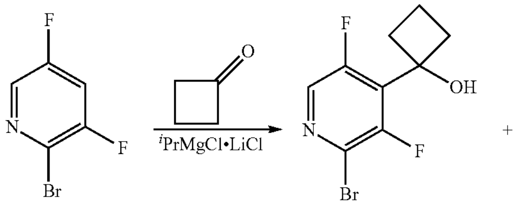

Intermediate alcohol 81

-continued

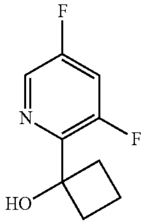

Intermediate alcohol 82

In a dried round-bottom flask equipped with a magnetic stirrer was dissolved 2-bromo-3,5-difluoropyridine (1 equiv, Combi-Blocks) in THF (0.52 M). The resulting solution was then cooled to −10° C. before Turbo Grignard (1.1 equiv, 1.3 M solution in THF, Sigma-Aldrich) was added dropwise over 5 min. After 15 min of stirring at −10° C., cyclobutanone (1.1 equiv, Combi-Blocks) was then added neat and dropwise over 5 min. The cooling bath was then removed and the reaction mixture was allowed to stir at RT for 1 h. Finally, the reaction was quenched with the addition of saturated aq. $NH_4Cl$ and extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex→EtOAc) afforded an inseparable 6:1 mixture of Intermediate alcohol 81 and Intermediate alcohol 82. This was used in the next step without further purification.

Intermediate Alcohol 83: Preparation of 1-(3,5-difluoro-2-methoxypyridin-4-yl)cyclobutan-1-ol

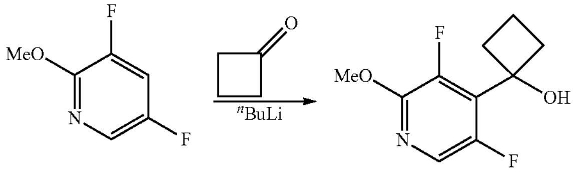

Intermediate alcohol 83

In a dried round-bottom flask equipped with a magnetic stirrer was dissolved 3,5-difluoro-2-methoxypyridine (1 equiv, Matrix Scientific) in THF (0.70 M). The resulting solution was then cooled to −78° C. before $^n$BuLi (1.1 equiv, 2.5 M solution in hexanes, Sigma-Aldrich) was added dropwise over 5 min to afford a dark purple solution. After 35 min of stirring at −78° C., cyclobutanone (1.1 equiv, Combi-Blocks) was then added neat and dropwise over 5 min. The resulting mixture was allowed to warm to RT over 30 min before the reaction was quenched with the addition of saturated aq. $NH_4Cl$. The aqueous phase was separated and backextracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex→EtOAc) afforded the title compound (57% yield).

Intermediate Alcohol 84: Preparation of 1-(pyrimidin-2-yl)cyclobutan-1-ol

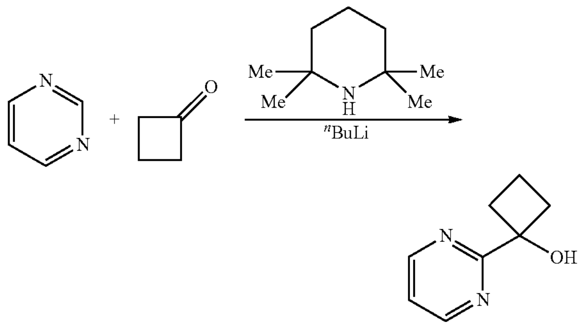

Intermediate alcohol 84

In a dried round-bottom flask equipped with a magnetic stirrer was dissolved 2,2,6,6-tetramethylpiperidine (1.5 equiv, Sigma-Alrdich) in THF (0.48 M). The resulting solution was then cooled to −30° C. before $^n$BuLi (1.1 equiv, 2.5 M solution in hexanes, Sigma-Aldrich) was added dropwise over 10 min to afford a yellow solution. After another 30 min of stirring at −30° C., the reaction solution was cooled further to −78° C. and pyrimidine (1 equiv, Sigma-Aldrich) was added dropwise over 5 min. Finally, cyclobutanone (1.1 equiv, Combi-Blocks) was added neat and dropwise to reaction mixture at −78° C. over a period of 10 min. After another 60 min of stirring at −78° C., the reaction was quenched with the addition of saturated aq. $NH_4Cl$. The aqueous phase was separated and backextracted with DCM (5×). The organic extracts were the combined, dried over $Na_2SO_4$, filtered and the filtrate concentrated in vacuo. Purification of the crude product thus obtained by way of column chromatography ($SiO_2$, gradient elution: Hex→EtOAc) afforded the title compound as a yellow oil (5% yield).

The following alcohol was prepared in an analogous fashion to Intermediate alcohol 84 but substituting pyrimidine with pyridazine (Sigma-Aldrich):

| Name | Structure |
| --- | --- |
| Intermediate alcohol 85 | 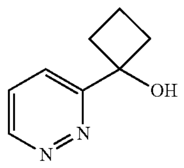 [SMILES: OC1(c2cccnn2)CCC1] |

Intermediate Alcohol 86: Preparation of 1-(6-methoxypyridazin-4-yl)cyclobutan-1-ol

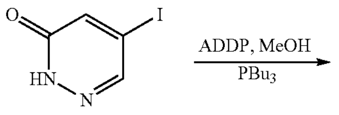

-continued

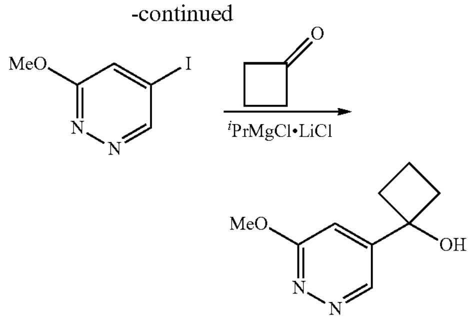

Intermediate alcohol 86

Step 1: In a dried round-bottom flask equipped with a magnetic stirrer was combined 5-iodopyridazin-3(2H)-one (1 equiv, Combi-Blocks), methanol (1.5 equiv, EMD), and 1,1'-(azodicarbonyl)dipiperidine (2 equiv, Sigma-Aldrich) in a 1:1 (v/v) solution of THF and toluene (0.15 M). The resulting orange reaction solution was then cooled to 0° C. before tributylphosphine (2 equiv, Sigma-Aldrich) was added dropwise over 5 min. The now thick, pale yellow suspension was stirred at RT for 15 min and then heated at 50° C. for 60 min. The reaction was quenched with the addition of water and then extracted with EtOAc (3×). The combined organic extracts were washed further with water and brine, dried over $MgSO_4$, filtered and the filtrate concentrated in vacuo. Purification of the crude product thus obtained by way of column chromatography ($SiO_2$, gradient elution:Hex→3:7 (v/v) Hex:EtOAc) afforded 5-iodo-3-methoxypyridazine (82% yield).

Step 2: In a dried round-bottom flask equipped with a magnetic stirrer was dissolved 5-iodo-3-methoxypyridazine (1 equiv) from the previous step in THF (0.15 M). The resulting solution was then cooled to −10° C. before Turbo Grignard (1.2 equiv, 1.3 M solution in THF, Sigma-Aldrich) was added dropwise over 5 min. After 15 min of stirring at −10° C., cyclobutanone (1.1 equiv, Combi-Blocks) was then added neat and dropwise over 5 min. The cooling bath was then removed and the reaction mixture was allowed to stir at RT for 1 h. Finally, the reaction was quenched with the addition of water and extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution: Hex→EtOAc) afforded the title compound as a pale yellow oil (20% yield).

Intermediate Alcohol 87: Preparation of 1-(5-((triisopropylsilyl)oxy)pyridin-3-yl)cyclobutan-1-ol

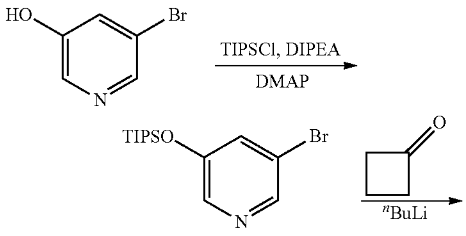

-continued

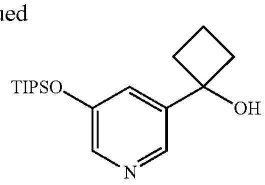

Intermediate alcohol 87

Step 1: In a dried round-bottom flask equipped with a magnetic stirrer was combined 5-bromopyridin-3-ol (1 equiv, Combi-Blocks), triisopropylsilyl chloride (1.1 equiv, Sigma-Aldrich), DIPEA (2 equiv, Sigma-Aldrich) and DMAP (0.05 equiv, Sigma-Aldrich) in dichloromethane (0.2 M). The resulting solution was stirred at RT for 48 h. The volatiles were then removed in vacuo and the resulting residue was directly subjected to purification by way of column chromatography ($SiO_2$, gradient elution:Hex→3:2 (v/v) Hex:EtOAc) to afford 3-bromo-5-((triisopropylsilyl)oxy)pyridine (>99% yield).

In a dried round-bottom flask equipped with a magnetic stirrer was dissolved 3-bromo-5-((triisopropylsilyl)oxy)pyridine (1 equiv) from the previous step in THF (0.13 M). The resulting solution was then cooled to −78° C. before $^{n}$BuLi (1.1 equiv, 2.5 M solution in hexanes, Sigma-Aldrich) was added dropwise over 5 min to afford a yellow solution. After 30 min of stirring at −78° C., cyclobutanone (1.1 equiv, Combi-Blocks) was then added neat and dropwise over 3 min. The resulting mixture was allowed to warm to 0° C. over 30 min before the reaction was quenched with the addition of saturated aq. $NH_4Cl$. The aqueous phase was separated and backextracted with EtOAc. The combined organic extracts were washed further with water and brine, dried over $MgSO_4$, filtered and the filtrate concentrated in vacuo. Purification of the crude product thus obtained by way of reverse phase column chromatography (Cis, gradient elution: 9:1 (v/v) $H_2O$:MeCN+0.1% formic acid→MeCN+0.1% formic acid) afforded the title compound as a colorless oil (68% yield).

Intermediate amide 1: Preparation of 6-(3-(2-chloroacetyl)-3,8-diazabicyclo[3.2.1]octan-8-yl)nicotinonitrile

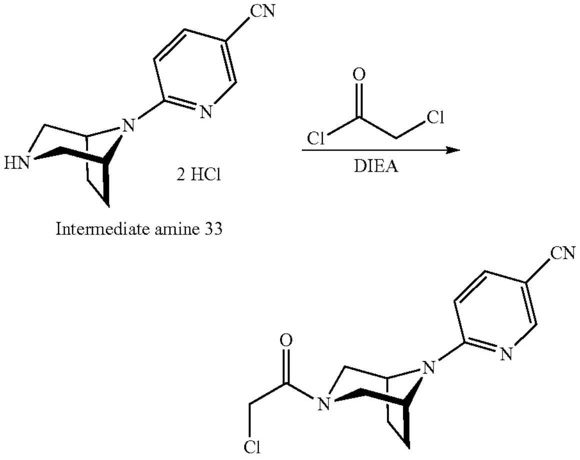

In a dried round-bottom flask equipped with a magnetic stirrer was dissolved Intermediate amine 33 (1 equiv) and DIEA (3.5 equiv, Sigma-Aldrich) in dichloromethane (0.12 M). To this was then added chloroacetyl chloride (1.2 equiv, Sigma-Aldrich) neat and dropwise over a period of 30 min. The resulting reaction mixture was stirred at RT for another 30 min. The reaction was then quenched with water and extracted with DCM. The combined organic extracts were washed further with water (2×) and brine, dried over $Na_2SO_4$, filtered and the filtrate in vacuo. The crude product thus obtained was purified further by way of column chromatography ($SiO_2$, gradient elution:Hex→1:1 (v/v) Hex:EtOAc) to afford the title compound as a white crystalline solid (69% yield).

The following amides were prepared in an analogous fashion to Intermediate amide 1 but substituting Intermediate amine 33 for the requisite amine:

| Name | Structure |
|---|---|
| Intermediate amide 2 | 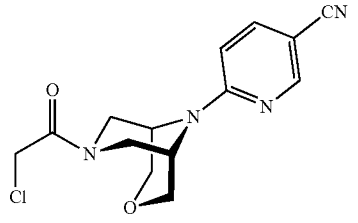 |
| Intermediate amide 3 | 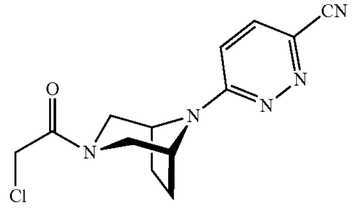 |
| Intermediate amide 4 | 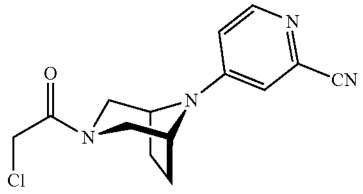 |

Intermediate amide 5: Preparation of 6-(3-(3-aminopropanoyl)-3,8-diazabicyclo[3.2.1]octan-8-yl)nicotinonitrile bis hydrochloride

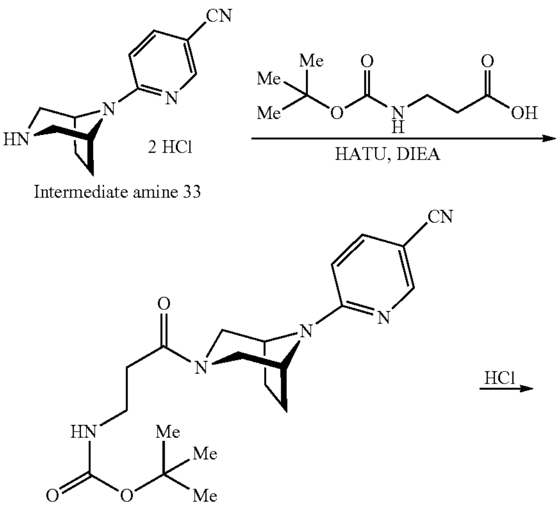

-continued

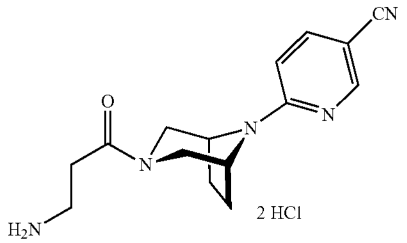

2 HCl

Intermediate amide 5

Step 1: In a dried round-bottom flask equipped with a magnetic stirrer was combined Intermediate amine 33 (1 equiv), 3-((tert-butoxycarbonyl)amino)propanoic acid (1.1 equiv, Sigma-Aldrich), and HATU (1.1 equiv, Combi-Blocks) in dichloromethane (0.1 M). To the reaction mixture was then added DIEA (3 equiv, Sigma-Aldrich) and the resulting solution was allowed to stir at RT for 20 min. The reaction mixture was then diluted with dichloromethane and washed further with water (3×). The organic layer was then concentrated in vacuo and the resulting residue was directly subjected to purification by way of column chromatography ($SiO_2$, gradient elution:Hex→EtOAc) to afford tert-butyl (3-(8-(5-cyanopyridin-2-yl)-3,8-diazabicyclo[3.2.1]octan-3-yl)-3-oxopropyl)carbamate (>99% yield).

Step 2: In a dried round-bottom flask equipped with a magnetic stirrer was dissolved tert-butyl (3-(8-(5-cyanopyridin-2-yl)-3,8-diazabicyclo[3.2.1]octan-3-yl)-3-oxopropyl) carbamate (1 equiv) from the previous step in dichloromethane (0.2 M). To this was then added HCl (4 equiv, 4 M solution in dioxane, Sigma-Aldrich) and the resulting suspension was stirred at RT for 5 h. The reaction mixture was added tert-butyl methyl ether and the resulting thick suspension was vigorously stirred at RT for 1 h. Finally, the suspension was filtered, washed further with tert-butyl methyl ether and air-dried to afford the title compound as a white crystalline solid (93% yield).

The following amide was prepared in an analogous fashion to Intermediate amide 5 but substituting 3-((tert-butoxycarbonyl)amino)propanoic acid for N-(tert-butoxycarbonyl) glycine (Sigma-Aldrich) in step 1:

| Name | Structure |
| --- | --- |
| Intermediate amide 6 | 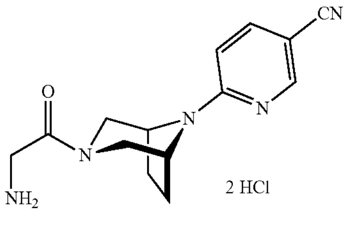 2 HCl |

Intermediate amide 7: Preparation of 6-(3-acryloyl-3,8-diazabicyclo[3.2.1]octan-8-yl)nicotinonitrile

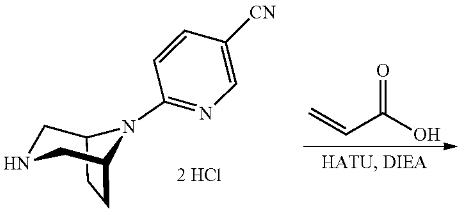

Intermediate amine 33

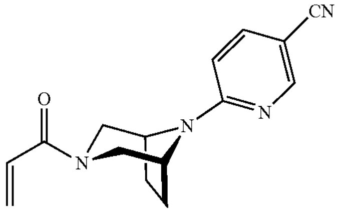

Intermediate amide 7

In a dried round-bottom flask equipped with a magnetic stirrer was combined Intermediate amine 33 (1 equiv), acrylic acid (1.1 equiv, Alfa Aesar), and HATU (1.2 equiv, Combi-Blocks) in dichloromethane (0.16 M). To the reaction mixture was then added DIEA (5 equiv, Sigma-Aldrich) and the resulting solution was allowed to stir at RT for 1 h. The reaction mixture was then diluted with DCM and washed further with water (3×). The organic layer was then concentrated in vacuo and the resulting residue was directly subjected to purification by way of column chromatography ($SiO_2$, gradient elution:Hex→EtOAc) to afford the title compound as a white solid (63% yield).

Intermediate iodide 1: Preparation of 4-iodo-2-(methoxy-$d_3$)pyridine

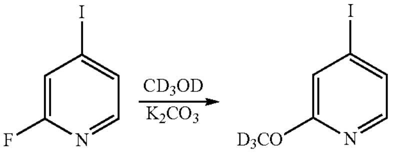

Intermediate iodide 1

In a dried round-bottom flask equipped with a magnetic stirrer was combined 2-fluoro-4-iodopyridine (1 equiv, Combi-Blocks) and potassium carbonate (1.2 equiv, Sigma-Aldrich) in methanol-$d_4$ (1.3 M). The resulting suspension was heated at reflux for 3 days. The reaction mixture was then diluted with EtOAc and washed further with water and brine. The organic layer was then dried over $MgSO_4$ and filtered. Concentration of the filtrate in vacuo afforded the crude title compound as a volatile liquid (>99% yield).

Intermediate acid 1: Preparation of 4,4-difluoro-4-(quinolin-5-yl)butanoic acid trifluoroacetic acid Salt

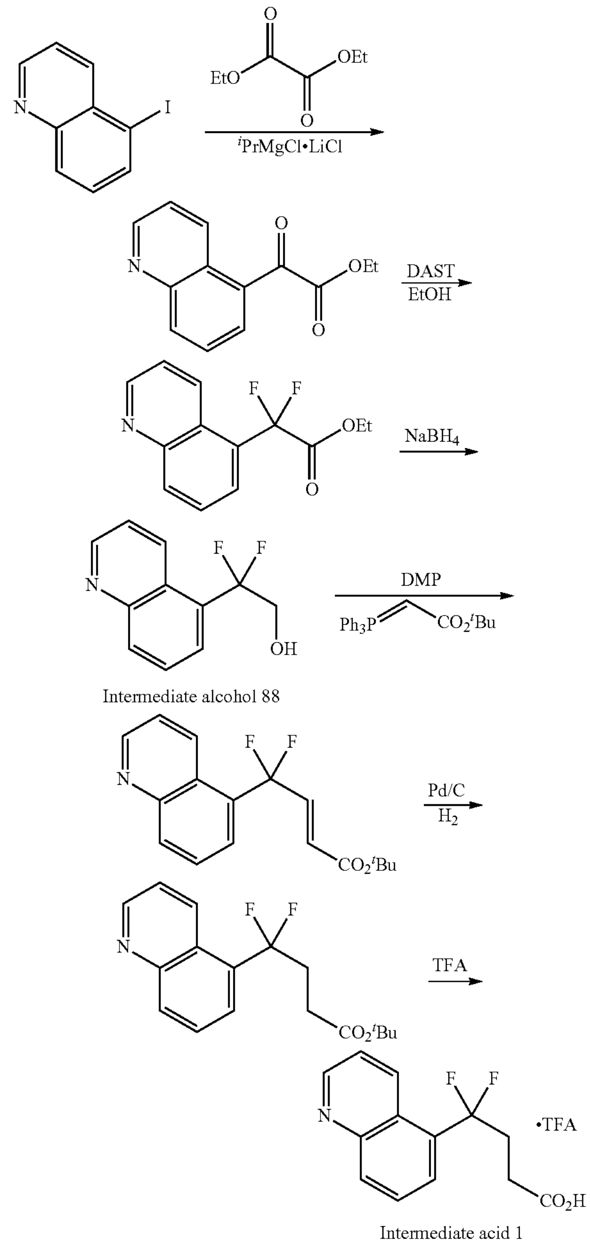

Intermediate alcohol 88

Intermediate acid 1

Step 1: In a dried round-bottom flask equipped with a magnetic stirrer was dissolved 5-iodoquinoline (1 equiv, Enamine) in THF (0.1 M). The resulting solution was then cooled to −10° C. before Turbo Grignard (1.1 equiv, 1.3 M solution in THF, Sigma-Aldrich) was added dropwise over 15 min, taking care to keep the internal reaction temperature below −5° C. After 60 min of stirring at −10° C., the now mustard yellow suspension was cooled further to −78° C. and diethyl oxalate (1.1 equiv, Sigma-Aldrich) was then added neat and dropwise over 10 min. The cooling bath was then removed and the reaction mixture was allowed to stir at RT for 16 h. Finally, the reaction was quenched with the addition of saturated aq. $NH_4Cl$ and extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution: 9:1 (v/v) Hex:EtOAc→3:7 (v/v) Hex:EtOAc) afforded ethyl 2-oxo-2-(quinolin-5-yl)acetate as a pale yellow oil (41% yield).

Step 2: In a Nalgene® bottle equipped with a magnetic stirrer was dissolved ethyl 2-oxo-2-(quinolin-5-yl)acetate (1 equiv) from the previous step in dichloromethane (0.1 M). To this was then added DAST (2.5 equiv, Sigma-Aldrich), along with two drops of ethanol, and the resulting solution was stirred at RT for 16 h. The reaction mixture was then quenched with ice water and extracted with dichloromethane (3×). The combined organic extracts were dried over $MgSO_4$, filtered and the filtrate concentrated in vacuo. Purification of the crude product thus obtained by way of column chromatography ($SiO_2$, gradient elution: 9:1 (v/v) Hex:EtOAc→3:7 (v/v) Hex:EtOAc) afforded ethyl 2,2-difluoro-2-(quinolin-5-yl)acetate as a pale yellow oil (82% yield).

Step 3: In a dried round-bottom flask equipped with a magnetic stirrer was dissolved ethyl 2,2-difluoro-2-(quinolin-5-yl)acetate (1 equiv) from the previous step in methanol (0.22 M). To this was then added at 0° C. sodium borohydride (10 equiv, Sigma-Aldrich) in one rapid portion and the resulting suspension was allowed to warm slowly to RT over 2 h. The reaction mixture was then poured into brine and extracted with EtOAc (3×). The combined organic extracts were washed sequentially with water, 1 M aq. NaOH and brine, dried over $MgSO_4$, filtered and the filtrate concentrated in vacuo. Purification of the crude product thus obtained by way of column chromatography ($SiO_2$, gradient elution: 9:1 (v/v) Hex:EtOAc→EtOAc) afforded 2,2-difluoro-2-(quinolin-5-yl)ethan-1-ol (Intermediate alcohol 88) as a pale yellow oil (98% yield).

Step 4: In a dried round-bottom flask equipped with a magnetic stirrer was dissolved Intermediate alcohol 88 (1 equiv) from the previous step in dichloromethane (0.20 M). To this was then added Dess-Martin Periodinane (1.5 equiv, Sigma-Aldrich) in one rapid portion and the resulting suspension was allowed to stir at RT for 30 min. Finally, (tert-butoxycarbonylmethylene)triphenylphosphorane (1.5 equiv, Acros) was added in one rapid portion and the now homogeneous solution was stirred at RT for another 60 min. The reaction was then quenched with the addition of 1 M aq. NaOH and extracted with tert-butyl methyl ether (2×). The combined organic extracts were washed further with water and brine, dried over $MgSO_4$, filtered and the filtrate concentrated in vacuo. Purification of the crude product thus obtained by way of column chromatography ($SiO_2$, gradient elution: 9:1 (v/v) Hex:EtOAc→3:7 (v/v) Hex:EtOAc) afforded tert-butyl (E)-4,4-difluoro-4-(quinolin-5-yl)but-2-enoate as a colorless oil (36% yield).

Step 5: In a dried round-bottom flask equipped with a magnetic stirrer was combined tert-butyl (E)-4,4-difluoro-4-(quinolin-5-yl)but-2-enoate (1 equiv) from the previous step and palladium black (0.2 equiv, 10% (w/w) over activated carbon, Sigma-Aldrich) in freshly deoxygenated EtOAc (0.20 M). The resulting suspension was evacuated and back-filled with hydrogen gas (3×). Once the gas exchange process was deemed complete, the reaction suspension was stirred at RT under a static hydrogen atmosphere for 3 h. The reaction was then quenched with the addition of chloroform, filtered through a pad of chloroform-wetted celite, and the filtrate concentrated in vacuo. Further purification of the crude product thus obtained by way of column chromatography ($SiO_2$, gradient elution: 9:1 (v/v) Hex:EtOAc→3:7 (v/v) Hex:EtOAc) afforded tert-butyl 4,4-difluoro-4-(quinolin-5-yl)butanoate as a colorless oil (69% yield).

Step 6: In a round-bottom flask equipped with a magnetic stirrer was dissolved tert-butyl 4,4-difluoro-4-(quinolin-5-yl)butanoate (1 equiv) from the previous step in dichloromethane (0.08 M). To this solution was then added TFA (50 equiv, Sigma-Aldrich) and the resulting mixture was stirred at RT for 90 mi. The volatiles were then removed in vacuo and the resulting residue was further azeotroped with toluene (3×). The title compound thus obtained was used in the next step without further purification (>99% yield).

The following acids were prepared in an analogous fashion to Intermediate acid 1 but substituting 5-iodoquinoline for the requisite (hetero)aryl bromide or (hetero)aryl iodide in step 1. For the synthesis of Intermediate acid 2, Intermediate acid 4, Intermediate acid 6, Intermediate acid 7, Intermediate acid 8, Intermediate acid 9, and Intermediate acid 11, step 5 was omitted:

| Name | Structure |
|---|---|
| Intermediate acid 2 | 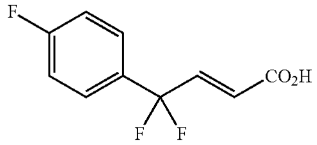 [SMILES: O=C(O)/C=C/C(F)(F)c1ccc(F)cc1] |
| Intermediate acid 3 | 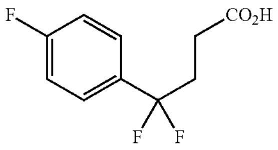 [SMILES: O=C(O)CCC(F)(F)c1ccc(F)cc1] |
| Intermediate acid 4 | 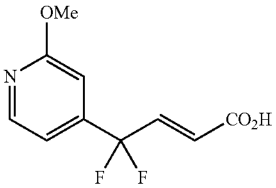 [SMILES: COc1cc(C(F)(F)/C=C/C(=O)O)ccn1] |
| Intermediate acid 5 | 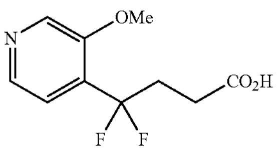 [SMILES: COc1cnccc1C(F)(F)CCC(=O)O] |
| Intermediate acid 6 | 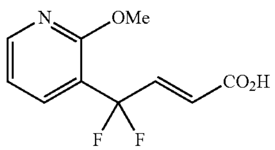 [SMILES: COc1ncccc1C(F)(F)/C=C/C(=O)O] |
| Intermediate acid 7 | 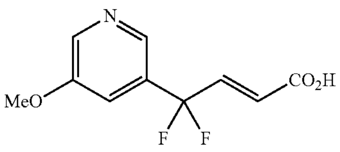 [SMILES: COc1cncc(C(F)(F)/C=C/C(=O)O)c1] |

-continued

| Name | Structure |
|---|---|
| Intermediate acid 8 | 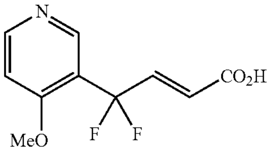 [SMILES: COc1ccncc1C(F)(F)/C=C/C(=O)O] |
| Intermediate acid 9 | 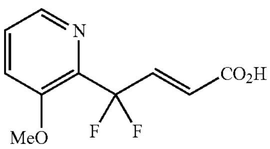 [SMILES: COc1cccnc1C(F)(F)/C=C/C(=O)O] |
| Intermediate acid 10 | 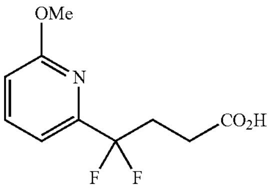 [SMILES: COc1cccc(C(F)(F)CCC(=O)O)n1] |
| Intermediate acid 11 | 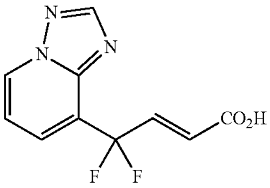 [SMILES: O=C(O)/C=C/C(F)(F)c1cccn2ncnc12] |

Intermediate acid 12: Preparation of 4,4-difluoro-4-(2-methoxypyridin-4-yl)butanoic acid

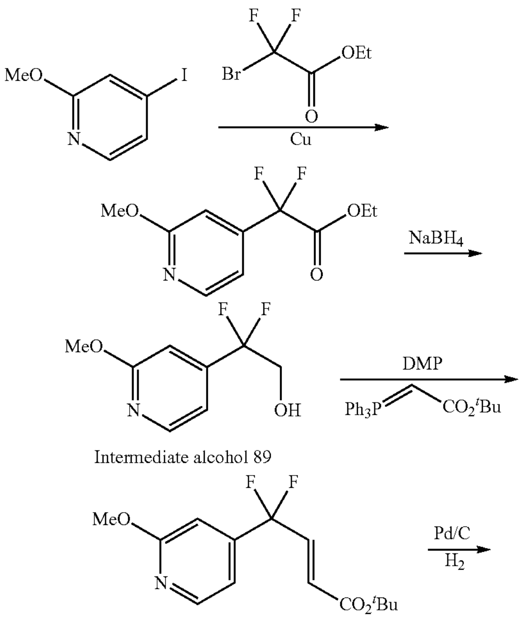

-continued

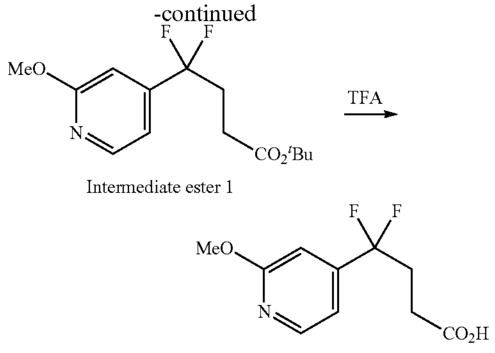

Intermediate ester 1

Intermediate acid 12

Step 1: In a sealable reaction vessel equipped with a magnetic stirrer and a Teflon screwcap was combined 4-iodo-2-methoxypyridine (1 equiv, Combi-Blocks), ethyl 2-bromo-2,2-difluoroacetate (1.5 equiv, Combi-Blocks), and copper powder (3 equiv, 325 mesh, Sigma-Aldrich) in DMSO (0.27 M). The resulting suspension was deoxygenated via sub-surface purging with nitrogen for 5 min before the reaction vessel was tightly sealed and heated at 60° C. for 16 h. The reaction suspension was then cooled to RT, filtered and the insolubles rinsed further with EtOAc. The organic filtrate was then washed further with saturated aq. $NH_4Cl$, water and brine, dried over $MgSO_4$, filtered and the filtrate concentrated in vacuo. Purification of the crude product thus obtained by way of column chromatography ($SiO_2$, gradient elution:Hex→2:3 (v/v) Hex:EtOAc) afforded ethyl 2,2-difluoro-2-(2-methoxypyridin-4-yl)acetate (41% yield).

Step 2: In a dried round-bottom flask equipped with a magnetic stirrer was dissolved ethyl 2,2-difluoro-2-(2-methoxypyridin-4-yl)acetate (1 equiv) from the previous step in methanol (0.11 M). To this was then added sodium borohydride (1.4 equiv, Sigma-Aldrich) in one rapid portion and the resulting mixture was stirred at RT for 30 min. The reaction mixture was then poured into water and extracted with EtOAc (2×). The combined organic extracts were washed further with water (2×) and brine, dried over $MgSO_4$, filtered and the filtrate concentrated in vacuo. Purification of the crude product thus obtained by way of column chromatography ($SiO_2$, gradient elution:Hex→EtOAc) afforded 2,2-difluoro-2-(2-methoxypyridin-4-yl)ethan-1-ol (Intermediate alcohol 89) as a colorless oil (83% yield).

Step 3: In a dried round-bottom flask equipped with a magnetic stirrer was dissolved Intermediate alcohol 89 (1 equiv) from the previous step in dichloromethane (0.18 M). To this was then added Dess-Martin Periodinane (1.2 equiv, Sigma-Aldrich) in one rapid portion and the resulting suspension was allowed to stir at RT for 3 h. Finally, (tert-butoxycarbonylmethylene)triphenylphosphorane (1.2 equiv, Acros) was added in one rapid portion and the now homogeneous solution was stirred at RT for another 3 h. The reaction was then quenched with water and extracted with DCM (2×). The combined organic extracts were washed further with water (3×) and brine, dried over $MgSO_4$, filtered and the filtrate concentrated in vacuo. Purification of the crude product thus obtained by way of column chromatography ($SiO_2$, gradient elution:Hex→2:3 (v/v) Hex:EtOAc) afforded tert-butyl (E)-4,4-difluoro-4-(2-methoxypyridin-4-yl)but-2-enoate as a colorless oil (53% yield).

Step 4: In a dried round-bottom flask equipped with a magnetic stirrer was combined tert-butyl (E)-4,4-difluoro-4-(2-methoxypyridin-4-yl)but-2-enoate (1 equiv) from the previous step and palladium black (0.1 equiv, 10% (w/w) over activated carbon, Sigma-Aldrich) in freshly deoxygenated EtOAc (0.11 M). The resulting suspension was evacuated and back-filled with hydrogen gas (3×). Once the gas exchange process was deemed complete, the reaction suspension was stirred at RT under a static hydrogen atmosphere for 4 h. The reaction was then quenched with the addition of chloroform, filtered through a pad of chloroform-wetted celite, and the filtrate concentrated in vacuo. Further purification of the crude product thus obtained by way of reverse phase column chromatography (Cis, gradient elution: 9:1 (v/v) $H_2O$:MeCN+0.1% formic acid→MeCN+0.1% formic acid) afforded tert-butyl 4,4-difluoro-4-(2-methoxypyridin-4-yl)butanoate (Intermediate ester 1) as a colorless oil (93% yield).

Step 5: In a dried round-bottom flask equipped with a magnetic stirrer was dissolved Intermediate ester 1 (1 equiv) from the previous step in dichloromethane (0.21 M). To this solution was then added TFA (20 equiv, Sigma-Aldrich) and the resulting mixture was stirred at RT for 3 h. The volatiles were then removed in vacuo and the resulting residue was further azeotroped with toluene (3×). The title compound thus obtained was used in the next step without further purification (>99% yield).

The following acids were prepared in an analogous fashion to Intermediate acid 12 but substituting 4-iodo-2-methoxypyridine for the requisite heteroaryl bromide or heteroaryl iodide in step 1. For the synthesis of Intermediate acid 14, Intermediate acid 15, and Intermediate acid 17, step 4 was omitted. For the synthesis of Intermediate acid 15, copper powder was also substituted for copper iodide (0.1 equiv, Sigma-Aldrich) and N,N,N',N'',N''-pentamethyldiethylenetriamine (1.5 equiv, Sigma-Aldrich), DMSO was substituted for MeCN, and the reaction was conducted at 80° C. instead of 60° C. in step 1. The following alcohol was prepared in an analogous fashion to Intermediate alcohol 89 but substituting 4-iodo-2-methoxypyridine for 8-bromo-[1,2,4]triazolo[1,5-a]pyridine:

| Name | Structure |
|---|---|
| Intermediate acid 13 | 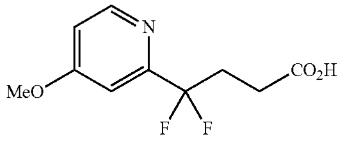 [SMILES: COc1ccnc(C(F)(F)CCC(=O)O)c1] |
| Intermediate acid 14 | 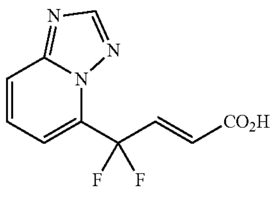 [SMILES: O=C(O)/C=C/C(F)(F)c1cccc2ncnn12] |
| Intermediate acid 15 | 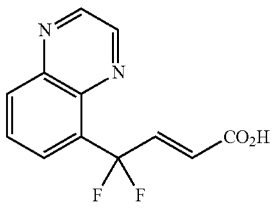 [SMILES: O=C(O)/C=C/C(F)(F)c1cccc2nccnc12] |

-continued

| Name | Structure |
|---|---|
| Intermediate acid 16 | 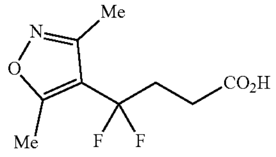 [SMILES: Cc1noc(C)c1C(F)(F)CCC(=O)O] |
| Intermediate acid 17 | 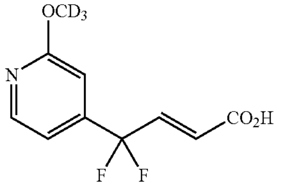 |
| Intermediate alcohol 90 | 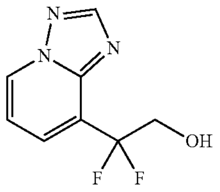 [SMILES: OCC(F)(F)c1cccn2ncnc12] |

Intermediate acid 12: Alternative Preparation of 4,4-difluoro-4-(2-methoxypyridin-4-yl)butanoic acid

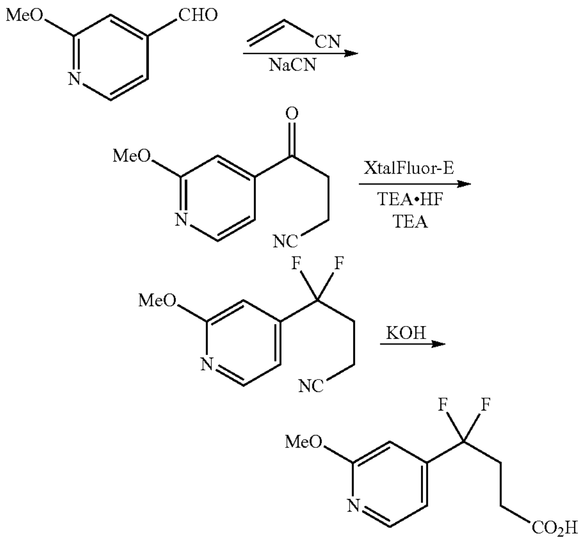

Intermediate acid 12

Step 1: In a dried round-bottom equipped with a magnetic stirrer was combined 2-methoxyisonicotinaldehyde (1 equiv, PharmaBlock, Inc) and sodium cyanide (0.25 equiv, Sigma-Aldrich) in MeCN (0.3 M). The resulting suspension was deoxygenated via sub-surface purging with nitrogen for 15 min before acrylonitrile (0.95 equiv, 14 M solution in MeCN, Acros) was added dropwise over 5 min. After 3.5 h of stirring at RT, the reaction was carefully quenched with glacial acetic acid (1 equiv, Sigma-Aldrich), diluted further with water and extracted with EtOAc (2×). The combined organic extracts were washed further with saturated aq. $NaHCO_3$ and brine, dried over $MgSO_4$ and filtered. Concentration of the filtrate in vacuo afforded 4-(2-methoxypyridin-4-yl)-4-oxobutanenitrile as a solid (92% yield).

Step 2: In a Nalgene® bottle equipped with a magnetic stirrer was dissolved 4-(2-methoxypyridin-4-yl)-4-oxobutanenitrile (1 equiv) from the previous step in dichloromethane (0.5 M). To this was then added sequentially triethylamine trihydrofluoride (5 equiv, Sigma-Aldrich), triethylamine (2.5 equiv, Sigma-Aldrich) and finally XtalFluor-E® (5 equiv, Sigma-Aldrich). The resulting reaction mixture was stirred under a nitrogen atmosphere at RT for 3 days. The reaction mixture was diluted with dichloromethane and then carefully added into ice. The organic layer was separated, washed sequentially with water, saturated aq. $NaHCO_3$ and brine, dried over $MgSO_4$, filtered and the filtrate concentrated in vacuo. Purification of the crude product thus obtained by way of column chromatography ($SiO_2$, gradient elution:Hex→EtOAc) afforded 4,4-difluoro-4-(2-methoxypyridin-4-yl)butanenitrile as a white solid (72% yield).

Step 3: In a round-bottom flask equipped with a magnetic stirrer was combined 4,4-difluoro-4-(2-methoxypyridin-4-yl)butanenitrile (1 equiv) from the previous step and potassium hydroxide (4 equiv, Alfa Aesar) in a 9:1 (v/v) solution of water and ethanol (0.30 M). The resulting solution was heated at 80° C. for 12 h. The reaction mixture was then cooled to RT and washed with tert-butyl methyl ether. The aqueous layer was separated, treated with activated charcoal and filtered through a pad of celite. The filtrate thus obtained was then cooled to 0° C. and its pH was carefully adjusted to ~2 with the dropwise addition of 3 M aq. HCl. The title compound was then isolated via vacuum filtration, washed further with water and hexanes, and dried in vacuo until constant weight (80% yield).

Intermediate acid 18: Preparation of 5,5-difluoro-5-(2-methoxypyridin-4-yl)pentanoic acid

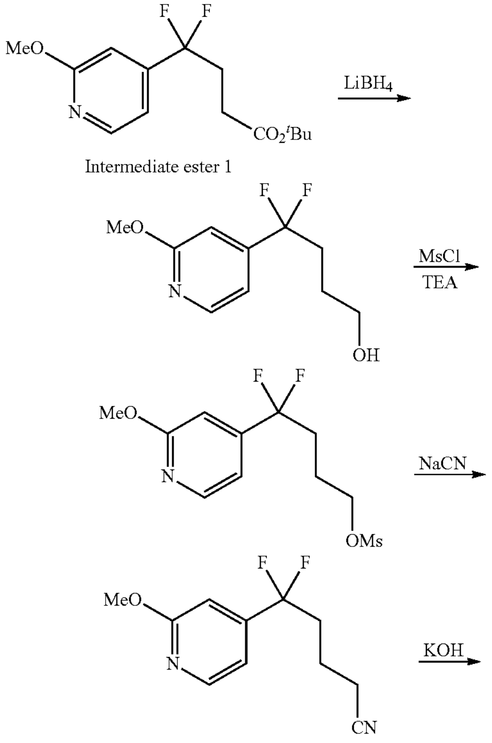

-continued

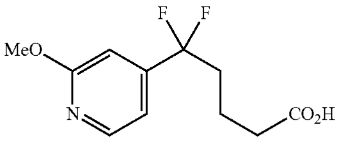

Intermediate acid 18

Step 1: In a dried round-bottom flask equipped with a magnetic stirrer was dissolved Intermediate ester 1 (1 equiv) in THF (0.29 M). To this was then added lithium borohydride (10 equiv, 2 M solution in THF, Sigma-Aldrich) and the resulting mixture was stirred at RT for 70 h. The unreacted lithium borohydride was then carefully quenched with 1 M aq. HCl which led to the vigorous evolution of gas. The pH of the resulting suspension was adjusted to ~7 with 1 M aq. NaOH and then extracted with EtOAc (3×). The combined organic extracts were washed further with water (3×) and brine, dried over $MgSO_4$ and filtered. Concentration of the filtrate in vacuo afforded 4,4-difluoro-4-(2-methoxypyridin-4-yl)butan-1-ol as a colorless syrup (97% yield).

Step 2: In a dried round-bottom flask equipped with a magnetic stirrer was combined 4,4-difluoro-4-(2-methoxypyridin-4-yl)butan-1-ol (1 equiv) from the previous step and triethylamine (2.5 equiv, Aldrich) in dichloromethane (0.14 M). To this was then added methanesulfonyl chloride (1.2 equiv, Sigma-Aldrich) neat and dropwise at RT and the resulting orange solution was stirred at RT for 1 h. The reaction mixture was then poured into water and extracted with DCM (2×). The combined organic extracts were dried over $Na_2SO_4$ and filtered. Concentration of the filtrate in vacuo afforded 4,4-difluoro-4-(2-methoxypyridin-4-yl)butyl methanesulfonate as a pale yellow oil (88% yield).

Step 3: In a dried round-bottom flask equipped with a magnetic stirrer was dissolved 4,4-difluoro-4-(2-methoxypyridin-4-yl)butyl methanesulfonate (1 equiv) from the previous step in DMF (0.21 M). To this was then added sodium cyanide (1 equiv, Sigma-Aldrich) and the resulting mixture was stirred at RT for 16 h. The now yellow reaction mixture was then diluted with water and extracted with a 1:1 (v/v) solution of Hex and EtOAc (2×). The combined organic extracts were washed with water and brine, dried over $MgSO_4$, filtered and the filtrate concentrated in vacuo. Further purification of the crude product thus obtained by way of column chromatography ($SiO_2$, gradient elution: Hex→1:1 (v/v) Hex:EtOAc) afforded 5,5-difluoro-5-(2-methoxypyridin-4-yl)pentanenitrile as a colorless oil (61% yield).

Step 4: In a round-bottom flask equipped with a magnetic stirrer was combined 5,5-difluoro-5-(2-methoxypyridin-4-yl)pentanenitrile (1 equiv) from the previous step and potassium hydroxide (4 equiv, Alfa Aesar) in a 1:1 (v/v) solution of ethylene glycol and water (0.14 M). The resulting solution was heated at 80° C. for 16 h. The reaction mixture was then cooled to RT, diluted with water and the pH adjusted to ~4 with 1 M aq. HCl. The resulting suspension was then extracted with EtOAc (2×). The combined organic extracts were washed with brine, dried over $Na_2SO_4$ and filtered. Concentration of the filtrate in vacuo afforded the title compound which was used in the next step without further purification (93% yield).

Intermediate acid 19: Preparation of (E)-3-(1-(2-methoxypyridin-4-yl)cyclobutyl)acrylic acid

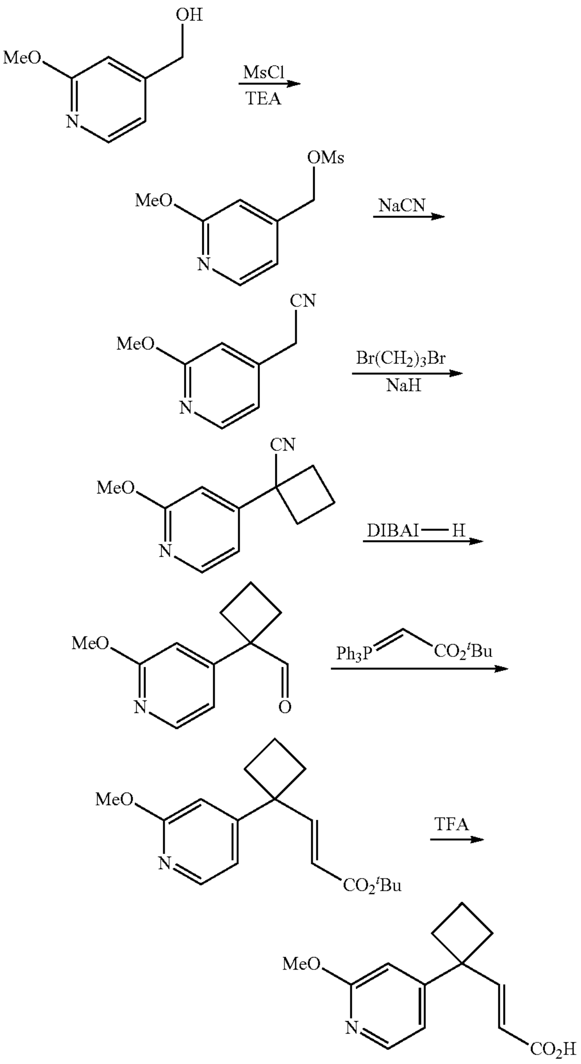

Intermediate acid 19

Step 1: In a dried round-bottom flask equipped with a magnetic stirrer was combined (2-methoxypyridin-4-yl)methanol (1 equiv, Combi-Blocks) and triethylamine (2.5 equiv, Aldrich) in dichloromethane (0.25 M). To this was then added methanesulfonyl chloride (1.2 equiv, Sigma-Aldrich) neat and dropwise at 0° C. and the resulting solution was stirred at 0° C. for 2 h. The reaction mixture was then poured into water and extracted with DCM (2×). The combined organic extracts were dried over $Na_2SO_4$ and filtered. Concentration of the filtrate in vacuo afforded (2-methoxypyridin-4-yl)methyl methanesulfonate as a pale yellow oil.

Step 2: In a dried round-bottom flask equipped with a magnetic stirrer was dissolved (2-methoxypyridin-4-yl)methyl methanesulfonate (1 equiv) from the previous step in DMF (0.32 M). To this was then added sodium cyanide (1.5 equiv, Sigma-Aldrich) and the resulting mixture was stirred at RT for 90 min. The now yellow reaction mixture was then diluted with water and extracted with a 1:1 (v/v) solution of Hex and EtOAc (2×). The combined organic extracts were washed with brine (3×), dried over $MgSO_4$, filtered and the filtrate concentrated in vacuo. Further purification of the crude product thus obtained by way of column chromatography ($SiO_2$, gradient elution:Hex→EtOAc) afforded 2-(2-methoxypyridin-4-yl)acetonitrile as a colorless oil (91% yield over two steps).

Step 3: In a dried round-bottom flask equipped with a magnetic stirrer was combined 2-(2-methoxypyridin-4-yl) acetonitrile (1 equiv) from the previous step and 1,3-dibromopropane (1.1 equiv, Sigma-Aldrich) in THF (0.1 M). To this was then added at 0° C. sodium hydride (2.5 equiv, 60% (w/w) dispersion in paraffin oil, Sigma-Aldrich) in one rapid portion and the resulting mixture was first stirred at 0° C. for 30 min and then at RT for 1.5 h. The reaction was then quenched with the addition of saturated aq. $NH_4Cl$ and extracted with EtOAc (2×). The combined organic extracts were washed with water and brine, dried over $MgSO_4$, filtered and the filtrate concentrated in vacuo. Further purification of the crude product thus obtained by way of column chromatography ($SiO_2$, gradient elution:Hex 4 EtOAc) afforded 1-(2-methoxypyridin-4-yl)cyclobutane-1-carbonitrile as a colorless oil (63% yield).

Step 4: In a dried round-bottom flask equipped with a magnetic stirrer was dissolved 1-(2-methoxypyridin-4-yl) cyclobutane-1-carbonitrile (1 equiv) from the previous step in toluene (0.12 M). To this was then added at −78° C. diisobutylaluminum hydride (2 equiv, 1 M solution in dichloromethane, Sigma-Aldrich) over a period of 5 min. The resulting reaction mixture was first stirred at −78° C. for 60 min and then at RT for another 60 min. The reaction mixture was then diluted with EtOAc and the resulting emulsion was broken with the addition of 2 M aq. $H_2SO_4$. The organic layer was separated and the aqueous layer was made basic with the addition of saturated aq. $NaHCO_3$. The resulting aqueous suspension was then backextracted with EtOAc (4×). All the organic extracts were combined, washed further with brine, dried over $Na_2SO_4$, filtered and the filtrate concentrated in vacuo. Purification of the crude product thus obtained by way of column chromatography ($SiO_2$, gradient elution:Hex→1:1 (v/v) Hex:EtOAc) afforded 1-(2-methoxypyridin-4-yl)cyclobutane-1-carbaldehyde as a colorless oil (79% yield).

Step 5: In a dried round-bottom flask equipped with a magnetic stirrer was dissolved 1-(2-methoxypyridin-4-yl) cyclobutane-1-carbaldehyde (1 equiv) from the previous step in dichloromethane (0.04 M). To this was then added (tert-butoxycarbonylmethylene)triphenylphosphorane (1 equiv, Acros) and the resulting mixture was stirred at RT for 3 h. The volatiles were then removed in vacuo and the crude product thus obtained was purified by way of column chromatography ($SiO_2$, gradient elution:Hex→2:3 (v/v) Hex:EtOAc) to afford tert-butyl (E)-3-(1-(2-methoxypyridin-4-yl)cyclobutyl)acrylate (51% yield).

Step 6: In a dried round-bottom flask equipped with a magnetic stirrer was dissolved tert-butyl (E)-3-(1-(2-methoxypyridin-4-yl)cyclobutyl)acrylate (1 equiv) from the previous step in dichloromethane (0.06 M). To this solution was then added TFA (80 equiv, Sigma-Aldrich) and the resulting mixture was stirred at RT for 16 h. The volatiles were then removed in vacuo and the resulting residue was further azeotroped with toluene (3×). The title compound thus obtained was used in the next step without further purification (>99% yield).

Intermediate acid 20: Preparation of racemic (2,2-difluoro-1-(5-methoxypyridin-3-yl)ethyl)glycine trifluoracetic acid Salt

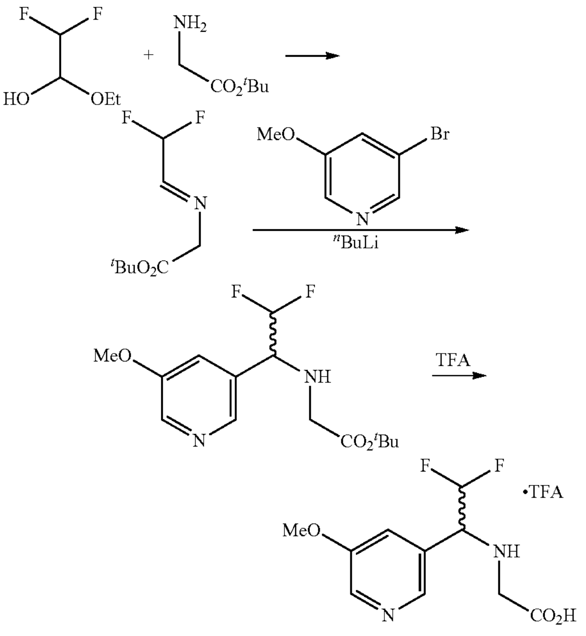

Intermediate acid 20

Step 1: In a dried round-bottom flask equipped with a magnetic stirrer was combined tert-butyl glycinate (1 equiv, Combi-Blocks) and difluoroacetaldehyde ethyl hemiacetal (1.05 equiv, AstaTech) in benzene (0.13 M). To the reaction vessel was then attached a Dean-Stark apparatus and the reaction mixture was heated at reflux for 18 h. The volatiles were then removed in vacuo to afford tert-butyl (E)-2-((2,2-difluoroethylidene)amino)acetate as a yellow oil (93% yield).

Step 2: In a dried round-bottom flask equipped with a magnetic stirrer was dissolved 3-bromo-5-methoxypyridine (1.1 equiv, Combi-Blocks) in diethyl ether (0.083 M). The resulting pale tan solution was then cooled to −78° C. before $^n$BuLi (1.1 equiv, 2.5 M solution in hexanes, Sigma-Aldrich) was added dropwise over 5 min to afford an orange solution. After 30 min of stirring at −78° C., tert-butyl (E)-2-((2,2-difluoroethylidene)amino)acetate (1 equiv, 0.45 M solution in ether) from the previous step was then added dropwise over 5 min. The resulting dark purple mixture was allowed to stir at −78° C. for 3 h before the reaction was quenched with the addition of saturated aq. $NH_4Cl$. The aqueous phase was separated and backextracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex→2:3 (v/v) EtOAc:Hex) afforded tert-butyl (2,2-difluoro-1-(5-methoxypyridin-3-yl)ethyl)glycinate as a colorless oil (10% yield).

Step 3: In a dried round-bottom flask equipped with a magnetic stirrer was dissolved tert-butyl (2,2-difluoro-1-(5-methoxypyridin-3-yl)ethyl)glycinate (1 equiv) from the previous step in dichloromethane (0.07 M). To this solution was then added TFA (80 equiv, Sigma-Aldrich) and the resulting mixture was stirred at RT for 48 h. The volatiles were then removed in vacuo and the resulting residue was further azeotroped with toluene (3×). The title compound thus obtained was used in the next step without further purification (>99% yield).

The following acid was prepared in an analogous fashion to Intermediate acid 20 but substituting 3-bromo-5-methoxypyridine for 1-bromo-2,4-difluorobenzene (Combi-Blocks) in step 2:

| Name | Structure |
|---|---|
| Intermediate acid 21 | 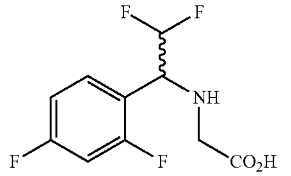 [SMILES: O=C(O)CNC(c1ccc(F)cc1F)C(F)F] |

Intermediate acid 22: Preparation of racemic 3-((1-(3,4-difluorophenyl)-2,2-difluoroethyl)amino)propanoic acid

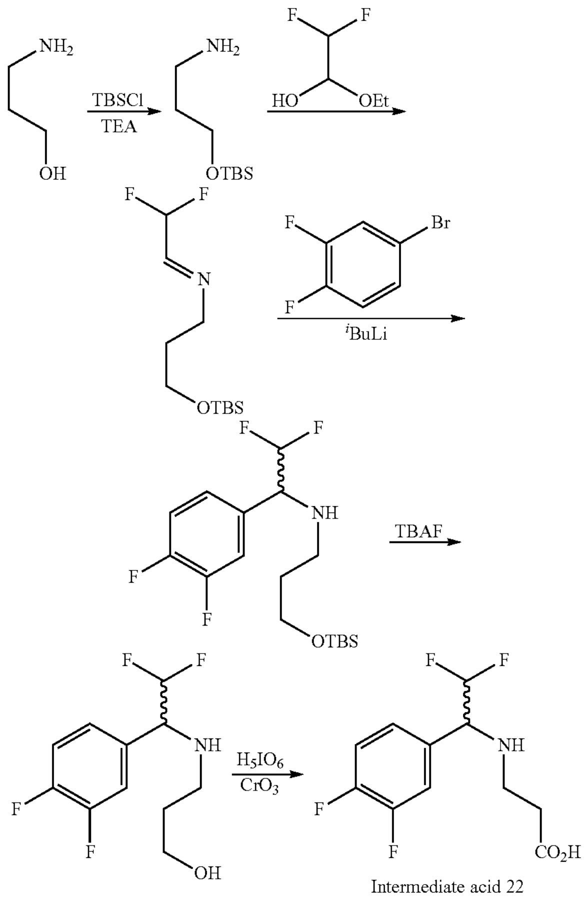

Intermediate acid 22

Step 1: In a dried round-bottom flask equipped with a magnetic stirrer was combined 3-aminopropan-1-ol (1 equiv, Combi-Blocks) and tert-butyldimethylsilyl chloride (1.05 equiv, Sigma-Aldrich) in dichloromethane (0.5 M). To the reaction mixture was then added triethylamine (1.3 equiv, Sigma-Aldrich) and the resulting solution was stirred at RT for 2 h. The reaction was then quenched with the addition of water and diluted with DCM. The organic layer was separated, washed further with water (2×) and brine, dried over $MgSO_4$ and filtered. Concentration of the filtrate in vacuo afforded 3-((tert-butyldimethylsilyl)oxy)propan-1-amine as a colorless oil (94% yield).

Step 2: In a dried round-bottom flask equipped with a magnetic stirrer was combined 3-((tert-butyldimethylsilyl)oxy)propan-1-amine (1 equiv) from the previous step and difluoroacetaldehyde ethyl hemiacetal (1.05 equiv, AstaTech) in benzene (0.26 M). To the reaction vessel was then attached a Dean-Stark apparatus and the reaction mixture was heated at reflux for 18 h. The volatiles were then removed in vacuo to afford (E)-N-(3-((tert-butyldimethylsilyl)oxy)propyl)-2,2-difluoroethan-1-imine as a colorless oil (94% yield).

Step 3: In a dried round-bottom flask equipped with a magnetic stirrer was dissolved 4-bromo-1,2-difluorobenzene (2 equiv, Combi-Blocks) in diethyl ether (0.13 M). The resulting colorless solution was then cooled to −78° C. before $^{n}$BuLi (1.9 equiv, 2.5 M solution in hexanes, Sigma-Aldrich) was added dropwise over 5 min to afford a pale yellow solution. After 10 min of stirring at −78° C., (E)-N-(3-((tert-butyldimethylsilyl)oxy)propyl)-2,2-difluoroethan-1-imine (1 equiv, 0.8 M solution in ether) from the previous step was then added dropwise over 5 min. The resulting bright yellow solution was allowed to stir at −78° C. for 3 h before the reaction was quenched with the addition of saturated aq. $NH_4Cl$. The aqueous phase was separated and back extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex$\rightarrow$3:7 (v/v) EtOAc:Hex) afforded 3-((tert-butyldimethylsilyl)oxy)-N-(1-(3,4-difluorophenyl)-2,2-difluoroethyl)propan-1-amine as a colorless oil (88% yield).

Step 4: In a dried round-bottom flask equipped with a magnetic stirrer was dissolved 3-((tert-butyldimethylsilyl)oxy)-N-(1-(3,4-difluorophenyl)-2,2-difluoroethyl)propan-1-amine (1 equiv) from the previous step in THF (0.25 M). To this solution was then added TBAF (1.2 equiv, 1 M solution in THF, Sigma-Aldrich) and the resulting mixture was stirred at RT for 90 min. The volatiles were then removed in vacuo and the resulting residue was directly subjected to purification by way of column chromatography ($SiO_2$, gradient elution:Hex 4 EtOAc) to afford 3-((1-(3,4-difluorophenyl)-2,2-difluoroethyl)amino)propan-1-ol as a colorless oil (91% yield).

Step 5: In a dried round-bottom flask equipped with a magnetic stirrer was dissolved 3-((1-(3,4-difluorophenyl)-2,2-difluoroethyl)amino)propan-1-ol (1 equiv) from the previous step and water (2 equiv) in MeCN (0.25 M). To the reaction mixture was then carefully added at 0° C., a freshly prepared (see, Zhao, M. et al., *Tetrahedron Lett.* 1998, p. 5323-5326) wet MeCN solution (0.44 M) of periodic acid (4.5 equiv, Sigma-Aldrich) and chromium(III) oxide (0.05 equiv, Sigma-Aldrich) over a period of 100 min. Following the completion of addition, the resulting mixture was stirred at 0° C. for an additional 30 min. The reaction was then quenched with addition of 2 M aq. $Na_2HPO_4$. The aqueous phase was separated and back extracted with toluene. The combined organic extracts were washed further with water (2×), saturated aq. $Na_2S_2O_3$ (2×) and brine, dried over $MgSO_4$ and filtered. Concentration of the filtrate in vacuo afforded the title compound as a colorless syrup (49% yield).

Intermediate acid 23: Preparation of (R)-3-((1-(4-fluorophenyl)-2-hydroxyethyl)amino)propanoic acid

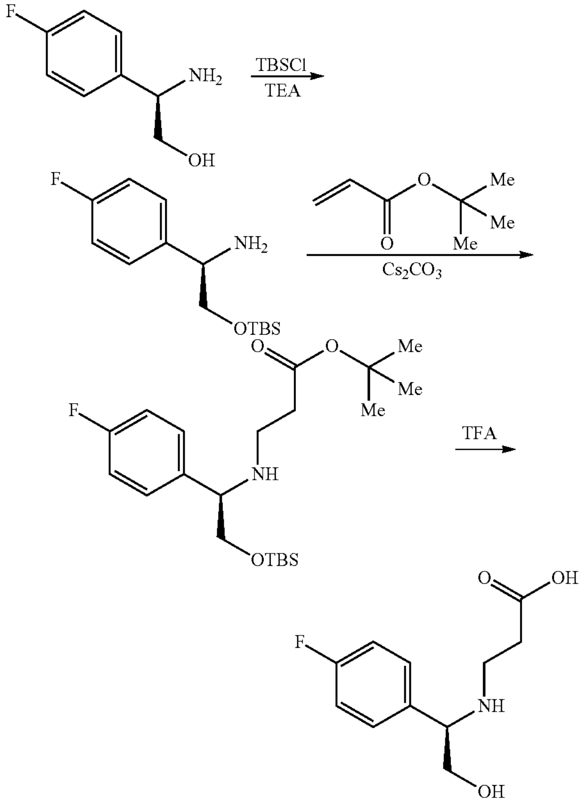

Intermediate acid 23

Step 1: In a dried round-bottom flask equipped with a magnetic stirrer was combined (R)-2-amino-1-(4-fluorophenyl)ethan-1-ol (1 equiv, AstaTech), DMAP (0.2 equiv, Sigma-Aldrich) and tert-butyldimethylsilyl chloride (2 equiv, Sigma-Aldrich) in dichloromethane (0.3 M). To the reaction mixture was then added triethylamine (3 equiv, Sigma-Aldrich) and the resulting solution was stirred at RT for 1 h. The reaction was then quenched with the addition of water and diluted with DCM. The organic layer was separated, washed further with water and brine, dried over $MgSO_4$, filtered, and the filtrate concentrated in vacuo. Purification of the crude product thus obtained by way of column chromatography ($SiO_2$, isocratic elution: 1:1 (v/v) EtOAc:Hex) afforded (R)-2-((tert-butyldimethylsilyl)oxy)-1-(4-fluorophenyl)ethan-1-amine as a yellow oil (76% yield).

Step 2: In a sealable reaction vessel equipped with a magnetic stirrer and a Teflon screwcap was suspended (R)-2-((tert-butyldimethylsilyl)oxy)-1-(4-fluorophenyl)ethan-1-amine (1 equiv) from the previous step, tert-butyl acrylate (6 equiv, TCI), and cesium carbonate (2 equiv, Sigma-Aldrich) in tert-butanol (0.085 M). The vessel was then tightly sealed and heated at 120° C. for 3 days. The volatiles were then removed in vacuo and the resulting residue was partitioned between water and tert-butyl methyl ether. The aqueous layer was separated and backextracted with tert-butyl methyl ether (3×). The combined organic extracts were washed further with water and brine, dried over $MgSO_4$, filtered, and the filtrate concentrated in vacuo. Purification of the crude product thus obtained by way of column chromatography ($SiO_2$, isocratic elution: 1:5 (v/v) EtOAc:Hex) afforded tert-butyl (R)-3-((tert-butyldimethylsilyl)oxy)-1-(4-fluorophenyl)ethyl)amino)propanoate as a colorless oil (39% yield).

Step 3: In a dried round-bottom flask equipped with a magnetic stirrer was dissolved tert-butyl (R)-3-((tert-butyldimethylsilyl)oxy)-1-(4-fluorophenyl)ethyl)amino) propanoate (1 equiv) from the previous step in dichloromethane (0.07 M). To this solution was then added TFA (50 equiv, Sigma-Aldrich) and the resulting mixture was stirred at RT for 24 h. The volatiles were then removed in vacuo and the resulting residue was further azeotroped with toluene (3×). The title compound thus obtained was used in the next step without further purification (>99% yield).

The following acid was prepared in an analogous fashion to Intermediate acid 23 but substituting (R)-2-amino-1-(4-fluorophenyl)ethan-1-ol for (S)-2-amino-1-(4-fluorophenyl) ethan-1-ol (Combi-Blocks) in step 1:

| Name | Structure |
|---|---|
| Intermediate acid 24 | 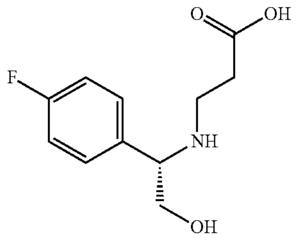 [SMILES: O=C(O)CCN[C@H](CO)c1ccc(F)cc1] |

Intermediate acid 25: Preparation of racemic 2-((1-phenylethyl)thio)acetic acid

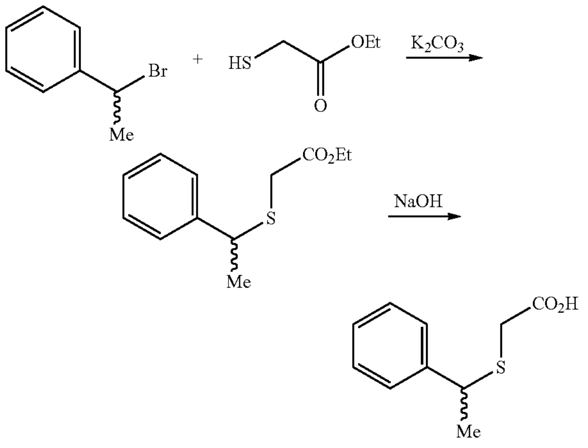

Intermediate acid 25

Step 1: In a dried round-bottom flask equipped with a magnetic stirrer was combined (1-bromoethyl)benzene (1 equiv, Combi-Blocks) and ethyl 2-mercaptoacetate (1.2 equiv, Sigma-Aldrich) in DMSO (0.38 M). To the reaction mixture was then added potassium carbonate (1.2 equiv, Sigma-Aldrich) portionwise over 5 min and the resulting suspension was stirred at RT for 48 h. The reaction was then quenched with the addition of water and diluted with EtOAc. The organic layer was separated, washed further with water (2×) and brine, dried over $MgSO_4$, filtered, and the filtrate concentrated in vacuo. Purification of the crude product thus obtained by way of column chromatography ($SiO_2$, gradient elution:Hex→1:1 (v/v) EtOAc:Hex) afforded ethyl 2-((1-phenylethyl)thio)acetate as a colorless oil (85% yield).

Step 2: In a round-bottom flask equipped with a magnetic stirrer was dissolved ethyl 2-((1-phenylethyl)thio)acetate (1 equiv) from the previous step in a 1:1 (v/v) solution of THF and methanol (0.2 M). To this solution was then added sodium hydroxide (3 equiv, 1 M solution in water, Fisher Scientific) and the resulting mixture was stirred at RT for 18 h. The pH of the reaction mixture was then adjusted to ~3 with 1 M aq. HCl and the volatiles were removed in vacuo. The resulting residue was then partitioned between water and EtOAc. The organic layer was separated, washed further with water and brine, dried over $Na_2SO_4$, and filtered. Concentration of the filtrate thus obtained in vacuo afforded the title compound as a colorless syrup (89% yield).

The following acids were prepared in an analogous fashion to Intermediate acid 25 but substituting (1-bromoethyl) benzene for the requisite benzyl halide in step 1. For the synthesis of Intermediate acid 27, Intermediate acid 28, and Intermediate acid 29, ethyl 2-mercaptoacetate was also substituted for methyl 3-mercaptopropanoate (TCI) in step 1. For the synthesis of Intermediate acid 30, ethyl 2-mercaptoacetate was also substituted for ethyl azetidine-3-carboxylate (Combi-Blocks) in step 1:

| Name | Structure |
|---|---|
| Intermediate acid 26 | 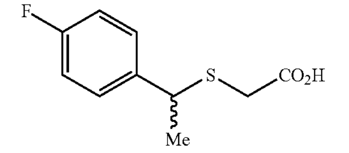 [SMILES: CC(SCC(=O)O)c1ccc(F)cc1] |
| Intermediate acid 27 | 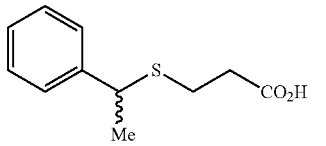 [SMILES: CC(SCCC(=O)O)c1ccccc1] |
| Intermediate acid 28 | 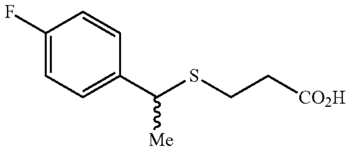 [SMILES: CC(SCCC(=O)O)c1ccc(F)cc1] |
| Intermediate acid 29 | 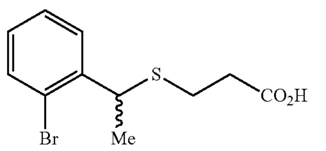 [SMILES: CC(SCCC(=O)O)c1ccccc1Br] |
| Intermediate acid 30 | 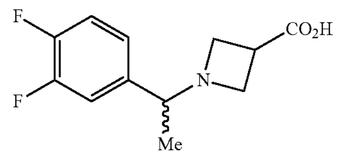 [SMILES: CC(c1ccc(F)c(F)c1)N1CC(C(=O)O)C1] |

Intermediate acid 31: Preparation of 3-hydroxy-3-(quinolin-5-yl)cyclobutane-1-carboxylic acid

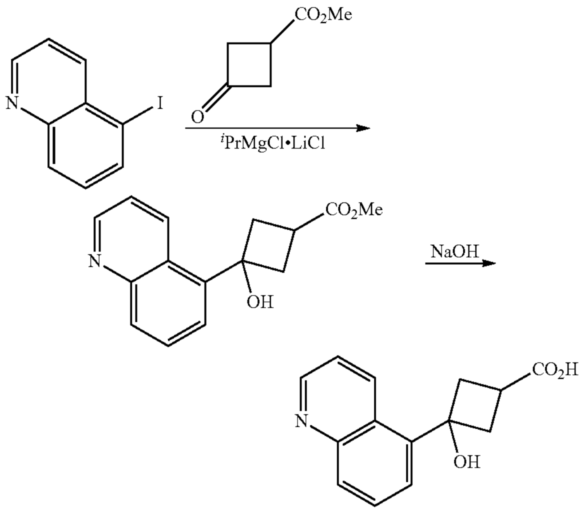

Intermediate acid 31

Step 1: In a dried round-bottom flask equipped with a magnetic stirrer was dissolved 5-iodoquinoline (1 equiv, Enamine) in THF (0.39 M). The resulting solution was then cooled to −40° C. before Turbo Grignard (1.1 equiv, 1.3 M solution in THF, Sigma-Aldrich) was added dropwise over 15 min, taking care to keep the internal reaction temperature below −15° C. After 60 min of stirring at −30° C., the now mustard yellow suspension was cooled further to −78° C. and methyl 3-oxocyclobutane-1-carboxylate (1.1 equiv, 0.7 M solution in THF, PharmaBlock Inc.) was then added dropwise over 10 min. The cooling bath was then removed and the reaction mixture was allowed to stir at RT for 16 h. Finally, the reaction was quenched with the addition of saturated aq. $NH_4Cl$ and extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex→EtOAc) afforded methyl 3-hydroxy-3-(quinolin-5-yl)cyclobutane-1-carboxylate as an inseparable mixture of cis- and trans-isomers (21% yield).

Step 2: In a round-bottom flask equipped with a magnetic stirrer was dissolved methyl 3-hydroxy-3-(quinolin-5-yl) cyclobutane-1-carboxylate (1 equiv) from the previous step in a 1:1 (v/v) solution of THF and methanol (0.13 M). To this solution was then added sodium hydroxide (3 equiv, 1 M solution in water, Fisher Scientific) and the resulting mixture was stirred at RT for 18 h. The pH of the reaction mixture was then adjusted to ~3 with 1 M aq. HCl and the volatiles were removed in vacuo. The resulting residue was then partitioned between water and EtOAc. The organic layer was separated, washed further with water and brine, dried over $Na_2SO_4$, and filtered. Concentration of the filtrate thus obtained in vacuo afforded the title compound as an inseparable mixture of cis- and trans-isomers (91% yield).

The following acid was prepared in an analogous fashion to Intermediate acid 31 but substituting 5-iodoquinoline for 5-iodoisoquinoline (AstaTech) in step 1:

| Name | Structure |
|---|---|
| Intermediate acid 32 | 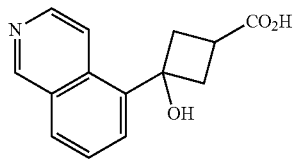 [SMILES: O=C(O)C1CC(O)(c2cccc3cnccc23)C1] |

Example 1: Preparation of 6-(3-(3-((1-(3,4-difluorophenyl)cyclopropyl)amino)propanoyl)-3,8-diazabicyclo[3.2.1]octan-8-yl)nicotinonitrile

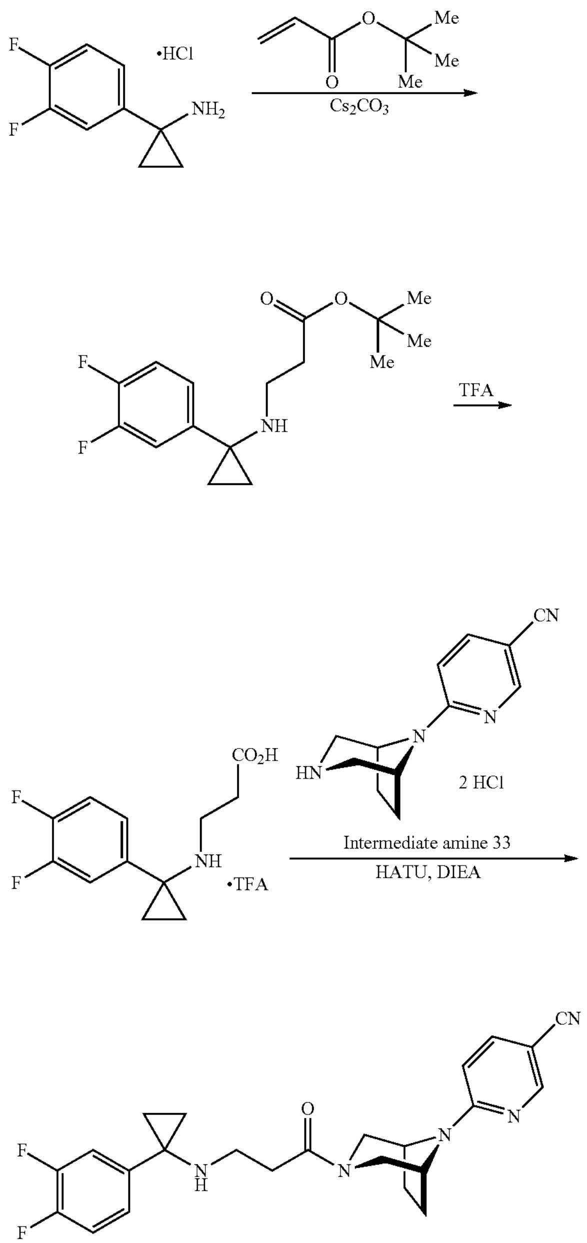

Example 1

Step 1: In a sealable reaction vessel equipped with a magnetic stirrer and a Teflon screwcap was suspended 1-(3,4-difluorophenyl)cyclopropyl amine hydrochloride (1 equiv, Combi-Blocks), tert-butyl acrylate (6 equiv, Combi-Blocks), and cesium carbonate (2 equiv, Sigma-Aldrich) in tert-butanol (0.15 M). The vessel was then tightly sealed and heated at 120° C. for 3 days. The volatiles were then removed in vacuo and the resulting residue was partitioned between water and tert-butyl methyl ether. The aqueous layer was separated and backextracted with tert-butyl methyl ether (3×). The combined organic extracts were washed further with water and brine, dried over $MgSO_4$, filtered, and the filtrate concentrated in vacuo. Purification of the crude product thus obtained by way of column chromatography ($SiO_2$, gradient elution:Hex→EtOAc) afforded tert-butyl 3-((1-(3,4-difluorophenyl)cyclopropyl)amino)propanoate as a colorless oil (39% yield).

Step 2: In a dried round-bottom flask equipped with a magnetic stirrer was dissolved tert-butyl 3-((1-(3,4-difluorophenyl)cyclopropyl)amino)propanoate (1 equiv) from the previous step in dichloromethane (0.07 M). To this solution was then added TFA (30 equiv, Sigma-Aldrich) and the resulting mixture was stirred at RT for 24 h. The volatiles were then removed in vacuo and the resulting residue was further azeotroped with toluene (3×). 3-((1-(3,4-Difluorophenyl)cyclopropyl)amino)propanoic acid thus obtained was used in the next step without further purification.

Step 3: In a dried round-bottom flask equipped with a magnetic stirrer was combined 3-((1-(3,4-difluorophenyl)cyclopropyl)amino)propanoic acid (1 equiv) from the previous step, Intermediate amine 33 (1.1 equiv), and HATU (1.2 equiv, Combi-Blocks) in DMF (0.39 M). To the reaction mixture was then added DIEA (5 equiv, Sigma-Aldrich) and the resulting solution was allowed to stir at RT for 20 min. The reaction mixture was then diluted with EtOAc and washed further with water (3×). The organic layer was then concentrated in vacuo and the resulting residue was directly subjected to purification by way of column chromatography ($SiO_2$, gradient elution:Hex→EtOAc→10:1 (v/v) EtOAc:MeOH) to afford the title compound as an off-white solid (83% yield). LCMS: m/z=438.1 $[M+H]^+$; $^1H$ NMR (DMSO-$d_6$): δ=8.51~8.50 (m, 1H), 7.98 (dd, J=9.0, 4.6 Hz, 1H), 7.40 (br s, 1H), 7.32 (br s, 1H), 7.12 (br s, 1H), 6.94 (d, J=8.5 Hz, 1H), 4.70 (br s, 2H), 4.13 (d, J=12.5 Hz, 1H), 3.61 (d, J=12.5 Hz, 1H), 3.21 (d, J=12.0 Hz, 1H), 3.17 (d, J=8.5 Hz, 1H), 2.75~2.73 (m, 1H), 2.64~2.61 (m, 1H), 2.32~2.29 (m, 1H), 1.91~1.86 (m, 3H), 1.80~1.76 (m, 1H), 1.62~1.59 (m, 1H), 0.92 (br s, 4H).

The following examples were prepared in an analogous fashion to Example 1 but substituting 1-(3,4-difluorophenyl)cyclopropyl amine hydrochloride for the requisite amine in step 1:

| Example | Starting Amine | Structure | LCMS (m/z) |
|---|---|---|---|
| 2 | 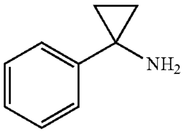 (Combi-Blocks) | 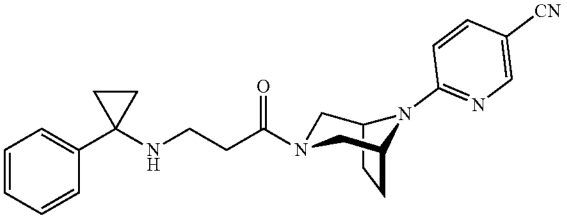 6-(3-(3-((1-phenylcyclopropyl)amino)propanoyl)-3,8-diazabicyclo[3.2.1]octan-8-yl)nicotinonitrile | 402.2 $[M + H]^+$ |
| 3 | 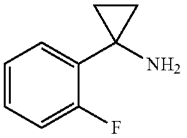 [SMILES: NC1(c2ccccc2F)CC1] (Combi-Blocks) | 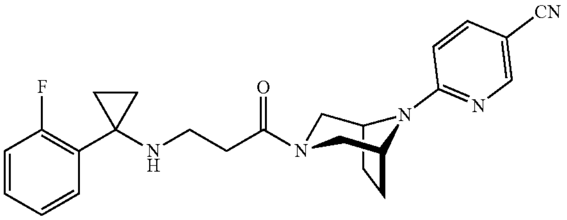 6-(3-(3-((1-(3-fluorophenyl)cyclopropyl)amino)propanoyl)-3,8-diazabicyclo[3.2.1]octan-8-yl)nicotinonitrile | 420.2 $[M + H]^+$ |
| 4 | 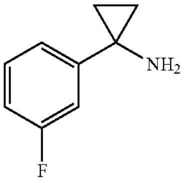 [SMILES: NC1(c2cccc(F)c2)CC1] (Combi-Blocks) | 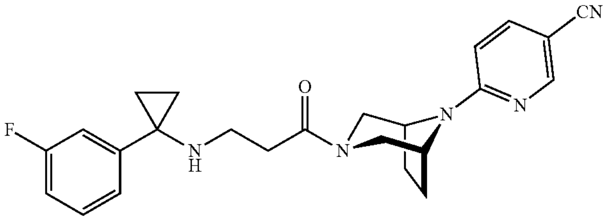 6-(3-(3-((1-(3-fluorophenyl)cyclopropyl)amino)propanoyl)-3,8-diazabicyclo[3.2.1]octan-8-yl)nicotinonitrile | 420.2 $[M + H]^+$ |
| 5 | 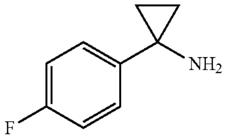 [SMILES: NC1(c2ccc(F)cc2)CC1] (Combi-Blocks) | 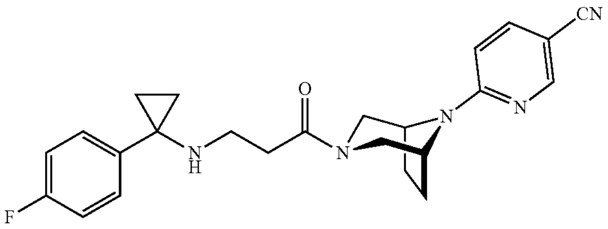 6-(3-(3-((1-(4-fluorophenyl)cyclopropyl)amino)propanoyl)-3,8-diazabicyclo[3.2.1]octan-8-yl)nicotinonitrile | 420.2 $[M + H]^+$ |
| 6 | 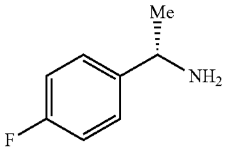 (Enamine) | 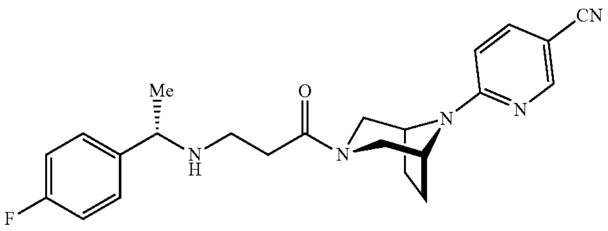 6-(3-(3-(((S)-1-(4-fluorophenyl)ethyl)amino)propanoyl)-3,8-diazabicyclo[3.2.1]octan-8-yl)nicotinonitrile | 408.2 $[M + H]^+$ |

-continued

| Example | Starting Amine | Structure | LCMS (m/z) |
|---|---|---|---|
| 7 | 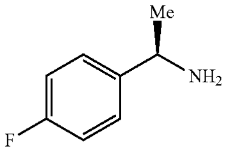 (Enamine) | 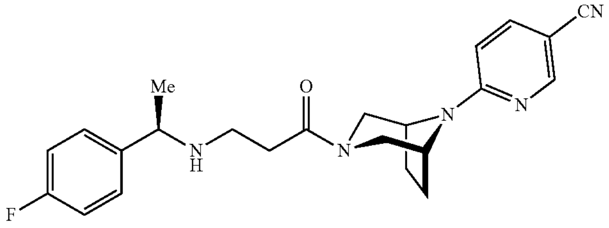 6-(3-(3-(((S)-1-(4-fluorophenyl)ethyl)amino)propanoyl)-3,8-diazabicyclo[3.2.1]octan-8-yl)nicotinonitrile | 408.2 $[M + H]^+$ |
| 8 | 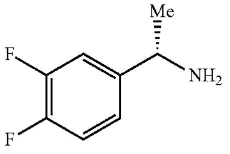 [SMILES: C[C@H](N)c1ccc(F)c(F)c1] (AstaTech) | 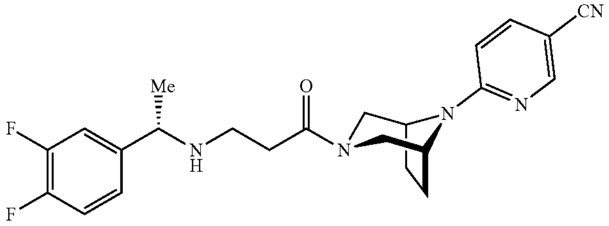 6-(3-(3-(((S)-1-(3,4-difluorophenyl)ethyl)amino)propanoyl)-3,8-diazabicyclo[3.2.1]octan-8-yl)nicotinonitrile | 426.1 $[M + H]^+$ |
| 9 | 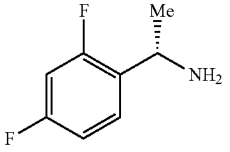 [SMILES: C[C@H](N)c1ccc(F)cc1F] (Combi-Blocks) | 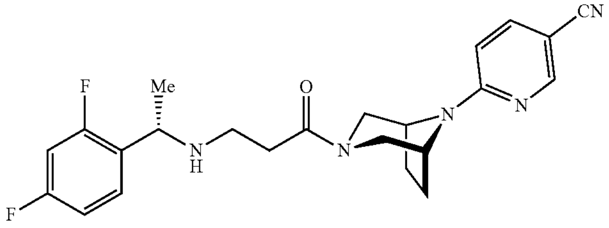 6-(3-(3-(((S)-1-(2,4-difluorophenyl)ethyl)amino)propanoyl)-3,8-diazabicyclo[3.2.1]octan-8-yl)nicotinonitrile | 426.1 $[M + H]^+$ |
| 10 | 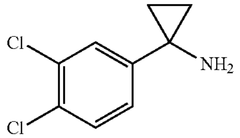 [SMILES: NC1(c2ccc(Cl)c(Cl)c2)CC1] (Enamine) | 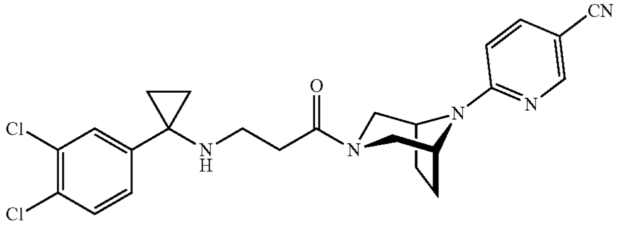 6-(3-(3-((1-(3,4-dichlorophenyl)cyclopropyl)amino)propanoyl)-3,8-diazabicyclo[3.2.1]octan-8-yl)nicotinonitrile | 470.0, 472.0 $[M + H]^+$ |
| 11 | 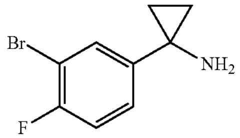 (Enamine) | 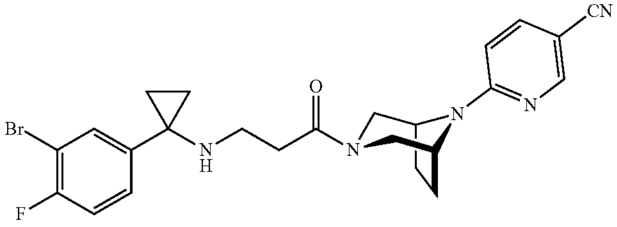 6-(3-(3-((1-(3-bromo-4-fluorophenyl)cyclopropyl)amino)propanoyl)-3,8-diazabicyclo[3.2.1]octan-8-yl)nicotinonitrile | 498.0, 500.0 $[M + H]^+$ |

-continued

| Example | Starting Amine | Structure | LCMS (m/z) |
|---|---|---|---|
| 12 | 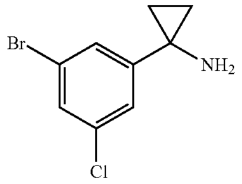 [SMILES: NC1(c2cc(Cl)cc(Br)c2)CC1] (Enamine) | 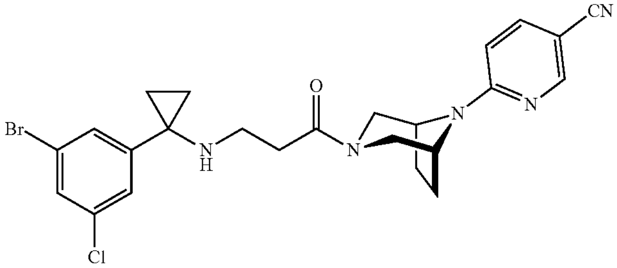 6-(3-(3-((1-(3-bromo-5-chlorophenyl)cyclopropyl)amino)propanoyl)-3,8-diazabicyclo[3.2.1]octan-8-yl)nicotinonitrile | 514.0, 516.0 $[M + H]^+$ |
| 13 | 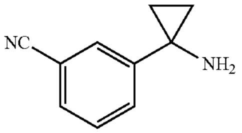 [SMILES: N#Cc1cccc(C2(N)CC2)c1] (Enamine) | 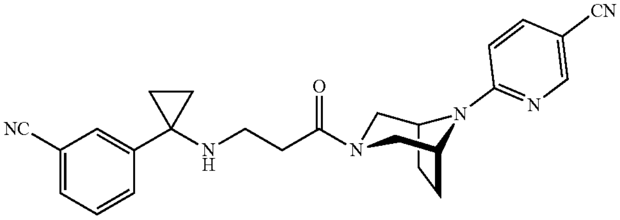 6-(3-(3-((1-(3-cyanophenyl)cyclopropyl)amino)propanoyl)-3,8-diazabicyclo[3.2.1]octan-8-yl)nicotinonitrile | 427.2 $[M + H]^+$ |
| 14 | 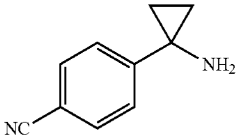 [SMILES: N#Cc1ccc(C2(N)CC2)cc1] (Enamine) | 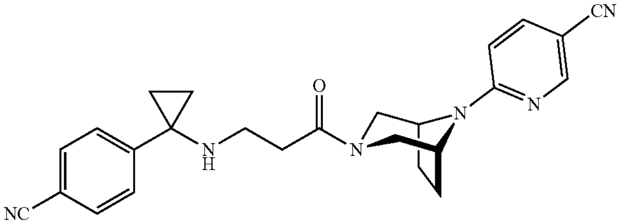 6-(3-(3-((1-(4-cyanophenyl)cyclopropyl)amino)propanoyl)-3,8-diazabicyclo[3.2.1]octan-8-yl)nicotinonitrile | 427.2 $[M + H]^+$ |
| 15 | 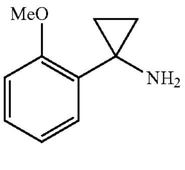 [SMILES: COc1ccccc1C1(N)CC1] (Enamine) | 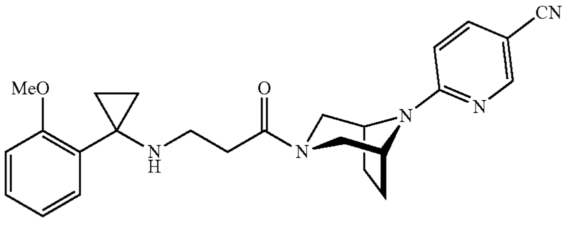 6-(3-(3-((1-(2-methoxyphenyl)cyclopropyl)amino)propanoyl)-3,8-diazabicyclo[3.2.1]octan-8-yl)nicotinonitrile | 432.1 $[M + H]^+$ |
| 16 | 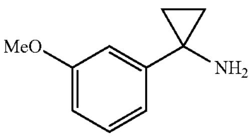 [SMILES: COc1cccc(C2(N)CC2)c1] (Enamine) | 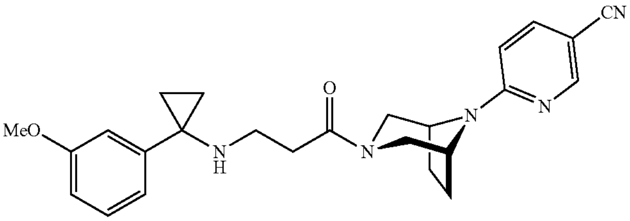 6-(3-(3-((1-(3-methoxyphenyl)cyclopropyl)amino)propanoyl)-3,8-diazabicyclo[3.2.1]octan-8-yl)nicotinonitrile | 432.1 $[M + H]^+$ |

-continued

| Example | Starting Amine | Structure | LCMS (m/z) |
|---|---|---|---|
| 17 | 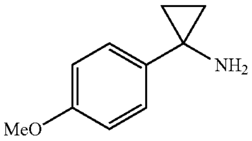 [SMILES: COc1ccc(C2(N)CC2)cc1] (Combi-Blocks) | 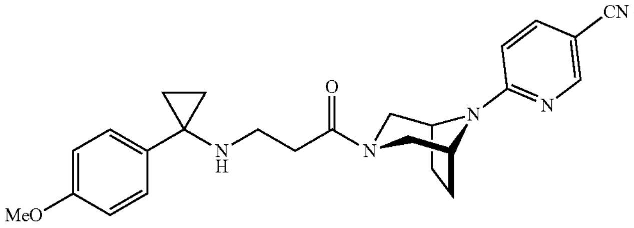 6-(3-(3-((1-(4-methoxyphenyl)cyclopropyl)amino)propanoyl)-3,8-diazabicyclo[3.2.1]octan-8-yl)nicotinonitrile | 432.1 $[M + H]^+$ |
| 18 | 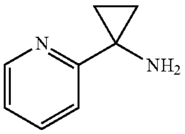 (Enamine) | 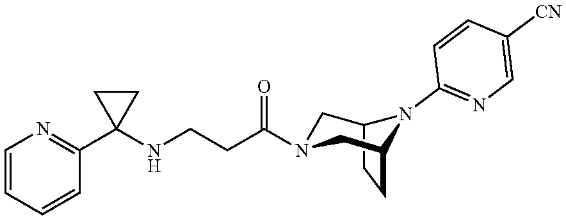 6-(3-(3-((1-(pyridin-2-yl)cyclopropyl)amino)propanoyl)-3,8-diazabicyclo[3.2.1]octan-8-yl)nicotinonitrile | 403.2 $[M + H]^+$ |
| 19 | 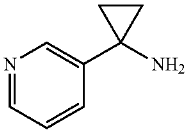 (Combi-Blocks) | 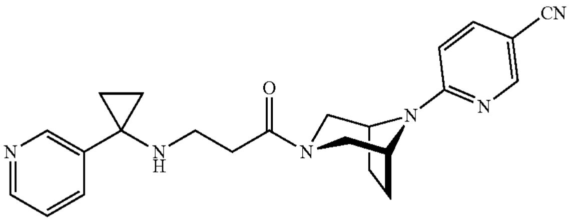 6-(3-(3-((1-(pyridin-3-yl)cyclopropyl)amino)propanoyl)-3,8-diazabicyclo[3.2.1]octan-8-yl)nicotinonitrile | 403.2 $[M + H]^+$ |
| 20 | 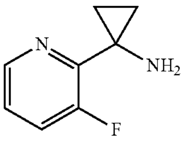 [SMILES: NC1(c2ncccc2F)CC1] (Enamine) | 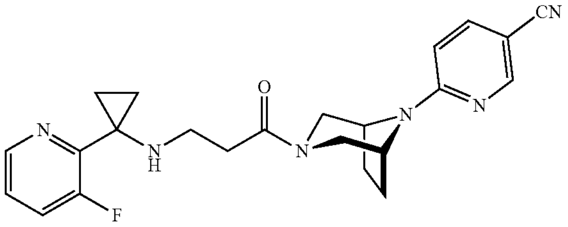 6-(3-(3-((1-(3-fluoropyridin-2-yl)cyclopropyl)amino)propanoyl)-3,8-diazabicyclo[3.2.1]octan-8-yl)nicotinonitrile | 421.1 $[M + H]^+$ |
| 21 | 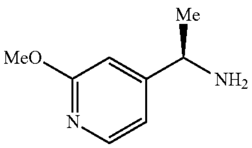 [SMILES: COc1cc([C@@H](C)N)ccn1] (ArkPharm) | 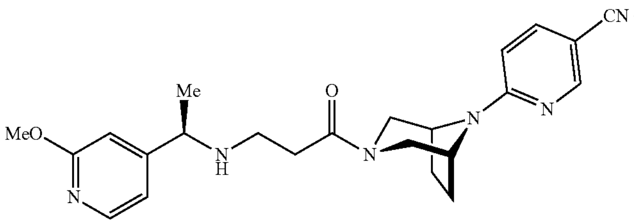 6-(3-(3-(((R)-1-(2-methoxypyridin-4-yl)ethyl)amino)propanoyl)-3,8-diazabicyclo[3.2.1]octan-8-yl)nicotinonitrile | 421.2 $[M + H]^+$ |

-continued

| Example | Starting Amine | Structure | LCMS (m/z) |
|---|---|---|---|
| 22 | 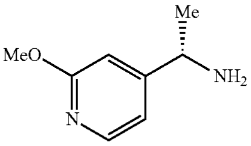 [SMILES: COc1cc([C@H](C)N)ccn1] (ArkPharm) | 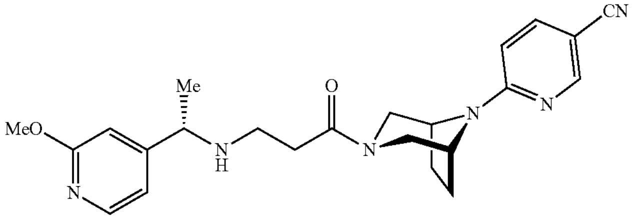 6-(3-(3-(((S)-1-(2-methoxypyridin-4-yl)ethyl)amino)propanoyl)-3,8-diazabicyclo[3.2.1]octan-8-yl)nicotinonitrile | 421.2 $[M + H]^+$ |
| 23 | 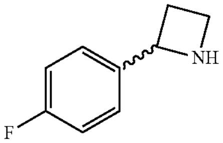 [SMILES: Fc1ccc(C2CCN2)cc1] (Enamine) | 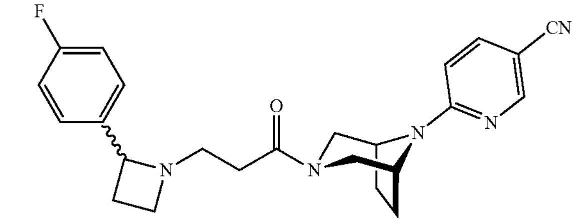 Racemic 6-(3-(3-(2-(4-fluorophenyl)azetidin-1-yl)propanoyl)-3,8-diazabicyclo[3.2.1]octan-8-yl)nicotinonitrile | 420.2 $[M + H]^+$ |
| 24 | 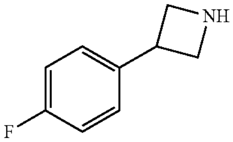 [SMILES: Fc1ccc(C2CNC2)cc1] (AstaTech) | 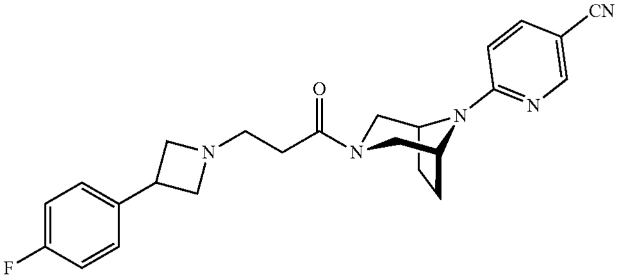 6-(3-(3-(4-(4-fluorophenyl)azetidin-1-yl)propanoyl)-3,8-diazabicyclo[3.2.1]octan-8-yl)nicotinonitrile | 420.2 $[M + H]^+$ |
| 25 | 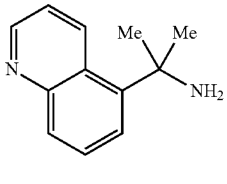 [SMILES: CC(C)(N)c1cccc2ncccc12] (Enamine) | 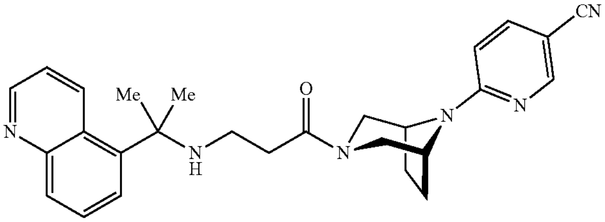 6-(3-(3-((2-(quinolin-5-yl)propan-2-yl)amino)propanoyl)-3,8-diazabicyclo[3.2.1]octan-8-yl)nicotinonitrile | 455.4 $[M + H]^+$ |
| 26 | 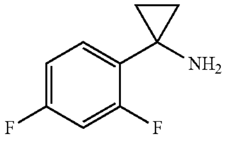 [SMILES: NC1(c2ccc(F)cc2F)CC1] (Combi-Blocks) | 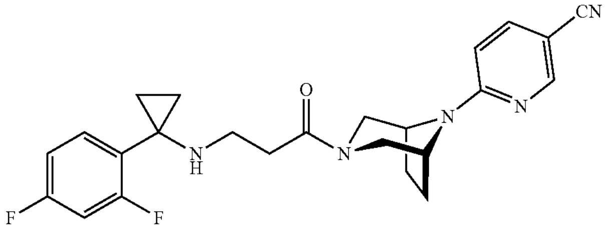 6-(3-(3-((1-(2,4-difluorophenyl)cyclopropyl)amino)propanoyl)-3,8-diazabicyclo[3.2.1]octan-8-yl)nicotinonitrile | 438.1 $[M + H]^+$ |

-continued

| Example | Starting Amine | Structure | LCMS (m/z) |
| --- | --- | --- | --- |
| 27 | 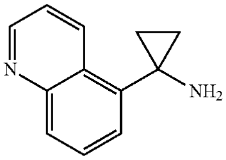 [SMILES: NC1(c2cccc3ncccc23)CC1] Intermediate amine 1 | 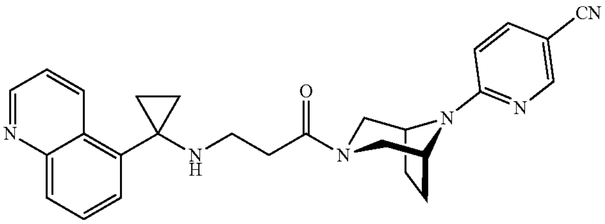 6-(3-(3-((1-(quinolin-5-yl)cyclopropyl)amino)propanoyl)-3,8-diazabicyclo[3.2.1]octan-8-yl)nicotinonitrile | 453.1 $[M + H]^+$ |
| 28 | 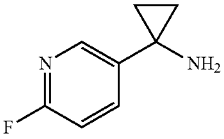 [SMILES: NC1(c2ccc(F)nc2)CC1] Intermediate amine 2 | 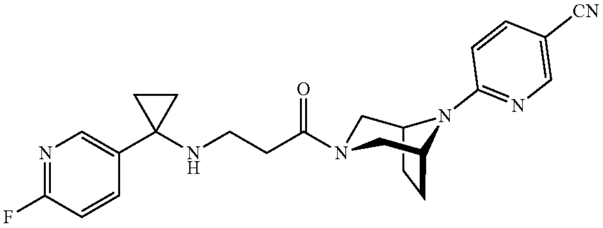 6-(3-(3-((1-(6-fluoropyridin-3-yl)cyclopropyl)amino)propanoyl)-3,8-diazabicyclo[3.2.1]octan-8-yl)nicotinonitrile | 421.2 $[M + H]^+$ |
| 29 | 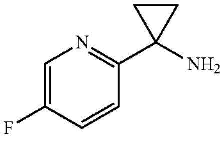 [SMILES: NC1(c2ccc(F)cn2)CC1] Intermediate amine 3 | 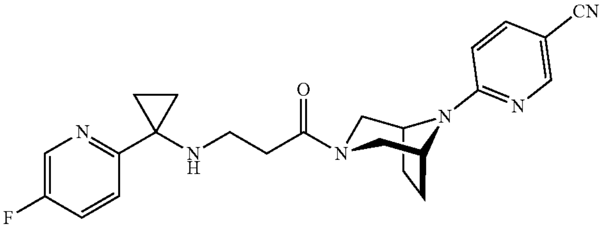 6-(3-(3-((1-(5-fluoropyridin-2-yl)cyclopropyl)amino)propanoyl)-3,8-diazabicyclo[3.2.1]octan-8-yl)nicotinonitrile | 421.2 $[M + H]^+$ |
| 30 | 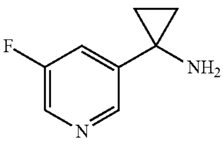 [SMILES: NC1(c2cncc(F)c2)CC1] Intermediate amine 4 | 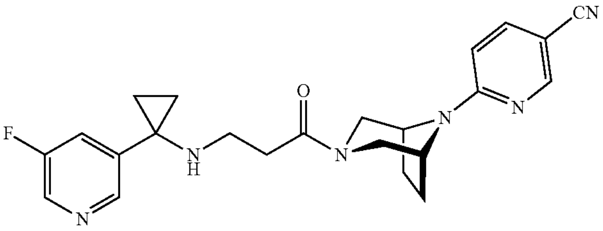 6-(3-(3-((1-(5-fluoropyridin-3-yl)cyclopropyl)amino)propanoyl)-3,8-diazabicyclo[3.2.1]octan-8-yl)nicotinonitrile | 421.2 $[M + H]^+$ |
| 31 | 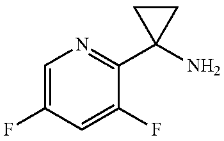 [SMILES: NC1(c2ncc(F)cc2F)CC1] Intermediate amine | 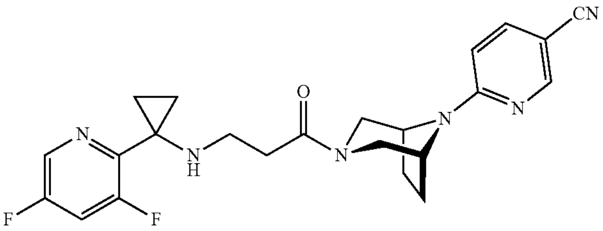 6-(3-(3-((1-(3,5-difluoropyridin-2-yl)cyclopropyl)amino)propanoyl)-3,8-diazabicyclo[3.2.1]octan-8-yl)nicotinonitrile | 439.1 $[M + H]^+$ |

-continued

| Example | Starting Amine | Structure | LCMS (m/z) |
|---|---|---|---|
| 32 | 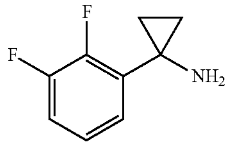 [SMILES: NC1(c2cccc(F)c2F)CC1] Intermediate amine 6 | 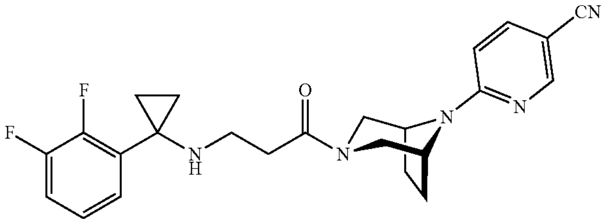 6-(3-(3-((1-(2,3-difluorophenyl)cyclopropyl)amino)propanoyl)-3,8-diazabicyclo[3.2.1]octan-8-yl)nicotinonitrile | 438.1 $[M + H]^+$ |
| 33 | 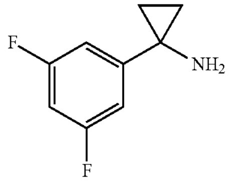 [SMILES: NC1(c2cc(F)cc(F)c2)CC1] Intermediate amine 7 | 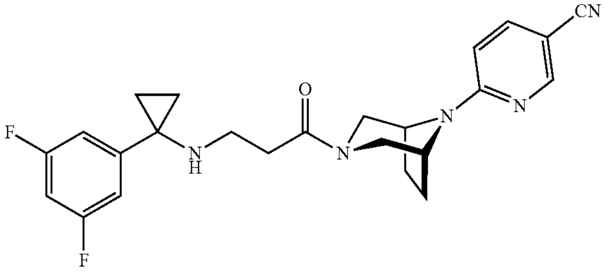 6-(3-(3-((1-(3,5-difluorophenyl)cyclopropyl)amino)propanoyl)-3,8-diazabicyclo[3.2.1]octan-8-yl)nicotinonitrile | 438.1 $[M + H]^+$ |
| 34 | 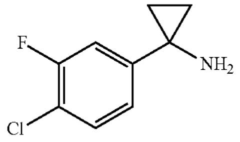 [SMILES: NC1(c2ccc(Cl)c(F)c2)CC1] Intermediate amine 10 | 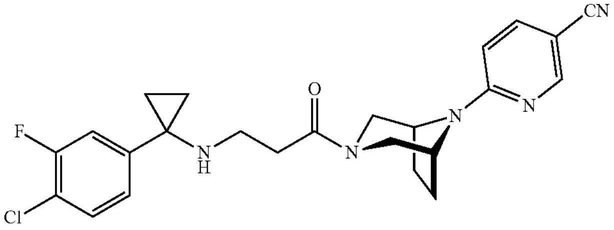 6-(3-(3-((1-(4-chloro-3-fluorophenyl)cyclopropyl)amino)propanoyl)-3,8-diazabicyclo[3.2.1]octan-8-yl)nicotinonitrile | 454.0, 456.0 $[M + H]^+$ |
| 35 | 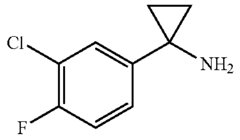 [SMILES: NC1(c2ccc(F)c(Cl)c2)CC1] Intermediate amine 11 | 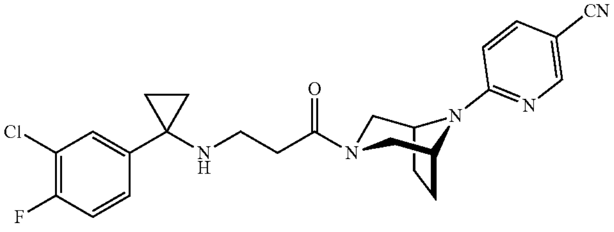 6-(3-(3-((1-(3-chloro-4-fluorophenyl)cyclopropyl)amino)propanoyl)-3,8-diazabicyclo[3.2.1]octan-8-yl)nicotinonitrile | 454.0, 456.0 $[M + H]^+$ |
| 36 | 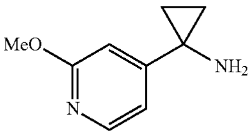 [SMILES: COc1cc(C2(N)CC2)ccn1] Intermediate amine 17 | 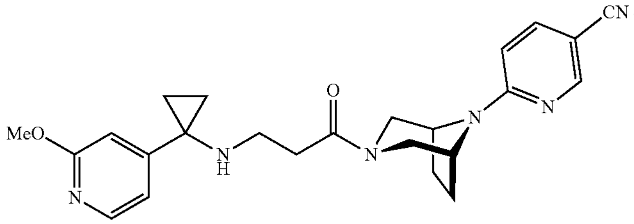 6-(3-(3-((1-(2-methoxypyridin-4-yl)cyclopropyl)amino)propanoyl)-3,8-diazabicyclo[3.2.1]octan-8-yl)nicotinonitrile | 433.1 $[M + H]^+$ |

-continued

| Example | Starting Amine | Structure | LCMS (m/z) |
| --- | --- | --- | --- |
| 37 | 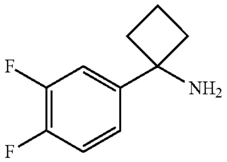 [SMILES: NC1(c2ccc(F)c(F)c2)CCC1] Intermediate amine 26 | 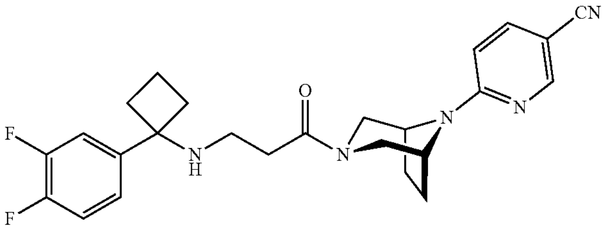 6-(3-(3-((1-(3,4-difluorophenyl)cyclobutyl)amino)propanoyl)-3,8-diazabicyclo[3.2.1]octan-8-yl)nicotinonitrile | 452.2 $[M + H]^+$ |
| 38 | 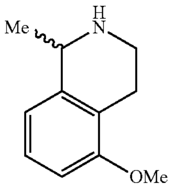 Intermediate amine 32 | 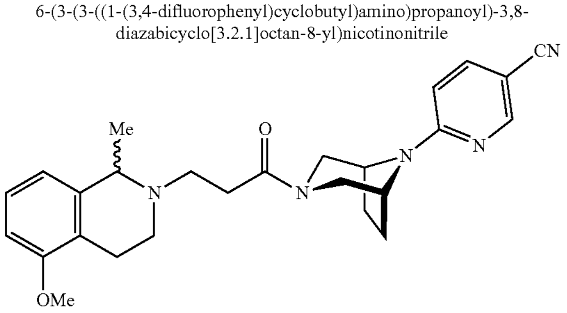 Racemic 6-(3-(3-(5-methoxy-1-methyl-3,4-dihydroisoquinolin-2(1H)-yl)propanoyl)-3,8-diazabicyclo[3.2.1]octan-8-yl)nicotinonitrile | 446.2 $[M + H]^+$ |

The following examples were prepared in an analogous fashion to Example 1 but substituting Intermediate amine 33 for the requisite amine in step 3:

| Example | Starting Amine | Structure | LCMS (m/z) |
| --- | --- | --- | --- |
| 39 | 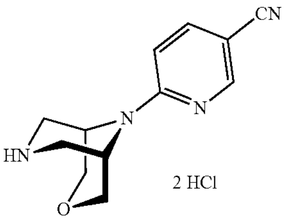 2 HCl Intermediate amine 34 | 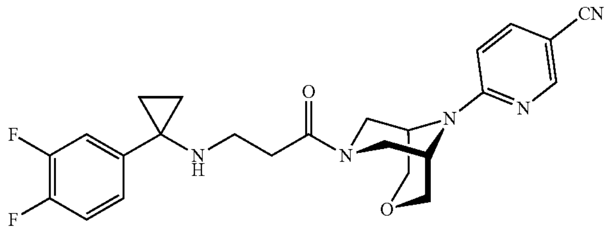 6-(7-(3-((1-(3,4-difluorophenyl)cyclopropyl)amino)propanoyl)-3-oxa-7,9-diazabicyclo[3.3.1]nonan-9-yl)nicotinonitrile | 454.1 $[M + H]^+$ |
| 40 | 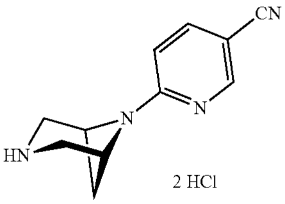 2 HCl Intermediate amine 35 | 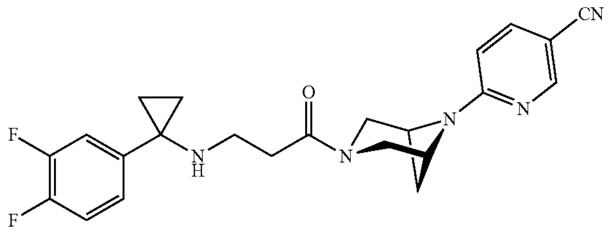 6-(3-(3-((1-(3,4-difluorophenyl)cyclopropyl)amino)propanoyl)-3,6-diazabicyclo[3.1.1]heptan-6-yl)nicotinonitrile | 424.1 $[M + H]^+$ |

-continued

| Example | Starting Amine | Structure | LCMS (m/z) |
| --- | --- | --- | --- |
| 41 | 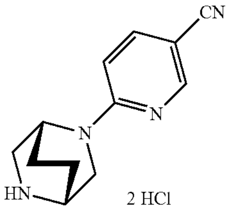 2 HCl<br>Intermediate amine 37 | 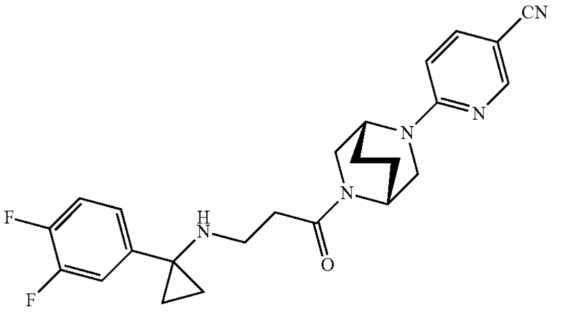<br>6-((1R,4R)-5-(3-((1-(3,4-difluorophenyl)cyclopropyl)amino)propanoyl)-2,5-diazabicyclo[2.2.2]octan-2-yl)nicotinonitrile | 438.1 $[M + H]^+$ |
| 42 | 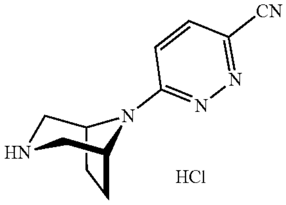 HCl<br>Intermediate amine 40 | 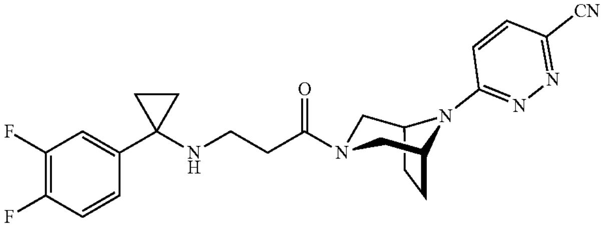<br>6-(3-(3-((1-(3,4-difluorophenyl)cyclopropyl)amino)propanoyl)-3,8-diazabicyclo[3.2.1]octan-8-yl)pyridazine-3-carbonitrile | 439.2 $[M + H]^+$ |
| 43 | 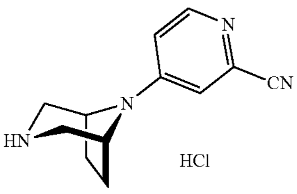 HCl<br>Intermediate amine 41 | 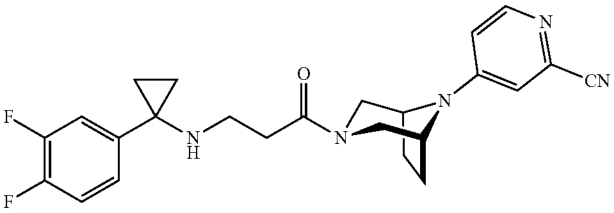<br>4-(3-(3-((1-(3,4-difluorophenyl)cyclopropyl)amino)propanoyl)-3,8-diazabicyclo[3.2.1]octan-8-yl)picolinonitrile | 438.2 $[M + H]^+$ |
| 44 | 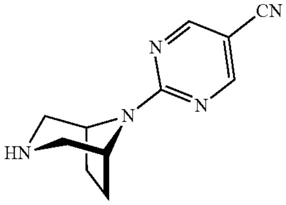<br>Intermediate amine 42 | 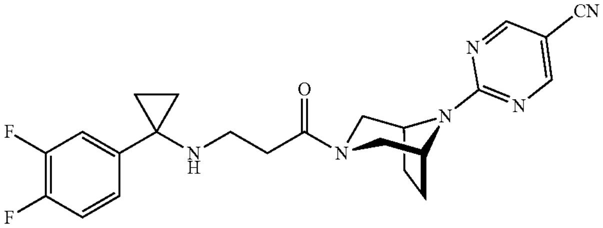<br>2-(3-(3-((1-(3,4-difluorophenyl)cyclopropyl)amino)propanoyl)-3,8-diazabicyclo[3.2.1]octan-8-yl)pyrimidine-5-carbonitrile | 439.2 $[M + H]^+$ |
| 45 | 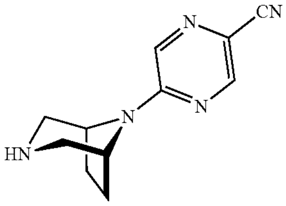<br>Intermediate amine 43 | 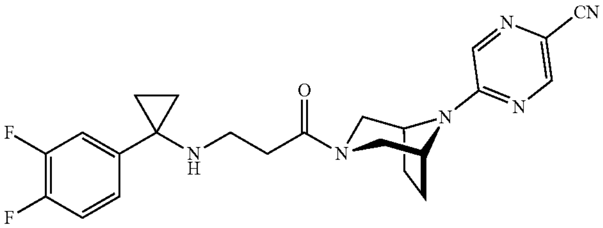<br>5-(3-(3-((1-(3,4-difluorophenyl)cyclopropyl)amino)propanoyl)-3,8-diazabicyclo[3.2.1]octan-8-yl)pyrazine-2-carbonitrile | 439.3 $[M + H]^+$ |

-continued

| Example | Starting Amine | Structure | LCMS (m/z) |
|---|---|---|---|
| 46 | 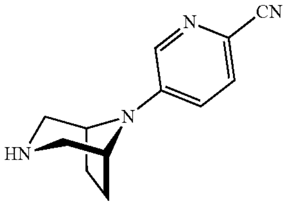 Intermediate amine 44 | 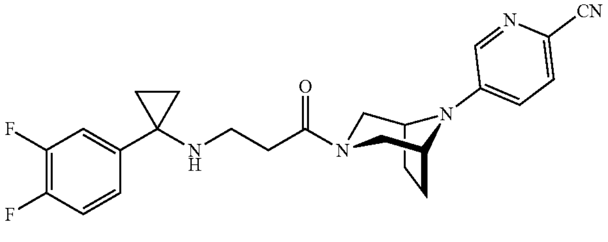 5-(3-(3-((1-(3,4-difluorophenyl)cyclopropyl)amino)propanoyl)-3,8-diazabicyclo[3.2.1]octan-8-yl)picolinonitrile | 438.3 $[M + H]^+$ |
| 47 | 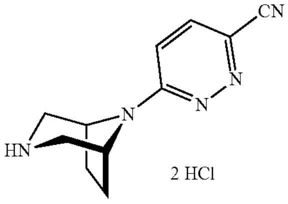 2 HCl Intermediate amine 46 | 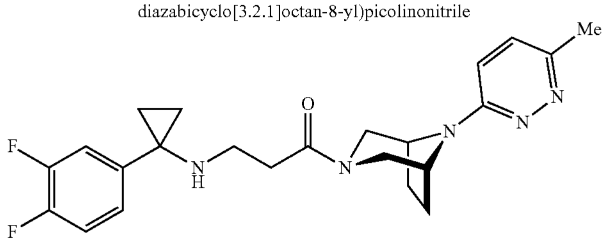 3-((1-(3,4-difluorophenyl)cyclopropyl)amino)-1-(8-(6-methylpyridazin-3-yl)-3,8-diazabicyclo[3.2.1]octan-3-yl)propan-1-one | 428.5 $[M + H]^+$ |

Example 48: Preparation of Racemic 6-(3-(3-((1-(quinolin-5-yl)ethyl)amino)propanoyl)-3,8-diazabicyclo[3.2.1]octan-8-yl)nicotinonitrile

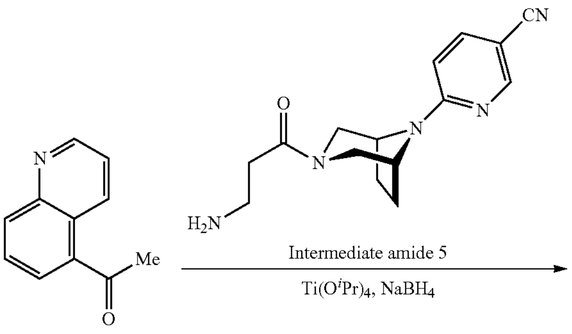

Intermediate ketone 1

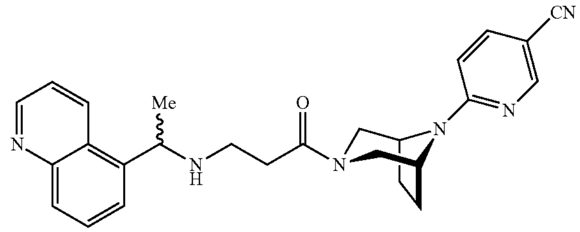

Example 48

In a dried round-bottom flask equipped with a magnetic stirrer was combined Intermediate ketone 1 (1.2 equiv) and Intermediate amide 5 (1 equiv) in methanol (0.12 M). To the reaction mixture was then added titanium(IV) isopropoxide (3 equiv, Combi-Blocks) and the resulting solution stirred at RT for 24 h. Finally, sodium borohydride (3 equiv, Sigma-Aldrich) was added in one rapid portion and the resulting mixture was stirred at RT for 1.5 h. The reaction mixture was then quenched with water and the volatiles were removed in vacuo. The resulting residue was directly subjected to purification by way of reverse phase column chromatography (Cis, gradient elution: 3:2 (v/v) $H_2O$:MeOH+0.1% $NH_4HCO_3$→2:3 (v/v) $H_2O$:MeOH+0.1% $NH_4HCO_3$) to afford the title compound as a white solid (17% yield). LCMS: m/z=441.2 $[M+H]^+$; $^1H$ NMR (Methanol-$d_4$) δ=8.91 8.78 (m, 2H), 8.43 (t, J=2.2 Hz, 1H), 7.99~ 7.90 (m, 1H), 7.87~ 7.70 (m. 3H), 7.65~ 7.50 (m, 1H), 6.84 (d, J=9.0 Hz, 1H), 4.71 (d, J=12.9 Hz, 1H), 4.24 (d, J=12.9 Hz, 1H), 3.73~3.60 (m, 1H), 3.31~ 3.22 (m, 1H), 2.97~2.41 (m, 5H), 2.01 (s, 2H), 1.87~1.66 (m, 2H), 1.51 (d, J=6.6 Hz, 3H).

The following examples were prepared in an analogous fashion to Example 48 but substituting Intermediate ketone 1 for the requisite ketone:

| Example | Starting Amine | Structure | LCMS (m/z) |
|---|---|---|---|
| 49 | 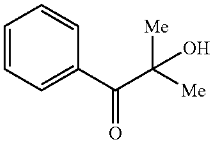 [SMILES: CC(C)(O)C(=O)c1ccccc1] (Combi-Blocks) | 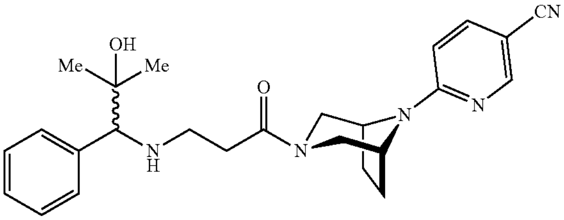 Racemic 6-(3-(3-((2-hydroxy-2-methyl-1-phenylpropyl)amino) propanoyl)-3,8-diazabicyclo[3.2.1]octan-8-yl)nicotinonitrile | 434.2 $[M + H]^+$ |
| 50 | 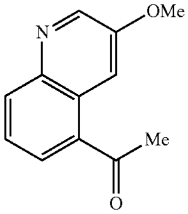 Intermediate ketone 3 | 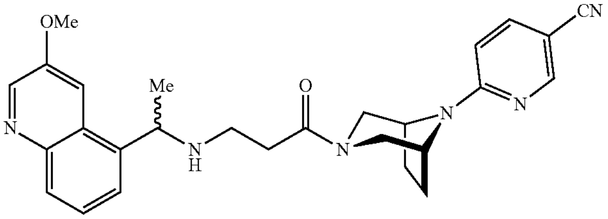 Racemic 6-(3-(3-((1-(3-methoxyquinolin-5-yl)ethyl)amino) propanoyl)-3,8-diazabicyclo[3.2.1]octan-8-yl)nicotinonitrile | 471.4 $[M + H]^+$ |
| 51 | 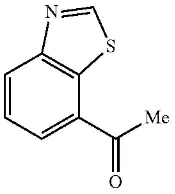 [SMILES: CC(=O)c1cccc2ncsc12] Intermediate ketone 4 | 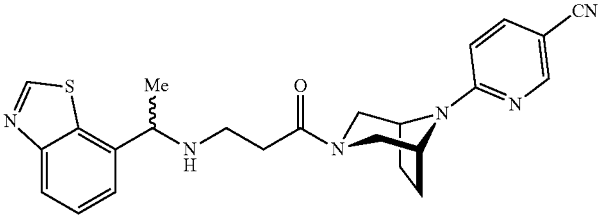 Racemic 6-(3-(3-((1-(benzo[d]thiazol-7-yl)ethyl)amino)propanoyl)-3,8-diazabicyclo[3.2.1]octan-8-yl)nicotinonitrile | 447.2 $[M + H]^+$ |
| 52 | 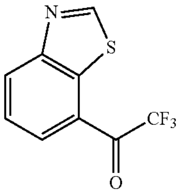 [SMILES: O=C(c1cccc2ncsc12)C(F)(F)F] Intermediate ketone 6 | 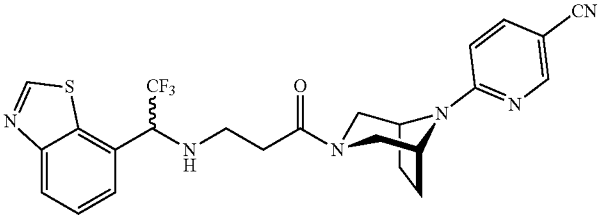 Racemic 6-(3-(3-((1-(benzo[d]thiazol-7-yl)-2,2,2-trifluoroethyl) amino)propanoyl)-3,8-diazabicyclo[3.2.1]octan-8-yl)nicotinonitrile | 501.5 $[M + H]^+$ |
| 53 | 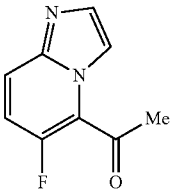 [SMILES: CC(=O)c1c(F)ccc2nccn12] Intermediate ketone 7 | 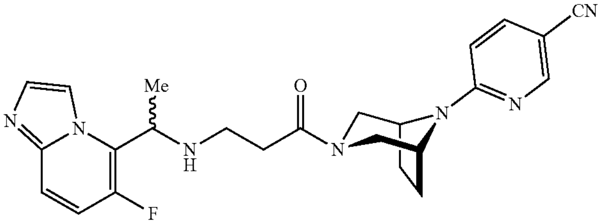 Racemic 6-(3-(3-((1-(6-fluoroimidazo[1,2-a]pyridin-5-yl)ethyl) amino)propanoyl)-3,8-diazabicyclo[3.2.1]octan-8-yl)nicotinonitrile | 448.4 $[M + H]^+$ |

Example 54: Preparation of racemic 6-(3-((1-([1,2,4]triazolo[1,5-a]pyridin-5-yl)ethyl)glycyl)-3,8-diazabicyclo[3.2.1]octan-8-yl)nicotinonitrile

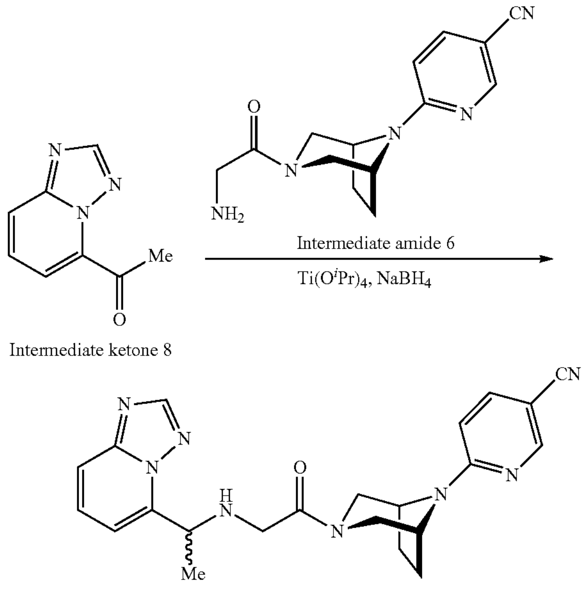

Intermediate ketone 8

Example 54

In a dried round-bottom flask equipped with a magnetic stirrer was combined Intermediate ketone 8 (1 equiv) and Intermediate amide 6 (1 equiv) in methanol (0.07 M). To the reaction mixture was then added titanium(IV) isopropoxide (3 equiv, Combi-Blocks) and the resulting solution was allowed to stir at RT for 1 h. Finally, sodium borohydride (3 equiv, Sigma-Aldrich) was added at 0° C. portionwise and the resulting mixture was stirred at 0° C. for 3.5 h. The reaction mixture was then quenched with water and the volatiles were removed in vacuo. The resulting residue was directly subjected to purification by way of reverse phase column chromatography (C18, gradient elution: 3:1 (v/v) $H_2O$:MeCN+0.1% $NH_4HCO_3$→1:1 (v/v) $H_2O$:MeOH+0.1% $NH_4HCO_3$) to afford the title compound as a white solid (37% yield). LCMS: m/z=417.5 $[M+H]^+$; $^1$H NMR (Methanol-$d_4$) δ=8.46 8.38 (m, 2H), 7.78~ 7.68 (m, 3H), 7.28 (q, J=4.6 Hz, 1H), 6.82 (d, J=9.0 Hz, 1H), 4.72~4.59 (m, 3H), 4.18 (d, J=13.1 Hz, 1H), 3.61~ 3.48 (m, 2H), 3.38~ 3.22 (m, 2H), 2.91 (dd, J=13.0, 5.4 Hz, 1H), 1.99 (s, 2H), 1.82~1.67 (m, 2H), 1.62 (dd, J=6.8, 2.8 Hz, 3H).

The following examples were prepared in an analogous fashion to Example 54 but substituting Intermediate ketone 8 for the requisite ketone. For the synthesis of Example 55 and Example 56, titanium(IV) isopropoxide was also substituted for acetic acid (10 equiv, Sigma-Aldrich) and sodium borohydride was also substituted for sodium cyanoborohydride (1.5 equiv, Sigma-Aldrich):

| Example | Starting Amine | Structure | LCMS (m/z) |
|---|---|---|---|
| 55 | 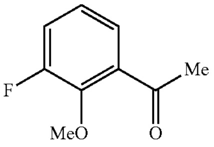 [SMILES: COc1c(F)cccc1C(C)=O] (Combi-Blocks) | 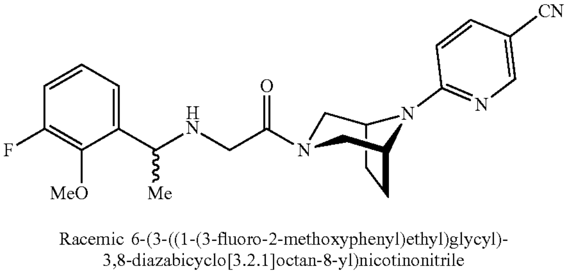 Racemic 6-(3-((1-(3-fluoro-2-methoxyphenyl)ethyl)glycyl)-3,8-diazabicyclo[3.2.1]octan-8-yl)nicotinonitrile | 424.2 $[M + H]^+$ |
| 56 | 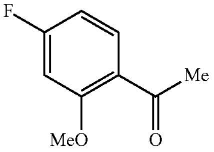 [SMILES: COc1cc(F)ccc1C(C)=O] (Combi-Blocks) | 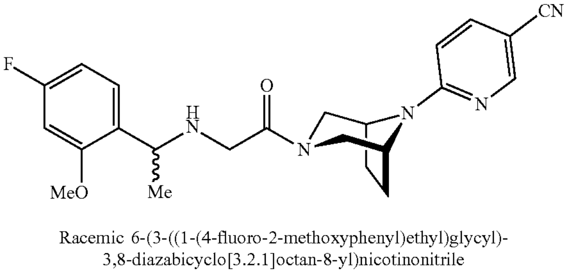 Racemic 6-(3-((1-(4-fluoro-2-methoxyphenyl)ethyl)glycyl)-3,8-diazabicyclo[3.2.1]octan-8-yl)nicotinonitrile | 424.1 $[M + H]^+$ |

-continued

| Example | Starting Amine | Structure | LCMS (m/z) |
|---|---|---|---|
| 57 | 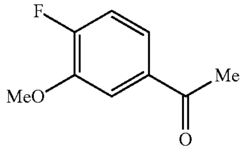 [SMILES: COc1cc(C(C)=O)ccc1F] (Combi-Blocks) | 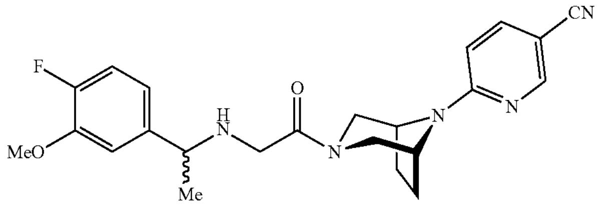 Racemic 6-(3-((1-(4-fluoro-3-methoxyphenyl)ethyl)glycyl)-3,8-diazabicyclo[3.2.1]octan-8-yl)nicotinonitrile | 424.2 $[M + H]^+$ |
| 58 | 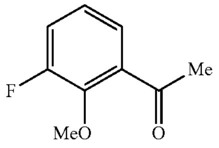 [SMILES: COc1c(F)cccc1C(C)=O] Intermediate ketone 9 | 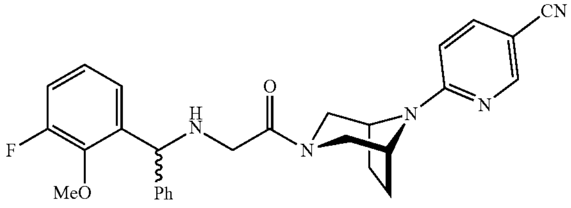 Racemic 6-(3-(((4-fluoro-3-methoxyphenyl)(phenyl)methyl)glycyl)-3,8-diazabicyclo[3.2.1]octan-8-yl)nicotinonitrile | 486.2 $[M + H]^+$ |

Example 59: Preparation of 6-(3-((1-(2,4-difluorophenyl)cyclopropyl)glycyl)-3,8-diazabicyclo[3.2.1]octan-8-yl)nicotinonitrile

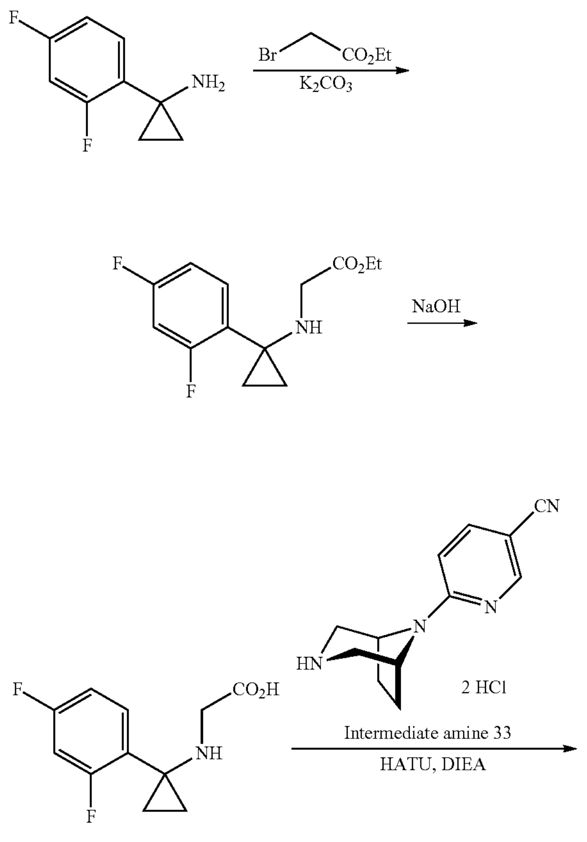

-continued

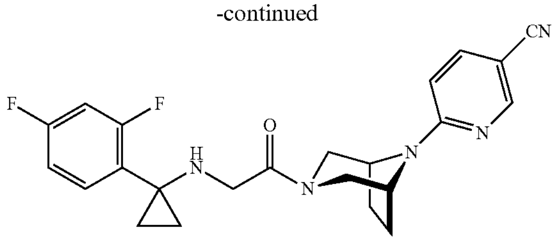

Example 59

Step 1: In a dried round-bottom flask equipped with a magnetic stirrer was dissolved 1-(2,4-difluorophenyl)cyclopropan-1-amine (1 equiv, Combi-Blocks) and potassium carbonate (2.5 equiv, Sigma-Aldrich) in a 6:1 (v/v) solution of MeCN and water (0.14 M). To this solution was then carefully added ethyl bromoacetate (1 equiv, Sigma-Aldrich) dropwise over a period of 5 min and the resulting mixture was stirred at RT for 16 h. The reaction mixture was then diluted with water and extracted with EtOAc. The combined organic extracts were washed further with water and brine, dried over $MgSO_4$, filtered, and the filtrate concentrated in vacuo. Purification of the crude product thus obtained by way of column chromatography ($SiO_2$, gradient elution:Hex→EtOAc) afforded ethyl (1-(3,4-difluorophenyl)cyclopropyl)glycinate as a colorless oil (66% yield).

Step 2: In a round-bottom flask equipped with a magnetic stirrer was dissolved ethyl (1-(3,4-difluorophenyl)cyclopropyl)glycinate (1 equiv) from the previous step in a 1:1 (v/v) solution of THF and methanol (0.11 M). To this solution was then added sodium hydroxide (3 equiv, 1 M solution in water, Fisher Scientific) and the resulting mixture was stirred at RT for 18 h. The pH of the reaction mixture was then adjusted to ~3 with 1 M aq. HCl and the volatiles were removed in vacuo. The resulting residue was then partitioned between water and 2-methyltetrahydrofuran. The organic layer was separated, washed further with brine, dried over $Na_2SO_4$, and filtered. Concentration of the filtrate thus obtained in vacuo afforded (1-(3,4-difluorophenyl)cyclopropyl)glycine as a white solid (99% yield).

Step 3: In a dried round-bottom flask equipped with a magnetic stirrer was combined (1-(3,4-difluorophenyl)cyclopropyl)glycine (1 equiv) from the previous step, Intermediate amine 33 (1.1 equiv), and HATU (1.2 equiv, Combi-Blocks) in DMF (0.21 M). To the reaction mixture was then added DIEA (5 equiv, Sigma-Aldrich) and the resulting solution was allowed to stir at RT for 3 h. The reaction mixture was then diluted with EtOAc and washed further with water (3×). The organic layer was then concentrated in vacuo and the resulting residue was directly subjected to purification by way of column chromatography ($SiO_2$, gradient elution:Hex→EtOAc→10:1 (v/v) EtOAc: MeOH) to afford the title compound as an off-white solid (47% yield). LCMS: m/z=424.1 $[M+H]^+$; $^1H$ NMR (DMSO-$d_6$): δ=8.49 (d, J=2.0 Hz, 1H), 7.87 (dd, J=9.0, 2.0 Hz, 1H), 7.43~7.38 (m, 1H), 7.15~7.11 (m, 1H), 6.97~6.93 (m, 1H), 6.89 (d, J=9.0 Hz, 1H), 4.66 (br s, 2H), 3.93 (d, J=12.5 Hz, 1H), 3.53 (d, J=12.5 Hz, 1H), 3.42~3.38 (m, 1H), 3.14~3.09 (m, 2H), 2.65 (d, J=12.5 Hz, 1H), 1.90~1.85 (m, 3H), 1.75~1.72 (m, 1H), 1.48~1.45 (m, 1H), 0.92~0.90 (m, 2H), 0.77~0.75 (in, 2H).

The following examples were prepared in an analogous fashion to Example 59 but substituting 1-(2,4-difluorophenyl)cyclopropan-1-amine for the requisite amine in step 1:

| Example | Starting Amine | Structure | LCMS (m/z) |
|---|---|---|---|
| 60 | 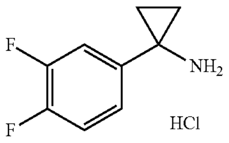 [SMILES: NC1(c2ccc(F)c(F)c2)CC1 ; Cl] HCl (Combi-Blocks) | 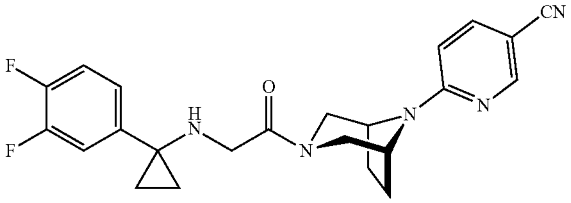 6-(3-((1-(3,4-difluorophenyl)cyclopropyl)glycyl)-3,8-diazabicyclo[3.2.1]octan-8-yl)nicotinonitrile | 424.1 $[M + H]^+$ |
| 61 | 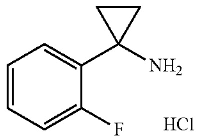 [SMILES: NC1(c2ccccc2F)CC1 ; Cl] HCl (Combi-Blocks) | 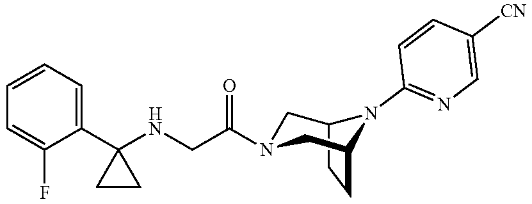 6-(3-((1-(2-fluorophenyl)cyclopropyl)glycyl)-3,8-diazabicyclo[3.2.1]octan-8-yl)nicotinonitrile | 406.2 $[M + H]^+$ |
| 62 | 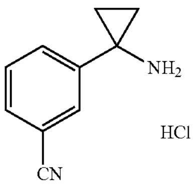 [SMILES: N#Cc1cccc(C2(N)CC2)c1 ; Cl] HCl (Enamine) | 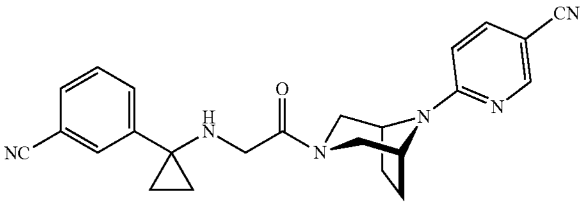 6-(3-((1-(3-cyanophenyl)cyclopropyl)glycyl)-3,8-diazabicyclo[3.2.1]octan-8-yl)nicotinonitrile | 413.1 $[M + H]^+$ |
| 63 | 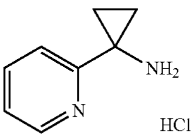 HCl (Enamine) | 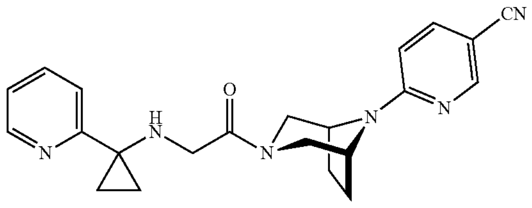 6-(3-((1-(pyridin-2-yl)cyclopropyl)glycyl)-3,8-diazabicyclo[3.2.1]octan-8-yl)nicotinonitrile | 489.1 $[M + H]^+$ |

-continued

| Example | Starting Amine | Structure | LCMS (m/z) |
| --- | --- | --- | --- |
| 64 | 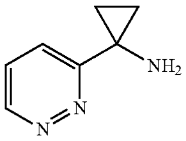<br>(AstaTech) | 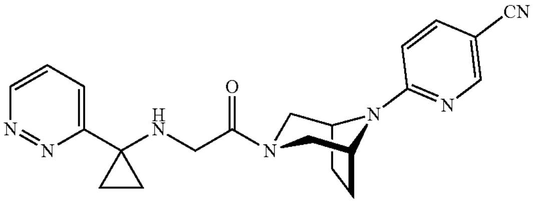<br>6-(3-((1-(pyridazin-3-yl)cyclopropyl)glycyl)-3,8-diazabicyclo[3.2.1]octan-8-yl)nicotinonitrile | 390.2 $[M + H]^+$ |
| 65 | 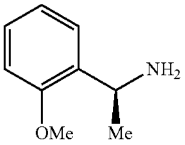 [SMILES: COc1ccccc1[C@H](C)N]<br>(Alfa Aesar) | 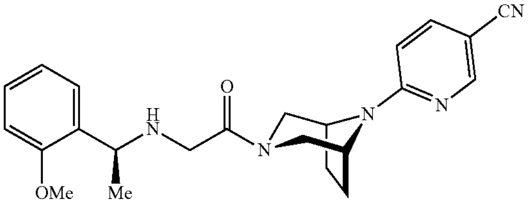<br>6-(3-(((S)-1-(2-methoxyphenyl)ethyl)glycyl)-3,8-diazabicyclo[3.2.1]octan-8-yl)nicotinonitrile | 406.2 $[M + H]^+$ |
| 66 | 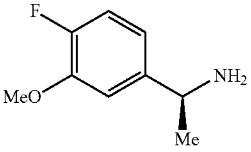 [SMILES: COc1cc([C@H](C)N)ccc1F]<br>(Combi-Blocks) | 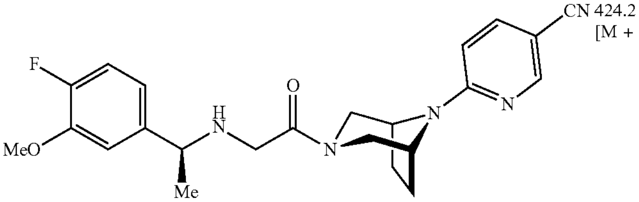<br>6-(3-(((S)-1-(4-fluoro-3-methoxyphenyl)ethyl)glycyl)-3,8-diazabicyclo[3.2.1]octan-8-yl)nicotinonitrile | 424.2 $[M + H]^+$ |
| 67 | 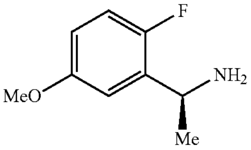 [SMILES: COc1ccc(F)c([C@H](C)N)c1]<br>(Combi-Blocks) | 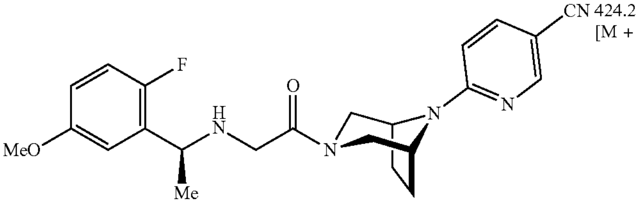<br>6-(3-(((S)-1-(2-fluoro-5-methoxyphenyl)ethyl)glycyl)-3,8-diazabicyclo[3.2.1]octan-8-yl)nicotinonitrile | 424.2 $[M + H]^+$ |
| 68 | 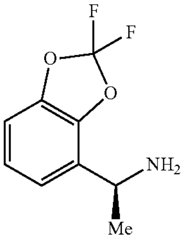 [SMILES: C[C@H](N)c1cccc2c1OC(F)(F)O2]<br>(AstaTech) | 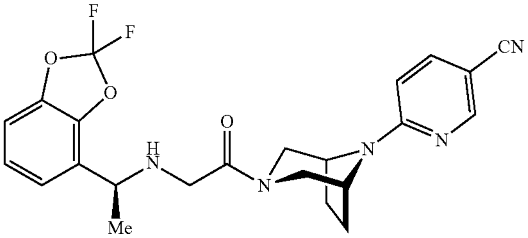<br>6-(3-(((S)-1-(2,2-difluorobenzo[d][1,3]dioxol-4-yl)ethyl)glycyl)-3,8-diazabicyclo[3.2.1]octan-8-yl)nicotinonitrile | 456.1 $[M + H]^+$ |

-continued

| Example | Starting Amine | Structure | LCMS (m/z) |
|---|---|---|---|
| 69 | 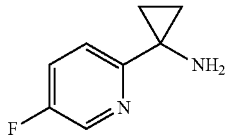 [SMILES: NC1(c2ccc(F)cn2)CC1]<br>Intermediate amine 3 | 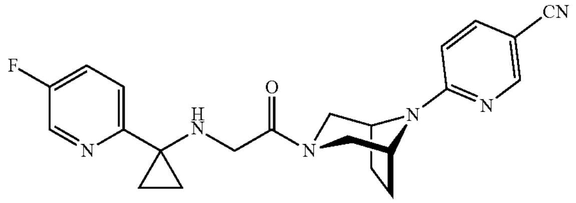<br>6-(3-((1-(5-fluoropyridin-2-yl)cyclopropyl)glycyl)-3,8-diazabicyclo[3.2.1]octan-8-yl)nicotinonitrile | 407.2 $[M + H]^+$ |
| 70 | 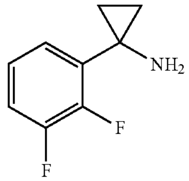 [SMILES: NC1(c2cccc(F)c2F)CC1]<br>Intermediate amine 6 | 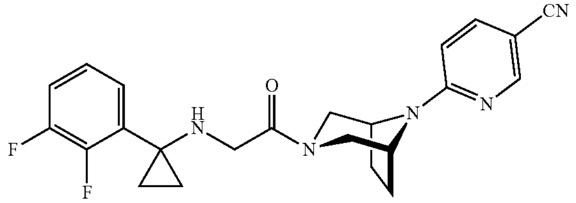<br>6-(3-((1-(2,3-difluorophenyl)cyclopropyl)glycyl)-3,8-diazabicyclo[3.2.1]octan-8-yl)nicotinonitrile | 424.1 $[M + H]^+$ |
| 71 | 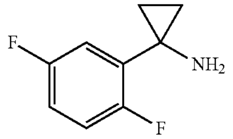 [SMILES: NC1(c2cc(F)ccc2F)CC1]<br>Intermediate amine 8 | 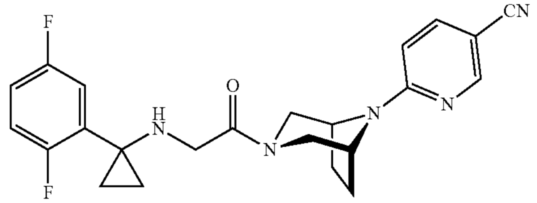<br>6-(3-((1-(2,5-difluorophenyl)cyclopropyl)glycyl)-3,8-diazabicyclo[3.2.1]octan-8-yl)nicotinonitrile | 424.1 $[M + H]^+$ |
| 72 | 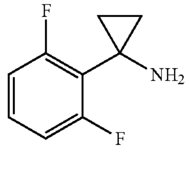 [SMILES: NC1(c2c(F)cccc2F)CC1]<br>Intermediate amine 9 | 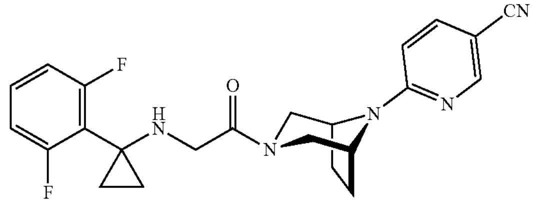<br>6-(3-((1-(2,6-difluorophenyl)cyclopropyl)glycyl)-3,8-diazabicyclo[3.2.1]octan-8-yl)nicotinonitrile | 424.1 $[M + H]^+$ |
| 73 | 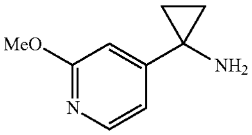 [SMILES: COc1cc(C2(N)CC2)ccn1]<br>Intermediate amine 17 | 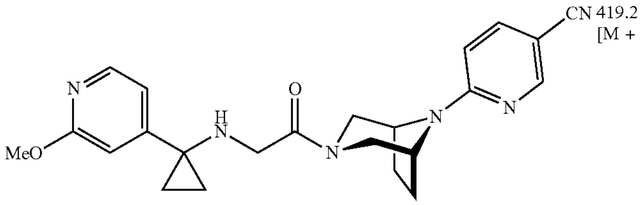<br>6-(3-((1-(2-methoxypyridin-4-yl)cyclopropyl)glycyl)-3,8-diazabicyclo[3.2.1]octan-8-yl)nicotinonitrile | 419.2 $[M + H]^+$ |

-continued

| Example | Starting Amine | Structure | LCMS (m/z) |
|---|---|---|---|
| 74 | 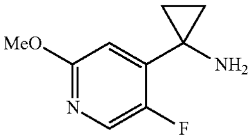 [SMILES: COc1cc(C2(N)CC2)c(F)cn1] Intermediate amine 18 | 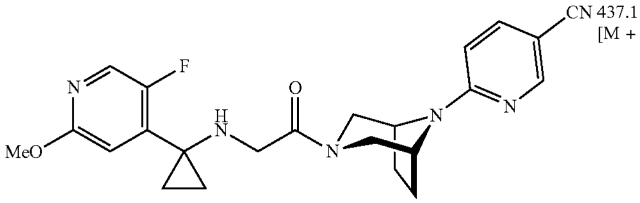 6-(3-((1-(5-fluoro-2-methoxypyridin-4-yl)cyclopropyl)glycyl)-3,8-diazabicyclo[3.2.1]octan-8-yl)nicotinonitrile | 437.1 $[M + H]^+$ |
| 75 | 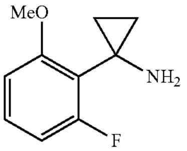 [SMILES: COc1cccc(F)c1C1(N)CC1] Intermediate amine 19 | 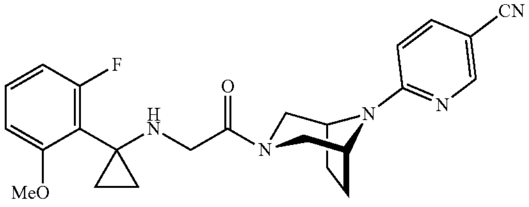 6-(3-((1-(2-fluoro-6-methoxyphenyl)cyclopropyl)glycyl)-3,8-diazabicyclo[3.2.1]octan-8-yl)nicotinonitrile | 436.1 $[M + H]^+$ |
| 76 | 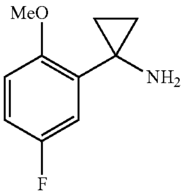 [SMILES: COc1ccc(F)cc1C1(N)CC1] Intermediate amine 20 | 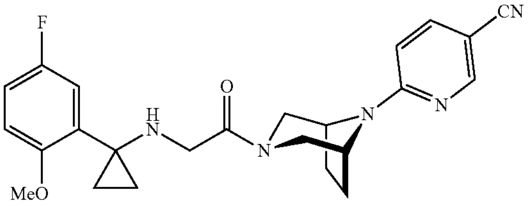 6-(3-((1-(5-fluoro-2-methoxyphenyl)cyclopropyl)glycyl)-3,8-diazabicyclo[3.2.1]octan-8-yl)nicotinonitrile | 436.1 $[M + H]^+$ |
| 77 | 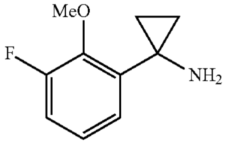 [SMILES: COc1c(F)cccc1C1(N)CC1] Intermediate amine 21 | 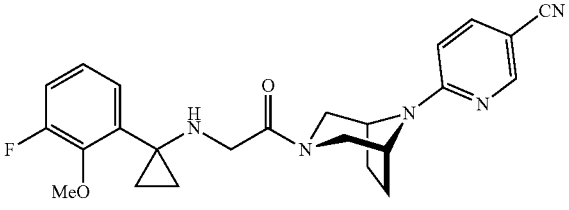 6-(3-((1-(3-fluoro-2-methoxyphenyl)cyclopropyl)glycyl)-3,8-diazabicyclo[3.2.1]octan-8-yl)nicotinonitrile | 436.1 $[M + H]^+$ |

The following examples were prepared in an analogous fashion to Example 59 but substituting Intermediate amine 33 for the requisite amine in step 3:

| Example | Starting Amine | Structure | LCMS (m/z) |
| --- | --- | --- | --- |
| 78 | 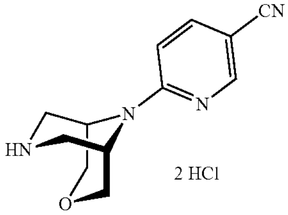 2 HCl Intermediate amine 34 | 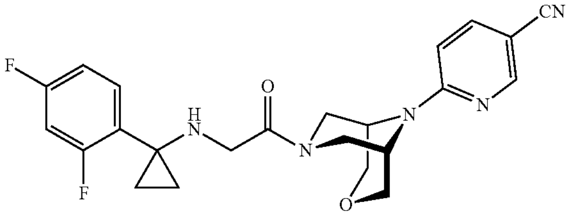 6-(7-((1-(2,4-difluorophenyl)cyclopropyl)glycyl)-3-oxa-7,9-diazabicyclo[3.3.1]nonan-9-yl)nicotinonitrile | 440.0 $[M + H]^+$ |
| 79 | 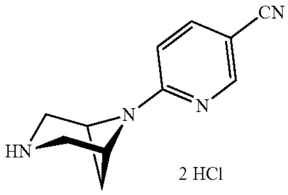 2 HCl Intermediate amine 35 | 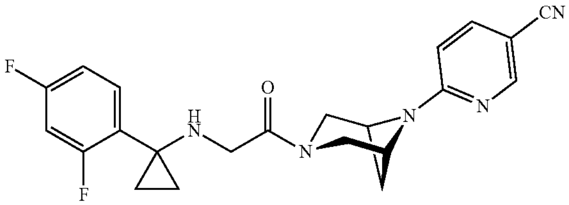 6-(3-((1-(2,4-difluorophenyl)cyclopropyl)glycyl)-3,6-diazabicyclo[3.1.1]heptan-6-yl)nicotinonitrile | 410.1 $[M + H]^+$ |
| 80 | 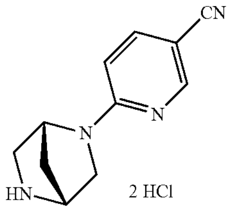 [SMILES: N#Cc1ccc(N2C[C@H]3C[C@@H]2CN3)nc1] 2 HCl Intermediate amine 36 | 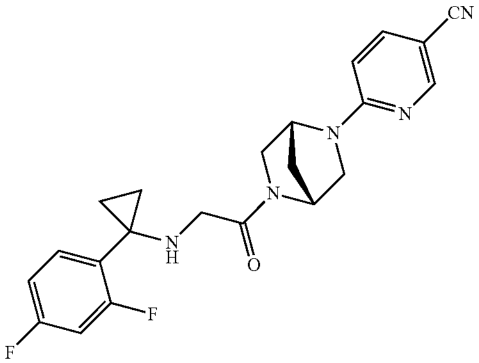 [SMILES: N#Cc1ccc(N2C[C@H]3C[C@@H]2CN3C(=O)CNC2(c3ccc(F)cc3F)CC2)nc1] 6-((1R,4R)-5-((1-(2,4-difluorophenyl)cyclopropyl)glycyl)-2,5-diazabicyclo[2.2.1]heptan-2-yl)nicotinonitrile | 410.2 $[M + H]^+$ |
| 81 | 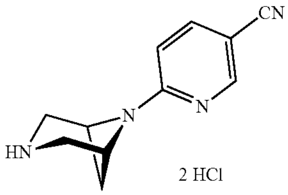 2 HCl Intermediate amine 37 | 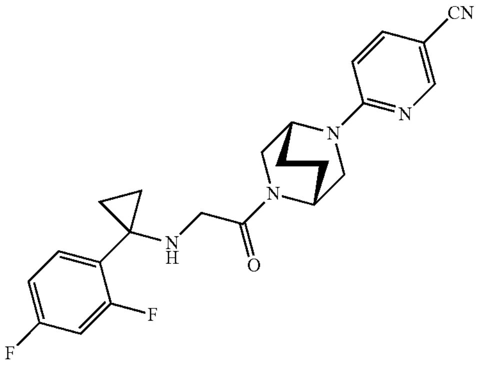 6-((1R,4R)-5-((1-(2,4-difluorophenyl)cyclopropyl)glycyl)-2,5-diazabicyclo[2.2.2]octan-2-yl)nicotinonitrile | 424.1 $[M + H]^+$ |

-continued

| Example | Starting Amine | Structure | LCMS (m/z) |
| --- | --- | --- | --- |
| 82 | 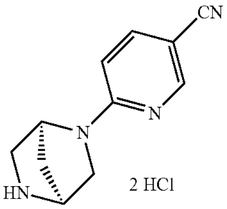 [SMILES: N#Cc1ccc(N2C[C@@H]3C[C@H]2CN3)nc1] 2 HCl Intermediate amine 38 | 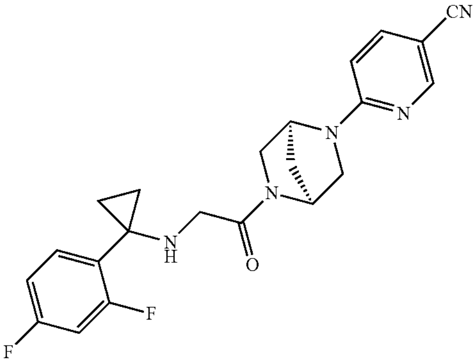 [SMILES: N#Cc1ccc(N2C[C@@H]3C[C@H]2CN3C(=O)CNC2(c3ccc(F)cc3F)CC2)nc1] 6-((1S,4S)-5-((1-(2,4-difluorophenyl)cyclopropyl)glycyl)-2,5-diazabicyclo[2.2.1]heptan-2-yl)nicotinonitrile | 410.2 $[M + H]^+$ |
| 83 | 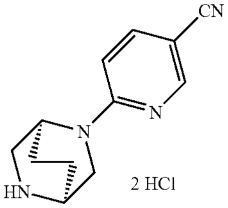 [SMILES: N#Cc1ccc(N2C[C@@H]3CC[C@H]2CN3)nc1] 2 HCl Intermediate amine 39 | 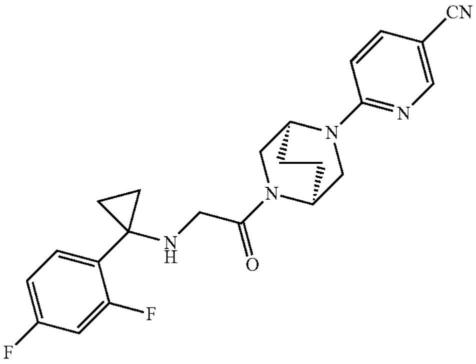 [SMILES: N#Cc1ccc(N2C[C@@H]3CC[C@H]2CN3C(=O)CNC2(c3ccc(F)cc3F)CC2)nc1] 6-((1S,4S)-5-((1-(2,4-difluorophenyl)cyclopropyl)glycyl)-2,5-diazabicyclo[2.2.2]octan-2-yl)nicotinonitrile | 424.1 $[M + H]^+$ |
| 84 | 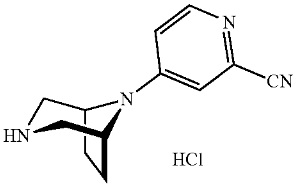 HCl Intermediate amine 41 | 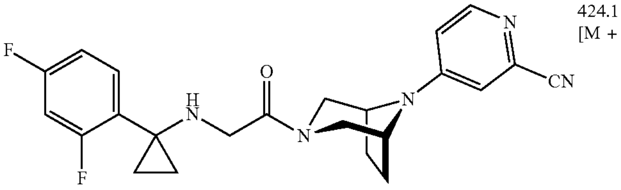 4-(3-((1-(2,4-difluorophenyl)cyclopropyl)glycyl)-3,8-diazabicyclo[3.2.1]octan-8-yl)picolinonitrile | 424.1 $[M + H]^+$ |
| 85 | 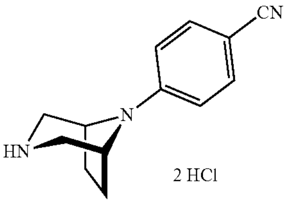 2 HCl Intermediate amine 45 | 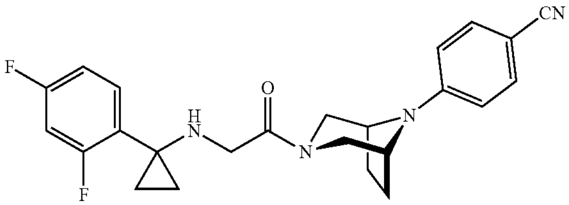 4-(3-((1-(2,4-difluorophenyl)cyclopropyl)glycyl)-3,8-diazabicyclo[3.2.1]octan-8-yl)benzonitrile | 423.1 $[M + H]^+$ |

-continued

| Example | Starting Amine | Structure | LCMS (m/z) |
|---|---|---|---|
| 86 | 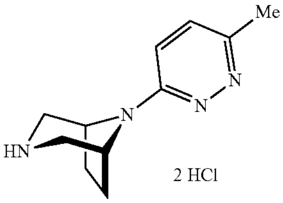 2 HCl<br>Intermediate amine 46 | 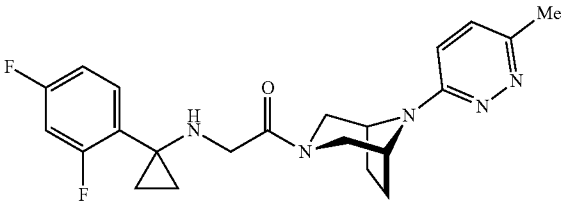<br>2-((1-(2,4-difluorophenyl)cyclopropyl)amino)-1-(8-(6-methylpyridazin-3-yl)-3,8-diazabicyclo[3.2.1]octan-3-yl)ethan-1-one | 414.2 [M + H]+ |

Example 87: Preparation of 6-(3-(((S)-1-(2,4-difluorophenyl)ethyl)glycyl)-3,8-diazabicyclo[3.2.1]octan-8-yl)nicotinonitrile

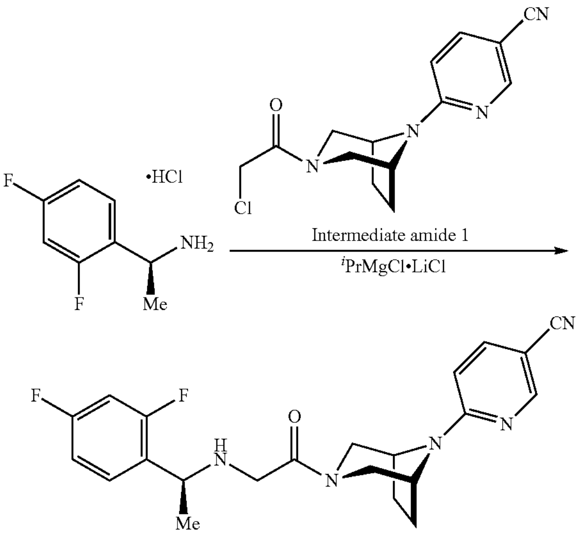

Example 87

In a round-bottom flask equipped with a magnetic stirrer was dissolved freshly freebased (S)-1-(2,4-difluorophenyl) ethan-1-amine hydrochloride (1 equiv, AstaTech) in THF (0.36 M). To this was then added Turbo Grignard (1.3 equiv, 1.3 M solution in THF, Sigma-Aldrich) dropwise over 15 min and the resulting mixture was allowed to stir at RT for another 3 h. Finally, Intermediate amide 1 was added (1 equiv) in one rapid portion and the reaction solution was heated at 80° C. for 16 h. After cooling to RT, the reaction was quenched with the addition of saturated aq. $NH_4Cl$ and extracted with EtOAc. The combined organic extracts were washed further with water and brine, dried over $MgSO_4$, filtered and the filtrate concentrated in vacuo. Purification of the crude product thus obtained by way of column chromatography ($SiO_2$, gradient elution:Hex→EtOAc→10:1 (v/v) EtOAc: MeOH) to afford the title compound as an off-white solid (11% yield). LCMS: m/z=412.1 $[M+H]^+$; $^1H$ NMR (DMSO-$d_6$): δ=8.49 (t, J=2.5 Hz, 1H), 7.87 (dt, J=9.0, 2.5 Hz, 1H), 7.54~7.48 (m, 1H), 7.16~7.10 (m, 1H), 7.08~7.02 (m, 1H), 6.90 (dd, J=9.0, 4.5 Hz, 1H), 4.70 (br s, 1H), 4.64 (br s, 1H), 4.11~4.06 (m, 1H), 4.10~3.94 (m, 1H), 3.50 (t, J=13.0 Hz, 1H), 3.36~3.31 (m, 1H), 3.16~3.11 (m, 1H), 3.09~3.03 (m, 1H), 2.77 (d, J=13.0 Hz, 1H), 1.94~1.83 (m, 2H), 1.77~1.69 (m, 1H), 1.64~1.55 (m, 1H), 1.26 (dd, J=6.5, 2.5 Hz, 3H).

The following examples were prepared in an analogous fashion to Example 87 but substituting (S)-1-(2,4-difluorophenyl)ethan-1-amine hydrochloride for the requisite amine:

| Example | Starting Amine | Structure | LCMS (m/z) |
|---|---|---|---|
| 88 | 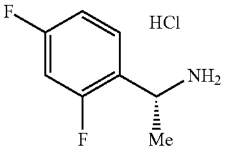 [SMILES: C[C@@H](N)c1ccc(F)cc1F ; Cl] HCl<br>(AstaTech) | 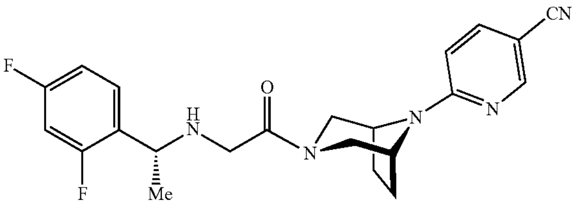<br>6-(3-(((S)-1-(2,4-difluorophenyl)ethyl)glycyl)-3,8-diazabicyclo[3.2.1]octan-8-yl)nicotinonitrile | 412.1 [M + H]+ |

-continued

| Example | Starting Amine | Structure | LCMS (m/z) |
| --- | --- | --- | --- |
| 89 | 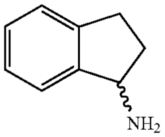<br>(Combi-Blocks) | 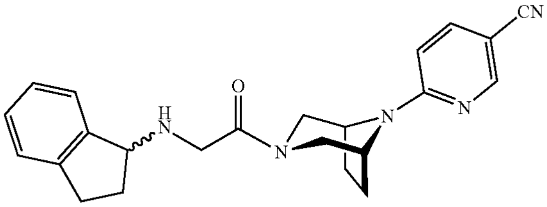<br>Racemic 6-(3-((2,3-dihydro-1H-inden-1-yl)glycyl)-3,8-diazabicyclo[3.2.1]octan-8-yl)nicotinonitrile | 388.2 $[M + H]^+$ |
| 90 | 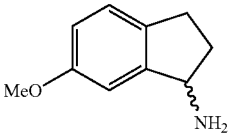 [SMILES: COc1ccc2c(c1)C(N)CC2]<br>(Combi-Blocks) | 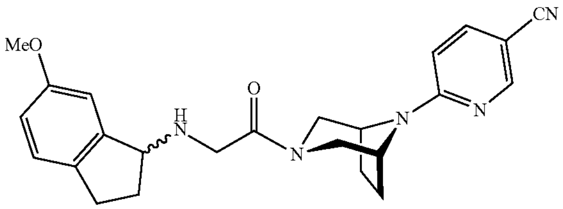<br>Racemic 6-(3-((6-methoxy-2,3-dihydro-1H-inden-1-yl)glycyl)-3,8-diazabicyclo[3.2.1]octan-8-yl)nicotinonitrile | 418.2 $[M + H]^+$ |
| 91 | 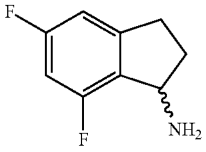 [SMILES: NC1CCc2cc(F)cc(F)c21]<br>(AstaTech) | 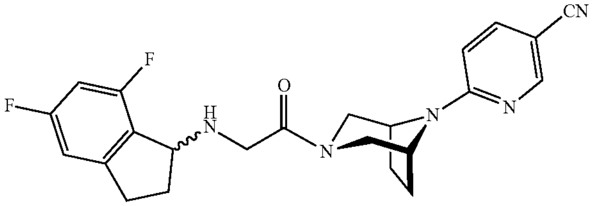<br>Racemic 6-(3-((5,7-difluoro-2,3-dihydro-1H-inden-1 yl)glycyl)-3,8-diazabicyclo[3.2.1]octan-8-yl)nicotinonitrile | 424.1 $[M + H]^+$ |
| 92 | 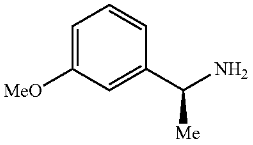 [SMILES: COc1cccc([C@H](C)N)c1]<br>(AstaTech) | 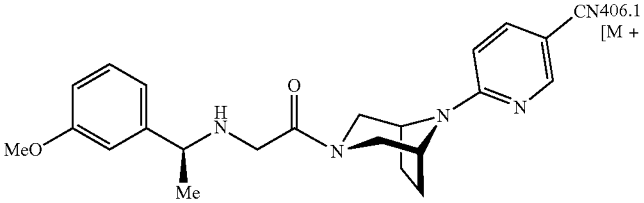<br>6-(3-(((S)-1-(3-methoxyphenyl)ethyl)glycyl)-3,8-diazabicyclo[3.2.1]octan-8-yl)nicotinonitrile | 406.1 $[M + H]^+$ |
| 93 | 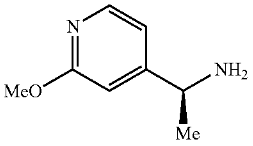 [SMILES: COc1cc([C@H](C)N)ccn1]<br>(AstaTech) | 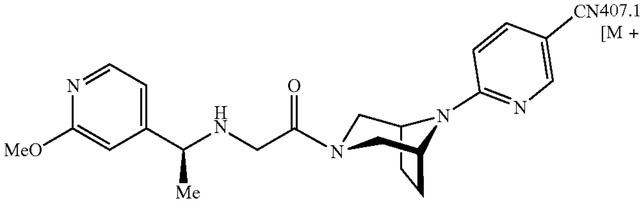<br>6-(3-(((S)-1-(2-methoxypyridin-4-yl)ethyl)glycyl)-3,8-diazabicyclo[3.2.1]octan-8-yl)nicotinonitrile | 407.1 $[M + H]^+$ |

-continued

| Example | Starting Amine | Structure | LCMS (m/z) |
|---|---|---|---|
| 94 | 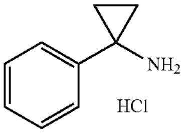 (Combi-Blocks) | 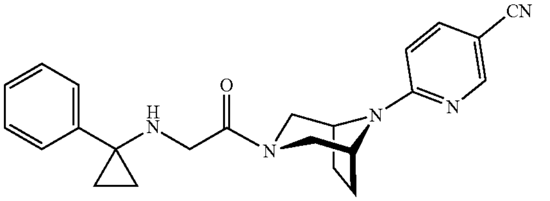 6-(3-((1-phenylcyclopropyl)glycyl)-3,8-diazabicyclo[3.2.1]octan-8-yl)nicotinonitrile | 388.2 $[M + H]^+$ |
| 95 | 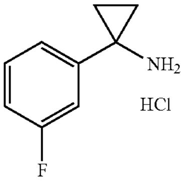 [SMILES: NC1(c2cccc(F)c2)CC1 ; Cl] (Combi-Blocks) | 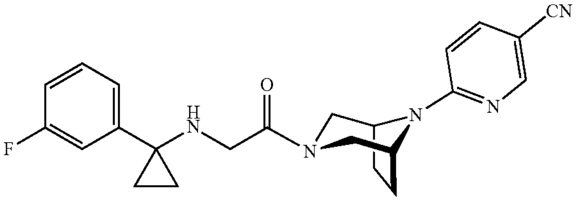 6-(3-((1-(3-fluorophenyl)cyclopropyl)glycyl)-3,8-diazabicyclo[3.2.1]octan-8-yl)nicotinonitrile | 406.1 $[M + H]^+$ |
| 96 | 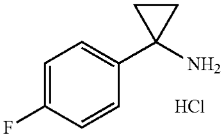 [SMILES: NC1(c2ccc(F)cc2)CC1 ; Cl] (Combi-Blocks) | 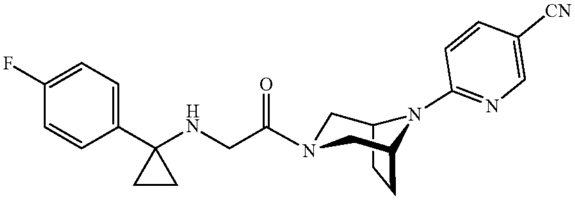 6-(3-((1-(4-fluorophenyl)cyclopropyl)glycyl)-3,8-diaabicyclo[3.2.1]octan-8-yl)nicotinonitrile | 406.1 $[M + H]^+$ |
| 97 | 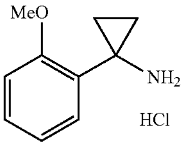 [SMILES: COc1ccccc1C1(N)CC1 ; Cl] (Combi-Blocks) | 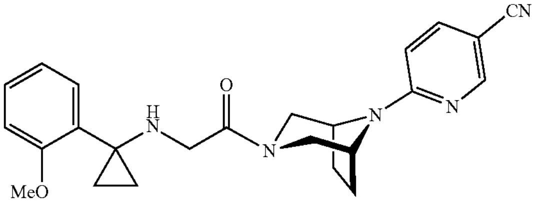 6-(3-((1-(2-methoxyphenyl)cyclopropyl)glycyl)-3,8-diazabicyclo[3.2.1]octan-8-yl)nicotinonitrile | 418.2 $[M + H]^+$ |
| 98 | 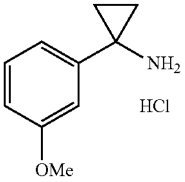 [SMILES: COc1cccc(C2(N)CC2)c1 ; Cl] (Combi-Blocks) | 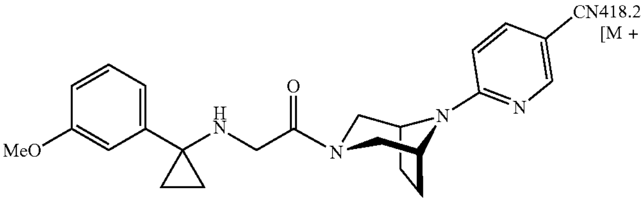 6-(3-((1-<3-methoxypheiiyl)cyclopropyl)glycyl)-3,8-diazabicyclo[3.2.1]octan-8-yl)nicotinonitrile | 418.2 $[M + H]^+$ |

-continued

| Example | Starting Amine | Structure | LCMS (m/z) |
|---|---|---|---|
| 99 | 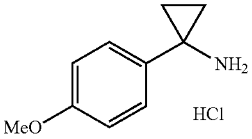 [SMILES: COc1ccc(C2(N)CC2)cc1 ; Cl]<br>HCl<br>(Combi-Blocks) | 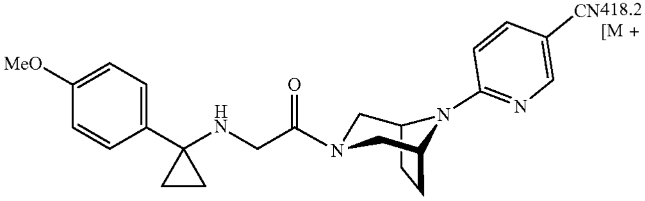<br>6-(3-((1-(3-methoxyphenyl)cyclopropYl)glycyl)-3,8-diazabicyclo[3.2.1]octan-8*yl)nicotinonitrile | 418.2 $[M + H]^+$ |
| 100 | 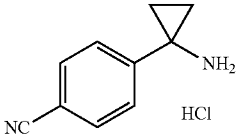 [SMILES: N#Cc1ccc(C2(N)CC2)cc1 ; Cl]<br>HCl<br>(Combi-Blocks) | 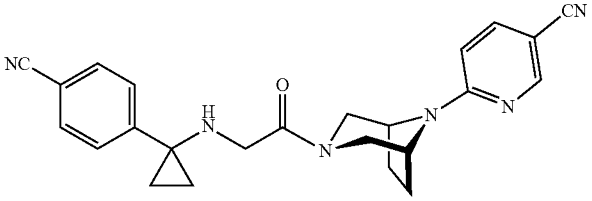<br>6-(3-((1-(4-cyanoplKml)cyclopropyl)glycyl)-3,8-diazabicyclo[3.2.1]oclaii-8-yl)mcotiiiomtrile | 413.1 $[M + H]^+$ |
| 101 | 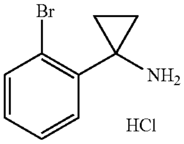 [SMILES: NC1(c2ccccc2Br)CC1 ; Cl]<br>HCl<br>(Enamine) | 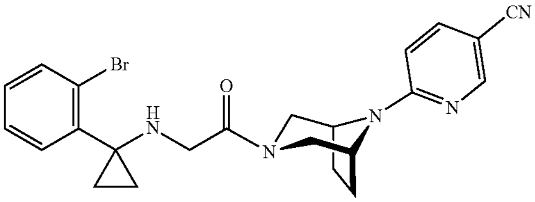<br>6-(3-((1-(2-bromophenyl)cyclopropyl)glycyl)-3,8-diazabicyclo[3.2.1]octan-8-yl)nicotinonitrile | 466.0, 468.0 $[M + H]^+$ |
| 102 | 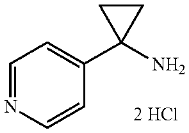<br>2 HCl<br>(Combi-Blocks) | 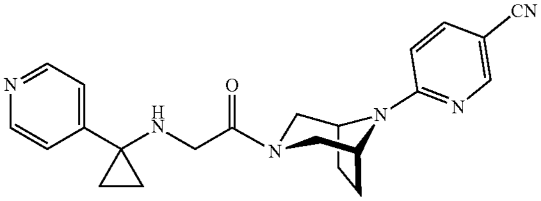<br>6-(3-((1-(pyridin-4-yl)cyclopropyl)glycyl)-3,8-diazabicyclo[3.2.1]octan-8-yl)nicotinonitrile | 389.1 $[M + H]^+$ |
| 103 | 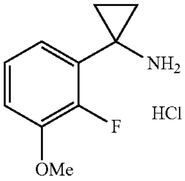 [SMILES: COc1cccc(C2(N)CC2)c1F ; Cl]<br>HCl<br>(Enamine) | 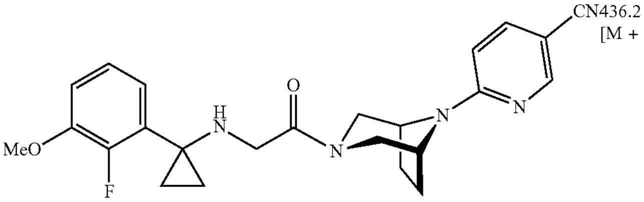<br>6-(3-((1-(2-fluoro-3-methoxyphenyl)cyclopropyl)glycyl)-3,8-diazabicyclo[3.2.1]octan-8-yl)nicotinonitrile | 436.2 $[M + H]^+$ |

-continued

| Example | Starting Amine | Structure | LCMS (m/z) |
|---|---|---|---|
| 104 | 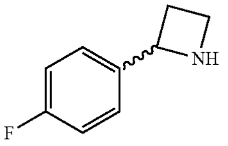 [SMILES: Fc1ccc(C2CCN2)cc1]<br>(Enamine) | 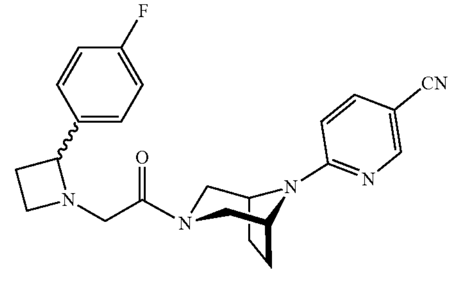<br>Racemic 6-(3-(2-(2-(4-fluorophenyl)azetidin-1-yl)acetyl>3,8-diazabicyclo[3.2.1]octan-8-yl)nicotinonitrile | 406.2 $[M + H]^+$ |
| 105 | 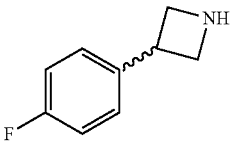<br>(AstaTech) | 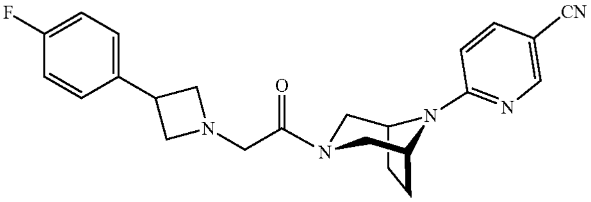<br>6-(3-(2-(3-(4-fluorophenyl)azetidin-1-yl)acetyl)-3,8-diazabicyclo[3.2.1]octan-8-yl)nicotinonitrile | 406.2 $[M + H]^+$ |
| 106 | 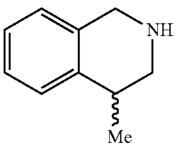 [SMILES: CC1CNCc2ccccc21]<br>(AstaTech) | 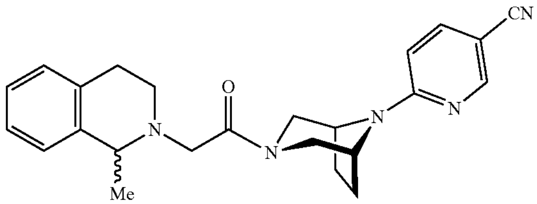<br>Racemic 6-(3-(2-(1-methyl-3,4-dihydroisoquinolin-2(1H)-yl)acetyl)-3,8-diazabicyclo[3.2.1]octan-8-yl)nicotinonitrile | 402.2 $[M + H]^+$ |
| 107 | 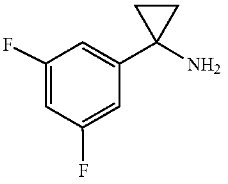 [SMILES: NC1(c2cc(F)cc(F)c2)CC1]<br>Intermediate amine 7 | 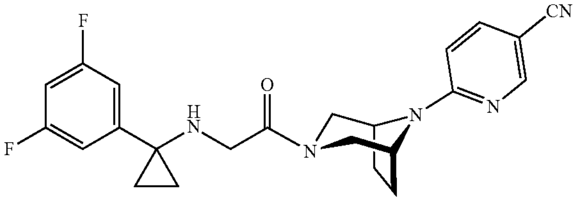<br>6-(3-((1-(3,5-difluorophenyl)cyclopropyl)glycyl)-3,8-diazabicyclo[3.2.1]octan-8-yl)nicotinonitrile | 421.1 $[M + H]^+$ |
| 108 | 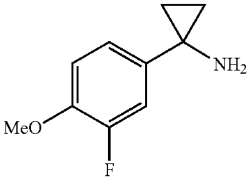 [SMILES: COc1ccc(C2(N)CC2)cc1F]<br>Intermediate amine 13 | 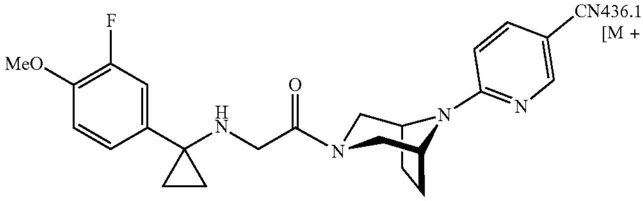<br>6-(3-((1-(3-fluoro-4-methoxyphenyl)cyclopropyl)glycyl>3,8-diazabicyclo[3.2.1]octan-8-yl)nicotinonitrile | 436.1 $[M + H]^+$ |

-continued

| Example | Starting Amine | Structure | LCMS (m/z) |
| --- | --- | --- | --- |
| 109 | 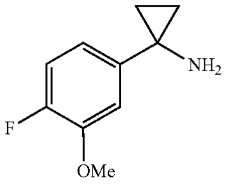 [SMILES: COc1cc(C2(N)CC2)ccc1F]<br>Intermediate amine 14 | 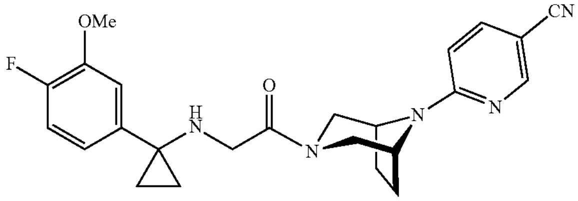<br>6-(3-((1-(4-fluoro-3-methoxyphenyl)cyclopropyl)glycyl)-3,8-diazabicyclo[3.2.1]octan-8-yl)nicotinonitrile | 436.1 $[M + H]^+$ |
| 110 | 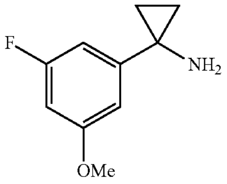 [SMILES: COc1cc(F)cc(C2(N)CC2)c1]<br>Intermediate amine 15 | 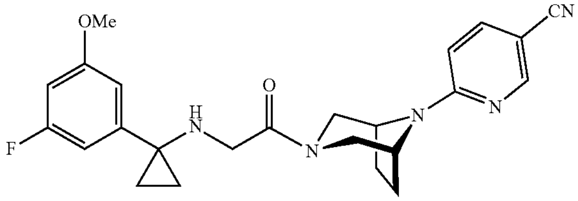<br>6-(3-((1-(3-fluoro-5-methoxyphenyl)cyclopropyl)glycyl)-3,8-diazabicyclo[3.2.1]octan-8-yl)nicotinonitrile | 436.1 $[M + H]^+$ |
| 111 | 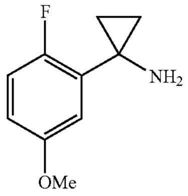 [SMILES: COc1ccc(F)c(C2(N)CC2)c1]<br>Intermediate amine 16 | 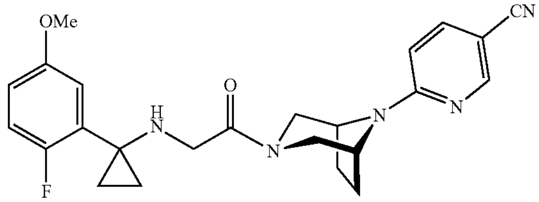<br>6-(3-((1-(2-fluoro-5-methoxyphenyl)cyclopropyl)glycyl)-3,8-diazabicyclo[3.2.1]octan-8-yl)nicotinonitrile | 436.1 $[M + H]^+$ |
| 112 | 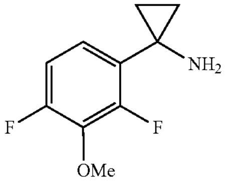 [SMILES: COc1c(F)ccc(C2(N)CC2)c1F]<br>Intermediate amine 22 | 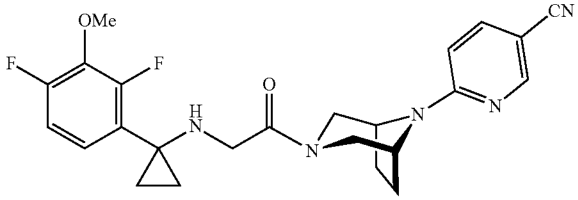<br>6-(3-((1-(2,4-difluoro-3-methoxyphenyl)cyclopropyl)glycyl)-3,8-diazabicyclo[3.2.1]octan-8-yl)nicotinonitrile | 454.1 $[M + H]^+$ |
| 113 | 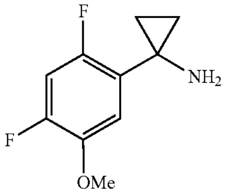 [SMILES: COc1cc(C2(N)CC2)c(F)cc1F]<br>Intermediate amine 23 | 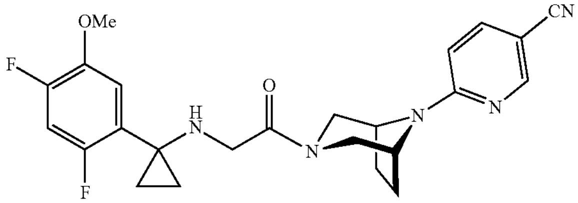<br>6-(3-((1-(2,4-difluoro-5-methoxyphenyl)cyclopropyl)glycyl)-3,8-diazabicyclo[3.2.1]octan-8-yl)nicotinonitrile | 454.1 $[M + H]^+$ |

-continued

| Example | Starting Amine | Structure | LCMS (m/z) |
| --- | --- | --- | --- |
| 114 | 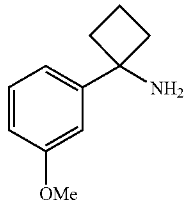 [SMILES: COc1cccc(C2(N)CCC2)c1] Intermediate amine 24 | 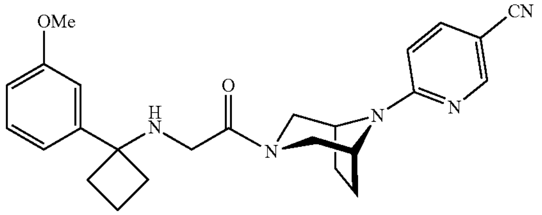 6-(3-((1-(3-methoxyphenyl)cyclobutyl)glycyl)-3,8-diazabicyclo[3.2.1]octan-8-yl)nicotinonitrile | 432.1 $[M+H]^+$ |
| 115 | 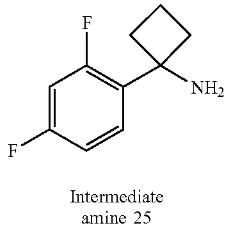 Intermediate amine 25 | 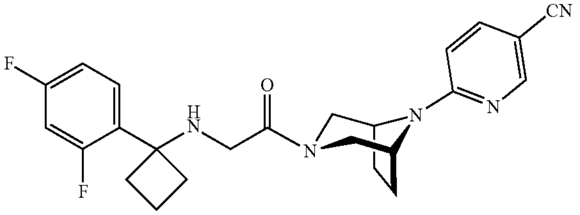 6-(3-((1-(2,4-difluorophenyl)cyclobutyl)glycyl)-3,8-diazabicyclo[3.2.1]octan-8-yl)nicotinonitrile | 438.1 $[M+H]^+$ |
| 116 | 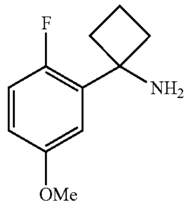 [SMILES: COc1ccc(F)c(C2(N)CCC2)c1] Intermediate amine 27 | 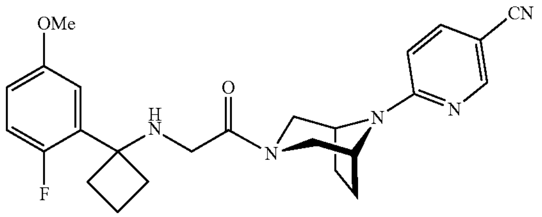 6-(3-((1-(2-fluoro-5-methoxyphenyl)cyclobutyl)glycyl)-3,8-diazabicyclo[3.2.1]octan-8-yl)nicotinonitrile | 450.1 $[M+H]^+$ |
| 117 | 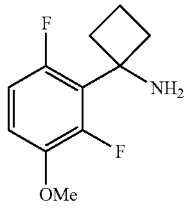 [SMILES: COc1ccc(F)c(C2(N)CCC2)c1F] Intermediate amine 28 | 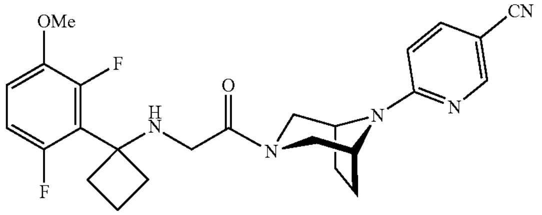 6-(3-((1-(2,6-difluoro-3-methoxyphenyl)cyclobutyl)glycyl)-3,8-diazabicyclo[3.2.1]octan-8-yl)nicotinonitrile | 468.1 $[M+H]^+$ |
| 118 | 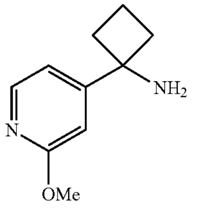 [SMILES: COc1cc(C2(N)CCC2)ccn1] Intermediate amine 29 | 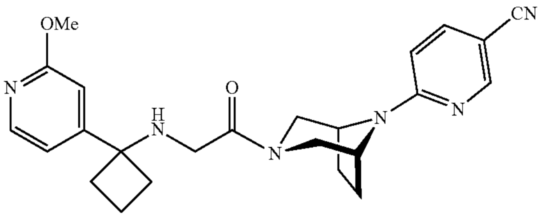 6-(3-((1-(2-methoxypyridin-4-yl)cyclobutyl)glycyl)-3,8-diazabicyclo[3.2.1]octan-8-yl)nicotinonitrile | 433.1 $[M+H]^+$ |

-continued

| Example | Starting Amine | Structure | LCMS (m/z) |
|---|---|---|---|
| 119 | 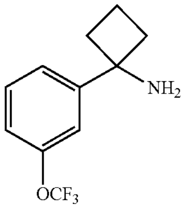<br>Intermediate amine 30 | 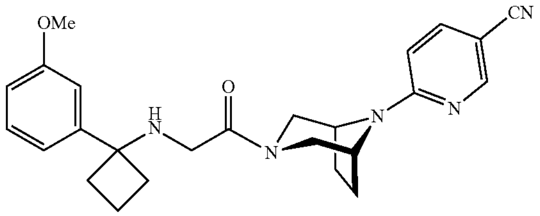<br>6-(3-((1-(3-(trifluoromethoxy)phenyl)cyclobutyl)glycyl)-3,8-diazabicyclo[3.2.1]octan-8-yl)nicotinonitrile | 486.1 $[M + H]^+$ |
| 120 | 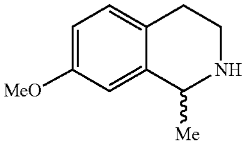<br>Intermediate amine 31 | 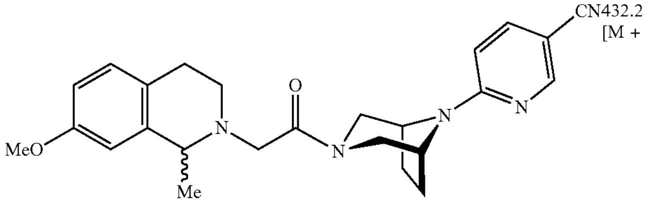<br>Racemic 6-(3-(2-(7-methoxy-1-methyl-3,4-dihydroisoquinolin-2(1H)-yl)acetyl)-3,8-diazabicyclo[3.2.1]octan-8-yl)nicotinonitrile | 432.2 $[M + H]^+$ |
| 121 | 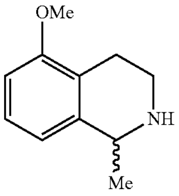 [SMILES: COc1cccc2c1CCNC2C]<br>Intermediate amine 32 | 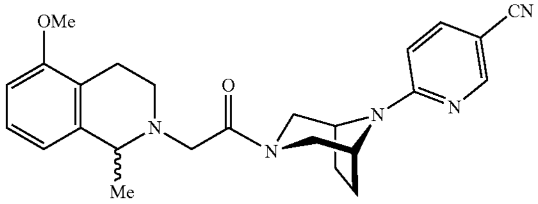<br>Racemic 6-(3-(2-(5-methoxy-1-methyl-3,4-dihydroisoquinolin-2(1H)-yl)acetyl)-3,8-diazabicyclo[3.2.1]octan-8-yl)nicotinonitrile | 432.2 $[M + H]^+$ |

Example 122: Preparation of 6-(3-(4,4-difluoro-4-(quinolin-5-yl) butanoyl)-3,8-diazabicyclo[3.2.1] octan-8-yl)nicotinonitrile

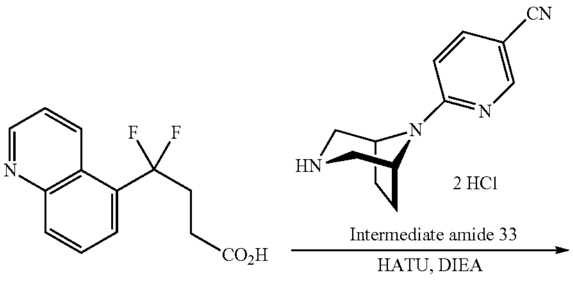

Intermediate acid 1

-continued

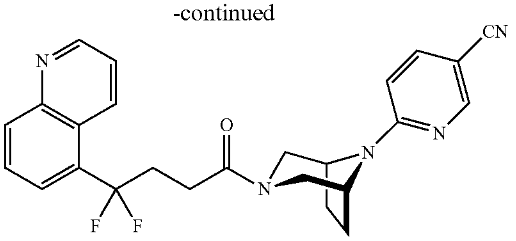

Example 122

In a dried round-bottom flask equipped with a magnetic stirrer was combined Intermediate acid 1 (1 equiv), Intermediate amine 33 (1.1 equiv), and HATU (1.2 equiv, Combi-Blocks) in DMF (0.08 M). To the reaction mixture was then added DIEA (5 equiv, Sigma-Aldrich) and the resulting yellow solution was allowed to stir at RT for 16 h. The reaction mixture was then diluted with EtOAc and washed sequentially with water, 1 M aq. NaOH, water and brine. The organic layer was then dried over $MgSO_4$, filtered and the filtrate concentrated in vacuo. Further purification by way of column chromatography ($SiO_2$, gradient elution:Hex→EtOAc→10:1 (v/v) EtOAc: MeOH) afforded the title compound as a white solid (90% yield). LCMS: m/z=448.1 $[M+H]^+$; $^1H$ NMR (DMSO-$d_6$): δ=8.98 (dd, J=4.0, 1.5 Hz, 1H), 8.64 (d, J=9.0 Hz, 1H), 8.51 (d, J=2.5 Hz, 1H), 8.17~8.15 (m, 1H), 7.88 (dd, J=9.0, 2.5 Hz, 1H), 7.83~ 7.81 (m, 2H), 7.64 (dd, J=9.0, 4.0 Hz, 1H), 6.91 (d, J=9.0 Hz, 1H), 4.70 (br s, 2H), 4.06 (d, J=8.5 Hz, 1H), 3.66 (d, J=12.5 Hz, 1H), 3.23 (d, J=12.5 Hz, 1H), 2.75~2.66 (m, 4H), 2.50~2.44 (m, 1H), 1.92~1.88 (m, 2H), 1.83~1.79 (m, 1H), 1.59~1.56 (m, 1H).

The following examples were prepared in an analogous fashion to Example 122 but substituting Intermediate acid 1 for the requisite acid:

| Example | Starting Acid | Structure | LCMS (m/z) |
|---|---|---|---|
| 123 | 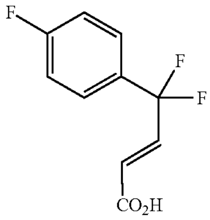 [SMILES: O=C(O)/C=C/C(F)(F)c1ccc(F)cc1] Intermediate acid 2 | 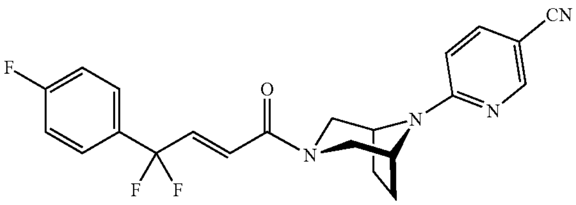 6-(3-((E)-4,4-difluoro-4-(4-fluorophenyl)but-2-enoyl)-3,8-diazabicyclo[3.2.1]octan-8-yl)nicotinonitrile | 413.1 [M + H]+ |
| 124 | 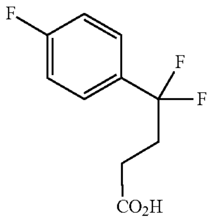 [SMILES: O=C(O)CCC(F)(F)c1ccc(F)cc1] Intermediate acid 3 | 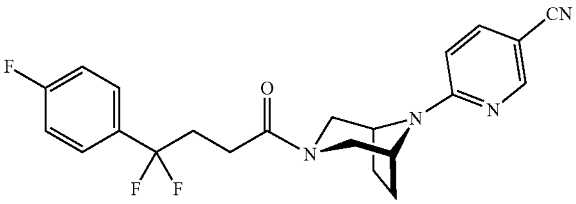 6-(3-(4,4-difluoro-4-(4-fluorophenyl)butanoyl)-3,8-diazabicyclo[3.2.1]octan-8-yl)nicotinonitrile | 415.2 [M + H]+ |
| 125 | 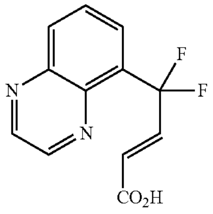 [SMILES: O=C(O)/C=C/C(F)(F)c1cccc2nccnc12] Intermediate acid 15 | 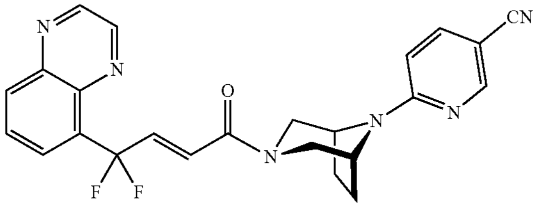 6-(3-((E)-4,4-difluoro-4-(quinoxalin-5-yl)but-2-enoyl)-3,8-diazabicyclo[3.2.1]octan-8-yl)nicotinonitrile | 447.0 [M + H]+ |
| 126 | 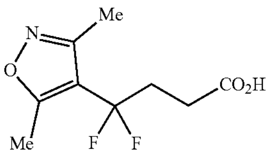 [SMILES: Cc1noc(C)c1C(F)(F)CCC(=O)O] Intermediate acid 16 | 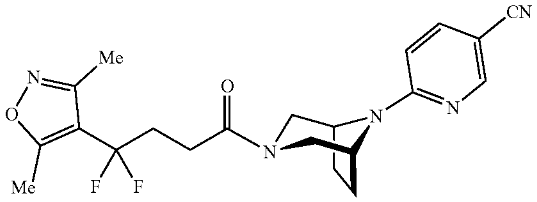 6-(3-(4-(3,5-dimethylisoxazol-4-yl)-4,4-difluorobutanoyl)-3,8-diazabicyclo[3.2.1]octan-8-yl)nicotinonitrile | 416.1 [M + H]+ |

-continued

| Example | Starting Acid | Structure | LCMS (m/z) |
|---|---|---|---|
| 127 | 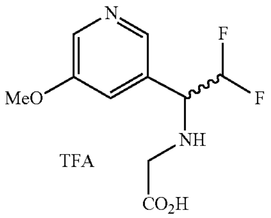 [SMILES: COc1cncc(C(NCC(=O)O)C(F)F)c1] TFA Intermediate acid 20 | 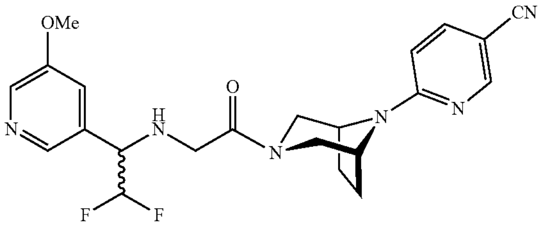 Racemic 6-(3-((2,2-difluoro-1-(5-methoxypyridin-3-yl)ethyl)glycyl)-3,8-diazabicyclo[3.2.1]octan-8-yl)nicotinonitrile | 443.0 $[M + H]^+$ |
| 128 | 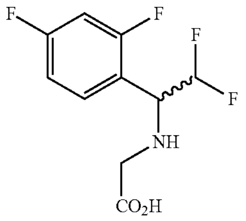 [SMILES: O=C(O)CNC(c1ccc(F)cc1F)C(F)F] Intermediate acid 21 | 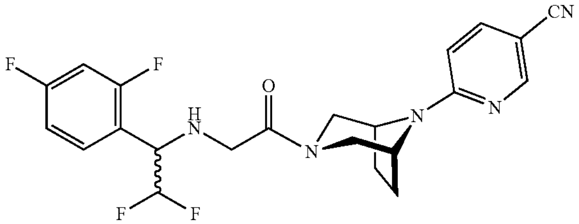 Racemic 6-(3-((1-(2.4-difluorophenyl)-2,2-difluoroethyl)glycyl)-3,8-diazabicyclo[3.2.1]octan-8-yl)nicotinonitrile | 448.0 $[M + H]^+$ |
| 129 | 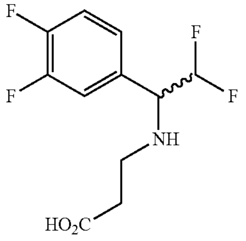 [SMILES: O=C(O)CCNC(c1ccc(F)c(F)c1)C(F)F] Intermediate acid 22 | 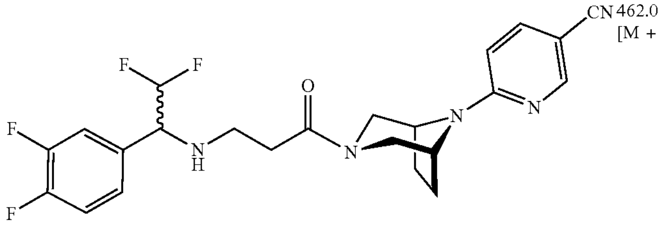 Racemic 6-(3-(3-((1-(3,4-difluorophenyl)-2,2-difluoroethyl)amino)propanoyl)-3,8-diazabicyclo[3.2.1]octan-8-yl)nicotinonitrile | 462.0 $[M + H]^+$ |
| 130 | 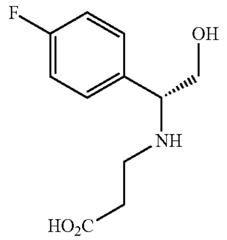 [SMILES: O=C(O)CCN[C@@H](CO)c1ccc(F)cc1] Intermediate acid 23 | 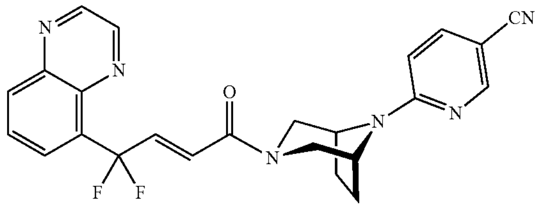 6-((3-(3-(((R)-1-(4-fluorophenyl)-2-hydroxyethyl)amino)propanoyl)-3,8-diazabicyclo[3.2.1]octan-8-yl)nicotinonitrile | 424.3 $[M + H]^+$ |
| 131 | 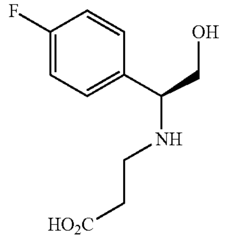 [SMILES: O=C(O)CCN[C@H](CO)c1ccc(F)cc1] Intermediate acid 24 | 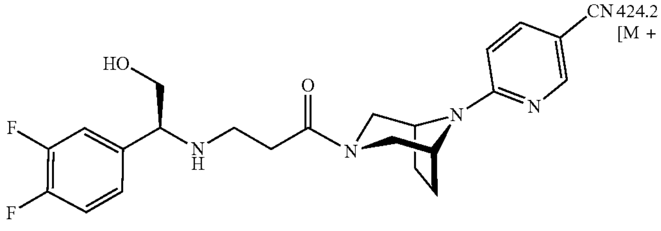 6-((3-(3-(((S)1-(4-fluorophenyl)-2-hydroxyethyl)amino)propanoyl)-3,8-diazabicyclo[3.2.1]octan-8-yl)nicotinonitrile | 424.2 $[M + H]^+$ |

-continued

| Example | Starting Acid | Structure | LCMS (m/z) |
|---|---|---|---|
| 132 | 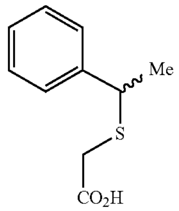 [SMILES: CC(SCC(=O)O)c1ccccc1] Intermediate acid 25 | 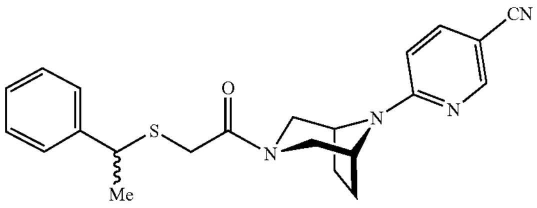 Racemic 6-(3-(2-((1-phenylethyl)thio)acetyl)-3,8-diazabicyclo[3.2.1]octan-8-yl)nicotinonitrile | 393.1 $[M + H]^+$ |
| 133 | 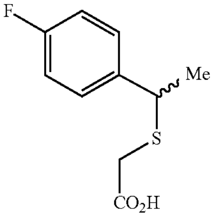 [SMILES: CC(SCC(=O)O)c1ccc(F)cc1] Intermediate acid 26 | 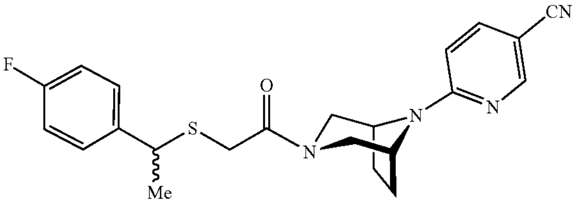 Racemic 6-(3-(2-((1-(4-fluorophenyl)ethyl)thio)acetyl)-3,8-diazabicyclo[3.2.1]octan-8-yl)nicotinonitrile | 411.1 $[M + H]^+$ |
| 134 | 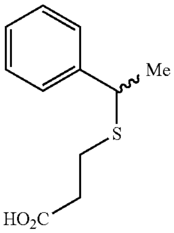 [SMILES: CC(SCCC(=O)O)c1ccccc1] Intermediate acid 27 | 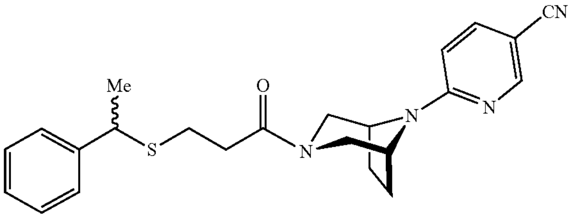 Racemic 6-(3-(3-((1-phenylethyl)thio)propanoyl)-3,8-diazabicyclo[3.2.1]octan-8-yl)nicotinonitrile | 407.1 $[M + H]^+$ |
| 135 | 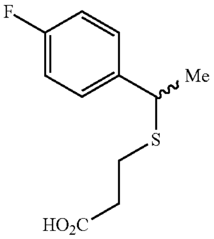 [SMILES: CC(SCCC(=O)O)c1ccc(F)cc1] Intermediate acid 28 | 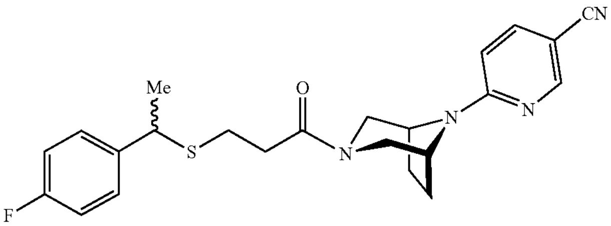 Racemic 6-((3-((1-(4-fluorophenyl)ethyl)thio)propanoyl)-3,8-diazabicyclo[3.2.1]octan-8-yl)nicotinonitrile | 425.1 $[M + H]^+$ |
| 136 | 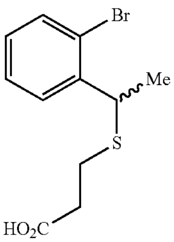 [SMILES: CC(SCCC(=O)O)c1ccccc1Br] Intermediate acid 29 | 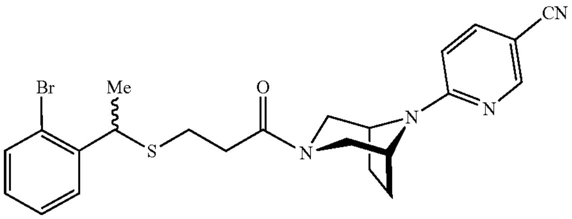 Racemic 6-((3-((1-(2-bromophenyl)ethyl)thio)propanoyl)-3,8-diazabicyclo[3.2.1]octan-8-yl)nicotinonitrile | 485.0, 487.0 $[M + H]^+$ |

-continued

| Example | Starting Acid | Structure | LCMS (m/z) |
|---|---|---|---|
| 137 | 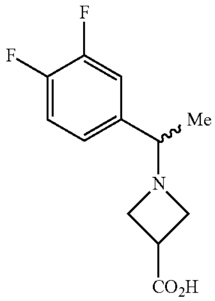 [SMILES: CC(c1ccc(F)c(F)c1)N1CC(C(=O)O)C1]<br>Intermediate acid 30 | 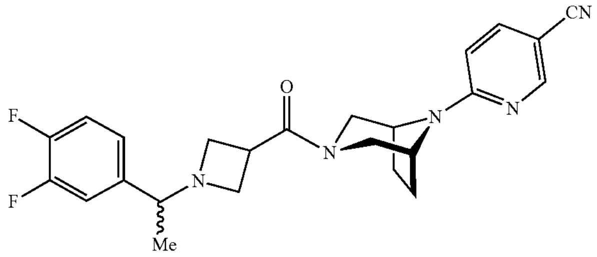<br>Racemic 6-(3-(1-(1-(3,4-difluorophenyl)ethyl)azetidine-3-carbonyl)-3,8-diazabicyclo[3.2.1]octan-8-yl)nicotinonitrile | 138.1 $[M + H]^+$ |

Example 138: Preparation of 6-(3-(4,4-difluoro-4-(2-methoxypyridin-4-yl)butanoyl)-3,8-diazabicyclo[3.2.1]octan-8-yl)nicotinonitrile

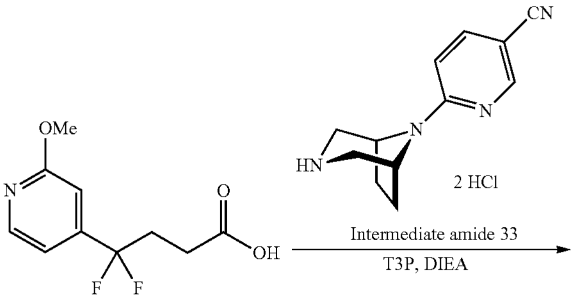

Intermediate acid 12

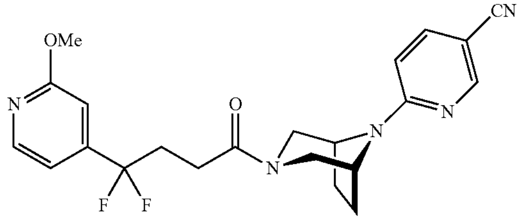

Example 138

In a dried round-bottom flask equipped with a magnetic stirrer was combined Intermediate acid 12 (1 equiv), Intermediate amine 33 (1.2 equiv), and DIEA (5 equiv, Sigma-Aldrich) in dichloromethane (0.28 M). To the reaction mixture was then added propylphosphonic anhydride (1.4 equiv, 50 wt % solution in EtOAc, Sigma-Aldrich) and the resulting yellow solution was allowed to stir at RT for 1.5 h. The reaction mixture was then diluted with EtOAc and washed sequentially with 1 M aq. NaOH, water and brine. The organic layer was then dried over $MgSO_4$, filtered and the filtrate concentrated in vacuo. Further purification by way of column chromatography ($SiO_2$, gradient elution:Hex 4 EtOAc→10:1 (v/v) EtOAc: MeOH) afforded the title compound as a white solid (82% yield). LCMS: m/z=428.1 $[M+H]^+$; $^1H$ NMR (DMSO-$d_6$): δ=8.50 (d, J=2.5 Hz, 1H), 8.29 (d, J=5.0 Hz, 1H), 7.88 (dd, J=9.0, 2.5 Hz, 1H), 7.11 (dd, J=5.0, 1.0 Hz, 1H), 3.93 (s, 1H), 6.91 (d, J=9.0 Hz, 1H), 4.69 (br s, 2H), 4.06 (d, J=12.0 Hz, 1H), 3.88 (s, 3H), 3.62 (d, J=13.0 Hz, 1H), 3.22 (d, J=11.5 Hz, 1H), 2.73 (d, J=12.0 Hz, 1H), 2.61~2.51 (m, 1H), 2.49~2.37 (m, 2H), 2.36~2.28 (m, 1H), 1.94~1.83 (m, 2H), 1.81~1.77 (m, 1H), 1.61~1.53 (in, 1H).

The following examples were prepared in an analogous fashion to Example 138 but substituting Intermediate acid 12 for the requisite acid:

| Example | Starting Acid | Structure | LCMS (m/z) |
|---|---|---|---|
| 139 | 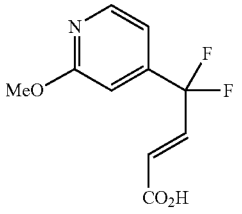 [SMILES: COc1cc(C(F)(F)/C=C/C(=O)O)ccn1]<br>Intermediate acid 4 | 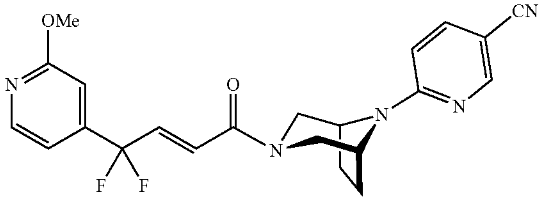<br>6-(3-((E)-4,4-difluoro-4-(2-methoxypyridin-4-yl)but-2-enoyl)-3,8-diazabicyclo[3.2.1]octan-8-yl)nicotinonitrile | 426.1 $[M + H]^+$ |

-continued

| Example | Starting Acid | Structure | LCMS (m/z) |
| --- | --- | --- | --- |
| 140 | 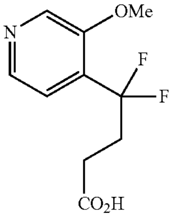 [SMILES: COc1cnccc1C(F)(F)CCC(=O)O]<br>Intermediate acid 5 | 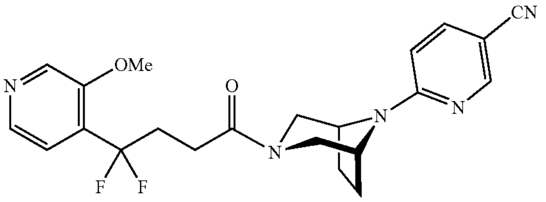<br>6-(3-(4,4-difluoro-4-(3-methoxypyridin-4-yl)butanoyl)-3,8-diazabicyclo[3.2.1]octan-8-yl)nicotinonitrile | 428.1 $[M + H]^+$ |
| 141 | 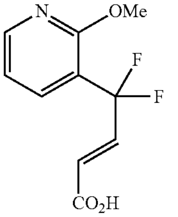 [SMILES: COc1ncccc1C(F)(F)/C=C/C(=O)O]<br>Intermediate acid 6 | 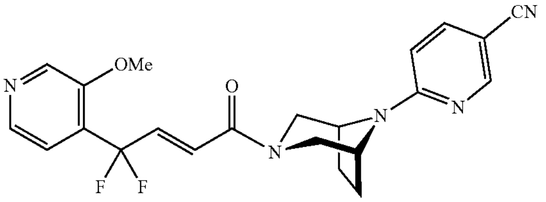<br>6-(3-((E)-4,4-difluoro-4-(2-methoxypyridin-3-yl)but-2-enoyl)-3,8-diazabicyclo[3.2.1]octan-8-yl)nicotinonitrile | 426.1 $[M + H]^+$ |
| 142 | 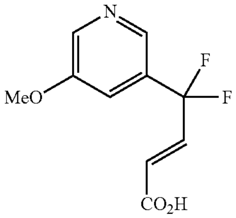 [SMILES: COc1cncc(C(F)(F)/C=C/C(=O)O)c1]<br>Intermediate acid 7 | 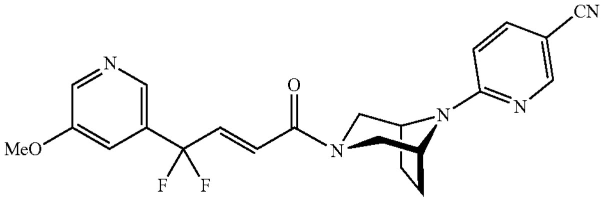<br>6-(3-((E)-4,4-difluoro-4-(5-methoxypyridin-3-yl)but-2-enoyl)-3,8-diazabicyclo[3.2.1]octan-8-yl)nicotinonitrile | 426.1 $[M + H]^+$ |
| 143 | 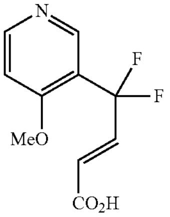 [SMILES: COc1ccncc1C(F)(F)/C=C/C(=O)O]<br>Intermediate acid 8 | 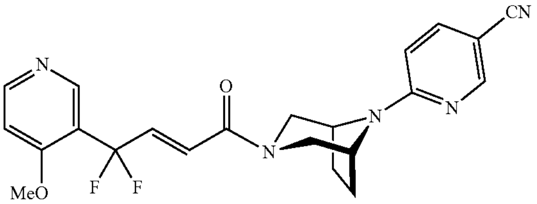<br>6-(3-((E)-4,4-difluoro-4-(4-methoxypyridin-3-yl)but-2-enoyl)-3,8-diazabicyclo[3.2.1]octan-8-yl)nicotinonitrile | 426.1 $[M + H]^+$ |
| 144 | 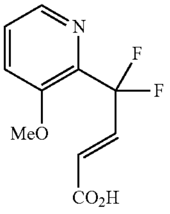 [SMILES: COc1cccnc1C(F)(F)/C=C/C(=O)O]<br>Intermediate acid 9 | 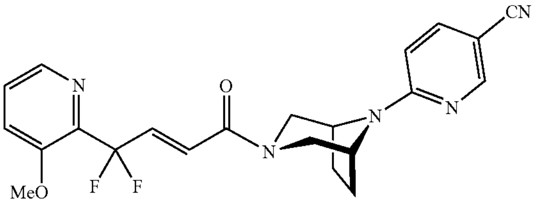<br>6-(3-((E)-4,4-difluoro-4-(3-methoxypyridin-2-yl)but-2-enoyl)-3,8-diazabicyclo[3.2.1]octan-8-yl)nicotinonitrile | 426.1 $[M + H]^+$ |

-continued

| Example | Starting Acid | Structure | LCMS (m/z) |
|---|---|---|---|
| 145 | 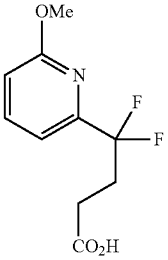 [SMILES: COc1cccc(C(F)(F)CCC(=O)O)n1]<br>Intermediate acid 10 | 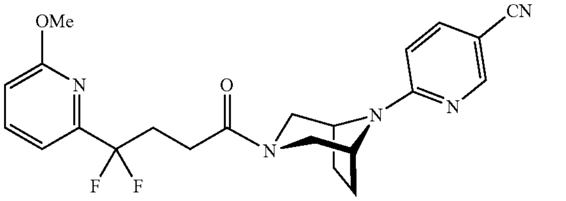<br>6-(3-(4,4-difluoro-4-(6-methoxypyridin-2-yl)butanoyl)-3,8-diazabicyclo[3.2.1]octan-8-yl)nicotinonitrile | 428.1 $[M + H]^+$ |
| 146 | 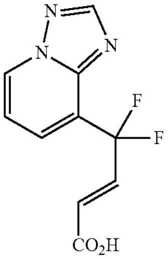 [SMILES: O=C(O)/C=C/C(F)(F)c1cccn2ncnc12]<br>Intermediate acid 11 | 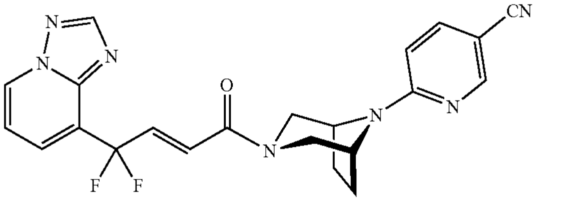<br>6-(3-((E)-4-([1,2,4]triazolo[1,5-a]pyridin-8-yl)-4,4-difluorobut-2-enoyl)-3,8-diazabicyclo[3.2.1]octan-8-yl)nicotinonitrile | 436.0 $[M + H]^+$ |
| 147 | 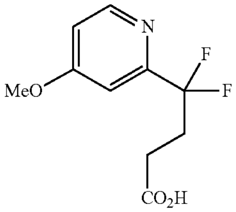 [SMILES: COc1ccnc(C(F)(F)CCC(=O)O)c1]<br>Intermediate acid 13 | 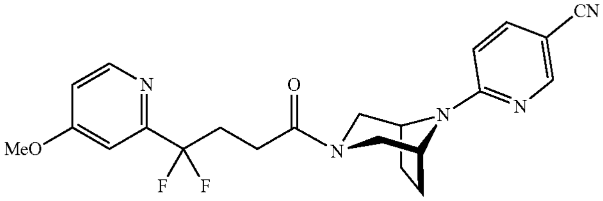<br>6-(3-(4,4-difluoro-4-(4-methoxypyridin-2-yl)butanoyl)-3,8-diazabicyclo[3.2.1]oxtan-8-yl)nicotinonitrile | 428.1 $[M + H]^+$ |
| 148 | 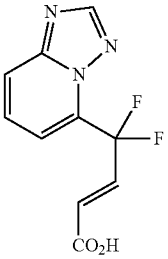 [SMILES: O=C(O)/C=C/C(F)(F)c1cccc2ncnn12]<br>Intermediate acid 14 | 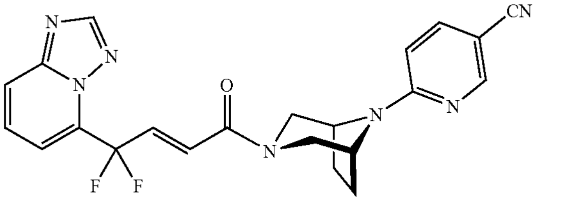<br>6-(-3-((E)- 4-([1,2,4]triazolo[1,5-a]pyridin-5-yl)-4,4-difluorobut-2-enoyl)-3,8-diazabicyclo[3.2.1]octan-8-yl)nicotinonitrile | 436.0 $[M + H]^+$ |

-continued

| Example | Starting Acid | Structure | LCMS (m/z) |
|---|---|---|---|
| 149 | 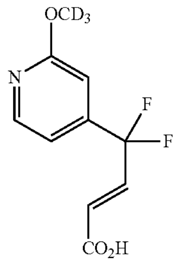<br>Intermediate acid 17 | 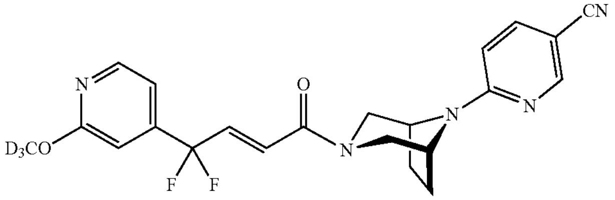<br>6-(3-((E)-4,4-difluoro-4-(2-(methoxy-$d_3$)pyridin-4-yl)but-2-enoyl)-3,8-diazabicyclo[3.2.1]octan-8-yl)nicotinonitrile | 429.1 $[M + H]^+$ |
| 150 | 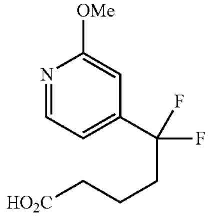 [SMILES: COc1cc(C(F)(F)CCCC(=O)O)ccn1]<br>Intermediate acid 18 | 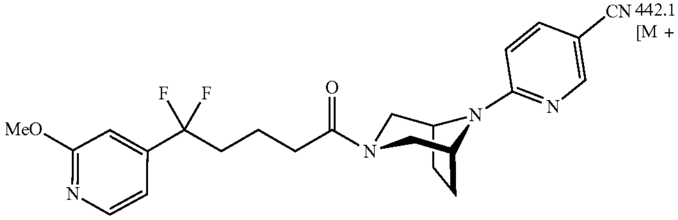<br>6-(3-(5,5-difluoro-5-(2-methoxypyridin-4-yl)pentanoyl)-3,8-diazabicyclo[3.2.1]octan-8-yl)nicotinonitrile | 442.1 $[M + H]^+$ |
| 151 | 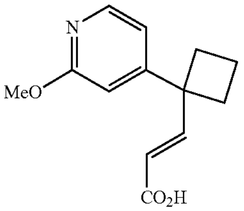 [SMILES: COc1cc(C2(/C=C/C(=O)O)CCC2)ccn1]<br>Intermediate acid 19 | 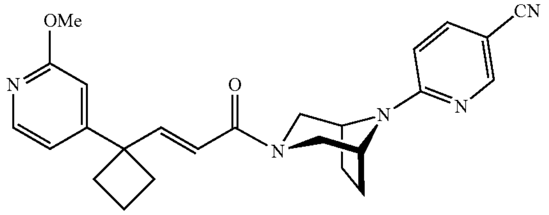<br>6-(3-((E)-3-(1-(2-methoxypyridin-4-yl)cyclobutyl)acryloyl)-3,8-diazabicyclo[3.2.1]octan-8-yl)nicotinonitrile | 430.1 $[M + H]^+$ |
| 152 | 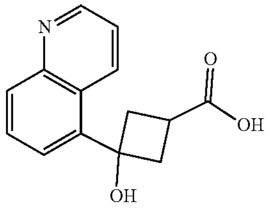 [SMILES: O=C(O)C1CC(O)(c2cccc3ncccc23)C1]<br>Intermediate acid 31 | 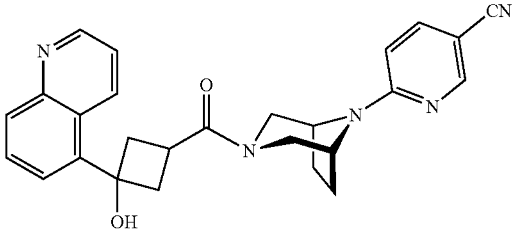<br>6-(3-(3-hydroxy-3-(quinolin-5-yl)cyclobutane-1-carbonyl)-3,8-diazabicyclo[3.2.1]octan-8-yl)nicotinonitrile | 440.1 $[M + H]^+$ |
| 153 | 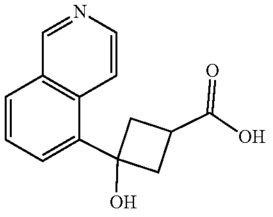 [SMILES: O=C(O)C1CC(O)(c2cccc3cnccc23)C1]<br>Intermediate Acid 32 | 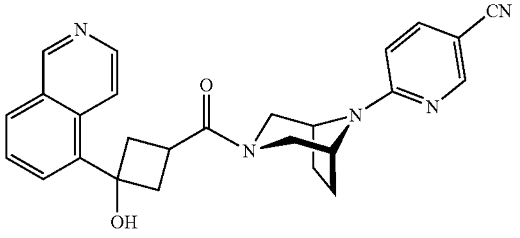<br>6-(3-(3-hydroxy-3-(quinolin-5-yl)cyclobutane-1-carbonyl)-3,8-diazabicyclo[3.2.1]octan-8-yl)nicotinonitrile | 440.1 $[M + H]^+$ |

The following examples were prepared in an analogous fashion to Example 138 but substituting Intermediate amine 33 for the requisite amine:

| Example | Starting Amine | Structure | LCMS (m/z) |
|---|---|---|---|
| 154 | 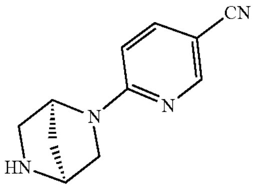 [SMILES: N#Cc1ccc(N2C[C@@H]3C[C@H]2CN3)nc1] Intermediate amine 38 | 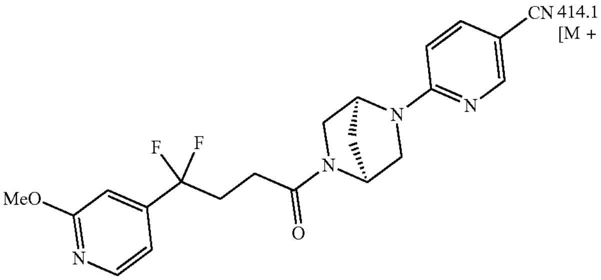 6-((1S,4S)-5-(4,4-difluoro-4-(2-methoxypyridin-4-yl)butanoyl)-2,5-diazabicyclo[2.2.1]heptan-2-yl)nicotinonitrile | 414.1 [M + H]+ |
| 155 | 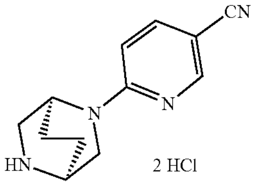 [SMILES: N#Cc1ccc(N2C[C@@H]3CC[C@H]2CN3)nc1] 2 HCl Intermediate amine 39 | 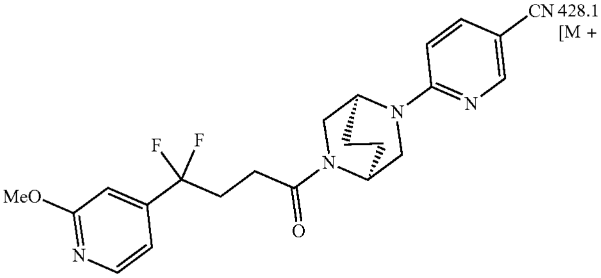 6-((1S,4S)-5-(4,4-difluoro-4-(2-methoxypyridin-4-yl)butanoyl)-2,5-diazabicyclo[2.2.2]octan-2-yl)nicotinonitrile | 428.1 [M + H]+ |
| 156 | 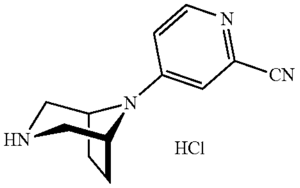 HCl Intermediate amine 41 | 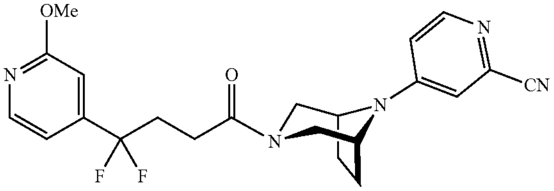 4-(3-(4,4-difluoro-4-(2-methoxypyridin-4-yl)butanoyl)-3,8-diazabicyclo[3.2.1]octan-8-yl)picolinonitrile | 428.1 [M + H]+ |
| 157 | 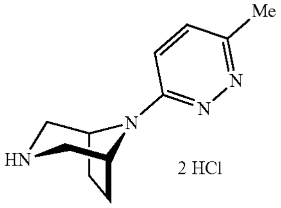 2 HCl Intermediate amine 46 | 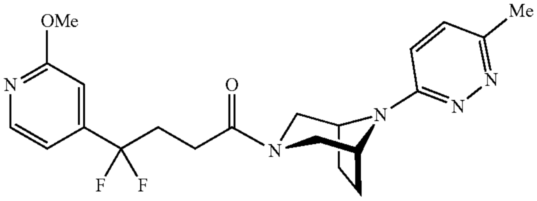 4,4-difluoro-4-(2-methoxypyridin-4-yl)-1-(8-(6-methylpyridazin-3-yl)-3,8-diazabicyclo[3.2.1]octan-3-yl)butan-1-one | 418.1 [M + H]+ |

Example 158: Preparation of 6-(3-(4-([1,2,4]triazolo [1,5-a]pyridin-8-yl)-4,4-difluorobutanoyl)-3,8-diazabicyclo[3.2.1]octan-8-yl)nicotinonitrile

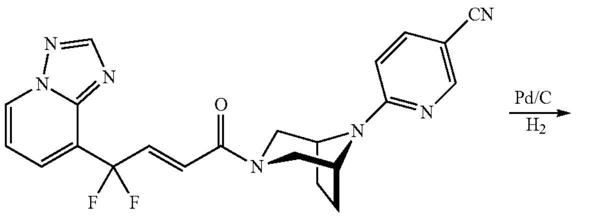

Example 146

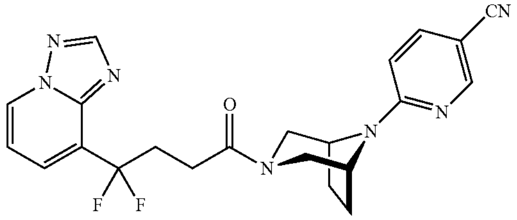

Example 158

In a dried round-bottom flask equipped with a magnetic stirrer was combined Example 146 (1 equiv) and palladium black (0.1 equiv, 10% (w/w) over activated carbon, Sigma-Aldrich) in a 20:1 (v/v) solution of EtOAc and methanol (0.1 M). The resulting suspension was evacuated and back-filled with hydrogen gas (3×). Once the gas exchange process was deemed complete, the reaction suspension was stirred at RT under a static hydrogen atmosphere for 2 h. The reaction suspension was then filtered and the filtrate concentrated in vacuo. Further purification of the crude product thus obtained by way of column chromatography ($SiO_2$, gradient elution:Hex→EtOAc→10:1 (v/v) EtOAc: MeOH) afforded the title compound as a white solid (27% yield). LCMS: m/z=438.1 $[M+H]^+$; $^1H$ NMR (DMSO-$d_6$): δ=9.10 (d, J=6.5 Hz, 1H), 8.57 (s, 1H), 8.50 (dd, J=2.5, 1.0 Hz, 1H), 7.87 (dd, J=9.5, 2.5 Hz, 1H), 7.83 (d, J=7.5 Hz, 1H), 7.29 (t, J=7.5 Hz, 1H), 6.90 (d, J=9.0 Hz, 1H), 4.67 (br s, 2H), 4.50~ 4.00 (m, 1H), 3.56 (d, J=12.0 Hz, 1H), 3.19 (d, J=11.5 Hz, TH), 2.95~2.76 (m, 2H), 2.75~2.67 (in, TH), 2.62~2.55 (in, TH), 2.38~2.30 (m, 1H), 1.92~1.83 (m, 2H), 1.81~1.74 (m, 1H), 1.61~1.54 (in, 1H).

The following examples were prepared in an analogous fashion to Example 158 but substituting Example 146 for the requisite alkene:

| Example | Starting Alkene | Structure | LCMS (m/z) |
|---|---|---|---|
| 159 | 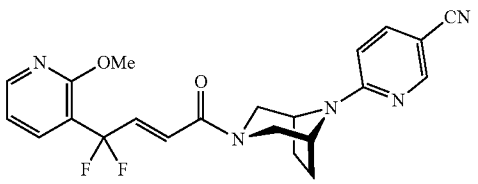 Example 141 | 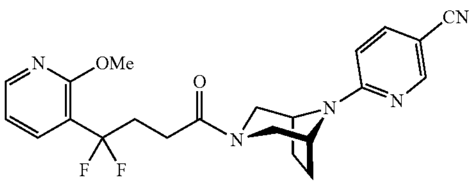 6-(3-(4,4-difluoro-4-(2-methoxypyridin-3-yl)butanoyl)-3,8-diazabicyclo[3.2.1]octan-8-yl)nicotinonitrile | 428.1 $[M + H]^+$ |
| 160 | 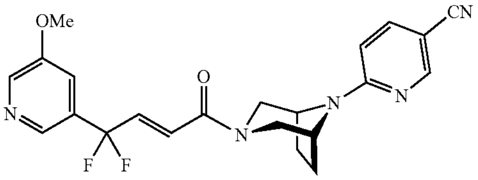 Example 142 | 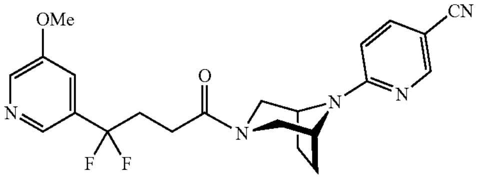 6-(3-(4,4-difluoro-4-(5-methoxypyridin-3-yl)butanoyl)-3,8-diazabicyclo[3.2.1]octan-8-yl)nicotinonitrile | 428.1 $[M + H]^+$ |
| 161 | 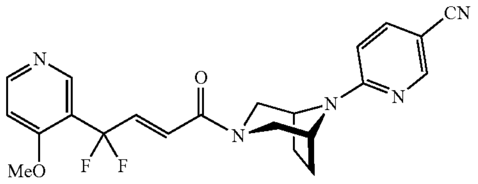 Example 143 | 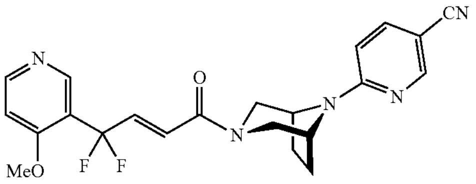 6-(3-(4,4-difluoro-4-(4-methoxypyridin-3-yl)butanoyl)-3,8-diazabicyclo[3.2.1]octan-8-yl)nicotinonitrile | 428.1 $[M + H]^+$ |

-continued

| Example | Starting Alkene | Structure | LCMS (m/z) |
|---|---|---|---|
| 162 | 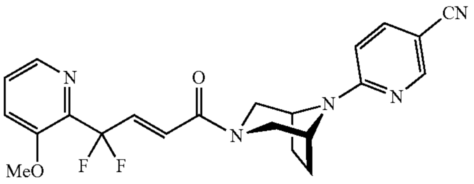 Example 144 | 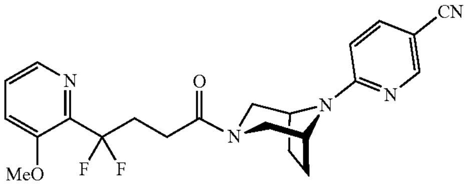 6-(3-(4,4-difluoro-4-(3-methoxypyridin-2-yl)butanoyl)-3,8-diazabicyclo[3.2.1]octan-8-yl)nicotinonitrile | 428.1 $[M + H]^+$ |
| 163 | 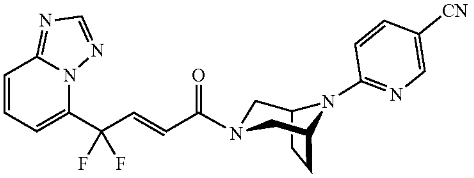 Example 145 | 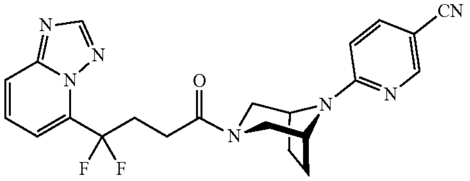 6-(3-(4-([1,2,4]triazolo[1,5-a]pyridin-5-yl)-4,4-difluorobutanoyl)-3,8-diazabicyclo[3.2.1]octan-8-yl)nicotinonitrile | 438.1 $[M + H]^+$ |
| 164 | 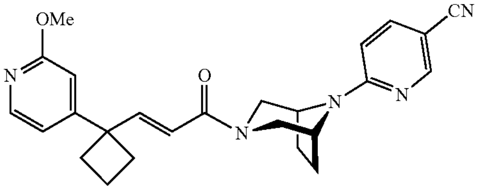 Example 146 | 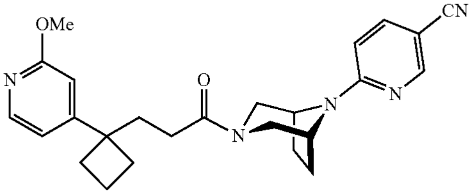 6-(3-(3-(1-(2-methoxypyridin-4-yl)cyclobutyl)propanoyl)-3,8-diazabicyclo[3.2.1]octan-8-yl)nicotinonitrile | 432.2 $[M + H]^+$ |
| 165 | 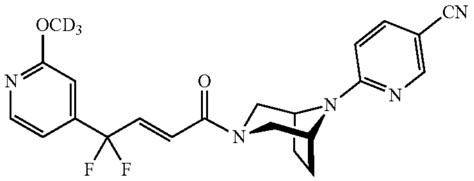 Example 149 | 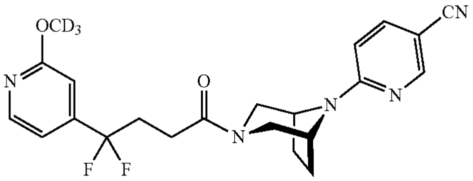 6-(3-(4,4-difluoro-4-(2-(methoxy-$d_3$)pyridin-4-yl)butanoyl)-3,8-diazabicyclo[3.2.1]octan-8-yl)nicotinonitrile | 431.1 $[M + H]^+$ |

Example 166: Preparation of 6-(3-(2-(difluoro(2-methoxypyridin-4-yl)methyl)cyclopropane-1-carbonyl)-3,8-diazabicyclo[3.2.1]octan-8-yl)nicotinonitrile

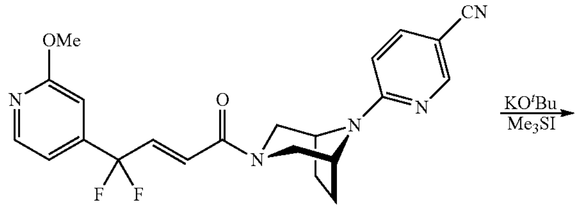

Example 139

-continued

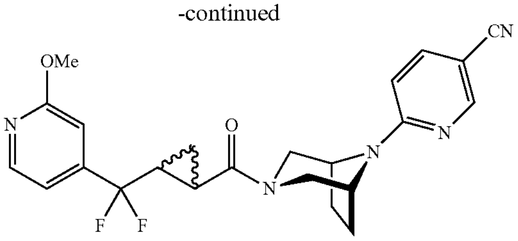

Example 166

In a dried round-bottom flask equipped with a magnetic stirrer was dissolved trimethylsulfonium iodide (1.5 equiv, Sigma-Aldrich) in DMSO (0.1 M). To this was then added potassium tert-butoxide (1.5 equiv, Sigma-Aldrich) in one rapid portion and the resulting golden yellow solution was allowed to stir at RT for 30 min. Finally, Example 139 (1 equiv) was added and the now brown solution was allowed to stir at RT for 6 h. The reaction mixture was diluted with water and extracted with EtOAc. The combined organic extracts were washed further with water, 1 M aq. NaOH and brine, dried over $MgSO_4$, filtered and the filtrate concentrated in vacuo. Further purification of the crude product thus obtained by way of column chromatography ($SiO_2$, gradient elution:Hex→EtOAc→10:1 (v/v) EtOAc: MeOH) afforded the title compound as a 1.2:1 mixture of cis- and trans-isomers (71% yield). LCMS: m/z=440.1 $[M+H]^+$; $^1$H NMR (DMSO-$d_6$): δ=8.52 (d, J=2.0 Hz, 1H, isomers A & B), 8.34 (d, J=5.0 Hz, 0.55H, isomer A), 8.30 (d, J=5.0 Hz, 0.45H, isomer B), 7.90~ 7.88 (m, 1H, isomers A & B), 7.22 (dd, J=5.0, 2.0 Hz, 0.55H, isomer A), 7.15 (dd, J=5.0, 2.0 Hz, 0.45H, isomer B), 7.05 (s, 0.55H, isomer A), 7.96 (s, 0.45H, isomer B), 6.93 (dd, J=2.0 Hz, 0.55H, isomer A), 6.92 (dd, J=2.0 Hz, 0.45H, isomer B), 4.74~4.66 (m, 2H, isomers A & B), 4.14~ 4.02 (m, 2H, isomers A & B), 3.90 (s, 1.64H, isomer A), 3.88 (s, 1.36H, isomer B), 3.32~ 3.23 (m, 1H, isomers A & B), 2.81~2.76 (m, 1H, isomers A & B), 2.38~2.33 (m, 1H, isomers A & B), 2.10~2.07 (m, 1H, isomers A & B), 1.95~1.78 (m, 2H, isomers A & B), 1.62~1.49 (m, 1H, isomers A & B), 1.35~1.10 (m, 3H).

Example 167: Preparation of Racemic 6-(3-(2-((1-(4-fluorophenyl)ethyl)sulfinyl)acetyl)-3,8-diazabicyclo[3.2.1]octan-8-yl)nicotinonitrile

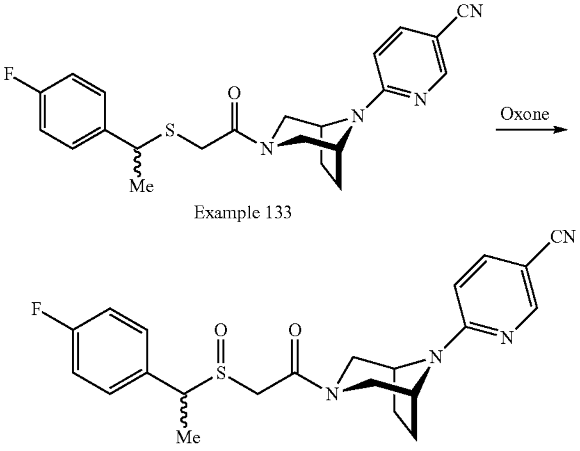

Example 133

Example 167

In a round-bottom flask equipped with a magnetic stirrer was dissolved Example 133 (1 equiv) in methanol (0.07 M). To this was then added at 0° C. Oxone® (1 equiv, 0.1 M solution in water, Sigma-Aldrich) dropwise over a period of 5 min. The cooling bath was then removed and the reaction mixture was stirred at RT for 3 h. The reaction suspension was then filtered through a bed of celite and the filtrate was diluted with water and EtOAc. The organic layer was separated, washed further with water and brine, dried over $Na_2SO_4$, filtered and the filtrate concentrated in vacuo. Purification of the crude product thus obtained by way of column chromatography ($SiO_2$, gradient elution:Hex→EtOAc→10:1 (v/v) EtOAc: MeOH) afforded the title compound as a 4:1 mixture of isomers (43% yield). LCMS: m/z=427.1 $[M+H]^+$; $^1$H NMR (DMSO-$d_6$): δ=8.52 (d, J=2.5 Hz, 0.8H, isomer A), 8.51 (d, J=2.5 Hz, 0.2H, isomer B), 7.89 (dd, J=9.0, 2.0 Hz, 0.8H, isomer A), 7.88 (dd, J=9.0, 2.0 Hz, 0.2H, isomer B), 7.43~ 7.36 (m, 1.6H, isomer A), 7.36~ 7.29 (m, 0.4H, isomer B), 6.94 (d, J=9.0 Hz, 0.8H, isomer A), 6.91 (d, J=9.0 Hz, 0.2H, isomer B), 4.72 (br s, 1.6H, isomer A), 4.65 (br s, 0.4H, isomer B), 4.28~ 4.05 (m, 2H, isomers A & B), 3.91~ 3.46 (m, 3H, isomers A & B), 3.29~ 3.06 (m, 2H, isomers A & B), 2.81~2.77 (m, 1H, isomers A & B), 1.97~1.89 (m, 3H, isomers A & B), 1.60~1.54 (m, 4H, isomers A & B).

The following examples were prepared in an analogous fashion to Example 167 but substituting Example 133 for the requisite sulfide. For the synthesis of Example 172, Example 173, Example 174, Example 175, and Example 176, the amount of Oxone® used for the oxidation was increased from 1 equiv to 3 equiv:

| Example | Starting Sulfide | Structure | LCMS (m/z) |
| --- | --- | --- | --- |
| 168 | 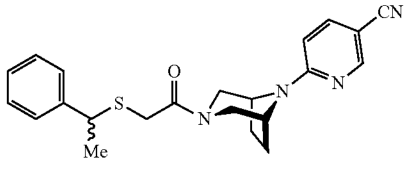 Example 132 | 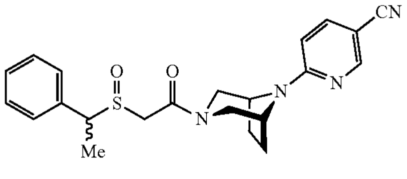 Racemic 6-(3-(2-((1-phenylethyl)sulfinyl)acetyl)-3,8-diazabicyclo[3.2.1]octan-8-yl)nicotinonitrile | 409.1 $[M + H]^+$ |

-continued

| Example | Starting Sulfide | Structure | LCMS (m/z) |
|---|---|---|---|
| 169 | 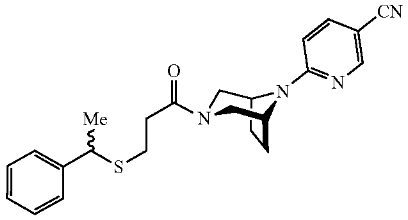<br>Example 134 | 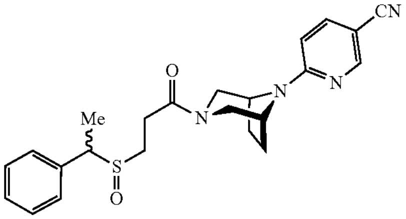<br>Racemic 6-(3-(3-((1-phenylethyl)sulfinyl)propanoyl)-3,8-diazabicyclo[3.2.1]octan-8-yl)nicotinonitrile | 423.1 [M + H]$^+$ |
| 170 | 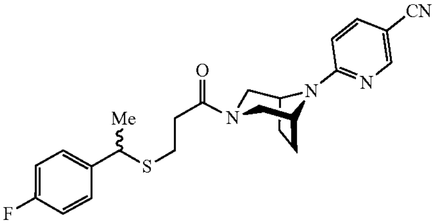<br>Example 135 | 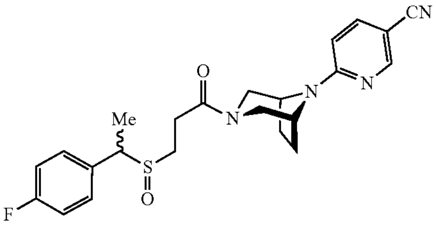<br>Racemic 6-(3-(3-((1-(4-fluorophenyl)ethyl)sulfinyl) propanoyl)-3,8-diazabicyclo[3.2.1]octan-8-yl) nicotinonitrile | 441.1 [M + H]$^+$ |
| 171 | 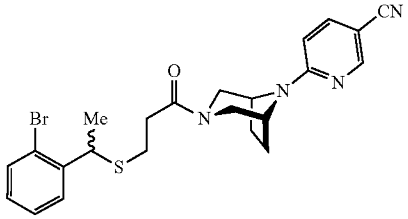<br>Example 136 | 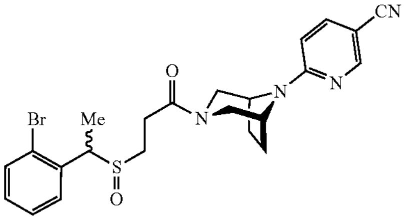<br>Racemic 6-(3-(3-((1-(2-bromophenyl)ethyl)sulflnyl) propanoyl)-3,8-diazabicyclo[3.2.1]octan-8-yl) nicotinonitrile | 501.0, 503.0 [M + H]$^+$ |
| 172 | 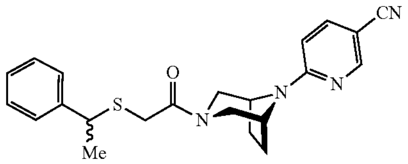<br>Example 132 | 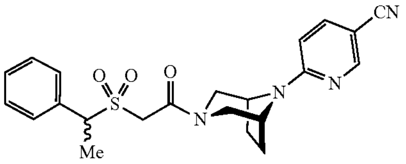<br>Racemic 6-(3-(2-((1-phenylethyl)sulfonyl)acetyl)-3,8-diazabicyclo[3.2.1]octan-8-yl)nicotinonitrile | 425.1 [M + H]$^+$ |
| 173 | 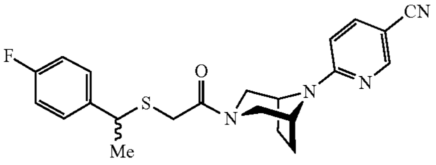<br>Example 133 | 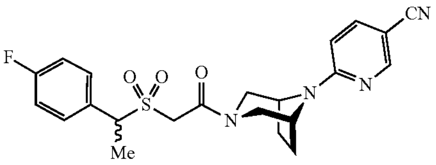<br>Racemic 6-(3-(2-((1-(4-fluorophenyl)ethyl)sulfonyl) acetyl)-3,8-diazabicyclo[3.2.1]octan-8-yl)nicotinonitrile | 443.0 [M + H]$^+$ |

-continued

| Example | Starting Sulfide | Structure | LCMS (m/z) |
|---|---|---|---|
| 174 | 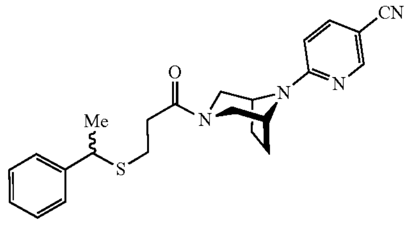 Example 134 | 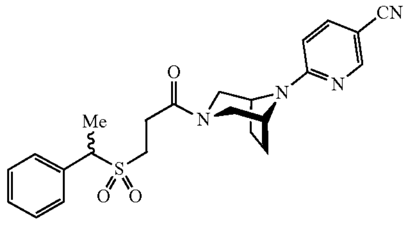 Racemic 6-(3-(3-((1-phenylethyl)sulfonyl)propanoyl)-3,8-diazabicyclo[3.2.1]octan-8-yl)nicotinonitrile | 439.0 $[M + H]^+$ |
| 175 | 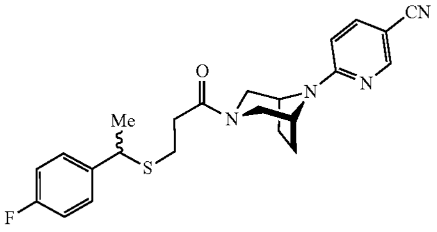 Example 135 | 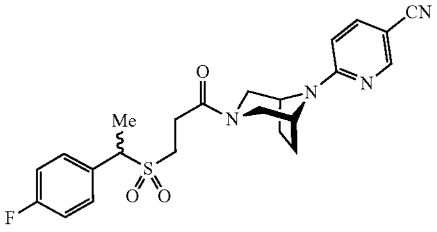 Racemic 6-(3-(3-((1-(4-fluorophenyl)ethyl)sulfonyl) propanoyl)-3,8-diazabicyclo[3.2.1]octan-8-yl) nicotinonitrile | 457.0 $[M + H]^+$ |
| 176 | 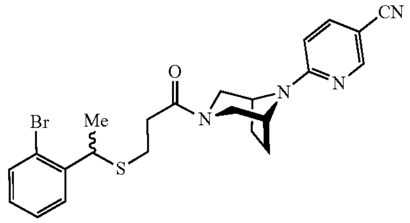 Example 136 | 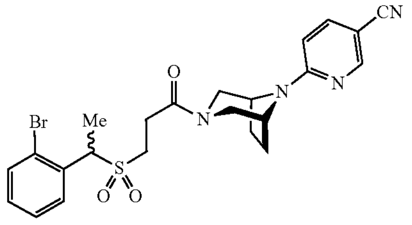 Racemic 6-(3-(3-((1-(2-bromophenyl)ethyl)sulfonyl) propanoyl)-3,8-diazabicyclo[3.2.1]octan-8-yl) nicotinonitrile | 516.9, 518.9 $[M + H]^+$ |

Example 177: Preparation of 6-(3-(2-(1-(3,4-difluorophenyl)cyclopropoxy)acetyl)-3,8-diazabicyclo[3.2.1]octan-8-yl)nicotinonitrile

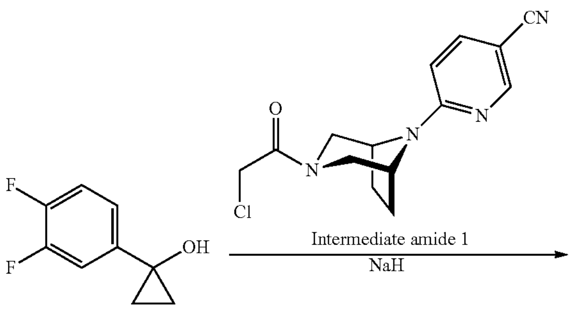

Intermediate alcohol 15

-continued

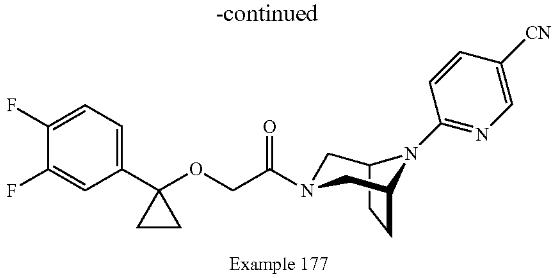

Example 177

In a dried round-bottom flask equipped with a magnetic stirrer was combined Intermediate alcohol 15 (1 equiv) and Intermediate amide 1 (1 equiv) in THF (0.17 M). To this was then added sodium hydride (1.5 equiv, 60% (w/w) dispersion in paraffin oil, Sigma-Aldrich) in one rapid portion and the resulting mixture was allowed to stir at RT for 1 h. The reaction was carefully quenched with water and extracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution:Hex→EtOAc→10:1 (v/v)

EtOAc: MeOH) afforded the title compound as a white solid (64% yield). LCMS: m/z=425.1 $[M+H]^+$; $^1H$ NMR (DMSO-$d_6$): δ=8.50 (d, J=2.0 Hz, 1H), 7.88 (dd, J=9.0, 2.5 Hz, 1H), 7.41~7.35 (m, 1H), 7.35~7.30 (m, 1H), 7.13~7.11 (m, 1H), 6.92 (d, J=9.0 Hz, 1H), 4.71 (br s, 1H), 4.66 (br s, 1H), 4.17~3.99 (m, 3H), 3.48 (d, J=12.5 Hz, 1H), 3.18 (d, J=12.0 Hz, 1H), 2.74 (d, J=12.5 Hz, 1H), 1.90~1.80 (m, 3H), 1.62~1.58 (m, 1H), 1.27~1.25 (m, 2H), 1.02~1.00 (m, 2H).

The following examples were prepared in an analogous fashion to Example 177 but substituting Intermediate alcohol 15 for the requisite alcohol:

| Example | Starting Alcohol | Structure | LCMS (m/z) |
|---|---|---|---|
| 178 | 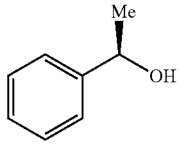 (Combi-Blocks) | 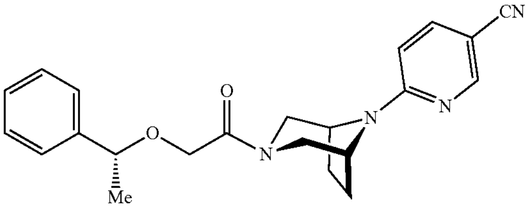 6-(3-(2-((R)-1-phenylethoxy)acetyl)-3,8-diazabicyclo[3.2.1]octan-8-yl)nicotinonitrile | 377.1 $[M + H]^+$ |
| 179 | 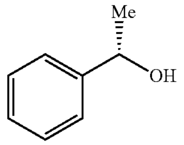 (Combi-Blocks) | 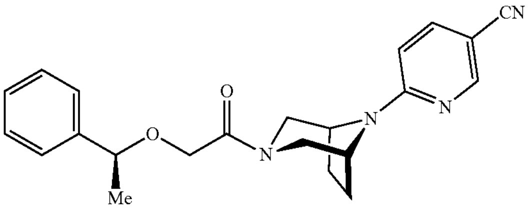 6-(3-(2-((S)-1-phenylethoxy)acetyl)-3,8-diazabicyclo[3.2.1]octan-8-yl)nicotinonitrile | 377.1 $[M + H]^+$ |
| 180 | 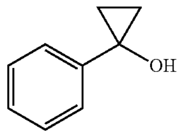 (Enamine) | 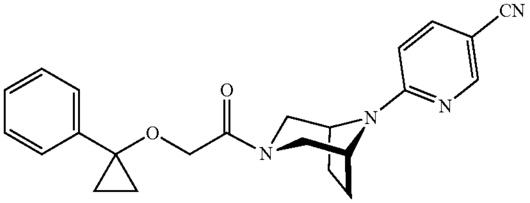 6-(3-(2-(1-phenylcyclopropoxy)acetyl)-3,8-diazabicyclo[3.2.1]octan-8-yl)nicotinonitrile | 389.1 $[M + H]^+$ |
| 181 | 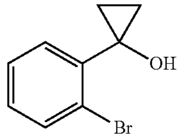 [SMILES: OC1(c2ccccc2Br)CC1] (Enamine) | 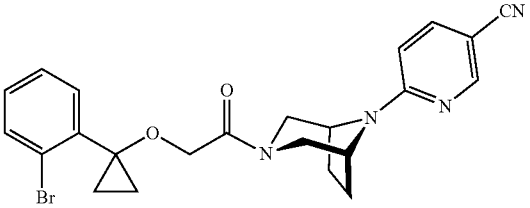 6-(3-(2-(1-(2-bromophenyl)cyclopropoxy)acetyl)-3,8-diazabicyclo[3.2.1]octan-8-yl)nicotinonitrile | 466.9, 468.9 $[M + H]^+$ |
| 182 | 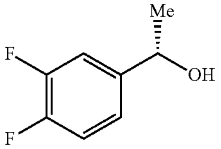 [SMILES: C[C@H](O)c1ccc(F)c(F)c1] (Enamine) | 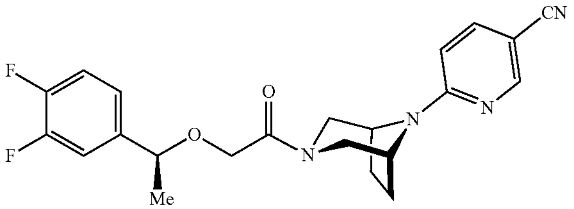 6-(3-(2-((S)-1-(3,4-difluorophenyl)ethoxy)acetyl)-3,8-diazabicyclo[3.2.1]octan-8-yl)nicotinonitrile | 413.1 $[M + H]^+$ |

-continued

| Example | Starting Alcohol | Structure | LCMS (m/z) |
| --- | --- | --- | --- |
| 183 | 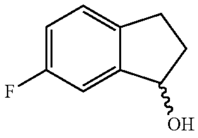 (AstaTech) | 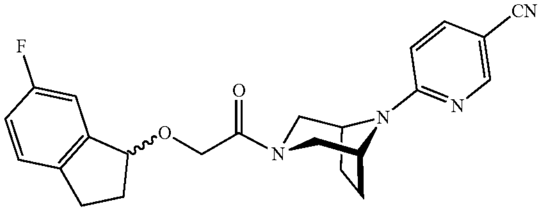 Racemic 6-(3-(2-((6-fluoro-2,3-dihydro-1H-inden-1-yl)oxy)acetyl)-3,8-diazabicyclo[3.2.1]octan-8-yl)nicotinonitrile | 429.3 $[M + H]^+$ |
| 184 | 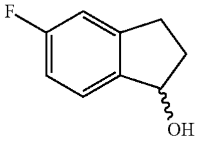 (AstaTech) | 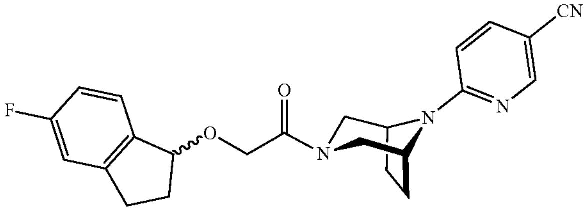 Racemic 6-(3-(2-((5-fluoro-2,3-dihydro-1H-inden-1-yl)oxy)acetyl)-3,8-diazabicyclo[3.2.1]octan-8-yl)nicotinonitrile | 429.3 $[M + H]^+$ |
| 185 | 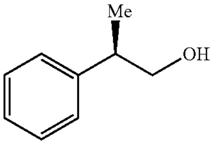 (Enamine) | 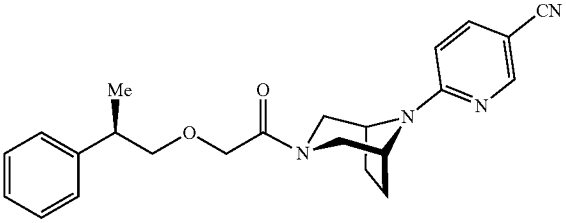 6-(3-(2-((S)-2-phenylpropoxy)acetyl)-3,8-diazabicyclo[3.2.1]octan-8-yl)nicotinonitrile | 391.2 $[M + H]^+$ |
| 186 | 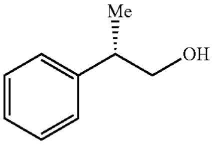 (Enamine) | 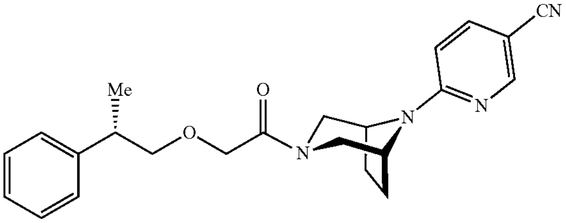 6-(3-(2-((S)-2-phenylpropoxy)acetyl)-3,8-diazabicyclo[3.2.1]octan-8-yl)nicotinonitrile | 391.2 $[M + H]^+$ |
| 187 | 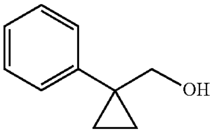 [SMILES: OCC1(c2ccccc2)CC1] (Enamine) | 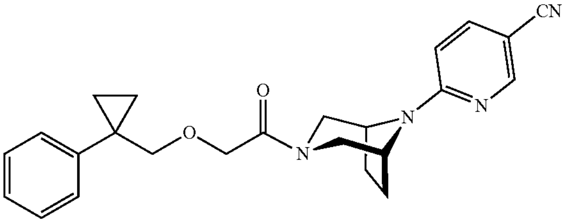 6-(3-(2-((1-phenylcyclopropyl)methoxy)acetyl)-3,8-diazabicyclo[3.2.1]octan-8-yl)nicotinonitrile | 403.1 $[M + H]^+$ |

-continued

| Example | Starting Alcohol | Structure | LCMS (m/z) |
|---|---|---|---|
| 188 | 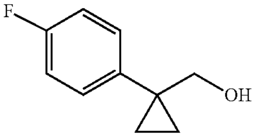 [SMILES: OCC1(c2ccc(F)cc2)CC1] (Enamine) | 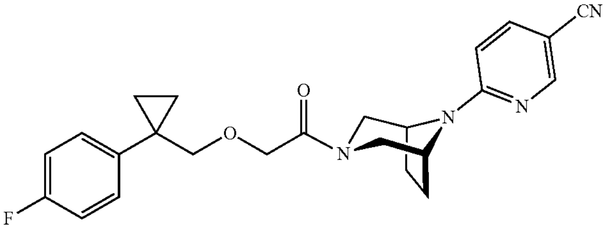 6-(3-(2-((1-(4-fluorophenyl)cyclopropyl)methoxy)acetyl)-3,8-diazabicyclo[3.2.1]octan-8-yl)nicotinonitrile | 423.5 $[M + H]^+$ |
| 189 | 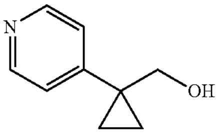 [SMILES: OCC1(c2ccncc2)CC1] (Enamine) | 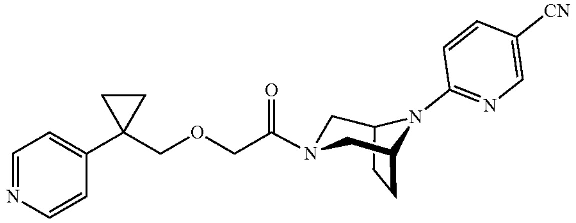 6-(3-(2-((1-(pyridin-4-yl)cyclopropyl)methoxy)acetyl)-3,8-diazabicyclo[3.2.1]octan-8-yl)nicotinonitrile | 404.1 $[M + H]^+$ |
| 190 | 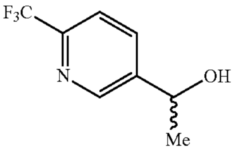 [SMILES: CC(O)c1ccc(C(F)(F)F)nc1] (AstaTech) | 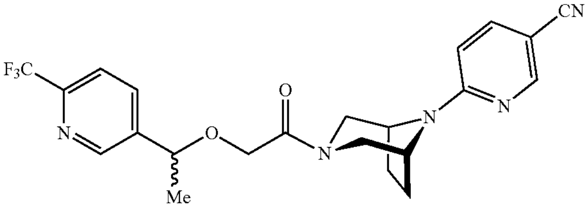 6-(3-(2-(1-(6-(trifluoromethyl)pyridin-3-yl)ethoxy)acetyl)-3,8-diazabicyclo[3.2.1]octan-8-yl)nicotinonitrile | 446.3 $[M + H]^+$ |
| 191 | 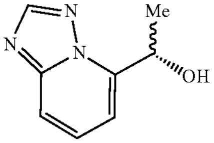 Intermediate alcohol 1 | 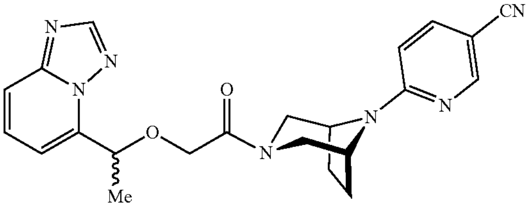 Racemic 6-(3-(2-(1-([1,2,4]triazolo[1,5-a]pyridin-5-yl) ethoxy)acetyl)-3,8-diazabicyclo[3.2.1]octan-8-yl)nicotinonitrile | 418.3 $[M + H]^+$ |
| 192 | 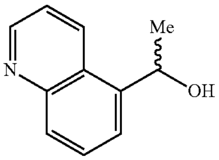 [SMILES: CC(O)c1cccc2ncccc12] Intermediate alcohol 2 | 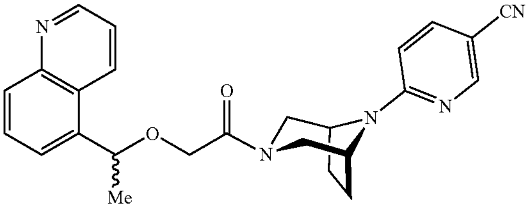 Racemic 6-(3-(2-(1-(quinolin-5-yl)ethoxy)acetyl)-3,8-diazabicyclo[3.2.1]octan-8-yl)nicotinonitrile | 428.1 $[M + H]^+$ |

-continued

| Example | Starting Alcohol | Structure | LCMS (m/z) |
|---|---|---|---|
| 193 | 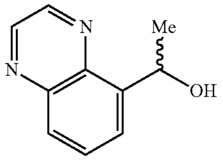 [SMILES: CC(O)c1cccc2nccnc12] Intermediate alcohol 3 | 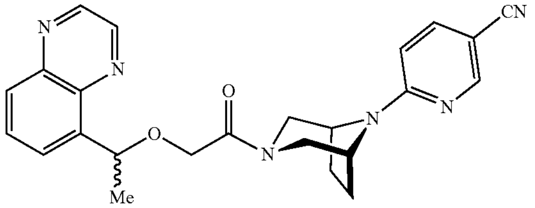 Racemic 6-(3-(2-(1-(quinoxalin-5-yl)ethoxy)acetyl)-3,8-diazabicyclo[3.2.1]octan-8-yl)nicotinonitrile | 429.1 [M + H]$^+$ |
| 194 | 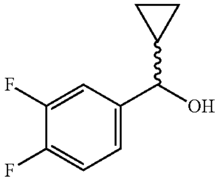 [SMILES: OC(c1ccc(F)c(F)c1)C1CC1] Intermediate alcohol 4 | 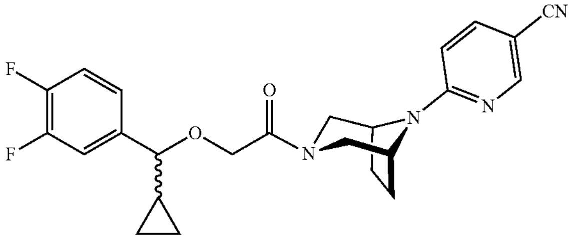 Racemic 6-(3-(2-(cyclopropyl(3,4-difluorophenyl)methoxy)acetyl)-3,8-diazabicyclo[3.2.1]octan-8-yl)nicotinonitrile | 439.1 [M + H]$^+$ |
| 195 | 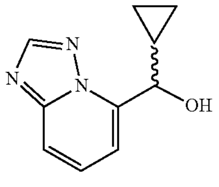 [SMILES: OC(c1cccc2ncnn12)C1CC1] Intermediate alcohol 5 | 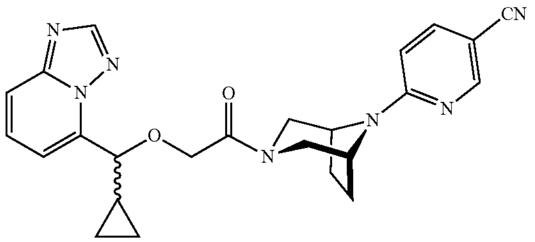 Racemic 6-(3-(2-([1,2,4]triazolo[1,5-a]pyridin-5-yl(cyclopropyl) methoxy)acetyl)-3,8-diazabicyclo[3.2.1]octan-8-yl)nicotinonitrile | 444.1 [M + H]$^+$ |
| 196 | 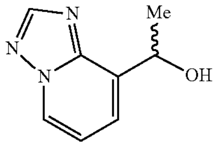 [SMILES: CC(O)c1cccn2ncnc12] Intermediate alcohol 6 | 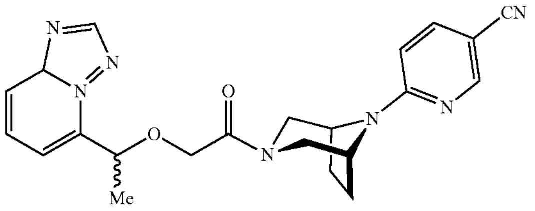 Racemic 6-(3-(2-(1-([1,2,4]triazolo[1,5-a]pyridin-8-yl)ethoxy)acetyl)-3,8-diazabicyclo[3.2.1]octan-8-yl)nicotinonitrile | 418.3 [M + H]$^+$ |
| 197 | 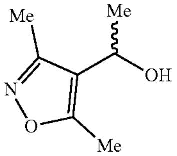 Intermediate alcohol 7 | 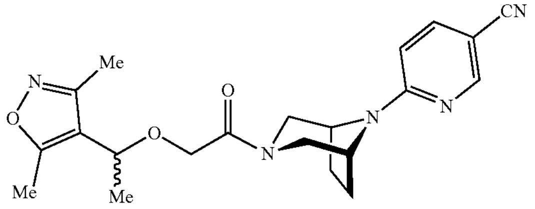 Racemic 6-(3-(2-(1-(3,5-dimethylisoxazol-4-yl)ethoxy)acetyl)-3,8-diazabicyclo[3.2.1]octan-8-yl)nicotinonitrile | 396.2 [M + H]$^+$ |

-continued

| Example | Starting Alcohol | Structure | LCMS (m/z) |
|---|---|---|---|
| 198 | 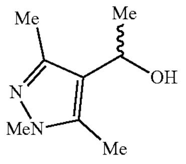 Intermediate alcohol 8 | 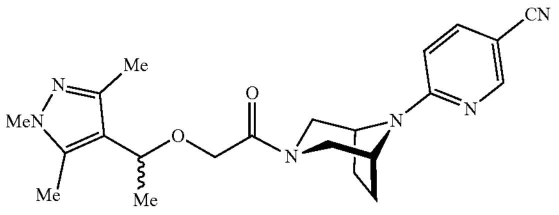 Racemic 6-(3-(2-(1-(1,3,5-trimethyl-1H-pyrazol-4-yl)ethoxy)acetyl)-3,8-diazabicyclo[3.2.1]octan-8-yl)nicotinonitrile | 409.2 $[M + H]^+$ |
| 199 | 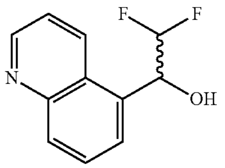 [SMILES: OC(c1cccc2ncccc12)C(F)F] Intermediate alcohol 9 | 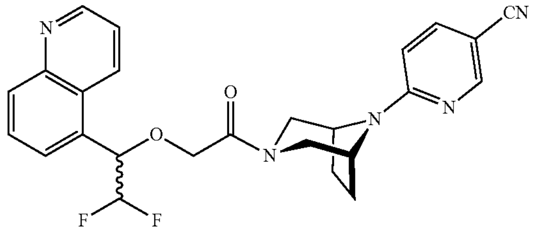 Racemic 6-(3-(2-(2,2-difluoro-1-(quinolin-5-yl)ethoxy)acetyl)-3,8-diazabicyclo[3.2.1]octan-8-yl)nicotinonitrile | 464.0 $[M + H]^+$ |
| 200 | 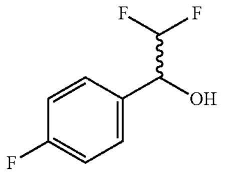 [SMILES: OC(c1ccc(F)cc1)C(F)F] Intermediate alcohol 10 | 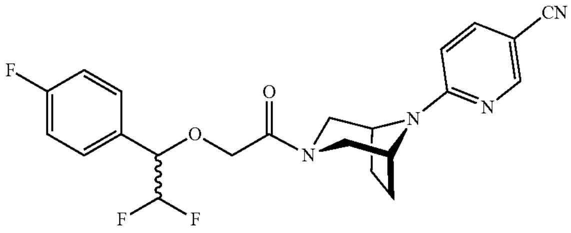 Racemic 6-(3-(2-(2,2-difluoro-1-(4-fluorophenyl)ethoxy)acetyl)-3,8-diazabicyclo[3.2.1]octan-8-yl)nicotinonitrile | 431.1 $[M + H]^+$ |
| 201 | 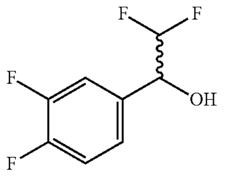 [SMILES: OC(c1ccc(F)c(F)c1)C(F)F] Intermediate alcohol 11 | 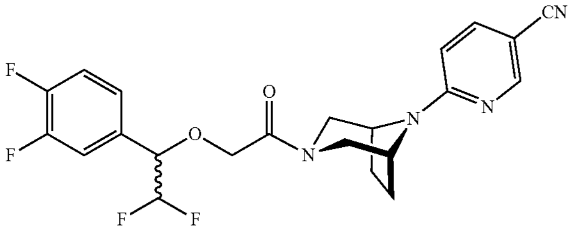 Racemic 6-(3-(2-(1-(3,4-difluorophenyl)-2,2-difluoroethoxy)acetyl)-3,8-diazabicyclo[3.2.1]octan-8-yl)nicotinonitrile | 449.0 $[M + H]^+$ |
| 202 | 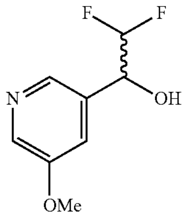 [SMILES: COc1cncc(C(O)C(F)F)c1] Intermediate alcohol 12 | 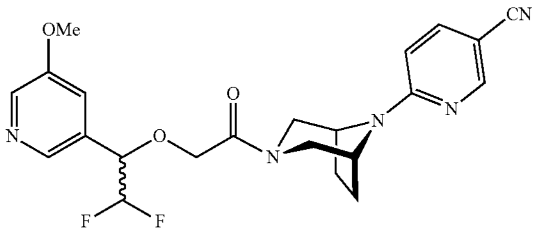 Racemic 6-(3-(2-(2,2-difluoro-1-(5-methoxypyridin-3-yl)ethoxy)acetyl)-3,8-diazabicyclo[3.2.1]octan-8-yl)nicotinonitrile | 444.1 $[M + H]^+$ |

-continued

| Example | Starting Alcohol | Structure | LCMS (m/z) |
|---|---|---|---|
| 203 | 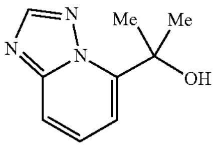 [SMILES: CC(C)(O)c1cccc2ncnn12] Intermediate alcohol 13 | 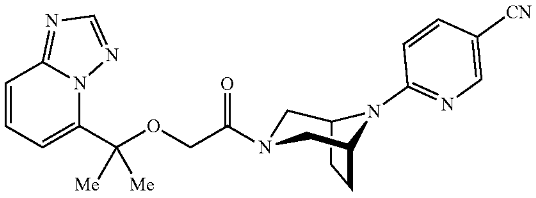 Racemic 6-(3-(2-((2-([1,2,4]triazolo[1,5-a]pyridin-5-yl)propan-2-yl)oxy)acetyl)-3,8-diazabicyclo[3.2.1]octan-8-yl)nicotinonitrile | 432.3 $[M + H]^+$ |
| 204 | 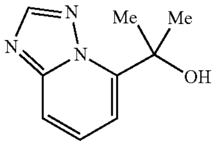 [SMILES: CC(C)(O)c1cccc2ncnn12] Intermediate alcohol 14 | 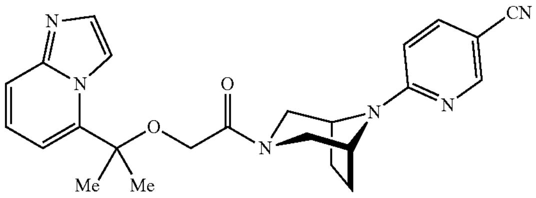 Racemic 6-(3-(2-((2-(imidazo[1,2-a]pyridin-5-yl)propan-2-yl)oxy)acetyl)-3,8-diazabicyclo[3.2.1]octan-8-yl)nicotinonitrile | 431.5 $[M + H]^+$ |
| 205 | 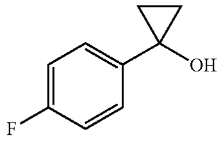 [SMILES: OC1(c2ccc(F)cc2)CC1] Intermediate alcohol 16 | 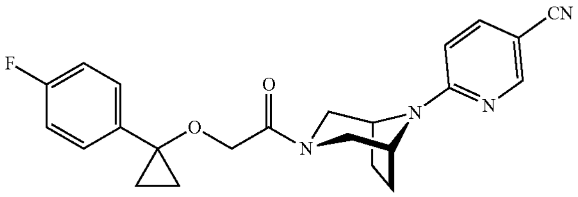 6-(3-(2-(1-(4-fluorophenyl)cyclopropoxy)acetyl)-3,8-diazabicyclo[3.2.1]octan-8-yl)nicotinonitrile | 407.1 $[M + H]^+$ |
| 206 | 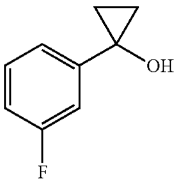 [SMILES: OC1(c2cccc(F)c2)CC1] Intermediate alcohol 17 | 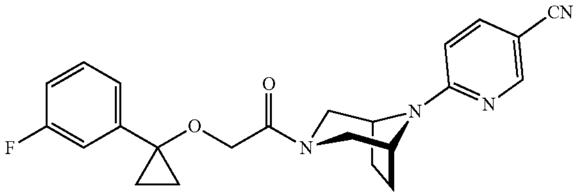 6-(3-(2-(1-(3-fluorophenyl)cyclopropoxy)acetyl)-3,8-diazabicyclo[3.2.1]octan-8-yl)nicotinonitrile | 407.1 $[M + H]^+$ |
| 207 | 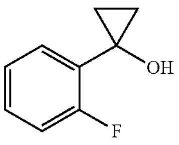 [SMILES: OC1(c2ccccc2F)CC1] Intermediate alcohol 18 | 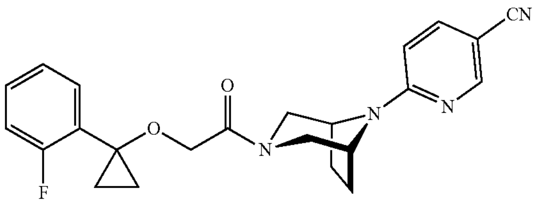 6-(3-(2-(1-(2-fluorophenyl)cyclopropoxy)acetyl)-3,8-diazabicyclo[3.2.1]octan-8-yl)nicotinonitrile | 407.1 $[M + H]^+$ |

-continued

| Example | Starting Alcohol | Structure | LCMS (m/z) |
|---|---|---|---|
| 208 | 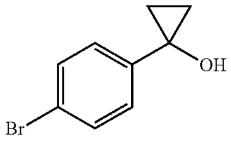 [SMILES: OC1(c2ccc(Br)cc2)CC1] Intermediate alcohol 19 | 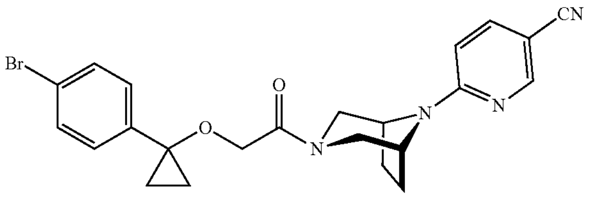 6-(3-(2-(1-(4-bromophenyl)cyclopropoxy)acetyl)-3,8-diazabicyclo[3.2.1]octan-8-yl)nicotinonitrile | 466.9, 468.9 $[M + H]^+$ |
| 209 | 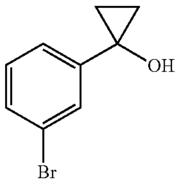 [SMILES: OC1(c2cccc(Br)c2)CC1] Intermediate alcohol 20 | 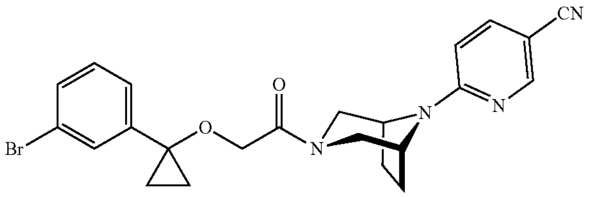 6-(3-(2-(1-(3-bromophenyl)cyclopropoxy)acetyl)-3,8-diazabicyclo[3.2.1]octan-8-yl)nicotinonitrile | 466.9, 468.9 $[M + H]^+$ |
| 210 | 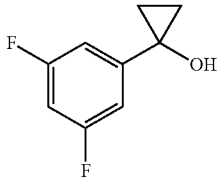 [SMILES: OC1(c2cc(F)cc(F)c2)CC1] Intermediate alcohol 21 | 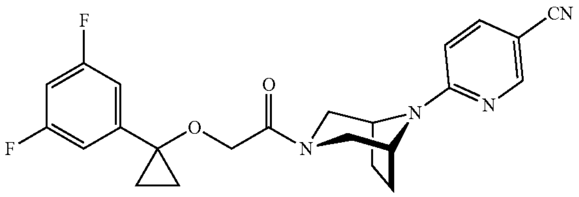 6-(3-(2-(1-(3,5-difluorophenyl)cyclopropoxy)acetyl)-3,8-diazabicyclo[3.2.1]octan-8-yl)nicotinonitrile | 425.1 $[M + H]^+$ |
| 211 | 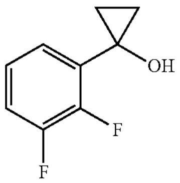 [SMILES: OC1(c2cccc(F)c2F)CC1] Intermediate alcohol 22 | 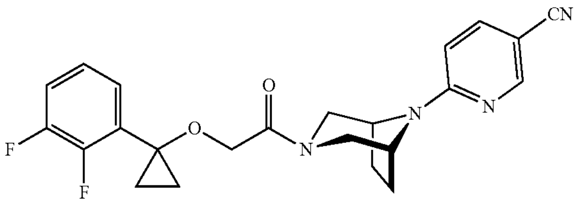 6-(3-(2-(1-(2,3-difluorophenyl)cyclopropoxy)acetyl)-3,8-diazabicyclo[3.2.1]octan-8-yl)nicotinonitrile | 425.1 $[M + H]^+$ |
| 212 | 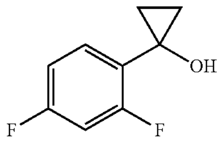 [SMILES: OC1(c2ccc(F)cc2F)CC1] Intermediate alcohol 23 | 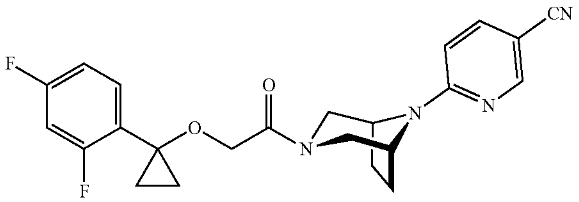 6-(3-(2-(1-(2,3-difluorophenyl)cyclopropoxy)acetyl)-3,8-diazabicyclo[3.2.1]octan-8-yl)nicotinonitrile | 425.1 $[M + H]^+$ |

-continued

| Example | Starting Alcohol | Structure | LCMS (m/z) |
|---|---|---|---|
| 213 | 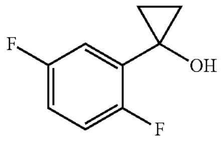 [SMILES: OC1(c2cc(F)ccc2F)CC1] Intermediate alcohol 24 | 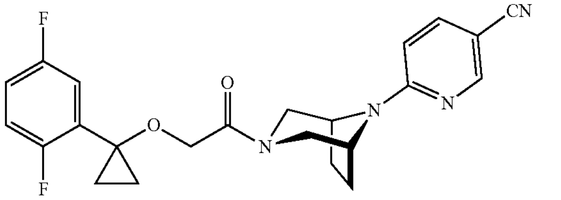 6-(3-(2-(1-(2,5-difluorophenyl)cyclopropoxy)acetyl)-3,8-diazabicyclo[3.2.1]octan-8-yl)nicotinonitrile | 425.1 [M + H]+ |
| 214 | 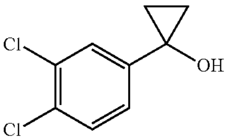 [SMILES: OC1(c2ccc(Cl)c(Cl)c2)CC1] Intermediate alcohol 25 | 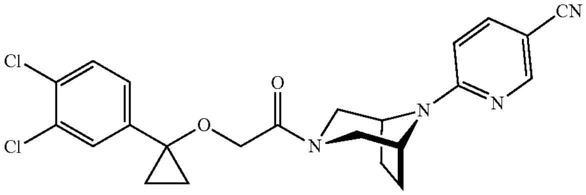 6-(3-(2-(1-(3,4-dichlorophenyl)cyclopropoxy)acetyl)-3,8-diazabicyclo[3.2.1]octan-8-yl)nicotinonitrile | 456.9, 458.9 [M + H]+ |
| 215 | 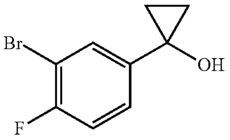 Intermediate alcohol 26 | 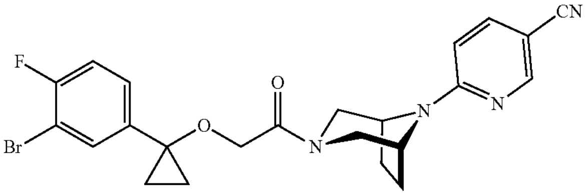 6-(3-(2-(1-(3-bromo-4-fluorophenyl)cyclopropoxy)acetyl)-3,8-diazabicyclo[3.2.1]octan-8-yl)nicotinonitrile | 487.0, 489.0 [M + H]+ |
| 216 | 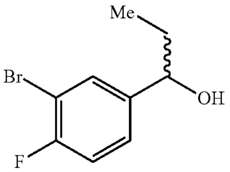 [SMILES: CCC(O)c1ccc(F)c(Br)c1] Intermediate alcohol 27 | 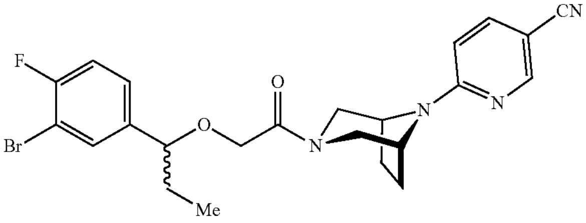 Racemic 6-(3-(2-(1-(3-bromo-4-fluorophenyl)propoxy)acetyl)-3,8-diazabicyclo[3.2.1]octan-8-yl)nicotinonitrile | 485.0, 487.0 [M + H]+ |
| 217 | 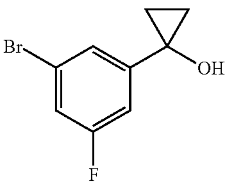 [SMILES: OC1(c2cc(F)cc(Br)c2)CC1] Intermediate alcohol 28 | 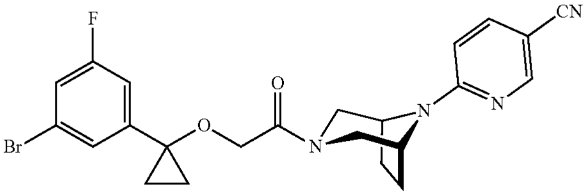 6-(3-(2-(1-(3-bromo-5-fluorophenyl)cyclopropoxy)acetyl)-3,8-diazabicyclo[3.2.1]octan-8-yl)nicotinonitrile | 487.0, 489.0 [M + H]+ |

-continued

| Example | Starting Alcohol | Structure | LCMS (m/z) |
|---|---|---|---|
| 218 | 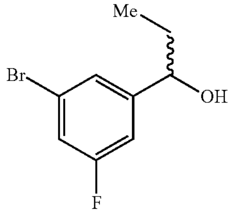 [SMILES: CCC(O)c1cc(F)cc(Br)c1]<br>Intermediate alcohol 29 | 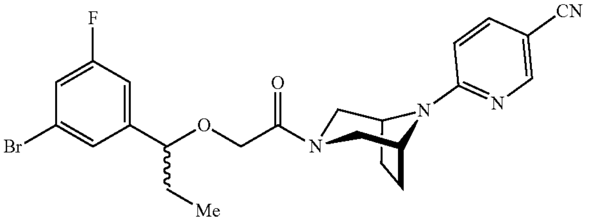<br>Racemic 6-(3-(2-(1-(3-bromo-5-fluorophenyl)propoxy)acetyl)-3,8-diazabicyclo[3.2.1]octan-8-yl)nicotinonitrile | 485.0, 487.0 $[M + H]^+$ |
| 219 | 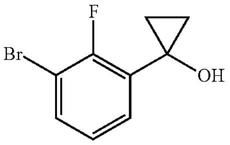<br>Intermediate alcohol 30 | 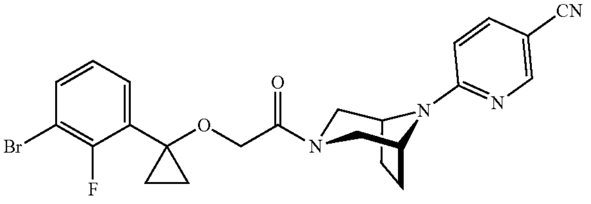<br>6-(3-(2-(1-(3-bromo-2-fluorophenyl)cyclopropoxy)acetyl)-3,8-diazabicyclo[3.2.1]octan-8-yl)nicotinonitrile | 485.0, 487.0 $[M + H]^+$ |
| 220 | 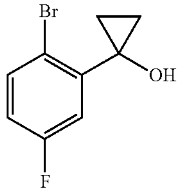 [SMILES: OC1(c2cc(F)ccc2Br)CC1]<br>Intermediate alcohol 31 | 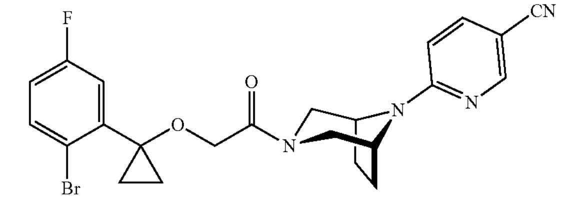<br>6-(3-(2-(1-(2-bromo-5-fluorophenyl)cyclopropoxy)acetyl)-3,8-diazabicyclo[3.2.1]-8-yl)nicotinonitrile | 485.0, 487.0 $[M + H]^+$ |
| 221 | 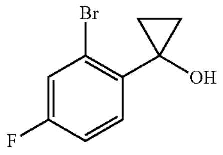 [SMILES: OC1(c2ccc(F)cc2Br)CC1]<br>Intermediate alcohol 32 | 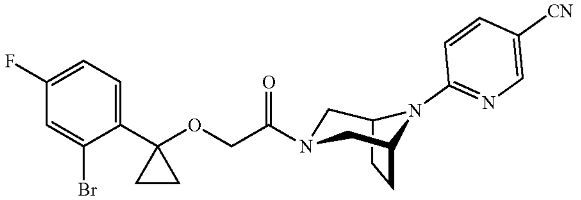<br>6-(3-(2-(1-(2-bromo-4-fluorophenyl)cyclopropoxy)acetyl)-3,8-diazabicyclo[3.2.1]octan-8-yl)nicotinonitrile | 485.0, 487.0 $[M + H]^+$ |
| 222 | 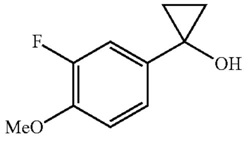 [SMILES: COc1ccc(C2(O)CC2)cc1F]<br>Intermediate alcohol 33 | 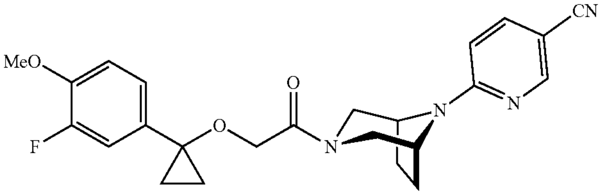<br>6-(3-(2-(1-(3-fluoro-4-methoxyphenyl)cyclopropoxy)acetyl)-3,8-diazabicyclo[3.2.1]octan-8-yl)nicotinonitrile | 437.2 $[M + H]^+$ |

-continued

| Example | Starting Alcohol | Structure | LCMS (m/z) |
|---|---|---|---|
| 223 | 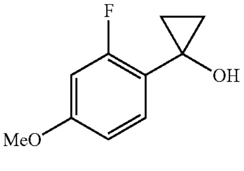 [SMILES: COc1ccc(C2(O)CC2)c(F)c1] Intermediate alcohol 34 | 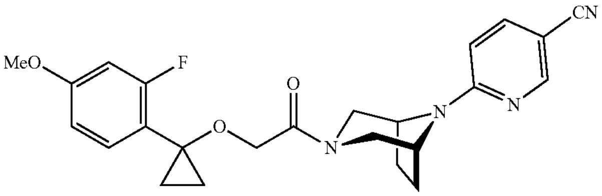 6-(3-(2-(1-(2-fluoro-4-methoxyphenyl)cyclopropoxy)acetyl)-3,8-diazabicyclo[3.2.1]octan-8-yl)nicotinonitrile | 437.2 $[M + H]^+$ |
| 224 | 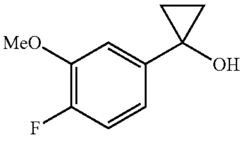 [SMILES: COc1cc(C2(O)CC2)ccc1F] Intermediate alcohol 35 | 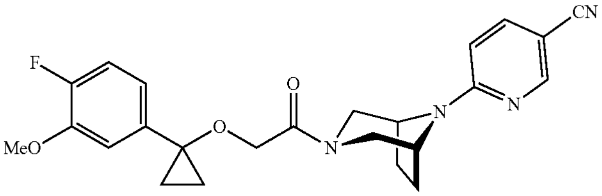 6-(3-(2-(1-(4-fluoro-3-methoxyphenyl)cyclopropoxy)acetyl)-3,8-diazabicyclo[3.2.1]octan-8-yl)nicotinonitrile | 437.2 $[M + H]^+$ |
| 225 | 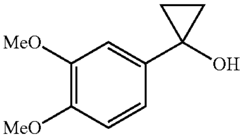 [SMILES: COc1ccc(C2(O)CC2)cc1OC] Intermediate alcohol 36 | 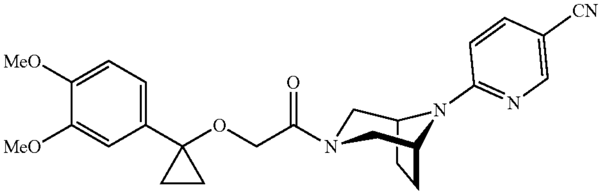 6-(3-(2-(1-(3,4-dimethoxyphenyl)cyclopropoxy)acetyl)-3,8-diazabicyclo[3.2.1]octan-8-yl)nicotinonitrile | 449.2 $[M + H]^+$ |
| 226 | 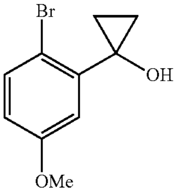 [SMILES: COc1ccc(Br)c(C2(O)CC2)c1] Intermediate alcohol 37 | 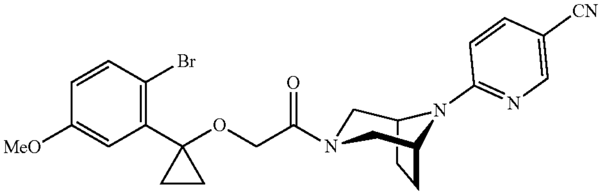 6-(3-(2-(1-(2-bromo-5-methoxyphenyl)cyclopropoxy)acetyl)-3,8-diazabicyclo[3.2.1]octan-8-yl)nicotinonitrile | 497.0, 499.0 $[M + H]^+$ |
| 227 | 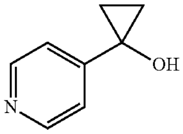 Intermediate alcohol 38 | 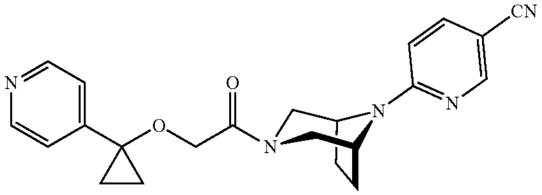 6-(3-(2-(1-(pyridin-4-yl)cyclopropoxy)acetyl)-3,8-diazabicyclo[3.2.1]octan-8-yl)nicotinonitrile | 390.1 $[M + H]^+$ |

-continued

| Example | Starting Alcohol | Structure | LCMS (m/z) |
|---|---|---|---|
| 228 | 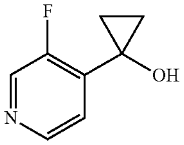 [SMILES: OC1(c2ccncc2F)CC1] Intermediate alcohol 39 | 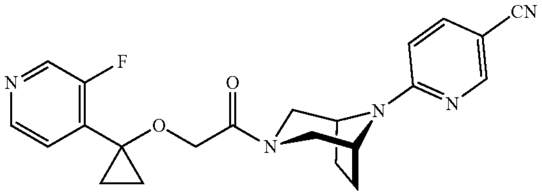 6-(3-(2-(1-(3-fluoropyridin-4-yl)cyclopropoxy)acetyl)-3,8-diazabicyclo[3.2.1]octan-8-yl)nicotinonitrile | 408.1 $[M + H]^+$ |
| 229 | 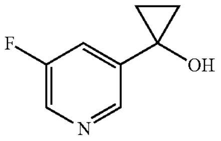 [SMILES: OC1(c2cncc(F)c2)CC1] Intermediate alcohol 40 | 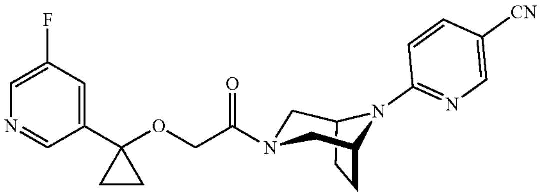 6-(3-(2-(1-(5-fluoropyridin-3-yl)cyclopropoxy)acetyl)-3,8-diazabicyclo[3.2.1]octan-8-yl)nicotinonitrile | 408.1 $[M + H]^+$ |
| 230 | 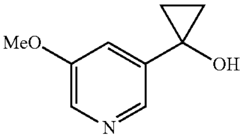 [SMILES: COc1cncc(C2(O)CC2)c1] Intermediate alcohol 41 | 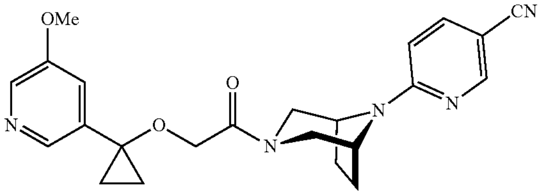 6-(3-(2-(1-(5-methoxypyridin-3-yl)cyclopropoxy)acetyl)-3,8-diazabicyclo[3.2.1]octan-8-yl)nicotinonitrile | 420.1 $[M + H]^+$ |
| 231 | 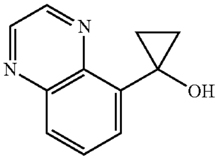 [SMILES: OC1(c2cccc3nccnc23)CC1] Intermediate alcohol 42 | 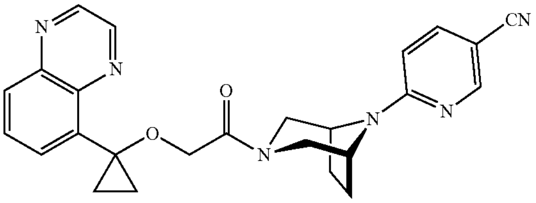 6-(3-(2-(1-(quinoxalin-5-yl)cyclopropoxy)acetyl)-3,8-diazabicyclo[3.2.1]octan-8-yl)nicotinonitrile | 441.3 $[M + H]^+$ |
| 232 | 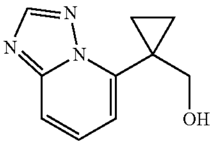 [SMILES: OCC1(c2cccc3ncnn23)CC1] Intermediate alcohol 43 | 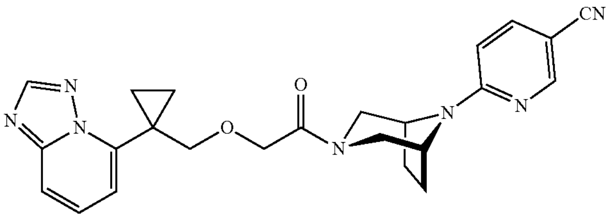 6-(3-(2-((1-([1,2,4]triazolo[1,5-a]pyridin-5-yl)cyclopropyl)methoxy)acetyl)-3,8-diazabicyclo[3.2.1]octan-8-yl)nicotinonitrile | 444.20 $[M + H]^+$ |

-continued

| Example | Starting Alcohol | Structure | LCMS (m/z) |
|---|---|---|---|
| 233 | 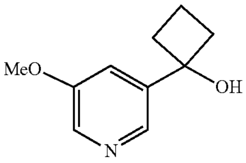 [SMILES: COc1cncc(C2(O)CCC2)c1]<br>Intermediate alcohol 44 | 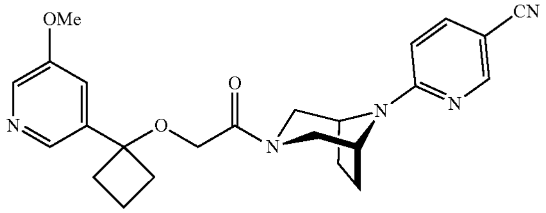<br>6-(3-(2-(1-(5-methoxypyridin-3-yl)cyclobutoxy)acetyl)-3,8-diazabicyclo[3.2.1]octan-8-yl)nicotinonitrile | 434.1 $[M + H]^+$ |
| 234 | 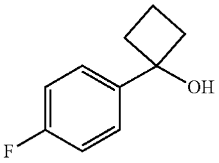 [SMILES: OC1(c2ccc(F)cc2)CCC1]<br>Intermediate alcohol 45 | 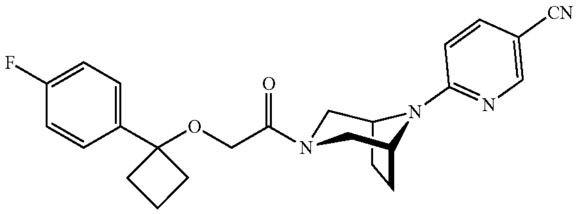<br>6-(3-(2-(1-(4-fluorophenyl)cyclobutoxy)acetyl)-3,8-diazabicyclo[3.2.1]octan-8-yl)nicotinonitrile | 443.0 $[M + H]^+$ |
| 235 | 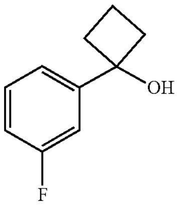 [SMILES: OC1(c2cccc(F)c2)CCC1]<br>Intermediate alcohol 46 | 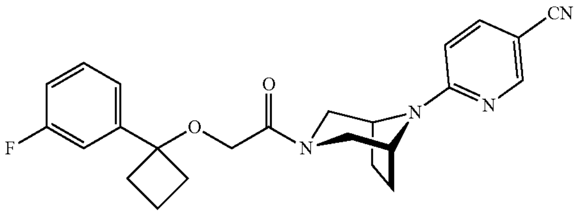<br>6-(3-(2-(1-(3-fluorophenyl)cyclobutoxy)acetyl)-3,8-diazabicyclo[3.2.1]octan-8-yl)nicotinonitrile | 443.0 $[M + H]^+$ |
| 236 | 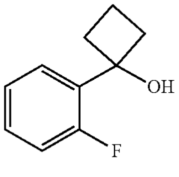 [SMILES: OC1(c2ccccc2F)CCC1]<br>Intermediate alcohol 47 | 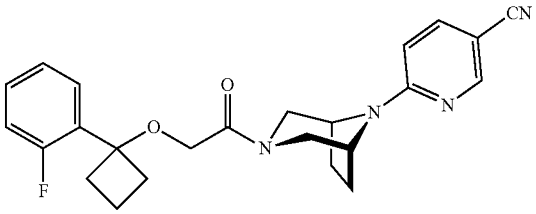<br>6-(3-(2-(1-(2-fluorophenyl)cyclobutoxy)acetyl)-3,8-diazabicyclo[3.2.1]octan-8-yl)nicotinonitrile | 443.0 $[M + H]^+$ |
| 237 | 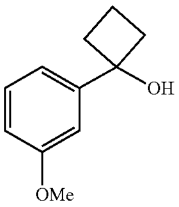 [SMILES: COc1cccc(C2(O)CCC2)c1]<br>Intermediate alcohol 48 | 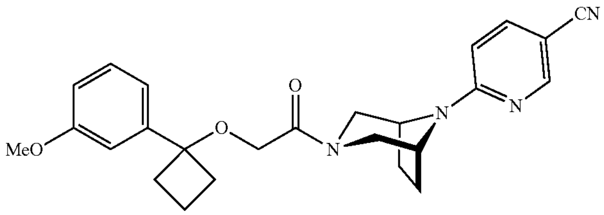<br>6-(3-(2-(1-(3-methoxyphenyl)cyclobutoxy)acetyl)-3,8-diazabicyclo[3.2.1]octan-8-yl)nicotinonitrile | 455.1 $[M + H]^+$ |

-continued

| Example | Starting Alcohol | Structure | LCMS (m/z) |
|---|---|---|---|
| 238 | 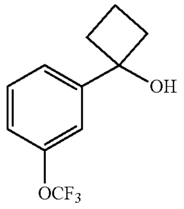 [SMILES: OC1(c2cccc(OC(F)(F)F)c2)CCC1] Intermediate alcohol 49 | 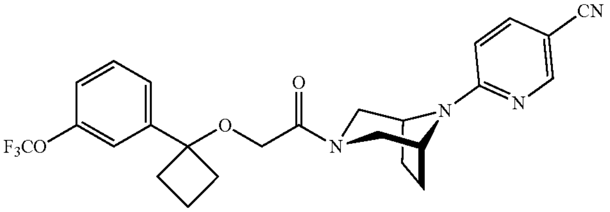 6-(3-(2-(1-(3-(trifluoromethoxy)phenyl)cyclobutoxy)acetyl)-3,8-diazabicyclo[3.2.1]octan-8-yl)nicotinonitrile | 487.0 $[M + H]^+$ |
| 239 | 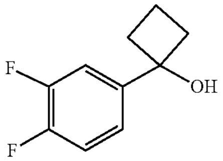 [SMILES: OC1(c2ccc(F)c(F)c2)CCC1] Intermediate alcohol 50 | 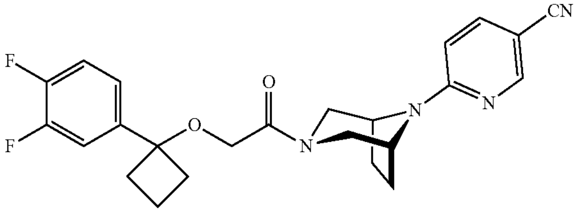 (3-(2-(1-(3,4-difluorophenyl)cyclobutoxy)acetyl)-3,8-diazabicyclo[3.2.1]octan-8-yl)nicotinonitrile | 462.0 $[M + H]^+$ |
| 240 | 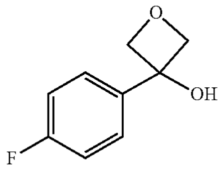 [SMILES: OC1(c2ccc(F)cc2)COC1] Intermediate alcohol 51 | 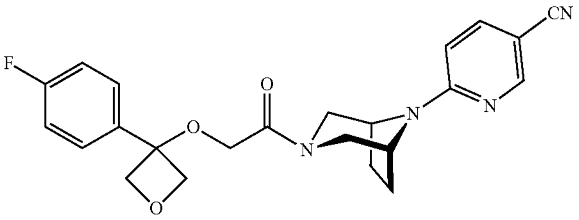 (3-(2-((3-(4-fluorophenyl)oxetan-3-yl)oxy)acetyl)-3,8-diazabicyclo[3.2.1]octan-8-yl)nicotinonitrile | 423.1 $[M + H]^+$ |
| 241 | 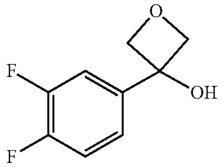 [SMILES: OC1(c2ccc(F)c(F)c2)COC1] Intermediate alcohol 52 | 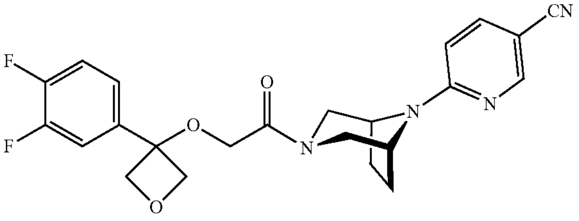 (3-(2-((3-(3,4-difluorophenyl)oxetan-3-yl)oxy)acetyl)-3,8-diazabicyclo[3.2.1]octan-8-yl)nicotinonitrile | 441.0 $[M + H]^+$ |
| 242 | 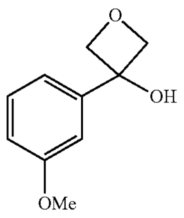 [SMILES: COc1cccc(C2(O)COC2)c1] Intermediate alcohol 53 | 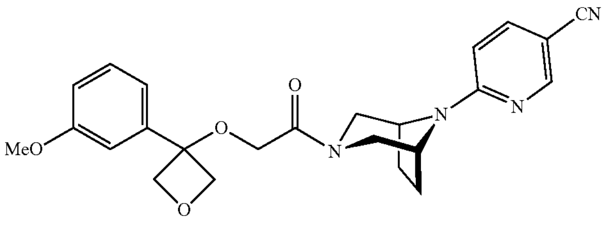 (3-(2-((3-(3-methoxyphenyl)oxetan-3-yl)oxy)acetyl)-3,8-diazabicyclo[3.2.1]octan-8-yl)nicotinonitrile | 435.1 $[M + H]^+$ |

-continued

| Example | Starting Alcohol | Structure | LCMS (m/z) |
|---|---|---|---|
| 243 | 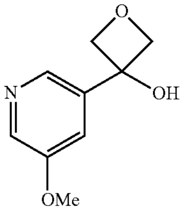 [SMILES: COc1cncc(C2(O)COC2)c1] Intermediate alcohol 54 | 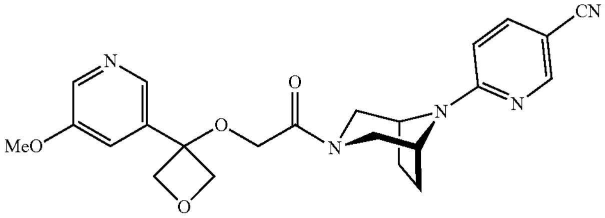 6-(3-(2-((3-(5-methoxypyridin-3-yl)oxetan-3-yl)oxy)acetyl)-3,8-diazabicyclo [3.2.1]octan-8-yl)nicotinonitrile | 436.1 [M + H]+ |
| 244 | 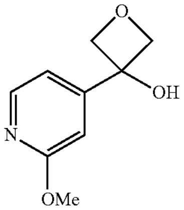 [SMILES: COc1cc(C2(O)COC2)ccn1] Intermediate alcohol 55 | 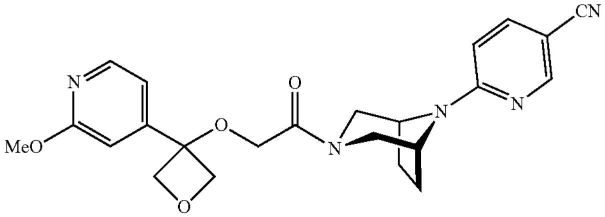 6-(3-(2-((3-(2-methoxypyridin-4-yl)oxetan-3-yl)oxy)acetyl)-3,8-diazabicyclo[3.2.1]octan-8-yl)nicotinonitrile | 436.1 [M + H]+ |
| 245 | 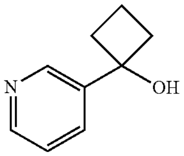 [SMILES: OC1(c2cccnc2)CCC1] Intermediate alcohol 56 | 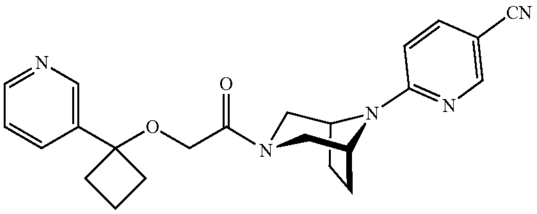 6-(3-(2-(1-(pyridin-3-yl)cyclobutoxy)acetyl)-3,8-diazabicyclo[3.2.1]octan-8-yl)nicotinonitrile | 404.1 [M + H]+ |
| 246 | 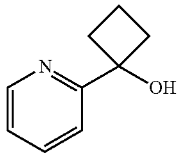 [SMILES: OC1(c2ccccn2)CCC1] Intermediate alcohol 57 | 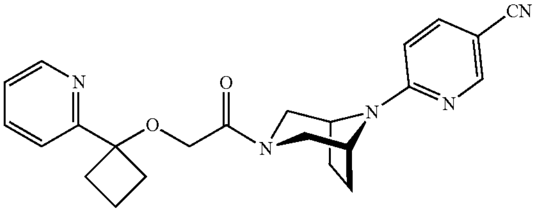 6-(3-(2-(1-(pyridin-2-yl)cyclobutoxy)acetyl)-3,8-diazabicyclo[3.2.1]octan-8-yl)nicotinonitrile | 404.1 [M + H]+ |
| 247 | 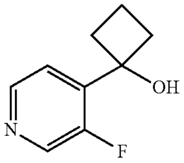 [SMILES: OC1(c2ccncc2F)CCC1] Intermediate alcohol 58 | 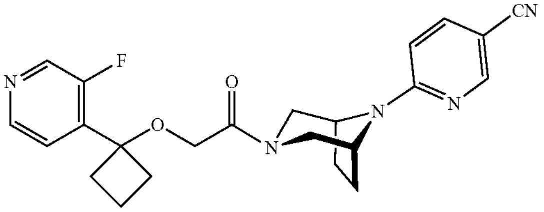 6-(3-(2-(1-(3-fluoropyridin-4-yl)cyclobutoxy)acetyl)-3,8-diazabicyclo[3.2.1]octan-8-yl)nicotinonitrile | 422.2 [M + H]+ |

-continued

| Example | Starting Alcohol | Structure | LCMS (m/z) |
|---|---|---|---|
| 248 | 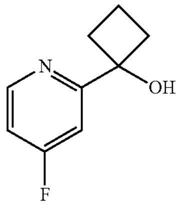 [SMILES: OC1(c2cc(F)ccn2)CCC1] Intermediate alcohol 59 | 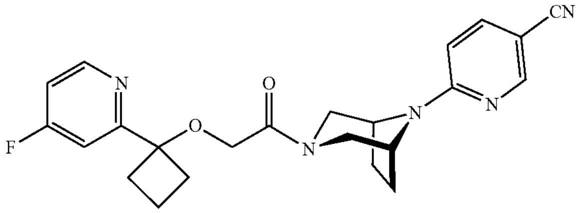 6-(3-(2-(1-(4-fluoropyridin-2-yl)cyclobutoxy)acetyl)-3,8-diazabicyclo[3.2.1]octan-8-yl)nicotinonitrile | 422.1 $[M + H]^+$ |
| 249 | 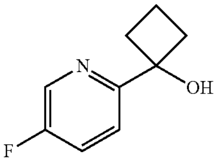 [SMILES: OC1(c2ccc(F)cn2)CCC1] Intermediate alcohol 60 | 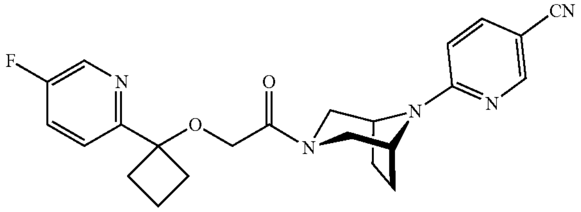 6-(3-(2-(1-(5-fluoropyridin-2-yl)cyclobutoxy)acetyl)-3,8-diazabicyclo[3.2.1]octan-8-yl)nicotinonitrile | 422.1 $[M + H]^+$ |
| 250 | 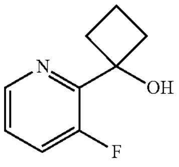 [SMILES: OC1(c2ncccc2F)CCC1] Intermediate alcohol 61 | 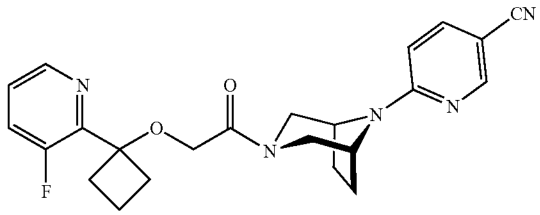 6-(3-(2-(1-(3-fluoropyridin-2-yl)cyclobutoxy)acetyl)-3,8-diazabicyclo[3.2.1]octan-8-yl)nicotinonitrile | 422.1 $[M + H]^+$ |
| 251 | 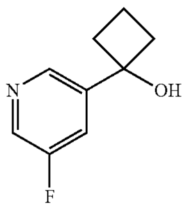 [SMILES: OC1(c2cncc(F)c2)CCC1] Intermediate alcohol 62 | 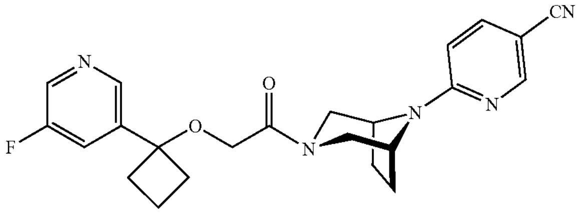 6-(3-(2-(1-(5-fluoropyridin-3-yl)cyclobutoxy)acetyl)-3,8-diazabicyclo[3.2.1]octan-8-yl)nicotinonitrile | 422.2 $[M + H]^+$ |
| 252 | 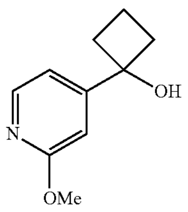 [SMILES: COc1cc(C2(O)CCC2)ccn1] Intermediate alcohol 63 | 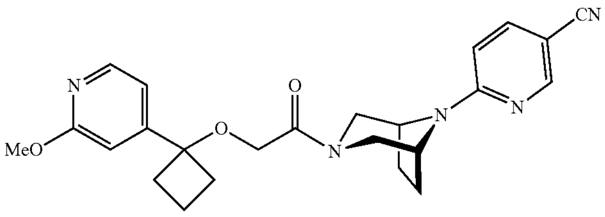 6-(3-(2-(1-(2-methoxypyridin-4-yl)cyclobutoxy)acetyl)-3,8-diazabicyclo[3.2.1]octan-8-yl)nicotinonitrile | 434.1 $[M + H]^+$ |

-continued

| Example | Starting Alcohol | Structure | LCMS (m/z) |
|---|---|---|---|
| 253 | 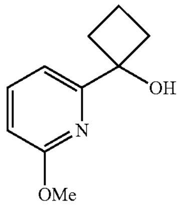 [SMILES: COc1cccc(C2(O)CCC2)n1] Intermediate alcohol 64 | 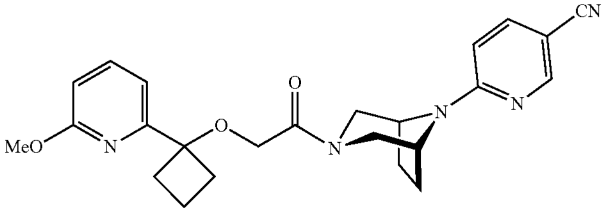 6-(3-(2-(1-(6-methoxypyridin-2-yl)cyclobutoxy)acetyl)-3,8-diazabicyclo[3.2.1]octan-8-yl)nicotinonitrile | 434.1 $[M + H]^+$ |
| 254 | 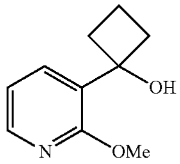 [SMILES: COc1ncccc1C1(O)CCC1] Intermediate alcohol 65 | 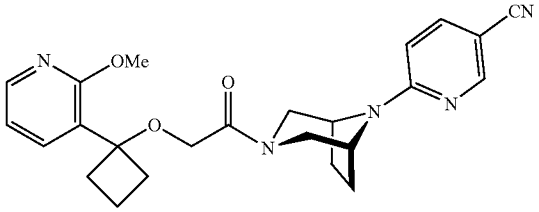 6-(3-(2-(1-(2-methoxypyridin-3-yl)cyclobutoxy)acetyl)-3,8-diazabicyclo[3.2.1]octan-8-yl)nicotinonitrile | 434.1 $[M + H]^+$ |
| 255 | 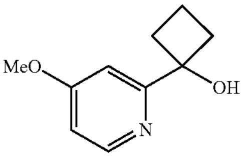 [SMILES: COc1ccnc(C2(O)CCC2)c1] Intermediate alcohol 66 | 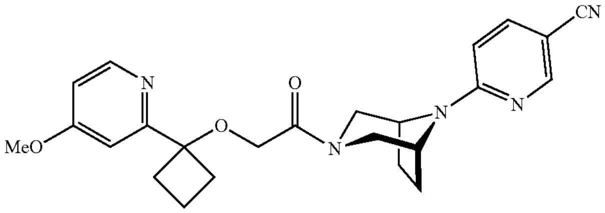 6-(3-(2-(1-(4-methoxypyridin-2-yl)cyclobutoxy)acetyl)-3,8-diazabicyclo[3.2.1]octan-8-yl)nicotinonitrile | 434.1 $[M + H]^+$ |
| 256 | 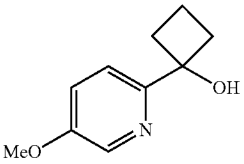 [SMILES: COc1ccc(C2(O)CCC2)nc1] Intermediate alcohol 67 | 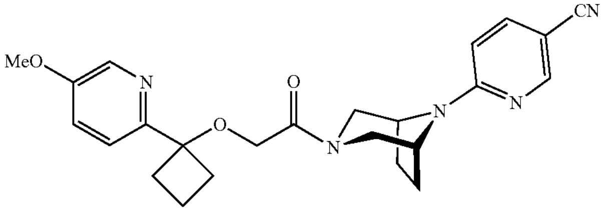 6-(3-(2-(1-(5-methoxypyridin-2-yl)cyclobutoxy)acetyl)-3,8-diazabicyclo[3.2.1]octan-8-yl)nicotinonitrile | 434.1 $[M + H]^+$ |
| 257 | 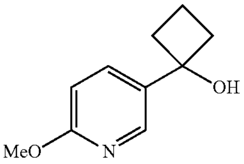 [SMILES: COc1ccc(C2(O)CCC2)cn1] Intermediate alcohol 68 | 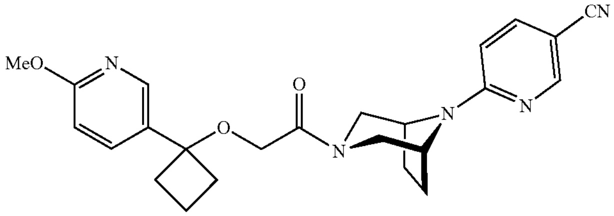 6-(3-(2-(1-(6-methoxypyridin-3-yl)cyclobutoxy)acetyl)-3,8-diazabicyclo[3.2.1]octan-8-yl)nicotinonitrile | 434.1 $[M + H]^+$ |

-continued

| Example | Starting Alcohol | Structure | LCMS (m/z) |
|---|---|---|---|
| 258 | 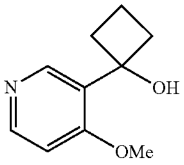 [SMILES: COc1ccncc1C1(O)CCC1] Intermediate alcohol 69 | 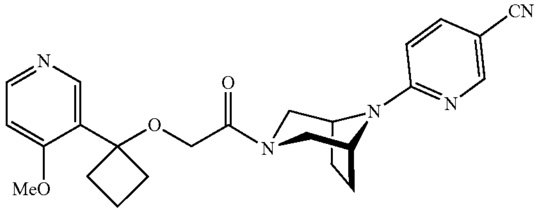 6-(3-(2-(1-(4-methoxypyridin-3-yl)cyclobutoxy)acetyl)-3,8-diazabicyclo[3.2.1]octan-8-yl)nicotinonitrile | 434.1 [M + H]+ |
| 259 | 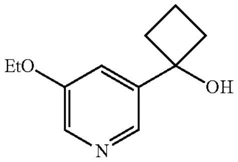 Intermediate alcohol 70 | 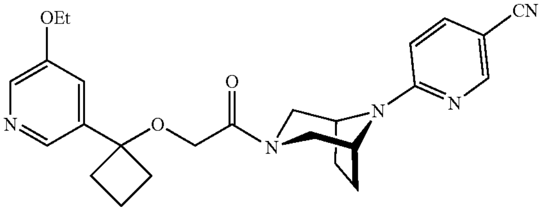 6-(3-(2-(1-(5-ethoxypyridin-3-yl)cyclobutoxy)acetyl)-3,8-diazabicyclo[3.2.1]octan-8-yl)nicotinonitrile | 448.1 [M + H]+ |
| 260 | 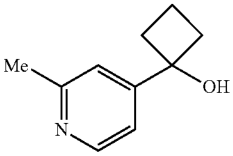 [SMILES: Cc1cc(C2(O)CCC2)ccn1] Intermediate alcohol 71 | 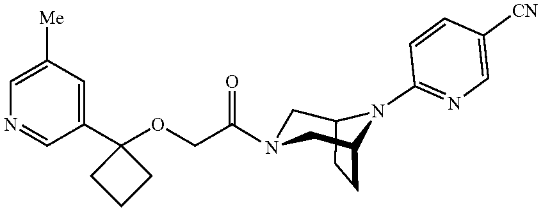 6-(3-(2-(1-(2-methylpyridin-4-yl)cyclobutoxy)acetyl)-3,8-diazabicyclo[3.2.1]octan-8-yl)nicotinonitrile | 418.1 [M + H]+ |
| 261 | 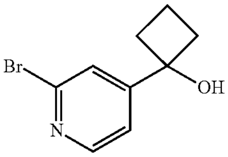 [SMILES: OC1(c2ccnc(Br)c2)CCC1] Intermediate alcohol 72 | 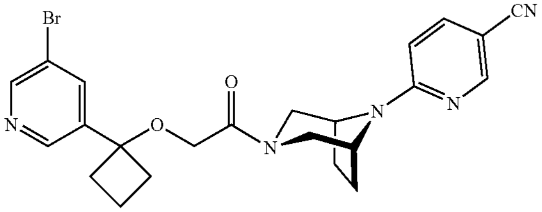 6-(3-(2-(1-(2-bromopyridin-4-yl)cyclobutoxy)acetyl)-3,8-diazabicyclo[3.2.1]octan-8-yl)nicotinonitrile | 482.0, 484.0 [M + H]+ |
| 262 | 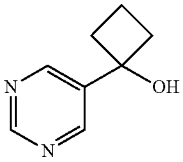 [SMILES: OC1(c2cncnc2)CCC1] Intermediate alcohol 73 | 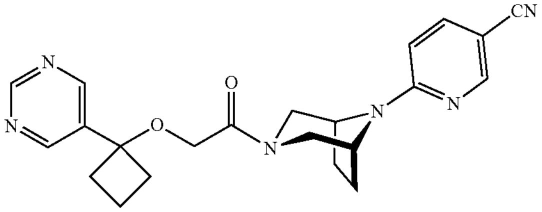 6-(3-(2-(1-(pyrimidin-5-yl)cyclobutoxy)acetyl)-3,8-diazabicyclo[3.2.1]octan-8-yl)nicotinonitrile | 405.2 [M + H]+ |

-continued

| Example | Starting Alcohol | Structure | LCMS (m/z) |
|---|---|---|---|
| 263 | 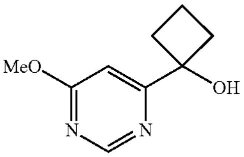 [SMILES: COc1cc(C2(O)CCC2)ncn1] Intermediate alcohol 74 | 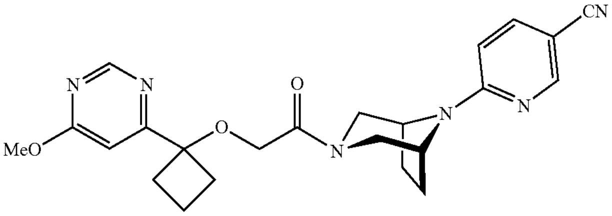 6-(3-(2-(1-(6-methoxypyrimidin-4-yl)cyclobutoxy)acetyl)-3,8-diazabicyclo[3.2.1]octan-8-yl)nicotinonitrile | 435.1 $[M + H]^+$ |
| 264 | 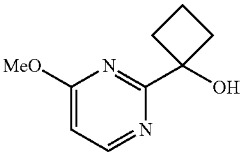 [SMILES: COc1ccnc(C2(O)CCC2)n1] Intermediate alcohol 75 | 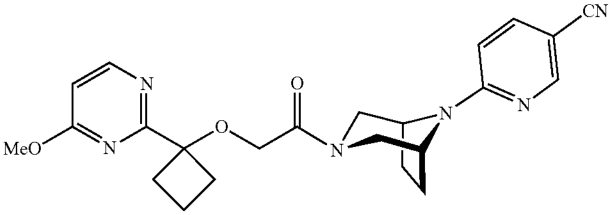 6-(3-(2-(1-(4-methoxypyrimidin-2-yl)cyclobutoxy)acetyl)-3,8-diazabicyclo[3.2.1]octan-8-yl)nicotinonitrile | 435.1 $[M + H]^+$ |
| 265 | 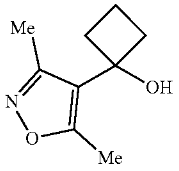 Intermediate alcohol 76 | 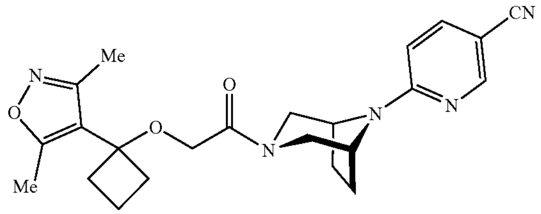 6-(3-(2-(1-(3,5-dimethylisoxazol-4-yl)cyclobutoxy)acetyl)-3,8-diazabicyclo[3.2.1]octan-8-yl)nicotinonitrile | 422.1 $[M + H]^+$ |
| 266 | 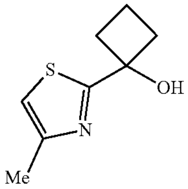 [SMILES: Cc1csc(C2(O)CCC2)n1] Intermediate alcohol 77 | 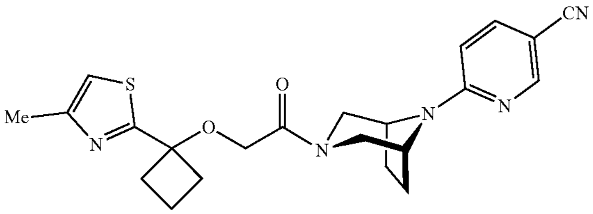 6-(3-(2-(1-(4-methylthiazol-2-yl)cyclobutoxy)acetyl)-3,8-diazabicyclo[3.2.1]octan-8-yl)nicotinonitrile | 424.1 $[M + H]^+$ |
| 267 | 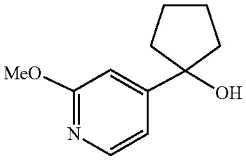 [SMILES: COc1cc(C2(O)CCCC2)ccn1] Intermediate alcohol 78 | 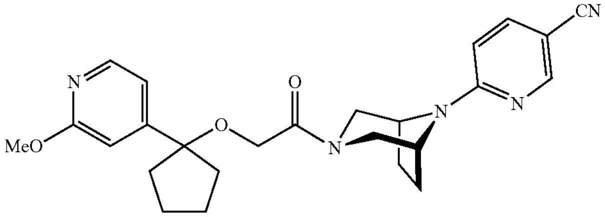 6-(3-(2-((1-(2-methoxypyridin-4-yl)cyclopentyl)oxy)acetyl)-3,8-diazabicyclo[3.2.1]octan-8-yl)nicotinonitrile | 448.1 $[M + H]^+$ |

-continued

| Example | Starting Alcohol | Structure | LCMS (m/z) |
| --- | --- | --- | --- |
| 268 | 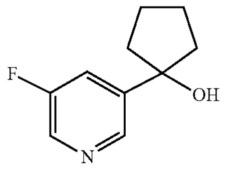 [SMILES: OC1(c2cncc(F)c2)CCCC1] Intermediate alcohol 79 | 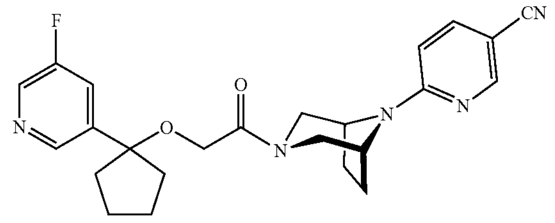 6-(3-(2-((1-(5-fluoropyridin-3-yl)cyclopentyl)oxy)acetyl)-3,8-diazabicyclo[3.2.1]octan-8-yl)nicotinonitrile | 436.2 [M + H]$^+$ |
| 269 | 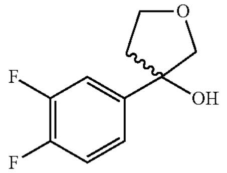 [SMILES: OC1(c2ccc(F)c(F)c2)CCOC1] Intermediate alcohol 80 | 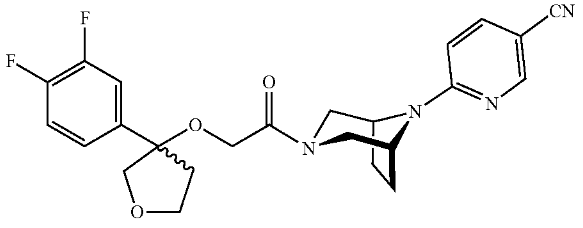 Racemic 6-(3-(2-((3-(3,4-difluorophenyl)tetrahydrofuran-3-yl)oxy)acetyl)-3,8-diazabicyclo [3.2.1]octan-8-yl)nicotinonitrile | 499.3 [M + H]$^+$ |
| 270 | 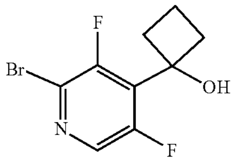 [SMILES: OC1(c2c(F)cnc(Br)c2F)CCC1] Intermediate alcohol 81 | 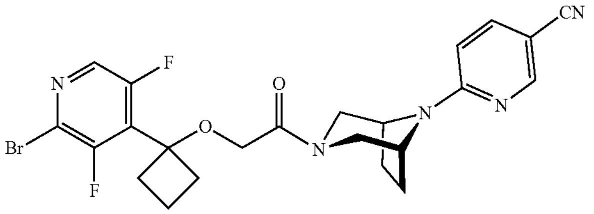 6-(3-(2-(1-(2-bromo-3,5-difluoropyridin-4-yl)cyclobutoxy)acetyl)-3,8-diazabicyclo[3.2.1]octan-8-yl)nicotinonitrile | 517.9, 519.9 [M + H]$^+$ |
| 271 | 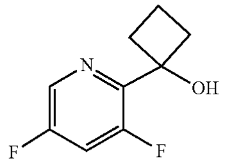 [SMILES: OC1(c2ncc(F)cc2F)CCC1] Intermediate alcohol 82 | 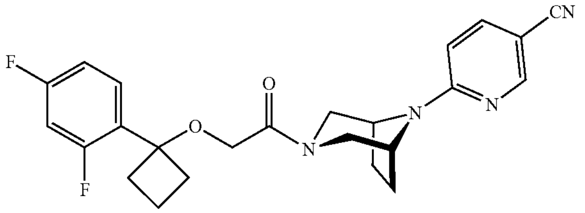 6-(3-(2-(1-(3,5-difluoropyridin-2-yl)cyclobutoxy)acetyl)-3,8-diazabicyclo[3.2.1]octan-8-yl)nicotinonitrile | 440.0 [M + H]$^+$ |
| 272 | 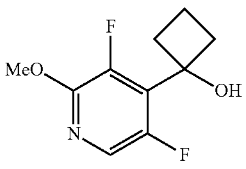 [SMILES: COc1ncc(F)c(C2(O)CCC2)c1F] Intermediate alcohol 83 | 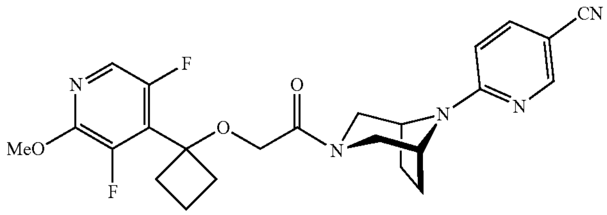 6-(3-(2-(1-(3,5-difluoro-2-methoxypyridin-4-yl)cyclobutoxy)acetyl)-3,8-diazabicyclo[3.2.1]octan-8-yl)nicotinonitrile | 470.0 [M + H]$^+$ |

-continued

| Example | Starting Alcohol | Structure | LCMS (m/z) |
|---|---|---|---|
| 273 | 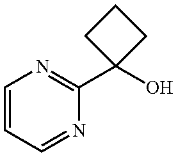 [SMILES: OC1(c2ncccn2)CCC1]<br>Intermediate alcohol 84 | 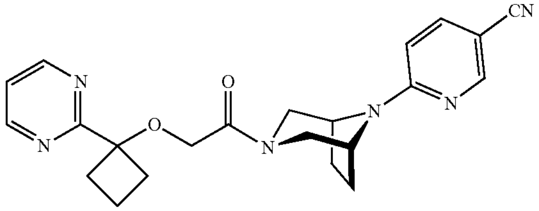<br>6-(3-(2-(1-(pyrimidin-2-yl)cyclobutoxy)acetyl)-3,8-diazabicyclo[3.2.1]octan-8-yl)nicotinonitrile | 405.2 [M + H]+ |
| 274 | 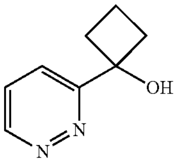 [SMILES: OC1(c2cccnn2)CCC1]<br>Intermediate alcohol 85 | 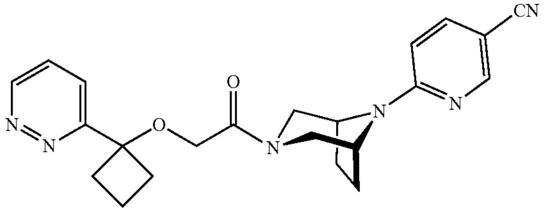<br>6-(3-(2-(1-(pyridazin-3-yl)cyclobutoxy)acetyl)-3,8-diazabicyclo[3.2.1]octan-8-yl)nicotinonitrile | 405.1 [M + H]+ |
| 275 | 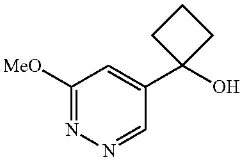 [SMILES: COc1cc(C2(O)CCC2)cnn1]<br>Intermediate alcohol 86 | 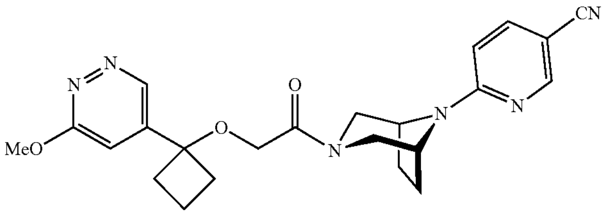<br>6-(3-(2-(1-(6-methoxypyridazin-4-yl)cyclobutoxy)acetyl)-3,8-diazabicyclo[3.2.1]octan-8-yl)nicotinonitrile | 435.1 [M + H]+ |
| 276 | 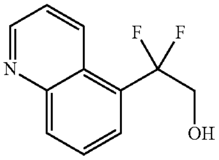 [SMILES: OCC(F)(F)c1cccc2ncccc12]<br>Intermediate alcohol 88 | 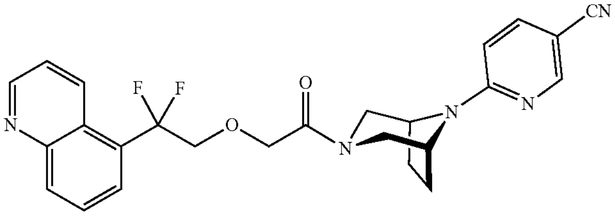<br>6-(3-(2-(2,2-difluoro-2-(quinolin-5-yl)ethoxy)acetyl)-3,8-diazabicyclo[3.2.1]octan-8-yl)nicotinonitrile | 464.0 [M + H]+ |
| 277 | 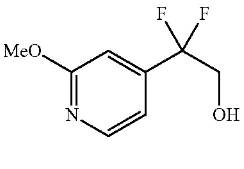 [SMILES: COc1cc(C(F)(F)CO)ccn1]<br>Intermediate alcohol 89 | 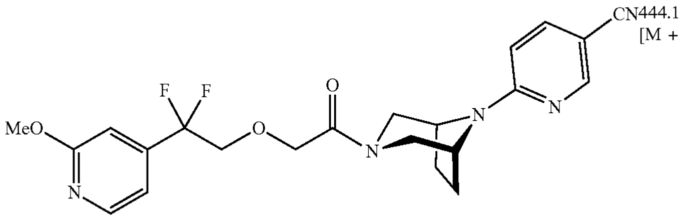<br>6-(3-(2-(2,2-difluoro-2-(2-methoxypyridin-4-yl)ethoxy)acetyl)-3,8-diazabicyclo[3.2.1]octan-8-yl)nicotinonitrile | 444.1 [M + H]+ |

-continued

| Example | Starting Alcohol | Structure | LCMS (m/z) |
|---|---|---|---|
| 278 | 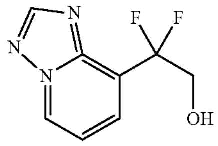 Intermediate alcohol 90 | 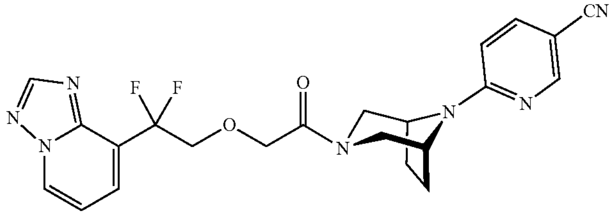 6-(3-(2-(2-([1,2,4]triazolo[1,5-a]pyridin-8-yl)-2,2-difluoroethoxy)acetyl)-3,8-diazabicyclo[3.2.1]octan-8-yl)nicotinonitrile | 454.2 [M + H]+ |

The following examples were prepared in an analogous fashion to Example 177 but substituting Intermediate amide 1 for the requisite amide. For the synthesis of Example 281 and Example 282, Intermediate alcohol 15 was also substituted for Intermediate alcohol 44 and Intermediate alcohol 58, respectively:

| Example | Starting Amide | Structure | LCMS (m/z) |
|---|---|---|---|
| 279 | 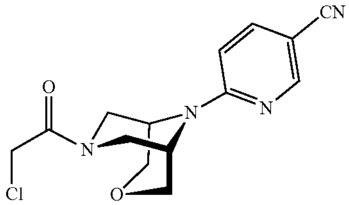 Intermediate amide 2 | 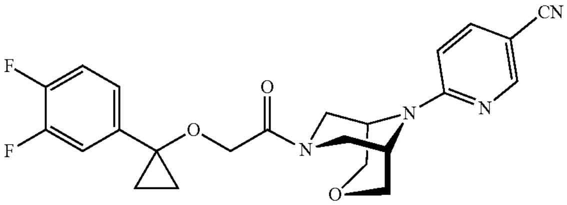 6-(7-(2-(1-(3,4-difluorophenyl)cyclopropoxy)acetyl)-3-oxa-7,9-diazabicyclo[3.3.1]nonan-9-yl)nicotinonitrile | 441.3 [M + H]+ |
| 280 | 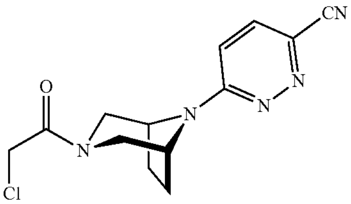 Intermediate amide 3 | 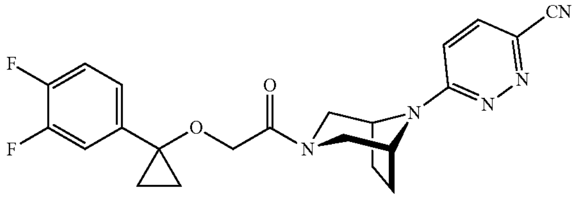 6-(3-(2-(1-(3,4-difluorophenyl)cyclopropoxy)acetyl)-3,8-diazabicyclo[3.2.1]octan-8-yl)pyridazine-3-carbonitrile | 426.2 [M + H]+ |
| 281 | 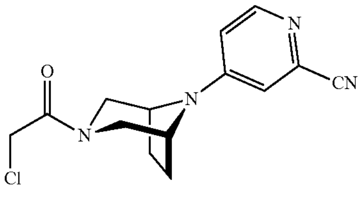 Intermediate amide 4 | 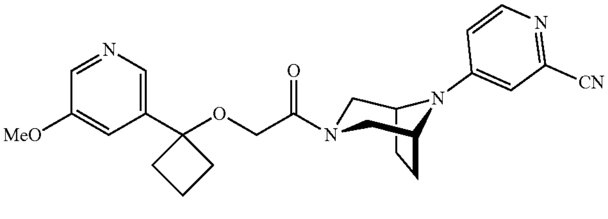 4-(3-(2-(1-(5-methoxypyridin-3-yl)cyclobutoxy)acetyl)-3,8-diazabicyclo[3.2.1]octan-8-yl)picolinonitrile | 434.2 [M + H]+ |

-continued

| Example | Starting Amide | Structure | LCMS (m/z) |
|---|---|---|---|
| 282 | 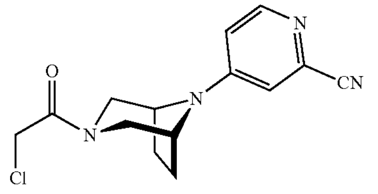 Intermediate amide 4 | 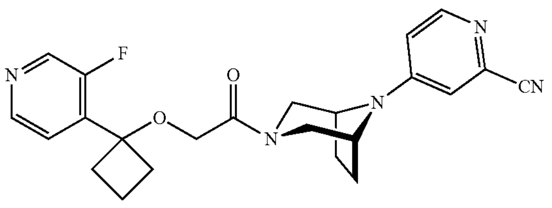 4-(3-(2-(1-(3-fluoropyridin-4-yl)cyclobutoxy)acetyl)-3,8-diazabicyclo[3.2.1]octan-8-yl)picolinonitrile | 422.1 $[M + H]^+$ |

Example 283: Preparation of 6-((1S,4S)-5-(2-(1-(3,4-difluorophenyl)cyclopropoxy)acetyl)-2,5-diazabicyclo[2.2.2]octan-2-yl)nicotinonitrile

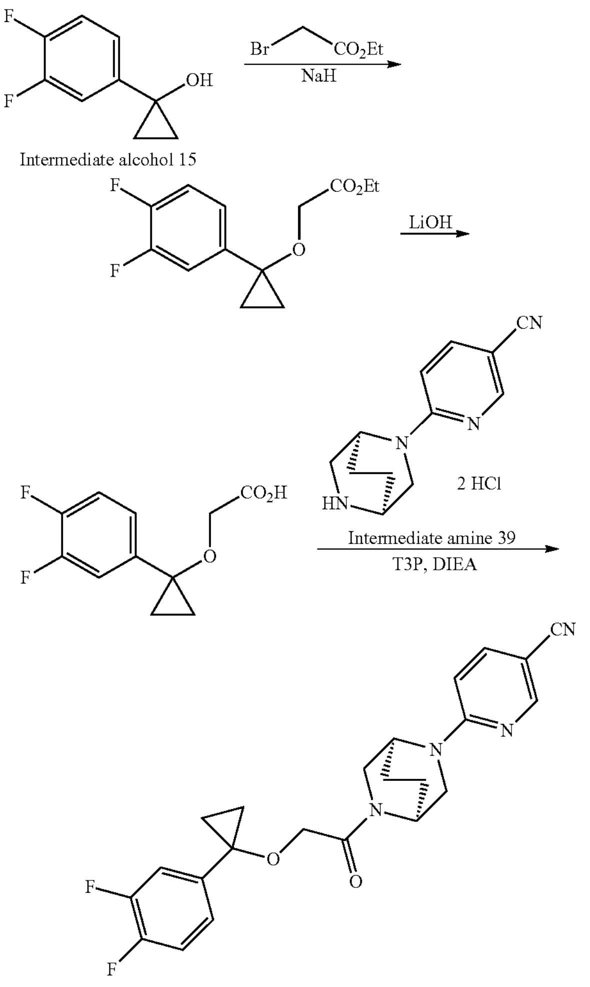

Example 283

Step 1: In a round-bottom flask equipped with a magnetic stirrer was combined Intermediate alcohol 15 (1 equiv) and ethyl bromoacetate (1.3 equiv, Sigma-Aldrich) in THF (0.59 M). To this was then added sodium hydride (1.5 equiv, 60% (w/w) dispersion in paraffin oil, Sigma-Aldrich) in one rapid portion and the resulting mixture was allowed to stir at RT for 1 h. The reaction was carefully quenched with water and extracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution:Hex→EtOAc) afforded ethyl 2-(1-(3,4-difluorophenyl)cyclopropoxy)acetate a colorless oil (27% yield).

Step 2: In a round-bottom flask equipped with a magnetic stirrer was dissolved ethyl 2-(1-(3,4-difluorophenyl)cyclopropoxy)acetate (1 equiv) from the previous step in a 2:1 (v/v) solution of THF and methanol (0.23 M). To this solution was then added lithium hydroxide (2 equiv, 1 M solution in water) and the resulting mixture was stirred at RT for 18 h. The pH of the reaction mixture was then adjusted to ~3 with 1 M aq. HCl and the volatiles were removed in vacuo. The resulting residue was then partitioned between water and EtOAc. The organic layer was separated, washed further with brine, dried over $Na_2SO_4$, and filtered. Concentration of the filtrate thus obtained in vacuo afforded 2-(1-(3,4-difluorophenyl)cyclopropoxy)acetic acid as a thick syrup (47% yield).

Step 3: In a dried round-bottom flask equipped with a magnetic stirrer was combined 2-(1-(3,4-difluorophenyl)cyclopropoxy)acetic acid (1 equiv) from the previous step, Intermediate amine 39 (1 equiv), and DIEA (5 equiv, Sigma-Aldrich) in dichloromethane (0.25 M). To the reaction mixture was then added propylphosphonic anhydride (1.4 equiv, 50 wt % solution in EtOAc, Sigma-Aldrich) and the resulting yellow solution was allowed to stir at RT for 3 h. The reaction mixture was then diluted with EtOAc and washed sequentially with 1 M aq. NaOH, water and brine. The organic layer was then dried over $MgSO_4$, filtered and the filtrate concentrated in vacuo. Further purification by way of column chromatography ($SiO_2$, gradient elution: Hex→EtOAc) afforded the title compound as a white solid (49% yield). LCMS: m/z=425.1 $[M+H]^+$; $^1H$ NMR (DMSO-$d_6$): δ=8.47 (s, 1H), 7.85 (d, J=8.0 Hz, 1H), 7.44~7.31 (m, 2H), 7.17~7.11 (m, 1H), 6.60~4.0 (m, 5H), 3.65~3.56 (m, 2H), 3.55~3.40 (m, 2H), 1.90~1.75 (m, 4H), 1.30~1.24 (m, 2H), 1.05~0.99 (in, 2H).

The following examples were prepared in an analogous fashion to Example 283 but substituting Intermediate amine 39 for the requisite amine in step 3:

| Example | Starting Amine | Structure | LCMS (m/z) |
|---|---|---|---|
| 284 | 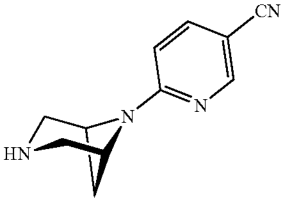 Intermediate amine 35 | 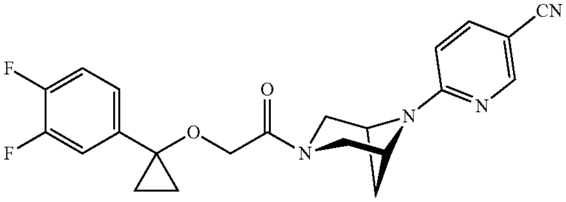 6-(3-(2-(1-(3,4-difluorophenyl)cyclopropoxy)acetyl)-3,6-diazabicyclo[3.1.1]heptan-6-yl)nicotinonitrile | 411.1 [M + H]+ |
| 285 | 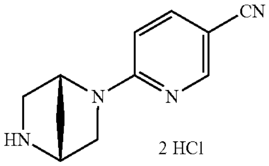 [SMILES: N#Cc1ccc(N2C[C@H]3C[C@@H]2CN3)nc1] 2 HCl Intermediate amine 36 | 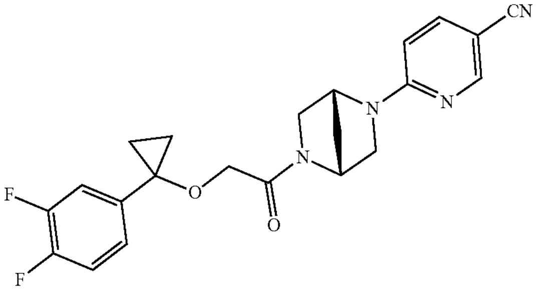 [SMILES: N#Cc1ccc(N2C[C@H]3C[C@@H]2CN3C(=O)COC2(c3ccc(F)c(F)c3)CC2)nc1] 6-((1R,4R)-5-(2-(1-(3,4-difluorophenyl)cyclopropoxy)acetyl)-2,5-diazabicyclo[2.2.1]heptan-2-yl)nicotinonitrile | 411.1 [M + H]+ |
| 286 | 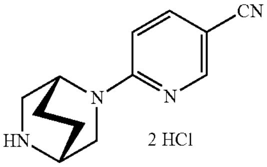 2 HCl Intermediate amine 37 | 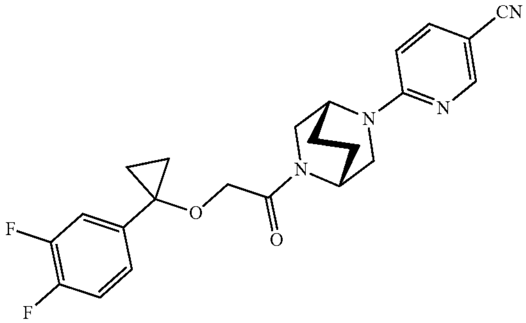 6-((1R,4R)-5-(2-(1-(3,4-difluorophenyl)cyclopropoxy)acetyl)-2,5-diazabicyclo[2.2.2]octan-2-yl)nicotinonitrile | 425.1 [M + H]+ |
| 287 | 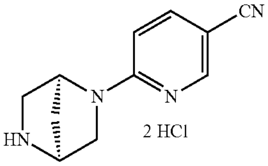 2 HCl Intermediate amine 38 | 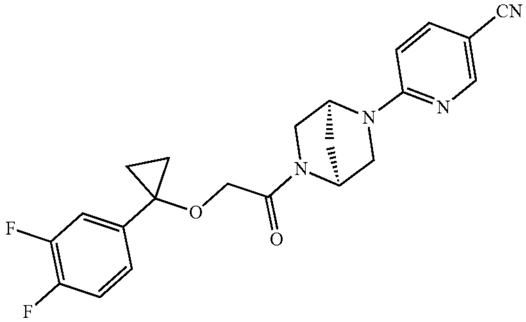 6-((1S,4S)-5-(2-(1-(3,4-difluorophenyl)cyclopropoxy)acetyl)-2,5-diazabicyclo[2.2.1]heptan-2-yl)nicotinonitrile | 411.1 [M + H]+ |

Example 288: Preparation of 6-(3-(3-((1-(3-cyano-4-fluorophenyl)cyclopropyl)amino)propanoyl)-3,8-diazabicyclo[3.2.1]octan-8-yl)nicotinonitrile formic acid Salt

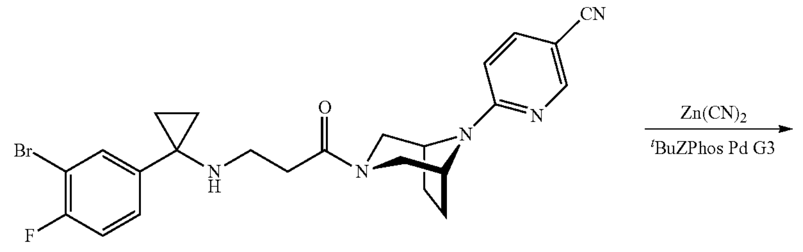

Example 11

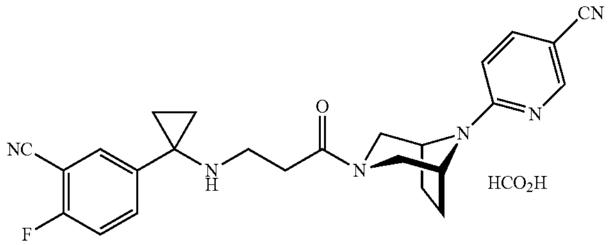

Example 288

In a sealable reaction vessel equipped with a magnetic stirrer and a Teflon screwcap was combined Example 11 (1 equiv) and zinc cyanide (0.66 equiv, Alfa Aesar) in a 5:1 (v/v) solution of water and THF (0.04 M). The reaction mixture was then deoxygenated via sub-surface purging with $N_2$ for 10 min. Finally, $^{t}$BuXPhos Pd G3 (0.05 equiv, Sigma-Aldrich) was added in one rapid fashion and the reaction vessel was tightly sealed and heated at 40° C. for 16 h. The reaction mixture was allowed to cool to RT, quenched with saturated aq. $NaHCO_3$ and extracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution:Hex→EtOAc→10:1 (v/v) EtOAc: MeOH) followed by reverse-phase column chromatography ($C_{1-8}$, gradient elution: 9:1 (v/v) $H_2O$:MeCN+0.100 formic acid 4~MeCN+ 0.1% formic acid) afforded the title compound as a white solid (10% yield). LCMS: m/z=445.1 $[M+H]^+$; $^1H$ NMR (DMSO-$d_6$): δ=8.50 (d, J=2.0 Hz, 1H), 8.15 (s, formic acid), 7.87 (dd, J=9, 2.5 Hz, 1H), 7.83 (dd, J=6.5, 2.5 Hz, 1H), 7.72~7.68 (m, 1H), 7.42 (t, J=9.0 Hz, 1H), 6.92 (d, J=9.0 Hz, 1H), 4.71 (br s, 2H), 4.14 (d, J=12.5 Hz, 1H), 3.62 (d, J=12.5 Hz, 2H), 3.21 (d, J=12.5 Hz, 2H), 2.74 (d, J=12.5 Hz, 1H), 2.60~2.57 (m, 2H), 2.33~2.27 (m, 1H), 1.91~1.89 (m, 2H), 1.80~1.76 (m, 1H), 1.62~1.59 (m, 1H), 0.95~0.94 (in, 4H).

The following examples were prepared in an analogous fashion to Example 288 but substituting Example 11 for the requisite halide:

| Example | Starting Halide | Structure | LCMS (m/z) |
|---|---|---|---|
| 289 | 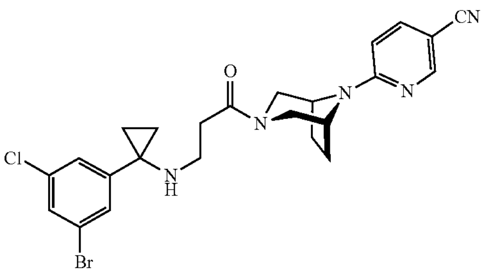 Example 12 | 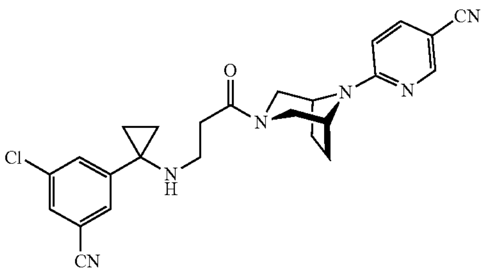 6-(3-(3-((1-(3-chloro-5-cyanophenyl)cyclopropyl)amino) propanoyl)-3,8-diazabicyclo[3.2.1]octan-8-yl)nicotinonitrile | 461.0, 463.0 $[M + H]^+$ |

-continued

| Example | Starting Halide | Structure | LCMS (m/z) |
| --- | --- | --- | --- |
| 290 | 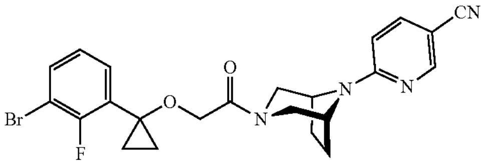 Example 219 | 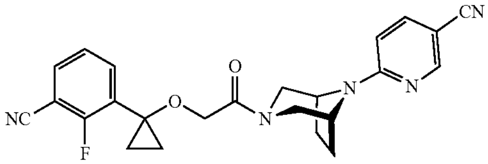 6-(3-(2-(1-(3-cyano-2-fluorophenyl)cyclopropoxy)acetyl)-3,8-diazabicyclo[3.2.1]octan-8-yl)nicotinonitrile | 432.1 $[M+H]^+$ |
| 291 | 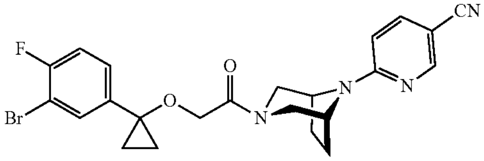 Example 215 | 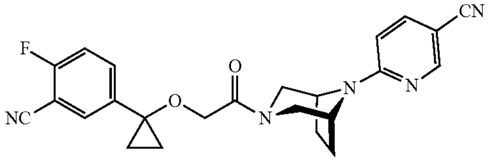 6-(3-(2-(1-(3-cyano-4-fluorophenyl)cyclopropoxy)acetyl)-3,8-diazabicyclo[3.2.1]octan-8-yl)nicotinonitrile | 432.1 $[M+H]^+$ |
| 292 | 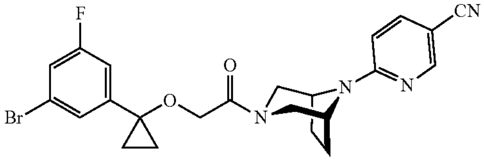 Example 217 | 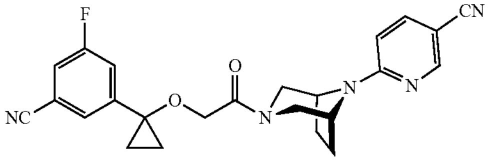 6-(3-(2-(1-(3-cyano-5-fluorophenyl)cyclopropoxy)acetyl)-3,8-diazabicyclo[3.2.1]octan-8-yl)nicotinonitrile | 432.1 $[M+H]^+$ |

Example 293: Preparation of 6-(3-(2-(1-(2-cyano-5-methoxyphenyl)cyclopropoxy)acetyl)-3,8-diazabicyclo[3.2.1]octan-8-yl)nicotinonitrile

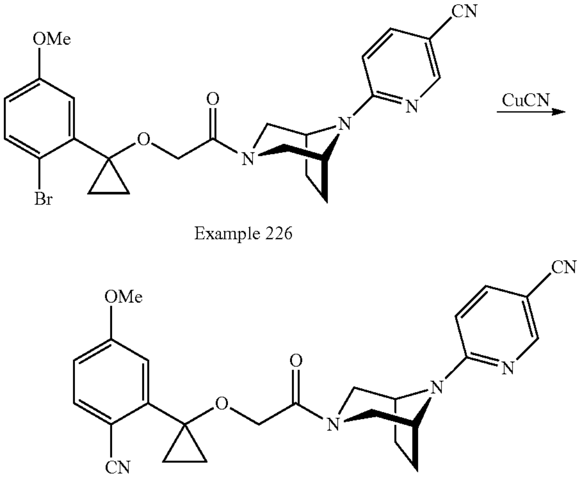

Example 226

Example 293

In a sealable reaction vessel equipped with a magnetic stirrer and a Teflon screwcap was combined Example 224 (1 equiv) and copper(I) cyanide (2 equiv, Sigma-Aldrich) in NMP (0.14 M). The reaction vessel was tightly sealed and heated at 170° C. for 12 h. The reaction mixture was allowed to cool to RT, diluted with water and extracted with EtOAc. The combined organic extracts were washed further with water (2×) and brine, dried over $Na_2SO_4$, filtered and the filtrate concentrated in vacuo. Purification of the crude product thus obtained by way of column chromatography ($SiO_2$, gradient elution:Hex→EtOAc→10:1 (v/v) EtOAc:MeOH) followed by reverse-phase column chromatography (Cis, gradient elution: 9:1 (v/v) $H_2O$:MeCN+0.1% formic acid→MeCN+0.1% formic acid) afforded the title compound as a white solid (22% yield). LCMS: m/z=444.1 $[M+H]^+$; $^1$H NMR (DMSO): δ=8.50 (d, J=2.0 Hz, 1H), 7.88, (dd, J=9.0, 2.0 Hz, 1H), 7.75 (d, J=8.5 Hz, 1H), 7.08 (d, J=2.5 Hz, 1H), 7.04 (dd, J=8.5, 2.5 Hz, 1H), 6.90 (d, J=9.0 Hz, 1H), 4.65 (br s, 2H). 3.99 (s, 2H), 3.95 (d, J=12.5 Hz, 1H), 3.85 (s, 3H), 3.46 (d, J=13.0 Hz, 1H), 3.14 (d, J=12.0 Hz, 1H), 2.62 (d, J=12.5 Hz, 1H), 1.91~1.84 (m, 3H), 1.57~1.50 (m, 1H), 1.29~1.20 (m, 2H), 1.08~1.02 (m, 1H), 1.02~0.96 (in, 1H).

The following examples were prepared in an analogous fashion to Example 293 but substituting Example 226 for the requisite halide:

| Example | Starting Halide | Structure | LCMS (m/z) |
|---|---|---|---|
| 294 | 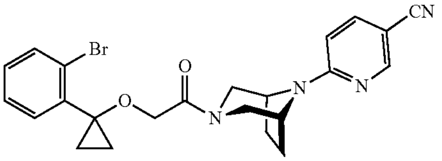 Example 181 | 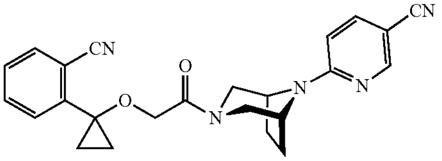 6-(3-(2-(1-(2-cyanophenyl)cyclopropoxy)acetyl)-3,8-diazabicyclo[3.2.1]octan-8-yl)nicotinonitrile | 414.1 [M + H]+ |
| 295 | 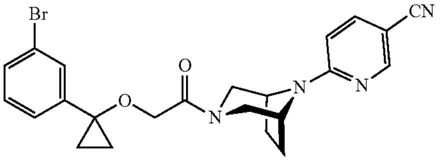 Example 209 | 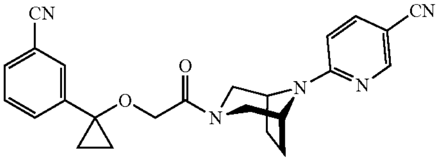 6-(3-(2-(1-(3-cyanophenyl)cyclopropoxy)acetyl)-3,8-diazabicyclo[3.2.1]octan-8-yl)nicotinonitrile | 414.1 [M + H]+ |
| 296 | 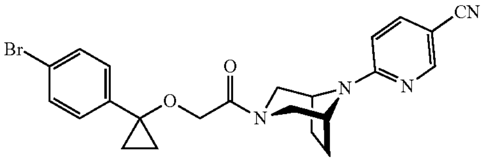 Example 208 | 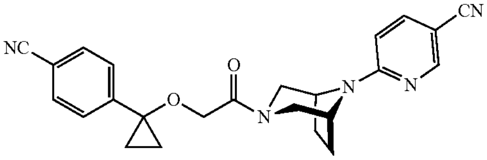 6-(3-(2-(1-(4-cyanophenyl)cyclopropoxy)acetyl)-3,8-diazabicyclo[3.2.1]octan-8-yl)nicotinonitrile | 414.1 [M + H]+ |
| 297 | 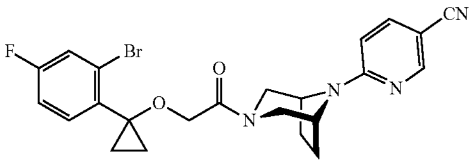 Example 221 | 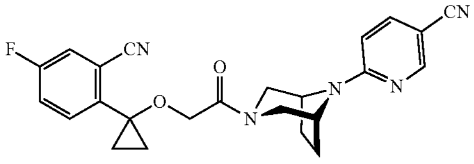 6-(3-(2-(1-(2-cyano-4-fluorophenyl)cyclopropoxy)acetyl)-3,8-diazabicyclo[3.2.1]octan-8-yl)nicotinonitrile | 432.1 [M + H]+ |
| 298 | 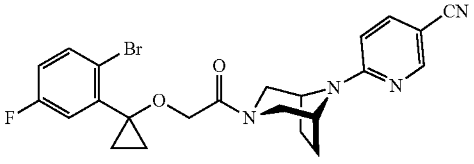 Example 220 | 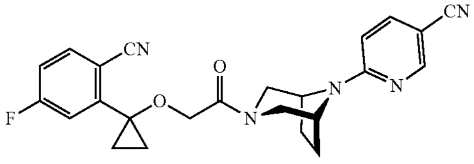 6-(3-(2-(1-(2-cyano-5-fluorophenyl)cyclopropoxy)acetyl)-3,8-diazabicyclo[3.2.1]octan-8-yl)nicotinonitrile | 432.1 [M + H]+ |

Example 299: Preparation of 6-(3-(2-(1-(1-methyl-6-oxo-1,6-dihydropyridin-2-yl)cyclobutoxy)acetyl)-3,8-diazabicyclo[3.2.1]octan-8-yl)nicotinonitrile

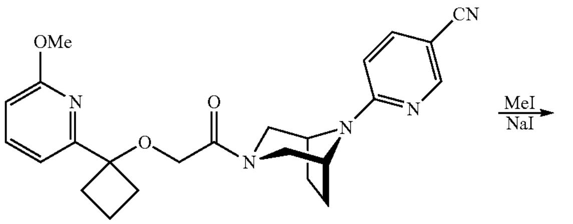

Example 253

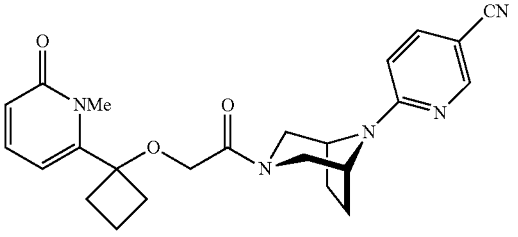

Example 299

In a sealable reaction vessel equipped with a magnetic stirrer and a Teflon screwcap was combined Example 253 (1 equiv), iodomethane (55 equiv, Sigma-Aldrich), and sodium iodide (3 equiv, Sigma-Aldrich) in MeCN (0.11 M). The reaction vessel was tightly sealed and heated at 80° C. for 3 days. The reaction mixture was allowed to cool to RT, diluted with water and extracted with EtOAc. The combined organic extracts were washed further with water (2×) and brine, dried over $Na_2SO_4$, filtered and the filtrate concentrated in vacuo. Purification of the crude product thus obtained by way of column chromatography ($SiO_2$, gradient elution:Hex→EtOAc→10:1 (v/v) EtOAc: MeOH) afforded the title compound as a white solid (58% yield). LCMS: m/z=434.1 $[M+H]^+$; $^1$H NMR (DMSO): δ=8.50 (d, J=2.0 Hz, 1H), 7.88, (dd, J=8.5, 2.0 Hz, 1H), 7.36, (dd, J=9.0, 7.5 Hz, 1H), 6.91 (d, J=9 Hz, 1H), 6.38 (dd, J=9.0, 1.0 Hz, 1H), 6.31 (dd, J=7.0, 1.5 Hz, 1H), 4.68 (br s, 2H), 4.00~ 3.95 (m, 2H), 3.77 (d, J=13.0 Hz, 1H), 3.51 (d, J=13.0 Hz, 1H), 3.41 (s, 3H), 3.20 (d, J=13.0 Hz, 1H), 2.72, (d, J=12.5 Hz, 1H), 2.57~2.50 (m, 2H), 2.42~2.35 (m, 2H), 1.95~1.80 (m, 4H), 1.70~1.61 (m, 1H), 1.57~1.50 (in, 1H).

The following examples were prepared in an analogous fashion to Example 299 but substituting Example 253 for the requisite methoxypyridine:

| Example | Starting Methoxypyridine | Structure | LCMS (m/z) |
|---|---|---|---|
| 300 | 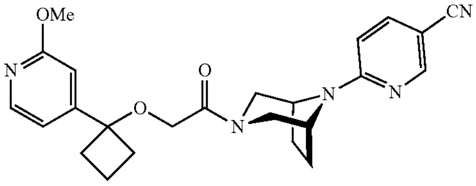 Example 252 | 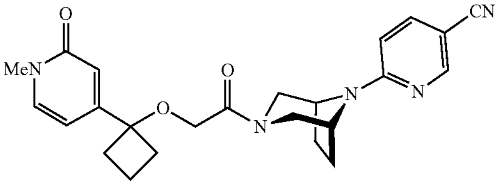 6-(3-(2-(1-(1-methyl-2-oxo-1,2-dihydropyridm-4-yl) cyclobutoxy)acetyl)-3,8-diazabicyclo[3.2.1]octan-8-yl)nicotinonitrile | 434.1 $[M + H]^+$ |
| 301 | 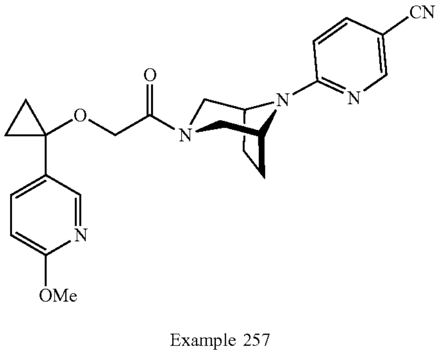 Example 257 | 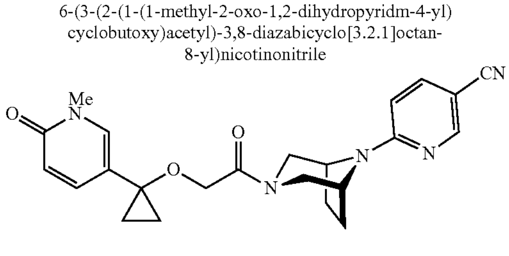 6-(3-(2-(1-(1-methyl-6-oxo-1,6-dihydropyridin-3-yl) cyclopropoxy)acetyl)-3,8-diazabicyclo[3.2.1]octan-8-yl)nicotinonitrile | 434.1 $[M + H]^+$ |
| 302 | 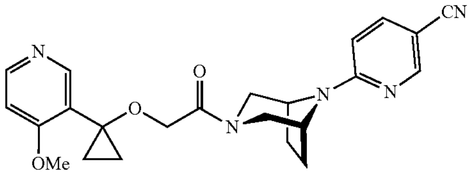 Example 258 | 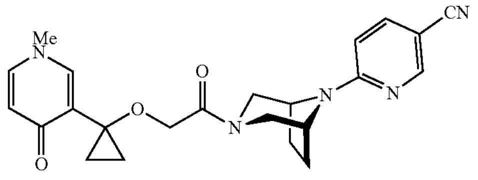 6-(3-(2-(1-(1-methyl-4-oxo-1,4-dihydropyridin-3-yl) cyclopropoxy)acetyl)-3,8-diazabicyclo[3.2.1]octan-8-yl)nicotinonitrile | 434.1 $[M + H]^+$ |

Example 303: Preparation of 6-(3-(3-(1-(3,4-difluorophenyl)cyclobutoxy)propanoyl)-3,8-diazabicyclo[3.2.1]octan-8-yl)nicotinonitrile

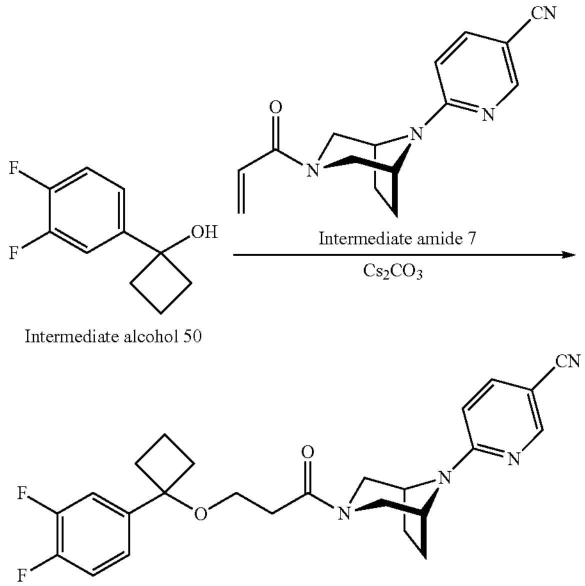

Example 303

In a sealable reaction vessel equipped with a magnetic stirrer and a Teflon screwcap was combined Intermediate alcohol 50 (1 equiv), Intermediate amide 7 (1 equiv), and cesium carbonate (1.5 equiv, Sigma-Aldrich) in tert-butanol (0.19 M). The reaction vessel was tightly sealed and heated at 60° C. for 18 h. The reaction mixture was allowed to cool to RT, diluted with water and extracted with EtOAc. The combined organic extracts were washed further with water (2×) and brine, dried over $Na_2SO_4$, filtered and the filtrate concentrated in vacuo. Purification of the crude product thus obtained by way of column chromatography ($SiO_2$, gradient elution:Hex→EtOAc) afforded the title compound as a white solid (16% yield). LCMS: m/z=453.0 $[M+H]^+$; $^1$H NMR (DMSO): δ=8.50 (d, J=1.5 Hz, 1H), 7.88 (dd, J=9.0, 2.0 Hz, 1H), 7.44~ 7.38 (m, 2H), 7.27~ 7.25 (m, 1H), 6.92 (d, J=9.0 Hz, 1H), 4.70 (br s, 2H), 4.13 (d, J=13.0 Hz, 1H), 3.67 (d, J=12.5 Hz, 1H), 3.22~ 3.17 (m, 3H), 2.73 (d, J=13.0 Hz, 1H), 2.65~2.59 (m, 1H), 2.41~2.36 (m, 1H), 2.31~2.28 (m, 4H), 1.91~1.81 (m, 4H), 1.61~1.56 (m, 2H).

The following examples were prepared in an analogous fashion to Example 303 but substituting Intermediate alcohol 50 for the requisite alcohol:

| Example | Starting Alcohol | Structure | LCMS (m/z) |
|---|---|---|---|
| 304 | 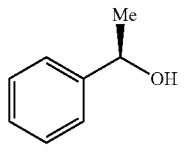 (Combi-Blocks) | 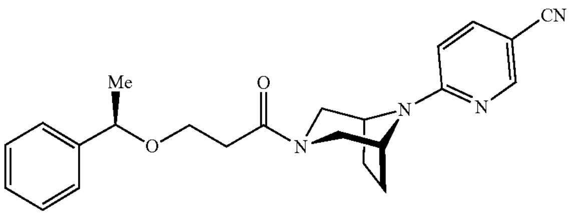 6-(3-(3-((R)-1-phenylethoxy)propanoyl)-3,8-diazabicyclo[3.2.1]octan-8-yl)nicotinonitrile | 391.2 $[M + H]^+$ |
| 305 | 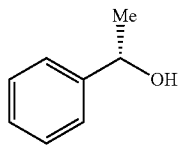 (Combi-Blocks) | 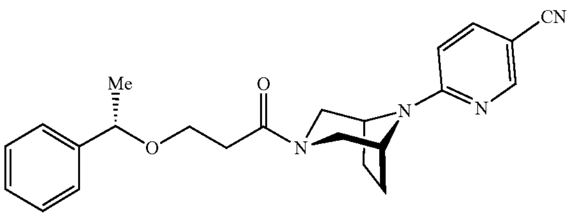 6-(3-(3-((S)-1-phenylethoxy)propanoyl)-3,8-diazabicyclo[3.2.1]octan-8-yl)nicotinonitrile | 391.2 $[M + H]^+$ |

-continued

| Example | Starting Alcohol | Structure | LCMS (m/z) |
|---|---|---|---|
| 306 | 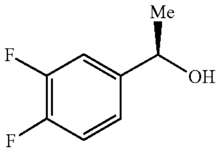 (Enamine) | 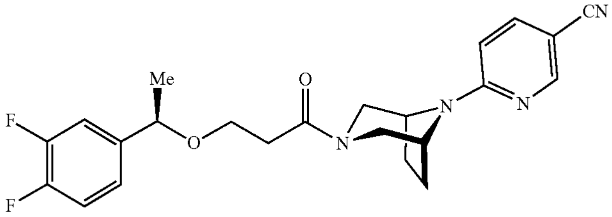 6-(3-(3-((R)-1-(3,4-difluorophenyl)ethoxy)propanoyl)-3,8-diazabicyclo[3.2.1]octan-8-yl)nicotinonitrile | 427.1 $[M + H]^+$ |
| 307 | 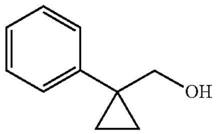 [SMILES: OCC1(c2ccccc2)CC1] (Enamine) | 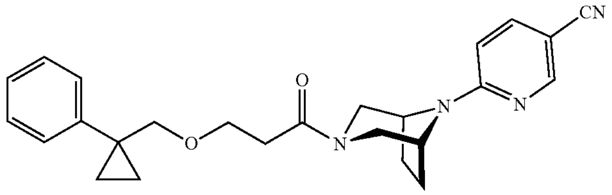 6-(3-(3-((1-phenylcyclopropyl)methoxy)propanoyl)-3,8-diazabicyclo[3.2.1]octan-8-yl)nicotinonitrile | 417.1 $[M + H]^+$ |
| 308 | 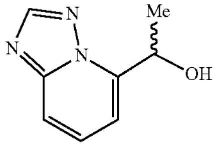 [SMILES: CC(O)c1cccc2ncnn12] Intermediate alcohol 1 | 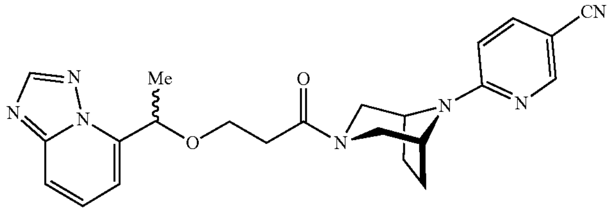 6-(3-(3-(1-([1,2,4]triazolo[1,5-a]pyridin-5-yl)ethoxy)propanoyl)-3,8-diazabicyclo[3.2.1]octan-8-yl)nicotinonitrile | 432.1 $[M + H]^+$ |
| 309 | 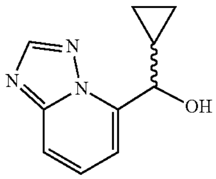 [SMILES: OC(c1cccc2ncnn12)C1CC1] Intermediate alcohol 5 | 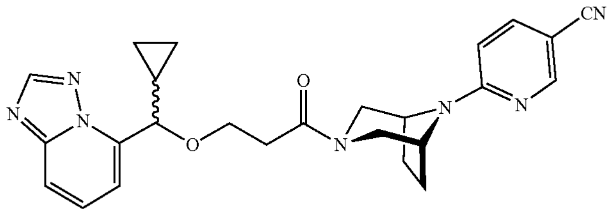 6-(3-(3-([1,2,4]triazolo[1,5-a]pyridin-5-yl(cyclopropyl)methoxy)propanoyl)-3,8-diazabicyclo[3.2.1]octan-8-yl)nicotinonitrile | 458.1 $[M + H]^+$ |
| 310 | 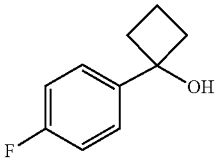 [SMILES: OC1(c2ccc(F)cc2)CCC1] Intermediate alcohol 45 | 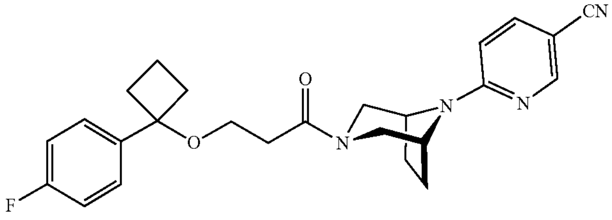 6-(3-(3-(1-(4-fluorophenyl)cyclobutoxy)propanoyl)-3,8-diazabicyclo[3.2.1]octan-8-yl)nicotinonitrile | 435.1 $[M + H]^+$ |

Example 311: Preparation of 6-(3-(3-(1-(quinolin-5-yl)ethoxy)propanoyl)-3,8-diazabicyclo[3.2.1]octan-8-yl)nicotinonitrile

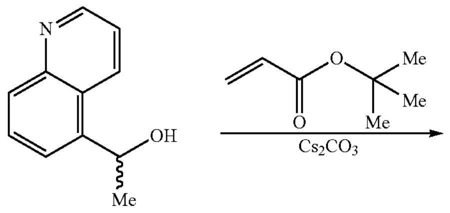

Intermediate alcohol 2

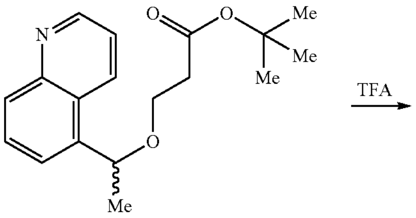

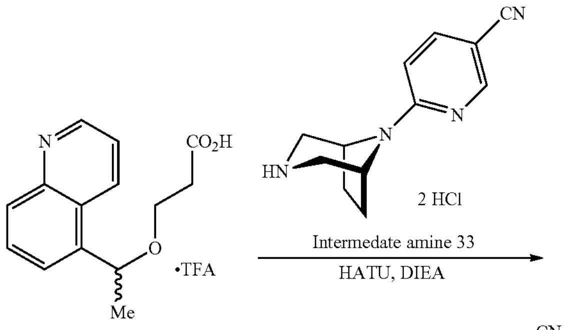

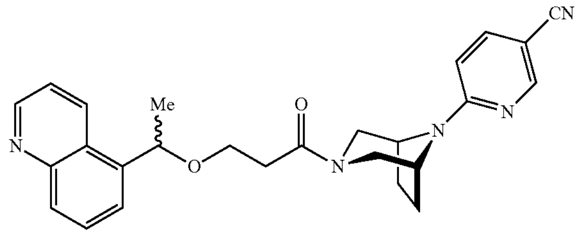

Example 311

Step 1: In a sealable reaction vessel equipped with a magnetic stirrer and a Teflon screwcap was combined Intermediate alcohol 2 (1 equiv), tert-butyl acrylate (5 equiv, Combi-Blocks), and cesium carbonate (1.2 equiv, Sigma-Aldrich) in tert-butanol (0.12 M). The vessel was then tightly sealed and heated at 60° C. for 16 h. The volatiles were then removed in vacuo and the resulting residue was partitioned between water and EtOAc. The aqueous layer was separated and backextracted with EtOAc (3×). The combined organic extracts were washed further with water and brine, dried over $MgSO_4$, filtered, and the filtrate concentrated in vacuo. Purification of the crude product thus obtained by way of column chromatography ($SiO_2$, gradient elution:Hex→EtOAc) afforded tert-butyl 3-(1-(quinolin-5-yl)ethoxy)propanoate as a colorless oil (34% yield).

Step 2: In a dried round-bottom flask equipped with a magnetic stirrer was dissolved tert-butyl 3-(1-(quinolin-5-yl)ethoxy)propanoate (1 equiv) from the previous step in dichloromethane (0.08 M). To this solution was then added TFA (230 equiv, Sigma-Aldrich) and the resulting mixture was stirred at RT for 2 h. The volatiles were then removed in vacuo and the resulting residue was further azeotroped with toluene (3×). 3-(1-(Quinolin-5-yl)ethoxy)propanoic acid trifluoroacetic acid salt thus obtained was used in the next step without further purification.

Step 3: In a dried round-bottom flask equipped with a magnetic stirrer was combined 3-(1-(quinolin-5-yl)ethoxy)propanoic acid trifluoroacetic acid salt (1 equiv) from the previous step, Intermediate amine 33 (1.1 equiv), and HATU (1.1 equiv, Combi-Blocks) in DMF (0.07 M). To the reaction mixture was then added DIEA (4 equiv, Sigma-Aldrich) and the resulting solution was allowed to stir at RT for 5 min. The reaction mixture was then diluted with EtOAc and washed further with water (3×). The organic layer was then concentrated in vacuo and the resulting residue was directly subjected to purification by way of column chromatography ($SiO_2$, gradient elution:Hex→EtOAc→10:1 (v/v) EtOAc:MeOH) to afford the title compound as an off-white solid (93% yield over two steps). LCMS: m/z=442.1 $[M+H]^+$; $^1H$ NMR (DMSO-$d_6$): δ=8.90~8.88 (m, 1H), 8.65 (d, J=8.5 Hz, 1H), 8.50 (t, J=2.5 Hz, 1H), 7.94~7.91 (m, 1H), 7.89~7.87 (m, 1H), 7.74~7.71 (m, 1H), 7.63 (t, J=8.0 Hz, 1H), 7.51 (dd, J=8.5, 4.0 Hz, 1H), 6.91 (d, J=9.5 Hz, 1H), 5.23~5.19 (m, 1H), 4.69 (br s, 2H), 4.11 (dd, J=12.5, 5.5 Hz, 1H), 3.71~3.57 (m, 2H), 3.54~3.51 (m, 1H), 3.17 (dd, J=25.5, 12.0 Hz, 1H), 2.74~2.67 (m, 2H), 2.55~2.45 (m, 1H), 1.91~1.78 (m, 3H), 1.60~1.54 (m, 1H), 1.48~1.46 (m, 3H).

The following example was prepared in an analogous fashion to Example 311 but substituting Intermediate alcohol 2 for Intermediate alcohol 3 in step 1:

| Example | Starting Amine | Structure | LCMS (m/z) |
| --- | --- | --- | --- |
| 312 | 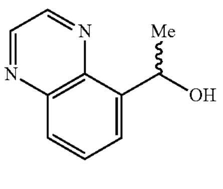 [SMILES: CC(O)c1cccc2nccnc12] Intermediate alcohol 3 | 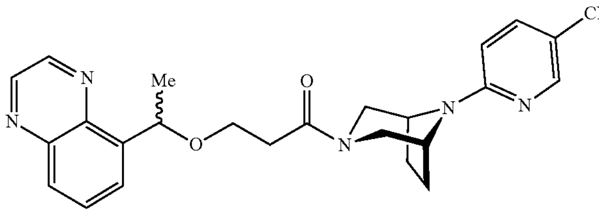 6-(3-(3-(1-(quinoxalin-5-yl)ethoxy)propanoyl)-3,8-diazabicyclo[3.2.1]octan-8-yl)nicotinonitrile | 443.1 $[M + H]^+$ |

Example 313: Preparation of 6-(3-(2-(1-(5-hydroxy-pyridin-3-yl)cyclobutoxy)acetyl)-3,8-diazabicyclo [3.2.1]octan-8-yl)nicotinonitrile

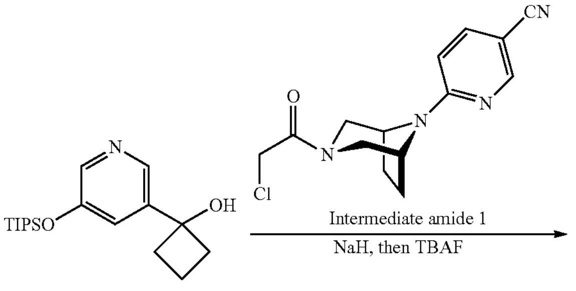

Intermediate alcohol 87

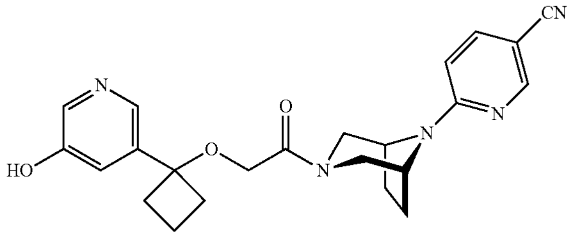

Example 313

In a dried round-bottom flask equipped with a magnetic stirrer was combined Intermediate alcohol 87 (1 equiv) and Intermediate amide 1 (1 equiv) in THF (0.22 M). To this was then added sodium hydride (1.5 equiv, 60% (w/w) dispersion in paraffin oil, Sigma-Aldrich) in one rapid portion and the resulting mixture was allowed to stir at RT for 1 h. The reaction was carefully quenched with water and extracted with EtOAc. The combined organic extracts were washed further with water (2×) and brine, dried over $MgSO_4$, filtered and the filtrate concentrated in vacuo. The resulting residue was then taken up in THF (0.03M) and TBAF (3 equiv, 1 M solution in THF, Sigma-Aldrich) was added dropwise. After 15 min of stirring at RT, the reaction was quenched with water and extracted with EtOAc. The combined organic extracts were washed further with water (2×) and brine, dried over $MgSO_4$, filtered and the filtrate concentrated in vacuo. Purification of the crude product thus obtained by way of column chromatography ($SiO_2$, gradient elution: Hex→EtOAc→10:1 (v/v) EtOAc: MeOH) afforded the title compound as a white solid (80% yield). LCMS: m/z=420.1 $[M+H]^+$; $^1H$ NMR (DMSO-$d_6$): δ=9.95 (s, 1H), 8.51 (d, J=2.0 Hz, 1H), 8.12 (d, J=1.5 Hz, 1H), 8.06 (d, J=2.5 Hz, 1H), 7.88 (dd, J=9.0, 2.5 Hz, 1H), 7.15~ 7.14 (m, 1H), 6.91 (d, J=9.0 Hz, 1H), 4.70 (br s, 2H), 4.04~ 4.02 (m, 1H), 3.77 (d, J=12.5 Hz, 1H), 3.66 (d, J=12.5 Hz, 1H), 3.55 (d, J=13.0 Hz, 1H), 3.20 (d, J=13.0 Hz, 1H), 2.75 (d, J=13.0 Hz, 1H), 2.37~2.34 (m, 4H), 1.93~1.82 (m, 4H), 1.63~1.57 (m, 1H).

Example 314: Preparation of 6-(3-(2-(1-(5-(2,2,2-trifluoroethoxy)pyridin-3-yl)cyclobutoxy)acetyl)-3,8-diazabicyclo[3.2.1]octan-8-yl)nicotinonitrile

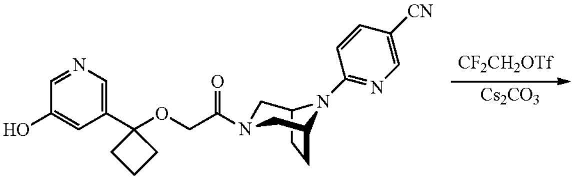

Example 313

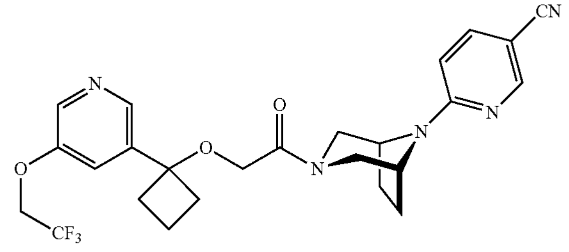

Example 314

In a dried round-bottom flask equipped with a magnetic stirrer was combined Example 313 (1 equiv) and cesium carbonate (1.3 equiv, Sigma-Aldrich) in DMF (0.065 M). To this was then added 2,2,2-trifluoroethyl trifluoromethanesulfonate (1.2 equiv, Sigma-Aldrich) and the resulting white suspension was allowed to stir at RT for 1 h. The reaction was diluted with brine and extracted with EtOAc. The combined organic extracts were dried over $MgSO_4$, filtered and the filtrate concentrated in vacuo. Purification of the crude product thus obtained by way of column chromatography ($SiO_2$, gradient elution:Hex→EtOAc) afforded the title compound as a viscous oil (80% yield). LCMS: m/z=502.0 $[M+H]^+$; $^1H$ NMR (DMSO-$d_6$): δ=8.50 (d, J=2.0 Hz, 1H), 8.37 (d, J=1.5 Hz, 1H), 8.34 (d, J=2.5 Hz, 1H), 7.88 (dd, J=9.0, 2.0 Hz, 1H), 7.53 (dd, J=2.5, 2.0 Hz, 1H), 6.91 (d, J=9.0 Hz, 1H), 4.90 (t, J=8.5 Hz, 2H), 4.69 (br s, 1H), 4.02 (d, J=13.5 Hz, 1H), 3.84 (d, J=13.5 Hz, 1H), 3.71 (d, J=13.5 Hz), 3.54 (d, J=12.5 Hz, 1H), 3.20 (d, J=12.0 Hz, 1H), 2.73 (d, J=12.5 Hz, 1H), 2.46~2.36 (m, 4H), 1.94~1.82 (m, 4H), 1.67~1.55 (m, 2H).

Example 315: Preparation of 6-(3-(2-(1-(5-(difluoromethoxy)pyridin-3-yl)cyclobutoxy)acetyl)-3,8-diazabicyclo[3.2.1]octan-8-yl)nicotinonitrile

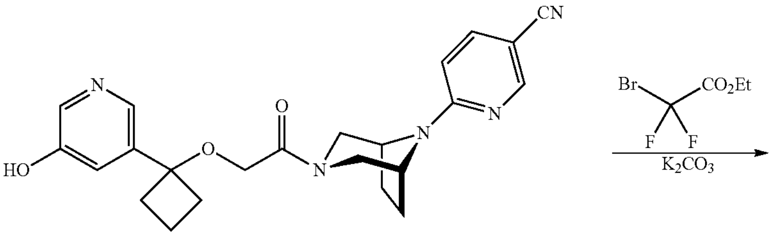

Example 313

-continued

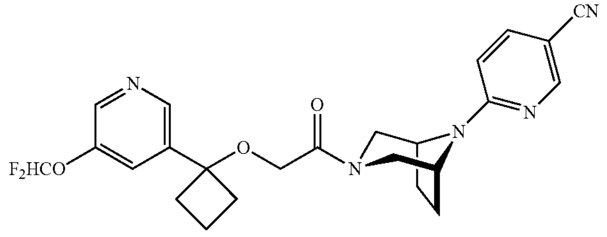

Example 315

In a sealable reaction vessel equipped with a magnetic stirrer and a Teflon screwcap was combined Example 313 (1 equiv), ethyl bromodifluoroacetate (1.5 equiv, Sigma-Aldrich), and potassium carbonate (1.5 equiv, Sigma-Aldrich) in acetone (0.067 M). The vessel was then tightly sealed and heated at 80° C. for 3 h. The volatiles were then removed in vacuo and the resulting residue was partitioned between water and EtOAc. The aqueous layer was separated and backextracted with EtOAc (3×). The combined organic extracts were washed further with water and brine, dried over $MgSO_4$, filtered, and the filtrate concentrated in vacuo. Purification of the crude product thus obtained by way of reverse phase column chromatography ($C_{18}$, gradient elution: 10:1 (v/v) $H_2O$:MeCN+0.1% formic acid→MeCN+0.1% formic acid) afforded the title compound as a white solid (15% yield). LCMS: m/z=470.0 $[M+H]^+$; $^1H$ NMR (DMSO-$d_6$): δ=8.57 (d, J=2.0 Hz, 1H), 8.50 (d, J=2.0 Hz, 1H), 8.43 (d, J=2.5 Hz, 1H), 7.88 (dd, J=9.0, 2.0 Hz, 1H), 7.68~ 7.66 (m, 1H), 7.36 (t, J=73.5 Hz, 1H), 6.91 (d, J=9.0 Hz, 1H), 4.69 (br s, 2H), 4.01 (d, J=13.0 Hz, 1H), 3.88 (d, J=13.5 Hz, 1H), 3.75 (d, J=13.5 Hz, 1H), 3.53 (d, J=12.5 Hz, 1H), 3.20 (d, J=12.0 Hz, 1H), 2.72 (d, J=12.5 Hz, 1H), 2.44~2.38 (m, 4H), 1.94~1.82 (m, 4H), 1.67~1.55 (m, 2H).

Example 316: Preparation of 6-(3-(2-(1-(3,5-difluoropyridin-4-yl)cyclobutoxy)acetyl)-3,8-diazabicyclo [3.2.1]octan-8-yl)nicotinonitrile

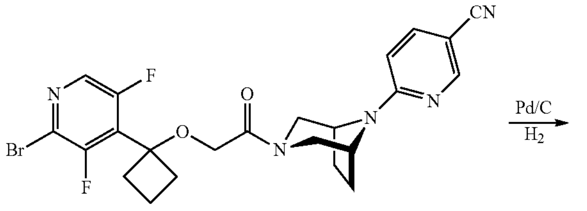

Example 270

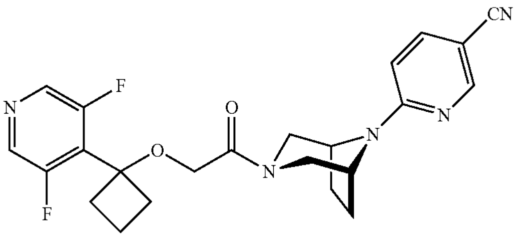

Example 316

In a dried round-bottom flask equipped with a magnetic stirrer was combined Example 270 (1 equiv) and palladium black (0.1 equiv, 10% (w/w) over activated carbon, Sigma-Aldrich) in a 1:1 (v/v) solution of EtOAc and methanol (0.1 M). The resulting suspension was evacuated and back-filled with hydrogen gas (3×). Once the gas exchange process was deemed complete, the reaction suspension was stirred at RT under a static hydrogen atmosphere for 3 days. The reaction suspension was then filtered and the filtrate concentrated in vacuo. Further purification of the crude product thus obtained by way of column chromatography ($SiO_2$, gradient elution:Hex→EtOAc→10:1 (v/v) EtOAc: MeOH) afforded the title compound as a white solid (28% yield). LCMS: m/z=440.1 $[M+H]^+$; 8.50 (d, J=2.0 Hz, 1H), 8.48 (s, 2H), 7.88 (dd, J=9.0, 2.5 Hz, 1H), 6.92 (d, J=9.0 Hz, 1H), 4.68 (br s, 2H), 4.01~ 3.90 (m, 3H), 3.52 (d, J=12.5 Hz, 1H), 3.21 (d, J=12.0 Hz, 1H), 2.66 (d, J=12.5 Hz, 1H), 2.62~2.55 (m, 2H), 2.54~2.48 (m, 2H), 2.22~2.13 (m, 1H), 1.93~1.84 (m, 4H), 1.55~1.50 (m, 1H).

Example 317: Preparation of racemic 6-(3-(5-hydroxy-4-(3-methoxyphenyl)pentanoyl)-3,8-diazabicyclo[3.2.1]octan-8-yl)nicotinonitrile

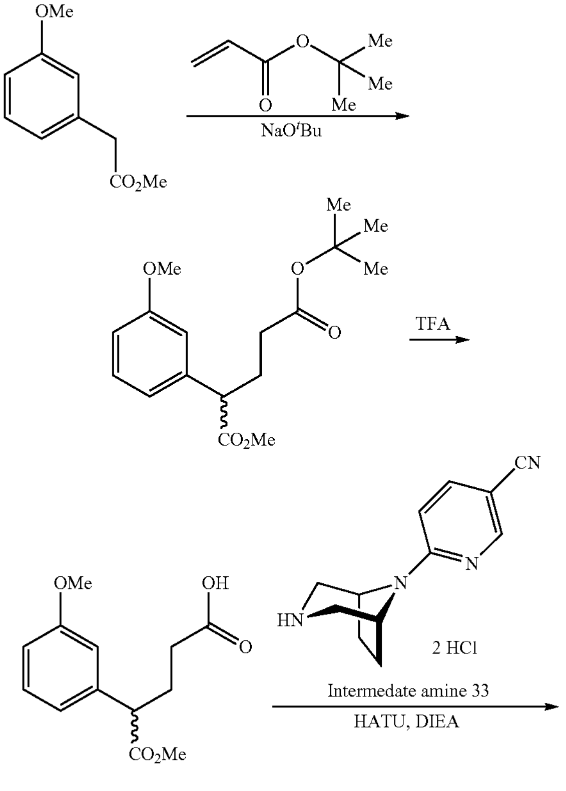

-continued

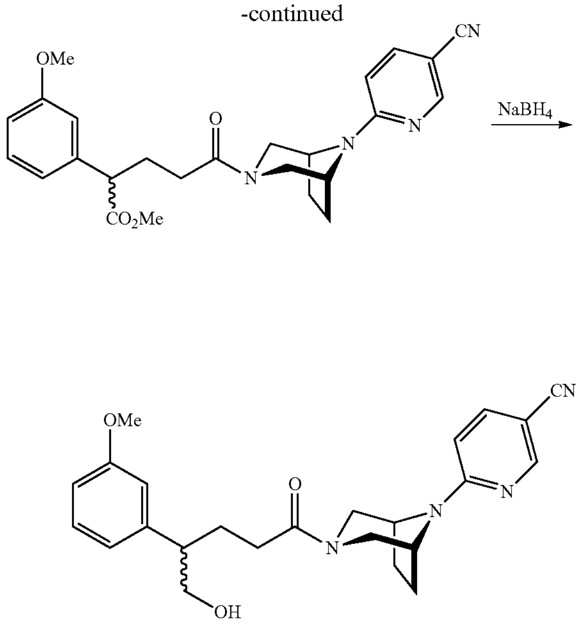

Example 317

Step 1: In a dried round-bottom flask equipped with a magnetic stirrer was combined methyl 2-(3-methoxyphenyl) acetate (1 equiv, Sigma-Aldrich) and tert-butyl acrylate (1.5 equiv, Combi-Blocks) in THF (0.46 M). To this solution was then added at 0° C. sodium tert-butoxide (2.5 equiv, Sigma-Aldrich) portionwise and the resulting mixture was stirred at 5° C. for 4 h. The volatiles were then removed in vacuo and the resulting residue was partitioned between water and DCM. The aqueous layer was separated and backextracted with DCM (3×). The combined organic extracts were washed further with water and brine, dried over $MgSO_4$, filtered, and the filtrate concentrated in vacuo. Purification of the crude product thus obtained by way of column chromatography ($SiO_2$, gradient elution:Hex→EtOAc) afforded 5-(tert-butyl) 1-methyl 2-(3-methoxyphenyl)pentanedioate as a yellow oil (47% yield).

Step 2: In a dried round-bottom flask equipped with a magnetic stirrer was dissolved 5-(tert-butyl) 1-methyl 2-(3-methoxyphenyl)pentanedioate (1 equiv) from the previous step in dichloromethane (0.52 M). To this solution was then added TFA (25 equiv, Sigma-Aldrich) and the resulting mixture was stirred at RT for 1 h. The volatiles were then removed in vacuo and the resulting residue was directly subjected to purification by way of column chromatography ($SiO_2$, gradient elution:Hex→EtOAc→10:1 (v/v) EtOAc: MeOH) to afford 5-methoxy-4-(3-methoxyphenyl)-5-oxo-pentanoic acid (92% yield).

Step 3: In a dried round-bottom flask equipped with a magnetic stirrer was combined 5-methoxy-4-(3-methoxyphenyl)-5-oxopentanoic acid (1 equiv) from the previous step, Intermediate amine 33 (1.1 equiv), and HATU (1.1 equiv, Combi-Blocks) in DMF (0.15 M). To the reaction mixture was then added DIEA (3 equiv, Sigma-Aldrich) and the resulting solution was stirred at RT for 1 h. The reaction mixture was then diluted with EtOAc and washed further with water (3×). The organic layer was then concentrated in vacuo and the resulting residue was directly subjected to purification by way of column chromatography ($SiO_2$, gradient elution:Hex→EtOAc→10:1 (v/v) EtOAc: MeOH) to afford methyl 5-(8-(5-cyanopyridin-2-yl)-3,8-diazabicyclo[3.2.1]octan-3-yl)-2-(3-methoxyphenyl)-5-oxopentanoate as a yellow oil (67% yield).

Step 4: In a dried round-bottom flask equipped with a magnetic stirrer was dissolved methyl 5-(8-(5-cyanopyridin-2-yl)-3,8-diazabicyclo[3.2.1]octan-3-yl)-2-(3-methoxyphenyl)-5-oxopentanoate (1 equiv) from the previous step in THF (0.044 M). To this was then added sodium borohydride (10 equiv, Sigma-Aldrich) and the resulting white suspension was heated at 80° C. for 16 h. After cooling to RT, the reaction was quenched with water and extracted with DCM. The combined organic extracts were dried over $MgSO_4$, filtered and the filtrate concentrated in vacuo. Purification by way of reverse phase column chromatography (Cis, gradient elution: 3:2 (v/v) $H_2O$:MeOH+0.10% $NH_4HCO_3$→2:3 (v/v) $H_2O$:MeOH+0.10% $NH_4HCO_3$) to afford the title compound as a white solid (28% yield). LCMS: m/z=421.1 $[M+H]^+$; $^1H$ NMR (Methanol-$d_4$) δ=8.47~ 8.39 (m, 1H), 7.76~ 7.71 (m, 1H), 7.27~ 7.15 (m. 1H), 6.88~ 6.76 (m, 4H), 4.69 (s, 2H), 4.24 (d, J=13.2 Hz, 1H), 3.78 (d, J=4.5 Hz, 3H), 3.73~ 3.60 (m, 2H), 3.52 (t, J=12.3 Hz, 1H), 3.31~ 3.17 (m, 1H), 2.91~2.73 (m, 2H), 2.40~2.24 (m, 3H), 2.28~2.10 (m, 2H), 1.88~1.74 (m, 3H).

The following examples were prepared via chiral chromatographic separation of the corresponding racemic mixture. For Example 318-entA and Example 318-entB, the separation was carried out with CHIRALPAK ID (2*25 cm; 5 m) as the stationary phase and 4:3:1 (v/v/v) $^i$PrOH:Hex:DCM+10 mM solution of $NH_3$ in MeOH as the mobile phase. For Example 319-entA and Example 319-entB, the separation was carried out with CHIRALPAK IE-3 (2*25 cm; 5 m) as the stationary phase and EtOH+8 mM solution of $NH_3$ in MeOH as the mobile phase. For Example 320-entA and Example 320-entB, the separation was carried out with CHIRALPAK IC (2*25 cm; 5 m) as the stationary phase and 3:2 (v/v) Hex: $^i$PrOH+8 mM solution of $NH_3$ in MeOH as the mobile phase. For Example 321-entA and Example 321-entB, the separation was carried out with CHIRALPAK ID (2*25 cm; 5 m) as the stationary phase and 2:1:1 (v/v/v) EtOH:Hex:DCM+10 mM solution of $NH_3$ in MeOH as the mobile phase. For Example 322-entA and Example 322-entB, the separation was carried out with CHIRALPAK IF-3 (2*25 cm; 5 m) as the stationary phase and 4:3:1 (v/v) EtOH:Hex:DCM+10 mM solution of $NH_3$ in MeOH as the mobile phase.

| Example | Starting Racemate | Analysis Conditions | RT (mm) |
|---|---|---|---|
| 318-entA<br>318-entB | 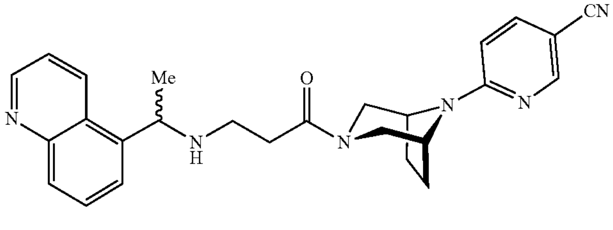<br>Example 48 | CHIRALPAK ID-3<br>(0.46 * 5 cm; 3 μm)<br>4:3:1 (v/v/v) $^{i}$PrOH:<br>Hex: DCM + 0.1% DEA<br>1 mL/min | 1.87<br>2.73 |
| 319-entA<br>319-entB | 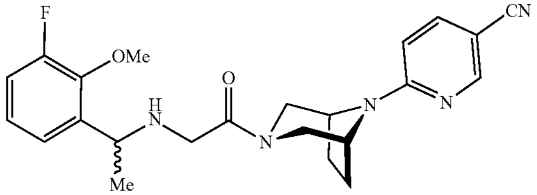<br>Example 55 | CHIRALPAK IE-3<br>(0.46 * 5 cm; 3 μm)<br>2:3 (v/v) EtOH: Hex +<br>0.1% DEA<br>1 mL/min | 3.92<br>4.61 |
| 320-entA<br>320-entB | 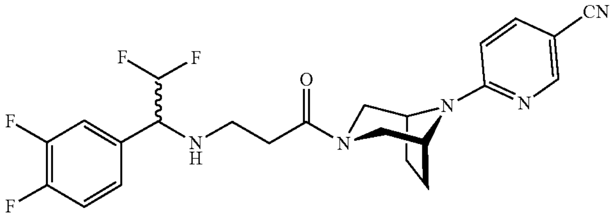<br>Example 129 | CHIRALPAK IC<br>(0.46 * 5 cm; 3 μm)<br>2:3 (v/w) $^{i}$PrOH: Hex +<br>0.1% DEA | 1.91<br>2.32 |
| 321-entA<br>321-entB | 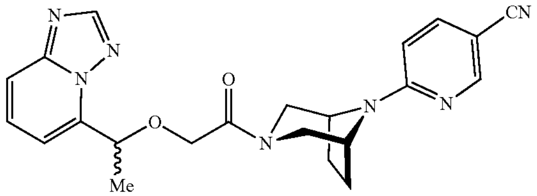<br>Example 191 | CHIRALPAK ID-3<br>(0.46 * 5 cm; 3 μm)<br>2:1:1 (v/v/v) EtOH: Hex:<br>DCM + 0.1% DEA<br>1 mL/min | 2.25<br>2.97 |
| 322-entA<br>322-entB | 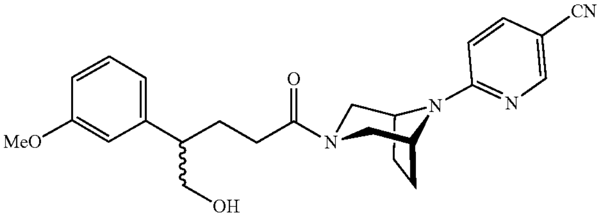<br>Example 317 | CHIRALPAK IF-3<br>(0.46 * 5 cm; 3 μm)<br>4:3:1 (v/w) EtOH: Hex:<br>DCM + 0.1% DEA<br>1 mL/min | 1.55<br>2.31 |

Biological Evaluations

Example 324: In Vitro Functional Assay of Muscarinic Acetylcholine Receptor Activity CHO-K1 cells stably expressing human $M_1$ receptor with aequorin (Perkin Elmer) were grown in F12 media (Gibco) containing 10% FBS (ATCC), 0.4 mg/mL geneticin (Sigma-Aldrich) and 0.25 mg/mL Zeocin (Invitrogen). Cells were grown as per the manufacturer's protocol. For compound testing, cells were grown to confluency and detached gently with Accutase (Sigma-Aldrich) followed by centrifugation for 5 min at 150× g. Cells were then re-suspended in assay buffer (i.e. DMEM/F-12 HEPES without phenol red (Invitrogen) with 0.1% BSA (Sigma-Aldrich)) at a density of $5\times10^6$ cells/ml. Under sterile conditions, 5 μM coelenterazine (Invitrogen) was added to the cells, mixed, then incubated at room temperature protected from light, with gentle agitation, for 4 h.

Primary compound plates were prepared in 100% DMSO in opaque 96-well plates (VWR) and serially diluted in half log increments. Secondary compound plates were prepared at 3× concentration in assay buffer. Compounds were added to white, clear bottom tissue culture treated 96-well plates (Fisher Scientific). Coelenterazine-loaded cells were then added at $5 \times 10^5$ cells/well.

Compounds and cells were incubated at room temperature for 30 min in the dark. Acetylcholine at the $EC_{80}$ concentration was added and calcium flux measured using a FlexStation 3 (Molecular Devices). Sigmoidal dose-response curves were generated by measuring luminescence over 40 sec and calculating the area under the curve. Dose response curves and $IC_{50}$ values were generated using Prism (GraphPad). Compounds were tested at a final concentration range of 100 μM to 10 μM in 0.1% DMSO. Results are shown in Table 1.

TABLE 1

| Example | $M_1$ $IC_{50}$ |
|---|---|
| 1 | A |
| 2 | C |
| 3 | C |
| 4 | B |
| 5 | B |
| 6 | D |
| 7 | D |
| 8 | C |
| 9 | C |
| 10 | A |
| 11 | A |
| 12 | C |
| 13 | B |
| 14 | D |
| 15 | B |
| 16 | B |
| 17 | C |
| 18 | D |
| 19 | C |
| 20 | D |
| 21 | C |
| 22 | D |
| 23 | D |
| 24 | E |
| 25 | A |
| 26 | B |
| 27 | A |
| 28 | A |
| 29 | D |
| 30 | C |
| 31 | C |
| 32 | B |
| 33 | B |
| 34 | A |
| 35 | B |
| 36 | D |
| 37 | A |
| 38 | D |
| 39 | C |
| 40 | D |
| 41 | B |
| 42 | A |
| 43 | B |
| 44 | C |
| 45 | B |
| 46 | A |
| 47 | B |
| 48 | A |
| 49 | D |
| 50 | A |
| 51 | B |
| 52 | A |
| 53 | B |
| 54 | B |
| 55 | A |
| 56 | A |
| 57 | A |
| 58 | B |
| 59 | A |

TABLE 1-continued

| Example | $M_1$ $IC_{50}$ |
|---|---|
| 60 | B |
| 61 | C |
| 62 | C |
| 63 | D |
| 64 | C |
| 65 | A |
| 66 | A |
| 67 | A |
| 68 | A |
| 69 | C |
| 70 | C |
| 71 | C |
| 72 | C |
| 73 | B |
| 74 | B |
| 76 | A |
| 76 | A |
| 77 | A |
| 78 | C |
| 79 | D |
| 80 | E |
| 81 | E |
| 82 | E |
| 83 | D |
| 84 | C |
| 85 | B |
| 86 | D |
| 87 | A |
| 88 | D |
| 89 | D |
| 90 | C |
| 91 | C |
| 92 | A |
| 93 | A |
| 94 | D |
| 95 | B |
| 96 | C |
| 97 | A |
| 98 | A |
| 99 | E |
| 100 | E |
| 101 | B |
| 102 | C |
| 103 | B |
| 104 | E |
| 105 | E |
| 106 | C |
| 107 | B |
| 108 | C |
| 109 | A |
| 110 | A |
| 111 | A |
| 112 | A |
| 113 | A |
| 114 | A |
| 115 | B |
| 116 | B |
| 117 | C |
| 118 | B |
| 119 | C |
| 120 | D |
| 121 | C |
| 122 | A |
| 123 | B |
| 124 | B |
| 125 | A |
| 126 | A |
| 127 | A |
| 128 | B |
| 129 | A |
| 130 | E |
| 131 | D |
| 132 | A |
| 133 | B |
| 134 | C |
| 135 | D |
| 136 | C |
| 137 | C |

TABLE 1-continued

| Example | $M_1$ $IC_{50}$ |
|---|---|
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | C |
| 151 | A |
| 152 | D |
| 153 | C |
| 154 | D |
| 155 | B |
| 156 | C |
| 157 | C |
| 158 | A |
| 159 | A |
| 160 | A |
| 161 | A |
| 162 | A |
| 163 | A |
| 164 | A |
| 165 | B |
| 166 | D |
| 167 | C |
| 168 | D |
| 169 | D |
| 170 | E |
| 171 | E |
| 172 | E |
| 173 | D |
| 174 | E |
| 175 | E |
| 176 | D |
| 177 | B |
| 178 | C |
| 179 | C |
| 180 | B |
| 181 | B |
| 182 | B |
| 183 | B |
| 184 | B |
| 185 | C |
| 186 | D |
| 187 | C |
| 188 | D |
| 189 | D |
| 190 | E |
| 191 | B |
| 192 | A |
| 193 | A |
| 194 | C |
| 195 | B |
| 196 | A |
| 197 | A |
| 198 | B |
| 199 | A |
| 200 | B |
| 201 | B |
| 202 | A |
| 203 | C |
| 204 | C |
| 205 | C |
| 206 | C |
| 207 | B |
| 208 | C |
| 209 | C |
| 210 | B |
| 211 | B |
| 212 | B |
| 213 | B |
| 214 | B |
| 215 | B |

TABLE 1-continued

| Example | $M_1$ $IC_{50}$ |
|---|---|
| 216 | A |
| 217 | B |
| 218 | A |
| 219 | B |
| 220 | A |
| 221 | B |
| 222 | D |
| 223 | E |
| 224 | B |
| 225 | C |
| 226 | A |
| 227 | C |
| 228 | B |
| 229 | C |
| 230 | A |
| 231 | B |
| 232 | A |
| 233 | A |
| 234 | B |
| 235 | B |
| 236 | C |
| 237 | A |
| 238 | C |
| 239 | A |
| 240 | C |
| 241 | D |
| 242 | B |
| 243 | C |
| 244 | D |
| 245 | C |
| 246 | D |
| 247 | A |
| 248 | C |
| 249 | B |
| 250 | C |
| 251 | C |
| 252 | B |
| 253 | A |
| 254 | A |
| 255 | A |
| 256 | D |
| 257 | D |
| 258 | A |
| 259 | B |
| 260 | B |
| 261 | B |
| 262 | C |
| 263 | B |
| 264 | A |
| 265 | A |
| 266 | C |
| 267 | B |
| 268 | B |
| 269 | C |
| 270 | A |
| 271 | C |
| 272 | B |
| 273 | C |
| 274 | B |
| 275 | B |
| 276 | A |
| 277 | C |
| 278 | A |
| 279 | D |
| 280 | C |
| 281 | A |
| 282 | B |
| 283 | C |
| 284 | D |
| 285 | E |
| 286 | E |
| 287 | D |
| 288 | B |
| 289 | C |
| 290 | D |
| 291 | C |
| 292 | C |
| 293 | A |

TABLE 1-continued

| Example | $M_1$ $IC_{50}$ |
|---|---|
| 294 | C |
| 295 | C |
| 296 | D |
| 297 | B |
| 298 | C |
| 299 | B |
| 300 | B |
| 301 | C |
| 302 | E |
| 303 | A |
| 304 | B |
| 305 | C |
| 306 | B |
| 307 | C |
| 308 | A |
| 309 | A |
| 310 | A |
| 311 | A |
| 312 | A |
| 313 | A |
| 314 | B |
| 315 | B |
| 316 | A |
| 317 | A |
| 318-entA | A |
| 318-entB | A |
| 319-entA | A |
| 319-entB | C |
| 320-entA | B |
| 320-entB | A |
| 321-entA | C |
| 321-entB | A |
| 322-entA | A |
| 322-entB | C |

A = $IC_{50}$ of less than 10 nM;
B = $IC_{50}$ less than 100 nM but greater than or equal to 10 nM;
C = $IC_{50}$ less than 1 μM (1,000 nM) but but greater than or equal to 100 nM;
D = $IC_{50}$ less than 10 μM (10,000 nM) but but greater than or equal to 1 μM (1,000 nM);
E = $IC_{50}$ greater than 1 μM (1,000 nM)

CHO-K1 cells stably expressing human $M_2$, $M_3$ and $M_4$ receptors, respectively, with aequonin (Perkin Elmer) were used to assess a test compound's ability to dose-dependently reverse the $EC_{80}$ acetylcholine response. The $IC_{50}$ of the compounds was calculated from the dose response curve. Results for select compounds are shown in Table 2.

TABLE 2

| Example | $M_2$ $IC_{50}$ | $M_3$ $IC_{50}$ | $M_4$ $IC_{50}$ |
|---|---|---|---|
| 1 | C | D | C |
| 59 | D | D | D |
| 87 | D | D | D |
| 118 | D | D | C |
| 138 | D | C | C |
| 147 | D | C | C |
| 158 | D | C | C |
| 162 | D | C | C |
| 177 | D | D | D |
| 210 | E | D | NT |
| 239 | D | D | D |
| 250 | E | D | NT |
| 304 | D | E | NT |
| 318-entA | D | D | D |
| 318-entB | D | D | D |
| 321-entB | D | C | NT |

A = $IC_{50}$ of less than 10 nM;
B = $IC_{50}$ less than 100 nM but greater than or equal to 10 nM;
C = $IC_{50}$ less than 1 μM (1,000 nM) but but greater than or equal to 100 nM;
D = $IC_{50}$ less than 10 μM (10,000 nM) but but greater than or equal to 1 μM (1,000 nM);
E = $IC_{50}$ greater than 1 μM (1,000 nM)

What is claimed is:

1. A compound, or a pharmaceutically acceptable salt thereof, having the structure of Formula (IA):

Formula (IA)

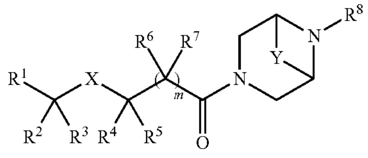

wherein:

X is a bond, —$C(R^9)(R^{10})$—, —O—, or —$CH_2O$—;

Y is a —$CH_2$— or —$CH_2CH_2$—;

$R^1$ is

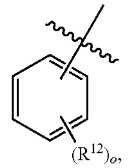 , 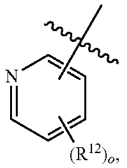 , 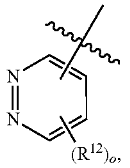 , 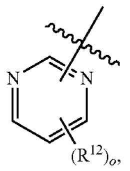 , or 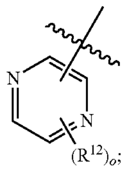 ;

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl; or $R^2$ and $R^3$ combine to form a cycloalkyl or heterocycloalkyl ring optionally substituted with halogen, $C_{1-6}$ alkyl, or $C_{3-6}$ cycloalkyl;

$R^4$ and $R^5$ are independently selected from hydrogen, deuterium, halogen, and $C_{1-3}$ alkyl; or $R^3$ and $R^4$ combine to form a cycloalkyl or heterocycloalkyl ring optionally substituted with halogen, $C_{1-6}$ alkyl, or $C_{3-6}$ cycloalkyl; or $R^4$ and $R^5$ combine to form a cycloalkyl or heterocycloalkyl ring optionally substituted with halogen, $C_{1-6}$ alkyl, or $C_{3-6}$ cycloalkyl;

$R^6$ and $R^7$ are independently selected from hydrogen, deuterium, halogen, and $C_{1-3}$ alkyl; or $R^3$ and $R^7$ combine to form a cycloalkyl or heterocycloalkyl ring optionally substituted with halogen, $C_{1-6}$ alkyl, or $C_{3-6}$ cycloalkyl; or $R^4$ and $R^6$ combine to form a cycloalkyl or heterocycloalkyl ring optionally substituted with halogen, $C_{1-6}$ alkyl, or $C_{3-6}$ cycloalkyl; or $R^5$ and $R^7$ combine to form a bond;

$R^8$ is

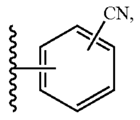 , 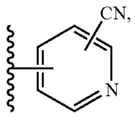 , 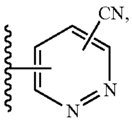 , 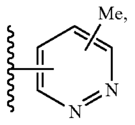 ,

-continued

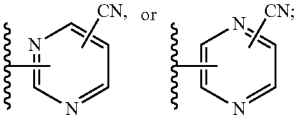

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^4$ and $R^{10}$ combine to form a cycloalkyl or heterocycloalkyl ring optionally substituted with halogen, $C_{1-6}$ alkyl, or $C_{3-6}$ cycloalkyl; or $R^6$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

each $R^{12}$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, or —$SF_5$;

m is 0 or 1; and o is 0, 1, 2, or 3.

2. The compound of claim 1, or a pharmaceutically acceptable salt thereof, having the structure of Formula (IIA):

Formula (IIA)

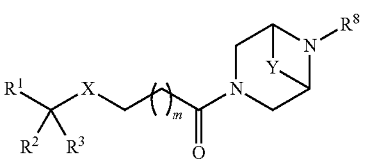

wherein:

X is a bond, —$C(R^9)(R^{10})$, —O—, or —$CH_2O$—;

Y is a —$CH_2$— or —$CH_2CH_2$—;

$R^1$ is

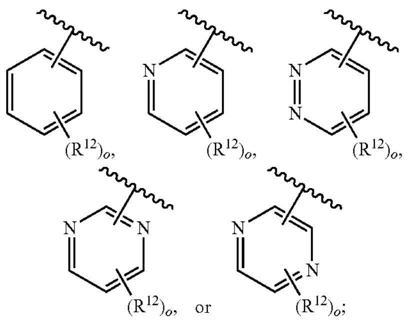

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

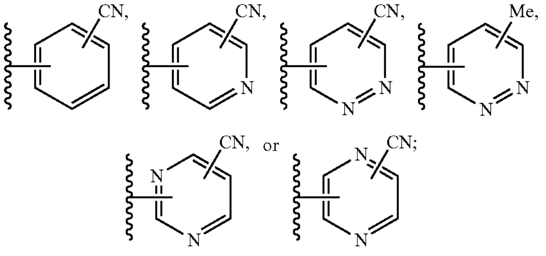

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

each $R^{12}$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, or —$SF_5$;

m is 0 or 1; and and o is 0, 1, 2, or 3.

3. The compound of claim 1, or a pharmaceutically acceptable salt thereof, having the structure of Formula (III):

Formula (III)

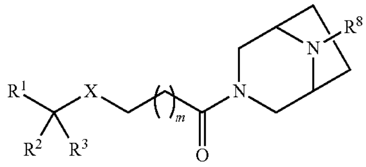

wherein:

X is a bond, —$C(R^9)(R^{10})$—, —O—, or —$CH_2O$—;

$R^1$ is

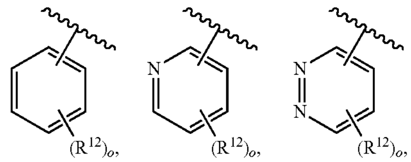

-continued

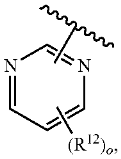 or 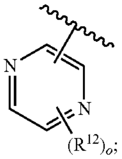

$R^2$ is hydrogen, deuterium, halogen, hydroxyl, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^3$ is halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl; or $R^2$ and $R^3$ combine to form a cycloalkyl or heterocycloalkyl ring optionally substituted with halogen, $C_{1-6}$ alkyl, or $C_{3-6}$ cycloalkyl;

$R^8$ is

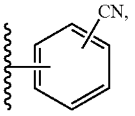 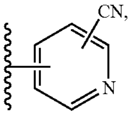 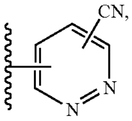 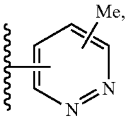

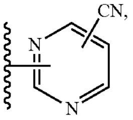 or 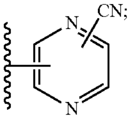

$R^9$ and $R^{10}$ are independently selected from hydrogen, deuterium, halogen, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, heterocycloalkyl, aryl or heteroaryl; or $R^3$ and $R^{10}$ combine to form a cycloalkyl or heterocycloalkyl ring optionally substituted with halogen, $C_{1-6}$ alkyl, or $C_{3-6}$ cycloalkyl; or $R^9$ and $R^{10}$ combine to form a cycloalkyl or heterocycloalkyl ring optionally substituted with halogen, $C_{1-6}$ alkyl, or $C_{3-6}$ cycloalkyl;

each $R^{12}$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, heterocycloalkyl, aryl, heteroaryl, or —$SF_5$;

m is 0 or 1; and and o is 0, 1, 2, or 3.

4. The compound of claim 1, or a pharmaceutically acceptable salt thereof, wherein X is a bond.

5. The compound of claim 1, or a pharmaceutically acceptable salt thereof, wherein $R^1$ is

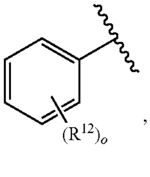 , 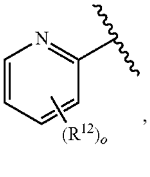 , 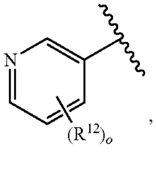 ,

-continued

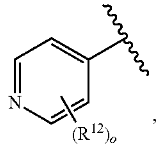 , 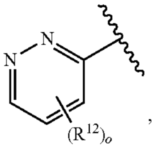 , 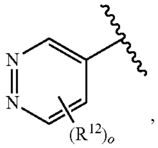 ,

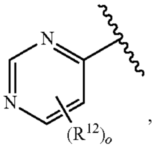 , 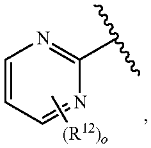 , 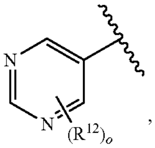 , or

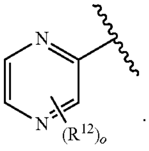 .

6. The compound of claim 1, or a pharmaceutically acceptable salt thereof, wherein $R^2$ is hydrogen, —F, —$CH_3$, —$CH_2CH_3$, —$CF_2H$, —$CF_3$, —$CH_2OH$, —$C(CH_3)_2OH$, or cyclopropyl.

7. The compound of claim 1, or a pharmaceutically acceptable salt thereof, wherein $R^3$ is —F, —$CH_3$, —$CH_2CH_3$, —$CF_2H$, —$CF_3$, —$CH_2OH$, —$C(CH_3)_2OH$, or cyclopropyl.

8. The compound of claim 1, or a pharmaceutically acceptable salt thereof, wherein m is 1.

9. The compound of claim 1, or a pharmaceutically acceptable salt thereof, wherein o is 1.

10. The compound of claim 1, or a pharmaceutically acceptable salt thereof, wherein $R^8$ is

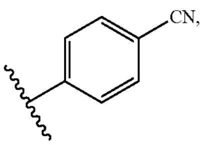 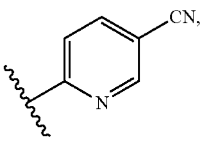

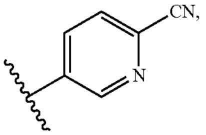 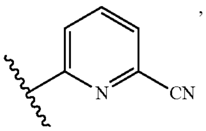 ,

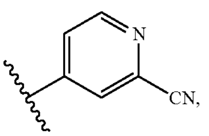 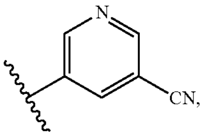

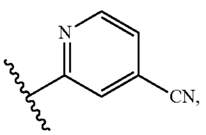 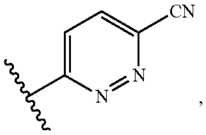 ,

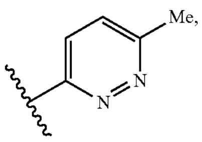 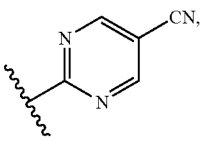 or

-continued
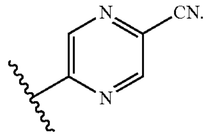
11. A pharmaceutical composition comprising a compound of claim 1, or a pharmaceutically acceptable salt thereof, and at least one pharmaceutically acceptable excipient.
12. A compound, which is
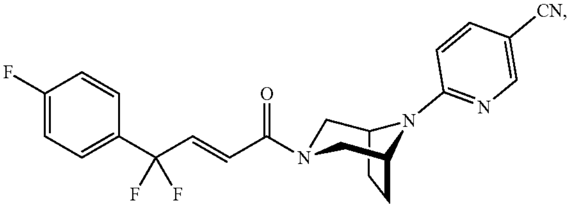
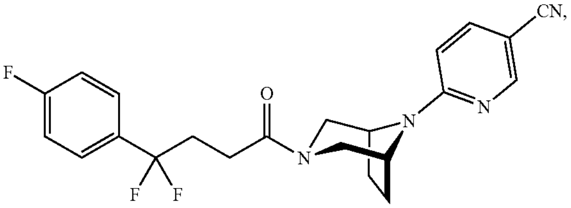
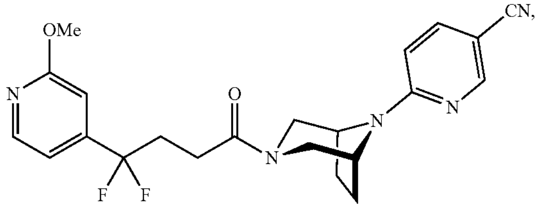
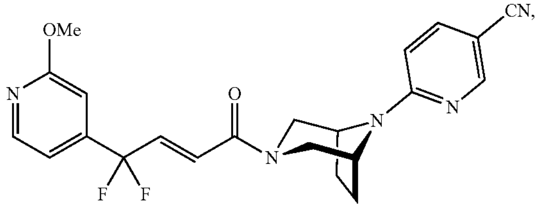
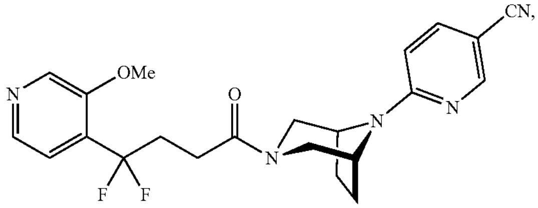
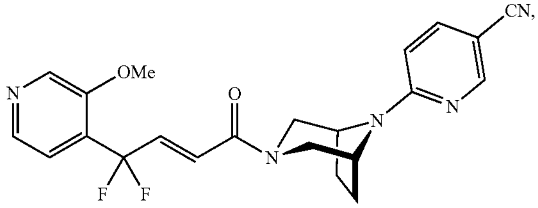
-continued
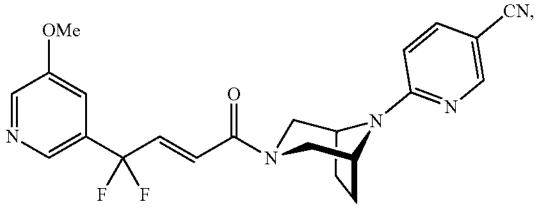
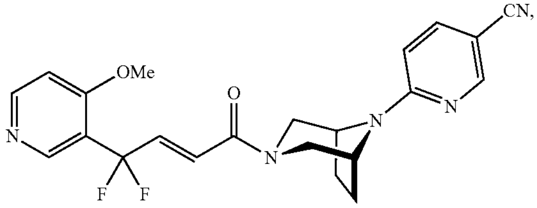
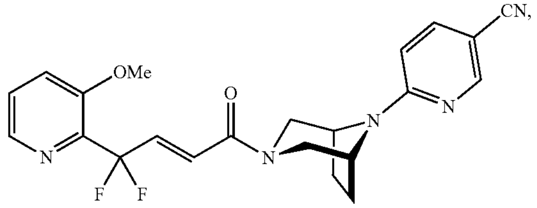
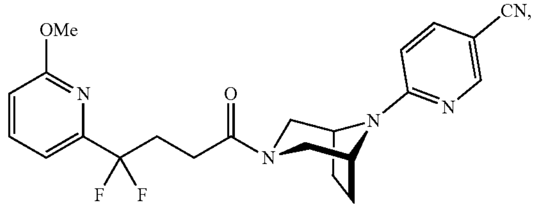
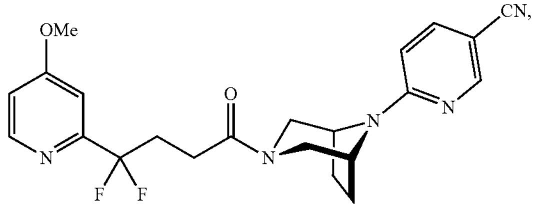
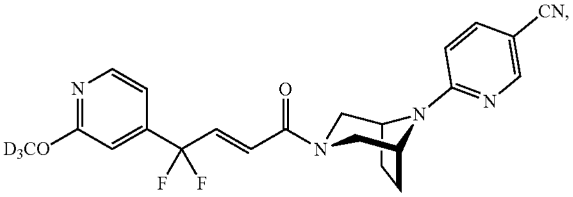
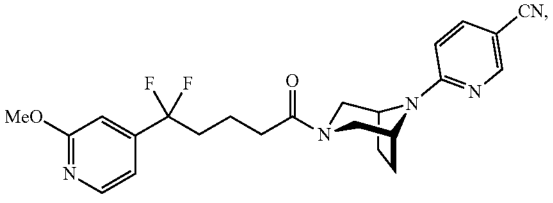
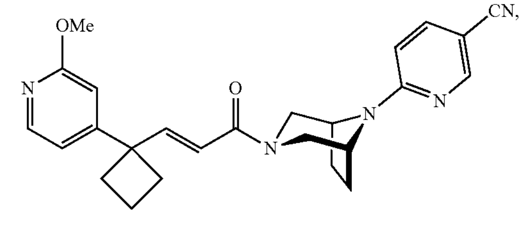

-continued
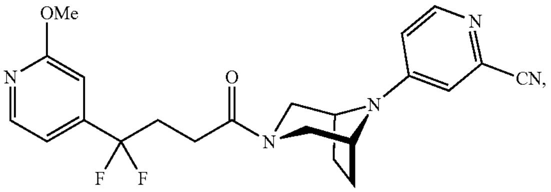
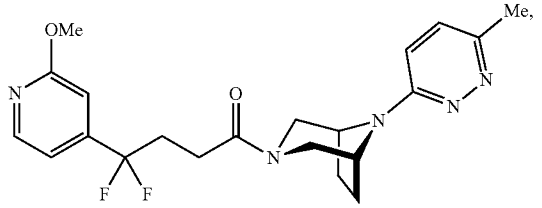
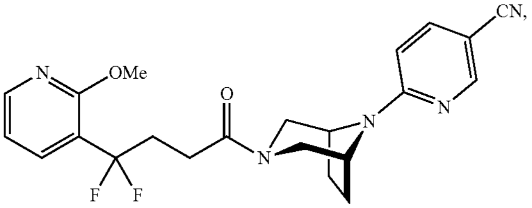
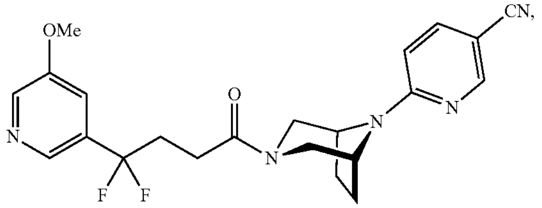
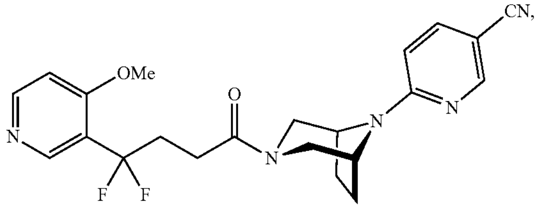
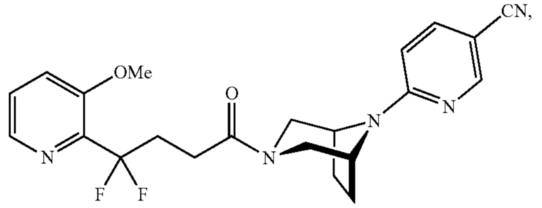
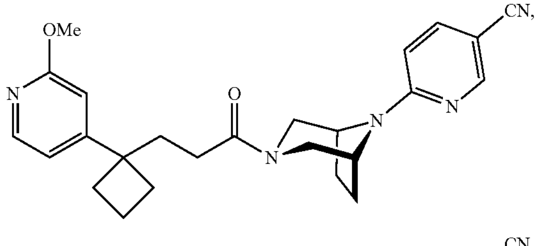
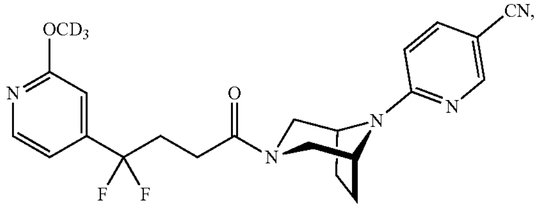
-continued
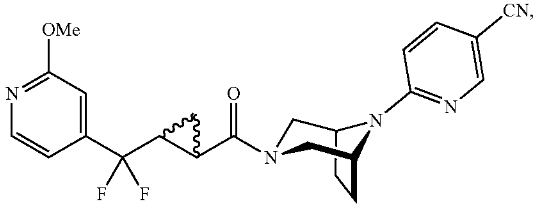
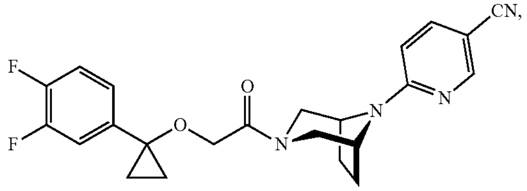
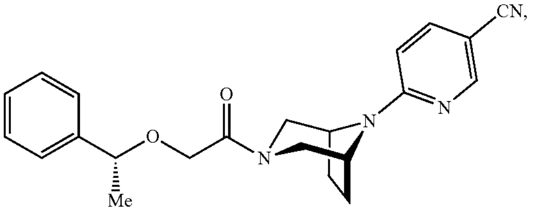
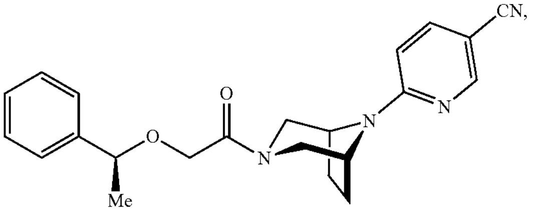
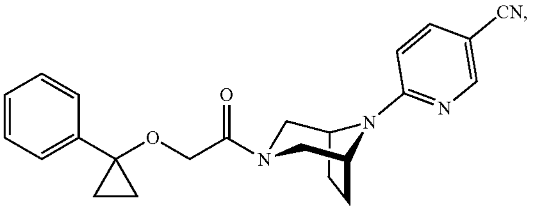
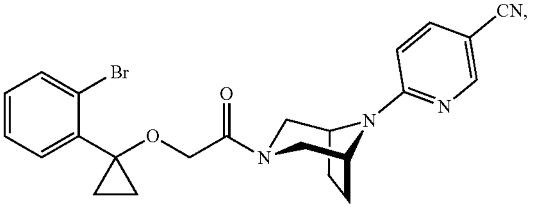
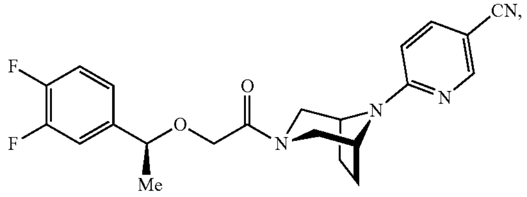
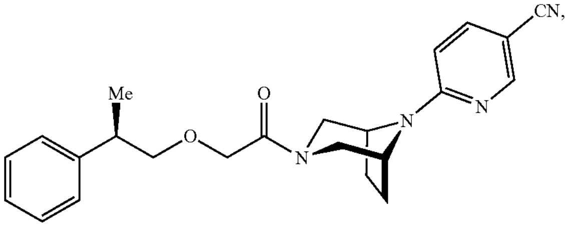

-continued
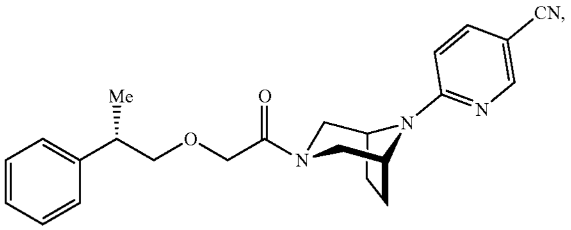
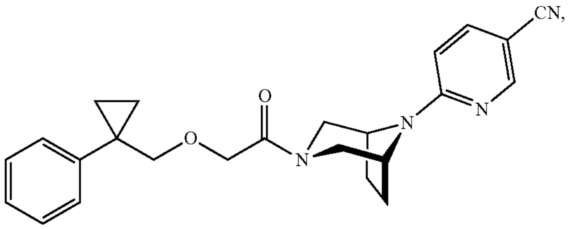
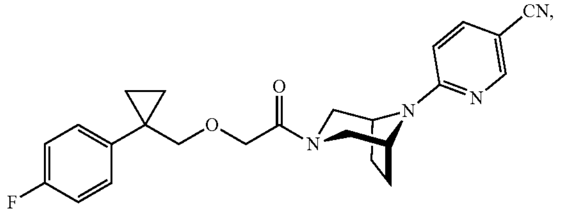
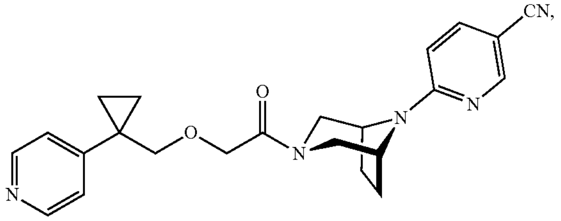
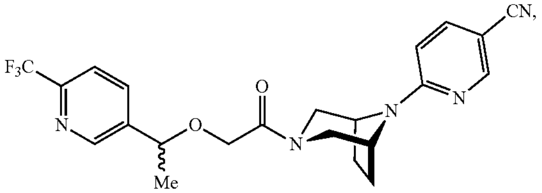
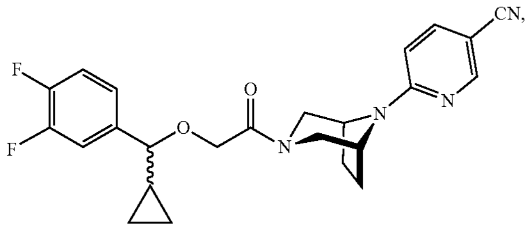
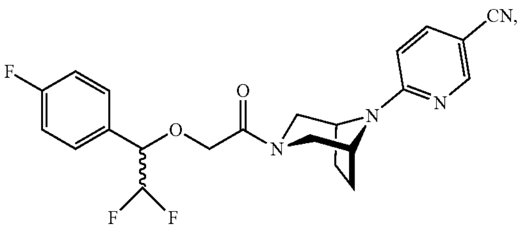
-continued
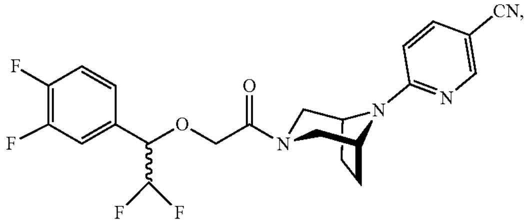
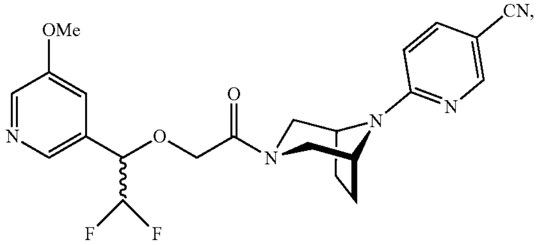
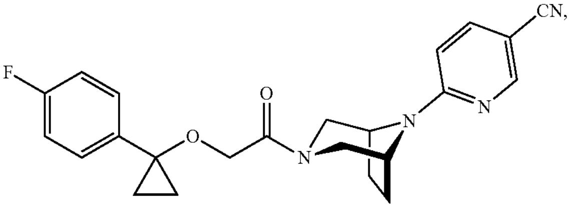
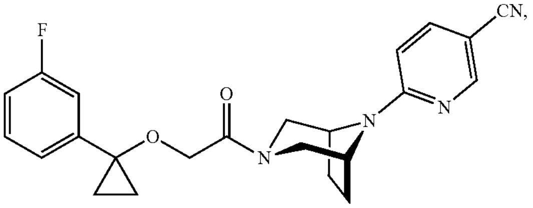
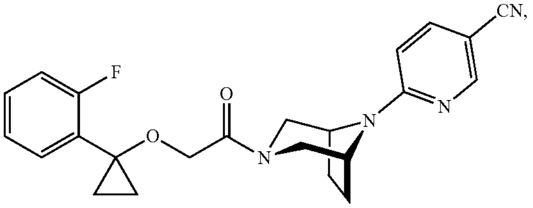
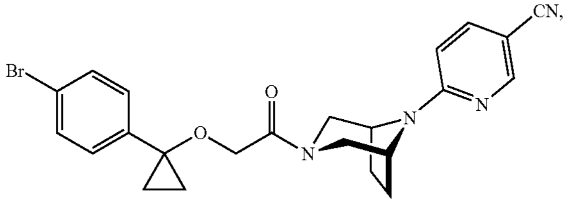
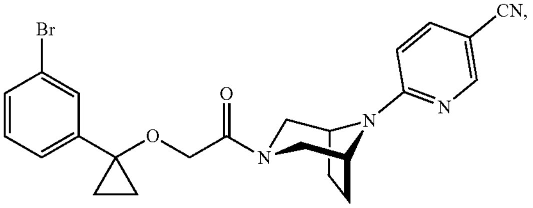
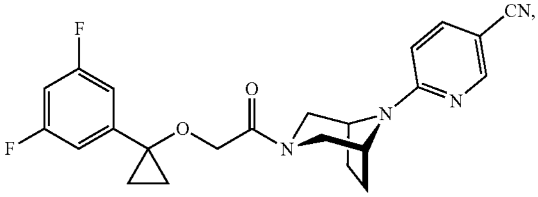

-continued
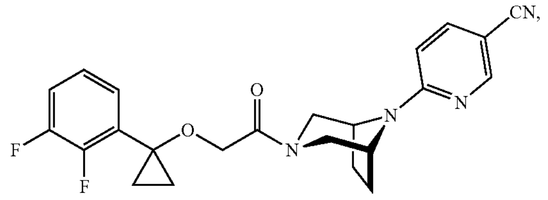
,
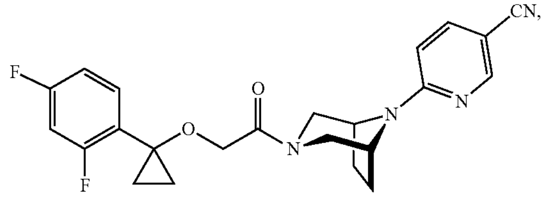
,
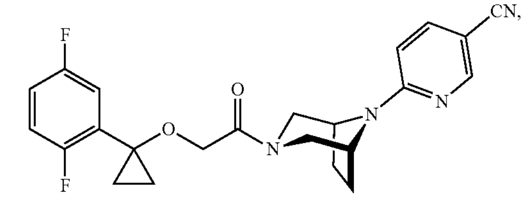
,
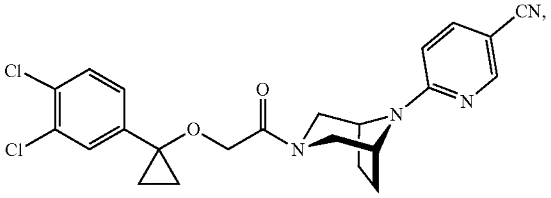
,
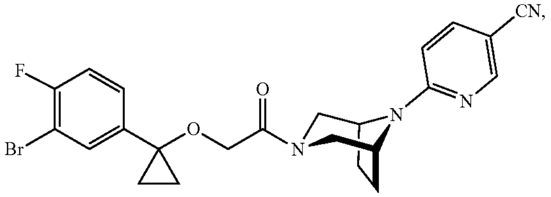
,
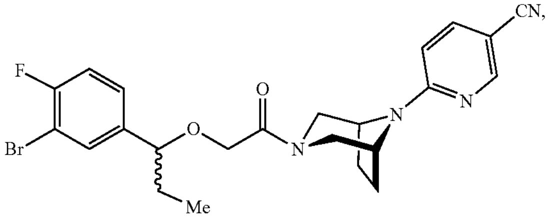
,
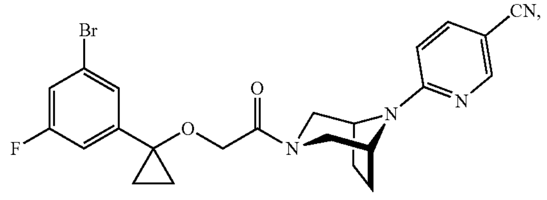
,
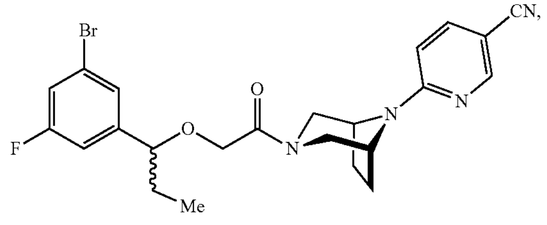
,
-continued
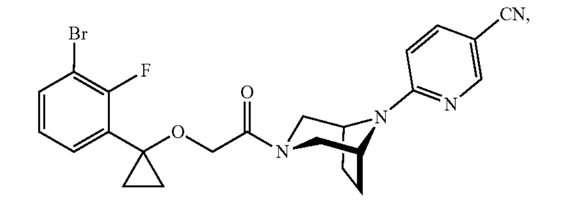
,
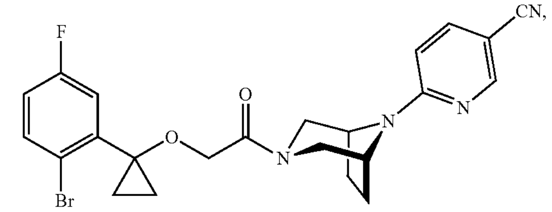
,
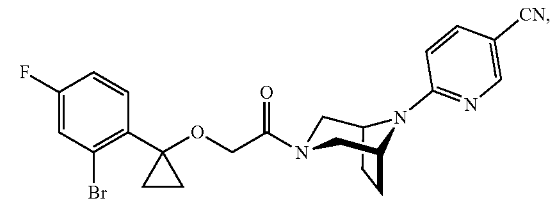
,
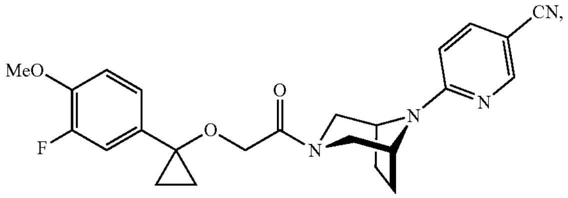
,
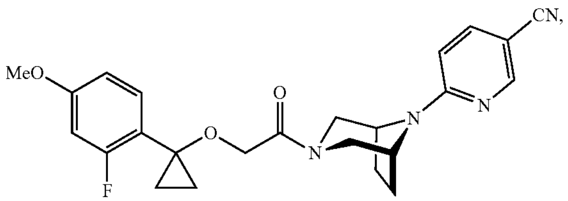
,
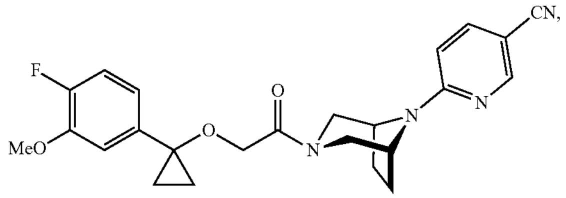
,
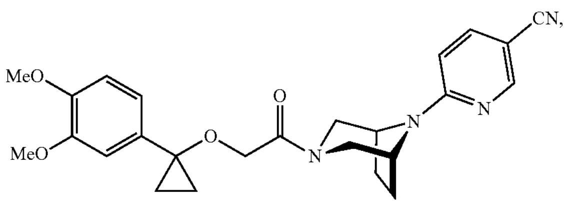
,
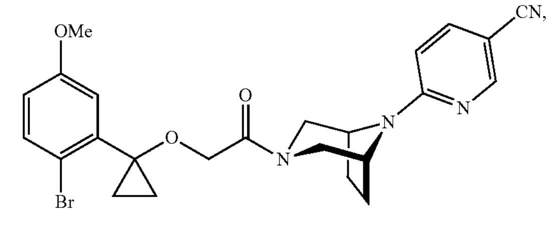
, -continued
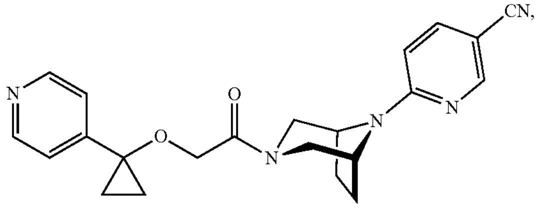
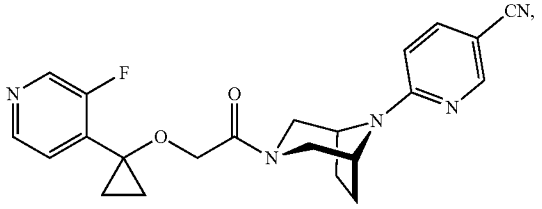
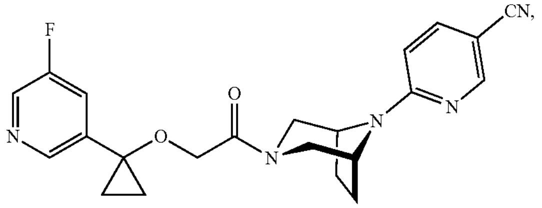
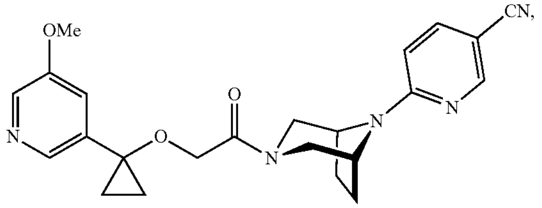
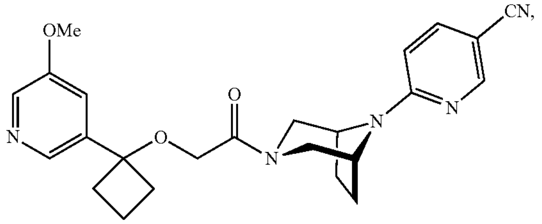
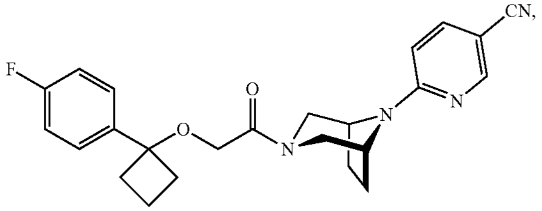
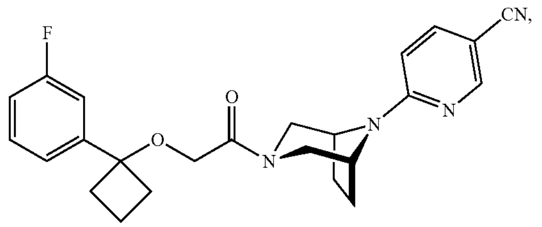
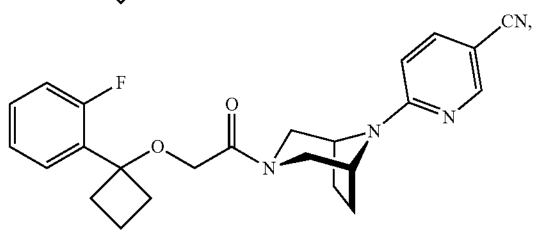
-continued
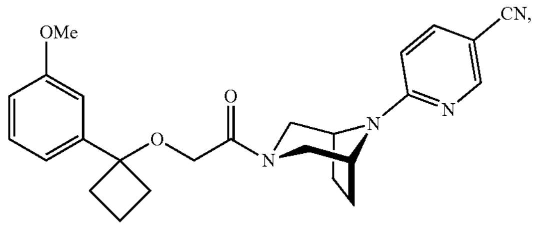
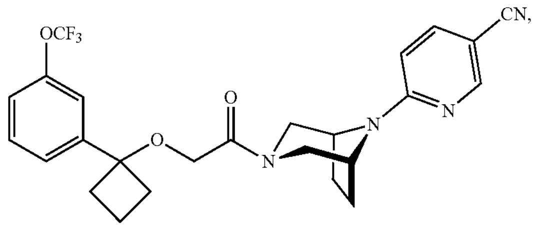
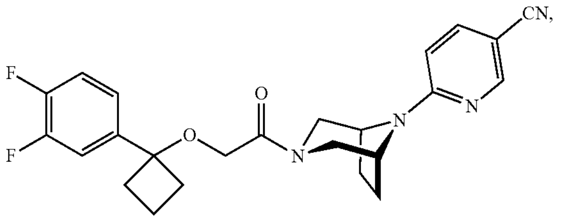
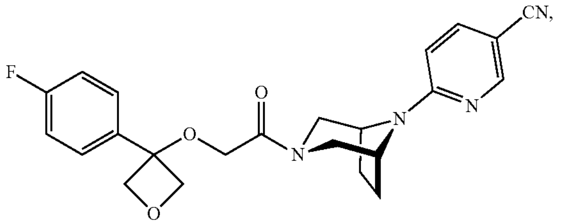
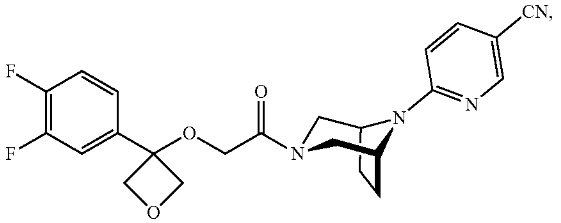
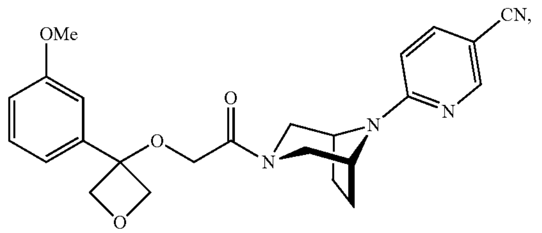
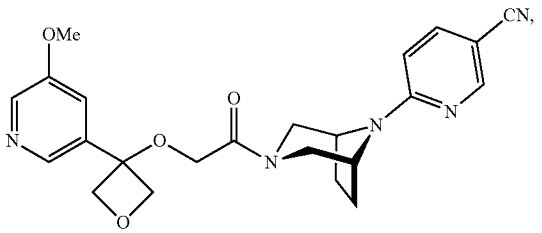

-continued
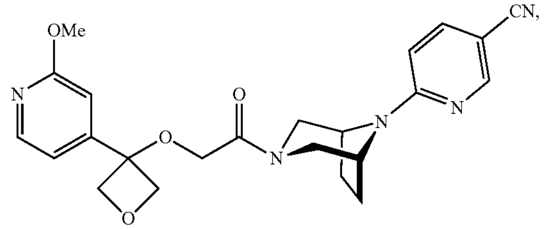
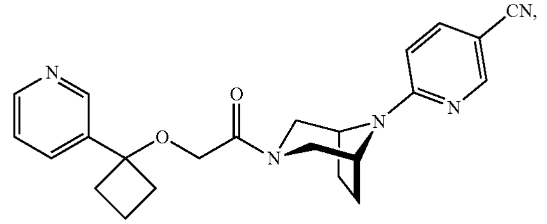
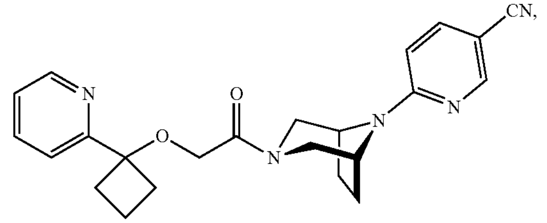
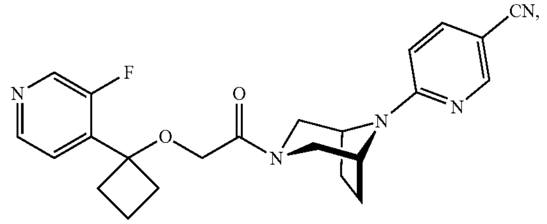
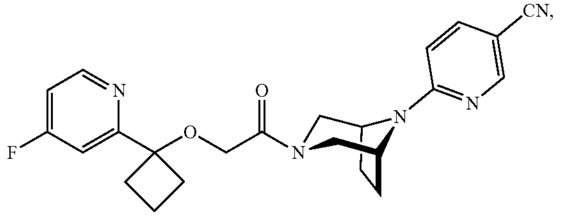
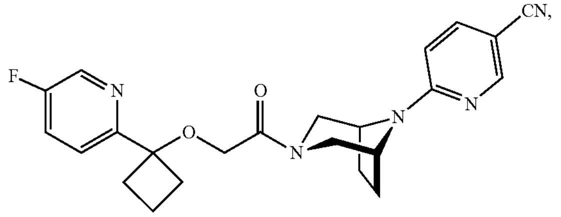
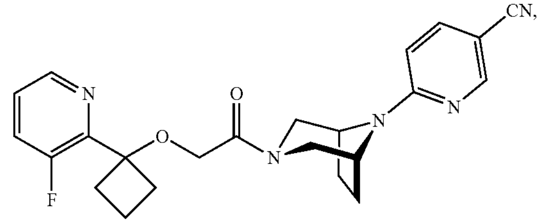
-continued
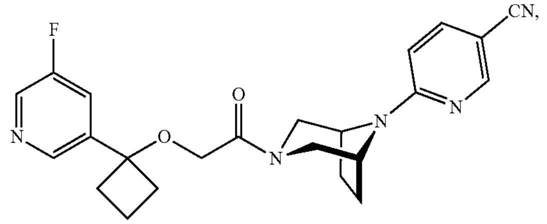
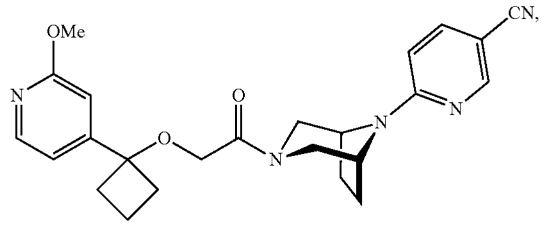
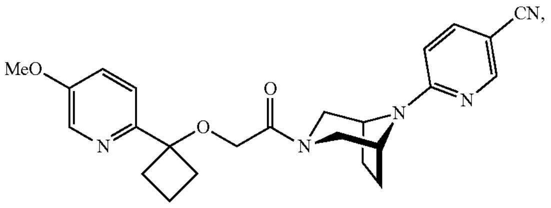
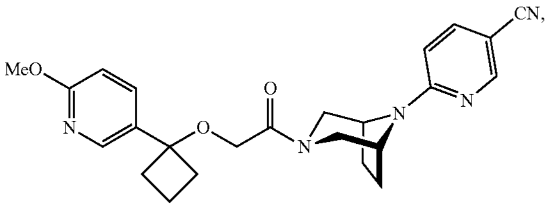
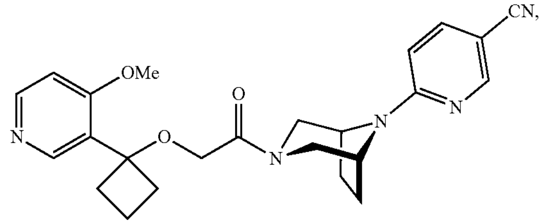
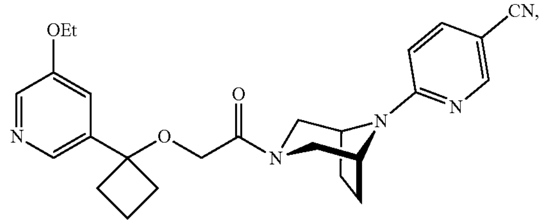
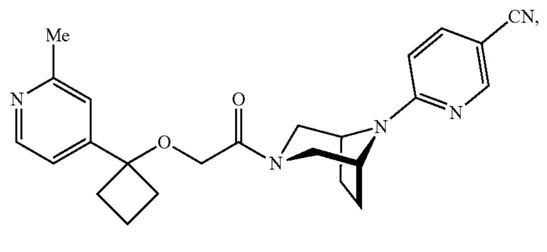

-continued
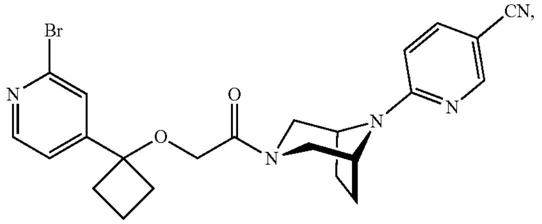
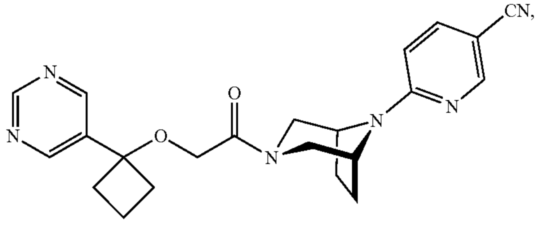
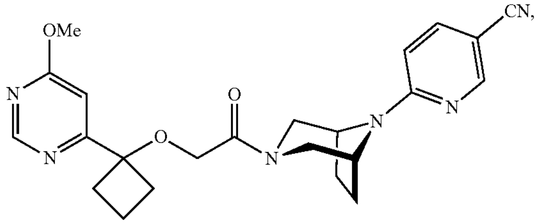
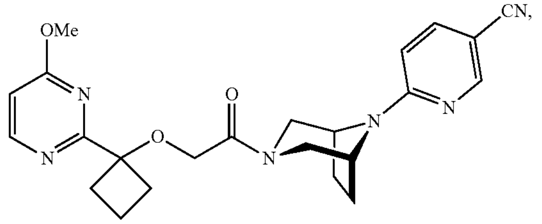
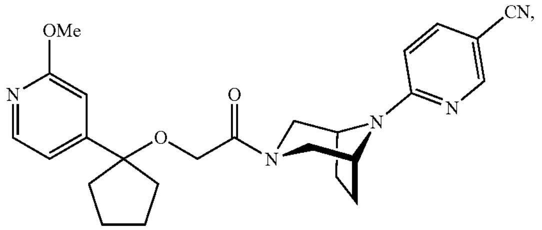
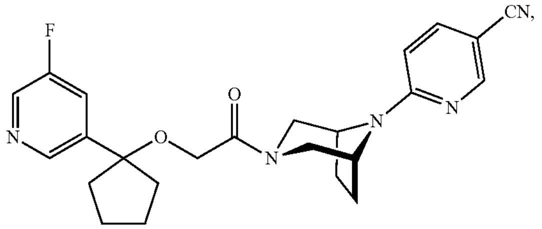
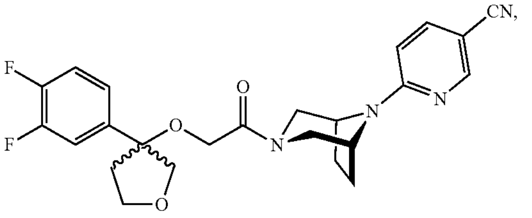
-continued
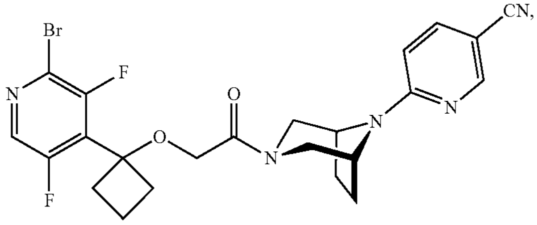
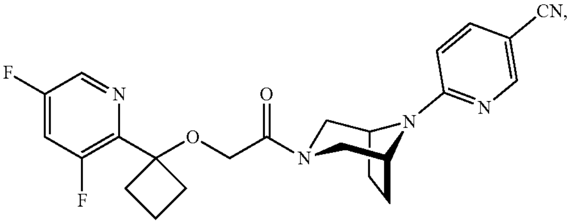
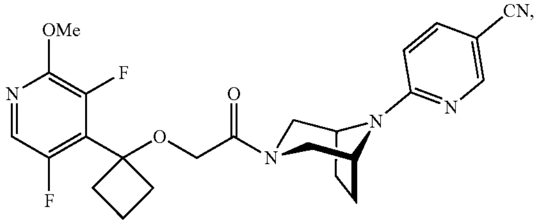
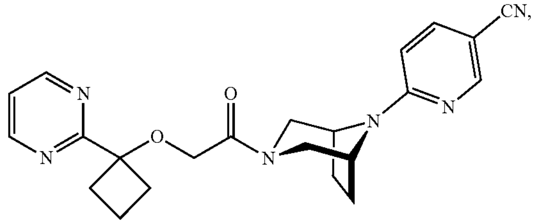
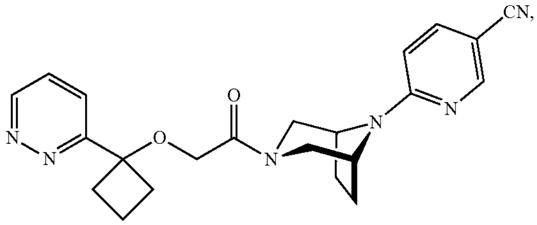
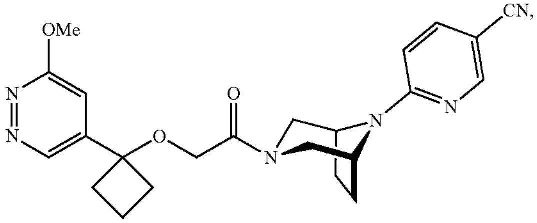
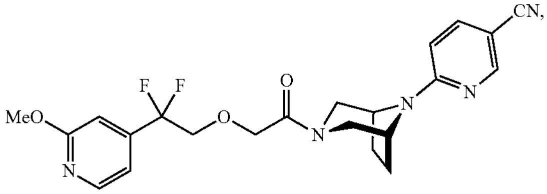
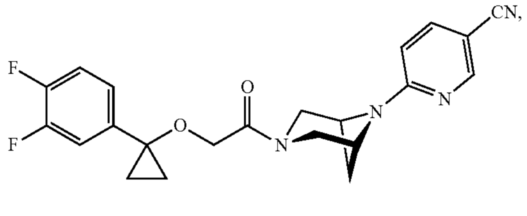

-continued
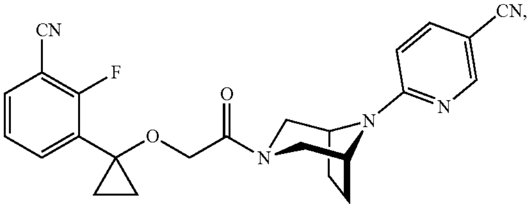
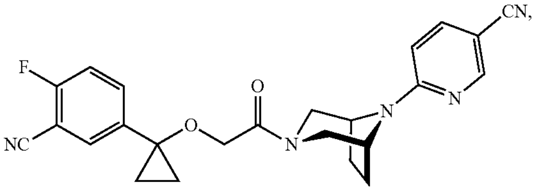
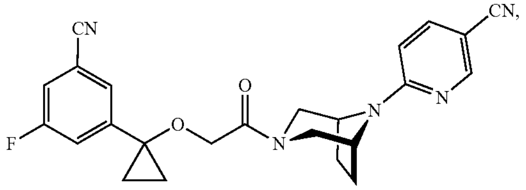
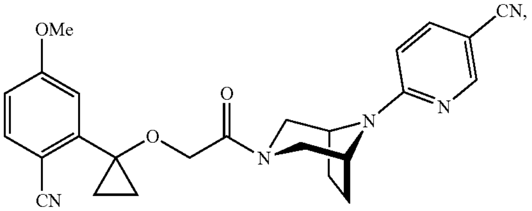
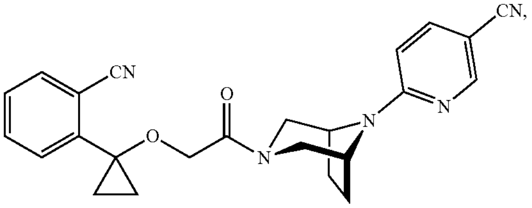
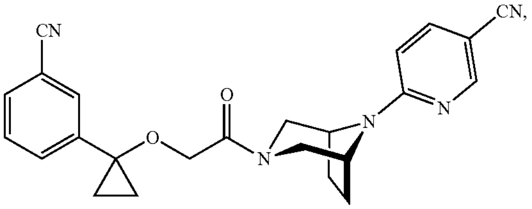
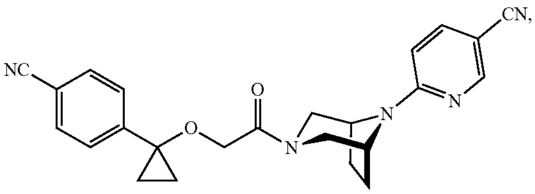
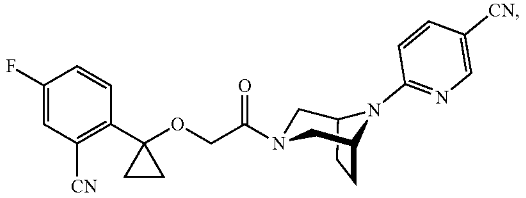
-continued
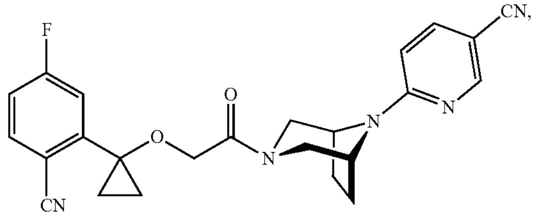
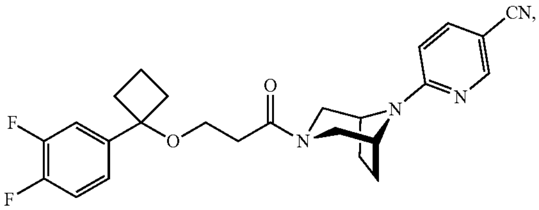
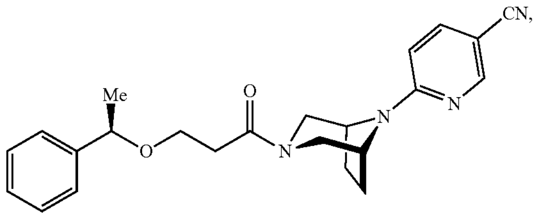
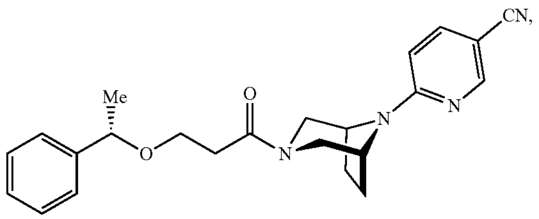
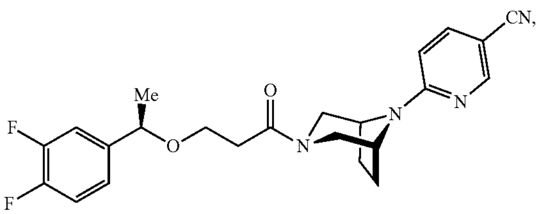
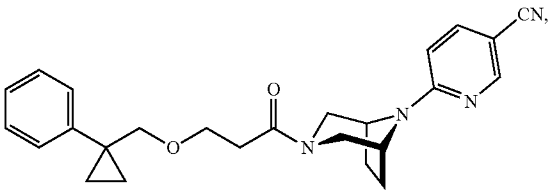
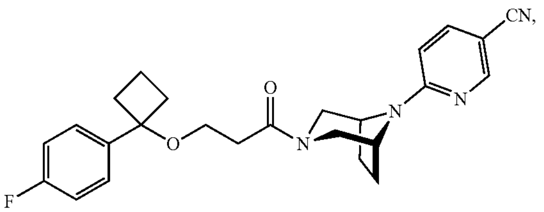
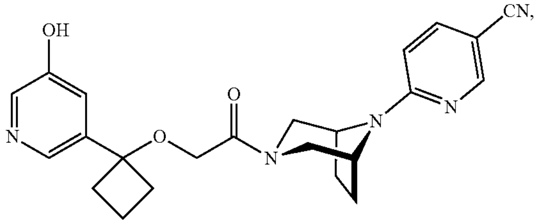

-continued
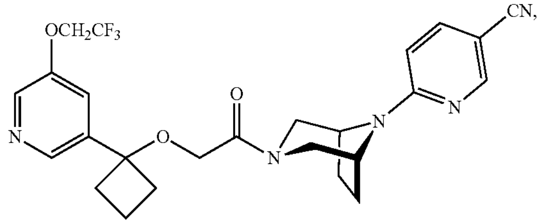
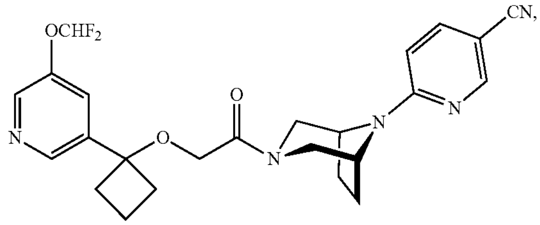
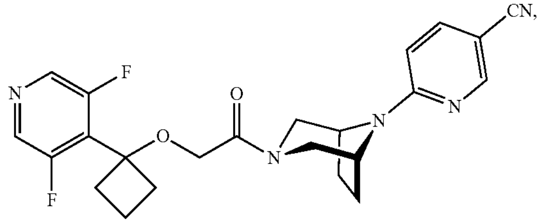
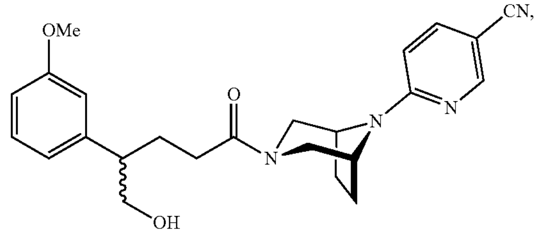
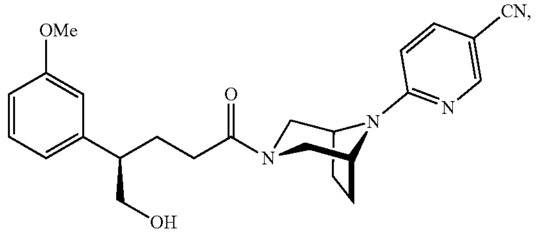
or
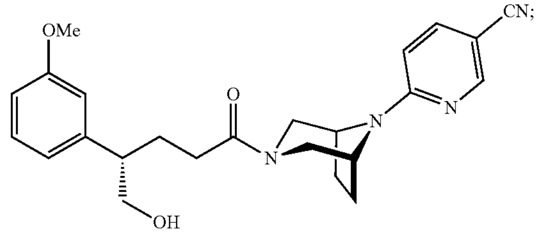
or a pharmaceutically acceptable salt thereof.
13. The compound of claim 12, wherein the compound is selected from the group consisting of
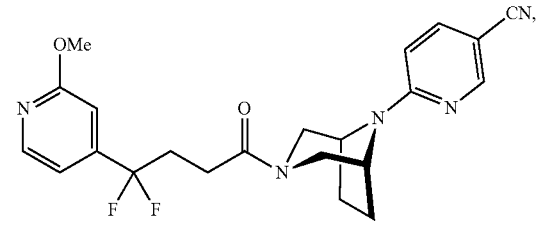
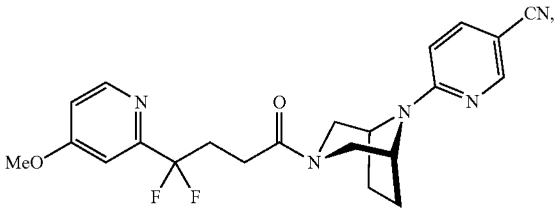
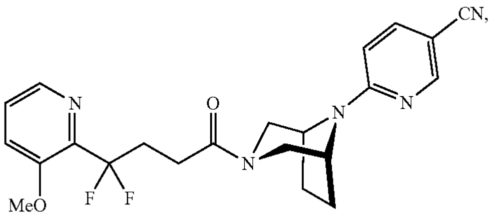
and
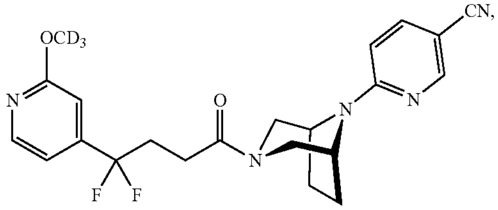
or a pharmaceutically acceptable salt thereof.
14. The compound of claim 13, wherein the compound is selected from the group consisting of
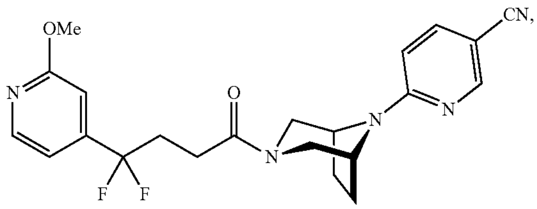
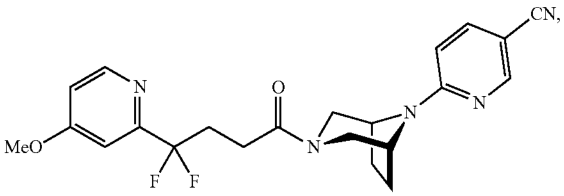
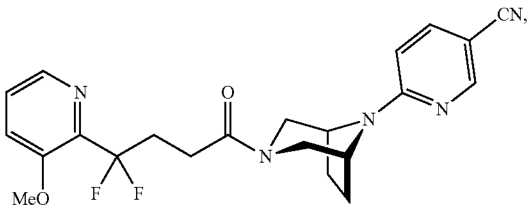
and -continued

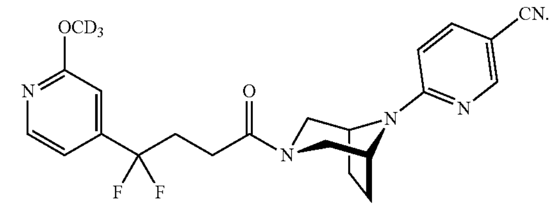

15. A compound, which is

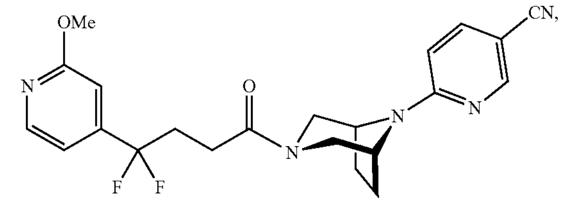

or a pharmaceutically acceptable salt thereof.

16. A compound, which is

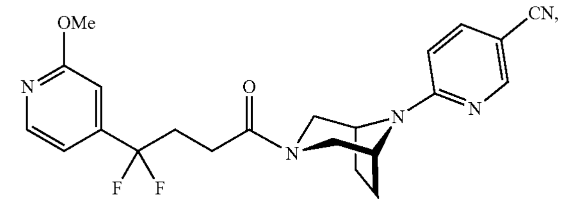

17. The compound of claim 13, wherein the compound is

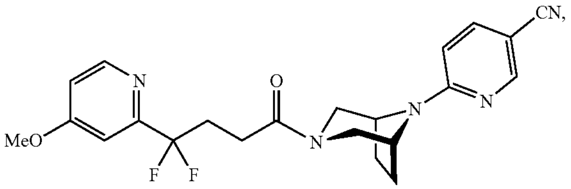

or a pharmaceutically acceptable salt thereof.

18. The compound of claim 17, wherein the compound is

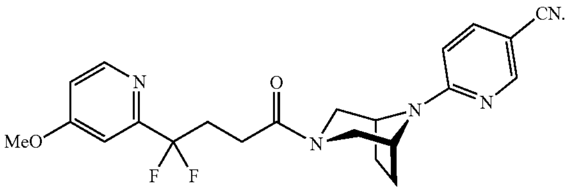

19. The compound of claim 13, wherein the compound is

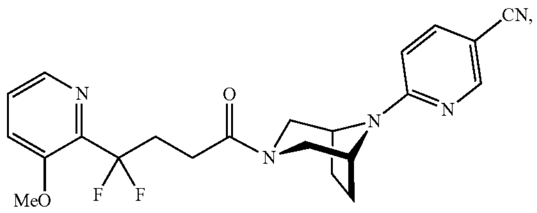

or a pharmaceutically acceptable salt thereof.

20. The compound of claim 19, wherein the compound is

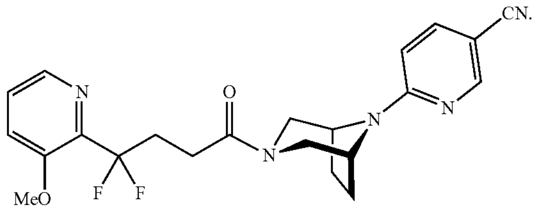

21. The compound of claim 13, wherein the compound is

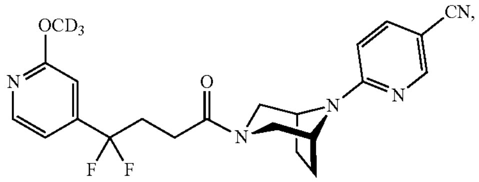

or a pharmaceutically acceptable salt thereof.

22. The compound of claim 21, wherein the compound is

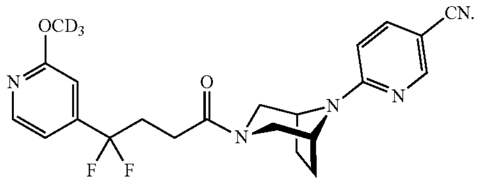

23. A pharmaceutical composition comprising the compound of claim 13, or a pharmaceutically acceptable salt thereof, and at least one pharmaceutically acceptable excipient.

24. A pharmaceutical composition comprising the compound of claim 14 and at least one pharmaceutically acceptable excipient.

25. A pharmaceutical composition comprising the compound of claim 15, or a pharmaceutically acceptable salt thereof, and at least one pharmaceutically acceptable excipient.

26. A pharmaceutical composition comprising the compound of claim 16 and at least one pharmaceutically acceptable excipient.

27. A pharmaceutical composition comprising the compound of claim 17, or a pharmaceutically acceptable salt thereof, and at least one pharmaceutically acceptable excipient.

28. A pharmaceutical composition comprising the compound of claim 18 and at least one pharmaceutically acceptable excipient.

29. A pharmaceutical composition comprising the compound of claim 19, or a pharmaceutically acceptable salt thereof, and at least one pharmaceutically acceptable excipient.

30. A pharmaceutical composition comprising the compound of claim 20 and at least one pharmaceutically acceptable excipient.

31. A pharmaceutical composition comprising the compound of claim 21, or a pharmaceutically acceptable salt thereof, and at least one pharmaceutically acceptable excipient.

32. A pharmaceutical composition comprising the compound of claim 22 and at least one pharmaceutically acceptable excipient.

33. The compound of claim 4, or a pharmaceutically acceptable salt thereof, wherein $R^1$ is

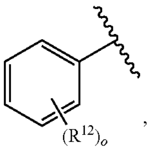,
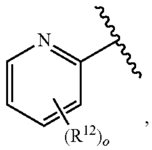,
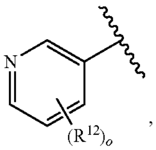,
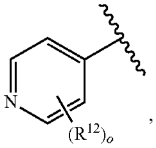,
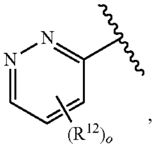,
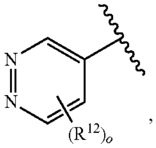,
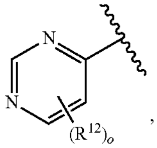,
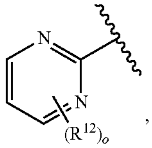,
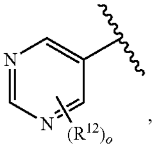, or
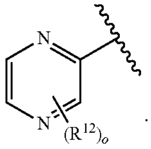.

34. The compound of claim 33, or a pharmaceutically acceptable salt thereof, wherein $R^2$ is hydrogen, —F, —$CH_3$, —$CH_2CH_3$, —$CF_2H$, —$CF_3$, —$CH_2OH$, —$C(CH_3)_2OH$, or cyclopropyl.

35. The compound of claim 34, or a pharmaceutically acceptable salt thereof, wherein $R^3$ is —F, —$CH_3$, —$CH_2CH_3$, —$CF_2H$, —$CF_3$, —$CH_2OH$, —$C(CH_3)_2OH$, or cyclopropyl.

36. The compound of claim 35, or a pharmaceutically acceptable salt thereof, wherein m is 1.

37. The compound of claim 36, or a pharmaceutically acceptable salt thereof, wherein o is 1.

38. The compound of claim 37, or a pharmaceutically acceptable salt thereof, wherein $R^8$ is

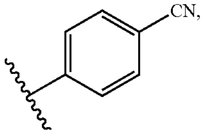
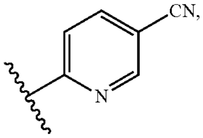
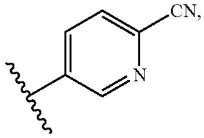,
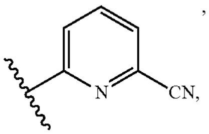
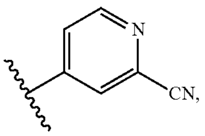
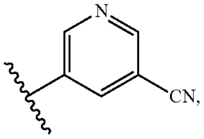
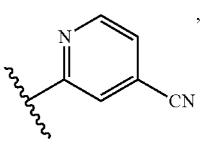,
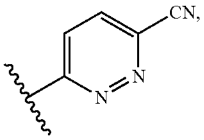
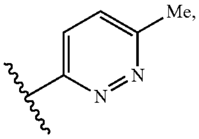
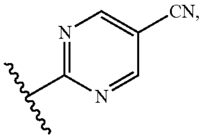 or
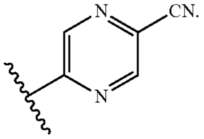

* * * * *